(12) United States Patent
Beckett et al.

(10) Patent No.: US 12,031,180 B2
(45) Date of Patent: Jul. 9, 2024

(54) METHODS, DEVICES, AND SYSTEMS FOR ANALYTE DETECTION AND ANALYSIS

(71) Applicant: Ultima Genomics, Inc., Newark, CA (US)

(72) Inventors: Nathan Beckett, Oakland, CA (US); Gilad Almogy, Palo Alto, CA (US); Nathan Caswell, Sunnyvale, CA (US); Jacob A. Wolf, Oakland, CA (US); Kristopher Barbee, Pleasanton, CA (US); Denis Pristinski, Dublin, CA (US); Mark Pratt, Bozeman, MT (US); Gene Polovy, Redwood City, CA (US); Osip Schwartz, Newark, CA (US); Stephanie Kubecka, San Jose, CA (US); Steven Menchen, Fremont, CA (US); Joseph Anthony, Oakland, CA (US); Jose Martin Sosa, San Jose, CA (US); Phillip You Fai Lee, South San Francisco, CA (US)

(73) Assignee: Ultima Genomics, Inc., Fremont, CA (US)

( * ) Notice: Subject to any disclaimer, the term of this patent is extended or adjusted under 35 U.S.C. 154(b) by 47 days.

(21) Appl. No.: 17/543,521

(22) Filed: Dec. 6, 2021

(65) Prior Publication Data
US 2022/0162696 A1 May 26, 2022

Related U.S. Application Data

(63) Continuation of application No. 17/308,241, filed on May 5, 2021, now Pat. No. 11,268,143, which is a continuation of application No. 16/953,071, filed on Nov. 19, 2020, now Pat. No. 11,118,223, which is a continuation of application No. PCT/US2020/022816, filed on Mar. 13, 2020, which is a continuation of application No. 16/677,067, filed on Nov. 7, 2019, now Pat. No. 10,830,703, and a continuation of application No. 16/677,115, filed on Nov. 7, 2019, now Pat. No. 10,852,518, and a continuation of application No. 16/445,798, filed on Jun. 19, 2019, now Pat. No. 10,900,078.

(60) Provisional application No. 62/914,293, filed on Oct. 11, 2019, provisional application No. 62/837,684, filed on Apr. 23, 2019, provisional application No. 62/818,549, filed on Mar. 14, 2019.

(51) Int. Cl.
*C12Q 1/6874* (2018.01)
*G01N 35/10* (2006.01)

(52) U.S. Cl.
CPC ....... *C12Q 1/6874* (2013.01); *G01N 35/1002* (2013.01)

(58) Field of Classification Search
None
See application file for complete search history.

(56) References Cited

U.S. PATENT DOCUMENTS

| | | |
|---|---|---|
| 3,707,723 A | 12/1972 | Levene |
| 4,611,881 A | 9/1986 | Schmidt et al. |
| 5,216,247 A | 6/1993 | Wang et al. |
| 5,307,146 A | 4/1994 | Porter et al. |
| 5,409,811 A | 4/1995 | Tabor et al. |
| 5,641,006 A | 6/1997 | Autrey et al. |
| 5,641,658 A | 6/1997 | Adams et al. |
| 5,674,716 A | 10/1997 | Tabor et al. |
| 5,800,997 A | 9/1998 | Beck |
| 6,139,831 A | 10/2000 | Shivashankar et al. |
| 6,320,609 B1 | 11/2001 | Buchanan et al. |
| 6,466,352 B1 | 10/2002 | Shahar et al. |
| 6,737,238 B2 | 5/2004 | Suzuki et al. |
| 7,623,289 B2 | 11/2009 | Harada |
| 7,689,022 B2 | 3/2010 | Weiner et al. |
| 7,906,285 B2 | 3/2011 | Drmanac |
| 7,939,264 B1 | 5/2011 | Densham |
| 8,431,903 B2 | 4/2013 | Duhr et al. |

(Continued)

FOREIGN PATENT DOCUMENTS

| | | |
|---|---|---|
| CN | 103547255 A | 1/2014 |
| CN | 107735664 A | 2/2018 |

(Continued)

OTHER PUBLICATIONS

Spencer et al., "Variations of the Earth's Rotation," Phys. Chem. Earth 1961, 4:186-210. (Year: 1961).*

(Continued)

*Primary Examiner* — Kaijiang Zhang
(74) *Attorney, Agent, or Firm* — Wilson Sonsini Goodrich & Rosati

(57) ABSTRACT

Provided are systems and methods for analyte detection and analysis. A system can comprise an open substrate. The open substrate may be configured to rotate or otherwise move. The open substrate can comprise an array of individually addressable locations, with analytes immobilized thereto. The substrate may be spatially indexed to identify nucleic acid molecules from one or more sources, and/or sequences thereof, with the respective one or more sources. A solution comprising a plurality of probes may be directed across the array to couple at least one of the plurality of probes with at least one of the analytes to form a bound probe. A detector can be configured to detect a signal from the bound probe via scanning of the substrate while minimizing temperature fluctuations of the substrate or optical aberrations caused by bubbles.

13 Claims, 84 Drawing Sheets

(56) References Cited

U.S. PATENT DOCUMENTS

| | | | |
|---|---|---|---|
| 8,475,739 B2 | 7/2013 | Holmes et al. | |
| 8,574,847 B2 | 11/2013 | Becker et al. | |
| 8,597,882 B2 | 12/2013 | Corbett et al. | |
| 8,772,473 B2 * | 7/2014 | Huang et al. | C12Q 1/6869 536/25.3 |
| 9,795,961 B1 | 10/2017 | Koh et al. | |
| 9,891,177 B2 | 2/2018 | Vazhaeparambil et al. | |
| 10,267,790 B1 | 4/2019 | Barbee et al. | |
| 10,273,528 B1 | 4/2019 | Barbee et al. | |
| 10,344,328 B2 | 7/2019 | Barbee et al. | |
| 10,512,911 B1 | 12/2019 | Beckett et al. | |
| 10,830,703 B1 | 11/2020 | Almogy et al. | |
| 10,852,518 B1 | 12/2020 | Almogy et al. | |
| 10,900,078 B2 | 1/2021 | Almogy et al. | |
| 11,118,223 B2 | 9/2021 | Almogy et al. | |
| 11,155,868 B2 | 10/2021 | Almogy et al. | |
| 11,268,143 B2 | 3/2022 | Beckett et al. | |
| 11,396,015 B2 | 7/2022 | Beckett et al. | |
| 11,499,962 B2 | 11/2022 | Barbee et al. | |
| 11,512,350 B2 | 11/2022 | Almogy et al. | |
| 11,591,651 B2 | 2/2023 | Almogy et al. | |
| 11,648,554 B2 | 5/2023 | Beckett et al. | |
| 11,732,298 B2 | 8/2023 | Almogy et al. | |
| 11,747,323 B2 | 9/2023 | Barbee et al. | |
| 2002/0006622 A1 | 1/2002 | Bradley et al. | |
| 2002/0009015 A1 | 1/2002 | Laugharn et al. | |
| 2002/0022261 A1 | 2/2002 | Anderson et al. | |
| 2002/0055112 A1 | 5/2002 | Patil et al. | |
| 2002/0072243 A1 | 6/2002 | Craighead et al. | |
| 2002/0074517 A1 | 6/2002 | Krutchinsky et al. | |
| 2002/0168652 A1 | 11/2002 | Werner et al. | |
| 2002/0172980 A1 | 11/2002 | Phan et al. | |
| 2002/0177144 A1 | 11/2002 | Remacle et al. | |
| 2003/0054376 A1 | 3/2003 | Mullis et al. | |
| 2003/0193589 A1 | 10/2003 | Lareau et al. | |
| 2004/0071888 A1 | 4/2004 | Chondroudis et al. | |
| 2005/0037484 A1 | 2/2005 | Staimer et al. | |
| 2005/0186580 A1 | 8/2005 | Dellinger et al. | |
| 2005/0237480 A1 | 10/2005 | Allbritton et al. | |
| 2006/0078934 A1 | 4/2006 | Desmet et al. | |
| 2006/0078935 A1 | 4/2006 | Werner et al. | |
| 2006/0263791 A1 | 11/2006 | Moon et al. | |
| 2007/0099289 A1 | 5/2007 | Irimia et al. | |
| 2007/0275193 A1 | 11/2007 | DeSimone et al. | |
| 2007/0290702 A1 | 12/2007 | Lee | |
| 2008/0038163 A1 | 2/2008 | Boege et al. | |
| 2008/0242560 A1 | 10/2008 | Gunderson et al. | |
| 2008/0254259 A1 | 10/2008 | Nishi et al. | |
| 2009/0098541 A1 | 4/2009 | Southern et al. | |
| 2009/0135385 A1 | 5/2009 | Gellrich et al. | |
| 2009/0263002 A1 | 10/2009 | Cremer et al. | |
| 2009/0263807 A1 | 10/2009 | Yotoriyama | |
| 2009/0305431 A1 | 12/2009 | Hodges et al. | |
| 2009/0308742 A1 | 12/2009 | Paranjape | |
| 2010/0041562 A1 | 2/2010 | Li et al. | |
| 2010/0101104 A1 | 4/2010 | Grzesiak et al. | |
| 2010/0151564 A1 | 6/2010 | Beebe et al. | |
| 2010/0167308 A1 | 7/2010 | Miller et al. | |
| 2010/0210475 A1 | 8/2010 | Lee et al. | |
| 2010/0330578 A1 | 12/2010 | Duhr et al. | |
| 2011/0086361 A1 | 4/2011 | Klunder et al. | |
| 2011/0178285 A1 | 7/2011 | Lebl et al. | |
| 2011/0312622 A1 | 12/2011 | Azimi et al. | |
| 2012/0068059 A1 | 3/2012 | Montes Usategui et al. | |
| 2012/0126142 A1 | 5/2012 | Matsui et al. | |
| 2012/0282708 A1 | 11/2012 | Corbett et al. | |
| 2012/0316074 A1 | 12/2012 | Saxonov | |
| 2013/0038719 A1 | 2/2013 | Canini et al. | |
| 2013/0076852 A1 | 3/2013 | Bai et al. | |
| 2014/0152888 A1 | 6/2014 | Staker et al. | |
| 2014/0162275 A1 | 6/2014 | Kotseroglou | |
| 2014/0261577 A1 | 9/2014 | Furukawa et al. | |
| 2014/0287423 A1 | 9/2014 | Nurse | |
| 2015/0071898 A1 | 3/2015 | Liu et al. | |
| 2015/0125346 A1 | 5/2015 | Schaff et al. | |
| 2015/0212310 A1 | 7/2015 | Fukuda et al. | |
| 2015/0270146 A1 | 9/2015 | Yoshihara et al. | |
| 2016/0032380 A1 | 2/2016 | Craighead et al. | |
| 2016/0041135 A1 | 2/2016 | Lannutti et al. | |
| 2016/0076025 A1 | 3/2016 | Boutell et al. | |
| 2016/0076978 A1 | 3/2016 | Dave et al. | |
| 2016/0184870 A1 | 6/2016 | Miura et al. | |
| 2016/0246170 A1 | 8/2016 | Bowen et al. | |
| 2016/0314575 A1 | 10/2016 | Matsuo et al. | |
| 2016/0319334 A1 | 11/2016 | Barany et al. | |
| 2017/0123198 A1 | 5/2017 | Singer et al. | |
| 2017/0136434 A1 | 5/2017 | Barnard et al. | |
| 2018/0207920 A1 | 7/2018 | Venkatesan et al. | |
| 2019/0271038 A1 | 9/2019 | Almogy et al. | |
| 2019/0271039 A1 | 9/2019 | Almogy et al. | |
| 2019/0291115 A1 | 9/2019 | Kaplan et al. | |
| 2019/0331903 A1 | 10/2019 | Wald et al. | |
| 2020/0164379 A1 | 5/2020 | Kaplan et al. | |
| 2020/0179925 A1 | 6/2020 | Beckett et al. | |
| 2020/0179926 A1 | 6/2020 | Beckett et al. | |
| 2020/0326327 A1 | 10/2020 | Barbee et al. | |
| 2021/0047688 A1 | 2/2021 | Almogy et al. | |
| 2021/0054454 A1 | 2/2021 | Almogy et al. | |
| 2021/0199647 A1 | 7/2021 | Beckett et al. | |
| 2021/0277464 A1 | 9/2021 | Beckett et al. | |
| 2021/0354126 A1 | 11/2021 | Beckett et al. | |
| 2022/0064727 A1 | 3/2022 | Almogy et al. | |

FOREIGN PATENT DOCUMENTS

| | | | |
|---|---|---|---|
| EP | 0865606 A1 | 9/1998 | |
| JP | 2000304688 A | 11/2000 | |
| JP | 2005345597 A | 12/2005 | |
| JP | 2010536009 A | 11/2010 | |
| WO | WO-0037680 A1 | 6/2000 | |
| WO | WO-0039625 A3 | 10/2000 | |
| WO | WO-03102535 A2 | 12/2003 | |
| WO | WO-03102535 A3 | 3/2004 | |
| WO | WO-2008016335 A1 | 2/2008 | |
| WO | WO-2014127379 A1 | 8/2014 | |
| WO | WO-2014143981 A1 | 9/2014 | |
| WO | WO-2014143981 A9 | 12/2014 | |
| WO | WO-2014143981 A8 | 12/2015 | |
| WO | WO-2018064297 A1 * | 4/2018 | C12Q 1/6869 |
| WO | WO-2018144582 A1 | 8/2018 | |
| WO | WO-2019099886 A1 | 5/2019 | |
| WO | WO-2020034143 A1 | 2/2020 | |
| WO | WO-2020118172 A1 | 6/2020 | |
| WO | WO-2020186243 A1 | 9/2020 | |
| WO | WO-2022072652 A1 | 4/2022 | |

OTHER PUBLICATIONS

Explanation of "Probe" in the Dictionary of Nutrition and Biochemistry. Retrieved from website on Jun. 30, 2023: https://kotobank.jp/word/%E3%83%97%E3%83%AD%E3%83%BC%E3%83%96-675975.

U.S. Appl. No. 17/962,163 Notice of Allowance dated Jun. 20, 2023.

Adessi et al. Solid phase DNA amplification: Charcterisation of primer attachment and amplification mechanisms, Nucl. Acids Res, 2000, 28(20):E87.

Bioptechs. Product information for the Bioptechs Objective Heather. Available at http://bioptechs.com/product/objective-heater/. Accessed on Jun. 25, 2019.

Brenner, et al. Gene expression analysis by massively parallel signature sequencing (MPSS) on microbead arrays. Nat Biotechnol. Jun. 2000;18(6):630-4.

Brenner et al. In vitro cloning of complex mixtures of DNA on microbeads: Physical separation of differentially expressed cDNAs, Proc. Natl. Acad. Sci. USA 2000, 97(4):1665-1670.

Co-pending U.S. Appl. No. 202017001174, inventors Almogy; Gilad et al., filed Aug. 24, 2020.

Co-pending U.S. Appl. No. 202017003400, inventors Almogy; Gilad et al., filed Aug. 26, 2020.

(56) References Cited

OTHER PUBLICATIONS

Dressman, et al. Transforming single DNA molecules into fluorescent magnetic particles for detection and enumeration of genetic variations. Proc Natl Acad Sci USA. 2003;100(15):8817-8822.
EP20180878612 European Search Report dated Jul. 14, 2021.
Lizardi, et al. Mutation detection and single-molecule counting using isothermal rolling-circle amplification. Nat Genet. Jul. 1998;19(3):225-32. .
MIT Technology Review. China's BGI says it can sequence a genome for just $100. Available at https://www.technologyreview.com/2020/02/26/905658/china-bgi-100-dollar-genome. Accessed on Feb. 19, 2021.
Mitra, et al. Digital genotyping and haplotyping with polymerase colonies. Proceedings of the National Academy of Sciences of the United States of America vol. 100, 10 (2003): 5926-31.
Mitra, et al. Fluorescent in situ sequencing on polymerase colonies, Anal. Biochem, 320:55-65. (2003).
PCT/US020/022816 International Search Report and Written Opinion dated Jul. 30, 2020.
PCT/US18/61598 International Search Report and Written Opinion dated Mar. 15, 2019.
Pemov, A. et al. DNA analysis with multiplex microarray-enhanced PCR. Nucleic acids research vol. 33:2 (2005).
Qin, et al. High-throughput, low-cost and rapid DNA sequencing using surface-coating techniques. bioRxiv (2020).
Reinartz, et al. Massively parallel signature sequencing (MPSS) as a tool for in-depth quantitative gene expression profiling in all organisms. Brief Funct Genomic Proteomic. Feb. 2002;1(1):95-104.
Spatial Transcriptomics. Workflow. Available at https://spatialtranscriptomics.com/workflow/. Accessed on Jun. 25, 2019.
Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.
U.S. Appl. No. 15/974,364 Office Action dated Aug. 7, 2018.
U.S. Appl. No. 15/974,543 Notice of Allowance dated Dec. 13, 2018.
U.S. Appl. No. 15/974,543 Office Action dated Aug. 7, 2018.
U.S. Appl. No. 16/445,798 Notice of Allowance dated Dec. 18, 2020.
U.S. Appl. No. 16/445,798 Notice of Allowance dated Dec. 4, 2020.
U.S. Appl. No. 16/445,798 Notice of Allowance dated Sep. 18, 2020.
U.S. Appl. No. 16/445,798 Office Action dated May 8, 2020.
U.S. Appl. No. 16/677,067 Notice of Allowance dated Aug. 12, 2020.
U.S. Appl. No. 16/677,067 Notice of Allowance dated Jul. 1, 2020.
U.S. Appl. No. 16/677,067 Notice of Allowance dated Jun. 19, 2020.
U.S. Appl. No. 16/677,067 Notice of Allowance dated Sep. 21, 2020.
U.S. Appl. No. 16/677,115 Notice of Allowance dated Aug. 21, 2020.
U.S. Appl. No. 16/677,115 Notice of Allowance dated Jul. 14, 2020.
U.S. Appl. No. 16/953,071 Notice of Allowance dated May 26, 2021.
U.S. Appl. No. 16/953,071 Notice of Allowance dated May 5, 2021.
U.S. Appl. No. 16/953,071 Office Action dated Apr. 22, 2021.
U.S. Appl. No. 16/953,071 Office Action dated Jan. 15, 2021.
U.S. Appl. No. 17/155,226 Notice of Allowance dated Aug. 27, 2021.
U.S. Appl. No. 17/155,226 Notice of Allowance dated Jul. 6, 2021.
U.S. Appl. No. 17/155,226 Office Action dated Mar. 18, 2021.
U.S. Appl. No. 17/308,241 Notice of Allowance dated Nov. 16, 2021.
U.S. Appl. No. 17/308,241 Office Action dated Jul. 26, 2021.
U.S. Appl. No. 15/974,364 Notice of Allowance dated Feb. 28, 2019.
U.S. Appl. No. 15/974,441 Notice of Allowance dated Nov. 21, 2018.
U.S. Appl. No. 15/974,441 Office Action dated Aug. 3, 2018. .
U.S. Appl. No. 16/445,798 Office Action dated Nov. 6, 2019.
U.S. Appl. No. 16/677,067 Office Action dated Feb. 28, 2020.
U.S. Appl. No. 16/677,115 Office Action dated Mar. 24, 2020.
Britannica, The Editors of Encyclopedia. "fluid". Encyclopedia Britannica, May 11, 2021, https://www.britannica.com/science/fluid-physics. Accessed on Jan. 21, 2022.
PCT/US2019/064916 International Search Report and Written Opinion dated Apr. 7, 2020.
PCT/US2021/052902 International Search Report and Written Opinion dated Feb. 17, 2022.
U.S. Appl. No. 16/665,540 Non-Final Office Action dated Jan. 10, 2022.
U.S. Appl. No. 16/665,559 Non-Final Office Action dated Feb. 7, 2022.
Co-pending U.S. Appl. No. 17/962,163, inventors Barbee; Kristopher et al., filed Oct. 7, 2022.
EP19894196.5 European Search Report dated Aug. 12, 2022.
He, R-Y., et al. Study of cell adhesion and migration by using a plasmon-enhanced total internal reflection fluorescence microscope. Imaging, Manipulation, and Analysis of Biomolecules, Cells, and Tissues IV. Vol. 6088. SPIE (2006).
U.S. Appl. No. 16/416,856 Final Office Action dated Oct. 5, 2022.
U.S.Appl. No. 16/862,196 Notice of Allowance dated Jul. 7, 2022.
EP20770906.4 Extended European Search Report dated Feb. 20, 2023.
Co-pending U.S. Appl. No. 18/224,378, inventors Barbee; Kristopher et al., filed Jul. 20, 2023.
U.S. Appl. No. 17/336,377 Office Action dated Sep. 28, 2023.

\* cited by examiner

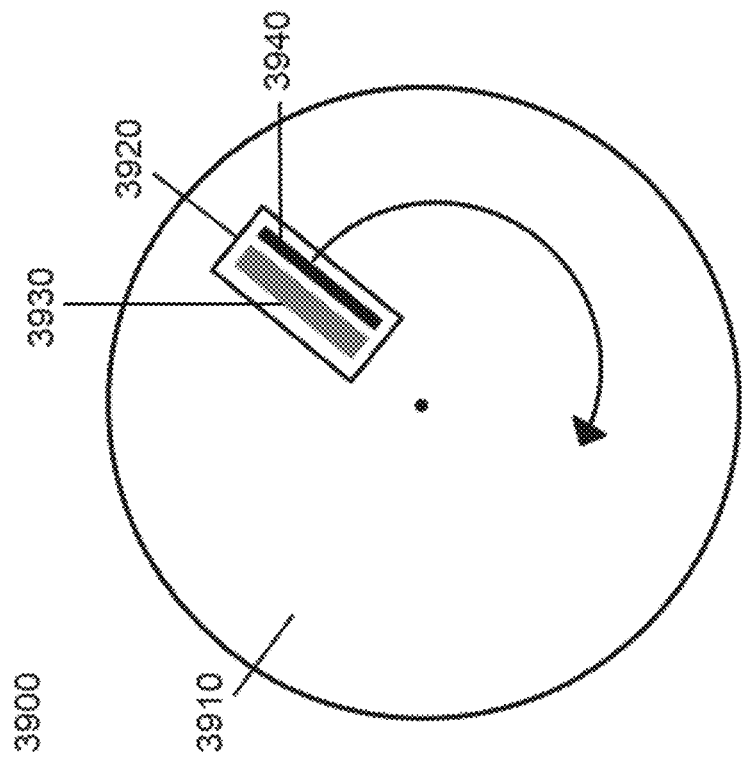
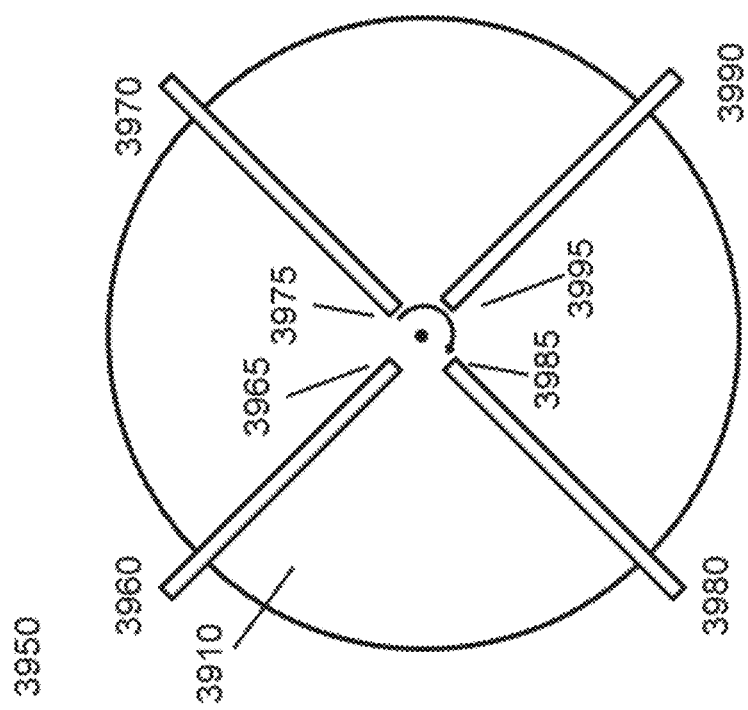
FIG. 12C

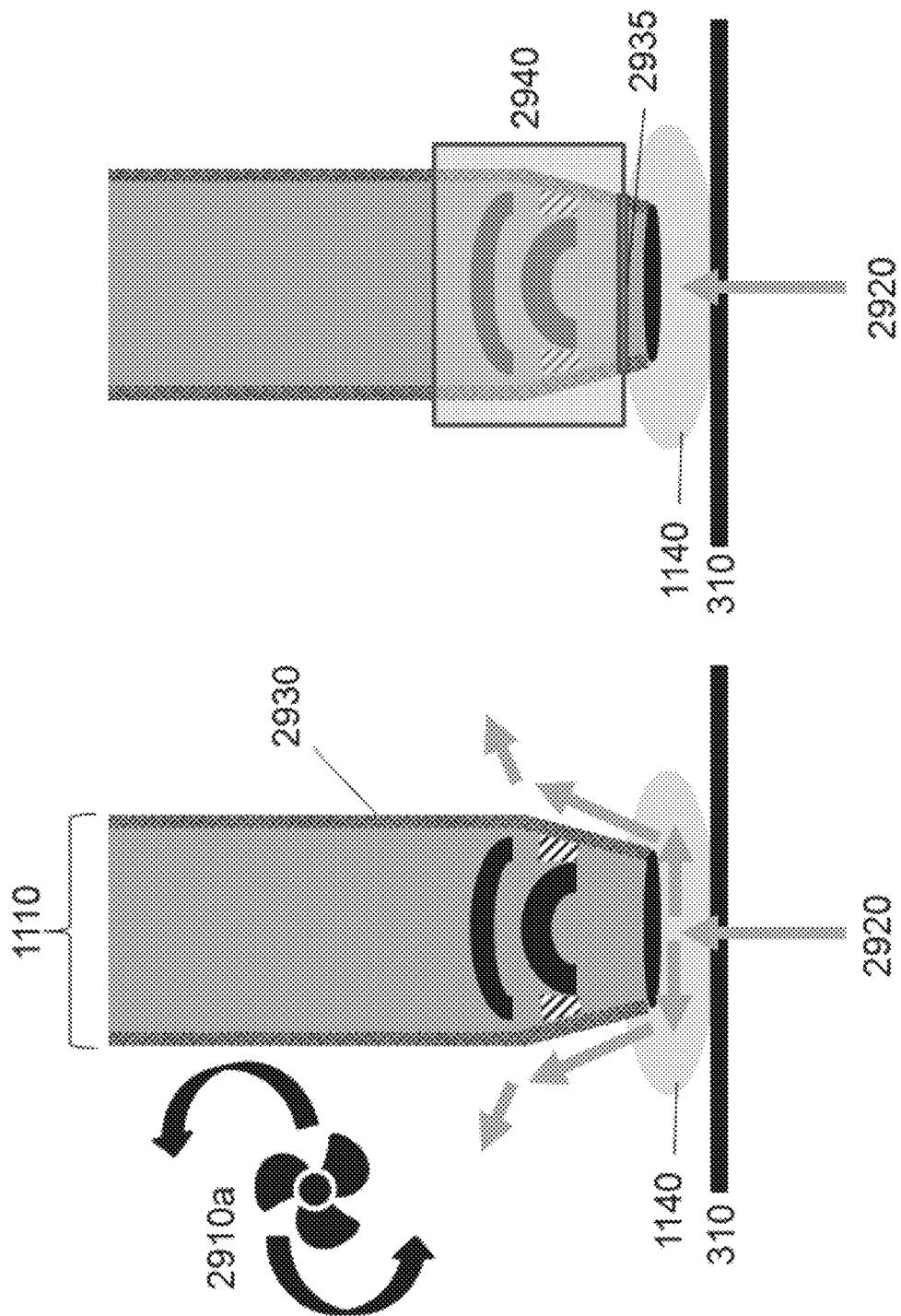

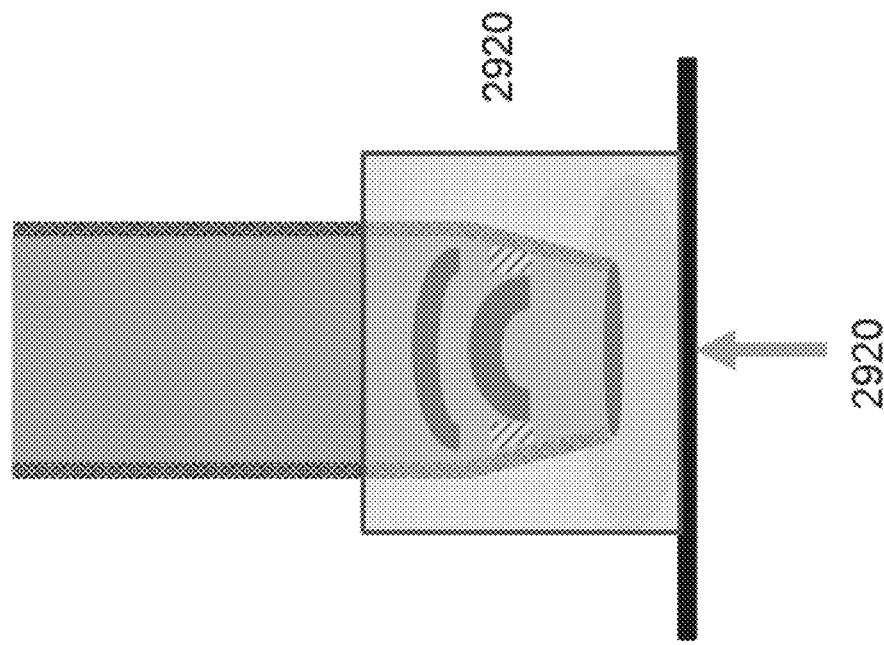
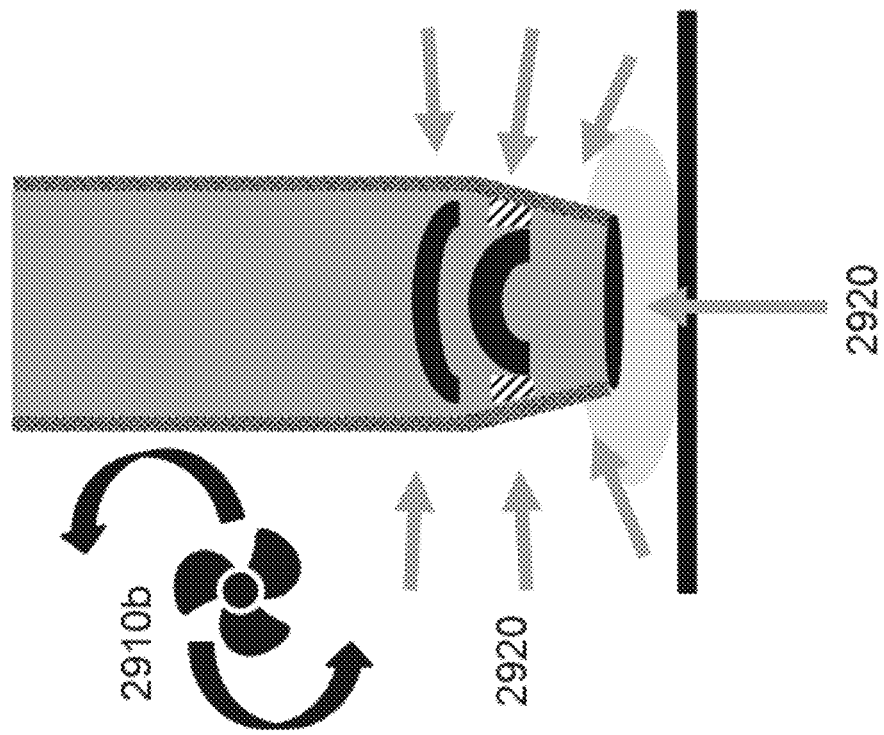
FIG. 17D
FIG. 17C

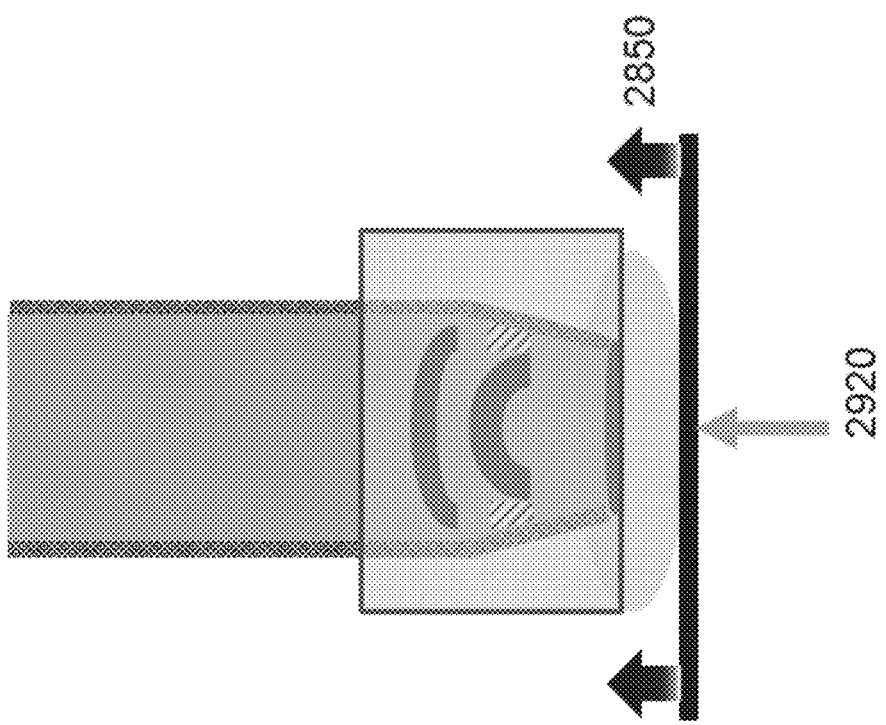

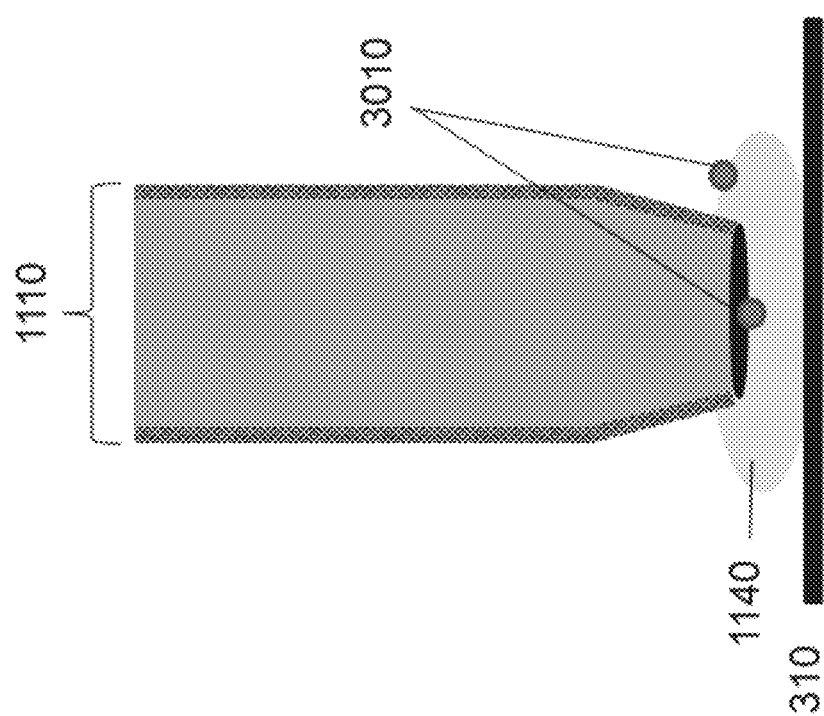

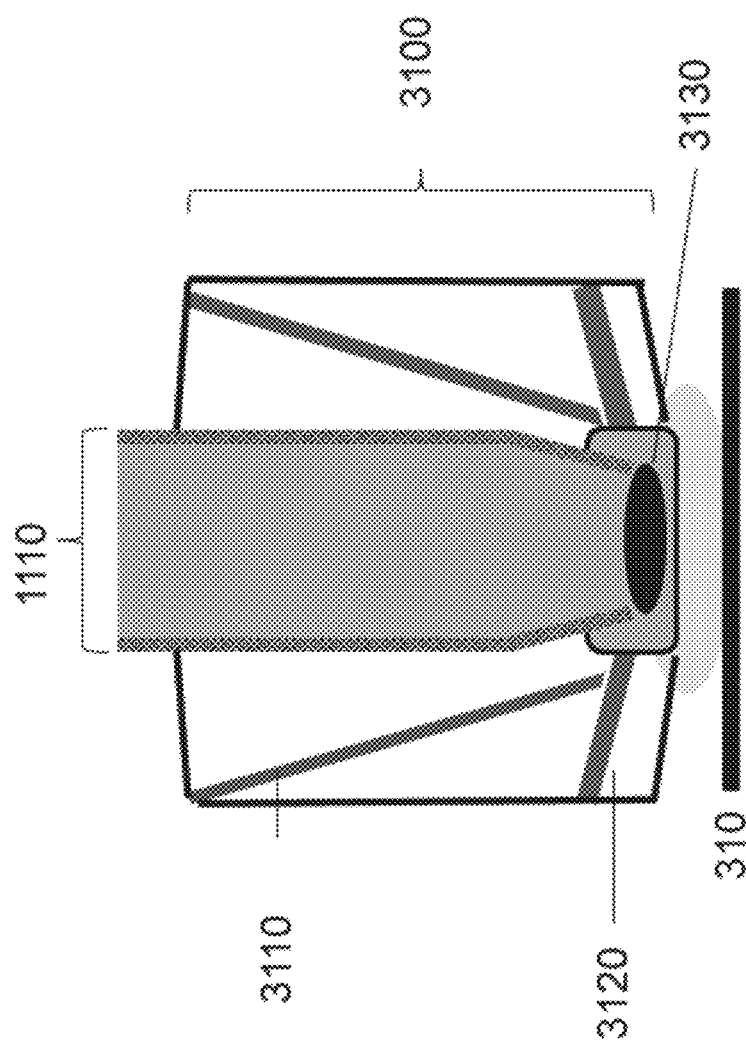

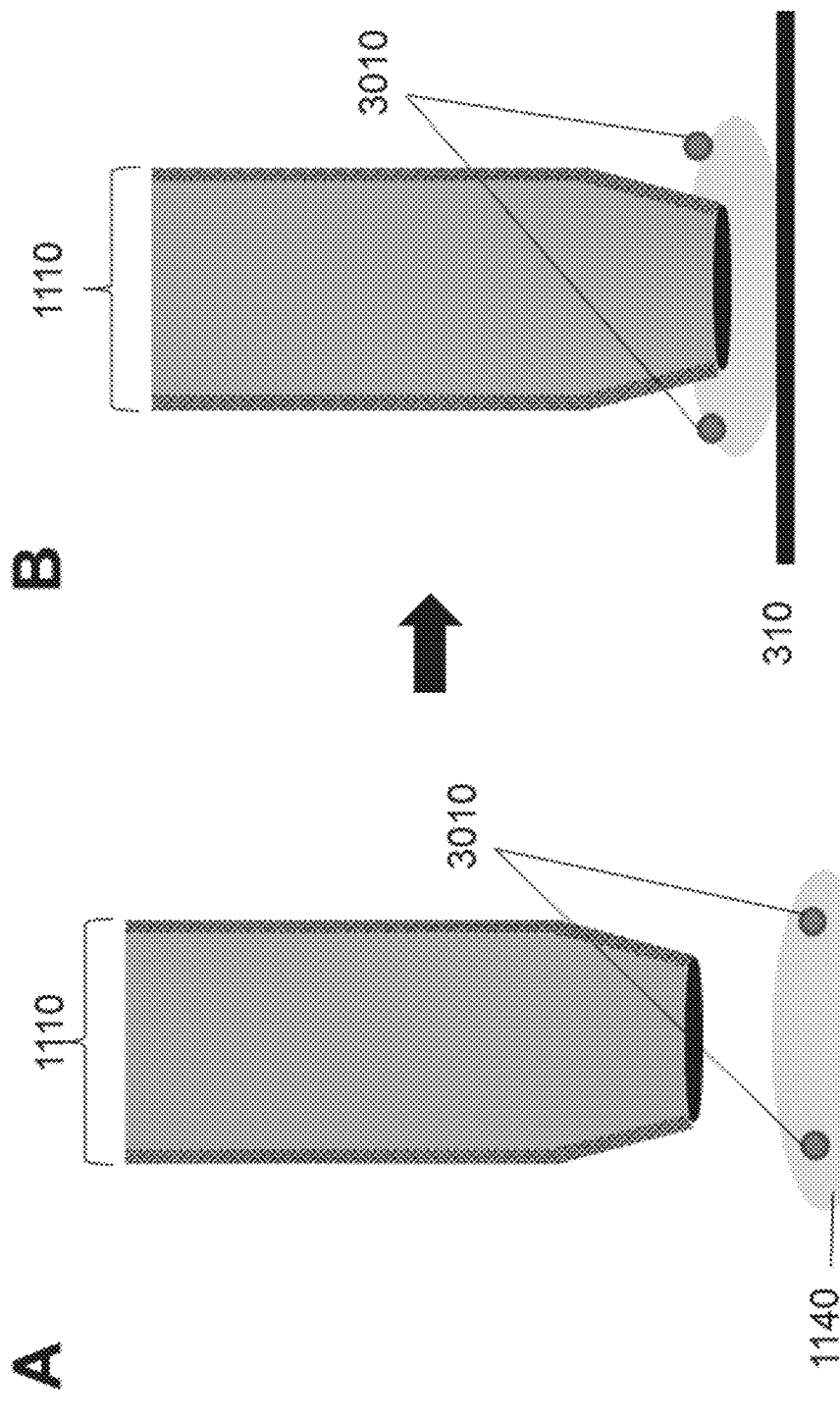

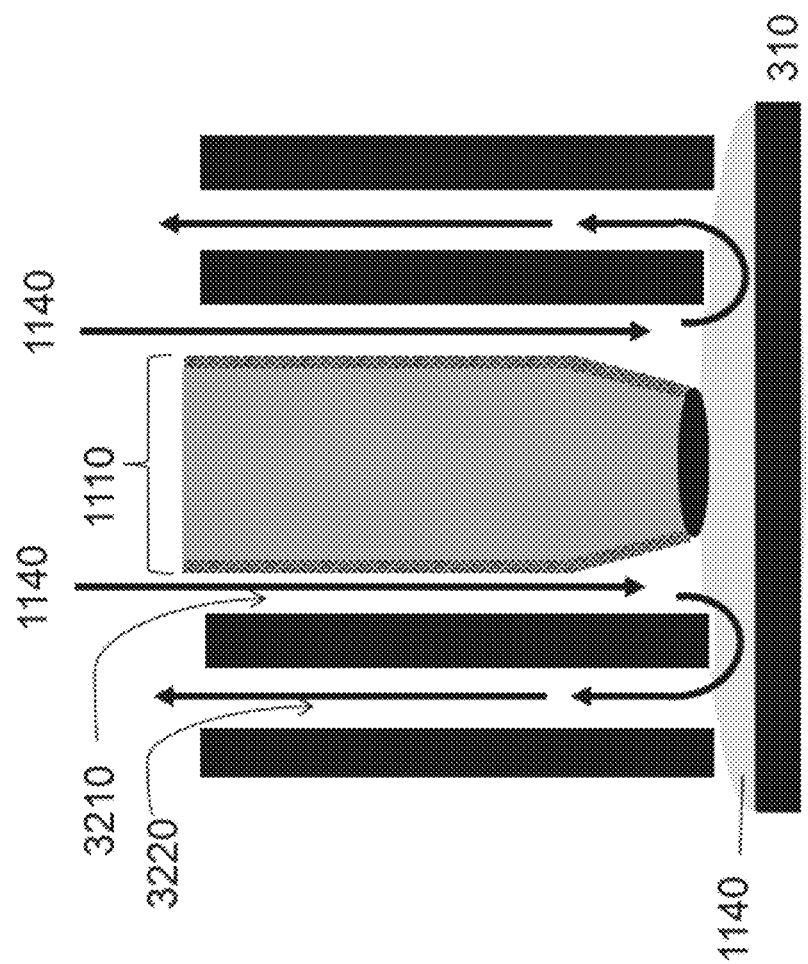

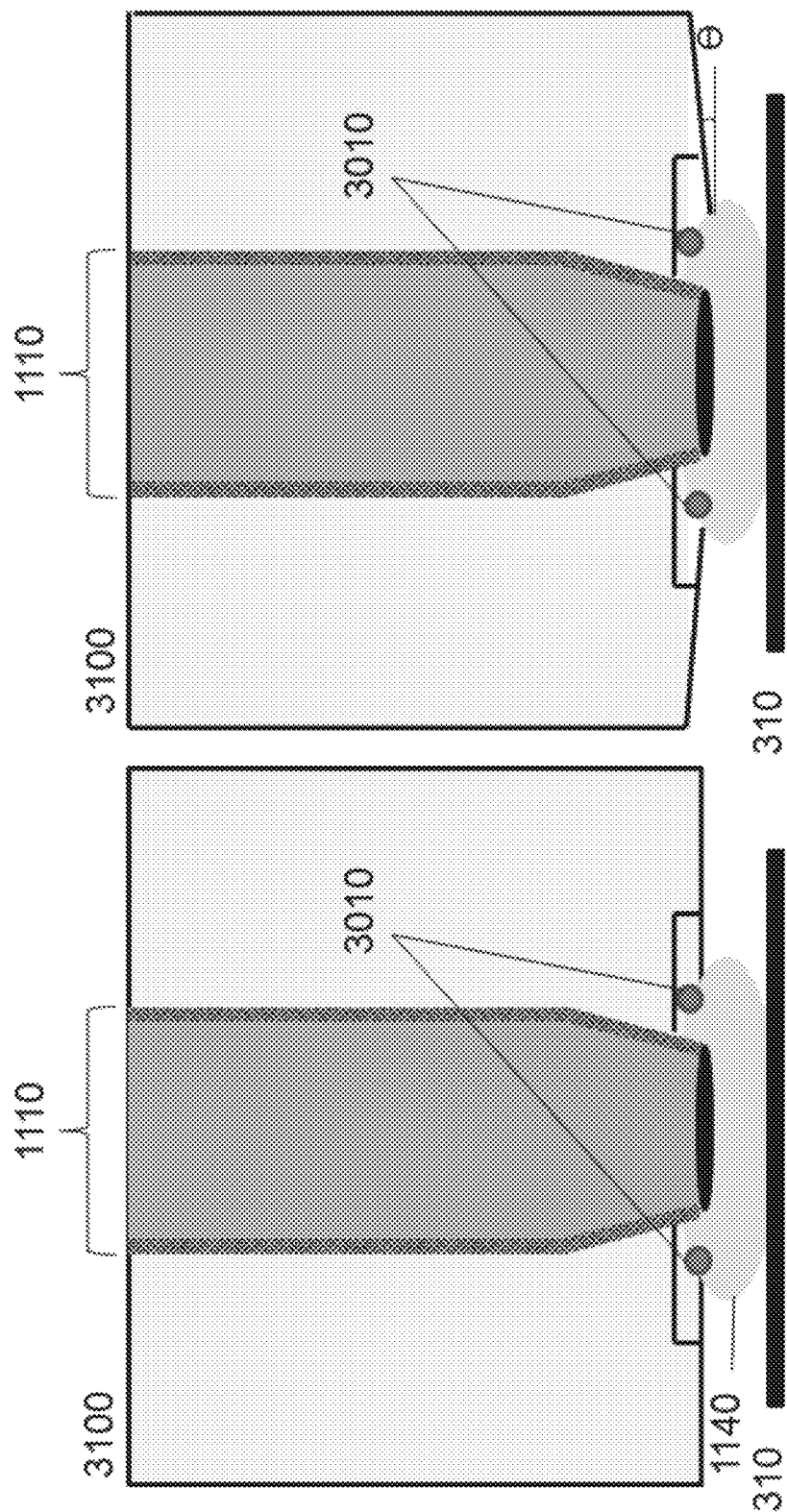

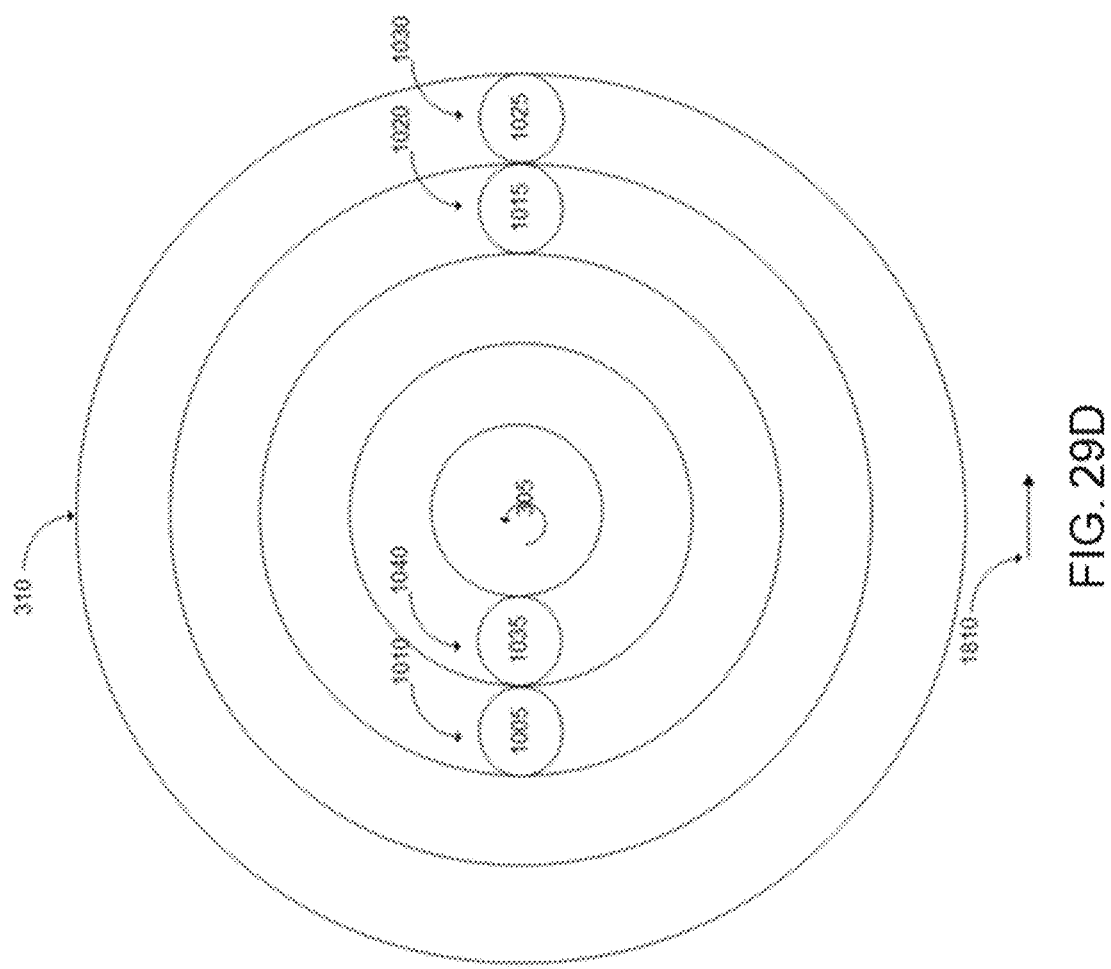

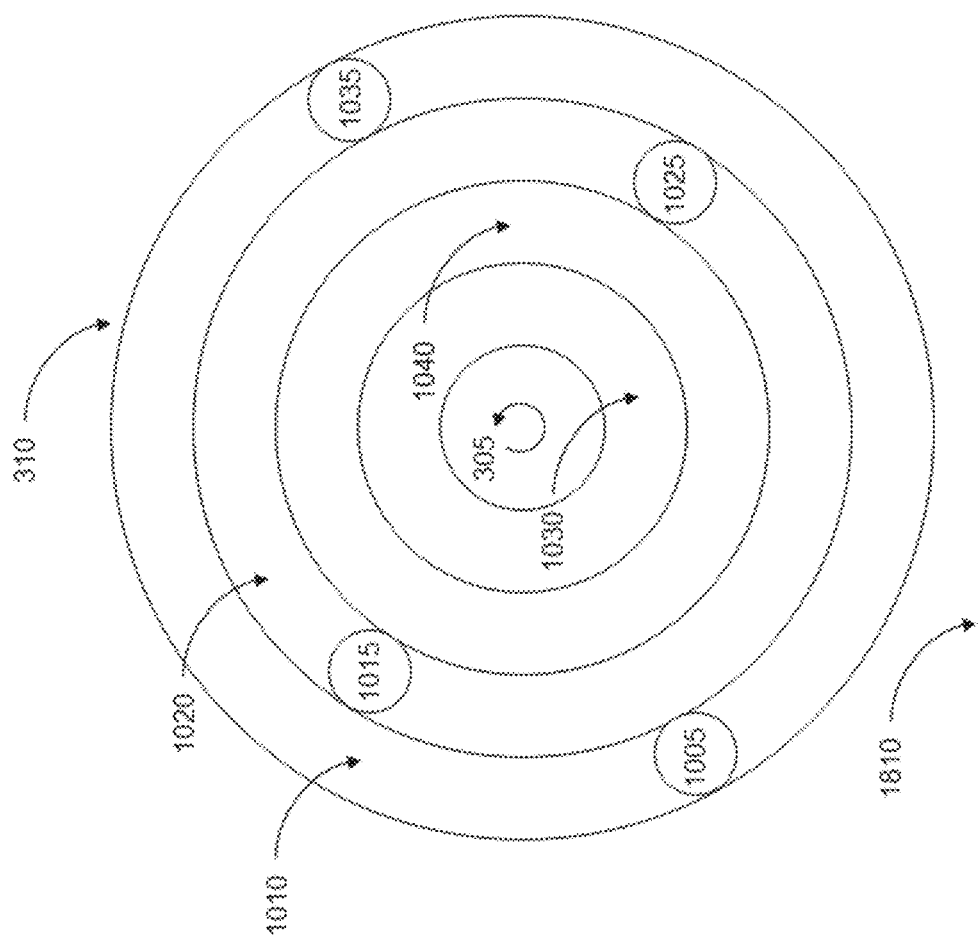

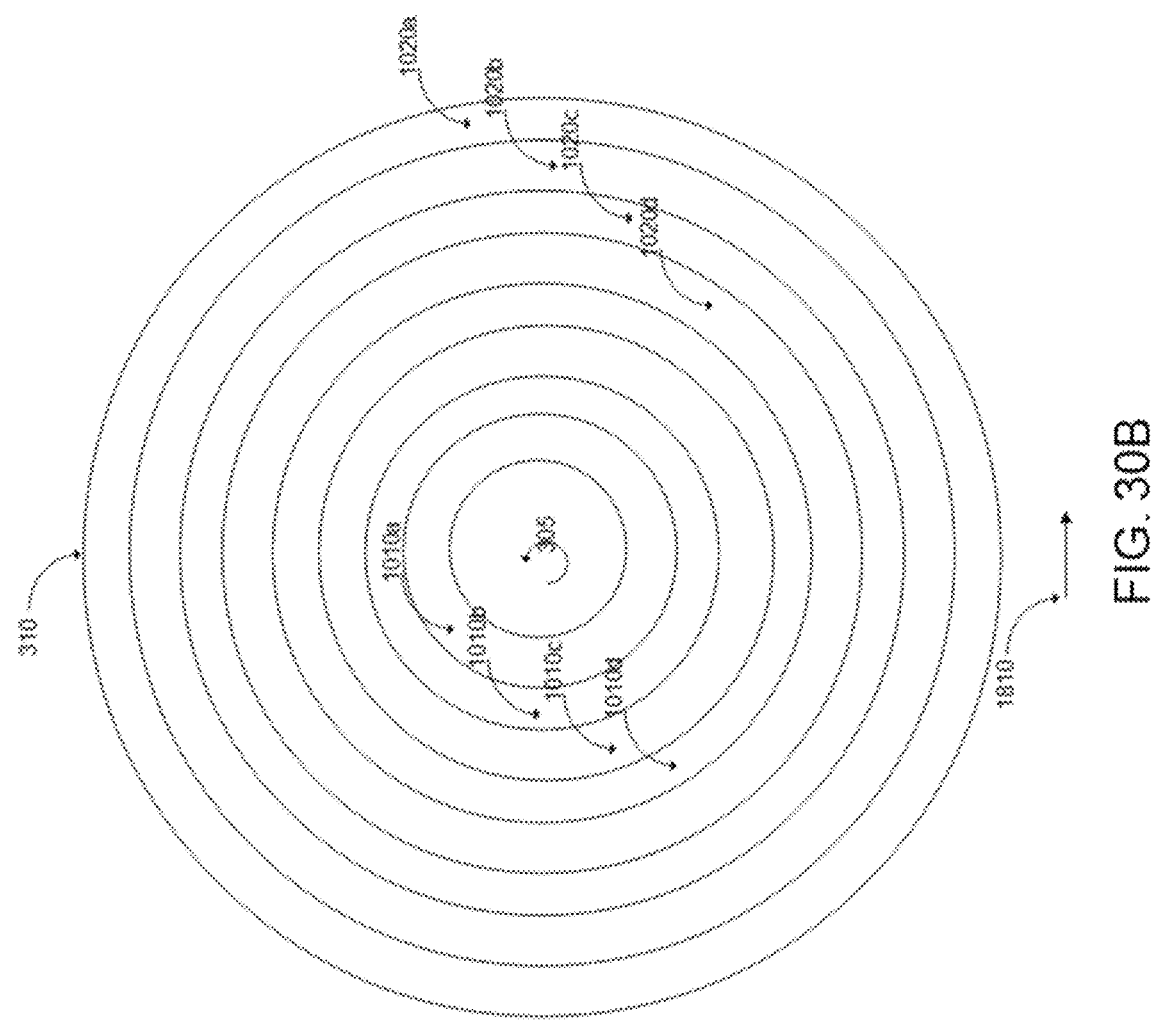

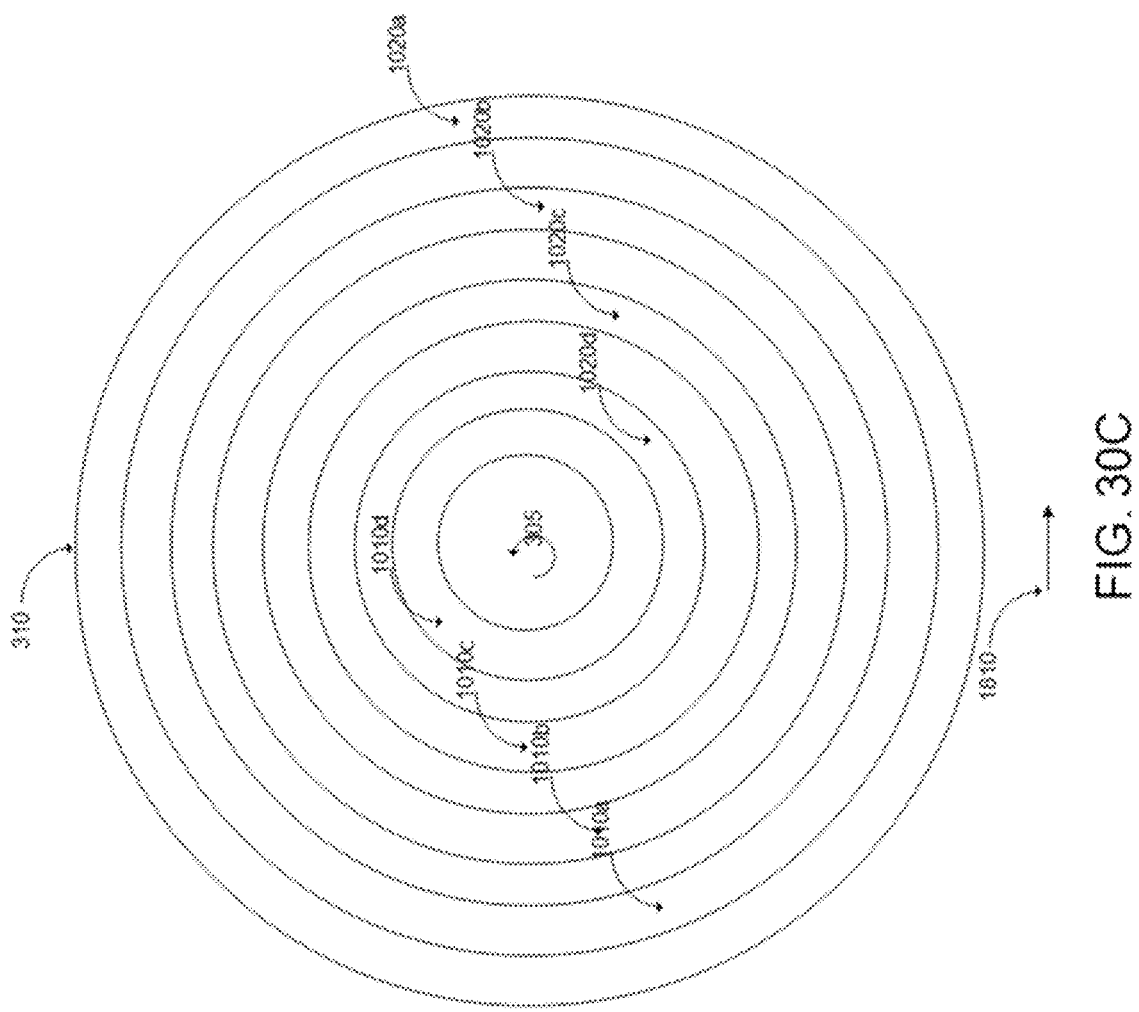

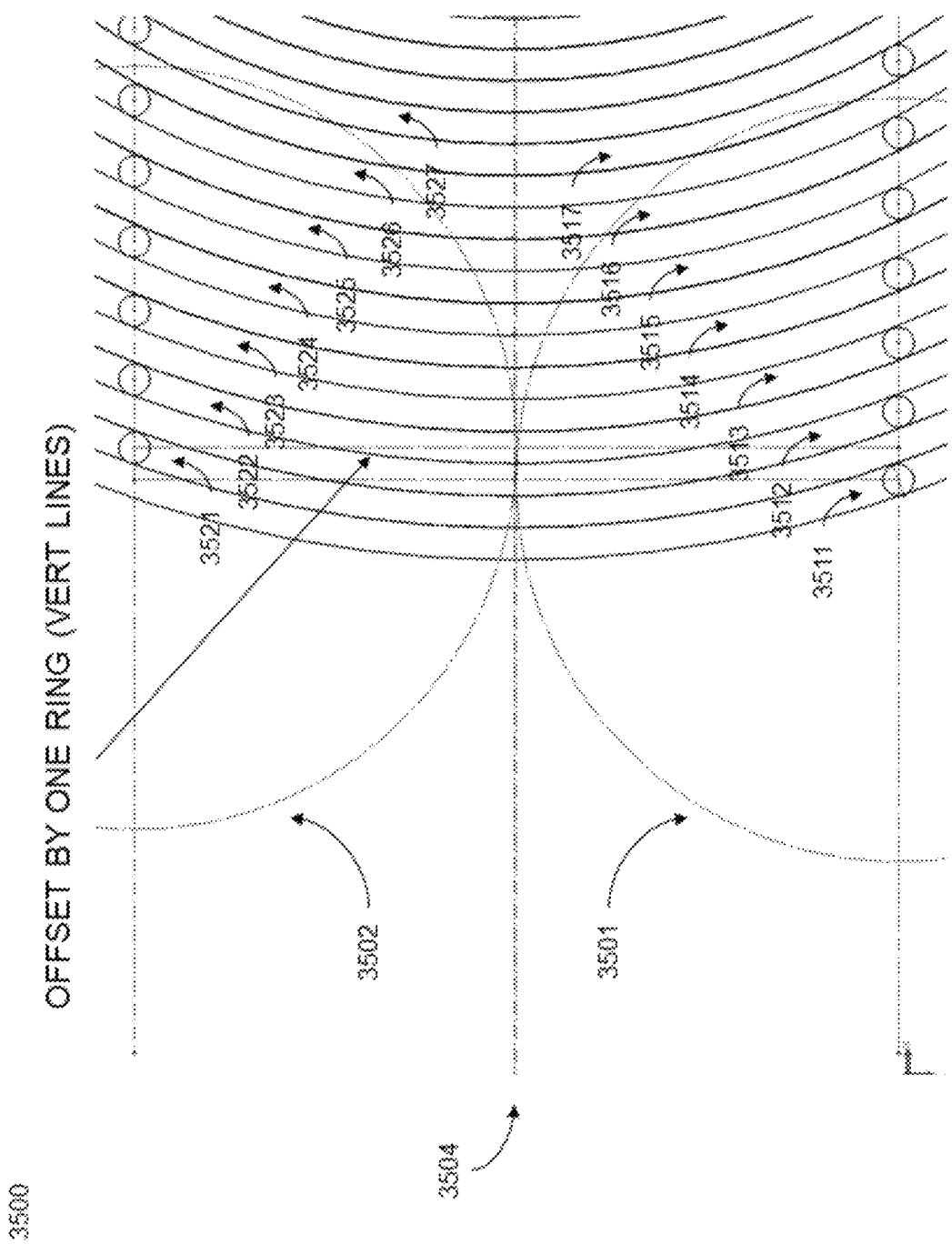

FIG. 38A

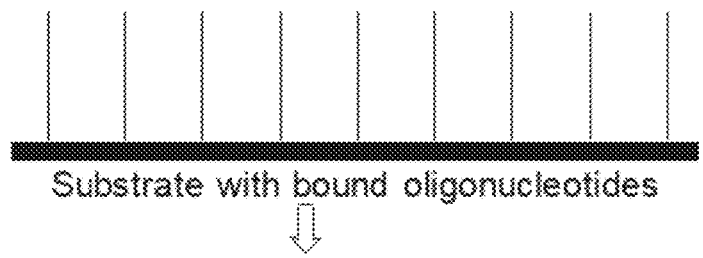
Substrate with bound oligonucleotides

FIG. 38B

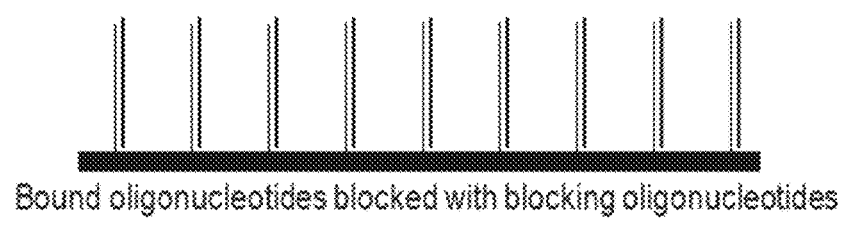
Bound oligonucleotides blocked with blocking oligonucleotides

FIG. 38C

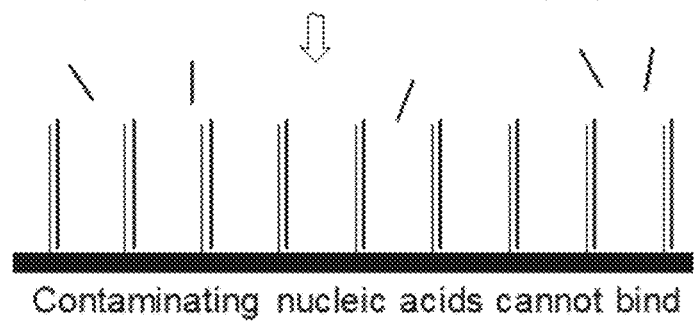
Contaminating nucleic acids cannot bind

Bound oligonucleotides are removed

FIG. 38D

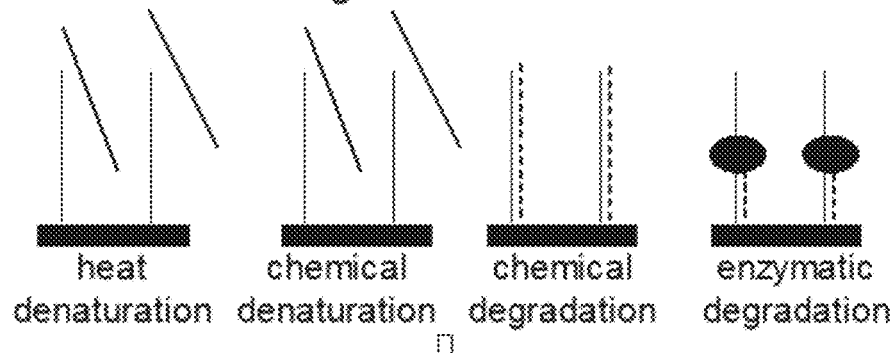

heat denaturation   chemical denaturation   chemical degradation   enzymatic degradation Relevant target nucleic acids can now bind to available substrate-bound oligonucleotides

METHODS, DEVICES, AND SYSTEMS FOR ANALYTE DETECTION AND ANALYSIS

CROSS-REFERENCE

This application is a continuation of Ser. No. 17/308,241, filed May 5, 2021, which is a continuation of U.S. application Ser. No. 16/953,071, filed Nov. 19, 2020, which is a continuation of International Patent App. No. PCT/US20/22816, filed Mar. 13, 2020, which claims benefit of: U.S. Provisional App. No. 62/818,549, filed Mar. 14, 2019; U.S. Provisional App. No. 62/837,684, filed Apr. 23, 2019; U.S. Provisional App. No. 62/914,293, filed Oct. 11, 2019; U.S. application Ser. No. 16/445,798, filed Jun. 19, 2019, now U.S. Pat. No. 10,900,078; U.S. application Ser. No. 16/677,067, filed Nov. 7, 2019, now U.S. Pat. No. 10,830,703; and U.S. application Ser. No. 16/677,115, filed Nov. 7, 2019, now U.S. Pat. No. 10,852,518, the entire contents of each of which are herein incorporated by reference.

BACKGROUND

Biological sample processing has various applications in the fields of molecular biology and medicine (e.g., diagnosis). For example, nucleic acid sequencing may provide information that may be used to diagnose a certain condition in a subject and in some cases tailor a treatment plan. Sequencing is widely used for molecular biology applications, including vector designs, gene therapy, vaccine design, industrial strain design and verification. Biological sample processing may involve a fluidics system and/or a detection system.

SUMMARY

Despite the prevalence of biological sample processing systems and methods, such systems and methods may have low efficiency that can be time-intensive and wasteful of valuable resources, such as reagents. Recognized herein is a need for methods and systems for sample processing and/or analysis with high efficiency.

The present disclosure provides methods, devices, and systems for sample processing and/or analysis. The methods, devices, and systems described herein may comprise an open substrate, or use thereof. The open substrate may comprise one or more analytes thereon. For example, the one or more analytes may be coupled, attached, immobilized, or otherwise associated, directly or indirectly (e.g., via an intermediary object, such as a binder or linker) with the open substrate. The open substrate may comprise an array. In some instances, an environment of the open substrate, such as the local environment surrounding the open substrate, may be controlled, such as to facilitate one or more reactions, or one or more detections. The methods, devices, and systems described herein may comprise immersion optics systems, or use thereof. An immersion optics system may be configured to detect analytes, or activities thereof, on the open substrate. The methods, devices, and systems described herein may comprise spatial indexing of the open substrate, or array thereof, or use thereof.

In various aspects, the present disclosure provides a method for scanning a surface, the method comprising: (a) scanning a scanning field comprising a portion of a surface using a scanning system, wherein the scanning field has an orientation with respect to a rotational axis of the surface; and (b) rotating (i) the surface about the rotational axis of the surface and (ii) the scanning field about a rotational axis of the scanning field such that the scanning field substantially maintains the orientation with respect to the rotational axis of the surface prior to, during, or subsequent to translation of the surface relative to the scanning field.

In some embodiments, the scanning field has a substantially rectilinear shape. In some embodiments, the scanning field has a long axis, and wherein the orientation comprises a line coinciding with the long axis of the scanning field passing through the rotational axis of the surface. In some embodiments, the scanning field traces an arc on the surface. In some embodiments, scanning the surface comprises imaging the surface. In some embodiments, the scanning field comprises an imaging field. In some embodiments, the scanning field traces a scanning path on the surface, and the scanning path comprises an imaging path. In some embodiments, the scanning system comprises an imaging system.

In some embodiments, the orientation comprises a long axis of the scanning field, wherein the long axis is parallel to a radial line passing through (i) the rotational axis of the surface and (ii) the rotational axis of the scanning field. In some embodiments, translation of the surface relative to the scanning field comprises translating in a direction that is not directly toward or away from the rotational axis of the surface. In some embodiments, translation of surface relative to the scanning field comprises translating along a translation path, wherein a line comprising a net displacement along the translation path does not intersect both the scanning field and the rotational axis of the surface.

In some embodiments, the scanning field rotates with respect to the surface around the rotational axis of the scanning field. In some embodiments, the rotational axis of the scanning field is substantially perpendicular to the surface. In some embodiments, the rotational axis of the scanning field is substantially parallel to the rotational axis of the surface. In some embodiments, the rotational axis of the scanning field passes through an axis of symmetry of the scanning field. In some embodiments, the scanning field is rotated by rotating an objective. In some embodiments, the scanning field is rotated by rotating a lens. In some embodiments, the scanning field is rotated by rotating a prism. In some embodiments, the scanning field is rotated by rotating a mirror. In some embodiments, the scanning field is rotated by rotating a camera. In some embodiments, scanning field is rotated by rotating a diffractive optical element (DOE). In some embodiments, the scanning field is rotated using a motor.

In some embodiments, the surface is substantially circular and wherein the scanning field is translated along a chord of the surface. In some embodiments, the surface is substantially circular and wherein the rotational axis of the scanning field is translated along a chord of the surface. In some embodiments, the chord does not pass through the rotational axis of the surface. In some embodiments, the scanning field is translated by moving the surface. In some embodiments, the scanning field is translated by moving the scanning system. In some embodiments, the scanning field traces a circle on the surface. In some embodiments, the scanning field traces a spiral on the surface. In some embodiments, rotating the surface and translation of the surface are performed simultaneously. In some embodiments, the translation of the surface is linear with respect to the rotational axis of the surface. In some embodiments, the translation of the surface is not substantially circular with respect to the surface. In some embodiments, the translation of the surface increases or decreases a distance between the rotational axis of the scanning field and the rotational axis of the surface.

In some embodiments, the scanning system comprises an objective in optical communication with the surface. In some embodiments, the scanning system comprises a camera. In some embodiments, the scanning field is in optical communication with a camera. In some embodiments, the camera is a time delay integration (TDI) camera having a line rate. In some embodiments, the camera is a multi-line TDI camera. In some embodiments, the camera comprises an array of sensors and the rotational axis of the scanning field passes through a center of the sensor array. In some embodiments, the line rate is set such that the camera takes an image when the scanning field has advanced along the surface from a first location to a second location, which second location is adjacent to the first location. In some embodiments, the line rate is variable. In some embodiments, the line rate is higher when the objective is located farther from the rotational axis of the surface.

In some embodiments, the scanning system further comprises a tube lens. In some embodiments, the scanning system comprises two objectives, the objective and a second objective, in optical communication with the surface. In some embodiments, the two objectives are on a same side of the surface with respect to a plane normal to the surface and intersecting the rotational axis of the surface. In some embodiments, the two objectives are on opposite sides of the surface with respect to a plane normal to the surface and intersecting the rotational axis of the surface. In some embodiments, the two objectives trace circular paths on the surface. In some embodiments, the circular paths are concentric. In some embodiments, the objective and the second objective trace alternating circular paths. In some embodiments, the objective traces the circular paths closer to the axis of rotation, and the second objective traces the circular paths farther from the rotational axis of the surface. In some embodiments, the two objectives trace individual spiral paths on the surface. In some embodiments, the spiral paths are interleafed. In some embodiments, the spiral paths are concentric and the objective traces the spiral path closer to the rotational axis of the surface, and the second objective traces the spiral path farther from the rotational axis of the surface. In some embodiments, the objective traces a first path, the first path having a first width corresponding to a first width of the scanning field, and wherein the second objective traces a second path, the second path having a second path width corresponding to a second width of a second scanning field. In some embodiments, the first path width and the second path width overlap by no more than 30%, no more than 20%, no more than 10%, no more than 5%, no more than 1%.

In some embodiments, the scanning system comprises four objectives in optical communication with the surface. In some embodiments, the four objectives are positioned on a same side of the surface with respect to a plane normal to the surface and intersecting the rotational axis of the surface. In some embodiments, a first two of the four objectives are positioned on a first side of the surface and a second two of the four objectives are positioned on a second side of the surface opposite the first side with respect to a plane normal to the surface and intersecting the rotational axis of the surface. In some embodiments, the scanning system comprises 5, 6, 7, 8, 9, 10, 11, 12, 13, or more objectives in optical communication with the surface.

In some embodiments, the surface is rotated at a constant angular velocity. In some embodiments, the camera is configured to take images at a given frequency and the surface is rotated relative to the objective at a variable angular velocity. In some embodiments, the angular velocity is varied such that, at the given frequency, the camera takes an image when the scanning field is at a first location and when the scanning field is at a second location, which second location is adjacent to the first location.

In some embodiments, the method further comprises illuminating a portion of the surface defined by an illumination field. In some embodiments, the illumination field is illuminated using a laser. In some embodiments, the illumination field is illuminated using a light emitting diode (LED) or a lamp. In some embodiments, a power of the laser is adjusted to maintain a constant brightness on the surface and/or not saturate the camera. In some embodiments, the illumination field at least partially overlaps with the scanning field. In some embodiments, the scanning field encompasses the illumination field. In some embodiments, the illumination field has a shape that is substantially similar to the scanning field. In some embodiments, the illumination field is a substantially rectilinear shape. In some embodiments, the illumination field has a long axis.

In some embodiments, the scanning system further comprises a plurality of illumination fields. In some embodiments, one or more of the plurality of illumination fields have a shape that is substantially linear. In some embodiments, the method further comprises rotating the illumination field such that the illumination field maintains a defined orientation with respect to the rotational axis of the surface. In some embodiments, the illumination field maintains a fixed orientation with respect to the scanning field. In some embodiments, the defined orientation comprises a line coinciding with the long axis of the illumination field passing through the rotational axis of the surface. In some embodiments, the defined orientation comprises the long axis of the illumination field being parallel to a radial line, wherein the radial line passes through the rotational axis of the surface and the rotational axis of the illumination field. In some embodiments, the scanning field and the illumination field are rotated together. In some embodiments, the long axis of the illumination field is parallel to the long axis of the scanning field. In some embodiments, the illumination field rotates around a rotational axis of the illumination field. In some embodiments, the rotational axis of the illumination field is substantially perpendicular to the surface. In some embodiments, the rotational axis of the illumination field is substantially parallel to the rotational axis of the surface. In some embodiments, the rotational axis of the illumination field passes through an axis of symmetry of the illumination field. In some embodiments, the rotational axis of the illumination field is the same as the rotational axis of the scanning field. In some embodiments, the illumination field is rotated by rotating a lens. In some embodiments, the illumination field is rotated by rotating a diffractive optical element (DOE). In some embodiments, the illumination field is rotated by rotating a prism. In some embodiments, the illumination field is rotated by rotating a mirror. In some embodiments, the illumination field is rotated by rotating a laser. In some embodiments, the illumination field is rotated using a motor.

In some embodiments, the method further comprises scanning a second portion of the surface defined by a second scanning field. In some embodiments, the second scanning field is scanned using a second scanning system. In some embodiments, the second scanning system comprises a second objective in optical communication with the surface. In some embodiments, the second objective is focused independently of a first objective. In some embodiments, the second objective has a fixed position relative to the first objective. In some embodiments, the second scanning field has an orientation with respect to the rotational axis of the surface. In some embodiments, the second scanning field is radially adjacent to the scanning field. In some embodiments, the scanning field and the second scanning field have the same orientation with respect to the rotational axis of the surface. In some embodiments, the second scanning field is rotated independently of the scanning field such that the second scanning field maintains the orientation with respect to the rotational axis of the surface. In some embodiments, the second scanning field is rotated in coordination with the scanning field.

In some embodiments, the first objective and the second objective are part of a scanning module, and the scanning module is translated relative to the surface along a line extending radially from the rotational axis of the surface. In some embodiments, the surface is substantially circular and wherein at least one of either the first objective or the second objective is not translated along a chord that passes through the rotational axis of the surface. In some embodiments, the first objective and second objective are on a same side of the surface with respect to a plane normal to the surface and intersecting the rotational axis of the surface, and both the first objective and the second objective are translated together toward or away from the rotational axis of the surface. In some embodiments, the first objective and second objective are on an opposite side of the surface with respect to a plane normal to the surface and intersecting the rotational axis of the surface. In some embodiments, (i) the first objective is translated toward the rotational axis of the surface when the second objective is translated away from the rotational axis of the surface or (ii) the first objective is translated away from the rotational axis of the surface when the second objective is translated toward the rotational axis of the surface.

In some embodiments, the surface is substantially circular and wherein the first objective and second objective are translated along parallel chords on either side of a plane normal to the surface and intersecting the rotational axis of the surface and equidistant from the rotational axis of the surface. In some embodiments, the surface is mounted on a rotational module. In some embodiments, the rotational module is translated relative to the scanning system. In some embodiments, the rotational module is stationary and the scanning module is translatable. In some embodiments, the scanning module is stationary and the rotational module is translatable. In some embodiments, the rotational module is mounted on a track. In some embodiments, the scanning module is mounted on a scanning module track. In some embodiments, the scanning module track is linear. In some embodiments, a plurality of surfaces are mounted on a plurality of rotational modules and wherein the plurality of rotational modules are mounted on a stage and the stage is rotated to bring each of the rotational modules in optical communication with the scanning module.

In some embodiments, subsequent to scanning the surface, the rotational module is moved to a chemistry module. In some embodiments, the method further comprises translating a second rotational module such that a second surface is in optical communication with the scanning module. In some embodiments, the surface comprises an array of nucleic acid colonies. In some embodiments, the nucleic acid colonies are labeled with a fluorophore. In some embodiments, an intensity of the fluorophore is indicative of a sequence of the nucleic acid colony. In some embodiments, a laser excites the fluorophore at a first wavelength and a camera detects an emission from the fluorophore at a second wavelength. In some embodiments, the laser illuminates an illumination field and the camera scans a scanning field.

In some embodiments, two or more of scanning, rotating the surface, rotating the scanning field, and translation occur simultaneously. In some embodiments, three or more of scanning, rotating the surface, rotating the scanning field, and translation occur simultaneously. In some embodiments, scanning, rotating the surface, rotating the scanning field, and translation occur independently. In some embodiments, the method further comprises repeating steps (a) and (b). In some embodiments, steps (a) and (b) are repeated for each base in a nucleic acid polymerization reaction, thereby sequencing the nucleic acid.

In various aspects, the present disclosure provides a scanning system comprising: a surface configured to rotate about a rotational axis of the surface; a detector in optical communication with the surface, wherein the detector has an scanning field comprising a first portion of the surface; and an illumination source configured to illuminate an illumination region comprising a second portion of the surface, wherein the illumination region and the scanning field at least partially overlap, wherein the detector is configured to maintain an orientation of the scanning field with respect to the rotational axis of the surface during (i) rotation of the surface about the rotational axis and (ii) translation of the surface relative to the scanning field.

In some embodiments, the scanning field traces an arc on the surface. In some embodiments, scanning the surface comprises imaging the surface. In some embodiments, the scanning field comprises an imaging field. In some embodiments, the scanning field traces a scanning path along the surface, and wherein the scanning path comprises an imaging path. In some embodiments, the scanning system comprises an imaging system. In some embodiments, the detector comprises a line scan camera. In some embodiments, the line scan camera comprises a TDI-line scan camera. In some embodiments, the TDI-line scan camera images a first scanning field on a first camera region. In some embodiments, the TDI-line scan camera images a second scanning field on a second camera region. In some embodiments, the TDI-line scan camera images a first scanning field on a first camera region and images the first scanning field on a second camera region. In some embodiments, the first camera region and the second camera region detect different wavelengths. In some embodiments, the first camera region and the second camera region detect different dynamic ranges.

In some embodiments, the surface is configured to translate along an axis of translation with respect to the scanning field. In some embodiments, the axis of translation intersects the rotational axis of the surface and a center point of the scanning field. In some embodiments, the axis of translation does not intersect the rotational axis of the surface and a center point of the scanning field. In some embodiments, an orientation of the scanning field changes from a first orientation to a second orientation with respect to the rotational axis of the surface upon translation of the surface. In some embodiments, the scanning field is configured to rotate about a rotational axis of the scanning field with respect to the rotational axis of the surface to correct the orientation of the scanning field from the second orientation to the first orientation with respect to the rotational axis of the surface. In some embodiments, the scanning field is configured to rotate by rotating an objective. In some embodiments, the scanning field is configured to rotate by rotating a lens. In some embodiments, the scanning field is configured to rotate by rotating a prism. In some embodiments, the scanning field is configured to rotate by rotating a mirror. In some embodiments, the scanning field is configured to rotate by rotating the detector. In some embodiments, the scanning field is configured to rotate by rotating a diffractive optical element (DOE).

In some embodiments, the illumination source comprises a laser or a light emitting diode (LED). In some embodiments, the illumination source comprises a substantially circular illumination profile. In some embodiments, the substantially circular illumination profile is expanded along a single axis. In some embodiments, the substantially circular illumination profile is expanded along a single axis using a cylindrical lens. In some embodiments, the scanning system further comprises a plurality of illumination sources having substantially circular illumination profiles, wherein the substantially circular illumination profiles are expanded along a single axis. In some embodiments, the illumination source passes through a grating.

In some embodiments, the first portion of the surface is configured to move with respect to the scanning field. In some embodiments, a first region of the first portion of the surface is configured to move at a first velocity with respect to the scanning field, and a second region of the first portion of the surface is configured to move at a second velocity with respect to the scanning field. In some embodiments, the first region is closer to the rotational axis of the surface than the second region and the first velocity slower than the second velocity. In some embodiments, an image of the first region is magnified on the detector by a first magnification factor and an image of the second region is magnified on the detector by a second magnification factor. In some embodiments, the first magnification factor and the second magnification factor are different.

In some embodiments, the scanning system further comprises a lens having a lens axis positioned in an optical path between the scanning field and the detector, wherein the lens axis is not perpendicular to the surface. In some embodiments, the scanning system further comprises an objective positioned in an optical path between the scanning field and the detector. In some embodiments, the objective is in fluidic contact with the surface. In some embodiments, the objective and the surface are different temperatures.

In some embodiments, the scanning system further comprises a temperature gradient across a fluid contacting the surface and the objective. In some embodiments, the objective comprises an insulating spacer in contact with the fluid. In some embodiments, the insulating spacer comprises an air gap. In some embodiments, the objective is heated to reduce the temperature gradient. In some embodiments, the objective is cooled to increase the temperature gradient. In some embodiments, the fluid is configured to exchange during rotation.

In some embodiments, the method further comprises (i) scanning a focal region of the surface using an autofocus system to generate a focal map of the focal region and (ii) adjusting a focus of the surface relative to the scanning system based on the focal map while scanning the scanning field. In some embodiments, the surface rotates about the rotational axis of the surface with respect to the scanning field while scanning the focal region of the surface using the autofocus system. In some embodiments, the focal region comprises the scanning field. In some embodiments, the focal region comprises a field in close proximity to the scanning field. In some embodiments, the focal region does not comprise the scanning field. In some embodiments, the focal region is scanned prior to scanning. In some embodiments, the focal region is scanned while scanning.

In some embodiments, the objective is configured to maintain fluidic contact with the surface while the surface is rotated about the rotational axis of the surface with respect to the objective. In some embodiments, the objective is configured to move in a direction approximately normal to the surface to leave and re-enter fluidic contact with the surface. In some embodiments, the objective is configured to retain a droplet of fluid adherent to the objective when the objective leaves fluidic contact with the surface. In some embodiments, the objective is configured to displace bubbles between the surface and the objective when the objective re-enters fluidic contact with the surface. In some embodiments, the scanning system further comprises an adaptor attached to the objective and configured to facilitate bubble displacement.

In some embodiments, the scanning system further comprises a chamber surrounding the surface and the objective configured to maintain a higher humidity in the chamber as compared to outside the chamber. In some embodiments, the chamber comprises a reservoir beneath the surface configured to collect fluid. In some embodiments, the reservoir comprises a fluid level, and wherein the reservoir is configured to maintain an approximately constant fluid level. In some embodiments, the reservoir is configured to dispense a volume of fluid approximately equal to a volume of fluid collected by the reservoir. In some embodiments, a top portion of the chamber is held at a first temperature, the objective is held at a second temperature, the surface is held at a third temperature, and the reservoir is held at a fourth temperature. In some embodiments, the first temperature is higher than the second temperature. In some embodiments, the third temperature is lower than the fourth temperature. In some embodiments, the second temperature is higher than the third temperature and lower than the first temperature.

In various aspects, the present disclosure provides a method for sequencing a nucleic acid molecule, the method comprising: (i) providing an array of nucleic acid molecules on an uncovered surface; (ii) dispersing a layer of a solution over the uncovered surface at a rate of at least 1 nanoliter per second when measured at a temperature of 25 degrees Celsius, wherein the solution comprises reagents including at least one nucleotide that incorporates into a growing nucleic acid strand that is complementary to a nucleic acid molecule of the array of nucleic acid molecules; and (iii) detecting one or more signals that are indicative of the nucleotide incorporated into the growing nucleic acid strand.

In various aspects, the present disclosure provides a method of processing a plurality of nucleic acid samples, comprising: (i) providing said plurality of nucleic acid samples, wherein said plurality of nucleic acid samples comprises a first nucleic acid sample comprising a first set of nucleic acid molecules and a second nucleic acid sample comprising a second set of nucleic acid molecules, wherein each sample of said plurality of nucleic acid samples has an identifiable sample origin; (ii) loading said first nucleic acid sample onto a first region of a substrate as a first array of said first set of nucleic acid molecules and loading said second nucleic acid sample onto a second region of said substrate as a second array of said second set of nucleic acid molecules, wherein said first region is different from said second region; (iii) dispersing a solution across said substrate, wherein said solution comprises reagents sufficient to react with nucleic acid molecules of said first array or said second array; (iv) detecting one or more signals that are indicative of a reaction between said reagents and said nucleic acid molecules of said first array or said second array; and (v) based at least in part on (a) said one or more signals and (b) locations, from said first region and said second region, from which said one or more signals are detected, analyzing said first nucleic acid sample and said second nucleic acid sample, and determine (1) a first subset of said nucleic acid molecules of said first array or said second array as originating from said first nucleic acid sample and (2) a second subset of said nucleic acid molecules of said first array or said second array as originating from said second nucleic acid sample.

In various aspects, the present disclosure provides a method for processing a plurality of nucleic acid samples, comprising: (i) providing said plurality of nucleic acid samples, wherein said plurality of nucleic acid samples comprises a first nucleic acid sample comprising a first set of nucleic acid molecules and a second nucleic acid sample comprising a second set of nucleic acid molecules; (ii) loading said first nucleic acid sample onto a substrate to associate said first set of nucleic acid molecules to a first array of individually addressable locations; (iii) imaging said substrate to identify said first array of individually addressable locations; (iv) loading said second nucleic acid sample onto a substrate to associate said second set of nucleic acid molecules to a second array of individually addressable locations; (v) imaging said substrate to identify said second array of individually addressable locations; (vi) dispersing a solution across said substrate, wherein said solution comprises reagents sufficient to react with nucleic acid molecules of said first array or said second array; (vii) detecting one or more signals that are indicative of a reaction between said reagents and said nucleic acid molecules of said first array or said second array; and (viii) based at least in part on (a) said one or more signals and (b) locations, from said first array of individually addressable locations and said second array of individually addressable locations, from which said one or more signals are detected, analyzing said first nucleic acid sample and said second nucleic acid sample, and determining (1) a first subset of said nucleic acid molecules of said first array or said second array as originating form said first nucleic acid sample and (20 a second subset of said nucleic acid molecules of said first array or said second array as originating from said second nucleic acid sample.

In various aspects, the present disclosure provides a method for processing a plurality of nucleic acid samples, wherein each of said plurality of nucleic acid samples comprises a fluorescent dye; (i) providing said plurality of nucleic acid samples, wherein each of said plurality of nucleic acid samples comprises a fluorescent dye; (ii) separating said plurality of nucleic acid samples into a first set of one or more samples and a second set of one or more samples; (iii) loading said first set of one or more samples onto a first set of regions on a substrate, with one sample per region in said first set of regions; (iv) imaging said substrate to identify (a) locations within said first set of regions and (b) locations within a second set of regions on said substrate, wherein said second set of regions are different from said first set of regions, where said first set of one or more samples are associated; (v) loading said second set of one or more samples onto said second set of regions on a substrate, with one sample per region in said second set of regions; (vi) imaging said substrate to identify (a) locations within said first set of regions and (b) locations within said second set of regions where said second set of one or more samples are associated; (vii) dispersing a solution across said substrate, wherein said solution comprises reagents sufficient to react with nucleic acid molecules of said first set of one or more samples or said second set of one or more samples; (viii) detecting one or more signals that are indicative of a reaction between said reagents and said nucleic acid molecules; and (ix) based at least in part on (a) said one or more signals and (b) locations, from said first set of regions and said second set of regions, from which said one or more signals are detected, analyzing said each of said plurality of nucleic acid samples.

In various aspects, the present disclosure provides a method for processing a biological analyte comprising: (i) moving a substrate through or along a reel, wherein a surface of said substrate comprises an array having immobilized thereto said biological analyte; (ii) bringing said surface of said substrate in contact with a reservoir comprising a solution, wherein said solution comprises a plurality of probes; (iii) subjecting said biological analyte to conditions sufficient to conduct a reaction between a probe of said plurality of probes and said biological analyte, to couple said probe to said biological analyte; and (iv) detecting one or more signals from said probe coupled to said biological analyte, thereby analyzing said biological analyte, wherein said substrate is moved through or along said reel in the same direction for at least two consecutive cycles of (ii)-(iv).

In various aspects, the present disclosure provides a system for analyzing a biological analyte, comprising: a substrate comprising a biological analyte, wherein said substrate is maintained at or above a first temperature that is higher than an ambient temperature of an environment exposed to said substrate; and an optical imaging objective in optical communication with said substrate and exposed to said environment, wherein said optical imaging objective is subject to a temperature gradient between said first temperature of said substrate and said ambient temperature of said environment, wherein said optical imaging objective comprises a first optical element and a second optical element adjacent to said first optical element, wherein said second optical element is disposed farther from said substrate than said first optical element, wherein said first optical element is configure to be at least partially immersed in an immersion fluid in contact with said substrate, wherein said second optical element is in optical communication with said substrate through said first optical element, and wherein said first optical element is configured such that a second temperature of said second optical element is maintained at or below a predetermined threshold.

In various aspects, the present disclosure provides a method for analyzing a biological analyte, comprising: (i) providing a substrate comprising a biological analyte, wherein said substrate is at a first temperature that is higher than an ambient temperature of an environment exposed to said substrate; (ii) providing an optical imaging objective in optical communication with said substrate and exposed to an environment, wherein said optical imaging objective is subject to a temperature gradient between said first temperature of said substrate and said ambient temperature of said environment, wherein said optical imaging objective comprises a first optical element and a second optical element adjacent to said first optical element, wherein said second optical element is disposed farther from said substrate than said first optical element, and wherein said first optical element is at least partially immersed in an immersion fluid in contact with said substrate; (iii) controlling or maintaining a second temperature of said first optical element to regulate a magnitude or location of said temperature gradient through said optical imaging objective such that a third temperature gradient through said optical element is maintained below a predetermined threshold; and (iv) using said optical imaging objective to detect one or more signals from said biological analyte, during movement of said substrate relative to said optical imaging objective.

In various aspects, the present disclosure provides a method for storing a substrate comprising a nucleic acid molecule-coated surface, comprising: (i) providing said substrate having a surface comprising a first set of nucleic acid molecules immobilized thereto, wherein nucleic acid molecules of said first set of nucleic acid molecules are configured to capture sample nucleic acid molecules derived from one or more nucleic acid samples; (ii) bringing said substrate comprising said surface comprising said first set of nucleic acid molecules into contact with a second set of nucleic acid molecules under conditions sufficient to yield a treated surface in which at least 90% of nucleic acid molecules of said first set of nucleic acid molecules are hybridized to nucleic acid molecules of said second set of nucleic acid molecules, wherein said second set of nucleic acid molecules are not said sample nucleic acid molecules; and (iii) storing said substrate having said treated surface for a time period of at least 1 hour.

In various aspects, the present disclosure provides a method for nucleic acid processing, comprising: (i) providing a substrate having a treated surface comprising a first set of nucleic acid molecules immobilized thereto, wherein at least 90% of nucleic acid molecules of said first set of nucleic acid molecules are hybridized to nucleic acid molecules of a second set of nucleic acid molecules, wherein nucleic acid molecules of said first set of nucleic acid molecules are configured to capture sample nucleic acid molecules derived from one or more nucleic acid samples, wherein said second set of nucleic acid molecules are not said sample nucleic acid molecules, and wherein said substrate having said treated substrate has been stored for a time period of at least 1 hour; and (ii) removing said nucleic acid molecules of said second set of nucleic acid molecules from said treated surface.

In various aspects, the present disclosure provides a kit, comprising: a substrate comprising a treated surface, wherein said treated surface comprises a plurality of pairs of bound nucleic acid molecules, wherein each pair of said plurality of pairs comprises a first nucleic acid molecule of a first set of nucleic acid molecules at least partially hybridized to a second nucleic acid molecule of a second set of nucleic acid molecules, wherein said first set of nucleic acid molecules is immobilized to said surface, wherein at least 90% of nucleic acid molecules of said first set of nucleic acid molecules are paired with a nucleic acid molecule of said second set of nucleic acid molecules, wherein nucleic acid molecules of said first set of nucleic acid molecules are configured to capture sample nucleic acid molecules derived from one or more nucleic acid samples when said nucleic acid molecules of said first set of nucleic acid molecules are not paired with nucleic acid molecules of said second set of nucleic acid molecules.

In various aspects, the present disclosure provides a kit, comprising: a substrate comprising a surface comprising a first set of nucleic acid molecules immobilized thereto, wherein said first set of nucleic acid molecules comprises one or more first nucleic acid molecules, which one or more first nucleic acid molecules are configured to capture sample nucleic acid molecules derived from one or more nucleic acid samples; and a solution comprising a second set of nucleic acid molecules, wherein said second set of nucleic acid molecules comprises one or more second nucleic acid molecules, which one or more second nucleic acid molecules are not said sample nucleic acid molecules; wherein said second set of nucleic acid molecules is selected such that, upon bringing said solution in contact with said surface, at least 70% of said one or more first nucleic acid molecules bind to a second nucleic acid molecule of said second set of nucleic acid molecules to generate one or more pairs of bound nucleic acid molecules, wherein each pair of said one or more pairs comprises (i) a first nucleic acid molecule of said first set of nucleic acid molecules and a second nucleic acid molecule of said second set of nucleic acid molecules, and (ii) a section of substantially complementary sequences.

In various aspects, the present disclosure provides a method for storing a substrate comprising a nucleic acid molecule-coated surface, comprising: (i) providing a substrate having a surface comprising a first set of nucleic acid molecules immobilized thereto, wherein nucleic acid molecules of said first set of nucleic acid molecules are configured to capture sample nucleic acid molecules derived from one or more nucleic acid samples, and wherein each nucleic acid molecule of said first set of nucleic acid molecules comprises a first nucleic acid sequence and a second nucleic acid sequence, which second nucleic acid sequence is substantially complementary to said first nucleic acid sequence; (ii) generating a treated surface by subjecting said surface to conditions sufficient to bind said first nucleic acid sequence of a nucleic acid molecule of said first set of nucleic acid molecules to said second nucleic acid sequence of said nucleic acid molecule to provide an immobilized hairpin molecule; and (iii) storing said substrate having said treated surface for a time period of at least 1 hour.

In various aspects, the present disclosure provides a method for storing a substrate comprising a nucleic acid molecule-coated surface, comprising: (i) providing a substrate having a surface comprising a first set of nucleic acid molecules immobilized thereto, wherein nucleic acid molecules of said first set of nucleic acid molecules are configured to capture sample nucleic acid molecules derived from one or more nucleic acid samples, and wherein each nucleic acid molecule of said nucleic acid molecules of said first set of nucleic acid molecules comprises a first nucleic acid sequence; (ii) providing a second set of nucleic acid molecules, wherein each nucleic acid molecule of said second set of nucleic acid molecules comprises a second nucleic acid sequence that is substantially complementary to said first nucleic acid sequence, and wherein said second set of nucleic acid molecules are not said sample nucleic acid molecules; (iii) bringing said surface comprising said first set of nucleic acid molecules into contact with said second set of nucleic acid molecules to generate a treated surface in which at least 70% of nucleic acid molecules of said first set of nucleic acid molecules are hybridized to nucleic acid molecules of said second set of nucleic acid molecules; and (iv) storing said treated surface for at least one hour, wherein, for each nucleic acid molecule of said first set of nucleic acid molecules hybridized to a nucleic acid molecule of said second set of nucleic acid molecules, said first nucleic acid sequence is hybridized to said second nucleic acid sequence, and wherein said first nucleic acid sequence hybridized to said second nucleic acid sequence at least partially denatures between about 40 degrees C. and 60 degrees C.

In various aspects, the present disclosure provides a method for detecting or analyzing an analyte, comprising: (i) providing an open substrate comprising a central axis, said open substrate comprising an array of analytes immobilized adjacent to said open substrate, wherein at least one analyte of said array of analytes is bound to a probe; and (ii) using a detector system to perform a non-linear scan of said open substrate to detect at least one signal or signal change from said bound probe, wherein said detector system comprises a line-scan camera and an illumination source, wherein said illumination source is configured to generate an illuminated region on said open substrate, wherein said open substrate comprises a first area and a second area, wherein said first area and said second area: (a) comprise different subsets of said array of analytes, (b) are at different radial positions of said open substrate with respect to said central axis, and (c) are spatially resolved by said detector system; and wherein said bound probe is disposed in said first area of said open substrate, and wherein said non-linear scan is performed during relative non-linear motion between said open substrate and one or both of (1) said line-scan camera and (2) said illuminated region.

In various aspects, the present disclosure provides an apparatus for analyte detection or analysis, comprising: a housing configured to receive an open substrate having an array of analytes immobilized adjacent thereto, wherein at least one analyte of said array of analytes is bound to a probe; and a detector system, wherein said detector system comprises a line-scan camera and an illumination source, wherein said illumination source is configured to generate an illuminated region on said open substrate, wherein said open substrate comprises a first area and a second area, wherein said first area and said second area: (a) comprise subsets of said array of immobilized analytes, (b) are at different radial positions of said open substrate with respect to said central axis, and (c) are spatially resolved by said detector system; wherein said bound probe is disposed in said first area of said open substrate, and wherein said detector system is programmed to perform a non-linear scan of said open substrate and detect at least one signal or signal change from said bound probe at said first area of said open substrate, wherein said non-linear scan is performed during relative non-linear motion between said open substrate and one or both of (1) said line-scan camera and (2) said illuminated region.

In various aspects, the present disclosure provides a computer-readable medium comprising non-transitory instructions stored thereon, which when executed cause one or more computer processors to implement a method for detecting or analyzing an analyte, the method comprising: providing an open substrate about a central axis, said open substrate comprising an array of analytes immobilized adjacent to said open substrate, wherein at least one analyte of said array of analytes is bound to a probe; and using a detector system to perform a non-linear scan of said open substrate to detect at least one signal or signal change from said bound probe, wherein said detector system comprises a line-scan camera and an illumination source, wherein said illumination source is configured to generate an illuminated region on said open substrate, wherein said open substrate comprises a first area and a second area, wherein said first area and said second area: (a) comprise different subsets of said array of analytes, (b) are at different radial positions of said open substrate with respect to said central axis, and (c) are spatially resolved by said detector system; wherein said bound probe is disposed in said first area of said open substrate; and wherein said non-linear scan is performed during relative non-linear motion between said open substrate and one or both of (1) said line-scan camera and (2) said illuminated region.

In various aspects, the present disclosure provides a method for nucleic acid sample processing, comprising: (i) providing a first source comprising a first set of nucleic acid molecules and a second source comprising a second set of nucleic acid molecules, wherein said first source is different than said second source; (ii) directing said first set of nucleic acid molecules from said first source to a substrate to yield said first set of nucleic acid molecules immobilized in a first array adjacent to said substrate; (iii) imaging said substrate to identify a first set of locations on said substrate with said first array adjacent to said substrate; (iv) directing said second set of nucleic acid molecules from said second source to said substrate to yield said second set of nucleic acid molecules immobilized in a second array adjacent to said substrate, wherein said second array is different than said first array; (v) imaging said substrate to identify a second set of locations on said substrate with said second array adjacent to said substrate; and (vi) using (a) signals detected from said first array and said second array and (b) locations from which said signals are detected to identify (1) said first set of nucleic acid molecules or sequences thereof with said first source and (2) said second set of nucleic acid molecules or sequences thereof with said second source, wherein said first set of locations and said second set of locations each comprise at least 1,000,000 locations.

In various aspects, the present disclosure provides a method for scanning a surface, comprising: (i) using a scanner to scan a scanning field comprising a portion of a surface, wherein the scanning field has an orientation with respect to a rotational axis of the surface; and (ii) rotating (a) the surface about the rotational axis of the surface and (b) the scanning field about a rotational axis of the scanning field to substantially maintain the orientation of the scanning field with respect to the rotational axis of the surface prior to, during, or subsequent to translation of the surface and the scanning field relative to one another.

In various aspects, the present disclosure provides a system, comprising: a scanner configured to scan a scanning field comprising a portion of a surface, wherein the scanning field has an orientation with respect to a rotational axis of the surface; and a controller configured to direct rotation of (i) the surface about the rotational axis of the surface and (ii) the scanning field about a rotational axis of the scanning field to substantially maintain the orientation of the scanning field with respect to the rotational axis of the surface prior to, during, or subsequent to translation of the surface and the scanning field relative to one another.

In various aspects, the present disclosure provides a method for analyzing a biological material, comprising: (i) activating a device comprising (a) a substrate comprising a surface having said biological material, wherein said surface is at a first temperature that is greater than an ambient temperature, (b) an optical imaging objective in optical communication with said surface, wherein said optical imaging objective comprises a temperature gradient between said first temperature and said ambient temperature, wherein said optical imaging objective comprises (1) a first optical element that is at least partially immersed in an immersion fluid in contact with said surface, and (2) a second optical element in optical communication with said surface through at least said first optical element, and wherein said second optical element is maintained at or below a second temperature different from said first temperature; and (ii) using said optical imaging objective to collect a signal from said surface having said biological material.

In various aspects, the present disclosure provides a system for analyzing a biological material, comprising: a platform configured to support a substrate comprising a surface having said biological material, wherein said surface is configured to be at a first temperature that is greater than an ambient temperature when said substrate is supported by said platform; an optical imaging objective configured to be in optical communication with said surface when said substrate is supported by said platform, wherein said optical imaging objective is configured to comprise a temperature gradient between said first temperature and said ambient temperature, wherein said optical imaging objective comprises (1) a first optical element that is configured to be at least partially immersed in an immersion fluid in contact with said surface, and (2) a second optical element in optical communication with said surface through at least said first optical element, and wherein said second optical element is configured to be maintained at or below a second temperature different from said first temperature; and one or more computer processors that are individually or collectively programmed to direct collection of a signal from said surface having said biological material using at least said optical imaging objective.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 8A illustrates rows of pixels for a time delay and integration (TDI) line-scan camera. FIG. 8B illustrates a trilinear pixel scheme for a color line-scan camera including red (R), green (G), and blue (B) pixels. FIG. 8C and FIG. 8D illustrate bilinear pixel schemes for a color line-scan camera including red, green, and blue pixels.

FIG. 12A-FIG. 12C illustrate schemes for detection of signals emitted by a material coupled to an open substrate. FIG. 12A illustrates a scheme in which an open substrate rotates and a detector system remains stationary during detection. FIG. 12B illustrates a scheme in which an open substrate remains stationary and a detector system rotates during detection.

FIG. 12C illustrates a scheme in which an open substrate rotates during delivery and dispersal of a solution to the open substrate (left panel) and remains stationary during detection with a rotating detector system (right panel).

FIG. 17A-FIG. 17B illustrate schematically exemplary methods to regulate temperature of the substrate.

FIG. 17C-FIG. 17D illustrate schematically exemplary methods to regulate temperature of the substrate.

FIG. 17E illustrates schematically exemplary methods to regulate temperature of the substrate.

FIG. 18 illustrates schematically bubble formation in a fluid.

FIG. 19 illustrates schematically an adapter for an optical imaging system.

FIG. 20A illustrates schematically an exemplary method to displace bubbles, showing a substrate with a fluid dispensed thereto.

FIG. 20B illustrates schematically an exemplary method to displace bubbles, showing an optical imaging objective in contact with the fluid.

FIG. 21 illustrates schematically a method for dispensing and removing immersion fluid onto a substrate.

FIG. 22A-FIG. 22B illustrate schematically a method for trapping bubbles and exemplary adapters for optical imaging objectives.

FIG. 29D shows motion of a substrate relative to four imaging heads.

FIG. 29E shows motion of a substrate relative to four imaging heads.

FIG. 30B shows successive ring paths of two imaging heads located on opposite sides of an axis of rotation of a substrate.

FIG. 30C shows staggered ring paths of two imaging heads located on the same side of an axis of rotation of a substrate.

FIG. 35C shows an example of imaging head positioning for optimal scanning efficiency;

FIG. 38A-FIG. 38D illustrate a method of making an oligonucleotide-coated surface resistant to nucleic acid contaminants.

FIG. 50A illustrates a method for loading beads onto specific regions of a substrate. FIG. 50B illustrates a method for loading a subset of beads onto specific regions of a substrate.

DETAILED DESCRIPTION

Figure 1:
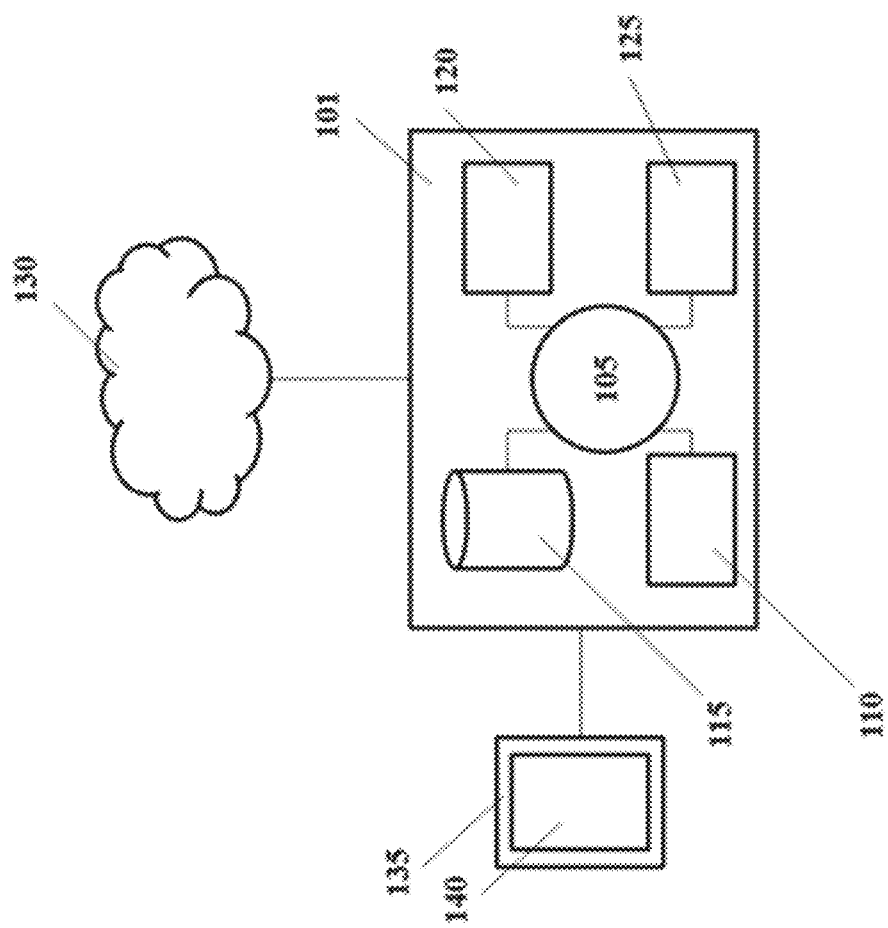
FIG. 1 shows a computer control system that is programmed or otherwise configured to implement methods provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "processing an analyte," as used herein, generally refers to one or more stages of interaction with one or more sample substances. Processing an analyte may comprise conducting a chemical reaction, biochemical reaction, enzymatic reaction, hybridization reaction, polymerization reaction, physical reaction, any other reaction, or a combination thereof with, in the presence of, or on, the analyte. Processing an analyte may comprise physical and/or chemical manipulation of the analyte. For example, processing an analyte may comprise detection of a chemical change or physical change, addition of or subtraction of material, atoms, or molecules, molecular confirmation, detection of the presence of a fluorescent label, detection of a Forster resonance energy transfer (FRET) interaction, or inference of absence of fluorescence. The term "analyte" may refer to molecules, cells, biological particles, or organisms. In some instances, a molecule may be a nucleic acid molecule, antibody, antigen, peptide, protein, or other biological molecule obtained from or derived from a biological sample. An analyte may originate from, and/or be derived from, a biological sample, such as from a cell or organism. An analyte may be synthetic.

The term "sequencing," as used herein, generally refers to a process for generating or identifying a sequence of a biological molecule, such as a nucleic molecule. Such sequence may be a nucleic acid sequence, which may include a sequence of nucleic acid bases. Sequencing may be single molecule sequencing or sequencing by synthesis, for example. Sequencing may be performed using template nucleic acid molecules immobilized on a support, such as a flow cell or one or more beads.

The term "biological sample," as used herein, generally refers to any sample from a subject or specimen. The biological sample can be a fluid or tissue from the subject or specimen. The fluid can be blood (e.g., whole blood), saliva, urine, or sweat. The tissue can be from an organ (e.g., liver, lung, or thyroid), or a mass of cellular material, such as, for example, a tumor. The biological sample can be a feces sample, collection of cells (e.g., cheek swab), or hair sample. The biological sample can be a cell-free or cellular sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell free DNA or cell free RNA. The nucleic acid molecules may be derived from a variety of sources including human, mammal, non-human mammal, ape, monkey, chimpanzee, reptilian, amphibian, avian, or plant sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject) or may be derived from tissue of the subject itself.

The term "subject," as used herein, generally refers to an individual from whom a biological sample is obtained. The subject may be a mammal or non-mammal. The subject may be an animal, such as a monkey, dog, cat, bird, or rodent. The subject may be a human. The subject may be a patient. The subject may be displaying a symptom of a disease. The subject may be asymptomatic. The subject may be undergoing treatment. The subject may not be undergoing treatment. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The terms "nucleic acid," "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or deoxyribonucleic acids (DNA) or ribonucleotides or ribonucleic acids (RNA), or analogs thereof. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, and isolated RNA of any sequence. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 20 kb, 30 kb, 40 kb, 50 kb, 100 kb, 200 kb, 300 kb, 400 kb, 500 kb, 1 megabase (Mb), or more. A nucleic acid molecule (e.g., polynucleotide) can comprise a sequence of four natural nucleotide bases: adenine (A); cytosine (C); guanine (G); and thymine (T) (uracil (U) for thymine (T) when the polynucleotide is RNA). A nucleic acid molecule may include one or more nonstandard nucleotide(s), nucleotide analog(s) and/or modified nucleotide(s).

Nonstandard nucleotides, nucleotide analogs, and/or modified analogs may include, but are not limited to, diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

The term "nucleotide," as used herein, generally refers to any nucleotide or nucleotide analog. The nucleotide may be naturally occurring or non-naturally occurring. The nucleotide analog may be a modified, synthesized or engineered nucleotide. The nucleotide analog may not be naturally occurring or may include a non-canonical base. The naturally occurring nucleotide may include a canonical base. The nucleotide analog may include a modified polyphosphate chain (e.g., triphosphate coupled to a fluorophore). The nucleotide analog may comprise a label. The nucleotide analog may be terminated (e.g., reversibly terminated). The nucleotide analog may comprise an alternative base.

The terms "amplifying," "amplification," and "nucleic acid amplification" are used interchangeably and generally refer to generating one or more copies of a nucleic acid or a template. For example, "amplification" of DNA generally refers to generating one or more copies of a DNA molecule. Moreover, amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, recombinase polymerase reaction (RPA), and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C.C. PNAS, 1989, 86, 4076-4080 and U.S. Pat. Nos. 5,409,811 and 5,674,716, each of which is herein incorporated by reference in its entirety.

The terms "dispense" and "disperse" may be used interchangeably herein. In some cases, dispensing may comprise dispersing and/or dispersing may comprise dispensing. Dispensing generally refers to distributing, depositing, providing, or supplying a reagent, solution, or other object, etc. Dispensing may comprise dispersing, which may generally refer to spreading.

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference).

The term "detector," as used herein, generally refers to a device that is capable of detecting a signal, including a signal indicative of the presence or absence of one or more incorporated nucleotides or fluorescent labels. The detector may detect multiple signals. The signal or multiple signals may be detected in real-time during, substantially during a biological reaction, such as a sequencing reaction (e.g., sequencing during a primer extension reaction), or subsequent to a biological reaction. In some cases, a detector can include optical and/or electronic components that can detect signals. The term "detector" may be used in detection methods. Non-limiting examples of detection methods include optical detection, spectroscopic detection, electrostatic detection, electrochemical detection, acoustic detection, magnetic detection, and the like. Optical detection methods include, but are not limited to, light absorption, ultraviolet-visible (UV-vis) light absorption, infrared light absorption, light scattering, Rayleigh scattering, Raman scattering, surface-enhanced Raman scattering, Mie scattering, fluorescence, luminescence, and phosphorescence. Spectroscopic detection methods include, but are not limited to, mass spectrometry, nuclear magnetic resonance (NMR) spectroscopy, and infrared spectroscopy. Electrostatic detection methods include, but are not limited to, gel-based techniques, such as, for example, gel electrophoresis. Electrochemical detection methods include, but are not limited to, electrochemical detection of amplified product after high-performance liquid chromatography separation of the amplified products.

The term "continuous area scanning," as used herein, generally refers to area scanning in rings, spirals, or arcs on a rotating substrate using an optical imaging system and a detector. Continuous area scanning may scan a substrate or array along a nonlinear path. Alternatively or in addition, continuous area scanning may scan a substrate or array along a linear or substantially linear path. The detector may be a continuous area scanning detector. The scanning direction may be substantially θ in an (R, θ) coordinate system in which the object rotation motion is in a θ direction. Across any field of view on the object (substrate) imaged by a scanning system, the apparent velocity may vary with the radial position (R) of the field point on the object as $$R\frac{d\theta}{dt}.$$

Continuous area scanning detectors may scan at the same rate for all image positions and therefore may not be able to operate at the correct scan rate for all imaged points in a curved (or arcuate or non-linear) scan. Therefore, the scan may be corrupted by velocity blur for imaged field points moving at a velocity different than the scan velocity. Continuous rotational area scanning may comprise an optical detection system or method that makes algorithmic, optical, and/or electronic corrections to substantially compensate for this tangential velocity blur, thereby reducing this scanning aberration. For example, the compensation is accomplished algorithmically by using an image processing algorithm that deconvolves differential velocity blur at various image positions corresponding to different radii on the rotating substrate to compensate for differential velocity blur. In some cases, the camera or scanner may apply or use a blur to compensate for differential velocity blur.

In another example, the compensation is accomplished by using an anamorphic magnification gradient. This may serve to magnify the substrate in one axis (anamorphic magnification) by different amounts at two or more substrate positions transverse to the scan direction. The anamorphic magnification gradient may modify the imaged velocities of the two or more positions to be substantially equal thereby compensating for tangential velocity differences of the two positions on the substrate. This compensation may be adjustable to account for different velocity gradients across the field of view at different radii on the substrate.

The imaging field of view may be segmented into two or more regions, each of which can be electronically controlled to scan at a different rate. These rates may be adjusted to the mean projected object velocity within each region. The regions may be optically defined using one or more beam splitters or one or more mirrors. The two or more regions may be directed to two or more detectors. The regions may be defined as segments of a single detector.

The term "continuous area scanning detector," as used herein, generally refers to an imaging array sensor capable of continuous integration over a scanning area wherein the scanning is electronically synchronized to the image of an object in relative motion. A continuous area scanning detector may comprise a time delay and integration (TDI) charge coupled device (CCD), Hybrid TDI, or complementary metal oxide semiconductor (CMOS) pseudo TDI device. For example, a continuous area scanning detector may comprise a TDI line-scan camera.

The term "open substrate", as used herein, generally refers to a substantially planar substrate in which a single active surface is physically accessible at any point from a direction normal to the substrate. Substantially planar may refer to planarity at a micrometer level or nanometer level. Alternatively, substantially planar may refer to planarity at less than a nanometer level or greater than a micrometer level (e.g., millimeter level).

The term "anamorphic magnification", as used herein, generally refers to differential magnification between two axes of an image. An anamorphic magnification gradient may comprise differential anamorphic magnification in a first axis across a displacement in the second axis. The magnification in the second axis may be unity or any other value that is substantially constant over the field.

The term "field of view", as used herein, generally refers to the area on the sample or substrate that is optically mapped to the active area of the detector.

Processing an Analyte Using an Open Substrate

Prior microfluidic systems have utilized substrates containing numerous long, narrow channels. The typical flow cell geometry for such substrates introduces a need to compromise between two competing requirements: 1) minimizing volume to minimize reagent usage; and 2) maximizing effective hydraulic diameter to minimize flow time. This trade-off may be especially important for washing operations, which may require large wash volumes and thus long amounts of time to complete. The tradeoff is illustrated by the Poiseuille equation that dictates flow in the laminar regime and is thus inherent to microfluidic systems that utilize such flow cell geometries. Such flow cell geometries may also be susceptible to contamination. Because such flow cell geometries allow for a finite, limited number of channels in the microfluidic systems, such finite number of channels may be shared between a plurality of different mixtures comprising different analytes, reagents, agents, and/or buffers. Contents of fluids flowing through the same channels may be contaminated.

Described herein are devices, systems, and methods for processing analytes using open substrates or flow cell geometries that can address at least the abovementioned problems. The devices, systems and methods may be used to facilitate any application or process involving a reaction or interaction between an analyte and a fluid (e.g., a fluid comprising reagents, agents, buffers, other analytes, etc.). Such reaction or interaction may be chemical (e.g., polymerase reaction) or physical (e.g., displacement). The systems and methods described herein may benefit from higher efficiency, such as from faster reagent delivery and lower volumes of reagents required per surface area. The systems and methods described herein may avoid contamination problems common to microfluidic channel flow cells that are fed from multiport valves which can be a source of carryover from one reagent to the next. The devices, systems, and methods may benefit from shorter completion time, use of fewer resources (e.g., various reagents), and/or reduced system costs. The open substrates or flow cell geometries may be used to process any analyte, such as but not limited to, nucleic acid molecules, protein molecules, antibodies, antigens, cells, and/or organisms, as described herein. The open substrates or flow cell geometries may be used for any application or process, such as, but not limited to, sequencing by synthesis, sequencing by ligation, amplification, proteomics, single cell processing, barcoding, and sample preparation, as described herein.

The systems and methods may utilize a substrate comprising an array (such as a planar array) of individually addressable locations. Each location, or a subset of such locations, may have immobilized thereto an analyte (e.g., a nucleic acid molecule, a protein molecule, a carbohydrate molecule, etc.). For example, an analyte may be immobilized to an individually addressable location via a support, such as a bead. A plurality of analytes immobilized to the substrate may be copies of a template analyte. For example, the plurality of analytes may have sequence homology. In other instances, the plurality of analytes immobilized to the substrate may be different. The plurality of analytes may be of the same type of analyte (e.g., a nucleic acid molecule) or may be a combination of different types of analytes (e.g., nucleic acid molecules, protein molecules, etc.). One or more surfaces of the substrate may be exposed to a surrounding open environment, and accessible from such surrounding open environment. For example, the array may be exposed and accessible from such surrounding open environment. In some cases, as described elsewhere herein, the surrounding open environment may be controlled and/or confined in a larger controlled environment.

Reagents may be dispensed to the substrate to multiple locations, and/or multiple reagents may be dispensed to the substrate to a single location, via different mechanisms. In some cases, dispensing (to multiple locations and/or of multiple reagents to a single location) may be achieved via relative motion of the substrate and the dispenser (e.g., nozzle). For example, a reagent may be dispensed to the substrate at a first location, and thereafter travel to a second location different from the first location due to forces (e.g., centrifugal forces, centripetal forces, inertial forces, etc.) caused by motion of the substrate. In another example, a reagent may be dispensed to a reference location, and the substrate may be moved relative to the reference location such that the reagent is dispensed to multiple locations of the substrate. In some cases, dispensing (to multiple locations and/or of multiple reagents to a single location) may be achieved without relative motion between the substrate and the dispenser. For example, multiple dispensers may be used to dispense reagents to different locations, and/or multiple reagents to a single location, or a combination thereof (e.g., multiple reagents to multiple locations). In another example, an external force (e.g., involving a pressure differential), such as wind, may be applied to one or more surfaces of the substrate to direct reagents to different locations across the substrate. In another example, the method for dispensing reagents (e.g., to multiple locations and/or of multiple reagents to a single location) may comprise vibration. In such an example, reagents may be distributed or dispensed onto a single region or multiple regions of the substrate (or a surface of the substrate). The substrate (or a surface thereof) may then be subjected to vibration, which may spread the reagent to different locations across the substrate (or the surface). Alternatively or in conjunction, the method may comprise using mechanical, electric, physical, or other means to dispense reagents to the substrate. For example, the solution may be dispensed onto a substrate and a physical scraper (e.g., a squeegee) may be used to spread the dispensed material or spread the reagents to different locations and/or to obtain a desired thickness or uniformity across the substrate. Beneficially, such flexible dispensing may be achieved without contamination of the reagents. In some instances, where a volume of reagent is dispensed to the substrate at a first location, and thereafter travels to a second location different from the first location, the volume of reagent may travel in a path or paths, such that the travel path or paths are coated with the reagent. In some cases, such travel path or paths may encompass a desired surface area (e.g., entire surface area, partial surface area(s), etc.) of the substrate.

Reagents may be dispensed over the uncovered surface or substrate at a desired flow rate. The flow rate of fluid dispensing may be about (e.g., at ambient temperature, or about 25 degrees Celsius) 1 picoliter/min, 10 picoliters/min, 100 picoliters/min, 1 nanoliter/min, 10 nanoliters/min, 100 nanoliters/min, 1 microliter/min, 10 microliters/min, 100 microliters/min, 1 milliliter/min, 10 milliliters/min, 100 milliliters/min, up to 1 liter/min. The flow rate of fluid dispensing may be between any of these flow rates. The flow rate of fluid dispensing may be at least any of these flow rates. Alternatively, the flow rate of fluid dispensing may be at most any of these flow rates. The flow rate may be tuned according to desired properties of the reagent or solution layer (e.g., thickness).

Solutions may comprise reagents, samples, or any useful substance. The solution may comprise a fluid that has desirable flow properties. For example, the fluid may have a temperature-variable viscosity. The solution may comprise a non-Newtonian fluid. The solution may comprise a power law fluid, such as a shear-thinning (thixotropic) or shear-thickening fluid. The solution may comprise a Newtonian fluid.

In some cases, the substrate may be rotatable about an axis. The analytes may be immobilized to the substrate during rotation. Reagents (e.g., nucleotides, antibodies, washing reagents, enzymes, etc.) may be dispensed onto the substrate prior to or during rotation (for instance, spun at a high rotational velocity) of the substrate to coat the array with the reagents and allow the analytes to interact with the reagents. For example, when the analytes are nucleic acid molecules and when the reagents comprise nucleotides, the nucleic acid molecules may incorporate or otherwise react with (e.g., transiently bind) one or more nucleotides. In another example, when the analytes are protein molecules and when the reagents comprise antibodies, the protein molecules may bind to or otherwise react with one or more antibodies. In another example, when the reagents comprise washing reagents, the substrate (and/or analytes on the substrate) may be washed of any unreacted (and/or unbound) reagents, agents, buffers, and/or other particles.

In some cases, the substrate may be movable in any vector or direction, as described elsewhere herein. For example, such motion may be non-linear (e.g., in rotation about an axis). In another example, such motion may be linear. In other examples, the motion may be a hybrid of linear and non-linear motion. The analytes may be immobilized to the substrate during any such motion. Reagents (e.g., nucleotides, antibodies, washing reagents, enzymes, etc.) may be dispensed onto the substrate prior to or during motion of the substrate to facilitate coating of the array with the reagents and allow the analytes to interact with the reagents.

In some cases, where the substrate is rotatable, high speed coating across the substrate may be achieved via tangential inertia directing unconstrained spinning reagents in a partially radial direction (that is, away from the axis of rotation) during rotation, a phenomenon commonly referred to as centrifugal force. High speed rotation may involve a rotational speed of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, at least 10,000 rpm, or greater. This mode of directing reagents across a substrate may be herein referred to as centrifugal or inertial pumping. Inertial forces may direct unconstrained reagents across the substrate in any direction during any type of motion (e.g., rotational motion, non-rotational motion, linear motion, non-linear motion, accelerated motion, etc.) of the substrate.

One or more signals (such as optical signals) may be detected from a detection area on the substrate prior to, during, or subsequent to, the dispensing of reagents to generate an output. For example, the output may be an intermediate or final result obtained from processing of the analyte. Signals may be detected in multiple instances. The dispensing, rotating (or other motion), and/or detecting operations, in any order (independently or simultaneously), may be repeated any number of times to process an analyte. In some instances, the substrate may be washed (e.g., via dispensing washing reagents) between consecutive dispensing of the reagents. One or more detection operations can be performed within a desired time frame. For example, the detection operation can be performed within about 1 minute, 50 seconds, 40 seconds, 30 seconds, 20 seconds, 10 seconds or less than 10 seconds. In some instances, at least two detection operations can be performed within 1 minute, 50 seconds, 40 seconds, 30 seconds, 20 seconds, 10 seconds or less than 10 seconds etc. In some instances, at least three detection operations can be performed within 1 minute, 50 seconds, 40 seconds, 30 seconds, 20 seconds, 10 seconds or less than 10 seconds.

Provided herein is a method for processing a biological analyte, comprising providing a substrate comprising an array having immobilized thereto the biological analyte, wherein the substrate is rotatable with respect to a central axis. In some instances, the array can be a planar array. In some instances, the array can be an array of wells. In some instances, the substrate can be textured and/or patterned. The method can comprise directing a solution across the substrate and bringing the solution in contact with the biological analyte during rotation of the substrate. The solution may be directed in a radial direction (e.g., outwards) with respect to the substrate to coat the substrate and contact the biological analytes immobilized to the array. In some instances, the solution may comprise a plurality of probes. In some instances, the solution may be a washing solution. The method can comprise subjecting the biological analyte to conditions sufficient to conduct a reaction between at least one probe of the plurality of probes and the biological analyte. The reaction may generate one or more signals from the at least one probe coupled to the biological analyte. The method can comprise detecting one or more signals, thereby analyzing the biological analyte.

In other cases, provided herein is a method for processing a biological analyte, comprising providing a substrate comprising an array having immobilized thereto the biological analyte, wherein the substrate is movable with respect to a reference axis. The method can comprise directing a solution across the substrate and bringing the solution in contact with the biological analyte during motion of the substrate. In some instances, the motion can be linear. In some instances, the motion can be non-linear. In some instances, the motion can be a hybrid between linear and non-linear motion.

In other cases, provided herein is a method for processing a biological analyte, comprising providing a substrate comprising an array having immobilized thereto the biological analyte. In some instances, the method can comprise dispensing a solution to two different locations on the substrate and/or array. In some instances, the method can comprise dispensing multiple solutions to a single location on the substrate and/or array, such as using multiple dispensers. In some instances, the method can comprise dispensing multiple solutions to multiple locations on the substrate and/or array. In some instances, the method can comprise dispensing a single solution to a single location. The substrate may be in relative motion with respect to one or more dispensers. The substrate may be stationary with respect to one or more dispensers. One or more dispensing operations can be performed within a desired time frame. For example, the dispensing operation can be performed within 1 minute, 50 seconds, 40 seconds, 30 seconds, 20 seconds, 10 seconds or less than 10 seconds. In some instances, at least two dispensing operations can be performed within 1 minute, 50 seconds, 40 seconds, 30 seconds, 20 seconds, 10 seconds or less than 10 seconds etc. In some instances, at least three dispensing operations can be performed within 1 minute, 50 seconds, 40 seconds, 30 seconds, 20 seconds, 10 seconds or less than 10 seconds.

Any operation or process of one or more methods disclosed herein may be performed within a desired time frame. In some instances, a combination of two or more operations or processes disclosed herein may be performed within a desired time frame. For example, the dispensing operation and the detection method may both be performed within 1 minute, 50 seconds, 40 seconds, 30 seconds, 20 seconds, 10 seconds or less than 10 seconds. In some instances, at least two dispensing and detection operations can be performed within 1 minute, 50 seconds, 40 seconds, 30 seconds, 20 seconds, 10 seconds or less than 10 seconds etc. In some instances, at least three dispensing and detection operations can be performed within 1 minute, 50 seconds, 40 seconds, 30 seconds, 20 seconds, 10 seconds or less than 10 seconds.

One or more methods disclosed herein may obviate the need for barcoding of analytes (e.g., nucleic acid molecules), which may be time-consuming and expensive. For example, alternative or in addition to barcoding, the substrate and/or array may be spatially indexed to identify the analytes, as described elsewhere herein. One or more methods disclosed herein may obviate the need for unique barcoding of individual analytes (e.g., individual nucleic acid molecules).

The biological analyte may be any analyte that comes from a sample. For instance, the biological analyte may be a macromolecule, e.g., a nucleic acid molecule, a carbohydrate, a protein, a lipid, etc. The biological analyte may comprise multiple macromolecular groups, e.g., glycoproteins, proteoglycans, ribozymes, liposomes, etc. The biological analyte may be an antibody, antibody fragment, or engineered variant thereof, an antigen, a cell, a peptide, a polypeptide, etc. In some cases, the biological analyte comprises a nucleic acid molecule. The nucleic acid molecule may comprise at least about 10, 100, 1000, 10,000, 100,000, 1,000,000, 10,000,000, 100,000,000, 1,000,000,000 or more nucleotides. Alternatively or in addition, the nucleic acid molecule may comprise at most about 1,000,000,000, 100, 000,000, 10,000,000, 1,000,000, 100,000, 10,000, 1000, 100, 10 or fewer nucleotides. The nucleic acid molecule may have a number of nucleotides that is within a range defined by any two of the preceding values. In some cases, the nucleic acid molecule may also comprise a common sequence, to which an N-mer may bind. An N-mer may comprise 1, 2, 3, 4, 5, or 6 nucleotides and may bind the common sequence. In some cases, the nucleic acid molecules may be amplified to produce a colony of nucleic acid molecules attached to the substrate or attached to beads that may associate with or be immobilized to the substrate. In some instances, the nucleic acid molecules may be attached to beads and subjected to a nucleic acid reaction, e.g., amplification, to produce a clonal population of nucleic acid molecules attached to the beads.

Nucleic acid molecules in any given nucleic acid sample may each comprise a key sequence. The key sequence may be a synthetic sequence. In some instances, the key sequence may be at most about 6 bases in length, 5 bases in length, 4 bases in length, 3 bases in length, 2 bases in length, or 1 base in length. Alternatively, the key sequence may be greater than 6 bases in length. The key sequence may be indicative of the originating sample. For example, the key sequence may be unique to a sample such that each sample of a plurality of samples has a unique key sequence. Individual analytes in a single sample may share the same key sequence. Alternatively, each sample may have a unique key sequence between its immediate neighboring samples when loaded onto the substrate. Beneficially, where two samples comprising different key sequences are loaded into adjacent or otherwise proximate regions on the substrate, nucleic acid molecules originating from different samples may be readily differentiated based on the different key sequences even where there is cross-contamination between regions (e.g., outlying nucleic acid molecules that are inadvertently loaded onto a neighboring region due to spillover, etc.) with relatively short reads (e.g., which are much shorter than reads of unique barcode sequences that are configured to differentiate individual molecules).

The substrate may be a solid substrate. The substrate may entirely or partially comprise one or more of rubber, glass, silicon, a metal such as aluminum, copper, titanium, chromium, or steel, a ceramic such as titanium oxide or silicon nitride, a plastic such as polyethylene (PE), low-density polyethylene (LDPE), high-density polyethylene (HDPE), polypropylene (PP), polystyrene (PS), high impact polystyrene (HIPS), polyvinyl chloride (PVC), polyvinylidene chloride (PVDC), acrylonitrile butadiene styrene (ABS), polyacetylene, polyamides, polycarbonates, polyesters, polyurethanes, polyepoxide, polymethyl methacrylate (PMMA), polytetrafluoroethylene (PTFE), phenol formaldehyde (PF), melamine formaldehyde (MF), urea-formaldehyde (UF), polyetheretherketone (PEEK), polyetherimide (PEI), polyimides, polylactic acid (PLA), furans, silicones, polysulfones, any mixture of any of the preceding materials, or any other appropriate material. The substrate may be entirely or partially coated with one or more layers of a metal such as aluminum, copper, silver, or gold, an oxide such as a silicon oxide ($Si_xO_y$, where x, y may take on any possible values), a photoresist such as SUB, a surface coating such as an aminosilane or hydrogel, polyacrylic acid, polyacrylamide dextran, polyethylene glycol (PEG), or any combination of any of the preceding materials, or any other appropriate coating. A substrate may be fully or partially opaque to visible light. In some cases, a substrate may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, at least 99.5%, or 100% opaque to visible light. The substrate may have an opacity that is within a range defined by any two of the preceding values. A substrate may be fully or partially transparent to visible light. In some cases, a substrate may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, at least 99.5%, or 100% transparent to visible light. The substrate may have a transparency that is within a range defined by any two of the preceding values. In some cases, an illumination power (e.g., a laser power) may be adjusted based on the opacity or transparency of the substrate. The one or more layers may have a thickness of at least 1 nanometer (nm), at least 2 nm, at least 5 nm, at least 10 nm, at least 20 nm, at least 50 nm, at least 100 nm, at least 200 nm, at least 500 nm, at least 1 micrometer (µm), at least 2 µm, at least 5 µm, at least 10 µm, at least 20 µm, at least 50 µm, at least 100 µm, at least 200 µm, at least 500 µm, or at least 1 millimeter (mm). The one or more layers may have a thickness that is within a range defined by any two of the preceding values. A surface of the substrate may be modified to comprise any of the binders or linkers described herein. A surface of the substrate may be modified to comprise active chemical groups, such as amines, esters, hydroxyls, epoxides, and the like, or a combination thereof. In some instances, such binders, linkers, active chemical groups, and the like may be added as an additional layer or coating to the substrate.

The substrate may have the general form of a cylinder, a cylindrical shell or disk, a rectangular prism, or any other geometric form. The substrate may have a thickness (e.g., a minimum dimension) of at least 100 µm, at least 200 µm, at least 500 µm, at least 1 mm, at least 2 mm, at least 5 mm, or at least 10 mm. The substrate may have a thickness that is within a range defined by any two of the preceding values. The substrate may have a first lateral dimension (such as a width for a substrate having the general form of a rectangular prism or a radius for a substrate having the general form of a cylinder) of at least 1 mm, at least 2 mm, at least 5 mm, at least 10 mm, at least 20 mm, at least 50 mm, at least 100 mm, at least 200 mm, at least 500 mm, or at least 1,000 mm. The substrate may have a first lateral dimension that is within a range defined by any two of the preceding values. The substrate may have a second lateral dimension (such as a length for a substrate having the general form of a rectangular prism) or at least 1 mm, at least 2 mm, at least 5 mm, at least 10 mm, at least 20 mm, at least 50 mm, at least 100 mm, at least 200 mm, at least 500 mm, or at least 1,000 mm. The substrate may have a second lateral dimension that is within a range defined by any two of the preceding values.

A surface of the substrate may be planar. A surface of the substrate may be uncovered and may be exposed to an atmosphere. Alternatively or in addition, a surface of the substrate may be textured or patterned. For example, the substrate may comprise grooves, troughs, hills, and/or pillars. The substrate may define one or more cavities (e.g., micro-scale cavities or nano-scale cavities). The substrate may define one or more channels. The substrate may have a regular textures and/or patterns across the surface of the substrate. For example, the substrate may have regular geometric structures (e.g., wedges, cuboids, cylinders, spheroids, hemispheres, etc.) above or below a reference level of the surface. Alternatively, the substrate may have irregular textures and/or patterns across the surface of the substrate. For example, the substrate may have any arbitrary structure above or below a reference level of the substrate. In some instances, a texture of the substrate may comprise structures having a maximum dimension of at most about 100%, 90%, 80%, 70%, 60%, 50%, 40%, 30%, 20%, 10%, 9%, 8%, 7%, 6%, 5%, 4%, 3%, 2%, 1%, 0.1%, 0.01%, 0.001%, 0.0001%, 0.00001% of the total thickness of the substrate or a layer of the substrate. In some instances, the textures and/or patterns of the substrate may define at least part of an individually addressable location on the substrate. A textured and/or patterned substrate may be substantially planar.

Figure 37A:
FIG. 37A-FIG. 37G illustrate different examples of cross-sectional surface profiles of a substrate.
Figure 37B:
Figure 37C:
Figure 37D:
Figure 37E:
Figure 37F:
Figure 37G:

For example, FIG. 37A-FIG. 37G illustrate different examples of cross-sectional surface profiles of a substrate. FIG. 37A illustrates a cross-sectional surface profile of a substrate having a completely planar surface. FIG. 37B illustrates a cross-sectional surface profile of a substrate having semi-spherical troughs or grooves. FIG. 37C illustrates a cross-sectional surface profile of a substrate having pillars, or alternatively or in conjunction, wells. FIG. 37D illustrates a cross-sectional surface profile of a substrate having a coating. FIG. 37E illustrates a cross-sectional surface profile of a substrate having spherical particles. FIG. 37F illustrates a cross-sectional surface profile of FIG. 37B, with a first type of binders seeded or associated with the respective grooves. FIG. 37G illustrates a cross-sectional surface profile of FIG. 37B, with a second type of binders seeded or associated with the respective grooves.

The substrate may comprise an array. For instance, the array may be located on a lateral surface of the substrate. The array may be a planar array. The array may have the general shape of a circle, annulus, rectangle, or any other shape. The array may comprise linear and/or non-linear rows. The array may be evenly spaced or distributed. The array may be arbitrarily spaced or distributed. The array may have regular spacing. The array may have irregular spacing. The array may be a textured array. The array may be a patterned array. The array may comprise a plurality of individually addressable locations. The individually addressable locations may be arranged in any convenient pattern. For example, the individually addressable locations may be randomly oriented on the array. The plurality of individually addressable locations may form separate radial regions around a disk-shaped substrate. The plurality of individually addressable locations may form a square, rectangle, disc, circular, annulus, pentagonal, hexagonal, heptagonal, octagonal, array, or any other pattern. One or more types of individually addressable locations may be generated. The one or more types of individually addressable locations may form alternating regions of the different types of individually addressable locations. The one or more types of individually addressable locations may form blocked regions of the different types of individually addressable locations. For example, in cases when two types (A and B) of individually addressable locations are desired, the individually addressable locations may be arrayed as alternating ABABAB, blocked AAABBB, or random, e.g. ABBAAB, AABBBA, BABBAA, etc. The types of individually addressable locations may be arrayed in any useful pattern, such as a square, rectangle, disc, annulus, pentagon, hexagon, radial pattern, etc. In some cases, the two types of individually addressable locations may have different chemical, physical, and/or biological properties (e.g., hydrophobicity, charge, color, topography, size, dimensions, geometry, etc.). For example, a first type of individually addressable location may bind a first type of biological analyte but not a second type of biological analyte, and a second type of individually addressable location may bind the second type of biological analyte but not the first type of biological analyte.

The analyte to be processed may be immobilized to the array. The array may comprise one or more binders described herein, such as one or more physical or chemical linkers or adaptors, that are coupled to a biological analyte. For instance, the array may comprise a linker or adaptor that is coupled to a nucleic acid molecule. Alternatively or in addition, the biological analyte may be coupled to a bead, which bead may be immobilized to the array. In some cases, a subset of the array may not be coupled to a sample or analyte. For example, in substrates that are configured to rotate about a central axis, the samples may not be coupled to a plurality of individually addressable locations of the array located near the central axis. In some cases, the array may be coupled to a sample or an analyte, but not all of the array may be processed. For example, the substrate may be coupled to a sample or analyte (e.g., comprising nucleic acid molecules), but the region of the array that is in proximity to the border of the array may not be subjected to further processing (e.g., detection).

The individually addressable locations may comprise locations of analytes or groups of analytes that are accessible for manipulation. The manipulation may comprise placement, extraction, reagent dispensing, seeding, heating, cooling, or agitation. The extraction may comprise extracting individual analytes or groups of analytes. For instance, the extraction may comprise extracting at least 2, at least 5, at least 10, at least 20, at least 50, at least 100, at least 200, at least 500, or at least 1,000 analytes or groups of analytes. Alternatively or in addition, the extraction may comprise extracting at most 1,000, at most 500, at most 200, at most 100, at most 50, at most 20, at most 10, at most 5, or at most 2 analytes or groups of analytes. The manipulation may be accomplished through, for example, localized microfluidic, pipet, optical, laser, acoustic, magnetic, and/or electromagnetic interactions with the analyte or its surroundings.

In some cases, the individually addressable locations may be indexed, e.g., spatially, such that the analyte immobilized or coupled to each individually addressable location may be identified. In some embodiments, the individually addressable locations are indexed by demarcating part of the substrate. In some embodiments, the surface of the substrate is demarcated using etching. In some embodiments, the surface of the substrate is demarcated using a notch in the surface. In some embodiments, the surface of the substrate is demarcated using a dye or ink. In some embodiments, the surface of the substrate is demarcated by depositing a topographical mark on the surface. In some embodiments, a sample, such as a control nucleic acid sample, may be used to demarcate the surface of the substrate. As will be appreciated, a combination of positive demarcations and negative demarcations (lack thereof) may be used to index the individually addressable locations. In some instances, a single reference point or axis (e.g., single demarcation) may be used to index all individually addressable locations. In some embodiments, each of the individually addressable locations is indexed. In some embodiments, a subset of the individually addressable locations is indexed. In some embodiments, the individually addressable locations are not indexed, and a different region of the substrate is indexed.

Individually addressable locations, or individual regions comprising the individually addressable locations, may be indexed, or otherwise distinguished. In some instances, the individually addressable locations, or individual regions may be distinguished solely by sample loading (e.g., without physical demarcations). In some instances, a single region may be distinguished from other regions. In some instances, a single type of region may be distinguished from other types of regions. For example, different types of regions may comprise different types of analytes or different sets of samples. For example, a first type of region ("A") may comprise a first set of samples (or first type of sample), and a second type of region ("B") may comprise a second set of samples (or second type of sample). The substrate may comprise a set of multiple region A's and a set of multiple region B's, wherein the multiple region A's are distinguishable from the multiple region B's. Different samples may be loaded onto the different types of regions in a predetermined spatial configuration to allow such distinction.

In some cases, a key or barcode sequence on the sample may be used to distinguish and/or index the spatial locations, originating sample, or a combination thereof. For example, nucleic acid molecules in any given nucleic acid sample may each comprise a key sequence. The key sequence may be a synthetic sequence. The key sequence may be at most about 6 bases in length, 5 bases in length, 4 bases in length, 3 bases in length, 2 bases in length, or 1 base in length. Alternatively, the key sequence may be greater than 6 bases in length. The key sequence may be indicative of the originating sample. For example, the key sequence may be unique to a sample such that each sample of a plurality of samples has a unique key sequence. Individual analytes of a single sample may share a common key sequence. Alternatively, each sample may have a unique key sequence between its immediate neighboring samples when loaded onto the substrate. Beneficially, where two samples comprising different key sequences are loaded into adjacent or otherwise proximate regions on the substrate, nucleic acid molecules originating from different samples may be readily differentiated based on the different key sequences even where there is cross-contamination between regions (e.g., outlying nucleic acid molecules that are inadvertently loaded onto a neighboring region due to spillover, etc.) with relatively short reads (e.g., which are much shorter than reads of barcode sequences that are configured to differentiate individual molecules).

Figure 40:
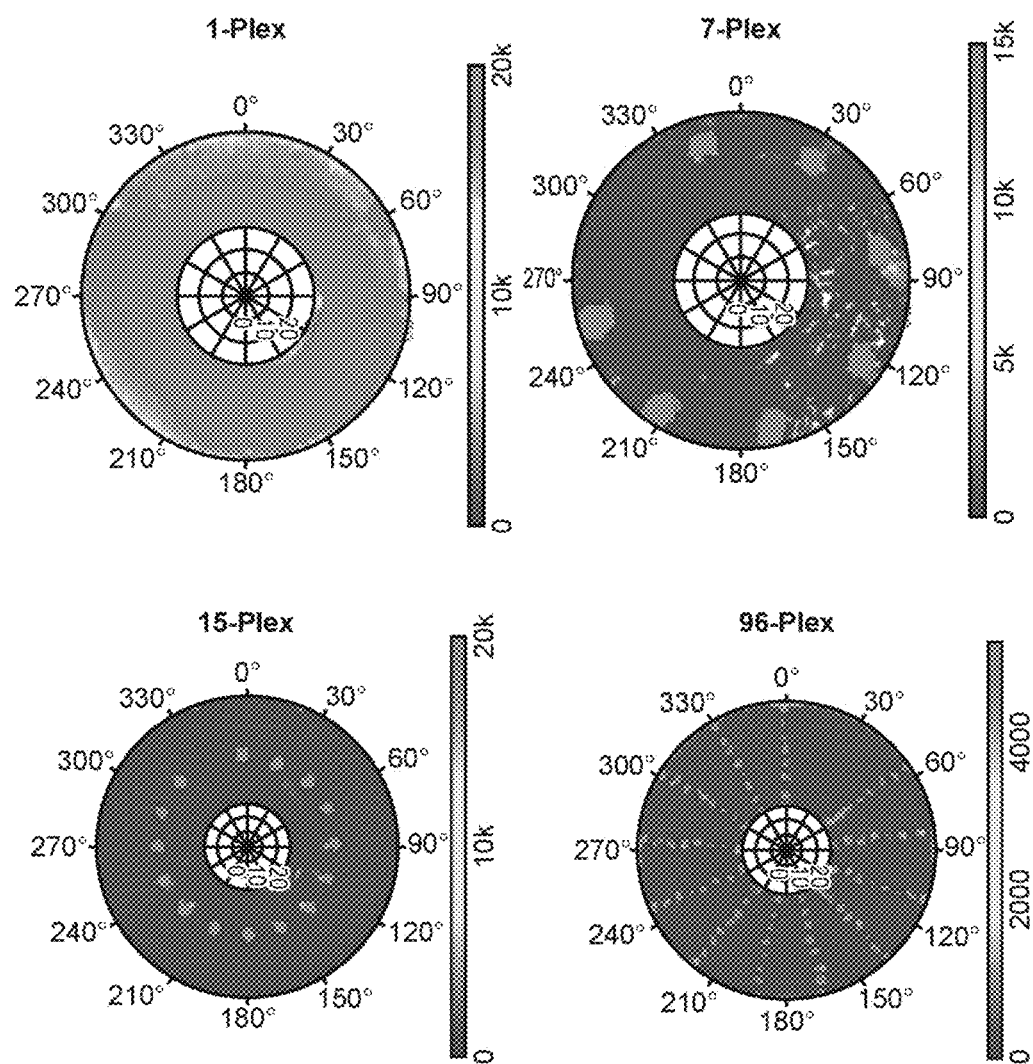
FIG. 40 illustrates multiplex sample processing schemes.

In some cases, spatial separation of analytes may be used to augment or replace the use of key or barcode sequences. For example, FIG. 40 illustrates schemes for analysis of analytes in a single region or in multiple regions, including 7, 15, and 96 regions. For example, as shown in FIG. 40, analytes may be distributed across the entire surface (upper left, "1-plex") distributed in discrete regions, including 7 regions (upper right, "7-plex"), 15 regions (lower left, "15-plex"), or 96 regions (lower right, "96-plex"). Analytes may be distributed in about 5, about 10, about 15, about 20, about 25, about 30, about 35, about 40, about 45, about 50, about 60, about 70, about 80, about 90, about 100, about 200, about 300, about 400, or about 500 regions. Analytes may be distributed in from 5 to 10, from 10 to 15, from 15 to 20, from 20 to 25, from 25 to 30, from 30 to 35, from 35 to 40, from 40 to 45, from 45 to 50, from 50 to 60, from 60 to 70, from 70 to 80, from 80 to 90, from 90 to 100, from 100 to 200, from 200 to 300, from 300 to 400, or from 400 to 500 regions. In some cases, each region may contain a different analyte.

In some cases, different types of regions may be used for sample processing. A first type of region ("A") may comprise a first set of samples (or first type of sample), and a second type of region ("B") may comprise a second set of samples (or second type of sample). The first type of region and the second type of region may be disposed apart from one another in an ordered fashion, as described elsewhere herein. In some cases, the first type of region and the second type of region may be disposed at a distance from a reference axis of the substrate. For example, the first type of region may be disposed at least 1 micrometer, 10 micrometers, 100 micrometers, 1 millimeter, 10 millimeters, 100 millimeters, 1 centimeter, 10 centimeters, 100 centimeters or more from the reference axis of the substrate. Similarly, the second type of region may be disposed at a distance from a reference axis of the substrate. For example, the first type of region may be disposed at least 1 micrometer, 10 micrometers, 100 micrometers, 1 millimeter, 10 millimeters, 100 millimeters, 1 centimeter, 10 centimeters, 100 centimeters or more from the reference axis of the substrate. Both types of regions may be disposed at least 1 micrometer, 10 micrometers, 100 micrometers, 1 millimeter, 10 millimeters, 100 millimeters, 1 centimeter, 10 centimeters, 100 centimeters or more from the reference axis of the substrate.

Figure 39B:
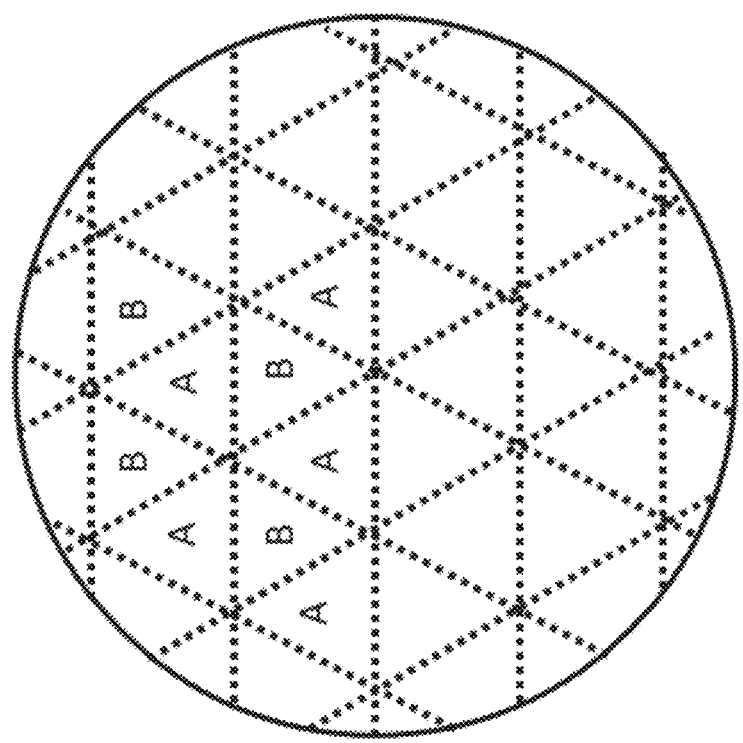
FIG. 39A-FIG. 39B illustrate two examples of spatial loading schemes.
Figure 39A:
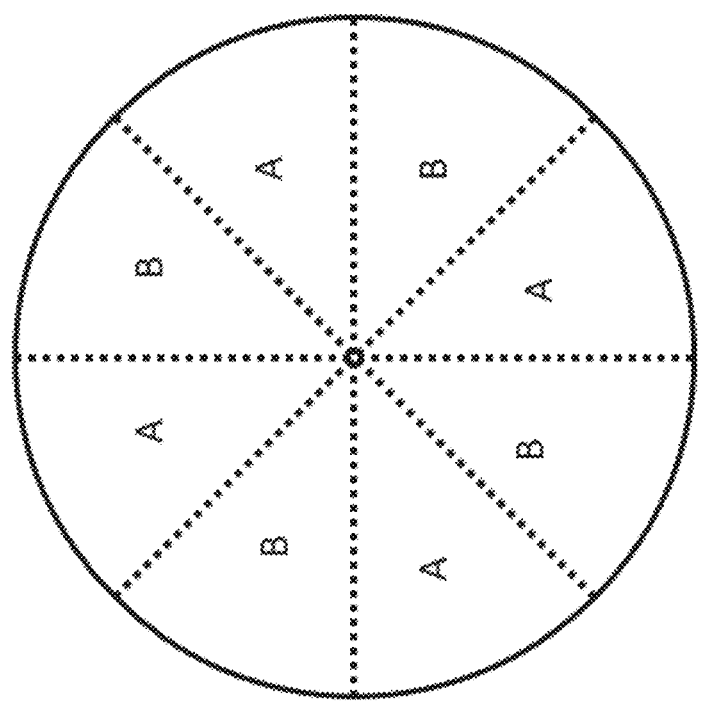

For example, FIG. 39A-FIG. 39B illustrate two examples of spatial loading schemes. In FIG. 39A, a substrate comprises two types of regions "A"s and "B"s which are disposed in radially alternating fashion with respect to a central axis of the substrate. In FIG. 39B, a substrate comprises two types of regions "A"s and "B"s which are disposed in triangularly alternating fashion across the substrate. Sample locations may be determined by loading a first set of samples to the A regions, wherein the first set of samples comprises a plurality of beads coupled to analytes of the first set of samples, and detecting the plurality of beads and/or analytes and their locations on the substrate, and then loading the second set of samples to the B regions, wherein the second set of samples comprises a plurality of beads coupled to analytes of the second set of samples, and detecting the plurality of beads and/or analytes and their locations on the substrate. Each sample in the first set of samples and the second set of samples may be associated with a label (e.g., fluorescent dye). Even though the first set of samples is primarily loaded onto the A regions, there may be some crossovers in which stray beads from the first set of samples are immobilized to the B regions. Even though the second set of samples is primarily loaded onto the B regions, there may be some crossovers in which stray beads from the second set of samples are immobilized to the A regions. The locations of the analytes of the first set of samples, including the cross-over beads, can be determined from the first image. The locations of the analytes of the second set of samples, including the cross-over beads, can be determined from the second image. Beneficially, where the same type of fluorescent dye identifies analytes of two different samples ("P" and "Q"), and "P" is deposited to an A region, and "Q" is deposited to a B region, based on the type of region where the fluorescent signal is detected, one may identify if the analyte is of the "P" sample or the "Q" sample. The different regions may be alternating. The plurality of regions may form any pattern, such as a triangular, square, rectangle, disc, circular, annulus, pentagonal, hexagonal, heptagonal, octagonal, array, or any other pattern. The plurality of regions may form irregular patterns. The plurality of regions may be discrete regions that are not patterned. The plurality of regions may be interleaved, interspersed, non-contiguous, and/or different in size.

While examples herein describe two types of regions, there may be any number of regions (e.g., alternating regions) to achieve the alternating spatial distinction described herein. For example, there may be at 1 at least 1, at least 2, at least 3, at least 4, at least 5, at least 6, at least 7, at least 8, at least 9, or at least 10 regions.

Figure 50A:
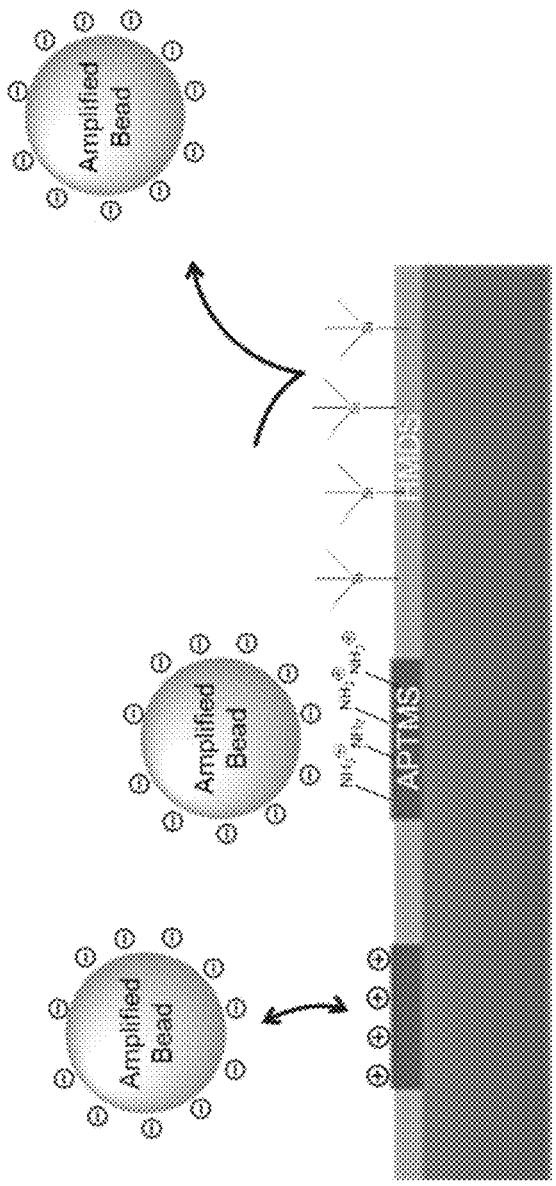
FIG. 50A and FIG. 50B illustrate methods for loading beads onto a substrate.
Figure 50B:
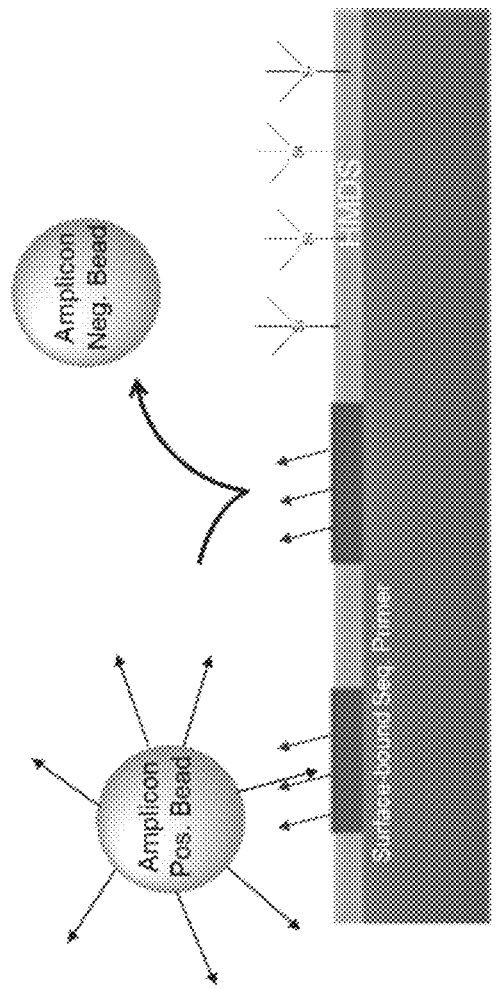

In some cases, an individually addressable location may comprise a distinct surface chemistry. The distinct surface chemistry may distinguish between different addressable locations. The distinct surface chemistry may distinguish between different regions. For example, a first location has a first affinity towards an object (e.g., a bead comprising nucleic acid molecules, e.g., amplicons, immobilized thereto) and a second location has a second, different affinity towards the object due to the distinct surface chemistries. The first location and the second location may or may not be located in the same region. The first location and the second location may or may not be disposed on the surface in alternating fashion. In another example, a first region (e.g., comprising a plurality of individually addressable locations) has a first affinity towards an object and a second region has a second, different affinity towards the object due to the distinct surface chemistries. A first location type or region type may comprise a first surface chemistry, and a second location type or region type may comprise a second surface chemistry. In some cases, a third location type or region type may comprise a third surface chemistry. For example, a first location type or region type may comprise a positively charged surface chemistry and/or a hydrophobic surface chemistry, and a second location type or region type may comprise a negatively charged surface chemistry and/or a hydrophilic surface chemistry, as shown in FIG. 50A. The same object (e.g., a bead comprising nucleic acid molecules, e.g., amplicons, immobilized thereto) may have higher affinity towards a first location type or region type compared to a second location type or region type. The same object may be attracted towards a first location type or region type and repelled from a second location type or region type. In other examples, a first location type or region type comprising a first surface chemistry (e.g., a positively charged surface chemistry or a negatively charged surface chemistry) may interact with (e.g., have an affinity towards) a first sample type (e.g., a bead comprising nucleic acid molecules, e.g., amplicons, immobilized thereto) and exclude a second sample type (e.g., a bead lacking nucleic acid molecules, e.g., amplicons, immobilized thereto, e.g., entirely or in substantial volume), for example as illustrated in FIG. 50B. In some cases, a surface chemistry may comprise an amine. In some cases, a surface chemistry may comprise a silane (e.g., tetramethylsilane). In some cases, the surface chemistry may comprise hexamethyldisilazane (HMDS). In some cases, the surface chemistry may comprise (3-aminopropyl) triethoxysilane (APTMS). In some cases, the surface chemistry may comprise a surface primer molecule or any oligonucleotide molecule that has any degree of affinity towards another molecule.

An individually addressable location of a plurality of locations (e.g., alternating locations) may have an area. In some cases, a location may have an area of about 0.1 square micron ($\mu m^2$), about 0.2 $\mu m^2$, about 0.25 $\mu m^2$, about 0.3 $\mu m^2$, about 0.4 $\mu m^2$, about 0.5 $\mu m^2$, about 0.6 $\mu m^2$, about 0.7 $\mu m^2$, about 0.8 $\mu m^2$, about 0.9 $\mu m^2$, about 1 $\mu m^2$, about 1.1 $\mu m^2$, about 1.2 $\mu m^2$, about 1.25 $\mu m^2$, about 1.3 $\mu m^2$, about 1.4 $\mu m^2$, about 1.5 $\mu m^2$, about 1.6 $\mu m^2$, about 1.7 $\mu m^2$, about 1.75 $\mu m^2$, about 1.8 $\mu m^2$, about 1.9 $\mu m^2$, about 2 $\mu m^2$, about 2.25 $\mu m^2$, about 2.5 $\mu m^2$, about 2.75 $\mu m^2$, about 3 $\mu m^2$, about 3.25 $\mu m^2$, about 3.5 $\mu m^2$, about 3.75 $\mu m^2$, about 4 $\mu m^2$, about 4.25 $\mu m^2$, about 4.5 $\mu m^2$, about 4.75 $\mu m^2$, about 5 $\mu m^2$, about 5.5 $\mu m^2$, or about 6 $\mu m^2$. A location may have an area that is within a range defined by any two of the preceding values. A location may have an area that is less than about 0.1 $\mu m^2$ or greater than about 6 $\mu m^2$. In some cases, a location may have a width of about 0.1 micron ($\mu m$), about 0.2 $\mu m$, about 0.25 $\mu m$, about 0.3 $\mu m$, about 0.4 $\mu m$, about 0.5 $\mu m$, about 0.6 $\mu m$, about 0.7 $\mu m$, about 0.8 $\mu m$, about 0.9 $\mu m$, about 1 $\mu m$, about 1.1 $\mu m$, about 1.2 $\mu m$, about 1.25 $\mu m$, about 1.3 $\mu m$, about 1.4 $\mu m$, about 1.5 $\mu m$, about 1.6 $\mu m$, about 1.7 $\mu m$, about 1.75 $\mu m$, about 1.8 $\mu m$, about 1.9 $\mu m$, about 2 $\mu m$, about 2.25 $\mu m$, about 2.5 $\mu m$, about 2.75 $\mu m$, about 3 $\mu m$, about 3.25 $\mu m$, about 3.5 $\mu m$, about 3.75 $\mu m$, about 4 $\mu m$, about 4.25 $\mu m$, about 4.5 $\mu m$, about 4.75 $\mu m$, about 5 $\mu m$, about 5.5 $\mu m$, or about 6 $\mu m$. In some cases, a location may have a width that is within a range defined by any two of the preceding values. A location may have a width that is less than about 0.1 $\mu m$ or greater than about 6 $\mu m$. Locations (e.g., of a same type) may be distributed on a substrate with a pitch determined by the distance between the center of a first location and the center of the closest or neighboring location (e.g., of the same type). Locations may be spaced with a pitch of about 0.1 micron ($\mu m$), about 0.2 $\mu m$, about 0.25 $\mu m$, about 0.3 $\mu m$, about 0.4 $\mu m$, about 0.5 $\mu m$, about 0.6 $\mu m$, about 0.7 $\mu m$, about 0.8 $\mu m$, about 0.9 $\mu m$, about 1 $\mu m$, about 1.1 $\mu m$, about 1.2 $\mu m$, about 1.25 $\mu m$, about 1.3 $\mu m$, about 1.4 $\mu m$, about 1.5 $\mu m$, about 1.6 $\mu m$, about 1.7 $\mu m$, about 1.75 $\mu m$, about 1.8 $\mu m$, about 1.9 $\mu m$, about 2 $\mu m$, about 2.25 $\mu m$, about 2.5 $\mu m$, about 2.75 $\mu m$, about 3 $\mu m$, about 3.25 $\mu m$, about 3.5 $\mu m$, about 3.75 $\mu m$, about 4 $\mu m$, about 4.25 $\mu m$, about 4.5 $\mu m$, about 4.75 $\mu m$, about 5 $\mu m$, about 5.5 $\mu m$, about 6 $\mu m$, about 6.5 $\mu m$, about 7 $\mu m$, about 7.5 $\mu m$, about 8 $\mu m$, about 8.5 $\mu m$, about 9 $\mu m$, about 9.5 $\mu m$, or about 10 $\mu m$. In some case the locations may be positioned with a pitch that is within a range defined by any two of the preceding values. The locations may be positioned with a pitch of less than about 0.1 $\mu m$ or greater than about 10 $\mu m$. In some cases, the pitch between any two locations of the same type may be determined as a function of a size of a loading object (e.g., bead). For example, where the loading object is a bead having a maximum diameter, the pitch may be at least about the maximum diameter of the loading object.

While examples herein generally describe the loading of two samples or two sets of samples, any number of samples, or sets of samples, may be immobilized to the substrate. For example, the substrate may have immobilized thereto at least 1, at least 2, at least 3, at least 4, at least 5, at least 6, at least 7, at least 8, at least 9, at least 10 samples, or sets of samples. In some cases, at least about 10, 100, 1000, 10,000, 100,000, 1,000,000, 10,000,000, 100,000,000, 1,000,000,000 or more samples, or sets of samples, may be immobilized. Alternatively or in addition, the substrate may comprise at most about 1,000,000,000, 100,000,000, 10,000,000, 1,000,000, 100,000, 10,000, 1000, 100, 10 or fewer samples, or sets of samples. When the sample is a nucleic acid sample, at least 1, at least 2, at least 3, at least 4, at least 5, at least 6, at least 7, at least 8, at least 9, at least 10 nucleic acid samples may be immobilized to the substrate. In some cases, at least about 10, 100, 1000, 10,000, 100,000, 1,000,000, 10,000,000, 100,000,000, 1,000,000,000 or more nucleic acid samples may be immobilized. Alternatively or in addition, the substrate may comprise at most about 1,000,000,000, 100,000,000, 10,000,000, 1,000,000, 100,000, 10,000, 1000, 100, 10 or fewer nucleic acid samples. Beneficially, multiple samples may be simultaneously processed on the same substrate, without needing to otherwise barcode the multiple samples (e.g., with a common barcode sequence per sample) to distinguish them.

Indexing may be performed using a detection method and may be performed at any convenient or useful step. A substrate that is indexed, e.g., demarcated, may be subjected to detection, such as optical imaging, to locate the indexed locations, individually addressable locations, and/or the biological analyte. Imaging may be performed using a detection unit. Imaging may be performed using one or more sensors. Imaging may not be performed using the naked eye. The substrate that is indexed may be imaged prior to loading of the biological analyte. Following loading of the biological analyte onto the individually addressable locations, the substrate may be imaged again, e.g. to determine occupancy or to determine the positioning of the biological analyte relative to the substrate. In some cases, the substrate may be imaged after iterative cycles of nucleotide addition (or other probe or other reagent), as described elsewhere herein. The indexing of the substrate and known initial position (individually addressable location) of the biological analyte may allow for analysis and identification of the sequence information for each individually addressable location and/or position. Additionally, spatial indexing may allow for identification of errors that may occur, e.g., sample contamination, sample loss, etc.

In some cases, indexing may be performed to identify, process, and/or analyze more than one type of biological analyte, as described above. For example, a first type of biological analyte, which may be labeled, may be loaded onto a first set of locations within a substrate. The substrate may be imaged for a first indexing step of the first type of biological analyte. A second type of biological analyte may be loaded onto a second set of locations within the substrate and imaged for a second indexing step of the second type of biological analyte. In some cases, the second type of biological analyte may be labeled in a way such that the second type of biological analyte is distinguishable from the first type of biological analyte. Alternatively, the first type of biological analyte and the second type of biological analyte may be labeled in substantially the same detectable manner (e.g., same dye), and the first and second images may be processed to generate a differential image, wherein overlapping signals are attributed to the locations of the first type of biological analyte and different signals are attributed to the locations of the second type of biological analyte. Alternatively, the first type of biological analyte and the second type of biological analyte may be labeled by cleavable (or otherwise removable) labels or tags (e.g., fluorescent tags), and the label cleaved after each imaging operation, such that only the relevant analyte locations are imaged at each imaging operation. Henceforth, the substrate may be analyzed and all of the locations comprising the first biological analyte may be attributed to the first biological analyte, and all of the locations comprising the second biological analyte may be attributed to the second analyte. In some cases, labeling of the first and second analyte may not be necessary, and the attribution of the location to either the first or second analyte may be performed based on spatial location alone. This process may be repeated for any number or types of biological analytes.

The array may be coated with binders. For instance, the array may be randomly coated with binders. Alternatively, the array may be coated with binders arranged in a regular pattern (e.g., in linear arrays, radial arrays, hexagonal arrays etc.). The array may be coated with binders on at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% of the number of individually addressable locations, or of the surface area of the substrate. The array may be coated with binders on a fraction of individually addressable locations, or of the surface areas of the substrate, that is within a range defined by any two of the preceding values. The binders may be integral to the array. The binders may be added to the array. For instance, the binders may be added to the array as one or more coating layers on the array.

The binders may immobilize biological analytes through non-specific interactions, such as one or more of hydrophilic interactions, hydrophobic interactions, electrostatic interactions, physical interactions (for instance, adhesion to pillars or settling within wells), and the like. The binders may immobilize biological analytes through specific interactions. For instance, where the biological analyte is a nucleic acid molecule, the binders may comprise oligonucleotide adaptors configured to bind to the nucleic acid molecule. Alternatively or in addition, such as to bind other types of analytes, the binders may comprise one or more of antibodies, oligonucleotides, nucleic acid molecules, aptamers, affinity binding proteins, lipids, carbohydrates, and the like. The binders may immobilize biological analytes through any possible combination of interactions. For instance, the binders may immobilize nucleic acid molecules through a combination of physical and chemical interactions, through a combination of protein and nucleic acid interactions, etc. The array may comprise at least about 10, 100, 1000, 10,000, 100,000, 1,000,000, 10,000,000, 100,000,000 or more binders. Alternatively or in addition, the array may comprise at most about 100,000,000, 10,000,000, 1,000,000, 100,000, 10,000, 1000, 100, 10 or fewer binders. The array may have a number of binders that is within a range defined by any two of the preceding values. In some instances, a single binder may bind a single biological analyte (e.g., nucleic acid molecule). In some instances, a single binder may bind a plurality of biological analytes (e.g., plurality of nucleic acid molecules). In some instances, a plurality of binders may bind a single biological analyte. Though examples herein describe interactions of binders with nucleic acid molecules, the binders may immobilize other molecules (such as proteins), other particles, cells, viruses, other organisms, or the like.

In some instances, each location, or a subset of such locations, may have immobilized thereto an analyte (e.g., a nucleic acid molecule, a protein molecule, a carbohydrate molecule, etc.). In other instances, a fraction of the plurality of individually addressable location may have immobilized thereto an analyte. A plurality of analytes immobilized to the substrate may be copies of a template analyte. For example, the plurality of analytes (e.g., nucleic acid molecules) may have sequence homology. In other instances, the plurality of analytes immobilized to the substrate may not be copies. The plurality of analytes may be of the same type of analyte (e.g., a nucleic acid molecule) or may be a combination of different types of analytes (e.g., nucleic acid molecules, protein molecules, etc.).

In some instances, the array may comprise a plurality of types of binders. For example, the array may comprise different types of binders to bind different types of analytes. For example, the array may comprise a first type of binders (e.g., oligonucleotides) configured to bind a first type of analyte (e.g., nucleic acid molecules), and a second type of binders (e.g., antibodies) configured to bind a second type of analyte (e.g., proteins), and the like. In another example, the array may comprise a first type of binders (e.g., first type of oligonucleotide molecules) to bind a first type of nucleic acid molecules and a second type of binders (e.g., second type of oligonucleotide molecules) to bind a second type of nucleic acid molecules, and the like. For example, the substrate may be configured to bind different types of analytes in certain fractions or specific locations on the substrate by having the different types of binders in the certain fractions or specific locations on the substrate.

A biological analyte may be immobilized to the array at a given individually addressable location of the plurality of individually addressable locations. An array may have any number of individually addressable locations. For instance, the array may have at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000, at least 2,000,000,000, at least 5,000,000,000, at least 10,000,000,000, at least 20,000,000,000, at least 50,000,000,000, or at least 100,000,000,000 individually addressable locations. The array may have a number of individually addressable locations that is within a range defined by any two of the preceding values. Each individually addressable location may be digitally and/or physically accessible individually (from the plurality of individually addressable locations). For example, each individually addressable location may be located, identified, and/or accessed electronically or digitally for mapping, sensing, associating with a device (e.g., detector, processor, dispenser, etc.), or otherwise processing. As described elsewhere herein, each individually addressable location may be indexed. Alternatively, the substrate may be indexed such that each individually addressable location may be identified during at least one step of the process. Alternatively or in addition, each individually addressable location may be located, identified, and/or accessed physically, such as for physical manipulation or extraction of an analyte, reagent, particle, or other component located at an individually addressable location.

Multiple biological analytes may be immobilized to the array at spatially discrete locations. Spatial separation of biological analytes may be obtained using masks or barriers, as described elsewhere herein. Alternatively or in conjunction, biological analytes may be separated using different fluid compositions. In some cases, the fluid compositions may be immiscible. For example, a first solution (e.g., an oil, organic solution, or other hydrophobic or oleophilic solution) may comprise a first biological analyte, and a second solution (e.g., a hydrophilic, aqueous, polar or ionic solution) may comprise a second biological analyte. The first and second solutions may be immiscible. The substrate may be exposed to the first solution in defined regions, e.g., using a mask (e.g., covering or shielding the other regions of the substrate). In some cases, the first biological analyte associates with defined regions (e.g., individually addressable locations), and the first solution may be removed from the substrate. The substrate may then be exposed to the second solution. The second biological analyte may then associate with the unoccupied sites of the substrate. Alternatively, the substrate may be pre-treated such that biological analytes may be loaded in discrete locations. In one non-limiting example, the substrate may be patterned with discrete hydrophobic and hydrophilic regions (e.g., using photolithography, soft lithography, etching, etc.) that can attract or repel a subset of the biological analytes. In another non-limiting example, an inert polymer such as polyethylene glycol (PEG) may be patterned in discrete regions to prevent attachment or the biological analyte to the substrate in the discrete regions.

Each individually addressable location may have the general shape or form of a circle, pit, bump, rectangle, or any other shape or form. Each individually addressable location may have a first lateral dimension (such as a radius for individually addressable locations having the general shape of a circle or a width for individually addressable locations having the general shape of a rectangle). The first lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The first lateral dimension may be within a range defined by any two of the preceding values. Each individually addressable location may have a second lateral dimension (such as a length for individually addressable locations having the general shape of a rectangle). The second lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The second lateral dimension may be within a range defined by any two of the preceding values. In some instances, each individually addressable locations may have or be coupled to a binder, as described herein, to immobilize an analyte thereto. In some instances, only a fraction of the individually addressable locations may have or be coupled to a binder. In some instances, an individually addressable location may have or be coupled to a plurality of binders to immobilize an analyte thereto.

The individually addressable locations may be generated using a variety of methods. In one embodiment, the method may comprise generation of individually addressable locations using one or more barriers. In some embodiments, the barrier may be removed during any convenient operation. For example, the barrier may be removed prior to or after coupling the analyte to the individually addressable locations. The barrier may be removed prior to or after loading of the solution comprising a plurality of probes. The barrier may be removed prior to or after subjecting the analyte to conditions sufficient to conduct a reaction between the probe and the analyte. The barrier may be removed prior to or after detection of one or more signals from the coupled probe and analyte. The barrier may be removed prior to or after detection of the coupled probe and analyte. The barrier may be removed prior to or after repeating any of the abovementioned processes. In some cases, the barriers may not be removed.

The barrier may comprise a physical, chemical, biological, or any other type of obstruction. In some embodiments, the barrier comprises a physical obstruction. In one such example, a mold may be used, wherein a portion of the mold may obstruct the movement of fluid to a specified region. The mold may be generated using a variety of means, such as injection molding, machining, heat treatment, fiber spinning, joining and bonding, casting, rolling, forging, 3D printing, etc. In some embodiments, the barrier may be configured to dissolve at any convenient step. The barrier may be configured to dissolve, evaporate, or sublime. In some cases, the barrier may be melted and removed. In some cases, removal of the barrier or part of the barrier may be achieved using an air knife. In some cases, the barrier comprises a chemical obstruction. In some cases, the barrier comprises a polymer. The barrier may comprise polyethylene glycol (PEG). In some cases, the barrier may comprise a solution. The solution may be viscous. The solution may have a temperature-variable viscosity. The solution may be a non-Newtonian fluid. The solution may be a power law fluid, such as a shear-thinning (e.g., thixotropic) or shear-thickening fluid. The solution may be a Newtonian fluid. In some embodiments, the barrier comprises a fluid that is immiscible with a loading solution. In some cases, the barrier is a hydrophobic region on the substrate.

A mask may be additionally or alternatively used to prevent coupling of the sample and/or biological analyte with a region of the substrate. Alternatively or in conjunction, a subset of the individually addressable locations comprising the biological analyte may be masked, e.g., to prevent coupling of the probe to the biological analyte. A mask may comprise a barrier, such as a physical, chemical or biological barrier. A mask may comprise a film with removed sections. In some cases, the mask may be interfaced with the substrate prior to introduction of the biological analyte. In such cases, introduction of the biological analyte may allow for coupling of the biological analyte to exposed regions of the mask-substrate interface, whereas the non-exposed regions may remain free of the biological analyte. At any convenient process, the substrate may be un-masked. Any combinations of masks may be used. For example, a first mask may be used to load a first biological analyte to a desired region. Subsequently, the first mask may be removed, and a second mask may be used to load a second biological analyte to a desired region. The first and second region may have overlapping regions or may remain spatially distinct. A barrier and mask may be used in conjunction or separately.

The analytes bound to the individually addressable locations may include, but are not limited to, molecules, cells, organisms, nucleic acid molecules, nucleic acid colonies, beads, clusters, polonies, DNA nanoballs, or any combination thereof (e.g., bead having attached thereto one or more nucleic acid molecules, e.g., one or more clonal populations of nucleic acid molecules). The bound analytes may be immobilized to the array in a regular, patterned, periodic, random, or pseudo-random configuration, or any other spatial arrangement. In some embodiments, the analytes are bound to bead(s) which may then associate with or be immobilized to the substrate or regions of the substrate (e.g., individually addressable locations). In some embodiments, the analytes comprise a bead or a plurality of beads. In some cases, the bead or plurality of beads may comprise another analyte (e.g., nucleic acid molecule) or a clonal population of other analytes (e.g., a nucleic acid molecule that has been amplified on the bead). Such other analytes may be attached or otherwise coupled to the bead. For example, an analyte may comprise a plurality of beads, each bead having a clonal population of nucleic acid molecules attached thereto. In some cases, the bead is magnetic, and application of a magnetic field or using a magnet may be used to direct the analytes or beads comprising the analytes to the individually addressable locations. In some cases, a fluid may be used to direct the analyte to the individually addressable locations. The fluid may be a ferrofluid, and a magnet may be used to direct the fluid to the individually addressable locations. The individually addressable locations may alternatively or in conjunction comprise a material that is sensitive to a stimulus, e.g., thermal, chemical, or electrical or magnetic stimulus. For example, the individually addressable location may comprise a photo-sensitive polymer or reagent that is activated when exposed to electromagnetic radiation. In some cases, a caged molecule may be used to reveal binding (e.g., biotin) moieties on the substrate. Subsequent exposure to a particular wavelength of light may result in un-caging of the binding moieties. A bead, e.g., with streptavidin, comprising the analyte may then associate with the uncaged binding moieties. In some cases, a subset of the individually addressable locations may not contain beads. In such cases, blank beads may be added to the substrate. The blank beads may then occupy the regions that are unoccupied by an analyte. In some cases, the blank beads have a higher binding affinity or avidity for the individually addressable locations than the beads comprising the analyte. In some cases, unoccupied locations may be destroyed. In some cases, unoccupied locations may be subjected to a process to remove any unbound analyte, e.g., aspiration, washing, air blasting etc. In some cases, the sample comprising the biological analyte may be loaded onto the substrate using a device, e.g., a microfluidic device, closed flow cell, etc. The loaded biological analyte may then associate with or be immobilized to the substrate or the individually addressable locations of the substrate. In such cases, the device may be removed following loading of the sample.

A biological analyte may be bound to any number of beads. Different biological analytes may be bound to any number of beads. The beads may be unique (i.e., distinct from each other). Any number of unique beads may be used. For instance, at least about 10, 100, 1000, 10,000, 100,000, 1,000,000, 10,000,000, 100,000,000 or more different beads may be used. Alternatively or in addition, at most about 100,000,000, 10,000,000, 1,000,000, 100,000, 10,000, 1000, 100, 10 or fewer different beads may be used. A number of different beads can be within a range defined by any two of the preceding values. The beads may be distinguishable from one another using a property of the beads, such as color, reflectance, anisotropy, brightness, fluorescence, etc.

A sample may be diluted such that the approximate occupancy of the individually addressable locations is controlled. A sample may be diluted at least to a dilution of 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:10000, 1:100000, 1:1000000, 1:10000000, 1:100000000. Alternatively, a sample may be diluted at most to a dilution of A sample may be diluted at least to a dilution of 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:10000, 1:100000, 1:1000000, 1:10000000, 1:100000000. A dilution between any of these dilution values may also be used.

Figure 49:
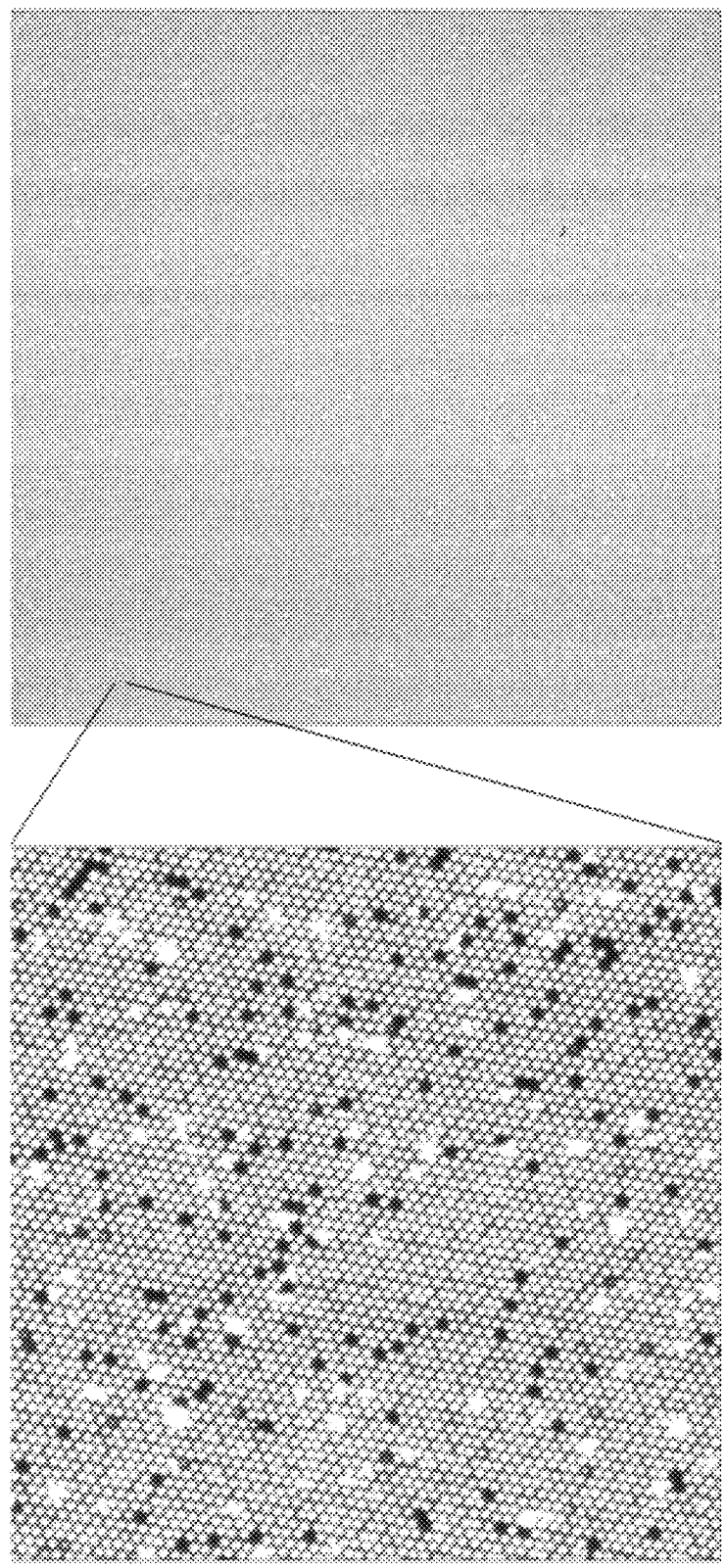
FIG. 49 shows an exemplary coating of a substrate with a hexagonal lattice of beads.

In some instances, a sample may comprise beads. Beads may be dispersed on a surface in any pattern, or randomly. Beads may be dispersed on one or more regions (e.g., a region having a particular surface chemistry) of a surface. In some cases, beads may be dispersed on a surface or a region of a surface in a hexagonal lattice, as shown in FIG. 49, which illustrates in the right panel a zoomed out image of a portion of a surface, and in the left panel a zoomed in image of a section of the portion of the surface. In some instances, a sample comprising beads may be dispersed on a surface comprising distinct locations/regions differentiated by surface chemistry (e.g., as illustrated in FIG. 50A and FIG. 50B). For example, a sample comprising beads may be dispersed on a surface comprising positively charged locations/regions and/or hydrophobic locations/regions. The beads may have a high affinity for a first location type or region type (e.g., positively charged). The beads may have a low affinity for a second location type or region type (e.g., hydrophobic). A location may comprise no more than 1, no more than 2, no more than 3, no more than 4, no more than 5, no more than 6, no more than 7, no more than 8, no more than 9, or no more than 10 beads per location. In some embodiments, a bead may be substantially centered within an individually addressable location. A location may have a width that is up to about 0.5 times, up to about 0.6 times, up to about 0.7 times, up to about 0.8 times, up to about 0.9 times, up to about 1 times, up to about 1.1 times, up to about 1.2 times, up to about 1.3 times, up to about 1.4 times, up to about 1.5 times, up to about 1.6 times, up to about 1.7 times, up to about 1.8 times, up to about 1.9 times, up to about 2 times, up to about 2.1 times, up to about 2.2 times, up to about 2.3 times, up to about 2.4 times, up to about 2.5 times, up to about 2.6 times, up to about 2.7 times, up to about 2.8 times, up to about 2.9 times, or up to about 3 times the diameter (e.g., maximum diameter) of the bead. In some embodiments, a region may be spaced with a pitch determined by the distance between the center of a first location and the center of the closest or neighboring location of the same type. A location may be spaced with a pitch that is at least about 1 times, at least about 1.2 times, at least about 1.4 times, at least about 1.6 times, at least about 1.8 times, at least about 2 times, at least about 2.2 times, at least about 2.4 times, at least about 2.6 times, at least about 2.8 times, at least about 3 times, at least about 3.2 times, at least about 3.4 times, at least about 3.6 times, at least about 3.8 times, at least about 4 times, at least about 4.2 times, at least about 4.4 times, at least about 4.6 times, at least about 4.8 times, or at least about 5 times the diameter (e.g., maximum diameter) of the bead. In some cases, one or more of a location size, a location spacing, a bead affinity, a location surface chemistry may be adjusted to reduce a deviation of a bead contact point from the center of a region.

A surface comprising a plurality of individually addressable locations may be loaded with beads. The beads may be loaded onto the surface at an occupancy determined by the number of locations of a given location type comprising at least one bead out of the total number of locations of the same location type. A surface comprising a plurality of locations may have occupancy of at least about 50%, at least about 60%, at least about 70%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99.5%, or up to about 100%. For example, a surface may have at least about 90% of the locations of a given location type loaded with at least one bead. Beads may land on the surface with a landing efficiency determined by the number of beads that bind to the surface out of the total number of beads dispensed on the surface. Beads may be dispensed onto a surface with a landing efficiency of at least about 10%, at least about 20%, at least about 30%, at least about 40%, at least about 50%, at least about 55%, at least about 60%, at least about 65%, at least about 70%, at least about 75%, at least about 80%, at least about 90%, up to about 100%. In some embodiments, one or more of a temperature, an incubation time, a surfactant, or a salt concentration of a solution comprising beads may be adjusted to increase bead occupancy. In some embodiments, one or more of a temperature, an incubation time, a surfactant, or a salt concentration of a solution comprising beads may be adjusted to increase bead loading efficiency.

In some cases, at least about 5%, 10%, 15%, 20%, 25%, 30%, 35%, 40%, 45%, 50%, 55%, 60%, 65%, 70%, 75%, 80%, 85%, 90%, or 95% of the available surface area of a substrate may be configured to accept a bead. Where less than 100% of the available surface area loads thereon a bead (e.g., have a bead immobilized thereto), the negative space (e.g., locations in which there is no bead) may be used as a reference to identify and/or index different individually addressable locations of the positive space (e.g., locations in which there is a bead). In an example, a single individually addressable location acting in negative space is sufficient to index the entire substrate. In such an example, the single individually addressable location will always remain 'dark' during imaging, such as during sequencing, as opposed to other individually addressable location in the positive space which will light up (e.g., fluoresce) at different points in time, such that the single individually addressable location which is always 'dark' may act as a reference against all other individually addressable locations. In other examples, multiple individually addressable locations acting in negative space may facilitate indexing of the substrate. Alternatively or in addition, a reference bead which is always 'bright' (e.g., always fluorescing regardless of time point) may be used as a reference to identify and/or index different individually addressable locations of the positive space. In such cases, even with 100% or substantially 100% of the available surface area loaded with beads, including the reference bead, the different individually addressable locations may be identified and/or indexed.

Figure 48:
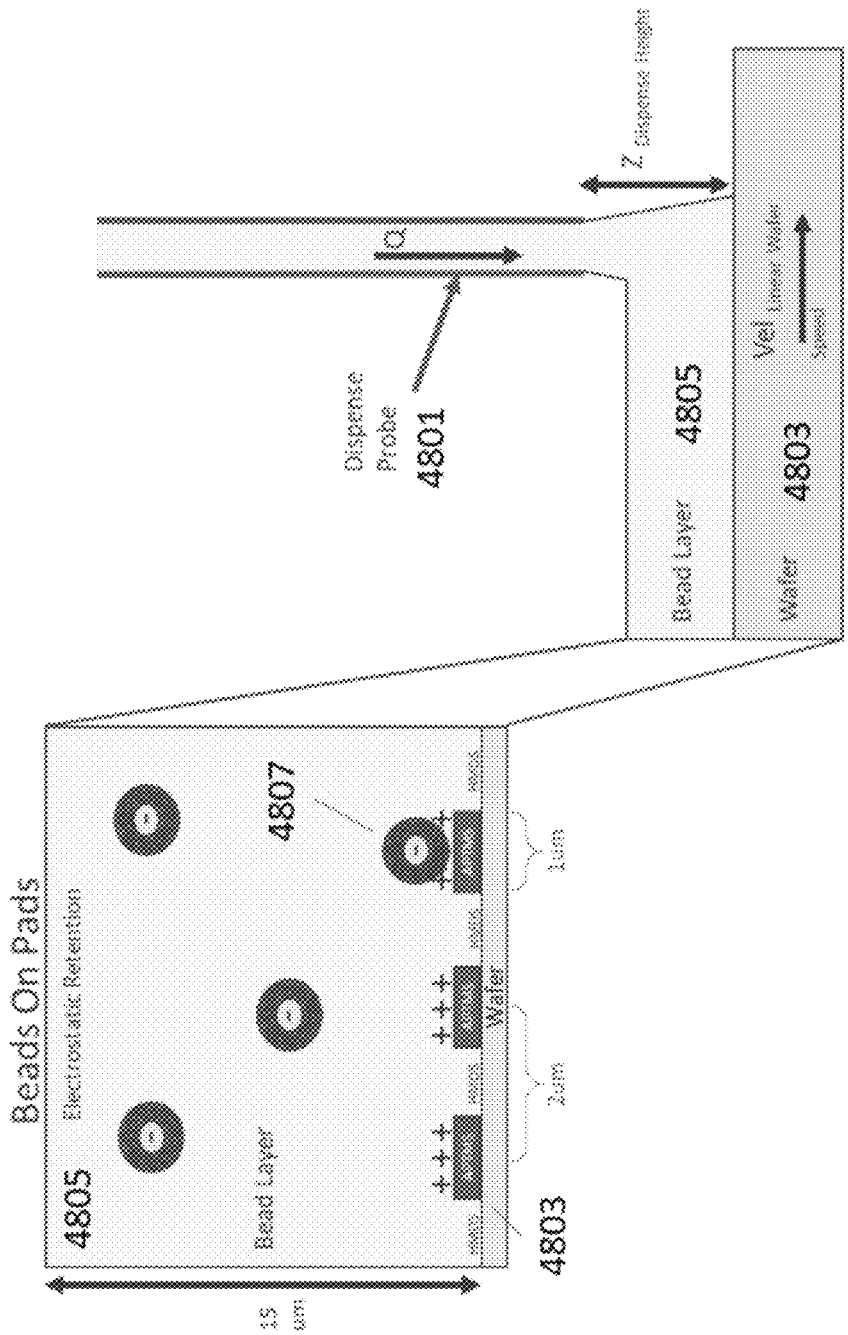
FIG. 48 shows a system and method for spiral loading a sample or a reagent onto a substrate.

A sample comprising beads may be dispensed on the surface. In some cases, the beads may be dispensed on the surface in a substantially spiral pattern. For example, the beads may be dispensed in a spiral pattern using the system shown in FIG. 48 and/or the method shown in FIG. 51. In some instances, the beads may be dispersed in a spiral pattern moving radially inward toward an axis of rotation of the surface. In some instances, the beads may be dispersed in a spiral pattern moving radially outward from an axis of rotation of the surface. As shown in FIG. 48, a sample (e.g., a sample comprising beads) may be dispensed from a dispense probe 4801 (e.g., a nozzle) to a substrate 4803 (e.g., a wafer) to form a layer 4805. The dispense probe may be positioned at a fixed height ("Z") above the substrate. In the illustrated example, the beads are retained in the layer 4805 by electrostatic retention, and may immobilize to the substrate. A set of beads may each comprise a population of amplified products (e.g., nucleic acid molecules) immobilized thereto, which amplified products accumulate to a negative charge on the bead with affinity to a positive charge. The substrate comprises alternating surface chemistry between distinguishable locations, in which a first location type comprises APTMS carrying a positive charge with affinity towards the negative charge of the amplified bead (e.g., a bead comprising amplified products immobilized thereto, and as distinguished from a negative bead which does not the comprise the same), and a second location type comprises HMDS which has lower affinity and/or is repellant of the amplified bead. Within the layer 4805 comprising the dispensed sample, an amplified bead may successfully land on a first location of the first location type (as in 4807). In the illustrated example, the location size is 1 micron, the pitch between the different locations of the same location type (e.g., first location type) is 2 microns, and the layer has a depth of 15 micron. In order to obtain a substantially spiral pattern, the substrate and/or the dispense probe may have angular and/or linear velocity with respect to each other.

Figure 51:
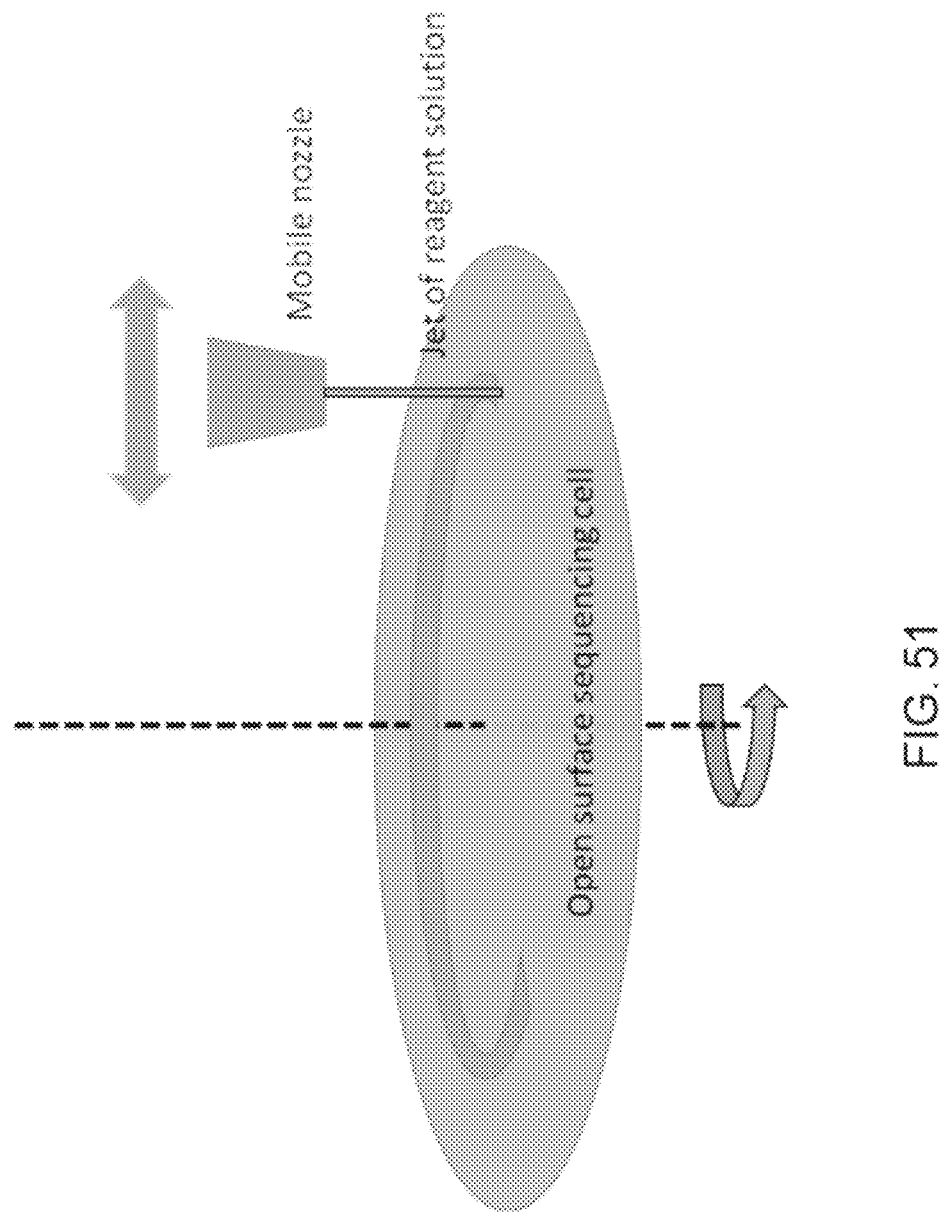
FIG. 51 illustrates a method for spiral loading a sample or a reagent onto an open substrate.

The sample may be dispensed as shown onto an open surface as illustrated in FIG. 51. In some cases, the substrate may be rotating relative to the dispensing probe. In some cases, the dispensing probe may be moving radially relative to the substrate with respect to the axis of rotation of the substrate. In some cases, the substrate may be moving linearly relative to the dispense probe. In some cases, the substrate may be rotating relative to the dispense probe while moving linearly relative to the dispense probe, thereby dispensing the sample in a spiral pattern. In some cases, the substrate may be rotating relative to the dispense probe while the dispense probe is moving radially relative to the substrate with respect to the axis of rotation of the substrate, thereby dispensing the sample in a spiral pattern. The substrate and the dispense probe may move in any configuration with respect to each other to achieve the substantially spiral pattern. The substrate may be rotating with a rotational frequency of no more than 60 rpm, no more than 50 rpm, no more than 40 rpm, no more than 30 rpm, no more than 25 rpm, no more than 20 rpm, no more than 15 rpm, no more than 14 rpm, no more than 13 rpm, no more than 12 rpm, no more than 11 rpm, no more than 10 rpm, no more than 9 rpm, no more than 8 rpm, no more than 7 rpm, no more than 6 rpm, no more than 5 rpm, no more than 4 rpm, no more than 3 rpm, no more than 2 rpm, or no more than 1 rpm. In some cases the rotational frequency may be within a range defined by any two of the preceding values. In some cases the substrate may be rotating with a rotational frequency of about 5 rpm.

A spiral dispensing pattern may have a path width determined by the width of a region coated by fluid dispensed during a single rotation of the surface. A spiral dispensing pattern may have a path pitch determined by the distance between the center of a fluid dispensing path at a first position and the center of a fluid dispensing path at a second position after one rotation of the substrate. In some instances, the path width may be greater than the path pitch. For example, the fluid dispensed along the path during a substrate rotation may overlap the fluid dispensed along the path during the preceding substrate rotation. In some instances, the path pitch may be greater than the path width. For example, the fluid dispensed along the path during a substrate rotation may be separated from the fluid dispensed along the path during the preceding substrate rotation. In some instances, the path width may be similar to the path pitch. For example, the fluid dispensed along the path during a substrate rotation not be substantially separated from the fluid dispensed along the path during the preceding substrate rotation, and the fluid dispensed along the path during a substrate rotation may not substantially overlap the fluid dispensed along the path during the preceding substrate rotation.

Figure 33:
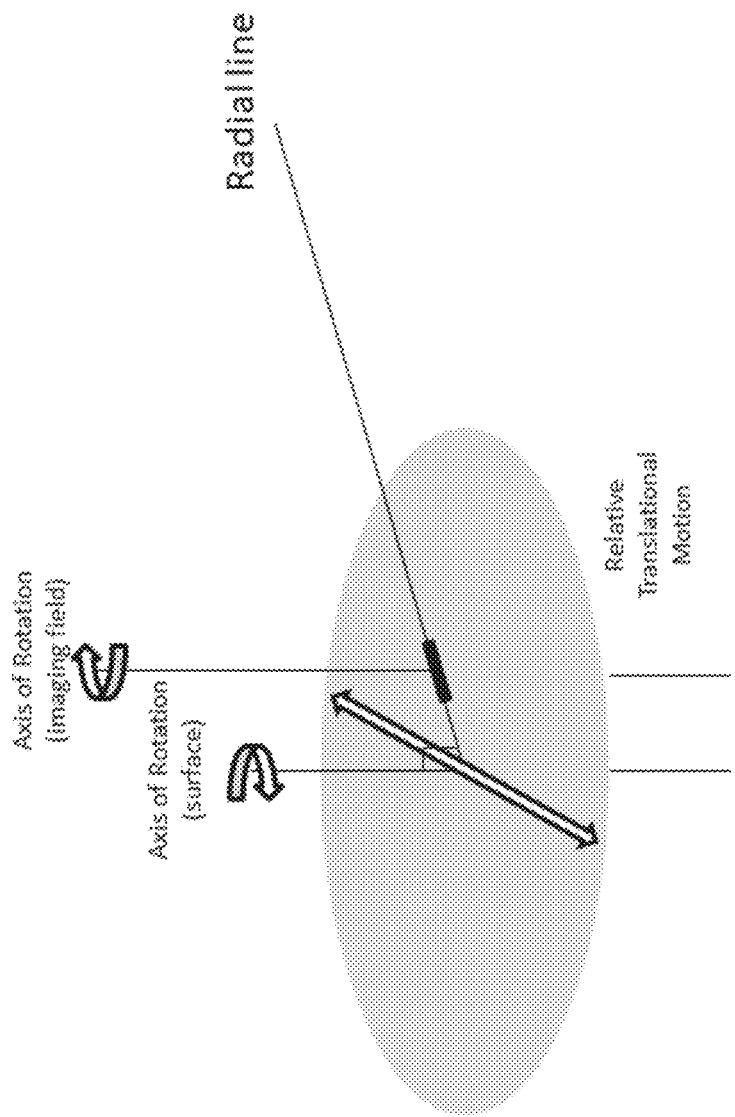
FIG. 33 illustrates schematically an axis of rotation and relative translation of a surface and an axis of rotation of an imaging field.

The substrate may be configured to rotate with respect to an axis. In some instances, the systems, devices, and apparatus described herein may further comprise a rotational unit configured to rotate the substrate. The rotational unit may comprise a motor and/or a rotor to rotate the substrate. Such motor and/or rotor may be mechanically connected to the substrate directly or indirectly via intermediary components (e.g., gears, stages, actuators, discs, pulleys, etc.). The rotational unit may be automated. Alternatively or in addition, the rotational unit may receive manual input. The axis of rotation may be an axis through the center of the substrate (e.g., as shown in FIG. 33). The axis may be an off-center axis. For instance, the substrate may be affixed to a chuck (such as a vacuum chuck) of a spin coating apparatus. The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational velocities during different operations described herein. The substrate may be configured to rotate with a rotational velocity that varies according to a time-dependent function, such as a ramp, sinusoid, pulse, or other function or combination of functions. The time-varying function may be periodic or aperiodic.

The substrate may be configured to move in any vector with respect to a reference point. In some instances, the systems, devices, and apparatus described herein may further comprise a motion unit configured to move the substrate. The motion unit may comprise any mechanical component, such as a motor, rotor, actuator, linear stage, drum, roller, pulleys, etc., to move the substrate. Such components may be mechanically connected to the substrate directly or indirectly via intermediary components (e.g., gears, stages, actuators, discs, pulleys, etc.). The motion unit may be automated. Alternatively or in addition, the motion unit may receive manual input. The substrate may be configured to move with any velocity. In some instances, the substrate may be configured to move with different velocities during different operations described herein. The substrate may be configured to move with a velocity that varies according to a time-dependent function, such as a ramp, sinusoid, pulse, or other function or combination of functions. The time-varying function may be periodic or aperiodic.

A solution may be provided to the substrate prior to or during rotation (or other motion) of the substrate to centrifugally (or otherwise inertially) direct the solution across the array. In some instances, the solution may be provided to the planar array during rotation of the substrate in pulses, thereby creating an annular wave of the solution moving radially outward. In some instances, the solution may be provided to the planar array during other motion of the substrate in pulses, thereby creating a wave of the solution moving in a certain direction. The pulses may have periodic or non-periodic (e.g., arbitrary) intervals. A series of pulses may comprise a series of waves producing a surface-reagent exchange. The surface-reagent exchange may comprise washing in which each subsequent pulse comprises a reduced concentration of the surface reagent. The solution may have a temperature different than that of the substrate, thereby providing a source or sink of thermal energy to the substrate or to an analyte located on the substrate. The thermal energy may provide a temperature change to the substrate or to the analyte. The temperature change may be transient. The temperature change may enable, disable, enhance, or inhibit a chemical reaction, such as a chemical reaction to be carried out upon the analyte. For example, the chemical reaction may comprise denaturation, hybridization, or annealing of nucleic acid molecules. The chemical reaction may comprise a step in a polymerase chain reaction (PCR), bridge amplification, or other nucleic acid amplification reaction. The temperature change may modulate, increase, or decrease a signal detected from the analyte.

The array may be in fluid communication with at least one sample inlet (of a fluid channel). The array may be in fluid communication with the sample inlet via a non-solid gap, e.g., an air gap. In some cases, the array may additionally be in fluid communication with at least one sample outlet. The array may be in fluid communication with the sample outlet via an airgap. The sample inlet may be configured to direct a solution to the array. The sample outlet may be configured to receive a solution from the array. The solution may be directed to the array using one or more dispensing nozzles. For example, the solution may be directed to the array using at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 dispensing nozzles. The solution may be directed to the array using a number of nozzles that is within a range defined by any two of the preceding values. In some cases, different reagents (e.g., nucleotide solutions of different types, different probes, washing solutions, etc.) may be dispensed via different nozzles, such as to prevent contamination. Each nozzle may be connected to a dedicated fluidic line or fluidic valve, which may further prevent contamination. A type of reagent may be dispensed via one or more nozzles. The one or more nozzles may be directed at or in proximity to a center of the substrate. Alternatively, the one or more nozzles may be directed at or in proximity to a location on the substrate other than the center of the substrate. Alternatively or in combination, one or more nozzles may be directed closer to the center of the substrate than one or more of the other nozzles. For instance, one or more nozzles used for dispensing washing reagents may be directed closer to the center of the substrate than one or more nozzles used for dispensing active reagents. The one or more nozzles may be arranged at different radii from the center of the substrate. Two or more nozzles may be operated in combination to deliver fluids to the substrate more efficiently. One or more nozzles may be configured to deliver fluids to the substrate as a jet, spray (or other dispersed fluid), and/or droplets. One or more nozzles may be operated to nebulize fluids prior to delivery to the substrate. For example, the fluids may be delivered as aerosol particles.

The solution may be dispensed on the substrate while the substrate is stationary; the substrate may then be subjected to rotation (or other motion) following the dispensing of the solution. Alternatively, the substrate may be subjected to rotation (or other motion) prior to the dispensing of the solution; the solution may then be dispensed on the substrate while the substrate is rotating (or otherwise moving).

Rotation of the substrate may yield a centrifugal force (or inertial force directed away from the axis) on the solution, causing the solution to flow radially outward over the array. In this manner, rotation of the substrate may direct the solution across the array. Continued rotation of the substrate over a period of time may dispense a fluid film of a nearly constant thickness across the array. The rotational velocity of the substrate may be selected to attain a desired thickness of a film of the solution on the substrate. The film thickness may be related to the rotational velocity by equation (1):

$$h(t) = \frac{\sqrt{3 \mu/2}}{\sqrt{2tp\omega^2 - 3 \mu C}} \quad (1)$$

Here, h(t) is the thickness of the fluid film at time t, p is the viscosity of the fluid, co is the rotational velocity, and C is a constant.

Alternatively or in combination, the viscosity of the solution may be chosen to attain a desired thickness of a film of the solution on the substrate. For instance, the rotational velocity of the substrate or the viscosity of the solution may be chosen to attain a film thickness of at least 10 nanometers (nm), at least 20 nm, at least 50 nm, at least 100 nm, at least 200 nm, at least 500 nm, at least 1 micrometer (µm), at least 2 µm, at least 5 µm, at least 10 µm, at least 20 µm, at least 50 µm, at least 100 µm. at least 200 µm, at least 500 µm, or at least 1 mm. The rotational velocity of the substrate and/or the viscosity of the solution may be chosen to attain a film thickness that is within a range defined by any two of the preceding values. The viscosity of the solution may be controlled by controlling a temperature of the solution. The thickness of the film may be measured or monitored. Measurements or monitoring of the thickness of the film may be incorporated into a feedback system to better control the film thickness. The thickness of the film may be measured or monitored by a variety of techniques. For instances, the thickness of the film may be measured or monitored by thin film spectroscopy with a thin film spectrometer, such as a fiber spectrometer.

In some instances, one or more factors such as the rotational velocity of the substrate, the acceleration of the substrate (e.g., the rate of change of velocity), viscosity of the solution, angle of dispensing (e.g., contact angle of a stream of reagents) of the solution, radial coordinates of dispensing of the solution (e.g., on center, off center, etc.), temperature of the substrate, temperature of the solution, and other factors may be adjusted and/or otherwise optimized to attain a desired wetting on the substrate and/or a film thickness on the substrate, such as to facilitate uniform coating of the substrate. In some cases, a surfactant may be added to the solution, or a surfactant may be added to the surface to facilitate uniform coating or to facilitate sample loading efficiency. Such optimization may prevent the solution from exiting the substrate along a relatively focused stream or travel path such that the fluid only contacts the substrate at partial surface areas (as opposed to the entire surface area)—in such cases, a significantly larger volume of reagents may have to be dispensed to achieve uniform and full coating of the substrate. Such optimization may also prevent the solution from scattering or otherwise reflecting or bouncing off the substrate upon contact and disturbing the surface fluid. Alternatively or in conjunction, the thickness of the solution may be adjusted using mechanical, electric, physical, or other mechanisms. For example, the solution may be dispensed onto a substrate and subsequently leveled using, e.g., a physical scraper such as a squeegee, to obtain a desired thickness of uniformity across the substrate.

In some cases, rotation of the substrate may be slow enough so as not to yield substantial centrifugal force (or inertial force directed away from the axis) on the solution. Beneficially, one or more reagents dispensed onto the substrate may remain substantially local to a landing location, e.g., without significantly and/or pre-emptively travelling outwards with respect to a rotational axis such as to invade another reaction space on the open substrate. The substrate may be rotating with a rotational frequency of no more than 60 rpm, no more than 50 rpm, no more than 40 rpm, no more than 30 rpm, no more than 25 rpm, no more than 20 rpm, no more than 15 rpm, no more than 14 rpm, no more than 13 rpm, no more than 12 rpm, no more than 11 rpm, no more than 10 rpm, no more than 9 rpm, no more than 8 rpm, no more than 7 rpm, no more than 6 rpm, no more than 5 rpm, no more than 4 rpm, no more than 3 rpm, no more than 2 rpm, or no more than 1 rpm. In some cases the rotational frequency may be within a range defined by any two of the preceding values. In some cases the substrate may be rotating with a rotational frequency of about 5 rpm. In some cases, the solution may be dispensed on the surface in a spiral pattern. For example, the solution may be dispensed in a spiral pattern using the system shown in FIG. 48 or FIG. 51. As shown in FIG. 48, a solution (e.g., a sample or a wash solution) may be dispensed from a dispense probe (e.g., a nozzle). In some embodiments, a solution may be dispensed from a plurality of dispense probes. For example, a first reagent in a solution may be dispensed from a first dispense probe, a second reagent in a solution may be dispensed from a second dispense probe, and a third reagent in a solution may be dispensed from a third dispense probe. The reagents dispensed from different dispense probes may combine on the substrate to form a homogenous solution. The dispense probe may be positioned at a fixed height above a substrate (e.g., a wafer). The reagent may be dispensed onto an open surface, as shown in FIG. 51. In some cases, the substrate may be rotating relative to the dispensing probe. In some cases, the dispensing probe may be moving radially relative to the substrate with respect to the axis of rotation of the substrate. In some cases, the substrate may be moving linearly relative to the dispense probe. In some cases, the substrate may be rotating relative to the dispense probe while moving linearly relative to the dispense probe, thereby dispensing the sample in a spiral pattern. In some cases, the substrate may be rotating relative to the dispense probe while the dispense probe is moving radially relative to the substrate with respect to the axis of rotation of the substrate, thereby dispensing the sample in a spiral pattern. The rotational velocity of the substrate, the rate of flow of the solution, or the viscosity of the solution may be chosen to attain a film thickness of at least 10 nanometers (nm), at least 20 nm, at least 50 nm, at least 100 nm, at least 200 nm, at least 500 nm, at least 1 micrometer (μm), at least 2 μm, at least 5 μm, at least 10 μm, at least 20 μm, at least 50 μm, at least 100 μm. at least 200 μm, at least 500 μm, or at least 1 mm.

In some cases, the solution may be heated prior to being dispensed on the substrate. The solution may be at a higher temperature than the ambient temperature. The solution may be heated to about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 45° C., about 50° C., about 55° C., about 60° C., about 65° C., about 70° C., about 75° C., about 80° C., about 85° C., about 90° C., about 95° C. prior to dispensing. In some cases, a solution may be heated to a temperature that is within a range defined by any two of the preceding values.

In some instances, the substrate may be rotated at a variable angular velocity. The angular velocity of the substrate may be varied such that the linear velocity of the substrate relative to a dispensing probe is substantially maintained as the radial distance of the dispensing probe from the axis of rotation of the substrate changes. For example, the angular velocity of the substrate may decrease as the dispensing probe dispenses a fluid in a spiral path progressing outward with respect to the axis of rotation of the substrate. In another example, the angular velocity of the substrate may increase as the dispensing probe dispenses a fluid in a spiral path progressing inward with respect to the axis of rotation of the substrate. In some instances, a dispensing probe may dispense a fluid at a variable flow rate. The flow rate of the dispensing probe may be varied such that the amount of fluid dispensed per unit area of the substrate is substantially maintained. For example, the flow rate of the dispensing probe may increase as the dispensing probe dispenses a fluid in a spiral path progressing outward with respect to the axis of rotation of the substrate. In another example, the flow rate of the dispensing probe may decrease as the dispensing probe dispenses a fluid in a spiral path progressing inward with respect to the axis of rotation of the substrate.

One or more solutions dispensed on a surface may undergo a reaction on the surface. For example, a first solution (e.g., comprising a reactant) dispensed on the surface may react with a second solution (e.g., comprising an enzyme) dispensed on the surface on top of the first solution. One or more solutions dispensed on a surface may deactivate or quench a chemical reaction. For example, a quenching solution (e.g., comprising EDTA or an acid) may be added to the substrate on top of a reaction to quench the reaction. A solution (e.g., a solution comprising a reactant, a solution comprising an enzyme, or a quenching solution) may be dispensed on the surface in a pattern (e.g., a spiral pattern). In some embodiments, a quenching solution is dispensed on the surface in the same pattern as a solution comprising a reactant, thereby maintaining a substantially constant reaction time at each point on the surface to which a solution is dispensed. In some embodiments, a quenching solution is dispensed on the surface in the same pattern as a solution comprising an enzyme, thereby maintaining a substantially constant reaction time at each point on the surface to which a solution is dispensed. For example, a solution comprising a reactant may be dispensed onto a surface in a spiral path directed inward toward an axis of rotation of the substrate. The solution comprising the reactant may be dispensed at a constant rate, and the substrate may rotated at a variable rate such that the volume dispensed per unit area is substantially constant. A solution comprising an enzyme may be dispensed along the same spiral path as the solution comprising the reagent. The solution comprising the enzyme may be dispensed a constant rate, and the substrate may rotated at a variable rate such that time between dispensing the solution comprising the reactant and the solution comprising the enzyme is substantially the same at any point along the spiral path. A quenching solution may be dispensed along the same spiral path as the solution comprising the enzyme. The quenching solution may be dispensed a constant rate, and the substrate may rotated at a variable rate such that time between dispensing the solution comprising the enzyme and the quenching solution is substantially the same at any point along the spiral path. Alternatively or in addition, similarly, one or more solutions dispensed on a surface may activate or catalyze a chemical reaction. For example, an activating solution (e.g., comprising catalysts) may be added to the substrate on top of a reaction (e.g., in the same dispense pattern) to activate or catalyze a reaction.

A variety of methods may be employed to dispense one or more solutions onto a substrate to ensure a substantially similar reaction time across an area of the substrate in contact with the one or more solutions. In some embodiments, a solution may be spin-coated onto a surface by dispensing the solution at or near the axis of rotation of a rotating substrate such that the centrifugal force of the rotating substrate facilitates the outward spread of the solution away from the axis of rotation. Spin-coating may be well-suited for dispensing one or more solutions that initiate or quench a reaction that occurs on a time scale that is slow relative to the dispensing time. In some embodiments, one or more solutions may be delivered directly to the reaction site without substantial displacement of the one or more solution from the point of delivery. Methods of direct delivery of a solution to the reaction site may include aerosol delivery of the solution, applying the solution using an applicator, curtain-coating the solution, slot-die coating, dispensing the solution from a translating dispense probe, dispensing the solution from an array of dispense probes, dipping the substrate into the solution, or contacting the substrate to a sheet comprising the solution.

Aerosol delivery may comprise delivering a solution to the substrate in aerosol form by directing the solution to the substrate using a pressure nozzle or an ultrasonic nozzle. Applying the solution using an applicator may comprise contacting the substrate with an applicator comprising the solution and translating the applicator relative to the substrate. For example, applying the solution using an applicator may comprise painting the substrate. The solution may be applied in a pattern by translating the applicator, rotating the substrate, translating the substrate, or a combination thereof. The pattern may be a spiral pattern. The pattern may be a circular pattern. Curtain-coating may comprise dispensing the solution from a dispense probe to the substrate in a continuous stream (e.g., a curtain or a flat sheet) and translating the dispense probe relative to the substrate. A solution may be curtain-coated in a pattern by translating the dispense probe, rotating the substrate, translating the substrate, or a combination thereof. The pattern may be a spiral pattern. The pattern may be a circular pattern. Slot-die coating may comprise dispensing the solution from a dispense probe positioned near the substrate such that the solution forms a meniscus between the substrate and the dispense probe and translating the dispense probe relative to the substrate. A solution may be slot-die coated in a pattern by translating the dispense probe, rotating the substrate, translating the substrate, or a combination thereof. The pattern may be a spiral pattern. The pattern may be a circular pattern. Dispensing the solution from a translating dispense probe may comprise translating the dispense probe relative to the substrate in a pattern (e.g., a spiral pattern, a circular pattern, a linear pattern, a striped pattern, a cross-hatched pattern, or a diagonal pattern). Dispensing the solution from an array of dispense probes may comprise dispensing the solution from an array of nozzles (e.g., a shower head) positioned above the substrate such that the solution is dispensed across an area of the substrate substantially simultaneously. Dipping the substrate into the solution may comprise dipping the substrate into a reservoir comprising the solution. In some embodiments, the reservoir may be a shallow reservoir to reduce the volume of the solution required to coat the substrate. Contacting the substrate to a sheet comprising the solution may comprise bringing the substrate in contact with a sheet of material (e.g., a porous sheet or a fibrous sheet) permeated with the solution. The solution may be transferred to the substrate. In some embodiments, the sheet of material may be a single-use sheet. In some embodiments, the sheet of material may be a reusable sheet. In some embodiments, a solution may be dispensed onto a substrate using the method illustrated in FIG. 51. As shown in FIG. 51, a jet of a solution may be dispensed from a nozzle to a rotating substrate. The nozzle may translate radially relative to the rotating substrate, thereby dispensing the solution in a spiral pattern onto the substrate.

One or more solutions or reagents may be delivered to a substrate by any of the delivery methods disclosed herein. In some embodiments, two or more solutions or reagents are delivered to the substrate using the same delivery method. In some embodiments, two or more solutions are delivered to the substrate such that the time between contacting a solution or reagent and a subsequent solution or reagent is substantially similar for each region of the substrate contacted to the one or more solutions or reagents. In some embodiments, a solution or reagent may be delivered as a single mixture. In some embodiments, the solution or reagent may be dispensed in two or more component solutions. For example, each component of the two or more component solutions may be dispensed from a distinct nozzle. The distinct nozzles may dispense the two or more component solutions substantially simultaneously to substantially the same region of the substrate such that a homogenous solution forms on the substrate. In some embodiments, dispensing of each component of the two or more components may be temporally separated. Dispensing of each component may be performed using the same method. For example, a first component and a second component are dispensed onto the substrate using the same method at substantially the same rate and in substantially the same pattern such that the time between contacting the first component and the second component is substantially similar for each region of the substrate contacted to the first component and the second component. In some embodiments, a first solution may start a reaction on the substrate (e.g., a solution comprising magnesium). In some embodiments, a second solution may stop a reaction on the substrate (e.g., a solution comprising ethylenediaminetetraacetic acid (EDTA)). In some embodiments, the time between starting the reaction and stopping the reaction may be substantially the same at each region of the substrate contacted to the first solution and the second solution. A first solution may form a substantially uniform film upon delivery to the substrate. A second solution may comprise a rapidly diffusing component that may diffuse rapidly upon contact with the first solution. In some embodiments, the rapidly diffusing component may start a reaction, or the rapidly diffusing component may stop a reaction.

In some embodiments, direct delivery of a solution or reagent may be combined with spin-coating. For example, a first solution may be delivered directly in a spiral pattern using any of the direct delivery methods disclosed herein. The spiral pattern may be directed inward toward an axis of rotation of the substrate. The first solution may start a reaction. A second solution may be delivered in the same pattern as the first solution. The second solution may stop the reaction. The second solution may wash away the first solution. The first solution and the second solution may be dispensed such that the reaction proceeds for a substantially fixed time at each spatial region of the substrate.

A solution may be incubated on the substrate. In some embodiments, the solution may be incubated on the substrate under conditions that maintain a layer of fluid on the surface. The solution may be incubated for at least about 5 minutes, up to about 10 minutes, up to about 15 minutes, up to about 20 minutes, up to about 25 minutes, up to about 30 minutes, up to about 35 minutes, up to about 40 minutes, up to about 45 minutes, up to about 50 minutes, up to about 55 minutes, up to about 60 minutes, up to about 65 minutes, up to about 70 minutes, up to about 75 minutes, up to about 80 minutes, up to about 85 minutes, or up to about 90 minutes. In some cases the incubation time may be within a range defined by any two of the preceding values. In some cases, the incubation may be for more than 90 minutes. In some instances, the layer of fluid may maintain a film thickness of at least 10 nanometers (nm), at least 20 nm, at least 50 nm, at least 100 nm, at least 200 nm, at least 500 nm, at least 1 micrometer (µm), at least 2 µm, at least 5 µm, at least 10 µm, at least 20 µm, at least 50 µm, at least 100 µm. at least 200 µm, at least 500 µm, or at least 1 mm during incubation. One or more of the temperature of the chamber, the humidity of the chamber, the rotation of the substrate, or the composition of the fluid may be adjusted such that the layer of fluid is maintained during incubation. In some instances, the substrate may be rotated at an rotational frequency of no more than 60 rpm, no more than 50 rpm, no more than 40 rpm, no more than 30 rpm, no more than 25 rpm, no more than 20 rpm, no more than 15 rpm, no more than 14 rpm, no more than 13 rpm, no more than 12 rpm, no more than 11 rpm, no more than 10 rpm, no more than 9 rpm, no more than 8 rpm, no more than 7 rpm, no more than 6 rpm, no more than 5 rpm, no more than 4 rpm, no more than 3 rpm, no more than 2 rpm, or no more than 1 rpm. In some cases the rotational frequency may be within a range defined by any two of the preceding values. In some cases the substrate may be rotating with a rotational frequency of about 5 rpm.

The substrate or a surface thereof may comprise other features that aid in solution or reagent retention on the substrate or thickness uniformity of the solution or reagent on the substrate. In some cases, the surface may comprise a raised edge (e.g., a rim) which may be used to retain solution on the surface. The surface may comprise a rim near the outer edge of the surface, thereby reducing the amount of the solution that flows over the outer edge.

The solution may be a reaction mixture comprising a variety of components. For example, the solution may comprise a plurality of probes configured to interact with the analyte. For example, the probes may have binding specificity to the analyte. In another example, the probes may not have binding specificity to the analyte. A probe may be configured to permanently couple to the analyte. A probe may be configured to transiently couple to the analyte. For example, a nucleotide probe may be permanently incorporated into a growing strand hybridized to a nucleic acid molecule analyte. Alternatively, a nucleotide probe may transiently bind to the nucleic acid molecule analyte. Transiently coupled probes may be subsequently removed from the analyte. Subsequent removal of the transiently coupled probes from an analyte may or may not leave a residue (e.g., chemical residue) on the analyte. A type of probe in the solution may depend on the type of analyte. A probe may comprise a functional group or moiety configured to perform specific functions. For example, a probe may comprise a label (e.g., dye). A probe may be configured to generate a detectable signal (e.g., optical signal), such as via the label, upon coupling or otherwise interacting with the analyte. In some instances, a probe may be configured to generate a detectable signal upon activation (e.g., application of a stimulus). In another example, a nucleotide probe may comprise reversible terminators (e.g., blocking groups) configured to terminate polymerase reactions (until unblocked). The solution may comprise other components to aid, accelerate, or decelerate a reaction between the probe and the analyte (e.g., enzymes, catalysts, buffers, saline solutions, chelating agents, reducing agents, other agents, etc.). In some instances, the solution may be a washing solution. In some instances, a washing solution may be directed to the substrate to bring the washing solution in contact with the array after a reaction or interaction between reagents (e.g., a probe) in a reaction mixture solution with an analyte immobilized on the array. The washing solution may wash away any free reagents from the previous reaction mixture solution.

A detectable signal, such as an optical signal (e.g., fluorescent signal), may be generated upon reaction between a probe in the solution and the analyte. For example, the signal may originate from the probe and/or the analyte. The detectable signal may be indicative of a reaction or interaction between the probe and the analyte. The detectable signal may be a non-optical signal. For example, the detectable signal may be an electronic signal. The detectable signal may be detected by one or more sensors. For example, an optical signal may be detected via one or more optical detectors in an optical detection scheme described elsewhere herein. The signal may be detected during rotation of the substrate. The signal may be detected following termination of the rotation. The signal may be detected while the analyte is in fluid contact with the solution. The signal may be detected following washing of the solution. In some instances, after the detection, the signal may be muted, such as by cleaving a label from the probe and/or the analyte, and/or modifying the probe and/or the analyte. Such cleaving and/or modification may be affected by one or more stimuli, such as exposure to a chemical, an enzyme, light (e.g., ultraviolet light), or temperature change (e.g., heat). In some instances, the signal may otherwise become undetectable by deactivating or changing the mode (e.g., detection wavelength) of the one or more sensors, or terminating or reversing an excitation of the signal. In some instances, detection of a signal may comprise capturing an image or generating a digital output (e.g., between different images).

The operations of directing a solution to the substrate and detection of one or more signals indicative of a reaction between a probe in the solution and an analyte in the array may be repeated one or more times. Such operations may be repeated in an iterative manner. For example, the same analyte immobilized to a given location in the array may interact with multiple solutions in the multiple repetition cycles. For each iteration, the additional signals detected may provide incremental, or final, data about the analyte during the processing. For example, where the analyte is a nucleic acid molecule and the processing is sequencing, additional signals detected for each iteration may be indicative of a base in the nucleic acid sequence of the nucleic acid molecule. The operations may be repeated at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 cycles to process the analyte. In some instances, a different solution may be directed to the substrate for each cycle. For example, at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 solutions may be directed to the substrate.

In some instances, a washing solution may be directed to the substrate between each cycle (or at least once during each cycle). For instance, a washing solution may be directed to the substrate after each type of reaction mixture solution is directed to the substrate. The washing solutions may be distinct. The washing solutions may be identical. The washing solution may be dispensed in pulses during rotation, creating annular waves as described herein. The washing solution may be dispensed in a continuous stream during rotation while the stream moves radially with respect to the axis of rotation of the substrate, thereby dispensing the washing solution in a spiral pattern. In some instances, the washing solution may be dispensed in a spiral pattern progressing outward with respect to an axis of rotation of the substrate. In some instances, the washing solution may be dispensed in a spiral pattern progressing inward with respect to an axis of rotation of the substrate. For example, at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 washing solutions may be directed to the substrate.

In some instances, a subset or an entirety of the solution(s) may be recycled after the solution(s) have contacted the substrate. Recycling may comprise collecting, filtering, and reusing the subset or entirety of the solution. The filtering may be molecule filtering.

Nucleic Acid Sequencing Using a Rotating Array

In some instances, a method for sequencing may employ sequencing by synthesis schemes wherein a nucleic acid molecule is sequenced base-by-base with primer extension reactions. For example, a method for sequencing a nucleic acid molecule may comprise providing a substrate comprising an array having immobilized thereto the nucleic acid molecule. The array may be a planar array. The substrate may be configured to rotate with respect to an axis. The method may comprise directing a solution comprising a plurality of nucleotides across the array prior to or during rotation of the substrate. Rotation of the substrate may facilitate coating of the substrate surface with the solution. The nucleic acid molecule may be subjected to a primer extension reaction under conditions sufficient to incorporate or specifically bind at least one nucleotide from the plurality of nucleotides into a growing strand that is complementary to the nucleic acid molecule. A signal indicative of incorporation or binding of at least one nucleotide may be detected, thereby sequencing the nucleic acid molecule.

In some instances, the method may comprise, prior to providing the substrate having immobilized thereto the nucleic acid molecule, immobilizing the nucleic acid molecule to the substrate. For example, a solution comprising a plurality of nucleic acid molecules comprising the nucleic acid molecule may be directed to the substrate prior to, during, or subsequent to rotation of the substrate, and the substrate may be subject to conditions sufficient to immobilize at least a subset of the plurality of nucleic acid molecules as an array on the substrate.

Figure 2:
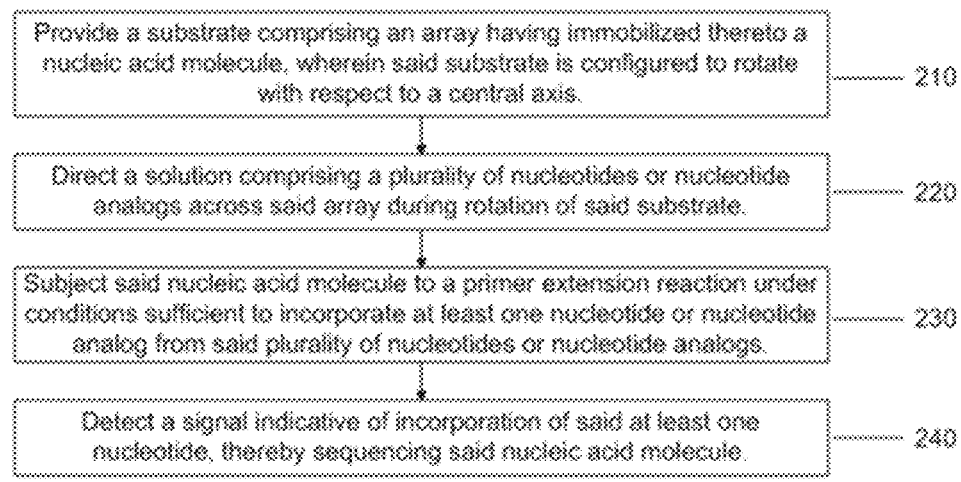
FIG. 2 shows a flowchart for an example of a method for sequencing a nucleic acid molecule.

FIG. 2 shows a flowchart for an example of a method 200 for sequencing a nucleic acid molecule. In a first operation 210, the method may comprise providing a substrate, as described elsewhere herein. The substrate may comprise an array of a plurality of individually addressable locations. The array may be a planar array. The array may be a textured array. The array may be a patterned array. For example, the array may define individually addressable locations with wells and/or pillars. A plurality of nucleic acid molecules, which may or may not be copies of the same nucleic acid molecule, may be immobilized to the array. Each nucleic acid molecule from the plurality of nucleic acid molecules may be immobilized to the array at a given individually addressable location of the plurality of individually addressable locations.

The substrate may be configured to rotate with respect to an axis. The axis may be an axis through the center or substantially center of the substrate. The axis may be an off-center axis. For instance, the substrate may be affixed to a chuck (such as a vacuum chuck) of a spin coating apparatus. The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational velocities during different operations described herein. The substrate may be configured to rotate with a rotational velocity that varies according to a time-dependent function, such as a ramp, sinusoid, pulse, or other function or combination of functions. The time-varying function may be periodic or aperiodic.

In a second operation 220, the method may comprise directing a solution across the array prior to or during rotation of the substrate. The solution may be centrifugally directed across the array. In some instances, the solution may be directed to the array during rotation of the substrate in pulses, thereby creating an annular wave of the solution moving radially outward. In some instances, the solution may be directed to the array during rotation of the substrate in a continuous stream while the stream moves radially with respect to an axis of rotation of the substrate, thereby directing the solution to the array in a spiral pattern. In some cases, the substrate may be configured to rotate with a velocity of no more than 60 rpm, no more than 50 rpm, no more than 40 rpm, no more than 30 rpm, no more than 25 rpm, no more than 20 rpm, no more than 15 rpm, no more than 14 rpm, no more than 13 rpm, no more than 12 rpm, no more than 11 rpm, no more than 10 rpm, no more than 9 rpm, no more than 8 rpm, no more than 7 rpm, no more than 6 rpm, no more than 5 rpm, no more than 4 rpm, no more than 3 rpm, no more than 2 rpm, or no more than 1 rpm. In some cases the rotational frequency may be within a range defined by any two of the preceding values. The solution may have a temperature different than that of the substrate, thereby providing a source or sink of thermal energy to the substrate or to a nucleic acid molecule located on the substrate. The thermal energy may provide a temperature change to the substrate or to the nucleic acid molecule. The temperature change may be transient. The temperature change may enable, disable, enhance, or inhibit a chemical reaction, such as a chemical reaction to be carried out upon the nucleic acid molecule. The chemical reaction may comprise denaturation, hybridization, or annealing of the plurality of nucleic acid molecules. The chemical reaction may comprise a step in a polymerase chain reaction (PCR), bridge amplification, or other nucleic acid amplification reaction. The temperature change may modulate, increase, or decrease a signal detected from the nucleic acid molecules (or from probes in the solution).

In some cases, a solution may comprise beads. The beads may be coated with a nucleic acid molecule to be sequenced. The solution comprising beads may be dispensed onto the substrate using the methods described herein. For example, the solution comprising beads may be dispensed onto the substrate in a spiral pattern, as illustrated in FIG. 48 or FIG. 51. In some cases, the beads may preferentially interact with a first region type of the substrate (e.g., a positively charged region), as illustrated in FIG. 50A. In some cases, a bead may not interact with a second region type of the substrate (e.g., a hydrophobic region). In some cases, a bead coated with a nucleic acid molecule may interact with a first region of the substrate (e.g., a positively charged region), and a bead that is not coated with a nucleic acid molecule may not interact with the first region type of the substrate, as shown in FIG. 50B.

In some instances, the solution may comprise probes configured to interact with nucleic acid molecules. For example, in some instances, such as for performing sequencing by synthesis, the solution may comprise a plurality of nucleotides (in single bases). The plurality of nucleotides may include nucleotide analogs, naturally occurring nucleotides, and/or non-naturally occurring nucleotides, collectively referred to herein as "nucleotides." The plurality of nucleotides may or may not be bases of the same type (e.g., A, T, G, C, etc.). For example, the solution may or may not comprise bases of only one type. The solution may comprise at least 1 type of base or bases of at least 2, at least 3, at least 4, at least 5, at least 6, at least 7, at least 8, at least 9, or at least 10 types. For instance, the solution may comprise any possible mixture of A, T, C, and G. In some instances, the solution may comprise a plurality of natural nucleotides and non-natural nucleotides. The plurality of natural nucleotides and non-natural nucleotides may or may not be bases of the same type (e.g., A, T, G, C). In some cases, the solution may comprise probes that are oligomeric (e.g., oligonucleotide primers). For example, in some instances, such as for performing sequencing by synthesis, the solution may comprise a plurality of nucleic acid molecules, e.g., primers, that comprise 1, 2, 3, 4, 5, 6, 7, 8, 9, 10, 20, 30, 40, 50, 60, 70, 80, 90, 100 or more nucleotide bases. The plurality of nucleic acid molecules may comprise nucleotide analogs, naturally occurring nucleotides, and/or non-naturally occurring nucleotides, collectively referred to herein as "nucleotides." The plurality of nucleotides may or may not be bases of the same type (e.g., A, T, G, C, etc.). For example, the solution may or may not comprise bases of only one type. The solution may comprise at least 1 type of base or bases of at least 2, at least 3, at least 4, at least 5, at least 6, at least 7, at least 8, at least 9, or at least 10 types. For instance, the solution may comprise any possible mixture of A, T, C, and G. In some instances, the solution may comprise a plurality of natural nucleotides and non-natural nucleotides. The plurality of natural nucleotides and non-natural nucleotides may or may not be bases of the same type (e.g., A, T, G, C).

One or more nucleotides of the plurality of nucleotides may be terminated (e.g., reversibly terminated). For example, a nucleotide may comprise a reversible terminator, or a moiety that is capable of terminating primer extension reversibly. Nucleotides comprising reversible terminators may be accepted by polymerases and incorporated into growing nucleic acid sequences analogously to non-reversibly terminated nucleotides. A polymerase may be any naturally occurring (i.e., native or wild-type) or engineered variant of a polymerase (e.g., DNA polymerase, Taq polymerase, etc.). Following incorporation of a nucleotide analog comprising a reversible terminator into a nucleic acid strand, the reversible terminator may be removed to permit further extension of the nucleic acid strand. A reversible terminator may comprise a blocking or capping group that is attached to the 3'-oxygen atom of a sugar moiety (e.g., a pentose) of a nucleotide or nucleotide analog. Such moieties are referred to as 3'-O-blocked reversible terminators. Examples of 3'-O-blocked reversible terminators include, for example, 3'-ONH$_2$ reversible terminators, 3'-O-allyl reversible terminators, and 3'-O-aziomethyl reversible terminators. Alternatively, a reversible terminator may comprise a blocking group in a linker (e.g., a cleavable linker) and/or dye moiety of a nucleotide analog. 3'-unblocked reversible terminators may be attached to both the base of the nucleotide analog as well as a fluorescing group (e.g., label, as described herein). Examples of 3'-unblocked reversible terminators include, for example, the "virtual terminator" developed by Helicos BioSciences Corp. and the "lightning terminator" developed by Michael L. Metzker et al. Cleavage of a reversible terminator may be achieved by, for example, irradiating a nucleic acid molecule including the reversible terminator. In some instances the plurality of nucleotides may not comprise a terminated nucleotide.

One or more nucleotides of the plurality of nucleotides may be labeled with a dye, fluorophore, or quantum dot. For example, the solution may comprise labeled nucleotides. In another example, the solution may comprise unlabeled nucleotides. In another example, the solution may comprise a mixture of labeled and unlabeled nucleotides. Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5-(or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, Atto 390, 425, 465, 488, 495, 532, 565, 594, 633, 647, 647N, 665, 680 and 700 dyes, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be one with linkers. For instance, a label may have a disulfide linker attached to the label. Non-limiting examples of such labels include Cy5-azide, Cy-2-azide, Cy-3-azide, Cy-3.5-azide, Cy5.5-azide and Cy-7-azide. In some cases, a linker may be a cleavable linker. In some cases, the label may be a type that does not self-quench or exhibit proximity quenching. Non-limiting examples of a label type that does not self-quench or exhibit proximity quenching include Bimane derivatives such as Monobromobimane. Alternatively, the label may be a type that self-quenches or exhibits proximity quenching. Non-limiting examples of such labels include Cy5-azide, Cy-2-azide, Cy-3-azide, Cy-3.5-azide, Cy5.5-azide and Cy-7-azide. In some instances, a blocking group of a reversible terminator may comprise the dye.

The solution may be directed to the array using one or more nozzles. In some cases, different reagents (e.g., nucleotide solutions of different types, washing solutions, etc.) may be dispensed via different nozzles, such as to prevent contamination. Each nozzle may be connected to a dedicated fluidic line or fluidic valve, which may further prevent contamination. A type of reagent may be dispensed via one or more nozzles. The one or more nozzles may be directed at or in proximity to a center of the substrate. Alternatively, the one or more nozzles may be directed at or in proximity to a location on the substrate other than the center of the substrate. Two or more nozzles may be operated in combination to deliver fluids to the substrate more efficiently.

The solution may be dispensed on the substrate while the substrate is stationary; the substrate may then be subjected to rotation following the dispensing of the solution. Alternatively, the substrate may be subjected to rotation prior to the dispensing of the solution; the solution may then be dispensed on the substrate while the substrate is rotating. Rotation of the substrate may yield a centrifugal force (or inertial force directed away from the axis) on the solution, causing the solution to flow radially outward over the array.

In a third operation 230, the method may comprise subjecting the nucleic acid molecule to a primer extension reaction. The primer extension reaction may be conducted under conditions sufficient to incorporate at least one nucleotide from the plurality of nucleotides into a growing strand that is complementary to the nucleic acid molecule. The nucleotide incorporated may or may not be labeled.

In some cases, the operation 230 may further comprise modifying at least one nucleotide. Modifying the nucleotide may comprise labeling the nucleotide. For instance, the nucleotide may be labeled, such as with a dye, fluorophore, or quantum dot. The nucleotide may be cleavably labeled. In some instances, modifying the nucleotide may comprise activating (e.g., stimulating) a label of the nucleotide.

In a fourth operation 240, the method may comprise detecting a signal indicative of incorporation of the at least one nucleotide. The signal may be an optical signal. The signal may be a fluorescence signal. The signal may be detected during rotation of the substrate. The signal may be detected following termination of the rotation. The signal may be detected while the nucleic acid molecule to be sequenced is in fluid contact with the solution. The signal may be detected following fluid contact of the nucleic acid molecule with the solution. The operation 240 may further comprise modifying a label of the at least one nucleotide. For instance, the operation 240 may further comprise cleaving the label of the nucleotide (e.g., after detection). The nucleotide may be cleaved by one or more stimuli, such as exposure to a chemical, an enzyme, light (e.g., ultraviolet light), or heat. Once the label is cleaved, a signal indicative of the incorporated nucleotide may not be detectable with one or more detectors.

The method 200 may further comprise repeating operations 220, 230, and/or 240 one or more times to identify one or more additional signals indicative of incorporation of one or more additional nucleotides, thereby sequencing the nucleic acid molecule. The method 200 may comprise repeating operations 220, 230, and/or 240 in an iterative manner. For each iteration, an additional signal may indicate incorporation of an additional nucleotide. The additional nucleotide may be the same nucleotide as detected in the previous iteration. The additional nucleotide may be a different nucleotide from the nucleotide detected in the previous iteration. In some instances, at least one nucleotide may be modified (e.g., labeled and/or cleaved) between each iteration of the operations 220, 230, or 240. For instance, the method may comprise repeating the operations 220, 230, and/or 240 at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 times. The method may comprise repeating the operations 220, 230, and/or 240 a number of times that is within a range defined by any two of the preceding values. The method 200 may thus result in the sequencing of a nucleic acid molecule of any size.

The method may comprise directing different solutions to the array during rotation of the substrate in a cyclical manner. For instance, the method may comprise directing a first solution containing a first type of nucleotide (e.g., in a plurality of nucleotides of the first type) to the array, followed by a second solution containing a second type of nucleotide, followed by a third type of nucleotide, followed by a fourth type of nucleotide, etc. In another example, different solutions may comprise different combinations of types of nucleotides. For example, a first solution may comprise a first canonical type of nucleotide (e.g., A) and a second canonical type of nucleotide (e.g., C), and a second solution may comprise the first canonical type of nucleotide (e.g., A) and a third canonical type of nucleotide (e.g., T), and a third solution may comprise the first canonical type, second canonical type, third canonical type, and a fourth canonical type (e.g., G) of nucleotide. In another example, a first solution may comprise labeled nucleotides, and a second solution may comprise unlabeled nucleotides, and a third solution may comprise a mixture of labeled and unlabeled nucleotides. The method may comprise directing at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 solutions to the array. The method may comprise directing a number of solutions that is within a range defined by any two of the preceding values to the array. The solutions may be distinct. The solutions may be identical.

The method may comprise directing at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 washing solutions to the substrate. For instance, a washing solution may be directed to the substrate after each type of nucleotide is directed to the substrate. The washing solutions may be distinct. The washing solutions may be identical. The washing solution may be dispensed in pulses during rotation, creating annular waves as described herein. The washing solution may be dispensed in a continuous stream during rotation while the stream moves radially with respect to the axis of rotation of the substrate, thereby dispensing the washing solution in a spiral pattern.

The method may further comprise recycling a subset or an entirety of the solution(s) after the solution(s) have contacted the substrate. Recycling may comprise collecting, filtering, and reusing the subset or entirety of the solution. The filtering may be molecule filtering.

The operations 220 and 230 may occur at a first location and the operation 240 may occur at a second location. The first and second locations may comprise first and second processing bays, respectively, as described herein (for instance, with respect to FIG. 23H). The first and second locations may comprise first and second rotating spindles, respectively, as described herein (for instance, with respect to FIG. 24). The first rotating spindle may be exterior or interior to the second rotating spindle. The first and second rotating spindles may be configured to rotate with different angular velocities. Alternatively, the operation 220 may occur at a first location and the operations 230 and 240 may occur at the second location.

The method may further comprise transferring the substrate between the first and second locations. Operations 220 and 230 may occur while the substrate is rotated at a first angular velocity and operation 240 may occur while the substrate is rotated at a second angular velocity. The first angular velocity may be less than the second angular velocity. The first angular velocity may be between about 0 rpm and about 100 rpm. The second angular velocity may be between about 100 rpm and about 1,000 rpm. Alternatively, the operation 220 may occur while the substrate is rotated at the first angular velocity and the operations 230 and 240 may occur while the substrate is rotated at the second angular velocity.

Many variations, alterations, and adaptations based on the method 200 provided herein are possible. For example, the order of the operations of the method 200 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated. Some of the operations may be manual. Some of the operations may be performed separately, e.g., in different locations or during different steps and/or processes. For example, directing a solution comprising a plurality of probes to the substrate may occur separately from the reaction and detection processes.

For example, in some cases, in the third operation 230, instead of facilitating a primer extension reaction, the nucleic acid molecule may be subject to conditions to allow transient binding of a nucleotide from the plurality of nucleotides to the nucleic acid molecule. The transiently bound nucleotide may be labeled. The transiently bound nucleotide may be removed, such as after detection (e.g., see operation 240). Then, a second solution may be directed to the substrate, this time under conditions to facilitate the primer extension reaction, such that a nucleotide of the second solution is incorporated (e.g., into a growing strand hybridized to the nucleic acid molecule). The incorporated nucleotide may be unlabeled. After washing, and without detecting, another solution of labeled nucleotides may be directed to the substrate, such as for another cycle of transient binding.

In some instances, such as for performing sequencing by ligation, the solution may comprise different probes. For example, the solution may comprise a plurality of oligonucleotide molecules. For example, the oligonucleotide molecules may have a length of about 2 bases, 3 bases, 4 bases, 5 bases, 6 bases, 7 bases, 8 bases, 9 bases, 10 bases or more. The oligonucleotide molecules may be labeled with a dye (e.g., fluorescent dye), as described elsewhere herein. In some instances, such as for detecting repeated sequences in nucleic acid molecules, such as homopolymer repeated sequences, dinucleotide repeated sequences, and trinucleotide repeated sequences, the solution may comprise targeted probes (e.g., homopolymer probe) configured to bind to the repeated sequences. The solution may comprise one type of probe (e.g., nucleotides). The solution may comprise different types of probes (e.g., nucleotides, oligonucleotide molecules, etc.). The solution may comprise different types of probes (e.g., oligonucleotide molecules, antibodies, etc.) for interacting with different types of analytes (e.g., nucleic acid molecules, proteins, etc.). Different solutions comprising different types of probes may be directed to the substrate any number of times, with or without detection between consecutive cycles (e.g., detection may be performed between some consecutive cycles, but not between some others), to sequence or otherwise process the nucleic acid molecule, depending on the type of processing.

Figure 3:
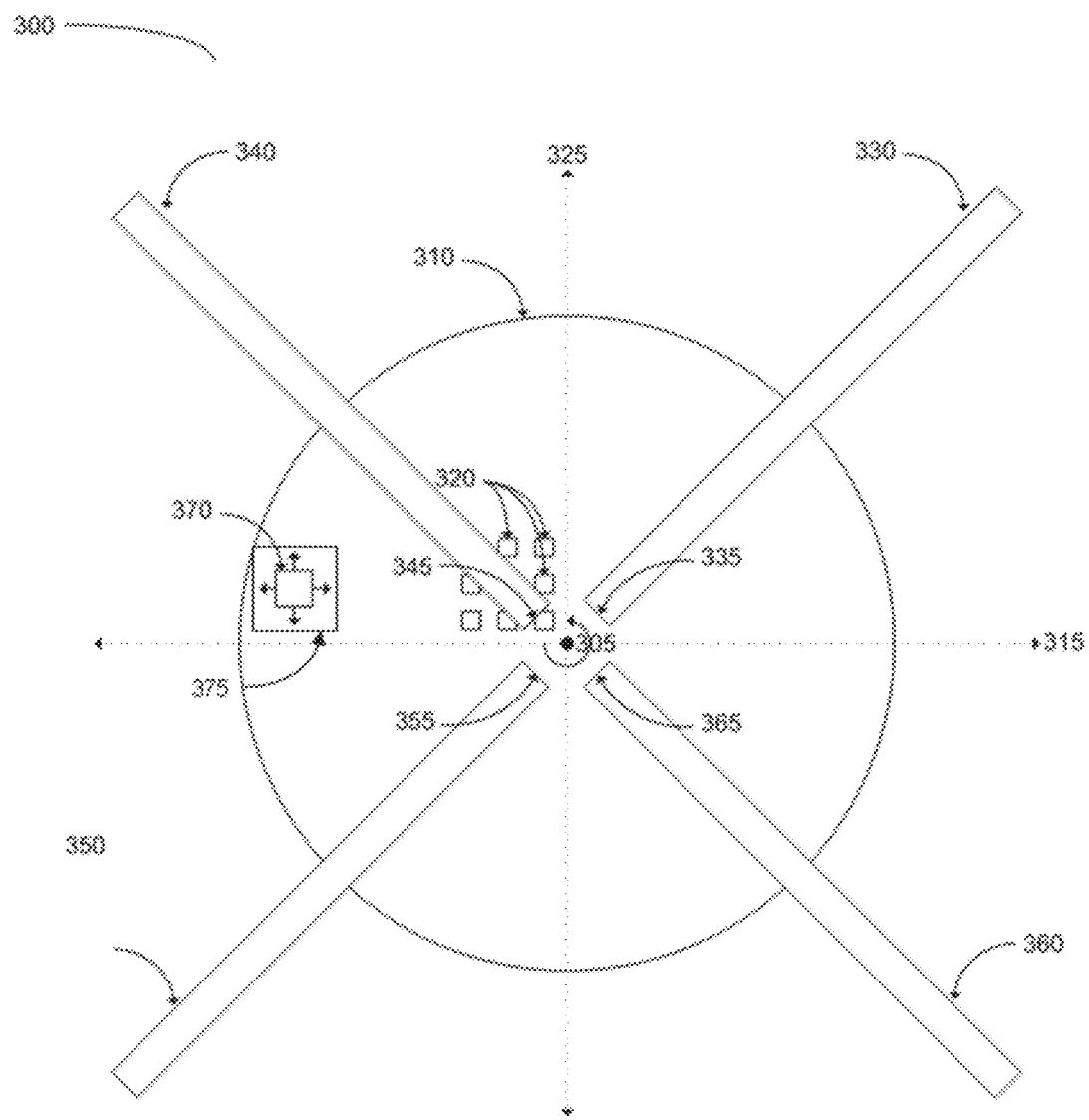
FIG. 3 shows a system for sequencing a nucleic acid molecule.

FIG. 3 shows a system 300 for sequencing a nucleic acid molecule or processing an analyte. The system may be configured to implement the method 200 or 1400. Although the systems (e.g., 300, 400, 500a, 500b, etc.) are described with respect to processing nucleic acid molecules, the systems may be used to process any other type of biological analyte, as described herein.

The system may comprise a substrate 310. The substrate may comprise any substrate described herein, such as any substrate described herein with respect to FIG. 2. The substrate may comprise an array. The substrate may be open. The array may comprise one or more locations 320 configured to immobilize one or more nucleic acid molecules or analytes. The array may comprise any array described herein, such as any array described herein with respect to method 200. For instance, the array may comprise a plurality of individually addressable locations. The array may comprise a linker (e.g., any binder described herein) that is coupled to the nucleic acid molecule to be sequenced. Alternatively or in combination, the nucleic acid molecule to be sequenced may be coupled to a bead; the bead may be immobilized to the array. The array may be textured. The array may be a patterned array. The array may be planar.

The substrate may be configured to rotate with respect to an axis 305. The axis may be an axis through the center of the substrate. The axis may be an off-center axis. The substrate may be configured to rotate at any rotational velocity described herein, such as any rotational velocity described herein with respect to method 200 or 1400.

The substrate may be configured to undergo a change in relative position with respect to first or second longitudinal axes 315 and 325. For instance, the substrate may be translatable along the first and/or second longitudinal axes (as shown in FIG. 3). Alternatively, the substrate may be stationary along the first and/or second longitudinal axes. Alternatively or in combination, the substrate may be translatable along the axis (as shown in FIG. 4). Alternatively or in combination, the substrate may be stationary along the axis. The relative position of the substrate may be configured to alternate between positions. The relative position of the substrate may be configured to alternate between positions with respect to one or more of the longitudinal axes or the axis. The relative position of the substrate may be configured to alternate between positions with respect to any of the fluid channels described herein. For instance, the relative position of the substrate may be configured to alternate between a first position and a second position. The relative position of the substrate may be configured to alternate between at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 positions. The relative position of the substrate may be configured to alternate between a number of positions that is within a range defined by any two of the preceding values. The first or second longitudinal axes may be substantially perpendicular with the axis. The first or second longitudinal axes may be substantially parallel with the axis. The first or second longitudinal axes may be coincident with the axis.

The system may comprise a first fluid channel 330. The first fluid channel may comprise a first fluid outlet port 335. The first fluid outlet port may be configured to dispense a first fluid to the array. The first fluid outlet port may be configured to dispense any fluid described herein, such as any solution described herein. The first fluid outlet port may be external to the substrate. The first fluid outlet port may not contact the substrate. The first fluid outlet port may be a nozzle. The first fluid outlet port may have an axis that is substantially coincident with the axis. The first fluid outlet port may have an axis that is substantially parallel to the axis.

The system may comprise a second fluid channel 340. The second fluid channel may comprise a second fluid outlet port 345. The second fluid outlet port may be configured to dispense a second fluid to the array. The second fluid outlet port may be configured to dispense any fluid described herein, such as any solution described herein. The second fluid outlet port may be external to the substrate. The second fluid outlet port may not contact the substrate. The second fluid outlet port may be a nozzle. The second fluid outlet port may have an axis that is substantially coincident with the axis. The second fluid outlet port may have an axis that is substantially parallel to the axis.

The first and second fluids may comprise different types of reagents. For instance, the first fluid may comprise a first type of nucleotide, such as any nucleotide described herein, or a nucleotide mixture. The second fluid may comprise a second type of nucleotide, such as any nucleotide described herein, or a nucleotide mixture. Alternatively, the first and second fluids may comprise the same type of reagents (e.g., same type of fluid is dispensed through multiple fluid outlet ports (e.g., nozzles) to increase coating speed). Alternatively or in combination, the first or second fluid may comprise a washing reagent. The first fluid channel 330 and the second fluid channel 340 may be fluidically isolated. Beneficially, where the first and second fluids comprise different types of reagents, each of the different reagents may remain free of contamination from the other reagents during dispensing.

The first fluid outlet port may be configured to dispense the first fluid during rotation of the substrate. The second fluid outlet port may be configured to dispense the second fluid during rotation of the substrate. The first and second fluid outlet ports may be configured to dispense at non-overlapping times. Alternatively, the first and second fluid outlet ports may be configured to dispense at overlapping times, such as when the first fluid and the second fluid comprise the same type of reagents. The substrate may be configured to rotate with a different speed or a different number of rotations when the first and second outlet ports dispense. Alternatively, the substrate may be configured to rotate with the same speed and number of rotations when the first and second outlet ports dispense. During rotation, the array may be configured to direct the first fluid in a substantially radial direction away from the axis. The first fluid outlet port may be configured to direct the first fluid to the array during at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, or at least 1,000,000 full rotations of the substrate. The first fluid outlet port may be configured to direct the first fluid to the array during a number of full rotations that is within a range defined by any two of the preceding values.

The system may comprise a third fluid channel 350 comprising a third fluid outlet port 355 configured to dispense a third fluid. The system may comprise a fourth fluid channel 360 comprising a fourth fluid outlet port 365 configured to dispense a fourth fluid. The third and fourth fluid channels may be similar to the first and second fluid channels described herein. The third and fourth fluids may be the same or different fluids as the first and/or second fluids. In some cases, at least 1, 2, 3, 4, 5, 6, 7, 8, 9, 10, 15, 20 or more fluids (or reagents) may be employed. For example, 5-10 fluids (or reagents) may be employed.

Although FIG. 3 shows a change in position of the substrate, as an alternative or in addition to, one or more of the first, second, third, and fourth fluid channels may be configured to undergo a change in position. For instance, any of the first, second, third, or fourth fluid channel may be translatable along the first and/or second longitudinal axes. Alternatively, any of the first, second, third, or fourth fluid channel may be stationary along the first and/or second longitudinal axes. Alternatively or in addition, any of the first, second, third, or fourth fluid channel may be translatable along the axis. Alternatively or in addition, any of the first, second, third, or fourth fluid channel may be stationary along the axis.

The relative position of one or more of the first, second, third, and fourth fluid channels may be configured to alternate between positions with respect to one or more of the longitudinal axes or the axis. For instance, the relative position of any of the first, second, third, or fourth fluid channel may be configured to alternate between a first position and a second position (e.g., by moving such channel, by moving the substrate, or by moving the channel and the substrate). The relative position of any of the first, second, third, or fourth fluid channel may be configured to alternate between at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more positions. The relative position of any of the first, second, third, or fourth fluid channel may be configured to alternate between a number of positions that is within a range defined by any two of the preceding values. The first or second longitudinal axes may be substantially perpendicular to the axis. The first or second longitudinal axes may be substantially parallel to the axis. The first or second longitudinal axes may be coincident with the axis.

Figure 4A:
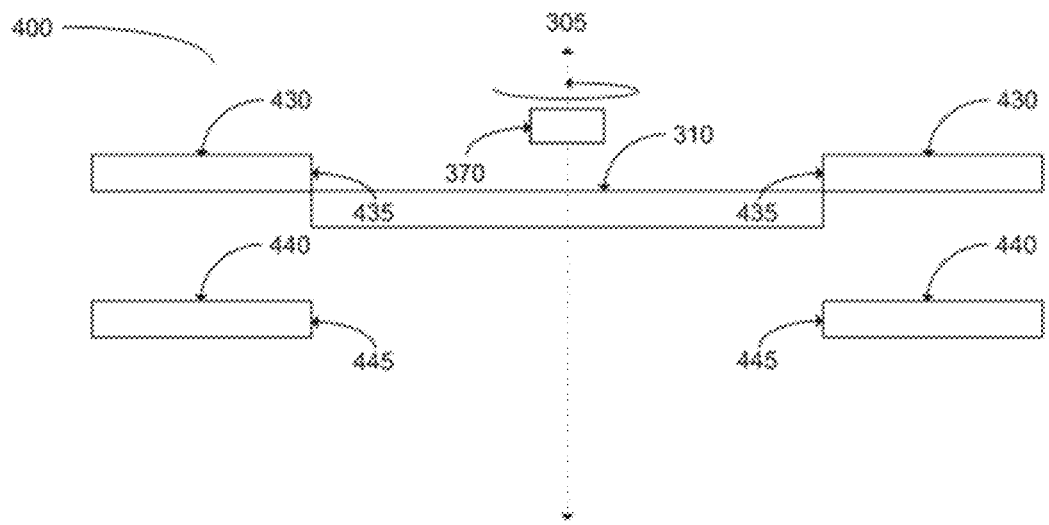
FIG. 4A shows a system for sequencing a nucleic acid molecule in a first vertical level.
Figure 4B:
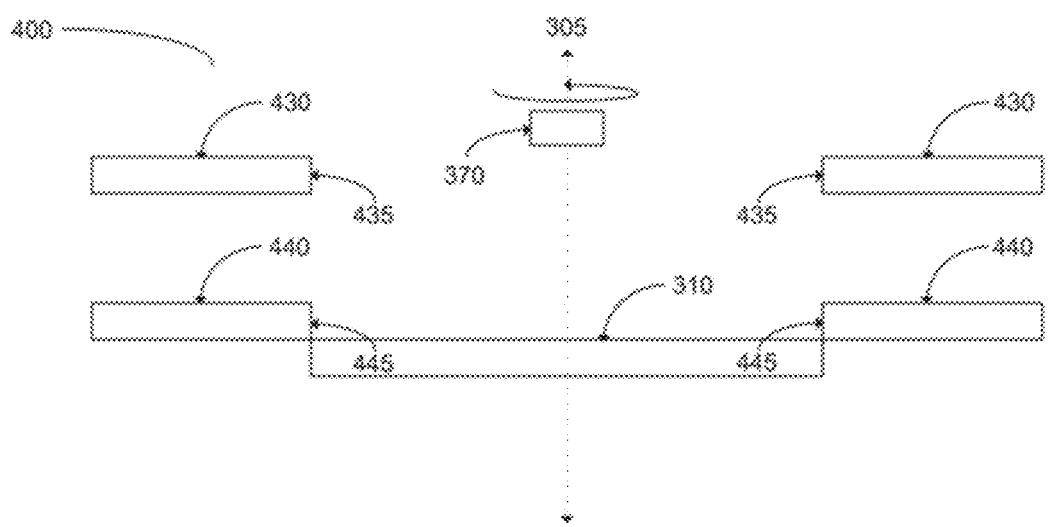
FIG. 4B shows a system for sequencing a nucleic acid molecule in a second vertical level.

In some instances, the system may comprise one or more fluid channels for receiving fluid from the substrate (not shown in FIG. 3). Referring to FIG. 4A-FIG. 4B, a fifth fluid channel 430 may comprise a first fluid inlet port 435. The first fluid inlet port may be located at a first level of the axis (as shown in FIG. 4). In some instances, the first fluid inlet port may surround the periphery of the substrate 310 (e.g., circularly). The first fluid inlet port may be downstream of and in fluid communication with the substrate 310 when the substrate is in a first position, such as with respect to the axis. The fifth fluid channel may be in fluid communication with the first fluid channel 330 (as shown in FIG. 3). For example, the first fluid inlet port may be configured to receive a solution passing from the first fluid outlet port to the substrate and thereafter off the substrate (e.g., due to inertial forces during rotation of the substrate). For instance, the first fluid inlet port may be configured to receive the solution in a recycling process such as the recycling process described herein with respect to method 200 or 1400. In some instances, the solution received by the fifth fluid channel via the first fluid inlet port may be fed back (e.g., after filtering) to the first fluid channel to be dispensed via the first fluid outlet port to the substrate. The fifth fluid channel and the first fluid channel may define at least part of a first cyclic fluid flow path. The first cyclic fluid flow path may comprise a filter, such as a filter described herein with respect to method 200 or 1400. The filter may be a molecular filter. In other instances, the solution received by the fifth fluid channel may be fed back (e.g., after filtering) to different fluid channels (other than the first fluid channel) to be dispensed via different fluid outlet ports.

The system may comprise a sixth fluid channel 440. The sixth fluid channel may comprise a second fluid inlet port 445. The second fluid inlet port may be located at a second level of the axis (as shown in FIG. 4). In some instances, the second fluid inlet port may surround the periphery of the substrate 310. The second fluid inlet port may be downstream of and in fluid communication with the substrate 310 when the substrate is in a second position, such as with respect to the axis. The sixth fluid channel may be in fluid communication with the second fluid channel 340. For example, the second fluid inlet port may be configured to receive a solution passing from the second fluid outlet port to the substrate and thereafter off the substrate. For instance, the second fluid inlet port may be configured to receive the solution in a recycling process such as the recycling process described herein with respect to method 200 or 1400. In some instances, the solution received by the sixth fluid channel via the second fluid inlet port may be fed back (e.g., after filtering) to the second fluid channel to be dispensed via the second fluid outlet port to the substrate. The sixth fluid channel and the second fluid channel may define at least part of a second cyclic fluid flow path. The second cyclic fluid flow path may comprise a filter, such as a filter described herein with respect to method 200 or 1400. The filter may be a molecular filter.

The system may comprise a shield (not shown) that prevents fluid communication between the substrate and the second fluid inlet port when the substrate is in the first position and between the substrate and the first fluid inlet port when the substrate is in the second position.

The system may further comprise one or more detectors 370. The detectors may be optical detectors, such as one or more photodetectors, one or more photodiodes, one or more avalanche photodiodes, one or more photomultipliers, one or more photodiode arrays, one or more avalanche photodiode arrays, one or more cameras, one or more charged coupled device (CCD) cameras, or one or more complementary metal oxide semiconductor (CMOS) cameras. The cameras may be TDI or other continuous area scanning detectors described herein, including, for example, TDI line-scan cameras. The detectors may be fluorescence detectors. The detectors may be in sensing communication with the array. For instance, the detectors may be configured to detect a signal from the array. The signal may be an optical signal. The signal may be a fluorescence signal. The detectors may be configured to detect the signal from the substrate during rotation of the substrate. The detectors may be configured to detect the signal from the substrate when the substrate is not rotating. The detectors may be configured to detect the signal from the substrate following termination of the rotation of the substrate. FIG. 3 shows an example region 375 on the substrate that is optically mapped to the detector.

Figure 11A:
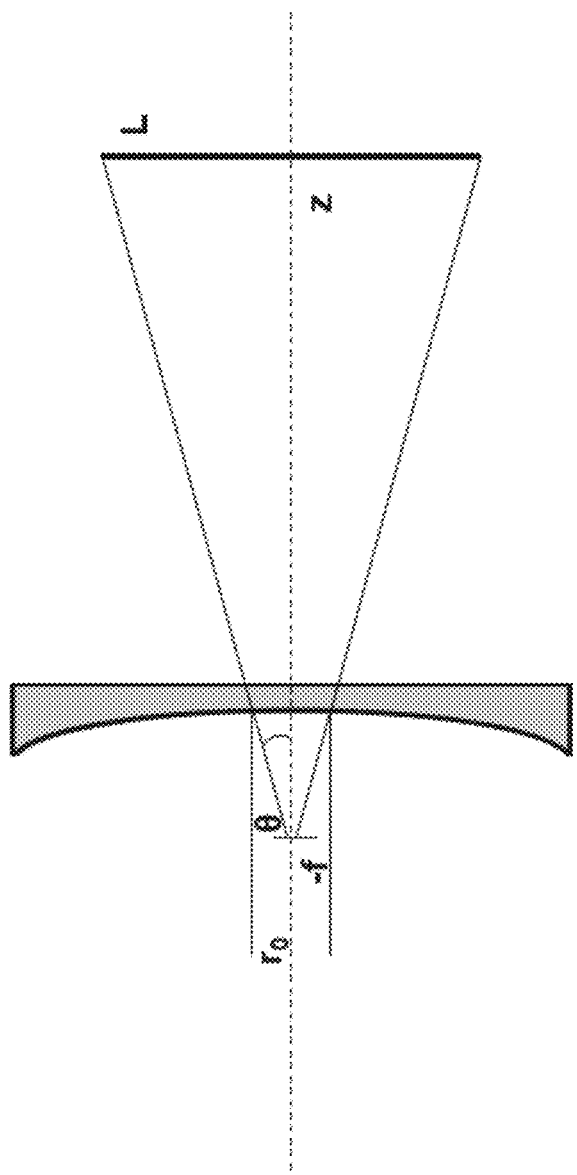
FIG. 11A illustrates schematically a scheme for expanding a laser beam to provide a laser line.
Figure 11B:
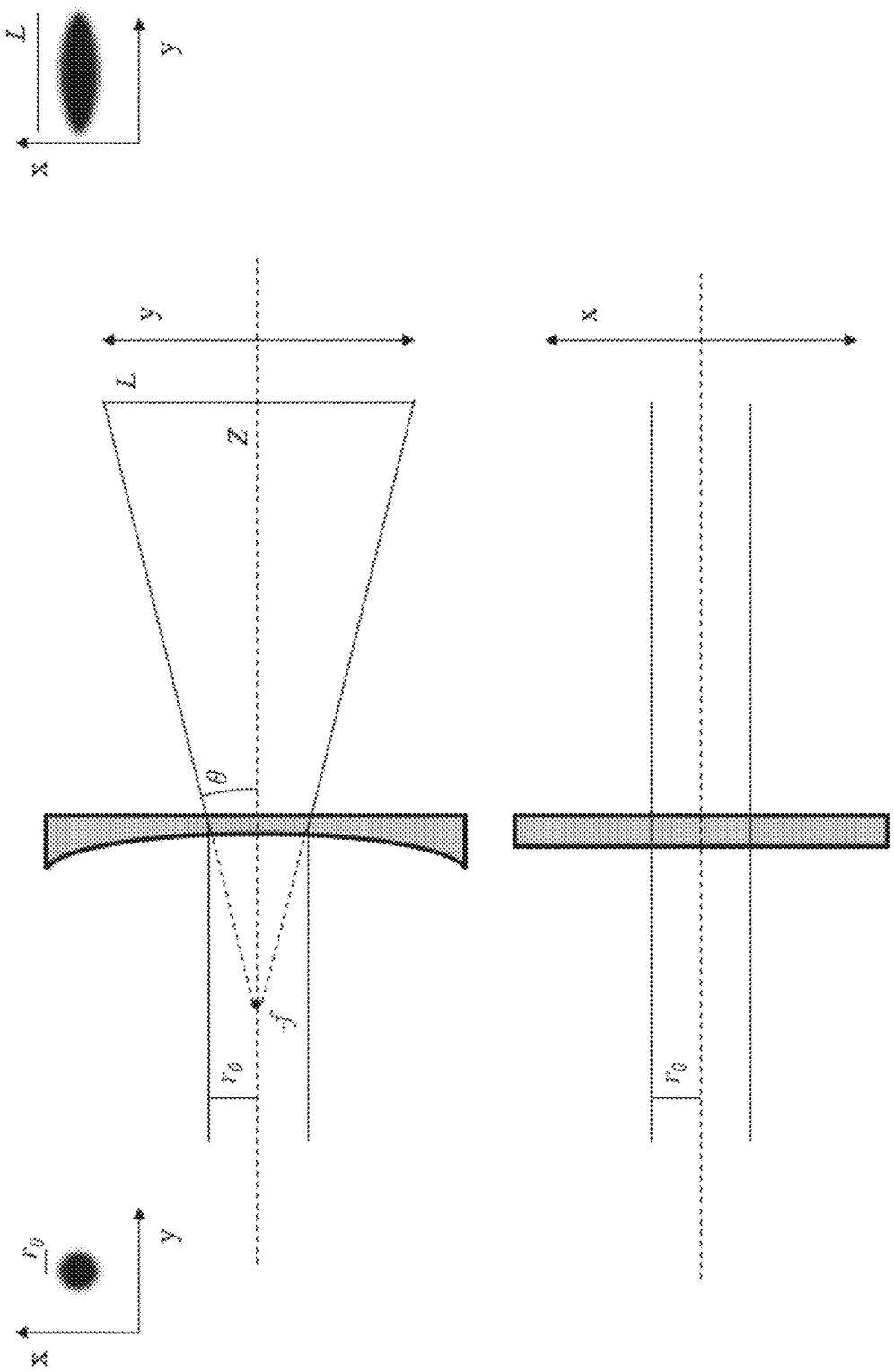
FIG. 11B illustrates schematically a scheme for expanding a laser beam to provide a laser line.

The system may comprise one or more sources (not shown in FIG. 3) configured to deliver electromagnetic radiation to the substrate. The sources may comprise one or more optical sources (e.g., illumination sources). The sources may comprise one or more incoherent or coherent optical sources. The sources may comprise one or more narrow bandwidth or broadband optical sources. The sources may be configured to emit optical radiation having a bandwidth of at most 1 hertz (Hz), at most 2 Hz, at most 5 Hz, at most 10 Hz, at most 20 Hz, at most 50 Hz, at most 100 Hz, at most 200 Hz, at most 500 Hz, at most 1 kilohertz (kHz), at most 2 kHz, at most 5 kHz, at most 10 kHz, at most 20 kHz, at most 50 kHz, at most 100 kHz, at most 200 kHz, at most 500 kHz, at most 1 megahertz (MHz), at most 2 MHz, at most 5 MHz, at most 10 MHz, at most 20 MHz, at most 50 MHz, at most 100 MHz, at most 200 MHz, at most 500 MHz, at most 1 gigahertz (GHz), at most 2 GHz, at most 5 GHz, at most 10 GHz, at most 20 GHz, at most 50 GHz, at most 100 GHz, or a bandwidth that is within a range defined by any two of the preceding values. The source may comprise one or more light emitting diodes (LEDs). The sources may comprise one or more lasers. The sources may comprise one or more single-mode laser sources. The sources may comprise one or more multi-mode laser sources. The sources may comprise one or more laser diodes. A laser may be a continuous wave laser or a pulsed laser. A beam of light emitted by a laser may be a Gaussian or approximately Gaussian beam, which beam may be manipulated using one or more optical elements (e.g., mirrors, lenses, prisms, waveplates, etc.). For example, a beam may be collimated. In some cases, a beam may be manipulated to provide a laser line (e.g., using one or more Powell lenses or cylindrical lenses). FIG. 11A shows an example of beam shaping using a cylindrical lens to provide a laser line. A collimated beam having a radius $r_0$ is incident upon a cylindrical plano-concave lens having a focal length $-f$. The beam will expand with a half-angle $\theta$ equivalent to $r_0/f$. The laser line will have a thickness of approximately $2r_0$ and a length L of approximately $2(r_0/f)(z+f)$ at a distance z from the lens. In some embodiments, a beam thickness may be expanded along a single axis, for example the y-axis, while the beam thickness remains substantially unchanged along a second axis, for example the x-axis, as shown in FIG. 11B.

Figure 11C:
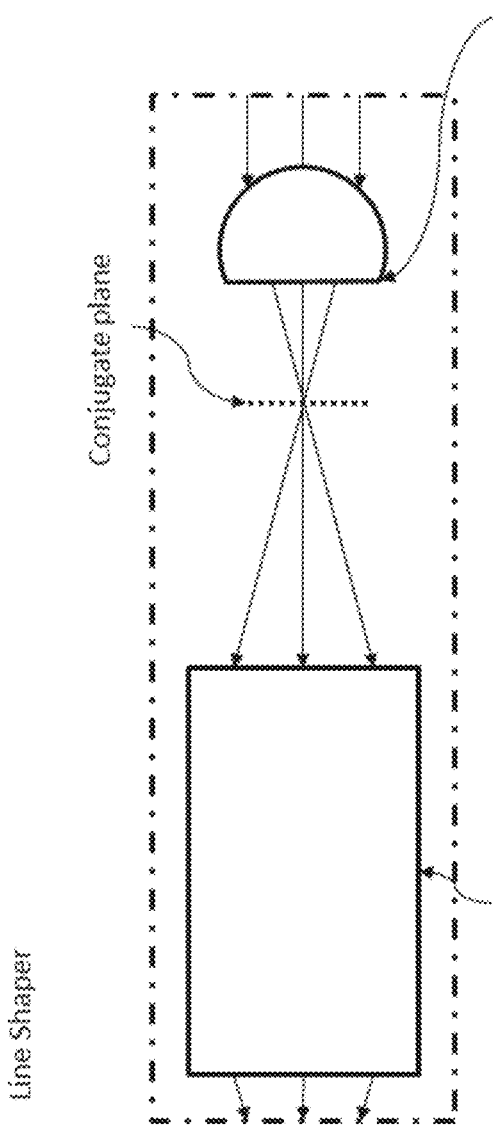
FIG. 11C shows an optical system for shaping a laser beam.

Expansion along a single axis may be achieved using a cylindrical lens, for example a plano-concave cylindrical lens having a focal length of −f along the axis of expansion. The beam shaping lens may be part of a line shaper element, as shown in FIG. 11C. The line shaper element may comprise one or more optical elements configured to expand a beam along a single axis. The line shaper element may further comprise one or more optical elements to collimate the expanded beam, for example a second cylindrical lens. In some embodiments, the second cylindrical lens is a plano-convex cylindrical lens. The expanded beam may result in a laser line, as shown in FIG. 11B. A laser line may impinge directly on a substrate or may be projected onto the substrate such that is approximately perpendicular to a central axis about which the open substrate may rotate.

The sources (e.g., optical or illumination sources) of a system may be configured to emit light comprising one or more wavelengths in the ultraviolet (about 100 nm to about 400 nm), visible (about 400 nm to about 700 nm), or infrared (about 700 nm to about 10,000 nm) regions of the electromagnetic spectrum, or any combination therefore. For instances, the sources may emit radiation comprising one or more wavelengths in the range from 600 nm to 700 nm. The sources may emit radiation, either individually or in combination, having an optical power of at least 0.05 watts (W), at least 0.1 W, at least 0.2 W, at least 0.5 W, at least 1 W, at least 2 W, at least 5 W, at least 10 W, or an optical power that is within a range defined by any two of the preceding values. The sources may be configured to interact with molecules on the substrate to generate detectable optical signals that may be detected by the optical detectors. For instance, the sources may be configured to generate optical absorption, optical reflectance, scattering, phosphorescence, fluorescence, or any other optical signal described herein.

The system may comprise a seventh, eighth, ninth, tenth, eleventh, twelfth, thirteenth, fourteenth, fifteenth, sixteenth, seventeenth, eighteenth, nineteenth, or twentieth fluid channel. Each fluid channel may comprise a fluid outlet port or a fluid inlet port in fluid communication with the substrate. For instance, the ninth, tenth, thirteenth, fourteenth, seventeenth, or eighteenth fluid channel may comprise a fluid outlet port. The seventh, eighth, eleventh, twelfth, fifteenth, sixteenth, nineteenth, or twentieth fluid channel may comprise a fluid inlet port. Alternatively, the system may comprise more than twenty fluid channels comprising a fluid outlet port or a fluid inlet port.

Thus, the system may comprise fifth, sixth, seventh, eighth, ninth, or tenth fluid outlet ports. The fifth, sixth, seventh, eighth, ninth, or tenth fluid outlet ports may be configured to dispense fifth, sixth, seventh, eighth, ninth, or tenth fluids to the array. The fifth, sixth, seventh, eighth, ninth, or tenth fluid outlet ports may be configured to dispense any fluid described herein, such as any solution described herein. The fifth, sixth, seventh, eighth, ninth, or tenth fluid outlet ports may be similar to the first, second, third, or fourth fluid outlet ports described herein. Alternatively, the system may comprise more than ten fluid outlet ports.

The fluid channels may be fluidically isolated from one another. For instance, the fluid channels may be fluidically isolated upstream of the first, second, third, fourth, fifth, sixth, seventh, eighth, ninth, or tenth fluid outlet ports. The fifth, sixth, seventh, eighth, ninth, or tenth fluid outlet ports may be external to the substrate. The fifth, sixth, seventh, eighth, ninth, or tenth fluid outlet ports may not contact the substrate. The fifth, sixth, seventh, eighth, ninth, or tenth fluid outlet ports may be a nozzle.

The system may comprise third, fourth, fifth, sixth, seventh, eighth, ninth, or tenth fluid inlet ports. The third, fourth, fifth, sixth, seventh, eighth, ninth, or tenth fluid inlet ports may be in fluid communication with the substrate when the substrate is in a third, fourth, fifth, sixth, seventh, eighth, ninth, or tenth position (e.g., with respect to the axis), respectively. Alternatively, the system may comprise more than ten fluid inlet ports.

The ninth, tenth, thirteenth, fourteenth, seventeenth, or eighteenth fluid channel may be in fluid communication with the seventh, eighth, eleventh, twelfth, fifteenth, or sixteenth, fluid channel, respectively; each pair of fluid channels may define at least part of a third, fourth, fifth, sixth, seventh, eighth, ninth, or tenth cyclic fluid flow path, respectively. Each cyclic fluid flow path may be configured similarly to the first or second cyclic fluid flow paths described herein, with the fluid inlet port of the cyclic fluid flow path configured to receive a solution passing from the fluid outlet port of the cyclic fluid flow path to the substrate. Each cyclic fluid flow path may be configured to receive the solution in a recycling process as described herein. Each cyclic fluid flow path may comprise a filter as described herein.

The fifth, sixth, seventh, eighth, ninth, or tenth fluids may comprise different types of reagents. For instance, the fifth, sixth, seventh, eighth, ninth, or tenth fluid may comprise a fifth, sixth, seventh, eighth, ninth, or tenth type of nucleotide, respectively, such as any nucleotide described herein. Alternatively or in combination, the fifth, sixth, seventh, eighth, ninth, or tenth fluid may comprise a washing reagent.

The fifth, sixth, seventh, eighth, ninth, or tenth fluid outlet port may be configured to dispense the fifth, sixth, seventh, eighth, ninth, or tenth fluid, respectively, during rotation of the substrate. The fifth, sixth, seventh, eighth, ninth, or tenth fluid outlet ports may be configured to dispense at overlapping or non-overlapping times.

FIG. 4A shows a system 400 for sequencing a nucleic acid molecule in a first vertical level. The system may be substantially similar to system 300 described herein or may differ from system 300 in the arrangement of one or more of its elements. The system 400 may comprise substrate 310 described herein. The system 400 may utilize vertical motion parallel to the axis 305 to expose (e.g., make available fluid communication) the substrate 310 to different fluid channels. The system may comprise first fluid channel 330 and first fluid outlet port 335 described herein. The system may comprise second fluid channel 340 and second fluid outlet port 345 described herein. The system may comprise third fluid channel 350 and third fluid outlet port 355 described herein. The system may comprise fourth fluid channel 360 and fourth fluid outlet port 365 described herein. The system may comprise detector 370 described herein. The detector may be in optical communication with the region shown. The system may comprise any optical source described herein (not shown in FIG. 4A).

The fifth fluid channel 430 and first fluid inlet port 435 may be arranged at a first level along the vertical axis, as shown in FIG. 4A and FIG. 4B. The sixth fluid channel 440 and second fluid inlet port 445 may be arranged at a second level along the vertical axis. In this manner, the system may be viewed as comprising first and second fluid flow paths, with each fluid flow path located at a different vertical level. The substrate 310 may be vertically movable between the first level and the second level, from the first level to the second level, and from the second level to the first level. As an alternative, the substrate may be vertically fixed, but the levels may be vertically movable with respect to the substrate 310. As another alternative, the substrate and the levels may be vertically movable.

The system 400 may comprise multiple levels. The levels may be vertically orientated relative to one another. The system may include at least 2, 3, 4, 5, 6, 7, 8, 9, 10, 20, 30, 40, 50, 100 or more levels. Each level may include one or more sub-levels (e.g., an incremental level between any two levels). Each level may be for dispensing and/or recovering a different fluid (or reagent). Some levels may be for dispensing the same fluid (or reagent).

While in the first vertical level, the substrate may be in fluid communication with the fifth fluid channel and the first fluid inlet port, but not the sixth fluid channel and the second fluid inlet port. The substrate may be isolated from the sixth fluid channel and the second fluid inlet port by a shield (not shown), as described herein. A first fluid or first solution described herein may be dispensed to the substrate while the substrate is in this first vertical level. For example, any excess of the first solution spinning off the substrate may be received by the first fluid inlet port while the substrate is at the first vertical level. In another example, a washing solution (e.g., dispensed from a different fluid outlet port than the first fluid) spinning off the substrate with some of the first fluid may be received by the first fluid inlet port while the substrate is at the first vertical level. The substrate may then be moved to a second vertical level by vertically moving the substrate. Alternatively, the fifth or sixth fluid channels may be moved vertically. Alternatively or in addition, the substrate and one or more of the fluid channels may be moved relative to the other (e.g., along the axis).

FIG. 4B shows the system 400 for sequencing a nucleic acid molecule in a second vertical level. While in the second vertical level, the substrate may be in fluid communication with the sixth fluid channel and the second fluid inlet port, but not the fifth fluid channel and the first fluid inlet port. The substrate may be isolated from the fifth fluid channel and the first fluid inlet port by a shield (not shown), as described herein. A second fluid or second solution described herein may be dispensed to the substrate while the substrate is in this second vertical position. Alternatively, the first solution may be removed while the substrate is in the second vertical position. In some cases, the first solution may be recycled while the substrate is in the second vertical position. The substrate may then be moved back to the first vertical level, or to another vertical level described herein, by vertically moving the substrate. Alternatively, the fifth or sixth fluid channels may be moved vertically. Alternatively or in addition, the substrate and one or more of the fluid channels may be moved relative to the other (e.g., along the axis).

The third, fourth, fifth, sixth, seventh, eighth, ninth, or tenth fluid inlet ports may be located at third, fourth, fifth, sixth, seventh, eighth, ninth, or tenth vertical levels, respectively. The substrate may be moved to the third, fourth, fifth, sixth, seventh, eighth, ninth, or tenth vertical levels by vertically moving the substrate or by vertically moving the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth fluid flow channels. At any of the first, second, third, fourth, fifth, sixth, seventh, eighth, ninth, tenth or more vertical levels, any fluid solution described herein may be dispensed to the substrate. At any of the first, second, third, fourth, fifth, sixth, seventh, eighth, ninth, tenth or more vertical levels, any fluid solution described herein may be removed from the substrate. At any of the first, second, third, fourth, fifth, sixth, seventh, eighth, ninth, tenth or more vertical levels, any fluid solution described herein may be recycled from the substrate.

Figure 5A:
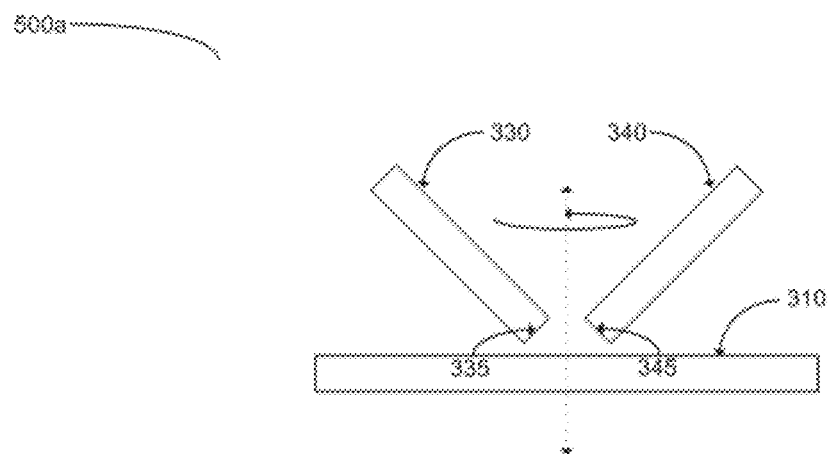
FIG. 5A shows a first example of a system for sequencing a nucleic acid molecule using an array of fluid flow channels.

FIG. 5A shows a first example of a system 500a for sequencing a nucleic acid molecule using an array of fluid flow channels. The system may be substantially similar to system 300 or 400 described herein and may differ from system 300 or 400 in the arrangement of one or more of its elements. The system 500a may utilize a geometrical arrangement of a plurality of fluid flow channels to expose the substrate to different fluids. The system 500a may comprise substrate 310 described herein. The system may comprise first fluid channel 330 and first fluid outlet port 335 described herein. The system may comprise second fluid channel 340 and second fluid outlet port 345 described herein. The system may comprise fifth fluid channel 430 and first fluid inlet port 435 described herein (not shown in FIG. 5A). The system may comprise sixth fluid channel 440 and second fluid inlet port 445 described herein (not shown in FIG. 5A). The system may comprise detector 370 described herein (not shown in FIG. 5A). The system may comprise any illumination source described herein (not shown in FIG. 5A).

The first fluid channel and first fluid outlet port may be arranged at a first position, as shown in FIG. 5A. The second fluid channel and second fluid outlet port may be arranged at a second position. The system may be configured to dispense a first fluid from the first fluid outlet port and a second fluid from the second fluid outlet port.

The system may comprise any of third, fourth, seventh, eighth, ninth, tenth, eleventh, twelfth, thirteenth, fourteenth, fifteenth, sixteenth, seventeenth, eighteenth, nineteenth, or twentieth fluid channels described herein. The system may comprise any of third, fourth, fifth, sixth, seventh, eighth, ninth, or tenth fluid outlet ports described herein. The system may comprise any of third, fourth, fifth, sixth, seventh, eighth, ninth, or tenth fluid inlet ports described herein.

The third, fourth, fifth, sixth, seventh, eighth, ninth, or tenth fluid outlet ports may be located at third, fourth, fifth, sixth, seventh, eighth, ninth, or tenth positions, respectively. The system may be configured to dispense a third, fourth, fifth, sixth, seventh, eighth, ninth, or tenth fluid from the third, fourth, fifth, sixth, seventh, eighth, ninth, or tenth fluid outlet port, respectively.

Any two or more of the first, second, third, fourth, seventh, eighth, ninth, tenth, eleventh, twelfth, thirteenth, fourteenth, fifteenth, sixteenth, seventeenth, eighteenth, nineteenth, twentieth, or more fluid channels may form an array of fluid flow channels. The array of fluid flow channels may be moveable. Alternatively, the array of fluid flow channels may be at a fixed location with respect to the substrate. Each fluid flow channel of the array of fluid flow channels may be positioned such that a longitudinal axis of the fluid flow channel forms an angle with the rotational axis of the substrate. The angle may have a value of at least 0 degrees, at least 5 degrees, at least 10 degrees, at least 15 degrees, at least 20 degrees, at least 25 degrees, at least 30 degrees, at least 35 degrees, at least 40 degrees, at least 45 degrees, at least 50 degrees, at least 55 degrees, at least 60 degrees, at least 65 degrees, at least 70 degrees, at least 75 degrees, at least 80 degrees, at least 85 degrees, or at least 90 degrees. The angle may have a value that is within a range defined by any two of the preceding values. Each fluid channel of the array of fluid channels may make a similar angle with the substrate. Alternatively, one or more fluid channels may make different angles with the substrate.

Figure 5B:
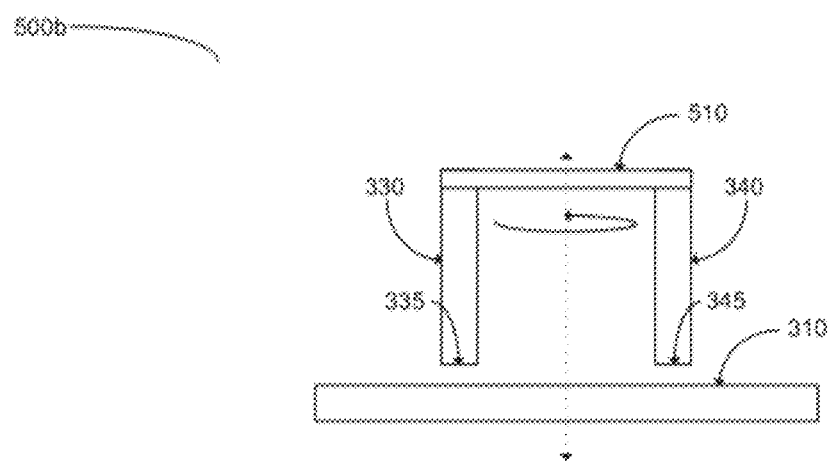
FIG. 5B shows a second example of a system for sequencing a nucleic acid molecule using an array of fluid flow channels.

FIG. 5B shows a second example of a system 500b for sequencing a nucleic acid molecule using an array of fluid flow channels.

The system may be substantially similar to system 300 or 400 described herein and may differ from system 300 or 400 in the arrangement of one or more of its elements. The system 500b may utilize a plurality of fluid flow channels configured to move relative to the substrate to expose the substrate to different fluids. The system 500b may comprise substrate 310 described herein. The system may comprise first fluid channel 330 and first fluid outlet port 335 described herein. The system may comprise second fluid channel 340 and second fluid outlet port 345 described herein. The system may comprise fifth fluid channel 430 and first fluid inlet port 435 described herein (not shown in FIG. 5B). The system may comprise sixth fluid channel 440 and second fluid inlet port 445 described herein (not shown in FIG. 5B). The system may comprise detector 370 described herein (not shown in FIG. 5B). The system may comprise any optical source described herein (not shown in FIG. 5B).

The first fluid channel and first fluid outlet port may be attached to a fluid dispenser 510. The fluid dispenser may be a moveable fluid dispenser, such as comprising a moveable gantry arm, as shown in FIG. 5B. As an alternative, the fluid dispenser may be fixed or stationary. The fluid dispenser may be configured to move to a first position to dispense a first fluid from the first fluid outlet port. The second fluid channel and second fluid outlet port may also be attached to the fluid dispenser. The fluid dispenser may be configured to move to a second position to dispense a second fluid from the second fluid outlet port.

The system may comprise any of third, fourth, seventh, eighth, ninth, tenth, eleventh, twelfth, thirteenth, fourteenth, fifteenth, sixteenth, seventeenth, eighteenth, nineteenth, or twentieth fluid channels described herein. The system may comprise any of third, fourth, fifth, sixth, seventh, eighth, ninth, or tenth fluid outlet ports described herein. The system may comprise any of third, fourth, fifth, sixth, seventh, eighth, ninth, or tenth fluid inlet ports described herein.

The third, fourth, fifth, sixth, seventh, eighth, ninth, or tenth fluid outlet ports may be attached to the fluid dispenser. The fluid dispenser may be configured to move to a third, fourth, fifth, sixth, seventh, eighth, ninth, or tenth position to dispense a third, fourth, fifth, sixth, seventh, eighth, ninth, or tenth fluid from the third, fourth, fifth, sixth, seventh, eighth, ninth, or tenth fluid outlet port, respectively. Alternatively, the fluid dispenser may be kept stationary and the substrate 310 may be moved to different positions to receive different fluids.

Figure 6:
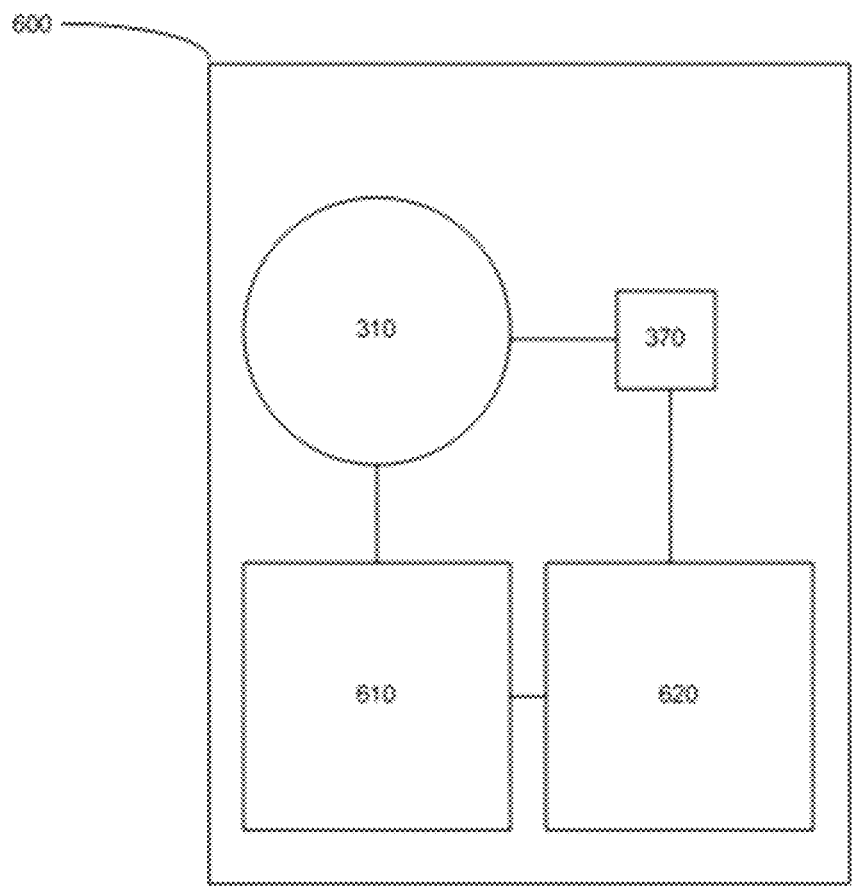
FIG. 6 shows a computerized system for sequencing a nucleic acid molecule.

FIG. 6 shows a computerized system 600 for sequencing a nucleic acid molecule. The system may comprise a substrate 310, such as a substrate described herein with respect to method 200 or 1400, or system 300. The system may further comprise a fluid flow unit 610. The fluid flow unit may comprise any element associated with fluid flow described herein, such as any or all of elements 330, 335, 340, 345, 350, 355, 360, 365, 430, 435, 440, 445, and 370 described herein with respect to system 300, 400, 500a, or 500b. The fluid flow unit may be configured to direct a solution comprising a plurality of nucleotides described herein to an array of the substrate prior to or during rotation of the substrate. The fluid flow unit may be configured to direct a washing solution described herein to an array of the substrate prior to or during rotation of the substrate. In some instances, the fluid flow unit may comprise pumps, compressors, and/or actuators to direct fluid flow from a first location to a second location. With respect to method 1400, the fluid flow system may be configured to direct any solution to the substrate 310. With respect to method 1400, the fluid flow system may be configured to collect any solution from the substrate 310. The system may further comprise a detector 370, such as any detector described herein with respect to system 300 or 400. The detector may be in sensing communication with the array of the substrate.

The system may further comprise one or more computer processors 620. The one or more processors may be individually or collectively programmed to implement any of the methods described herein. For instance, the one or more processors may be individually or collectively programmed to implement any or all operations of the methods of the present disclosure, such as method 200 or 1400. In particular, the one or more processors may be individually or collectively programmed to: (i) direct the fluid flow unit to direct the solution comprising the plurality of nucleotides across the array during or prior to rotation of the substrate; (ii) subject the nucleic acid molecule to a primer extension reaction under conditions sufficient to incorporate at least one nucleotide from the plurality of nucleotides into a growing strand that is complementary to the nucleic acid molecule; and (iii) use the detector to detect a signal indicative of incorporation of the at least one nucleotide, thereby sequencing the nucleic acid molecule.

While the rotational system has been described with respect to sequencing applications, such rotational schemes may be used for other applications (e.g., pre-sequencing applications, sample preparation, etc.), such as template seeding and surface amplification processes. For example, the reagents dispensed during or prior to rotation of the substrate may be tailored to the other applications. While the reagents dispensed to the substrate in the rotational system have been described with respect to nucleotides, any reagent that may react with a nucleic acid molecule (or any other molecule or cell) immobilized to the substrate, such as probes, adaptors, enzymes, and labelling reagents, may be dispensed to the substrate prior to, during, or subsequent to rotation to achieve high speed coating of the substrate with the dispensed reagents.

The systems described herein (such as any of systems 300, 400, 500a, or 500b, or any other system described herein), or any element thereof, may be environmentally controlled. For instance, the systems may be maintained at a specified temperature or humidity. The systems (or any element thereof) may be maintained at a temperature of at least 20 degrees Celsius (° C.), at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at most 100° C., at most 95° C., at most 90° C., at most 85° C., at most 80° C., at most 75° C., at most 70° C., at most 65° C., at most 60° C., at most 55° C., at most 50° C., at most 45° C., at most 40° C., at most 35° C., at most 30° C., at most 25° C., at most 20° C., or at a temperature that is within a range defined by any two of the preceding values.

Different elements of the system may be maintained at different temperatures or within different temperature ranges, such as the temperatures or temperature ranges described herein. Elements of the system may be set at temperatures above the dew point to prevent condensation. Elements of the system may be set at temperatures below the dew point to collect condensation.

Figure 7:
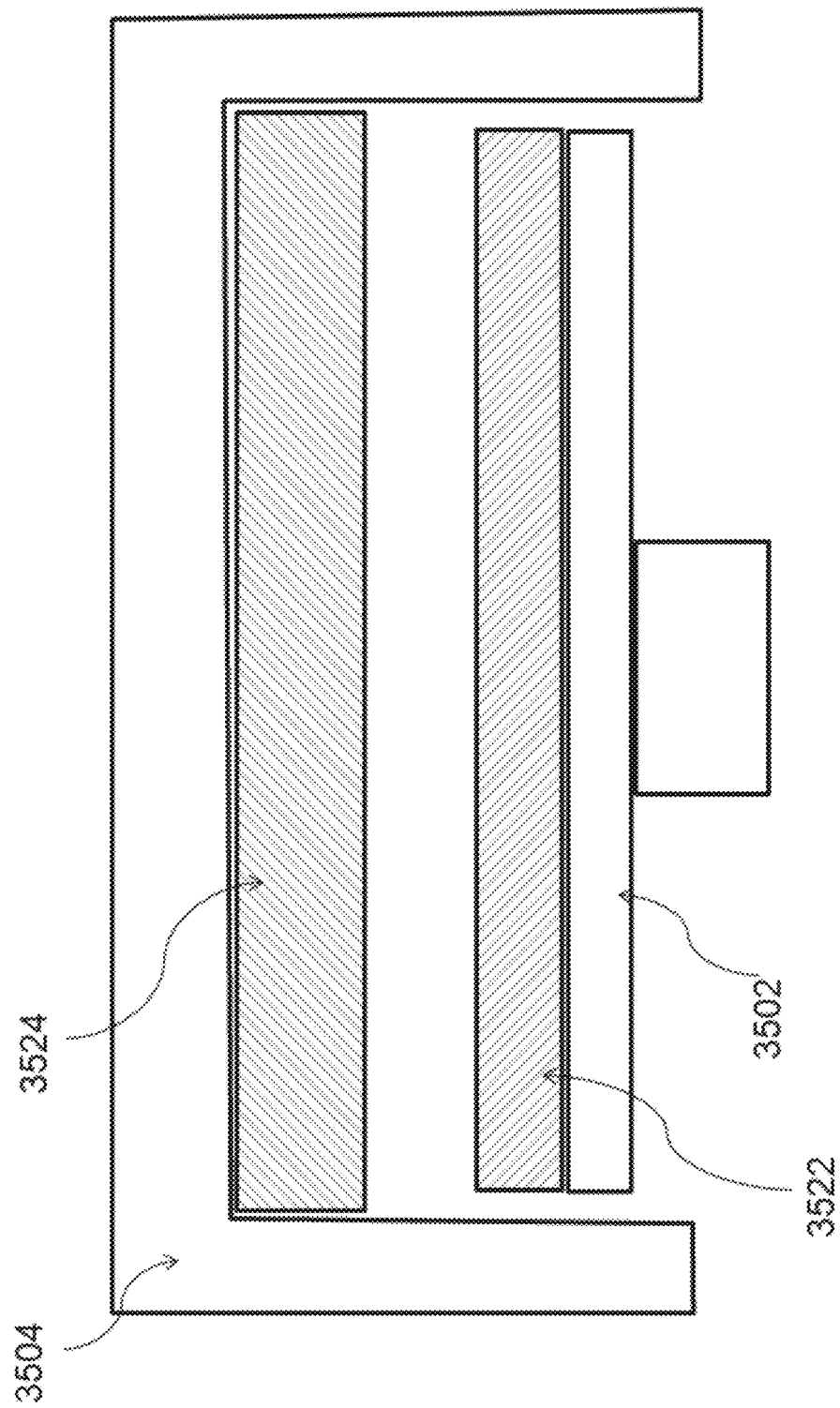
FIG. 7 illustrates a system with different environmental conditions in an open substrate system.

FIG. 7 illustrates a system with different environmental conditions in an open substrate system. An open substrate system may comprise a substrate 3502 and a container 3504 enclosing the substrate. The substrate 3502 may be any substrate described herein. The container 3504 may define a surrounding environment of the substrate 3502. In some instances, the surrounding environment may be confined and/or closed. In some instances, the surrounding environment may be sealed (e.g., hermetically sealed, frictionally sealed, pneumatically, etc.). In some instances, the surrounding environment may be sealed using a pressure differential (e.g., pneumatic pressure, mechanical pressure, etc.). The open substrate system may comprise at least two non-overlapping regions, a first region 3522 and a second region 3524, having different environmental conditions. In some instances, the first region 3522, contacting or in proximity to a surface of the substrate 3502, such as the surface that comprises one or more analytes as described herein, may be maintained at a first set of temperatures and first set of humidities. In some instances, the second region 3524, contacting or in proximity to a top portion of the container 3504 (or otherwise referred to herein as a lid or cover), may be maintained at a second set of temperatures and second set of humidities. The first set of temperatures and first set of humidities may be controlled such as to prevent or minimize evaporation of one or more reagents on the surface of the substrate. For example, the first set of temperatures and first set of humidities may be configured to prevent less than 80%, less than 70%, less than 60%, less than 50%, less than 40%, less than 30%, less than 20%, less than 10%, less than 5%, less than 4%, less than 3%, less than 2%, or less than 1% evaporation of the volume of the solution layer dispensed on the uncovered surface. The second set of temperatures and second set of humidities may also be controlled such as to enhance or restrict condensation. For example, the first set of temperatures may be the lowest temperatures within the surrounding environment of the open substrate system. For example, the second set of temperatures may be the highest temperatures within the surrounding environment of the open substrate system. In some instances, the environmental conditions of the different regions may be achieved by controlling the temperature of the enclosure. In some instances, the environmental conditions of the different regions may be achieved by controlling the temperature of selected parts or whole of the container. In some instances, the environmental conditions of the different regions may be achieved by controlling the temperature of selected parts or whole of the substrate. In some instances, the environmental conditions of the different regions may be achieved by controlling the temperature of reagents dispensed to the substrate. Any combination thereof may be used to control the environmental conditions of the different regions. Heat transfer may be achieved by any method, including for example, conductive, convective, and radiative methods. For example, the first region 3522 may be maintained at cooler temperatures by controlling the temperature of the substrate 3502, and the second region 3524 may be maintained at warmer temperatures by controlling the temperature of a top portion of the container 3504, via conduction.

The system may further comprise a reservoir beneath the substrate 3522 (not shown in FIG. 7). The reservoir may be configured to hold fluid. The reservoir may be configured to collect fluid, precipitation, or condensation from other surfaces, for example from the substrate 3522 or the top portion of the container 3504. Fluid may be removed from the reservoir. In some cases, fluid may be removed from the reservoir volumetrically. For example, fluid may be removed from the reservoir volumetrically to balance an amount of fluid added to the system. In some cases, fluid is continuously added to the system and fluid is continuously removed from the reservoir. The amount of fluid added may be equal to the amount of fluid removed. In some cases, a volume of fluid in the reservoir is held constant. The volume of fluid in the reservoir may be determined based on a relative humidity of the system. The relative humidity of the system may depend on the volume of fluid in the reservoir, the amount of fluid in the system, the temperature of the system, or any combination thereof.

Figure 47A:
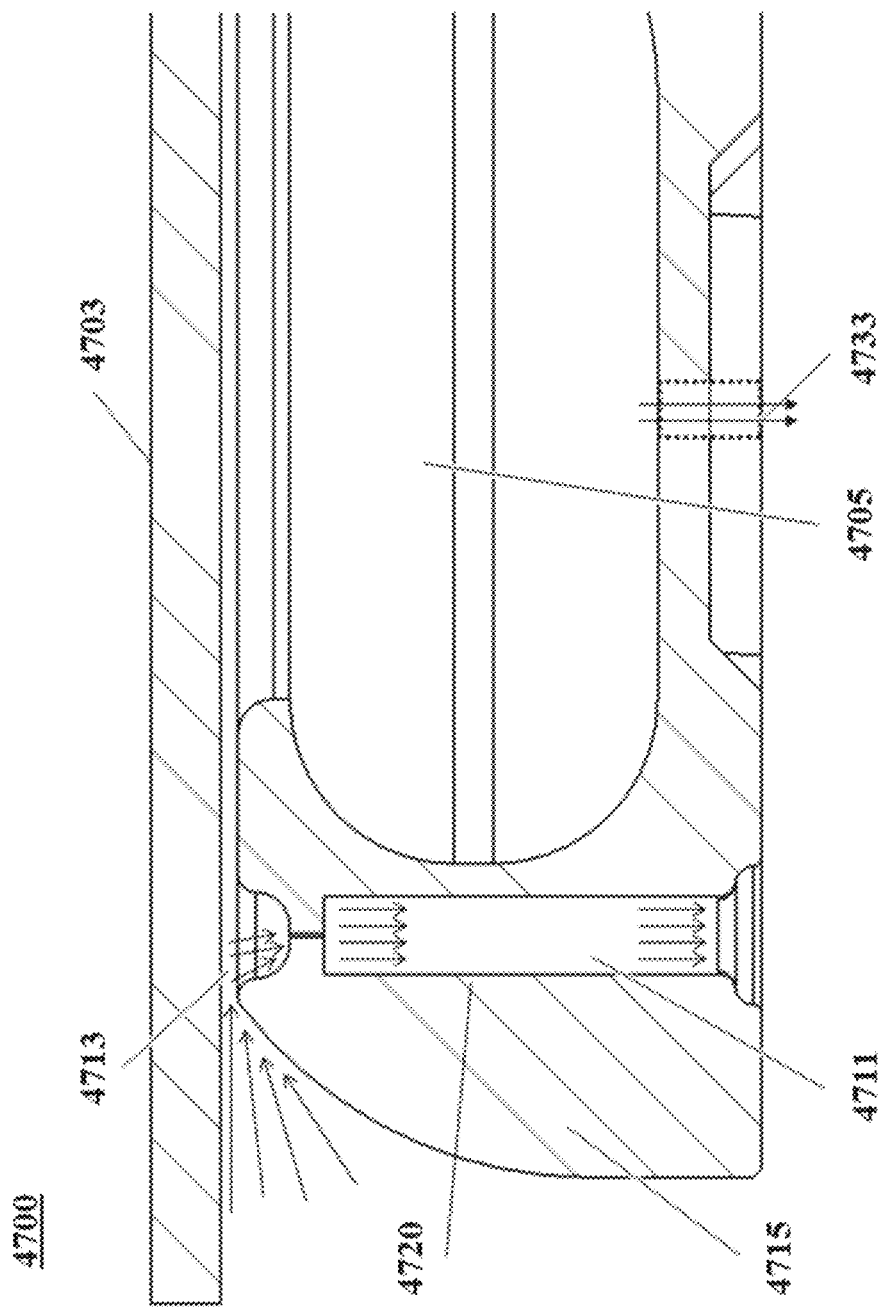
FIG. 47A illustrates a partial cross-sectional view of a barrier system maintaining a fluid barrier.
Figure 47B:
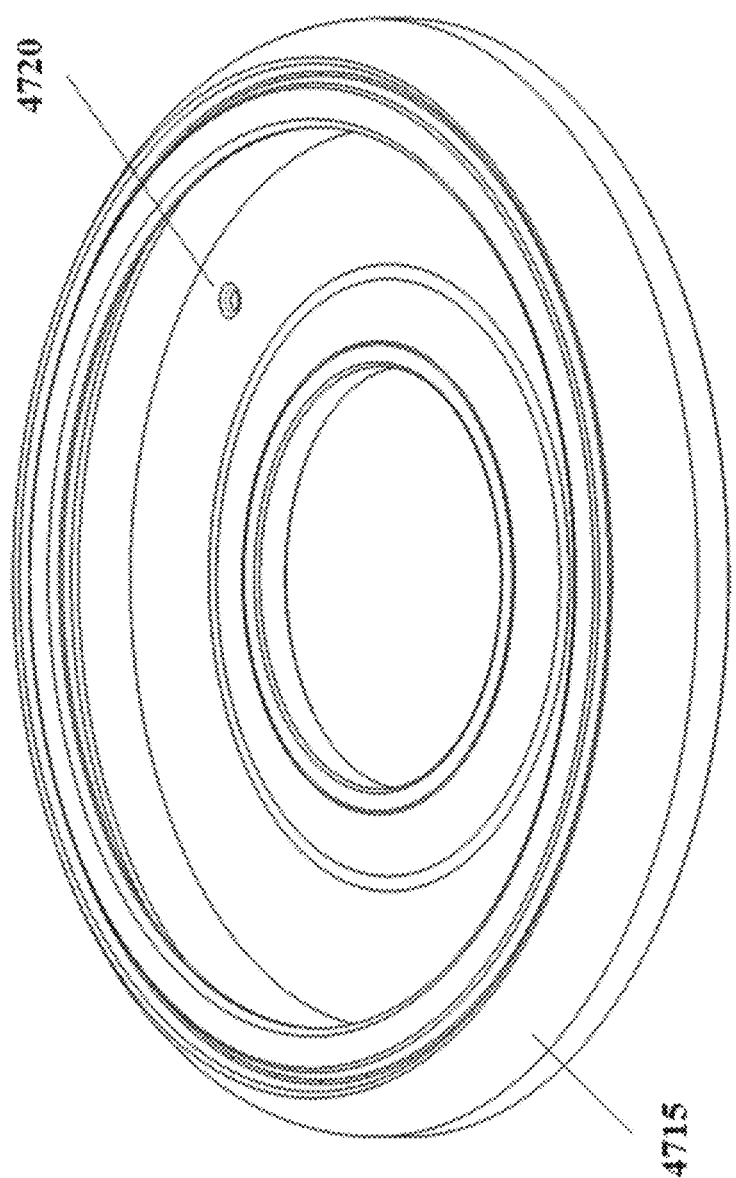
FIG. 47B illustrates a perspective view of a chamber of the barrier system of FIG. 47A.

An open substrate system of the present disclosure may comprise a barrier system configured to maintain a fluid barrier. FIG. 47A illustrates a partial cross-sectional view of a barrier system 4700 maintaining a fluid barrier 4713. FIG. 47B illustrates a perspective view of a chamber 4715 of the barrier system 4700. The barrier system 4700, and/or respective components thereof, may correspond to the system with different environmental conditions illustrated in FIG. 7, and/or respective components thereof. A substrate 310, shown for example in FIG. 15-FIG. 24, may be positioned within the barrier system 4700.

The barrier system 4700 comprises a sample environment 4705 defined by a plate 4703, the chamber 4715, and the fluid barrier 4713. The chamber 4715 and the plate 4703 may be separated by a physical gap. The sample environment 4705 may be isolated (and/or insulated) from an external environment 4707.

The fluid barrier 4713 may act as a transition region between the sample environment 4705 and the external environment 4707. A substrate (e.g., substrate 310 as shown in FIG. 15-FIG. 24) may be positioned within the sample environment 4705. The fluid barrier 4713 may comprise fluids (e.g., air) from the sample environment 4705, the external environment 4707, or both. The fluid barrier 4713 may be a low pressure region. The fluid barrier 4713 may have lower pressure than the sample environment, the external environment, or both. The fluid barrier 4713 may be maintained via a fluid flow unit, such as a pressure-altering apparatus 4711. The fluid barrier 4713 may comprise fluid in coherent motion or bulk motion.

The pressure-altering apparatus 4711 may be integral to the chamber 4715. For example, as illustrated in FIG. 47A and FIG. 47B, the pressure-altering apparatus may be integrated as a fluid channel 4720 in a wall of the chamber 4715. For example, suction may be applied through the fluid channel 4720 to draw in fluids from the external environment 4707, or sample environment 4705, or both, to generate a partial vacuum curtain (e.g., in coherent motion, in bulk motion, etc.), thereby creating the fluid barrier 4713. Otherwise, the fluid may be subjected to negative pressure. The fluid exhaust may be expelled at another end of the fluid channel. Alternatively or in addition to, the apparatus may not be integral to the chamber 4715. The fluid flow unit and/or the pressure-altering apparatus 4711 may be operated via one or more compressors (e.g., to generate negative pressure), pumps (e.g., to generate positive pressure), suction apparatus, and/or other devices to provide the lower pressure in the transition region. The chamber 4715 may comprise one or more fluid channels 4720 for implementing fluid barriers of the present disclosure.

While two pressure-altering apparatus 4711 is illustrated in FIG. 47A and FIG. 47B, it will be appreciated that there may be any number of such apparatus. For example, there may be at least about 2, 3, 4, 5, 6, 7, 8, 9, 10, 20, 30, 40, 50 or more such apparatus. Alternatively or in addition to, there may be at most about 50, 40, 30, 20, 10, 9, 8, 7, 6, 5, 4, 3, or 2 such apparatus. In some instances, one or more pressure-altering apparatus 4711 may be implemented as an annular fluid channel surrounding the sample environment region, or other fluid channel along a perimeter or boundary of the sample environment region. In some instances, one or more additional fluid flow channels (e.g., 4733) may be provided near a bottom of the chamber to draw in excess fluid (e.g., liquids, gases) from the sample environment region.

Beneficially, the fluid barrier 4713 may provide a low friction or zero friction seal between the sample environment 4705 and the external environment 4707. In some instances, a fluid flow rate through the fluid barrier 4713 may be at least about 5 liters per minute (L/min), 5.5 L/min, 6 L/min, 6.5 L/min, 7 L/min, 7.5 L/min, 8 L/min, 8.5 L/min, 9 L/min, 9.5 L/min, 10 L/min, 10.5 L/min, 11 L, 11.5 L/min, 12 L/min, 12.5 L/min, 13 L/min, 13.5 L/min, 14 L/min, 14.5 L/min, 15 L/min, or more. Alternatively or in addition to, the fluid flow rate may be at most about 15 L/min, 14.5 L/min, 14 L/min, 13.5 L/min, 13 L/min, 12.5 L/min, 12 L/min, 11.5 L/min, 11 L/min, 10.5 L/min, 10 L/min, 9.5 L/min, 9 L/min, 8.5 L/min, 8 L/min, 7.5 L/min, 7 L/min, 6.5 L/min, 6 L/min, 5.5 L/min, 5 L/min, or less. As will be appreciated the fluid flow rate may vary with different parameters (e.g., minimal distance between the plate and chamber, pressure, temperature, etc.). In some examples, for a gap of about 500 microns between the plate 4703 and the chamber 4715, the fluid flow rate can be about 10 L/min or about 13 milliliters per minute (mL/min) per millimeter (mm) along the circumference for a velocity of about 0.42 meters per second (m/s). The barrier systems, methods, and apparatus that can be used in the open substrate systems of the present disclosure are described in U.S. Pat. No. 10,512,911 and International Patent Application No. PCT/US19/64916, filed Dec. 6, 2019, each of which is entirely incorporated herein by reference.

Figure 15:
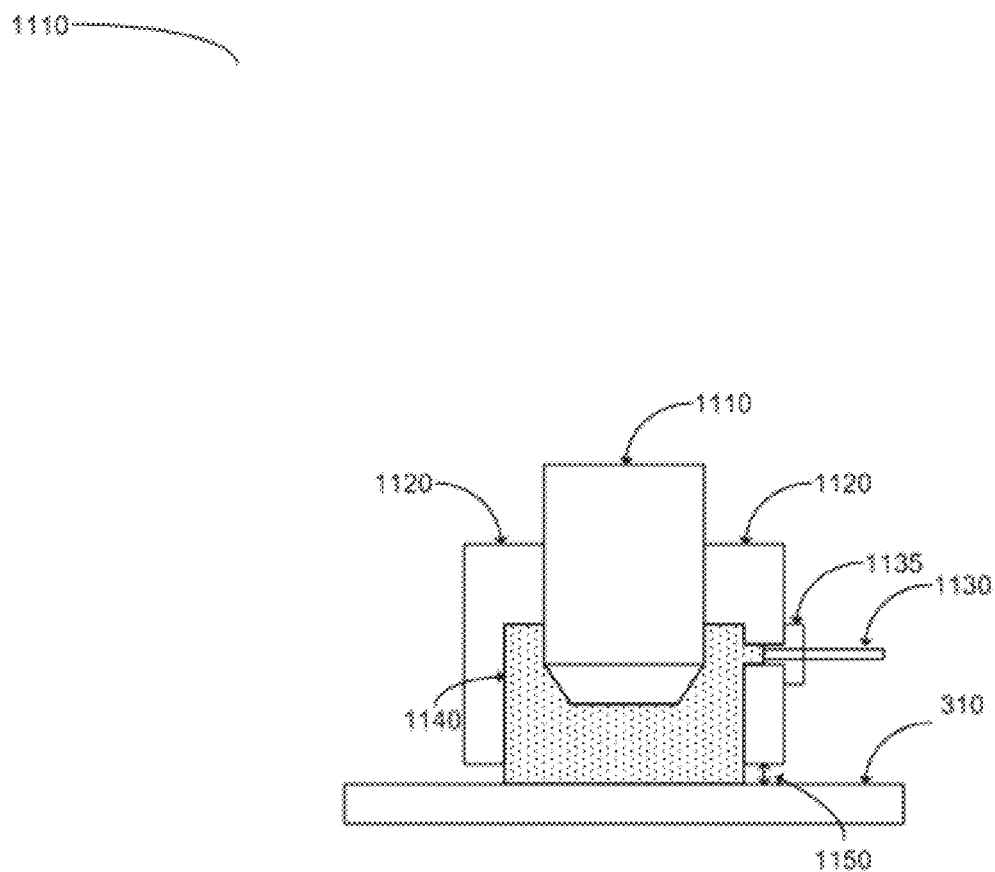
FIG. 15 shows a cross-sectional view of an immersion optical system.

The system may be temperature controlled. In some cases, the elements of the system may be held at different temperatures. The differential temperatures of individual elements in the system may control the accumulation of condensation or precipitation on the individual elements of the system. The top portion of the container 3504 may be held at a different temperature than the substrate 3502, an objective (for example, as shown in FIG. 15), or the reservoir. Alternatively or in addition, the substrate may be held at a different temperature than the top portion of the container, the objective, or the reservoir. Alternatively or in addition, the reservoir may be held at a different temperature than the top portion of the container, the objective, or the substrate. Alternatively or in addition, the objective may be held at a different temperature than the top portion of the container, the reservoir, or the substrate. In some cases, the top portion of the container is held at a higher temperature than at least one other element in the system to prevent the accumulation of condensation on the top surface of the container. In an exemplary configuration, the top portion of the container is held at the highest temperature, the substrate is held at the lowest temperature, and the reservoir and the objective are held at intermediate temperatures, thereby preventing condensation from forming on the top portion of the container or from forming or dripping onto the objective. In another example, the objective is held at the highest temperature, the top portion of the container is held at an intermediate temperature, and the substrate and the reservoir are held at lower temperatures than the top portion of the container, thereby preventing condensation from forming on the top portion of the container or from forming or dripping onto the objective. In some cases, the objective may be fully or partially surrounded by a seal. The seal may be configured to prevent moisture from the container surrounding the substrate (for example, as shown in FIG. 7) from reaching other optical components in the system (for example, as described with respect to FIG. 41). The seal may comprise a flexible material. The flexible seal may be configured to allow relative motion of individual elements of the system while maintaining the seal. In some embodiments, the flexible seal may stretch, expand, or contract. For example, the flexible seal may be configured to allow independent motion of two or more imaging heads, as described with respect to FIG. 29F-FIG. 29G. Alternatively or in addition, the seal may comprise a waterproof material. For example, the seal may be rubber, silicone, latex, plastic, Teflon, nitrile, elastin, an elastomer, or a polymer. The seal may surround the objective and contact the top portion of the container. In some cases, a portion of the objective comprising a front lens is not covered by the seal. The front lens of the objective may be exposed to the container surrounding the substrate. In some cases, the front lens of the objective may be in fluidic contact with the substrate.

The systems (or any element thereof) may be maintained at a relative humidity of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at most 100%, at most 95%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5%, or a relative humidity that is within a range defined by any two of the preceding values. The systems (or any element thereof) may be configured such that less than 80%, less than 70%, less than 60%, less than 50%, less than 40%, less than 30%, less than 20%, less than 10%, less than 5%, less than 4%, less than 3%, less than 2%, or less than 1% of the volume of the solution layer dispensed on the uncovered surface evaporates.

The systems (or any element thereof) may be contained within a sealed container, housing, or chamber that insulates the system (or any element thereof) from the external environment or atmosphere, allowing for the control of the temperature or humidity. An environmental unit (e.g., humidifiers, heaters, heat exchangers, compressors, etc.) may be configured to regulate one or more operating conditions in each environment. In some instances, each environment may be regulated by independent environmental units. In some instances, a single environmental unit may regulate a plurality of environments. In some instances, a plurality of environmental units may, individually or collectively, regulate the different environments. An environmental unit may use active methods or passive methods to regulate the operating conditions. For example, the temperature may be controlled using heating or cooling elements. The humidity may be controlled using humidifiers or dehumidifiers. In some instances, a part of the internal environment within the container or chamber may be further controlled from other parts of the internal environment. Different parts may have different local temperatures, pressures, and/or humidity. For example, the internal environment may comprise a first internal environment and a second internal environment separated by a seal.

Alternatively or in conjunction, the systems or methods described herein may comprise a solution comprising an agent that may reduce evaporation. For example, the solution may comprise glycerol, which can prevent evaporation of the solution.

In some instances, the seal may comprise an immersion objective lens, which is described in further detail elsewhere herein. For example, an immersion objective lens may be part of a seal that separates the internal environment in the container into a first internal environment having 100% (or substantially 100%) humidity and a second environment having one or more of an ambient temperature, pressure or humidity. The immersion objective lens may be in contact with one or more of a detector and imaging lens.

Substrate Preparation and Contaminant-Resistant Substrates

As described above, a substrate may comprise a surface comprising a plurality of binders coupled thereto. In some cases, the plurality of binders may comprise a plurality of nucleic acid molecules (e.g., a plurality of nucleic acid molecules that are directly coupled to the surface or that are indirectly coupled to the surface via a plurality of linkers, as described herein). Oligonucleotide (e.g., nucleic acid molecule)-coated surfaces (e.g., substantially planar substrates and/or particles, including substrates having a plurality of particles immobilized thereto) may be employed for various applications, including for capturing specific sequences of nucleic acid molecules for, e.g., gene expression analysis by hybridization capture (gene arrays), single nucleotide polymorphism (SNP) genotyping, capturing a subset of sequencing libraries (e.g., targeted capture or exome sequencing), synthesis of cDNA from mRNA via oligo-dT capture, and on-surface amplification of nucleic acid molecules for downstream analysis such as next generation sequencing. An oligonucleotide-coated surface may be prepared in advance of its use in any such application and may be stored between its generation and its eventual use (e.g., during transport from a manufacturing site to an operating site, sample processing and preparation, etc.). An oligonucleotide-coated surface may be stored for at least 1 hour, and in some cases may be stored for months or even years. During storage, an oligonucleotide-coated surface may come into contact with one or more solutions or other materials that may contain nucleic acid molecules, which may be considered contaminants. Contaminant nucleic acid molecules may hybridize to oligonucleotides coupled to a surface, leading to decreased efficiency in downstream analysis (e.g., during use in an application such as those described herein) and/or erroneous results in downstream analysis. For example, an oligonucleotide-coated surface prepared for use in a sequencing analysis may become contaminated with non-relevant sequencing libraries during handling of the surface prior to its use in the sequencing analysis (e.g., prior to placement of the substrate comprising the surface in a sequencing instrument or to commencement of an amplification process, such as a clonal amplification process).

Non-relevant interactions of oligonucleotides (e.g., binders) coupled to a surface of a substrate may be reduced by blocking the oligonucleotides that are attached to the surface (e.g., bound oligonucleotides) with oligonucleotides comprising sequences that are fully or partially complementary to the sequences of the oligonucleotides that are attached to the surface. Blocking oligonucleotides may be provided in solution and may be considered "free" oligonucleotides. For example, blocking oligonucleotides may fully or partially hybridize to all or a subset of the oligonucleotides coupled to a surface of a substrate, thereby providing a partially double-stranded nucleic acid molecule comprising a bound oligonucleotide and a blocking oligonucleotide. Such a partially double-stranded nucleic acid molecule may be resistant to hybridization to nucleic acid molecules with which the surface may come into contact, including potential contaminant nucleic acid molecules that may not be relevant to any eventual analysis such as eventual nucleic acid sequencing. Blocking oligonucleotides may be removed from the oligonucleotide-coated surface (e.g., via application of an appropriate stimulus, such as a chemical or thermal stimulus, or via enzymatic degradation) to provide an oligonucleotide-coated surface that may be ready to use in an analysis process (e.g., as described herein). The surface may undergo one or more washing processes (e.g., one or more wash flows) to remove blocking oligonucleotides. Removing the blocking oligonucleotides may provide the oligonucleotides coupled to the surface as free oligonucleotides that may participate in various reactions, including capture of complementary or partially complementary nucleic acid molecules of interest.

An oligonucleotide-coated surface may be stored for any useful amount of time. For example, an oligonucleotide-coated surface may be stored for at least 1 hour, such as at least 2 hours, 6 hours, 12 hours, 24 hours, 36 hours, 2 days, 3 days, 4 days, 5 days, 6 days, 1 week, 1 month, 2 months, 3 months, 4 months, 5 months, 6 months, 1 year, or longer. An oligonucleotide-coated surface may be stored under any useful conditions. For example, an oligonucleotide-coated surface may be stored under standard temperature and pressure conditions (e.g., room temperature), such as between about 18° C. to about 30° C., such as between about 20° C. to about 25° C., and about 1 atmosphere. An oligonucleotide-coated surface may be stored in a dry environment (e.g., in air or a nitrogen- or argon-enriched environment) or in a solution (e.g., a buffered solution such as saline sodium citrate).

An oligonucleotide-coated surface may be stored in a package or container, which package or container may contain one or more such oligonucleotide-coated surfaces. For example, multiple oligonucleotide-coated surfaces may be provided in a given package or container. A package or container comprising one or more oligonucleotide-coated surfaces may be a rigid package or container or a flexible package or container. For example, one or more oligonucleotide-coated surfaces, such as one or more substantially planar substrates comprising the one or more oligonucleotide-coated surfaces, may be provided in a flexible package. A package or container may comprise or be formed of, for example, a glass, plastic polymer, metal (e.g., metal foil), or any other material. A package or container comprising one or more oligonucleotide-coated surfaces may be sealed (e.g., hermetically sealed). A package or container comprising one or more oligonucleotide-coated surfaces may be resealable upon opening. For example, a first oligonucleotide-coated surface may be removed from the package or container and a second oligonucleotide-coated surface may be retained within the package or container. An oligonucleotide-coated surface may also be configured for storage outside of a package or container for a period of time, such as for at least about 1 hour, 2 hours, 6 hours, or longer (e.g., as described herein).

An oligonucleotide-coated surface may be prepared at a manufacturing and/or shipping site. Alternatively, an oligonucleotide-coated surface may be prepared by a user, such as a user of a sequencing instrument. In some cases, an oligonucleotide-coated surface comprising a plurality of blocking oligonucleotides coupled (e.g., hybridized) to a plurality of oligonucleotides coupled to the oligonucleotide-coated surface may be prepared at a manufacturing and/or shipping site. Alternatively, an oligonucleotide-coated surface comprising a plurality of blocking oligonucleotides coupled (e.g., hybridized) to a plurality of oligonucleotides coupled to the oligonucleotide-coated surface may be prepared by a user, such as a user of a sequencing instrument. A plurality of blocking oligonucleotides coupled to a plurality of oligonucleotides coupled to the oligonucleotide-coated surface may be removed by a user, such as a user of a sequencing instrument. For example, a plurality of blocking oligonucleotides coupled to a plurality of oligonucleotides coupled to the oligonucleotide-coated surface may be removed by a user shortly before a user makes use of the oligonucleotide-coated surface (e.g., as described herein, such as for a sequencing application).

An oligonucleotide-coated surface may be used one or more times for one or more applications. For example, an oligonucleotide-coated surface may be configured for one-time use. Alternatively, an oligonucleotide-coated surface may be configured to be used multiple times, for the same and/or different applications. For example, oligonucleotides coupled to a surface may be "recharged" for use in a subsequent application, or a surface may be washed clean and new oligonucleotides may be coupled to the surface for use in a subsequent application. In another example, an oligonucleotide-coated surface may comprise one or more different regions comprising one or more different oligonucleotides (e.g., binders) coupled thereto (e.g., as described herein). The one or more different oligonucleotides may be configured for use in one or more different applications. In an example, an oligonucleotide-coated surface comprises a first plurality of oligonucleotides coupled to a first region and a second plurality of oligonucleotides coupled to a second region, where the first plurality of oligonucleotides and the second plurality of oligonucleotides have different nucleic acid sequences. The first plurality of oligonucleotides may be configured to at least partially hybridize to a first plurality of blocking oligonucleotides, while the second plurality of oligonucleotides may be configured to at least partially hybridize to a second plurality of blocking oligonucleotides, where the first plurality of blocking oligonucleotides and the second plurality of blocking oligonucleotides have different nucleic acid sequences. The first plurality of blocking oligonucleotides hybridized to the first plurality of oligonucleotides coupled to the surface may be removable upon application of a first stimulus (e.g., as described herein) and the second plurality of blocking oligonucleotides hybridized to the second plurality of oligonucleotides coupled to the surface may be removable upon application of a second stimulus, which second stimulus differs from the first stimulus. Accordingly, the first and second pluralities of blocking oligonucleotides may be provided to the oligonucleotide-coated surface (e.g., at the same or different times) to provide a doubly-treated surface. The first plurality of blocking oligonucleotides hybridized to oligonucleotides of the first plurality of oligonucleotides coupled to the surface may be removed (e.g., after a first period of storage) by application of the first stimulus to provide the first plurality of oligonucleotides coupled to the first region free to participate in a first application such as a first sequencing assay. Application of the first stimulus may not affect the second plurality of blocking oligonucleotides coupled to the second plurality of oligonucleotides coupled to the second region. Accordingly, the second plurality of blocking oligonucleotides hybridized to oligonucleotides of the second plurality of oligonucleotides coupled to the surface may be retained during the duration of the first application. The second plurality of blocking oligonucleotides hybridized to oligonucleotides of the second plurality of oligonucleotides coupled to the surface may be removed (e.g., after a second period of storage) by application of the second stimulus to provide the second plurality of oligonucleotides coupled to the second region free to participate in a second application such as a second sequencing assay.

Oligonucleotides may be coupled to an oligonucleotide-coated surface via any useful mechanism, including, for example, non-specific interactions (e.g., one or more of hydrophilic interactions, hydrophobic interactions, electrostatic interactions, physical interactions (for instance, adhesion to pillars or settling within wells), and the like) or specific interactions (e.g., as described herein).

Oligonucleotides may be coupled to an oligonucleotide-coated surface randomly or semi-randomly. Alternatively, oligonucleotides may be coupled to an oligonucleotide-coated surface in a predetermined pattern (e.g., as described herein). In some cases, a substrate comprising an oligonucleotide-coated surface may comprise one or more different binders (e.g., dispersed with a plurality of oligonucleotides or disposed on a different region of the substrate). For example, a substrate comprising an oligonucleotide-coated surface may comprise a first set of oligonucleotides coupled to the surface and a second set of oligonucleotides coupled to the surface, where the oligonucleotides of the first set of oligonucleotides have a nucleic acid sequence that differs from a nucleic acid sequence of oligonucleotides of the second set of oligonucleotides. In an example, oligonucleotides of the first set of oligonucleotides may comprise a first nucleic acid sequence and oligonucleotides of the second set of oligonucleotides may comprise a second nucleic acid sequence that differs from the first nucleic acid sequence. In some cases, oligonucleotides of the first set of oligonucleotides and oligonucleotides of the second set of oligonucleotides may comprise a common third nucleic acid sequence, such as a poly(T) sequence.

Oligonucleotides may be coupled to one or more particles immobilized to a surface of a substrate. For example, a surface of a substrate may comprise a plurality of particles (e.g., beads) immobilized thereto (e.g., as described herein), which plurality of particles comprise a plurality of oligonucleotides coupled thereto. In some cases, each particle comprises a different plurality of oligonucleotides coupled thereto (e.g., a plurality of oligonucleotides comprising a nucleic acid sequence that differs from a nucleic acid sequence of another plurality of oligonucleotides coupled to a different particle). For example, each particle of a plurality of particles to a surface of a substrate may comprise a plurality of oligonucleotides coupled thereto, where all of the oligonucleotides coupled to a given particle comprise a common barcode sequence and where each plurality of oligonucleotides coupled to each different particle of the plurality of particles comprises a different barcode sequence (e.g., as described herein).

An oligonucleotide-coated surface may comprise any useful number of oligonucleotides coupled thereto (e.g., as described herein). For example, an oligonucleotide-coated surface may comprise at least 10, 100, 1,000, 10,000, 100,000, 1,000,000, 10,000,000, 100,000,000 or more oligonucleotides. In some cases, an oligonucleotide-coated surface comprises multiple regions comprising multiple different pluralities of oligonucleotides, which different pluralities of oligonucleotides may have the same or different nucleic acid sequences and may comprise the same or different numbers of oligonucleotides. For example, an oligonucleotide-coated surface may comprise a first region comprising a first plurality of oligonucleotides and a second region comprising a second plurality of oligonucleotides, where the first plurality of oligonucleotides and/or the second plurality of oligonucleotides comprises at least 10, 100, 1000, 10,000, 100,000, 1,000,000, 10,000,000, 100, 000,000 or more oligonucleotides. The density of oligonucleotides coupled to a region of a surface may be, for example, at least about 1,000 molecules per mm$^2$, such as at least about 10,000 molecules per mm$^2$, 100,000 molecules per mm$^2$, 1,000,000 molecules per mm$^2$, 10,000,000 molecules per mm$^2$, or more. The density of oligonucleotides coupled to a surface may vary by region. For example, a surface may comprise a first region comprising a first density of oligonucleotides coupled thereto and a second region comprising a second density of oligonucleotides coupled thereto, where the first density is higher than the second density.

Oligonucleotides coupled to a surface of a substrate may comprise one or more different nucleic acid sequences. For example, an oligonucleotide coupled to a surface of a substrate may comprise a barcode sequence, an adapter sequence, a primer sequence (e.g., a universal primer sequence), a poly(T) sequence, a random N-mer sequence, a flow cell adapter sequence, a sequencing primer, a unique molecular identifier, a key sequence, an index sequence, or any other useful sequence. One or more sequences of an oligonucleotide coupled to a surface may be configured to capture a particular sample molecule or population thereof. In some cases, an oligonucleotide-coated surface may comprise a plurality of oligonucleotides coupled thereto, wherein each oligonucleotide of the plurality of oligonucleotides comprises at least one common or shared sequence. For example, each oligonucleotide of a plurality of oligonucleotides coupled to an oligonucleotide-coated surface or a given region thereof may comprise a common barcode sequence. Alternatively or in addition, each oligonucleotide of the plurality of oligonucleotides coupled to an oligonucleotide-coated surface or a given region thereof may comprise a poly(T) sequence (e.g., for capture of sample nucleic acid molecules comprising a poly(A) sequence, such as mRNA molecules) or another specific capture sequence. In some cases, each oligonucleotide of a plurality of oligonucleotides coupled to an oligonucleotide-coated surface or a region thereof may comprise one or more common sequences (e.g., as described herein) and a different unique molecular identifier or key sequence.

Oligonucleotides coupled to a surface of a substrate may have any useful length. For example, an oligonucleotide coupled to a surface of a substrate may comprise at least 6 bases, such as 7, 8, 9, 10, 12, 14, 16, 18, 20, 25, 30, 35, or more bases. In some cases, only a portion of the bases of an oligonucleotide coupled to a surface of a substrate may be accessible to a blocking or other oligonucleotide. For example, one or more nucleotides of an oligonucleotide coupled to a surface of a substrate may comprise a blocking moiety and/or may be coupled to other moieties, such as a moiety immobilizing the oligonucleotide to the surface. In some cases, an oligonucleotide coupled to a surface of a substrate may comprise one or more reversible terminators.

Similarly, a blocking oligonucleotide may have any useful length. For example, a blocking oligonucleotide may comprise at least 6 bases, such as 7, 8, 9, 10, 12, 14, 16, 18, 20, 25, 30, 35, or more bases. In some cases, only a portion of the bases of a blocking oligonucleotide may be available to hybridize to an oligonucleotide coupled to an oligonucleotide-coated surface. For example, one of more nucleotides of a blocking oligonucleotide may comprise a blocking moiety and/or may be coupled to other moieties. In some cases, a blocking oligonucleotide may comprise one or more groups that may be substantially inert or unreactive (e.g., in a buffered solution). In some cases, a blocking oligonucleotide may comprise one or more reversible terminators.

Oligonucleotides coupled to a surface of a substrate may have any useful composition. Oligonucleotides coupled to a surface may comprise nucleotides, nucleotide analogs, non-standard nucleotides, and/or modified analogs (e.g., as described herein). For example, oligonucleotides coupled to a surface may comprise DNA nucleotides, RNA nucleotides, and/or a mixture thereof. Similarly, blocking oligonucleotides coupled to a surface may have any useful composition, provided that the blocking oligonucleotides comprise a nucleic acid sequence that is fully or partially complementary to oligonucleotides coupled to a surface of a substrate. Blocking oligonucleotides may comprise DNA nucleotides, RNA nucleotides, and/or a mixture thereof. In an example, an oligonucleotide coupled to a surface comprises DNA nucleotides and a blocking oligonucleotide configured to hybridize partially or completely to the oligonucleotide coupled to the surface comprises DNA nucleotides. In another example, an oligonucleotide coupled to a surface comprises RNA nucleotides and a blocking oligonucleotide configured to hybridize partially or completely to the oligonucleotide coupled to the surface comprises RNA nucleotides.

An oligonucleotide coupled to a surface may comprise an adapter or complement thereof. For example, an oligonucleotide may comprise a sequence complementary to a sequence of an adapter coupled to a sample nucleic acid molecule (e.g., a single-stranded sample nucleic acid molecule, such as a single-stranded sample RNA molecule). An adapter may be a single-stranded adapter and may have any useful composition. For example, an adapter may comprise DNA nucleotides, RNA nucleotides, or a combination thereof. An adapter may have any useful length and other properties. An adapter may be disposed at an end of an oligonucleotide that is distal from the surface to which the oligonucleotide is coupled. The adapter may comprise a barcode sequence (e.g., as described herein).

An oligonucleotide coupled to a surface and/or a blocking oligonucleotide may comprise a functional feature such as a terminator (e.g., reversible terminator), blocking moiety, or a label or reporter moiety. For example, a blocking oligonucleotide may comprise a label moiety such as a fluorescent label (e.g., a dye, as described herein). A label moiety or other functional feature may be linked to a nucleotide of an oligonucleotide via a linker moiety. For example, a nucleotide of a blocking oligonucleotide may comprise a label moiety (e.g., dye) linked to the base of the nucleotide via a linker moiety. The nucleotide may be disposed at an end of the blocking oligonucleotide. Alternatively or in addition, a nucleotide of a blocking oligonucleotide may comprise a terminator (e.g., reversible terminator). The terminator may be linked to the sugar of the nucleotide via a linker moiety. The nucleotide may be disposed at the end of the blocking oligonucleotide. Such functional features may facilitate control of the interaction between blocking oligonucleotides and oligonucleotides coupled to a surface of a substrate and/or provide a mechanism for identifying where blocking oligonucleotides have hybridized to oligonucleotides coupled to a surface. Alternatively or in addition, an oligonucleotide coupled to a surface may comprise a label or reporter moiety, which label or reporter moiety may emit a first signal when the oligonucleotide is uncoupled and a second signal when the oligonucleotide is coupled to a blocking oligonucleotide. For example, the second signal may be attenuated, decreased, quenched, or amplified relative to the first signal. In some cases, no detectable signal may be emitted by the label or reporter moiety when the oligonucleotide coupled to the surface is hybridized to a blocking oligonucleotide. In this manner, coupling between oligonucleotides coupled to a surface and blocking oligonucleotides may be monitored (e.g., to gauge the blocking efficiency of the blocking oligonucleotides). For example, oligonucleotides coupled a surface may each comprise a dye that emits a signal when the oligonucleotides are "free," which signal is severely attenuated when the oligonucleotides are "blocked" (e.g., hybridized to blocking oligonucleotides). By optically interrogating the surface before and after provision of the blocking oligonucleotides, the blocking efficiency of the blocking oligonucleotides (and thus the contamination resistance of the treated surface) can be gauged. In some cases, different fluorescent dyes may be used for different areas of a surface (e.g., for oligonucleotides having different nucleic acid sequences that may be coupled to different areas of the surface).

A treated surface comprising a plurality of oligonucleotides immobilized thereto and a plurality of blocking oligonucleotides coupled to oligonucleotides of the plurality of oligonucleotides may have any degree of "contamination resistance." The percentage of oligonucleotides of the plurality of oligonucleotides that are coupled to blocking oligonucleotides of the plurality of blocking oligonucleotides may be indicative of the resistance of the treated surface to contamination. In some cases, at least 50% of the oligonucleotides of the plurality of oligonucleotides may be coupled to blocking oligonucleotides. For example, at least 55%, 60%, 65%, 70%, 75%, 80%, 85%, 90%, 95%, 96%, 97%, 98%, 99%, or more of the oligonucleotides of the plurality of oligonucleotides may be coupled to blocking oligonucleotides. Coupling between oligonucleotides coupled to the surface and blocking oligonucleotides may be monitored via optical detection (e.g., as described herein) or any other useful method.

FIG. 38A-FIG. 38D illustrate a blocking oligonucleotide scheme. In FIG. 38A, a substrate comprising bound oligonucleotides is provided. In FIG. 38B, the bound oligonucleotides are blocked using blocking oligonucleotides (e.g., as described herein). As shown in FIG. 38C, contaminant nucleic acid molecules cannot bind to the bound oligonucleotides while the blocking oligonucleotides are coupled to the bound oligonucleotides. FIG. 38D shows removal of the blocking oligonucleotides using various mechanisms, including heat denaturation, chemical denaturation, chemical degradation, and enzymatic degradation. After the blocking oligonucleotides have been removed, relevant target nucleic acid molecules (e.g., from a sample for various applications such as sequencing) may be able to bind to substrate-bound oligonucleotides (e.g., substrate-bound oligonucleotides comprising sequences that are at least partially complementary to the target nucleic acid molecules, as described herein).

In an aspect, the present disclosure provides a method for storing a substrate comprising a nucleic acid molecule-coated surface. A substrate having a surface comprising a first set of nucleic acid molecules immobilized thereto may be provided. Nucleic acid molecules of the first set of nucleic acid molecules may be configured to capture sample nucleic acid molecules derived from one or more nucleic acid samples (e.g., nucleic acid samples for sequencing). The substrate comprising the surface comprising the first set of nucleic acid molecules may be brought into contact with a second set of nucleic acid molecules under conditions sufficient to yield a treated surface in which at least 70% (e.g., at least 75%, 80%, 85%, 90%, or more) of nucleic acid molecules of the first set of nucleic acid molecules may be hybridized to nucleic acid molecules of the second set of nucleic acid molecules, wherein the second set of nucleic acid molecules are not the sample nucleic acid molecules. Excess nucleic acid molecules of the second set of nucleic acid molecules may be washed away. The substrate having the treated surface may be stored for a period of time, such as at least 1 hour, 6 hours, 12 hours, 24 hours, 2 days, or longer. The treated surface may be stored under any useful conditions (e.g., as described herein). During storage of the treated surface, each nucleic acid molecule of the first set of nucleic acid molecules that is hybridized to a nucleic acid molecule of the second set of nucleic acid molecules may not hybridize to another nucleic acid molecule.

The second set of nucleic acid molecules may be provided to the surface of the substrate in a solution. Each nucleic acid molecule of the second set of nucleic acid molecules may comprise a sequence that is substantially complementary to a sequence of the first set of nucleic acid molecules. The sequence of the first set of nucleic acid molecules may comprise at least 6 bases, such as at least 10 bases, 20 bases, or more. Each nucleic acid molecule of the first set of nucleic acid molecules may comprise at least 6 bases, such as at least 10 bases, 20 bases, or more. The first set of nucleic acid molecules and/or the second set of nucleic acid molecules may comprise DNA nucleotides, RNA nucleotides, or a combination thereof. Each nucleic acid molecule of the first set of nucleic acid molecules may comprise the same nucleic acid sequence. In some cases, the first set of nucleic acid molecules may comprise one or more different nucleic acid sequences. The first set of nucleic acid molecules may comprise a first subset of nucleic acid molecules comprising a first nucleic acid sequence and a second subset of nucleic acid molecules comprising a second nucleic acid sequence, which first and second nucleic acid sequences are different. The first subset of nucleic acid molecules and the second subset of nucleic acid molecules may both comprise a third nucleic acid sequence. The third nucleic acid sequence may comprise a poly(T) sequence.

The nucleic acid molecules of the first set of nucleic acid molecules may be immobilized to the surface at independently addressable locations. The independently addressable locations may be substantially planar and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per mm$^2$, such as at least 100,000, 1,000,000, 10,000,000, or more molecules per mm$^2$. The surface of the substrate may be substantially planar. The substrate may comprise one or more particles immobilized thereto.

The method may further comprise, subsequent to a period of storage of the treated surface, removing nucleic acid molecules of the second set of nucleic acid molecules from the treated surface. The nucleic acid molecules may be removed via, for example, enzymatic degradation or via denaturing via chemical or thermal stimulation (e.g., application of a chemical stimulus such as sodium hydroxide). After removing these nucleic acid molecules, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

In another aspect, the present disclosure provides a method for preparing a substrate having a treated surface for use in nucleic acid processing. A substrate having a treated surface may be provided, which substrate comprises a first set of nucleic acid molecules immobilized thereto. At least 70% (e.g., at least 80%, 85%, 90%, 95%, or more) of nucleic acid molecules of the first set of nucleic acid molecules may be hybridized to nucleic acid molecules of a second set of nucleic acid molecules. Nucleic acid molecules of the first set of nucleic acid molecules may be configured to capture sample nucleic acid molecules derived from one or more nucleic acid samples. The second set of nucleic acid molecules is distinct from the sample nucleic acid molecules. The substrate having the treated substrate may have been stored for a time period of at least 1 hour, such as at least 6 hours, 12 hours, 24 hours, 2 days, or longer. The treated surface may have been stored under any useful conditions (e.g., as described herein). During storage of the treated surface, each nucleic acid molecule of the first set of nucleic acid molecules that is hybridized to a nucleic acid molecule of the second set of nucleic acid molecules may not hybridize to another nucleic acid molecule.

Nucleic acid molecules of the second set of nucleic acid molecules from the treated surface may be removed (e.g., as described herein). For example, the nucleic acid molecules may be removed from the treated surface via enzymatic degradation or via denaturing via chemical or thermal stimulation (e.g., application of a chemical stimulus such as sodium hydroxide). After removing these nucleic acid molecules, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

Each nucleic acid molecule of the second set of nucleic acid molecules may comprise a sequence that is substantially complementary to a sequence of the first set of nucleic acid molecules. The sequence of the first set of nucleic acid molecules may comprise at least 6 bases, such as at least 10 bases, 20 bases, or more. Each nucleic acid molecule of the first set of nucleic acid molecules may comprise at least 6 bases, such as at least 10 bases, 20 bases, or more. The first set of nucleic acid molecules and/or the second set of nucleic acid molecules may comprise DNA nucleotides, RNA nucleotides, or a combination thereof. Each nucleic acid molecule of the first set of nucleic acid molecules may comprise the same nucleic acid sequence. In some cases, the first set of nucleic acid molecules may comprise one or more different nucleic acid sequences. The first set of nucleic acid molecules may comprise a first subset of nucleic acid molecules comprising a first nucleic acid sequence and a second subset of nucleic acid molecules comprising a second nucleic acid sequence, which first and second nucleic acid sequences are different. The first subset of nucleic acid molecules and the second subset of nucleic acid molecules may both comprise a third nucleic acid sequence. The third nucleic acid sequence may comprise a poly(T) sequence.

The nucleic acid molecules of the first set of nucleic acid molecules may be immobilized to the surface at independently addressable locations. The independently addressable locations may be substantially planar and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per $mm^2$, such as at least 100,000, 1,000,000, 10,000,000, or more molecules per $mm^2$. The surface of the substrate may be substantially planar. The substrate may comprise one or more particles immobilized thereto.

In another aspect, the present disclosure provides a method for storing a substrate comprising a nucleic acid molecule-coated surface, comprising providing a substrate having a surface comprising a first set of nucleic acid molecules immobilized thereto. Nucleic acid molecules of the first set of nucleic acid molecules may be configured to capture sample nucleic acid molecules derived from one or more nucleic acid samples. Each nucleic acid molecule of the nucleic acid molecules of the first set of nucleic acid molecules may comprise a first nucleic acid sequence. A second set of nucleic acid molecules may also be provided, wherein each nucleic acid molecule of the second set of nucleic acid molecules comprises a second nucleic acid sequence that may be substantially complementary to the first nucleic acid sequence. The second set of nucleic acid molecules may be distinct from the sample nucleic acid molecules. The surface comprising the first set of nucleic acid molecules may be brought into contact with the second set of nucleic acid molecules to generate a treated surface in which at least 70% (e.g., at least 75%, 80%, 85%, 90%, 95%, or more) of nucleic acid molecules of the first set of nucleic acid molecules may be hybridized to nucleic acid molecules of the second set of nucleic acid molecules. For each nucleic acid molecule of the first set of nucleic acid molecules hybridized to a nucleic acid molecule of the second set of nucleic acid molecules, the first nucleic acid sequence may be hybridized to the second nucleic acid sequence. The first nucleic acid sequence hybridized to the second nucleic acid sequence may at least partially denature between about 40° C. and 60° C., such as between about 50° C. and 60° C. The treated surface may then be stored for a period of time, such as for at least one hour, 2 hours, 6 hours, 12 hours, 24 hours, 2 days, or longer. The treated surface may be stored under any useful conditions (e.g., as described herein). During storage of the treated surface, each nucleic acid molecule of the first set of nucleic acid molecules that is hybridized to a nucleic acid molecule of the second set of nucleic acid molecules may not hybridize to another nucleic acid molecule.

The second set of nucleic acid molecules may be provided to the surface of the substrate in a solution. The first nucleic acid sequence and the second nucleic acid sequence may each comprise at least 6 bases, such as at least 10 bases, 20 bases, or more. Each nucleic acid molecule of the second set of nucleic acid molecules may comprise at least 6 bases, such as at least 10 bases, 20 bases, or more. Similarly, each nucleic acid molecule of the first set of nucleic acid molecules may comprise at least 6 bases, such as at least 10 bases, 20 bases, or more. A given nucleic acid molecule of the first set of nucleic acid molecules and a given nucleic acid molecule of the second set of nucleic acid molecules may comprise the same number of nucleotides. Alternatively, a given nucleic acid molecule of the first set of nucleic acid molecules and a given nucleic acid molecule of the second set of nucleic acid molecules may comprise a different number of nucleotides. The first set of nucleic acid molecules and/or the second set of nucleic acid molecules may comprise DNA nucleotides, RNA nucleotides, or a combination thereof. In some cases, the first set of nucleic acid molecules may comprise one or more different nucleic acid sequences. The first set of nucleic acid molecules may comprise a first subset of nucleic acid molecules comprising the first nucleic acid sequence and a second subset of nucleic acid molecules comprising a third nucleic acid sequence, which first and third nucleic acid sequences are different. The first subset of nucleic acid molecules and the second subset of nucleic acid molecules may both comprise a fourth nucleic acid sequence. The fourth nucleic acid sequence may comprise a poly(T) sequence.

The nucleic acid molecules of the first set of nucleic acid molecules may be immobilized to the surface at independently addressable locations. The independently addressable locations may be substantially planar and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per mm$^2$, such as at least 100,000, 1,000,000, 10,000,000, or more molecules per mm$^2$. The surface of the substrate may be substantially planar and may comprise a plurality of wells. The substrate may comprise one or more particles immobilized thereto.

The method may further comprise, subsequent to a period of storage of the treated surface, removing nucleic acid molecules of the second set of nucleic acid molecules from the treated surface. The nucleic acid molecules may be removed via, for example, enzymatic degradation or via denaturing via chemical or thermal stimulation (e.g., application of a chemical stimulus such as sodium hydroxide). The nucleic acid molecules of the second set of nucleic acid molecules may be removed from said treated surface by denaturing said first nucleic acid sequence hybridized to the second nucleic acid sequence, e.g., by heating the treated surface or a solution in contact with the treated surface to between about 40° C. and 60° C. After removing these nucleic acid molecules, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

In some cases, a single nucleic acid molecule may play the role of both a nucleic acid molecule coupled to a surface and a blocking nucleic acid molecule. For example, a nucleic acid molecule coupled to a surface may comprise a first sequence and a second sequence, which second sequence may be complementary to the first sequence. The second sequence may hybridize to the first sequence to provide a hairpin molecule that is immobilized to the surface. Such a scheme may provide a higher blocking efficiency and thus a higher contamination resistance. The portion of the nucleic acid molecule including the second sequence may be separated from the immobilized portion of the nucleic acid molecule including the first sequence (e.g., by cleaving the molecule at a cleavage site disposed between the first and second sequences) and the portion of the nucleic acid molecule including the second sequence may be removed (e.g., via denaturation or enzymatic degradation) and washed away.

Accordingly, in another aspect, the present disclosure may provide a method for storing a substrate comprising a nucleic acid molecule-coated surface, comprising providing a substrate having a surface comprising a first set of nucleic acid molecules immobilized thereto, wherein nucleic acid molecules of the first set of nucleic acid molecules may be configured to capture sample nucleic acid molecules derived from one or more nucleic acid samples. Each nucleic acid molecule of the first set of nucleic acid molecules may comprise a first nucleic acid sequence and a second nucleic acid sequence, which second nucleic acid sequence is substantially complementary to the first nucleic acid sequence. The first sequence and the second sequence may each comprise at least 6 bases, such as at least 10 bases, 12 bases, 15 bases, 20 bases, or more. A treated surface may be generated by subjecting the surface to conditions sufficient to bind the first nucleic acid sequence of a nucleic acid molecule of the first set of nucleic acid molecules to the second nucleic acid sequence of the nucleic acid molecule to provide an immobilized hairpin molecule. The substrate having the treated surface may then be stored for a time period of at least 1 hour, such as at least 2 hours, 6 hours, 12 hours, 24 hours, 2 days, or longer. The treated surface may be stored under any useful conditions (e.g., as described herein). During storage of the treated surface, each nucleic acid molecule of the first set of nucleic acid molecules may not hybridize to another nucleic acid molecule. At least 70% (e.g., at least 75%, 80%, 85%, 90%, 95%, or more) of nucleic acid molecules of the first set of nucleic acid molecules may be present as immobilized hairpin molecules during storage of the treated surface.

The nucleic acid molecules of the first set of nucleic acid molecules may be immobilized to the surface at independently addressable locations. The independently addressable locations may be substantially planar and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per mm$^2$, such as at least 100,000, 1,000,000, 10,000,000, or more molecules per mm$^2$. The surface of the substrate may be substantially planar, and/or may comprise a plurality of wells. The substrate may comprise one or more particles immobilized thereto.

The first set of nucleic acid molecules may comprise one or more different nucleic acid sequences. For example, the first set of nucleic acid molecules may comprise a first subset of nucleic acid molecules comprising the first nucleic acid sequence and the second nucleic acid sequence, and a second subset of nucleic acid molecules comprising a third nucleic acid sequence and a fourth nucleic acid sequence. The third nucleic acid sequence may be substantially complementary to the fourth nucleic acid sequences. The first nucleic acid sequence may be different from the third and fourth nucleic acid sequences. The first subset of nucleic acid molecules and the second subset of nucleic acid molecules may both comprise a fifth nucleic acid sequence, which fifth nucleic acid sequence may comprise a poly(T) sequence.

The method may further comprise, subsequent to storage of the treated surface for a period of time, separating the second sequence from the first sequence of the immobilized hairpin molecule. Separating the first and second sequences may be achieved via enzymatic degradation or denaturation using a chemical or thermal stimulus (e.g., a chemical stimulus such as sodium hydroxide). After separating these sequences, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof. Each nucleic acid molecule of the first set of nucleic acid molecules may comprise a cleavable base. The cleavable base may be disposed between the first and second sequences of the nucleic acid molecule. Subsequent to separating the first and second sequences of the immobilized hairpin molecule, the nucleic acid molecule may be cleaved at the cleavable base, thereby removing the second sequence of the nucleic acid molecule from the surface.

The present disclosure also provides kits including treated surfaces and kits for preparing treated surfaces. A kit may include a substrate comprising a treated surface and one or more reagents for processing the treated surface (e.g., for removing blocking oligonucleotides from the treated surface and preparing the surface for use in a subsequent application). A kit may include a substrate comprising a surface and a plurality of oligonucleotides for coupling to the substrate. The kit may also include a plurality of blocking oligonucleotides configured to hybridize to the plurality of oligonucleotides, as well as reagents for removing the blocking oligonucleotides and/or preparing the surface for use in a subsequent application. A kit provided herein may also comprise reagents for use in a subsequent application, and/or instructions for storing, preparing, unblocking, or otherwise utilizing a surface of a substrate.

In an aspect, the present disclosure provides a kit comprising a substrate comprising a treated surface, wherein the treated surface comprises a plurality of pairs of bound nucleic acid molecules, wherein each pair of the plurality of pairs comprises a first nucleic acid molecule of a first set of nucleic acid molecules at least partially hybridized to a second nucleic acid molecule of a second set of nucleic acid molecules. The first set of nucleic acid molecules may be immobilized to the surface. At least 70% (e.g., 75%, 80%, 85%, 90%, 95%, or more) of nucleic acid molecules of the first set of nucleic acid molecules may be paired with a nucleic acid molecule of the second set of nucleic acid molecules. Nucleic acid molecules of the first set of nucleic acid molecules may be configured to capture sample nucleic acid molecules derived from one or more nucleic acid samples when the nucleic acid molecules of the first set of nucleic acid molecules are not paired with nucleic acid molecules of the second set of nucleic acid molecules.

The treated surface may be stored for a period of time, such as for at least 6 hours, 12 hours, 24 hours, 2 days, or longer. The treated surface may be stored under any useful conditions (e.g., as described herein). During storage of the treated surface, each nucleic acid molecule of the first set of nucleic acid molecules in each pair of the plurality of pairs may not hybridize to another nucleic acid molecule (e.g., a sample nucleic acid molecule).

The kit may comprise one or more reagents for processing nucleic acid molecules. For example, the kit may comprise a kit further comprising a chemical stimulus (e.g., sodium hydroxide) configured to remove second nucleic acid molecules from the treated surface.

The surface of the substrate may be substantially planar, and/or may comprise a plurality of wells. In some cases, the substrate may comprise one or more particles (e.g., beads) immobilized thereto. Nucleic acid molecules of the first set of nucleic acid molecules may be immobilized to the surface at independently addressable locations. The independently addressable locations may be substantially planar, and/or may comprise one or more wells. In some cases, a density of the first set of nucleic acid molecules on the surface may be at least 10,000 molecules per $mm^2$, such as at least 100,000, 1,000,000, 10,000,000, or more molecules per $mm^2$. Nucleic acid molecules of the first set of nucleic acid molecules may be immobilized to the surface according to a predetermined pattern or may be randomly distributed on the surface.

The second nucleic acid molecule may comprise a sequence that is substantially complementary to a sequence of the first nucleic acid molecule. The sequence of the first nucleic acid molecule and/or the second nucleic acid molecule may comprise at least 6 bases, such as at least 10, 12, 16, 20, or more bases. In some cases, the first nucleic acid molecule and the second nucleic acid molecule may comprise the same number of nucleotides. Alternatively, the first nucleic acid molecule and the second nucleic acid molecule may comprise different numbers of nucleotides. Each nucleic acid molecule of the second set of nucleic acid molecules may comprise at least 6 bases. The first and/or second set of nucleic acid molecules may comprise DNA nucleotides, RNA nucleotides, or a mixture thereof.

Each nucleic acid molecule of the first set of nucleic acid molecules may comprise the same nucleic acid sequence. Alternatively, the first set of nucleic acid molecules may comprise one or more different nucleic acid sequences. For example, the first set of nucleic acid molecules may comprise a first subset of nucleic acid molecules comprising a first nucleic acid sequence and a second subset of nucleic acid molecules comprising a second nucleic acid sequence. The first and second nucleic acid sequences may be different. The first and second subsets of nucleic acid molecules may both comprise a third nucleic acid sequence, which third nucleic acid sequence may comprise a poly(T) sequence.

In another aspect, the present disclosure provides a kit comprising a substrate comprising a surface comprising a first set of nucleic acid molecules immobilized thereto, wherein the first set of nucleic acid molecules comprises one or more first nucleic acid molecules. One or more first nucleic acid molecules may be configured to capture sample nucleic acid molecules derived from one or more nucleic acid samples. The kit may also comprise a solution comprising a second set of nucleic acid molecules, wherein the second set of nucleic acid molecules comprises one or more second nucleic acid molecules, which one or more second nucleic acid molecules are not said sample nucleic acid molecules. The second set of nucleic acid molecules may be selected such that, upon bringing the solution in contact with the surface, at least 70% of the one or more first nucleic acid molecules (e.g., at least 75%, 80%, 85%, 90%, 90%, or more) bind to a second nucleic acid molecule of the second set of nucleic acid molecules to generate one or more pairs of bound nucleic acid molecules. Each pair of the one or more pairs may comprise (i) a first nucleic acid molecule of the first set of nucleic acid molecules and a second nucleic acid molecule of the second set of nucleic acid molecules, and (ii) a section of substantially complementary sequences. Each nucleic acid molecule of the first set of nucleic acid molecules in each pair of the one or more pairs may not hybridize to another nucleic acid molecule (e.g., during storage of the treated surface). For example, paired nucleic acid molecules may not hybridize to a sample nucleic acid molecule.

The treated surface may be stored for a period of time, such as for at least 6 hours, 12 hours, 24 hours, 2 days, or longer. The treated surface may be stored under any useful conditions (e.g., as described herein).

The kit may comprise one or more reagents for processing nucleic acid molecules. For example, the kit may comprise a kit further comprising a chemical stimulus (e.g., sodium hydroxide) configured to remove second nucleic acid molecules from the treated surface.

The surface of the substrate may be substantially planar, and/or may comprise a plurality of wells. In some cases, the substrate may comprise one or more particles (e.g., beads) immobilized thereto. Nucleic acid molecules of the first set of nucleic acid molecules may be immobilized to the surface at independently addressable locations. The independently addressable locations may be substantially planar, and/or may comprise one or more wells. In some cases, a density of the first set of nucleic acid molecules on the surface may be at least 10,000 molecules per mm$^2$, such as at least 100,000, 1,000,000, 10,000,000, or more molecules per mm$^2$. Nucleic acid molecules of the first set of nucleic acid molecules may be immobilized to the surface according to a predetermined pattern or may be randomly distributed on the surface.

The section of substantially complementary sequences of each pair of the one or more pairs may comprise a first sequence of a first nucleic acid molecule of the one or more first nucleic acid molecules and a second sequence of a second nucleic acid molecule of the one or more second nucleic acid molecules. The first sequence may be substantially complementary to the second sequence. The first and second sequences may each comprise the same number of bases. In some cases, the first and second sequences may each comprise between about 6-20 bases. A first nucleic acid molecule of the one or more first nucleic acid molecules and a second nucleic acid molecule of the one or more second nucleic acid molecules may comprise the same number of nucleotides. Alternatively, a first nucleic acid molecule of the one or more first nucleic acid molecules and a second nucleic acid molecule of the one or more second nucleic acid molecules may comprise different numbers of nucleotides. Each nucleic acid molecule of the second set of nucleic acid molecules may comprise at least 6 bases. The first and/or second set of nucleic acid molecules may comprise DNA nucleotides, RNA nucleotides, or a mixture thereof. The sequence of a nucleic acid molecule of the first nucleic acid molecules and/or a nucleic acid molecule of the second nucleic acid molecules may comprise at least 6 bases, such as at least 10, 12, 16, 20, or more bases.

Each nucleic acid molecule of the first set of nucleic acid molecules may comprise the same nucleic acid sequence. Alternatively, the first set of nucleic acid molecules may comprise one or more different nucleic acid sequences. For example, the first set of nucleic acid molecules may comprise a first subset of nucleic acid molecules comprising a first nucleic acid sequence and a second subset of nucleic acid molecules comprising a second nucleic acid sequence. The first and second nucleic acid sequences may be different. The first and second subsets of nucleic acid molecules may both comprise a third nucleic acid sequence, which third nucleic acid sequence may comprise a poly(T) sequence.

Optical Systems for Imaging a Rotating Substrate

For a substrate exhibiting a smooth, stable rotational motion, it may be simpler or more cost-effective to image the substrate using a rotational motion system instead of a rectilinear motion system. Rotational motion, as used herein, may generally refer to motion in a polar coordinate system, comprising an angular component φ, and a radial component r, that is predominantly in an angular direction, φ. Prior optical imaging systems have utilized time delay and integration (TDI) cameras to achieve high duty cycles and maximum integration times per field point. A TDI camera (e.g., a TDI line-scan camera) may use a detection principle similar to a charge coupled device (CCD) camera. Compared to a CCD camera, the TDI camera may shift electric charge, row by row, across a sensor at the same rate as an image traverses the focal plane of the camera. In this manner, the TDI camera may allow longer image integration times while reducing artifacts such as blurring that may be otherwise associated with long image exposure times. A TDI camera may perform integration while simultaneously reading out and may therefore have a higher duty cycle than a camera that performs these functions in a serial manner. Use of a TDI camera to extend integration times may be important for high throughput fluorescent samples, which may be limited in signal production by fluorescent lifetimes. For instance, alternative imaging techniques, such as point scanning, may be precluded from use in high throughput systems as it may not be possible to acquire an adequate number of photons from a point in the limited amount of integration time required for high speeds due to limits imposed by fluorescence lifetimes of dye molecules.

Figure 8:
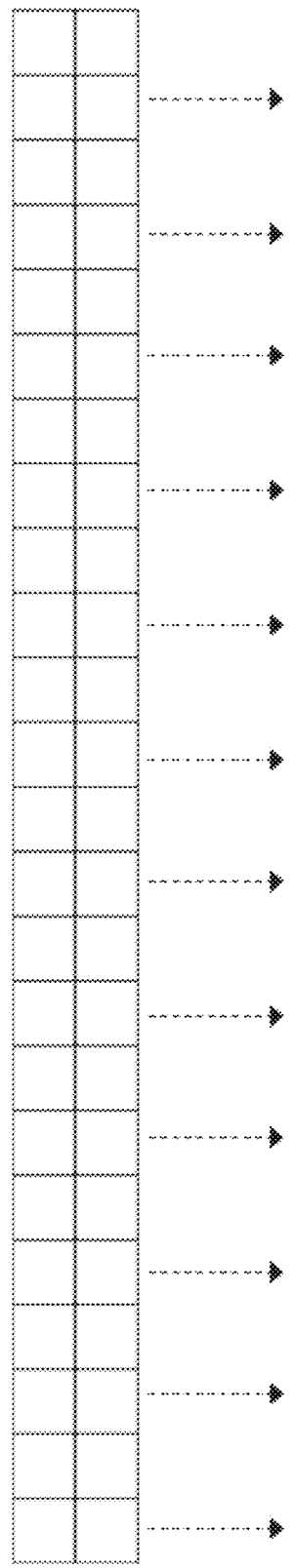
FIG. 8A-FIG. 8D illustrate schemes for line-scan cameras.

FIG. 8A-FIG. 8D illustrate example schemes for a line-scan camera. As shown in FIG. 8A, a TDI line-scan camera may comprise two or more vertically arranged rows of pixels (such as 3, 4, 5, 6, 7, 8, 9, 10, 24, 36, 48, 50, 60, 72, 84, 96, 100, 108, 120, 128, 132, 150, 200, 256, 512, 1024, 2000, 2048, 4000, 4096, 8000, 8192, 12000, 16000, 16384, or more pixels). During operation of the camera (e.g., movement of the camera relative to an open substrate), photoelectrons from each pixel in a given row may be summed into the row below the given row (e.g., in the direction of relative object motion) by shifting accumulated charges between pixel rows. FIG. 8B and FIG. 8C show pixel schemes for use in color line-scan cameras. Such cameras may include rows of pixels having different color filters to detect and/or block light of different wavelengths. For example, FIG. 8B shows a trilinear pixel scheme including rows of red, green, and blue filters. This trilinear pixel scheme may be replicated one or more times to facilitate TDI applications. FIG. 8C shows a bilinear pixel scheme including a row of alternating red and blue filters and a row of green filters. FIG. 8D shows an alternative bilinear pixel scheme including multiple Bayer patterns (e.g., 2×2 pixel arrays including a first row alternating blue and green pixels and a second row alternating green and red pixels). Like the trilinear scheme, the bilinear patterns may be replicated one or more times to facilitate TDI applications. The color line-scan schemes depicted in FIG. 8B-FIG. 8D may be substituted by alternative color combinations, including cyan, yellow, green, and magenta; red, green, blue, and emerald; cyan, magenta, yellow, and white; or any other color combination, in any arrangements (e.g., alternating, non-alternating).

Prior TDI detection schemes may be limited in their applicability to the imaging of rotating systems, such as the rotating nucleic acid sequencing systems described herein. When scanning a curved path, such as the curved path generated by the rotating systems described herein, a TDI sensor may only be able to shift charge (commonly referred to as clocking or line triggering) at the correct rate for a single velocity. For instance, the TDI sensor may only be able to clock at the correct rate along an arc located at a particular distance from the center of rotation. Locations at smaller distances from the center of rotation may clock too quickly, while locations at smaller distances from the center of rotation may clock too slowly. In either case, the mismatch between the rotational speed of the rotating system and the clock rate of the TDI sensor may cause blurring that varies with the distance of a location from the center of the rotating system. This effect may be referred to as tangential velocity blur. The tangential velocity blur may produce an image distortion of a magnitude a defined by equation (2):

$$\sigma = \frac{hw}{2R} = \frac{A}{2R} \quad (2)$$

Here, h, w, and A are the effective height, width, and area, respectively, of the TDI sensor projected to the object plan. These values may be adjusted using one of more optical elements (e.g., lenses, prisms, mirrors, etc.). R is the distance of the center of the field from the center of the rotating system. The effective height, width, and area of the sensor are the height, width, and area, respectively, that produce signal. In the case of fluorescence imaging, the effective height, width, and area of the sensor may be the height, width, and area, respectively, that correspond to illuminated areas on the sample. In addition to the tangential velocity blur effect, Equation (2) implies that increasing sensor area, which may be a goal of many imaging systems, may introduce imaging complications for TDI imaging of rotating systems. Consequently, prior TDI systems may require small image sensors to image rotating systems and may thus be unfit for simultaneous high-sensitivity and high-throughput imaging of such systems.

Described herein are systems and methods for imaging rotating systems that can address at least the abovementioned problems. The systems and methods described herein may benefit from higher efficiency, such as from faster imaging time.

Figure 9:
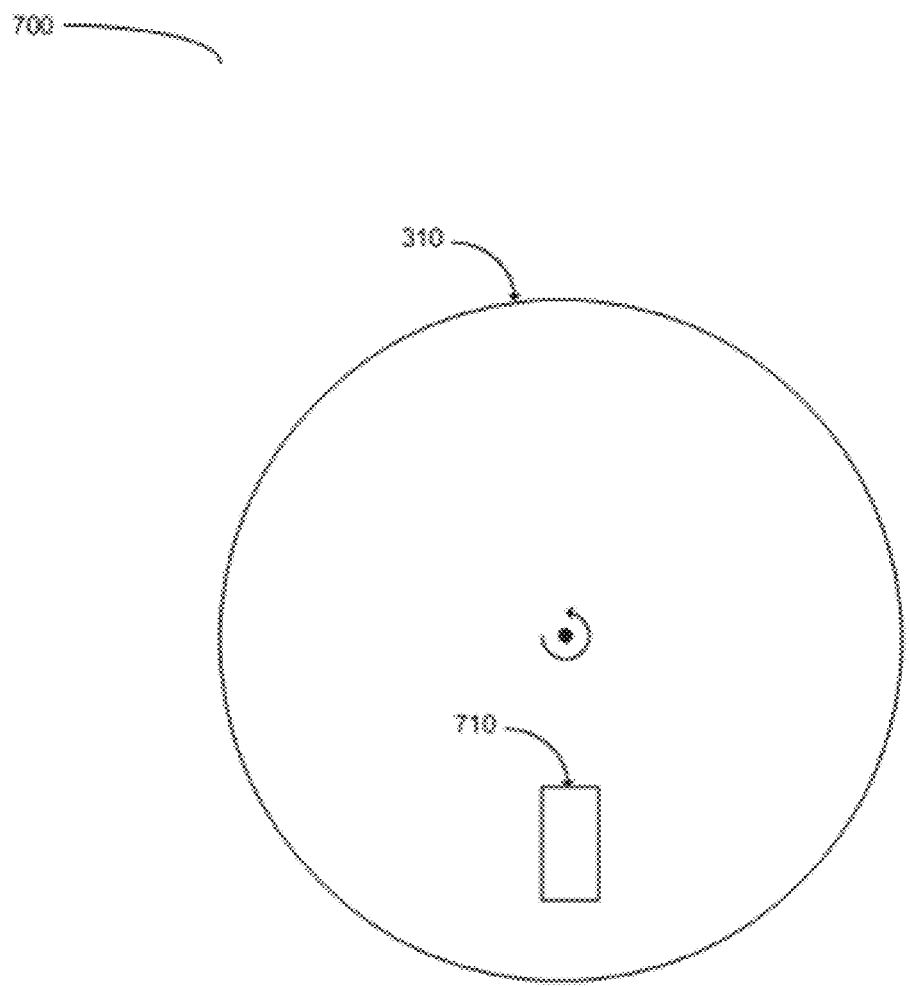
FIG. 9 shows an optical system for continuous area scanning of a substrate during rotational motion of the substrate.

FIG. 9 shows an optical system 700 for continuous area scanning of a substrate during rotational motion of the substrate. The term "continuous area scanning (CAS)," as used herein, generally refers to a method in which an object in relative motion is imaged by repeatedly, electronically or computationally, advancing (clocking or triggering) an array sensor at a velocity that compensates for object motion in the detection plane (focal plane). CAS can produce images having a scan dimension larger than the field of the optical system. TDI scanning may be an example of CAS in which the clocking entails shifting photoelectric charge on an area sensor during signal integration. For a TDI sensor, at each clocking step, charge may be shifted by one row, with the last row being read out and digitized. Other modalities may accomplish similar function by high speed area imaging and co-addition of digital data to synthesize a continuous or stepwise continuous scan.

The optical system may comprise one or more sensors 710. As shown, in FIG. 9, the sensors may detect an image optically projected from the sample. The optical system may comprise one or more optical elements, such as the optical element 810 described in the context of FIG. 8. An optical element may be, for example, a lens, prism, mirror, wave plate, filter, attenuator, grating, diaphragm, beam splitter, diffuser, polarizer, depolarizer, retroreflector, spatial light modulator, or any other optical element. The system may comprise a plurality of sensors, such as at least 2, at least 5, at least 10, at least 20, at least 50, at least 100, at least 200, at least 500, or at least 1,000 sensors. The system may comprise a at least 2, at least 4, at least 8, at least 16, at least 32, at least 64, at least 128, at least 256, at least 512, or at least 1,024 sensors. The plurality of sensors may be the same type of sensor or different types of sensors. Alternatively, the system may comprise at most about 1000, 500, 200, 100, 50, 20, 10, 5, 2, or fewer sensors. Alternatively, the system may comprise at most about 1024, 512, 256, 128, 64, 32, 16, 8, 4, 2, or fewer sensors. The system may comprise a number of sensors that is within a range defined by any two of the preceding values. The sensors may comprise image sensors. The sensors may comprise CCD cameras. The sensors may comprise CMOS cameras. The sensors may comprise TDI cameras (e.g., TDI line-scan cameras). The sensors may comprise pseudo-TDI rapid frame rate sensors. The sensors may comprise CMOS TDI or hybrid cameras. The sensors may be integrated together in a single package. The sensors may be integrated together in a single semiconductor substrate. The system may further comprise any optical source described herein (not show in FIG. 9).

The sensors may be configured to detect an image from a substrate, such as the substrate 310 described herein, during rotational motion of the substrate. The rotational motion may be with respect to an axis of the substrate. The axis may be an axis through the center of the substrate. The axis may be an off-center axis. The substrate may be configured to rotate at any rotational speed described herein. The rotational motion may comprise compound motion. The compound motion may comprise rotation and an additional component of radial motion. The compound motion may be a spiral (or substantially spiral). The compound motion may be a ring (or substantially ring-like).

Each sensor may be located at a conjugate focal plane with respect to the substrate. Each sensor may be in optical communication with the substrate. The conjugate focal plane may be the approximate plane in an imaging system (e.g., CAS sensor) at which an image of a region of the substrate forms. A sensor may be located at a plane conjugate to a plane comprising the substrate (e.g., an image plane). The conjugate focal plane may be segmented into a plurality of regions, such as at least 2, at least 5, at least 10, at least 20, at least 50, at least 100, at least 200, at least 500, or at least 1000 regions. The conjugate focal plane may be segmented into at least 2, at least 4, at least 8, at least 16, at least 32, at least 64, at least 128, at least 256, at least 512, or at least 1,024 regions. The conjugate focal plane may be segmented into a number of regions that is within a range defined by any two of the preceding values. The conjugate focal plane may be segmented into a plurality of regions along an axis substantially normal to a projected direction of the rotational motion. An angle between the axis and the projected direction of the rotational motion may be no more than 1 degree, no more than 2 degrees, no more than 3 degrees, no more than 4 degrees, no more than 5 degrees, no more than 6 degrees, no more than 7 degrees, no more than 8 degrees, no more than 9 degrees, no more than 10 degrees, no more than 11 degrees, no more than 12 degrees, no more than 13 degrees, no more than 14 degrees, or no more than 15 degrees from normal, or an angle that is within a range defined by any two of the preceding values. The conjugate focal plane may be segmented into a plurality of regions along an axis parallel to a projected direction of the rotational motion. The conjugate focal plane may be spatially segmented. For instance, the conjugate focal plane may be segmented by abutting or otherwise arranging a plurality of sensors in a single focal plane and clocking each of the sensors independently.

Alternatively or in combination, the conjugate focal plane may be segmented by optically splitting the conjugate focal plane into a plurality of separate focal paths, each of which may form a sub-image on an independent sensor of the plurality of sensors and which may be clocked independently. The focal path may be optically split using one or more optical elements, such as a lens array, mirror, or prism. Each sensor of the plurality of sensors may be in optical communication with a different region of the rotating substrate. For instance, each sensor may image a different region of the rotating substrate. Each sensor of the plurality of sensors may be clocked at a rate appropriate for the region of the rotating substrate imaged by the sensor, which may be based on the distance of the region from the center of the rotating substrate or the tangential velocity of the region. For example, a first sensor (e.g., a line-scan camera) imaging a first region through a first objective positioned farther from the axis of rotation of the rotating substrate may be clocked at a faster rate than a second sensor imaging a second region through a second objective positioned closer to the axis of rotation of the rotating substrate.

One or more of the sensors may be configured to be in optical communication with at least 2 of the plurality of regions in the conjugate focal plane. One or more of the sensors may comprise a plurality of segments. Each segment of the plurality of segments may be in optical communication with a region of the plurality of regions. Each segment of the plurality of segments may be independently clocked. The independent clocking of a segment may be linked to a velocity of an image in an associated region of the focal plane. The independent clocking may comprise TDI line rate or pseudo-TDI frame rate.

The system may further comprise a controller (not shown). The controller may be operatively coupled to the one or more sensors. The controller may be programmed to process optical signals from each region of the rotating substrate. For instance, the controller may be programmed to process optical signals from each region with independent clocking during the rotational motion. The independent clocking may be based at least in part on a distance of each region from a projection of the axis and/or a tangential velocity of the rotational motion. The independent clocking may be based at least in part on the angular velocity of the rotational motion. While a single controller has been described, a plurality of controllers may be configured to, individually or collectively, perform the operations described herein.

Figure 10A:
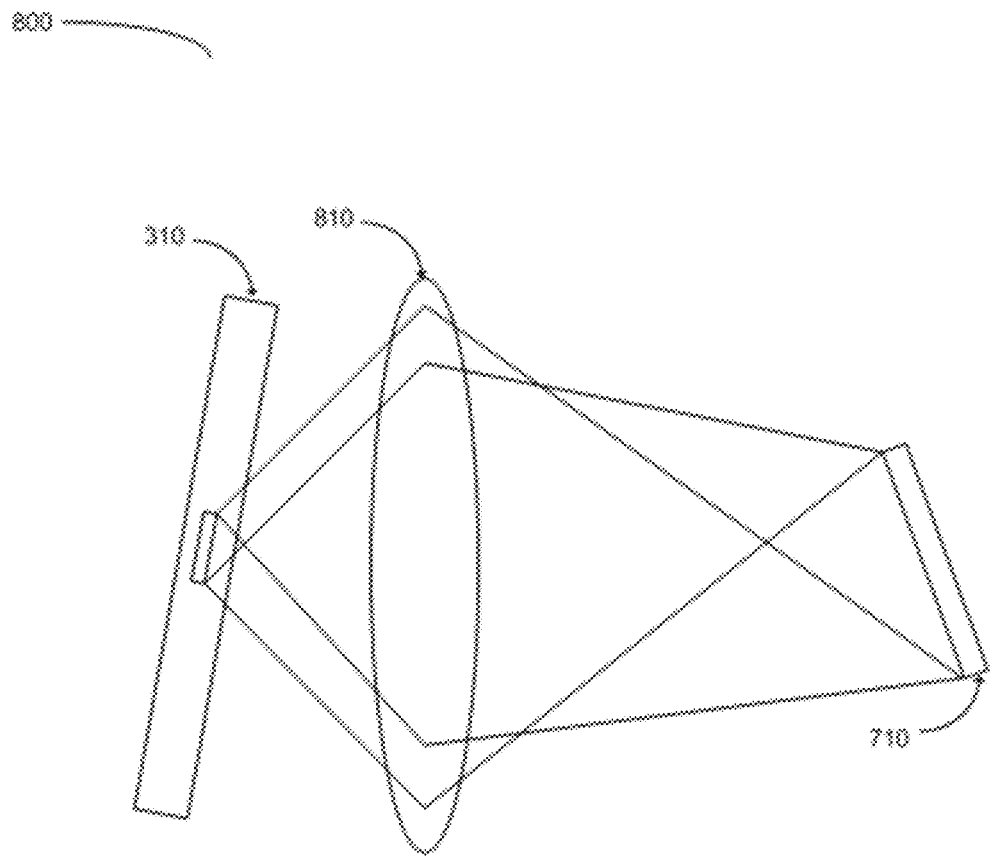
FIG. 10A shows an optical system for imaging a substrate during rotational motion of the substrate using tailored optical distortions.
Figure 10B:
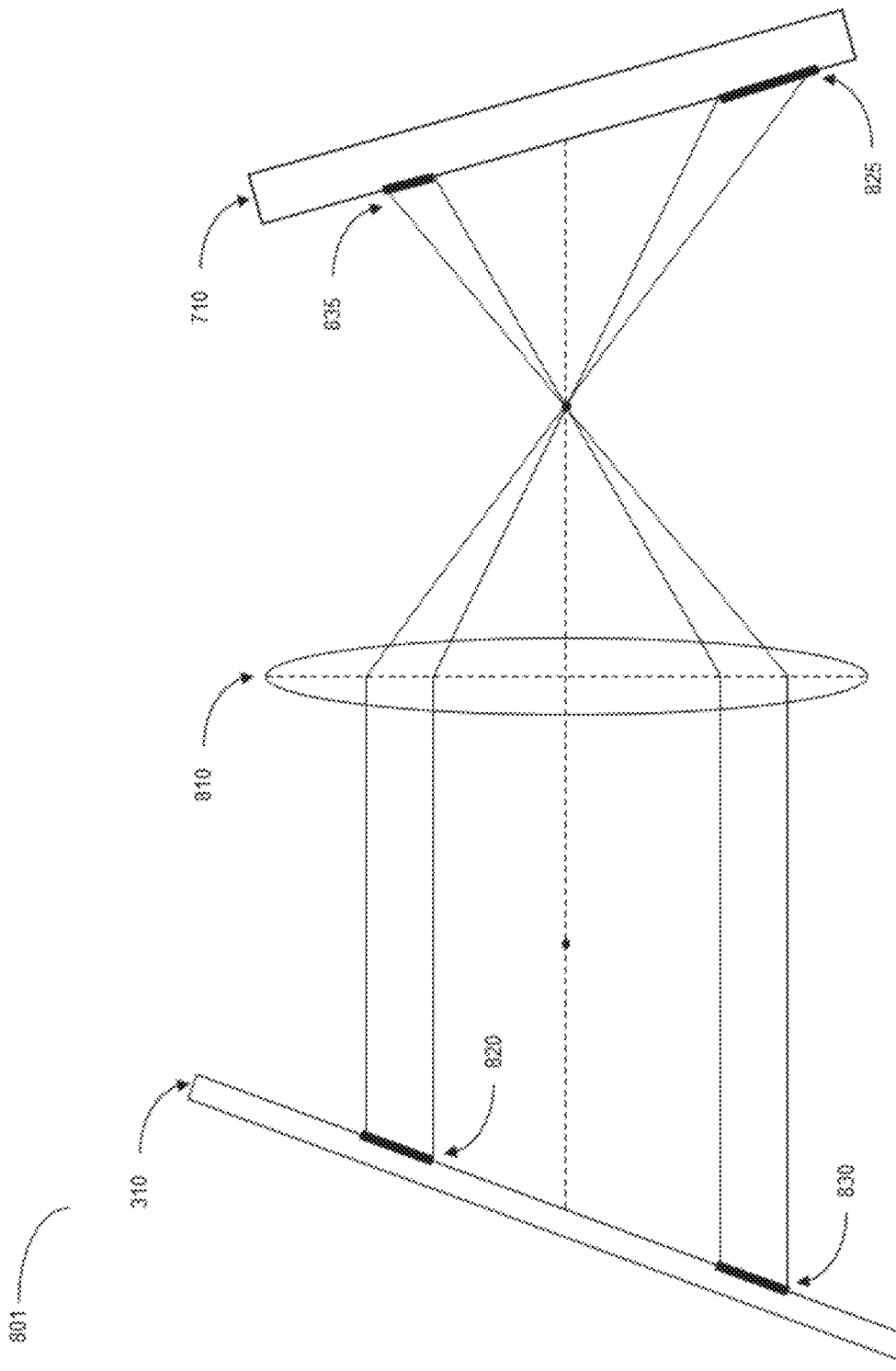
FIG. 10B shows an optical system for imaging a substrate during rotational motion of the substrate using tailored optical distortions.

FIG. 10A shows an optical system 800 for imaging a substrate during rotational motion of the substrate using tailored optical distortions. The optical system may comprise one or more sensors 710. The one or more sensors may comprise any sensors described herein. The optical system may comprise any optical sources described herein (not shown in FIG. 10A). FIG. 10B shows optical system 801 for imaging a substrate during rotational motion of the substrate using tailored optical distortions. The optical system may comprise one or more sensors 710. The one or more sensors may comprise any sensors described herein. The optical system may comprise any optical sources described herein (not shown in FIG. 10B). The optical system may comprise a lens 810, for example a plano-convex lens. In some embodiments, the substrate 310 is tilted with respect to the lens 810 and the detector 710. In some embodiments, the lens 810 is tilted with respect to the detector 710, thereby producing anamorphic magnification of light (e.g., fluorescence or scattered light) from the substrate. Anamorphic magnification may result in differential magnification of light from a first region of the substrate 820 and a second region of the substrate 830. The light from the first region of the substrate may be magnified by a first amount at a first position on the detector 825, and the light from the second region of the substrate may be magnified by a second amount at a second position on the detector 835. In some embodiments, the anamorphic magnification may occur along a single axis. In some embodiments, a cylindrical lens may be used to produce anamorphic magnification along a single axis.

The sensors may be configured to detect an image from a substrate, such as the substrate 310 described herein, during rotational motion of the substrate. The rotational motion may be with respect to an axis of the substrate. The axis may be an axis through the center of the substrate. The axis may be an off-center axis. The substrate may be configured to rotate at any rotational speed described herein.

The system 800 may further comprise an optical element 810. The optical element may be in optical communication with the sensor. The optical element may be configured to direct optical signals from the substrate to the sensor. The optical element may produce an optical magnification gradient across the sensor. At least one of the optical elements and the sensor may be adjustable. For instance, at least one of the optical elements and the sensor may be adjustable to generate an optical magnification gradient across the sensor. The optical magnification gradient may be along a direction substantially perpendicular to a projected direction of the rotational motion of the substrate. The optical element may be configured to rotate, tilt, or otherwise be positioned to engineer the optical magnification gradient. The optical element may produce a magnification that scales approximately as the inverse of the distance to the axis of the substrate. The magnification gradient may be produced by selecting a relative orientation of the substrate, optical element, and sensor. For instance, the magnification gradient may be produced by tilting the object and image planes as shown in FIG. 10A and FIG. 10B. The magnification gradient may display geometric properties. For instance, a ratio of a first optical magnification of a first region 820 at a maximum distance from the center of the substrate to a second optical magnification of a second region 830 at a minimum distance from the center of the substrate may be substantially equal to a ratio of the maximum distance to the minimum distance. In this manner, the first and second optical magnifications may be in the same ratio as the radii of their respective sample regions. Although the system 800 and system 801 as shown include a single optical element 810, the system 800 or system 801 may include a plurality of optical elements, such as at least 2, 3, 4, 5, 6, 7, 8, 9, 10, 20, 30, 40, 50, 100, or more optical elements. Various arrangements or configurations of optical elements may be employed. For example, the system 800 may include a lens and a mirror for directing light.

Figure 10C:
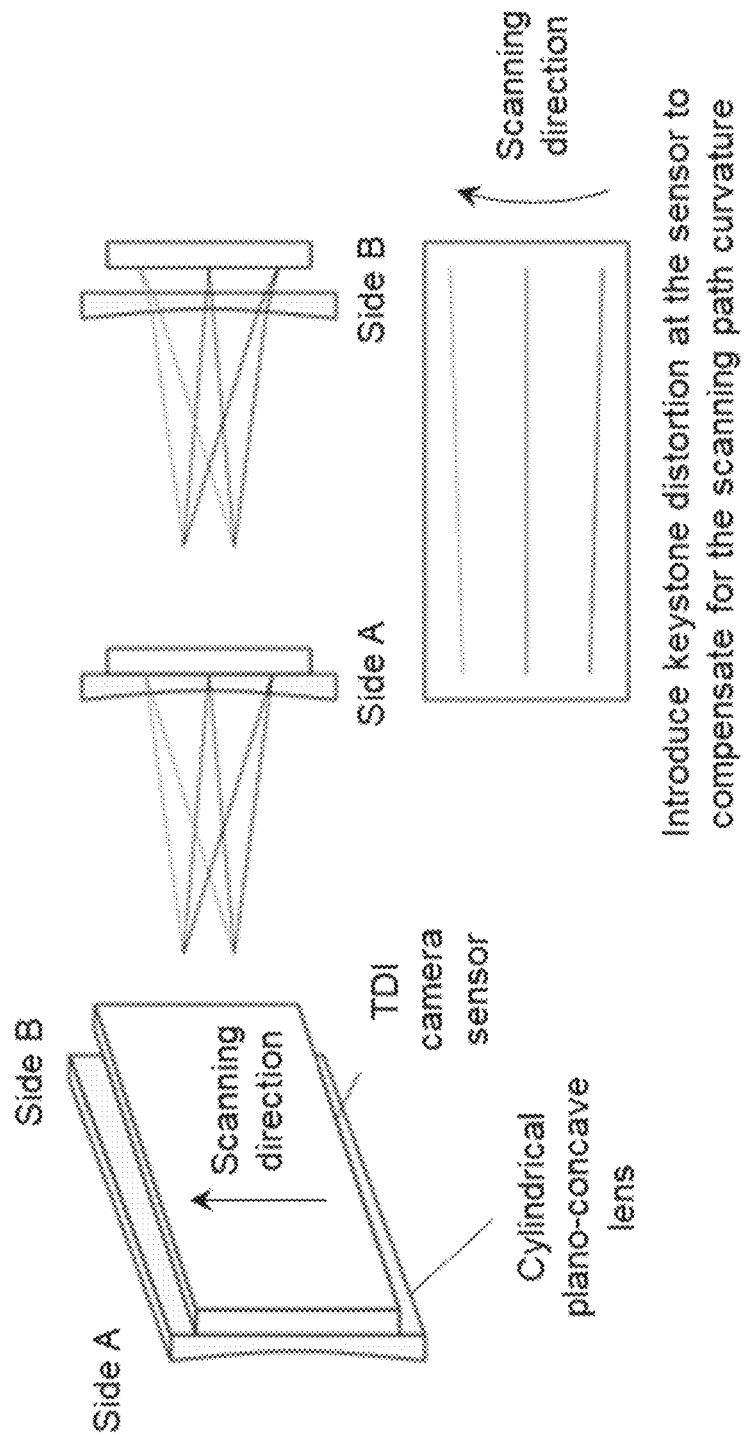
FIG. 10C shows an example of induced tailored optical distortions using a cylindrical lens.

The optical element may be a lens. The lens may be a field lens. The lens may be a cylindrical lens (for instance, as shown in FIG. 10C). The cylindrical lens may be plano-cylindrical. The lens may be plano-concave or plano-convex. The cylindrical lens may have a positive or negative curvature. The curvature of the cylindrical lens may vary. The curvature of the cylindrical lens may vary in a direction perpendicular to a projected direction of rotational motion. The shape of a surface of the lens may be conical. The lens may be tilted with respect to the sensor, thereby producing an anamorphic magnification gradient. The tilt of the lens may be adjustable, thereby producing an adjustable anamorphic magnification gradient.

FIG. 10C shows an example of induced tailored optical distortions using a cylindrical lens. As shown in FIG. 10C, a cylindrical lens may have a first side A and a second side B. The first side A may be located closer to an image sensor (such as a TDI camera sensor described herein) than the second side B. Such a configuration may be achieved by tilting the cylindrical lens in relation to the image sensor. In this manner, the cylindrical lens may direct light to different locations on the image sensor, with light passing through side B being directed more divergently than light passing through side A. In this manner, the cylindrical lens may provide an anamorphic magnification gradient across the image sensor, as depicted in FIG. 10C.

Tilting of the lens may provide an anamorphic magnification gradient across the sensor. The tilt and hence anamorphic gradient may be in a direction substantially perpendicular to the image motion on the sensor. The tilt of the lens may be adjustable. The adjustment may be automatic by using a controller. The adjustment may be coupled to the radius of the scanned substrate region relative to the substrate axis of rotation. The ratio of the minimum to maximum anamorphic magnification may be exactly or approximately in the ratio of the minimum to maximum projected radii relative to the substrate axis of rotation.

Alternatively or in combination, a gradient in the radius of curvature of the lens may provide an anamorphic magnification gradient across the sensor. The curvature gradient may be in a direction substantially direction perpendicular to the image motion on the sensor.

The system may further comprise a controller (not shown). The controller may be operatively coupled to the sensor and the optical element. The controller may be programmed to direct the adjustment of at least one of the sensors and the optical element to generate an optical magnification gradient across the sensor. The magnification gradient may be generated along a direction substantially perpendicular to a projected direction of the rotational motion. The controller may be programmed to direct adjustment of the sensor and/or the optical element to produce an anamorphic optical magnification gradient. The optical magnification gradient may be across the sensor in a direction substantially perpendicular to a projected direction of the rotational motion. The controller may be programmed to direct rotation or tilt of the optical element. The controller may be programmed to direct adjustment of the magnification gradient. For instance, the controller may be programmed to direct adjustment of the magnification gradient at least in part on a radial range of a field dimension relative to a projection about the axis of the substrate. The controller may be programmed to subject the rotational motion to the substrate. While a single controller has been described, a plurality of controllers may be configured to, individually or collectively, perform the operations described herein.

The optical systems described herein may utilize multiple scan heads. The multiple scan heads may be operated in parallel along different imaging paths. For instance, the scan heads may be operated to produce interleaved spiral scans, nested spiral scans, interleaved ring scans, nested ring scans, or a combination thereof. A scan head may comprise one or more of a detector element such as a camera (e.g., a TDI line-scan camera), an illumination source (e.g., as described herein), and one or more optical elements (e.g., as described herein).

Figure 13A:
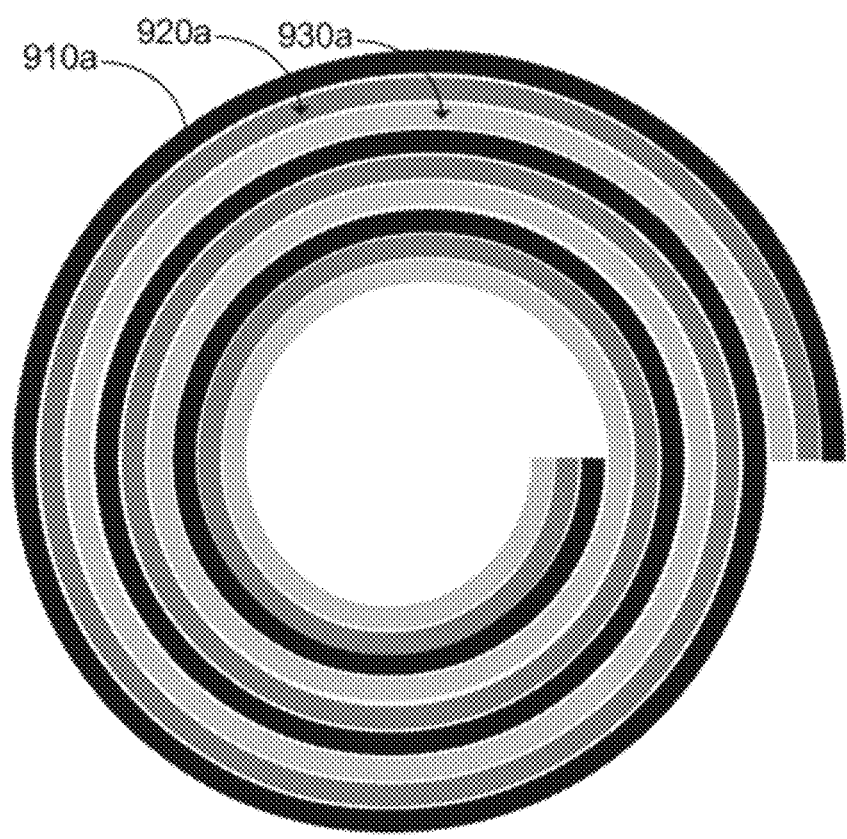
FIG. 13A shows a first example of an interleaved spiral imaging scan.

FIG. 13A shows a first example of an interleaved spiral imaging scan. A first region of a scan head may be operated along a first spiral path $910a$. A second region of a scan head may be operated along a second spiral path $920a$. A third region of a scan head may be operated along a third spiral path $930a$. Each of the first, second, and third regions may be independently clocked. The scan head may comprise any optical systems described herein. The use of multiple imaging scan paths may increase imaging throughput by increasing imaging rate.

Figure 13B:
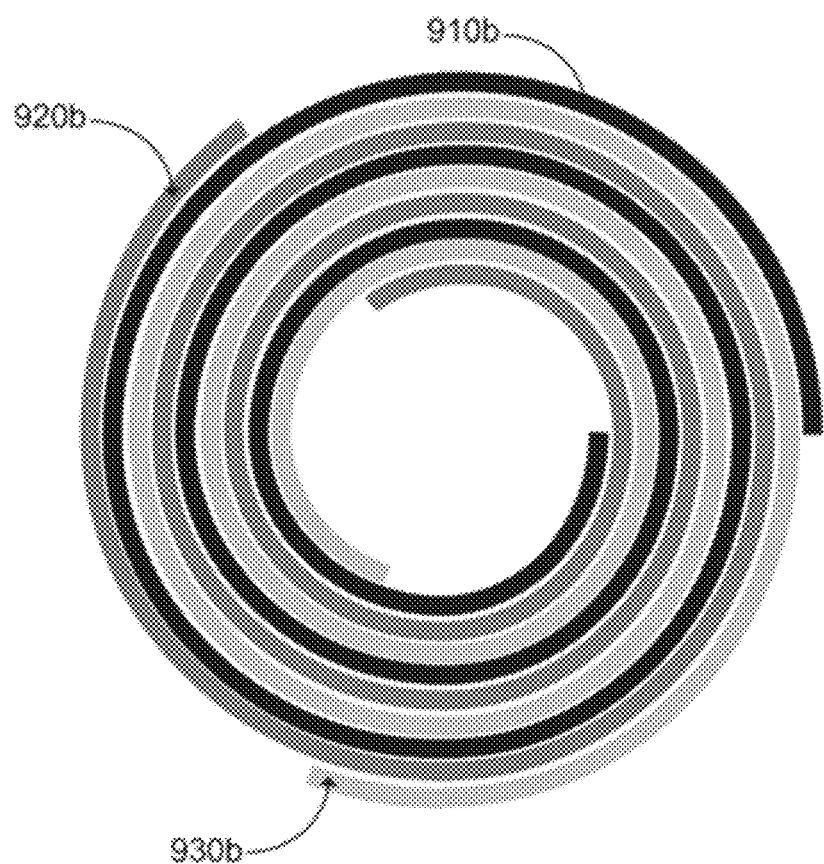
FIG. 13B shows a second example of an interleaved imaging scan.

FIG. 13B shows a second example of an interleaved spiral imaging scan. A first scan head may be operated along a first spiral path $910b$. A second scan head may be operated along a second spiral path $920b$. A third scan head may be operated along a third spiral path $930b$. Each of the first, second, and third scan heads may be independently clocked or clocked in unison. Each of the first, second, and third scan heads may comprise any optical systems described herein. The use of multiple imaging scan paths may increase imaging throughput by increasing net imaging rate. Throughput of the optical system can be multiplied by operating many scan heads of a field width in parallel. For example, each scan head may be fixed at a different angle relative to the center of substrate rotation.

Figure 13C:
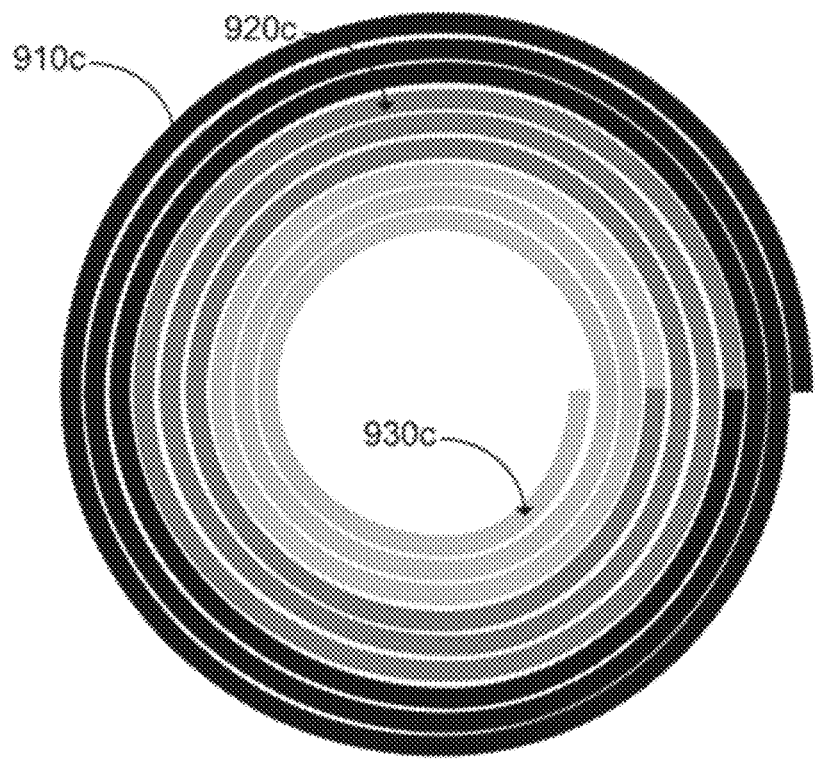
FIG. 13C shows an example of a nested imaging scan.

FIG. 13C shows an example of a nested spiral imaging scan. A first scan head may be operated along a first spiral path $910c$. A second scan head may be operated along a second spiral path $920c$. A third scan head may be operated along a third spiral path $930c$. Each of the first, second, and third scan heads may be independently clocked. Each of the first, second, and third scan heads may comprise any optical systems described herein. The use of multiple imaging scan paths may increase imaging throughput by increasing imaging rate. The scan heads may move together in the radial direction. Throughput of the optical system can be multiplied by operating many scan heads of a field width in parallel. For example, each scan head may be fixed at a different angle. The scans may be in discrete rings rather than spirals.

While FIG. 13A-FIG. 13C illustrate three imaging paths, there may be any number of imaging paths and any number of scan heads. For example, there may be at least about 2, 3, 4, 5, 6, 7, 8, 9, 10, or more imaging paths or scan heads. Alternatively, there may be at most about 10, 9, 8, 7, 6, 5, 4, 3, 2, or fewer imaging paths or scan heads. Each scan head may be configured to receive light having a wavelength within a given wavelength range. For instance, the first scan head may be configured to receive first light having a wavelength within a first wavelength range. The second scan head may be configured to receive second light having a wavelength within a second wavelength range. The third scan head may be configured to receive third light having a wavelength within a third wavelength range. Similarly, fourth, fifth, sixth, seventh, eighth, ninth, or tenth scan heads may be configured to receive fourth, fifth, sixth, seventh, eighth, ninth, or tenth light, respectively, each of the fourth, fifth, sixth, seventh, eighth, ninth, or tenth light having a wavelength within a fourth, fifth, sixth, seventh, eighth, ninth, or tenth wavelength range, respectively. The first, second, third, fourth, fifth, sixth, seventh, eighth, ninth, or tenth wavelength ranges may be identical. The first, second, third, fourth, fifth, sixth, seventh, eighth, ninth, or tenth wavelength ranges may partially overlap. Any 2, 3, 4, 5, 6, 7, 8, 9, or 10 of the first, second, third, fourth, fifth, sixth, seventh, eighth, ninth, or tenth wavelength ranges may be distinct. The first, second, third, fourth, fifth, sixth, seventh, eighth, ninth, or tenth wavelength ranges may be in the ultraviolet, visible, or near infrared regions of the electromagnetic spectrum. Each of the first, second, third, fourth, fifth, sixth, seventh, eighth, ninth, or tenth wavelength ranges may comprise a wavelength emitted by a fluorophore, dye, or quantum dot described herein. In this manner, the system may be configured to detect optical signals from a plurality of fluorophores, dyes, or quantum dots.

Scanning a surface may comprise detecting a focus of the surface relative to the detector. In some embodiments, scanning the surface comprises adjusting the focus of the surface relative to the detector. The optical systems of this disclosure may further comprise one or more autofocus systems to detect the position of the surface relative to an objective, as described elsewhere herein. An autofocus system may comprise an autofocus illumination source. The autofocus system may detect when the surface moves out of focus relative to the detector. The autofocus system may be configured to send a signal to a focusing system to adjust a position of the surface relative to the objective, thereby returning the surface to a focused position relative to the detector. In some embodiments the autofocus system may map part or all of a surface prior to scanning the surface to generate an autofocus map of the surface. The autofocus map of the surface may comprise surface textures, irregularities, or tilts that may impact the focus. The autofocus map of the surface may be used to anticipate a focal position of the surface and adjust the position of the surface relative to the objective to correct for the surface textures, irregularities, or tilts. In some embodiments, the autofocus system may map a first part of the surface (e.g., a first ring) before scanning the first part of the surface. The map of the first part of the surface may be used to anticipate and adjust the focus of the surface while scanning the first part of the surface. The map of the first part of the surface may be used to predict the focus of the surface while scanning a second part of the surface (e.g., a second ring). The second portion of the surface may be close to the first part of the surface so that the map of the first part of the surface may approximate a map of the second part of the surface. The autofocus system may map the second portion of the surface while scanning the second portion of the surface. The map of the second part of the surface may be used to anticipate and adjust the focus of the surface while scanning the third part of the surface (e.g., a third ring). In some embodiments, a map generated while scanning a third, fourth, fifth, sixth, seventh, eighth, ninth, tenth, eleventh, twelfth, or more portion of a surface may be used to anticipate and adjust the focus of the surface while scanning a fourth, fifth, sixth, seventh, eighth, ninth, tenth, eleventh, twelfth, thirtieth, or more part of the surface, respectively. Sequential surface portions may be positioned close together such that the map of a preceding part of the surface may approximate a map of the following part of the surface. In some embodiments, the autofocus system may map the entire surface before scanning. In some embodiments, the autofocus system adjust the focus while scanning without generating a map.

Figure 14:
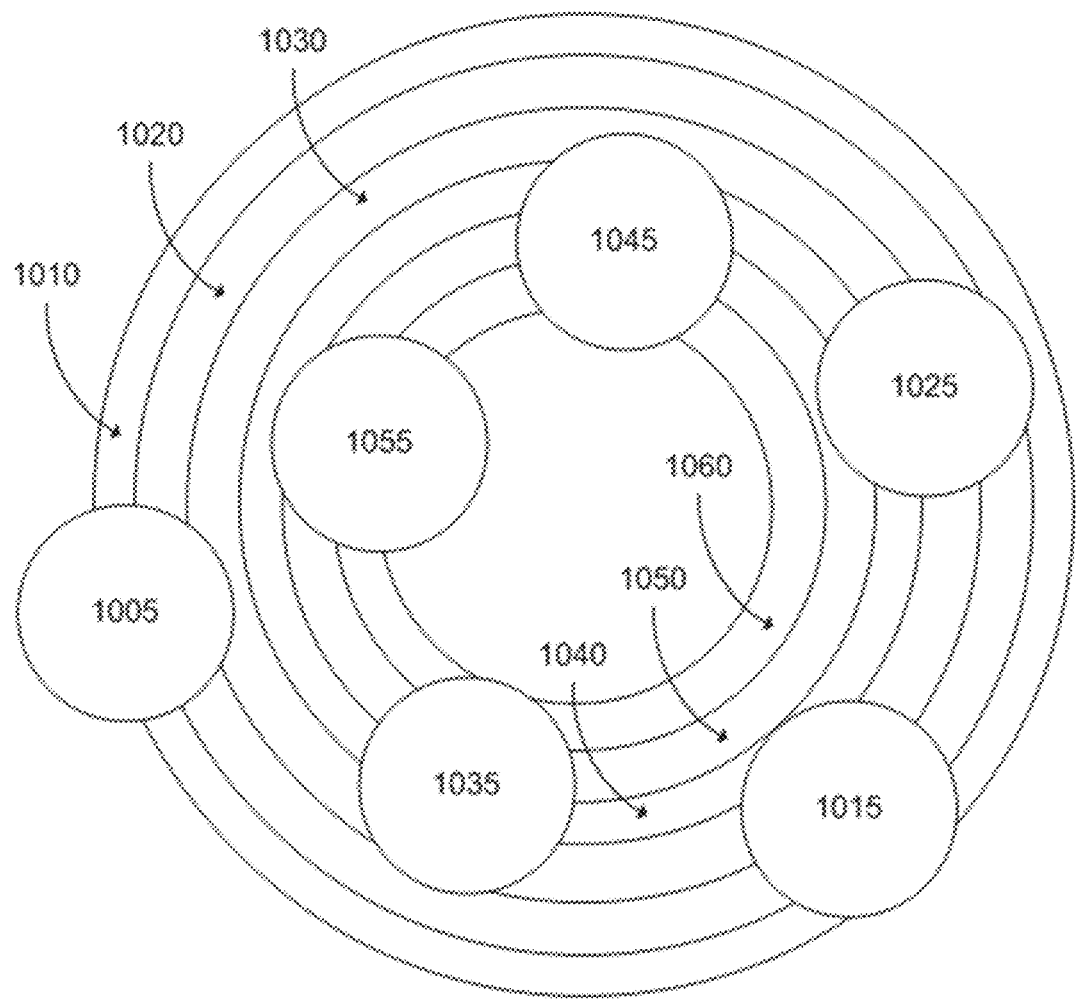
FIG. 14 shows a configuration for a nested circular imaging scan.

FIG. 14 shows a nested circular imaging scan. A first scan head 1005 may be operated along a first approximately circular path 1010. A second scan head 1015 may be operated along a second approximately circular path 1020. A third scan head 1025 may be operated along a third approximately circular path 1030. A fourth scan head 1035 may be operated along a fourth approximately circular path 1040. A fifth scan head 1045 may be operated along a fifth approximately circular path 1050. A sixth scan head 1055 may be operated along a sixth approximately circular path 1060. Each of the first, second, third, fourth, fifth, and sixth scan heads may be independently clocked. Each of the first, second, third, fourth, fifth, and sixth scan heads may comprise any optical systems described herein. Each of the first, second, third, fourth, fifth, and sixth scan heads may be configured to remain in a fixed location during scanning of a substrate. Alternatively, one or more of the first, second, third, fourth, fifth, and sixth scan heads may be configured to move during scanning of a substrate. The use of a plurality of scan heads imaging along approximately circular imaging paths may greatly increase imaging throughput. For instance, the configuration of scan heads depicted in FIG. 14 may allow all addressable locations on a substrate to be imaged during a single rotation of the substrate. Such a configuration may have the additional advantage of simplifying the mechanical complexity of an imaging system by requiring only one scanning motion (e.g., the rotation of the substrate).

While FIG. 14 illustrates six imaging paths and six scan heads, there may be any number of imaging paths and any number of scan heads. For example, there may be at least about 2, 3, 4, 5, 6, 7, 8, 9, 10, or more imaging paths or scan heads. Alternatively, there may be at most about 10, 9, 8, 7, 6, 5, 4, 3, 2, or less imaging paths or scan heads. Each scan head may be configured to receive light having a wavelength within a given wavelength range. For instance, the first scan head may be configured to receive first light having a wavelength within a first wavelength range. The second scan head may be configured to receive second light having a wavelength within a second wavelength range. The third scan head may be configured to receive third light having a wavelength within a third wavelength range. The fourth scan head may be configured to receive fourth light having a wavelength within a fourth wavelength range. The fifth scan head may be configured to receive fifth light having a wavelength within a fifth wavelength range. The sixth scan head may be configured to receive sixth light having a wavelength within a sixth wavelength range. Similarly, seventh, eighth, ninth, or tenth scan heads may be configured to receive seventh, eighth, ninth, or tenth light, respectively, each of the seventh, eighth, ninth, or tenth light having a wavelength within a seventh, eighth, ninth, or tenth wavelength range, respectively. The first, second, third, fourth, fifth, sixth, seventh, eighth, ninth, or tenth wavelength ranges may be identical. The first, second, third, fourth, fifth, sixth, seventh, eighth, ninth, or tenth wavelength ranges may partially overlap. Any 2, 3, 4, 5, 6, 7, 8, 9, or 10 of the first, second, third, fourth, fifth, sixth, seventh, eighth, ninth, or tenth wavelength ranges may be distinct. The first, second, third, fourth, fifth, sixth, seventh, eighth, ninth, or tenth wavelength ranges may be in the ultraviolet, visible, or near infrared regions of the electromagnetic spectrum. Each of the first, second, third, fourth, fifth, sixth, seventh, eighth, ninth, or tenth wavelength ranges may comprise a wavelength emitted by a fluorophore, dye, or quantum dot described herein. In this manner, the system may be configured to detect optical signals from a plurality of fluorophores, dyes, or quantum dots.

Figure 29A:
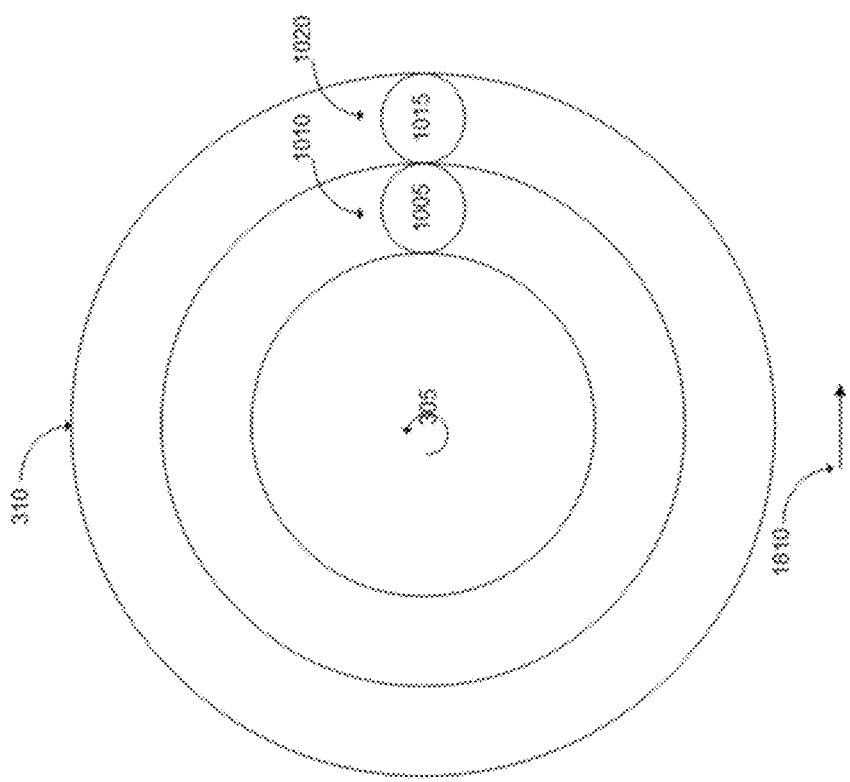
FIG. 29A shows motion of a substrate relative to two imaging heads located on the same side of an axis of rotation of the substrate.
Figure 29B:
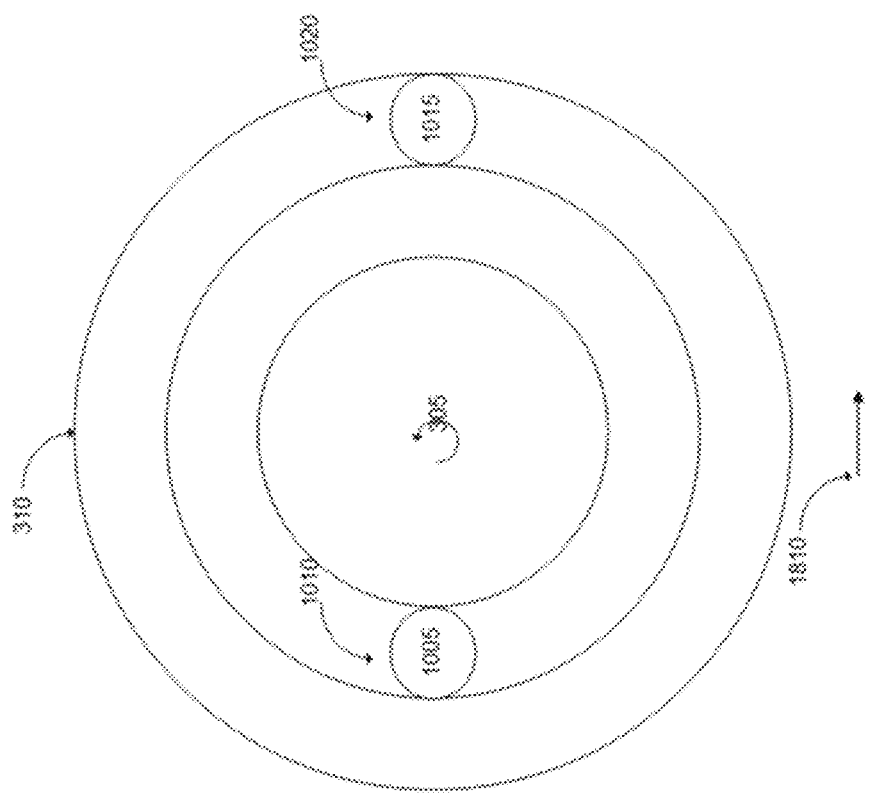
FIG. 29B shows motion of a substrate relative to two imaging heads located on opposite sides of an axis of rotation of the substrate.
Figure 29C:
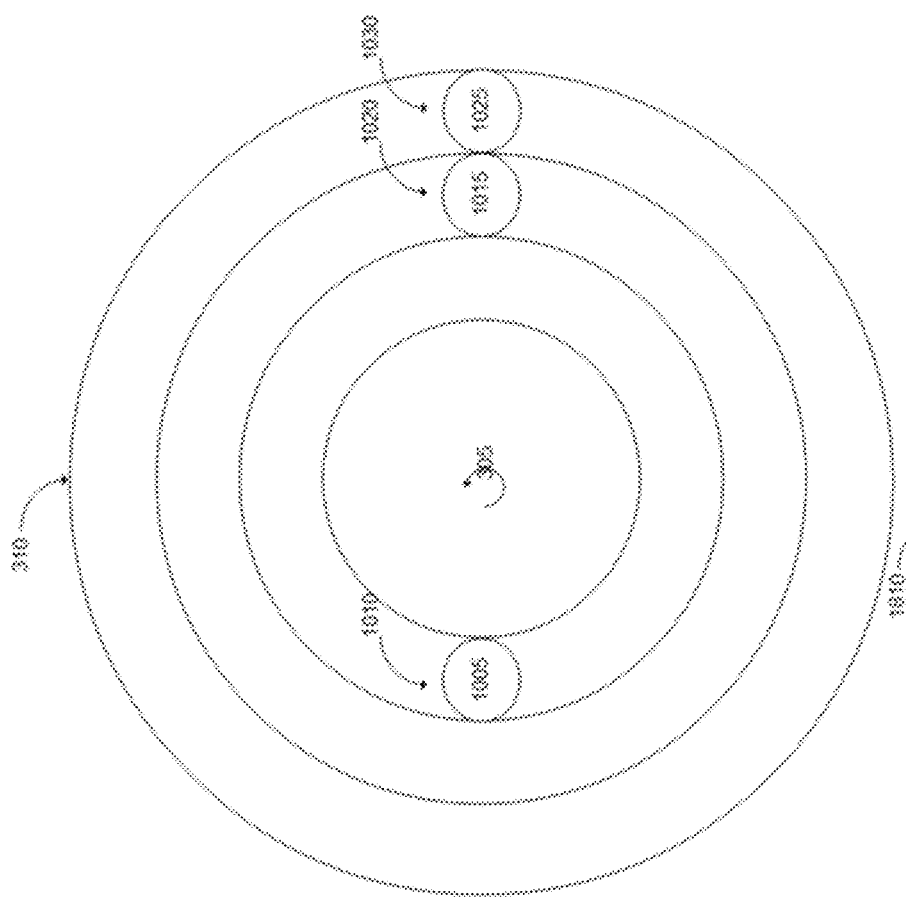
FIG. 29C shows motion of a substrate relative to three imaging heads.
Figure 30A:
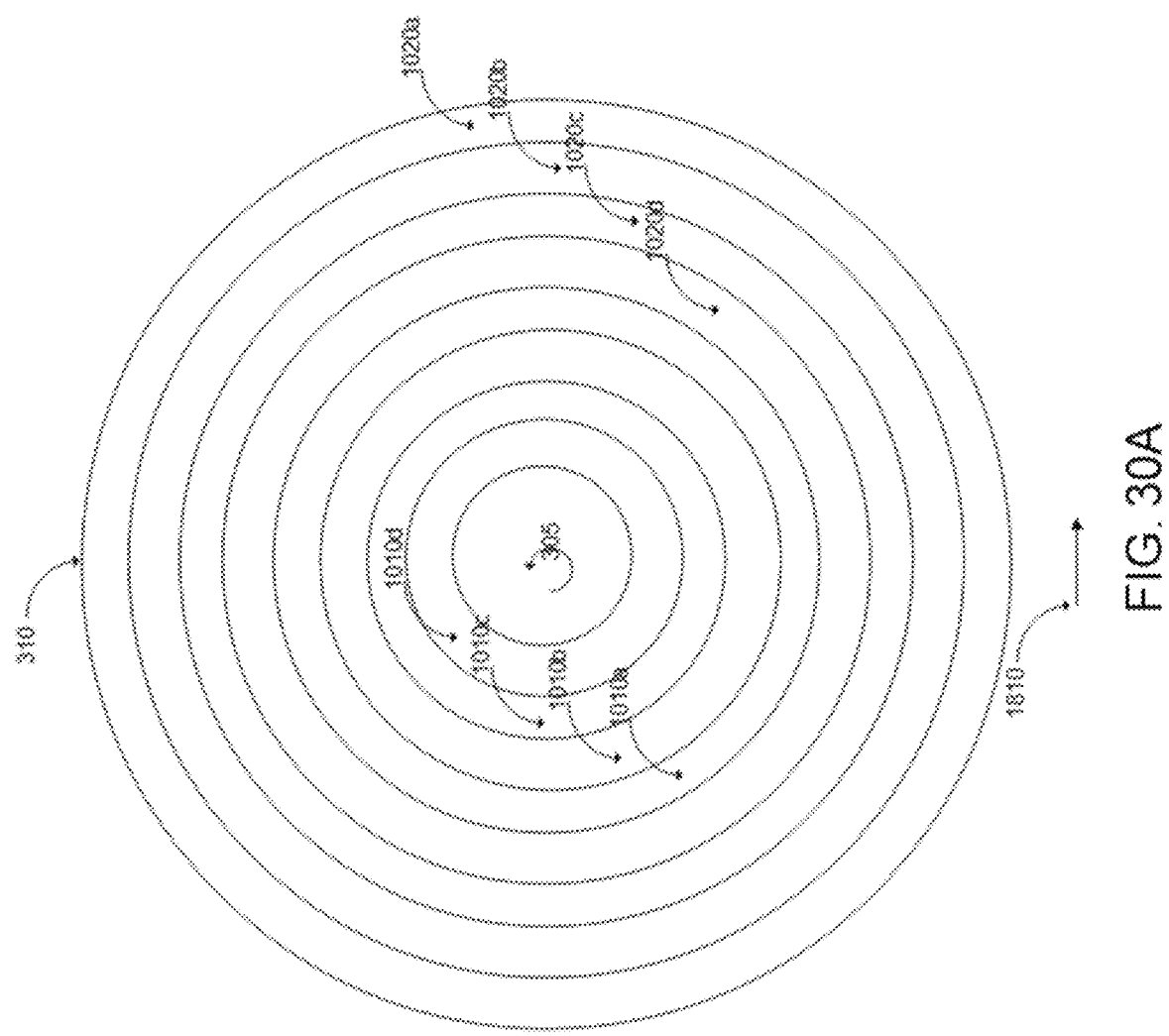
FIG. 30A shows successive ring paths of two imaging heads located on the same side of an axis of rotation of a substrate.
Figure 30D:
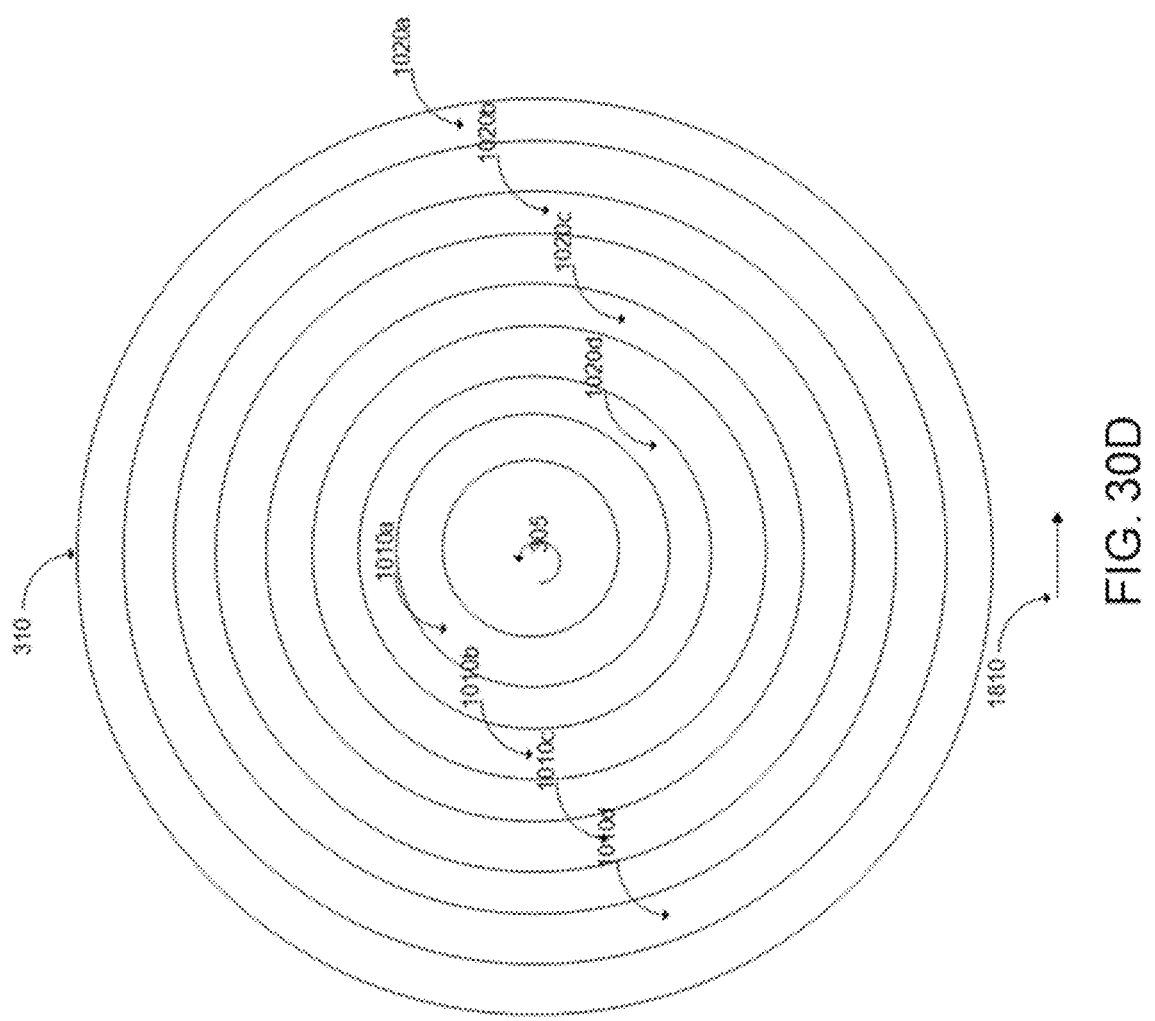
FIG. 30D shows staggered ring paths of two imaging heads located on opposite sides of an axis of rotation of a substrate.
Figure 31A:
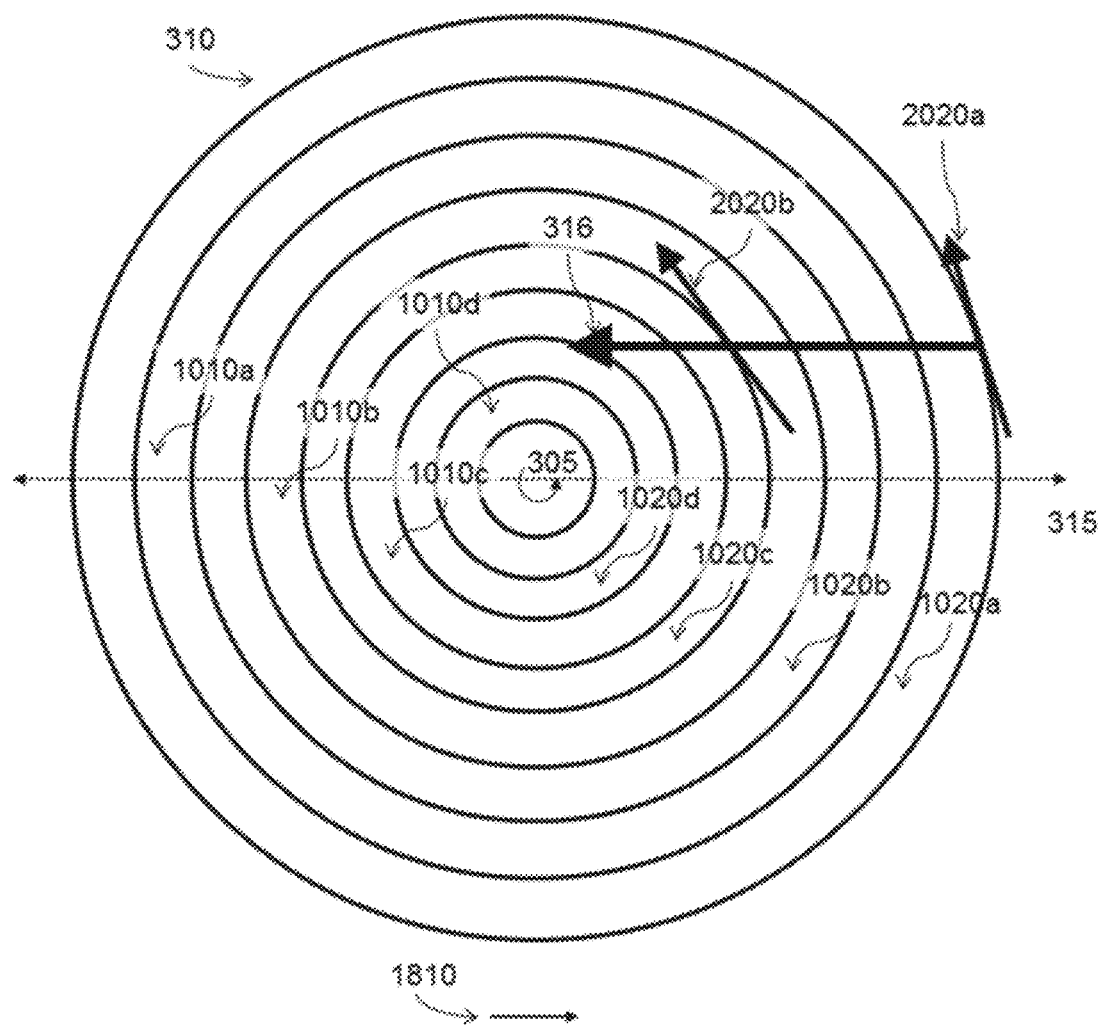
FIG. 31A shows rotating scan directions of imaging heads due to non-radial motion of a substrate.
Figure 31B:
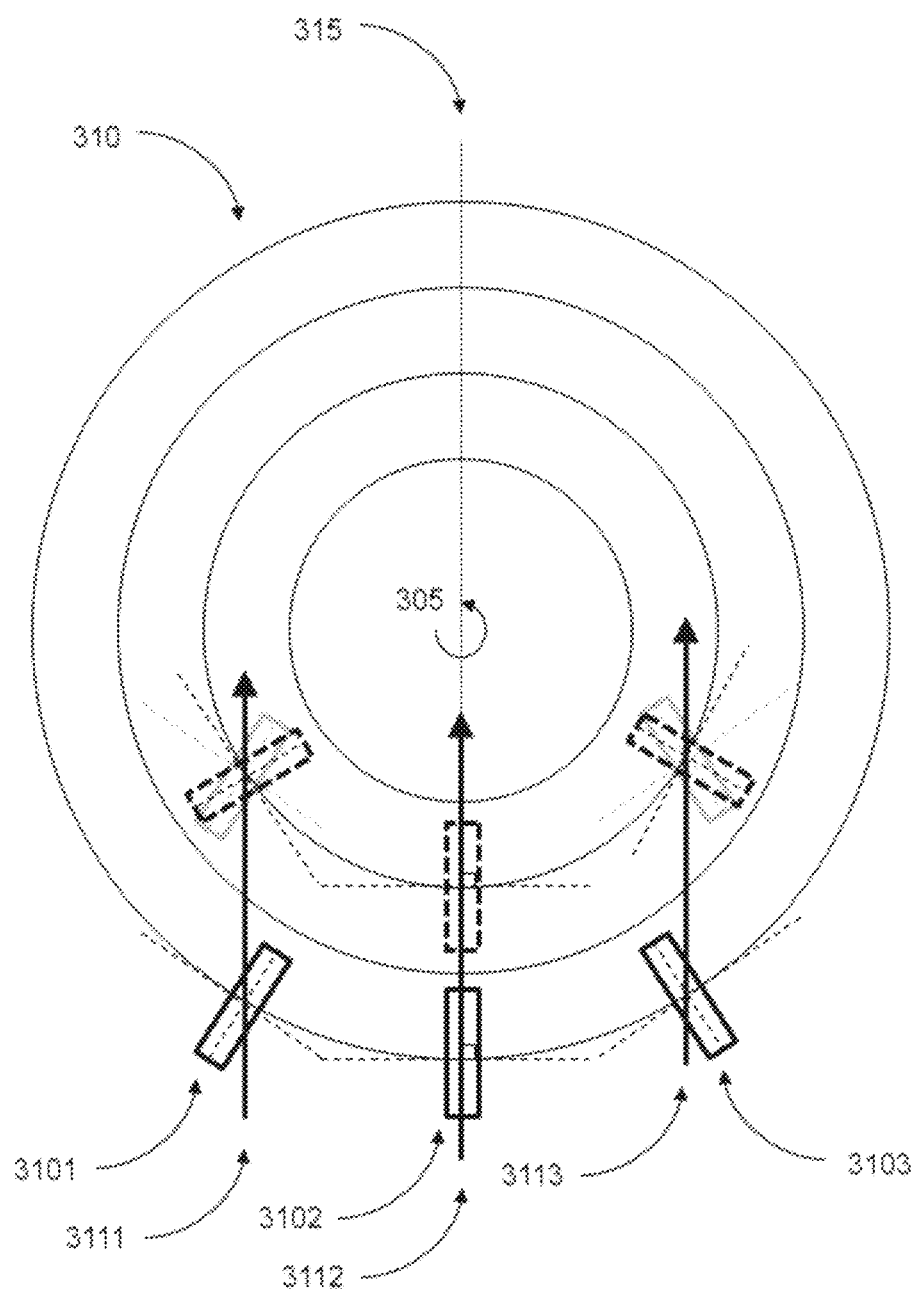
FIG. 31B shows rotating scan directions of imaging heads due to non-radial motion of a substrate.

FIG. 29A-FIG. 29D, FIG. 30A-FIG. 30D, and FIG. 31A-FIG. 31B show additional examples of imaging schemes involving multiple imaging heads. For example, FIG. 31B shows rotating scan directions of multiple imaging heads due to non-radial motion of a substrate.

FIG. 15 shows a cross-sectional view of an immersion optical system 1100. The system 1100 may be used to optically image the substrates described herein. The system 1100 may be integrated with any other optical system or system for nucleic acid sequencing described herein (such as any of systems 300, 400, 500*a*, 500*b*, 700, or 800), or any element thereof. The system may comprise an optical imaging objective 1110. The optical imaging objective may be an immersion optical imaging objective. The optical imaging objective may be configured to be in optical communication with a substrate, such as substrate 310 described herein. The optical imaging objective may be configured to be in optical communication with any other optical elements described herein. The optical imaging objective may be partially or completely surrounded by an enclosure 1120. The enclosure may partially or completely surround a sample-facing end of the optical imaging objective. The enclosure and fluid may comprise an interface between the atmosphere in contact with the substrate and the ambient atmosphere. The atmosphere in contact with the substrate and the ambient atmosphere may differ in relative humidity, temperature, and/or pressure. The enclosure may have a generally cup-like shape or form. The enclosure may be any container. The enclosure may be configured to contain a fluid or immersion fluid 1140 (such as water or an aqueous or organic solution) in which the optical imaging objective is to be immersed. The enclosure may be configured to maintain a minimal distance 1150 between the substrate and the enclosure in order to avoid contact between the enclosure and the substrate during rotation of the substrate. In some instances, air or a pressure differential may be used to maintain the minimal distance. The minimal distance may be at least 100 nm, at least 200 nm, at least 500 nm, at least 1 µm, at least 2 µm, at least 5 µm, at least 10 µm, at least 20 µm, at least 50 µm, at least 100 µm, at least 200 µm, at least 500 µm, at least 1 mm, or a distance that is within a range defined by any two of the preceding values. Even with a minimal distance, the enclosure may contain the fluid due to surface tension effects. The system may comprise a fluid flow tube 1130 configured to deliver fluid to the inside of the enclosure. The fluid flow tube may be connected to the enclosure through an adaptor 1135. The adaptor may comprise a threaded adaptor, a compression adaptor, or any other adaptor. An electrical field application unit (not shown) can be configured to regulate a hydrophobicity of one or more surfaces of a container to retain at least a portion of the fluid contacting the immersion objective lens and the open substrate, such as by applying an electrical field.

As used herein, the fluid contacting the immersion objective lens may be referred to as "immersion fluid" or "fluid". The immersion fluid may comprise any suitable immersion medium for imaging. For example, the immersion medium may comprise an aqueous solution. Non-limiting examples of aqueous immersion fluids include water. In some cases, the aqueous solution may comprise salts, surfactants, oils and/or any other chemicals or reagents useful in imaging. In some cases, the immersion medium comprises an organic solution. Non-limiting examples of organic immersion fluids include oils, perfluorinated polyethers, perfluorocarbons, and hydrofluorocarbons. In some cases, the immersion fluid may be substantially the same as the wash buffer, as described elsewhere herein, or any buffer used in the processes described herein. The immersion fluid may be tuned based on the optical requirements of the systems and methods described herein. For example, where a high numerical aperture (NA) is required, the appropriate immersion fluid (e.g., oil) may be used for imaging. In some cases, the immersion fluid may be selected to match an index of refraction of a solution on the substrate (e.g., a buffer), a surface (e.g., a coverslip or the substrate), or an optical component (e.g., an objective lens).

The optical imaging objective may be in fluidic contact with an open substrate. The open substrate may comprise a layer of fluid covering the surface of the substrate. The optical imaging objective may be configured to scan the surface comprising the layer of fluid. The layer of fluid on the surface may comprise the same fluid as the immersion fluid. The layer of fluid on the surface may comprise a different fluid than the immersion fluid. The layer of fluid on the surface may be miscible with the immersion fluid, or the layer of fluid on the surface may be immiscible with the immersion fluid. In some cases, the layer of fluid is deeper where it contacts the optical imaging objective than at other points on the surface. A portion of the layer of fluid may adhere to the optical imaging objective. In some cases, the portion of the layer of fluid may move with the optical imaging objective relative to the substrate during scanning. The optical imaging objective may remain in fluidic contact with the substrate during scanning. The optical imaging objective may be configured to have a long travel distance in a vertical direction relative to the substrate. In some cases, the optical imaging objective may be configured to lift away from the substrate such that the optical imaging objective is no longer in fluidic contact with the substrate. For example, the optical imaging objective may be lifted away from the substrate while fluid is being dispensed on the substrate. A portion of the layer of fluid, the immersion fluid, or both may adhere to the optical imaging objective when it leaves fluidic contact with the substrate. The portion of the layer of fluid adhering to the optical imaging objective may prevent bubbles from forming or accumulating between the substrate and the optical imaging objective when the optical imaging objective re-enters fluidic contact with the substrate.

The optical imaging objective may be configured to scan a side of the substrate that does not comprise a layer of fluid. For example, the optical imaging objective may be configured to scan a bottom surface of the substrate. In some cases, the optical imaging objective may not be in fluidic contact with the substrate. For example, the optical imaging objective may be an air objective.

The fluid may be in contact with the substrate. The optical imaging objective and enclosure may be configured to provide a physical barrier between a first location in which chemical processing operations are performed and a second location in which detection operations are performed. In this manner, the chemical processing operations and the detection operations may be performed with independent operation conditions and contamination of the detector may be avoided. The first and second locations may have different humidities, temperatures, pressures, or atmospheric admixtures.

A system of the present disclosure may be contained in a container or other closed environment. For example, a container may isolate an internal environment 1160 from an external environment 1170. The internal environment 1160 may be controlled such as to localize temperature, pressure, and/or humidity, as described elsewhere herein. In some instances, the external environment 1170 may be controlled. In some instances, the internal environment 1160 may be further partitioned, such as via, or with aid of, the enclosure 1120 to separately control parts of the internal environment (e.g., first internal environment for chemical processing operations, second internal environment for detection operations, etc.). The different parts of the internal environment may be isolated via a seal. For example, the seal may comprise the immersion objective described herein.

A system of the present disclosure may be configured to analyze a dynamic (e.g., rotating or otherwise moving) open substrate (e.g., as described herein) using a stationary detector system. Alternatively or additionally, one or more components of a detector system may be in motion. For example, a detector system may comprise a sensor (e.g., camera) and an illumination source. The sensor may be in motion while an optical element (e.g., prism) remains stationary. The illumination source may move in tandem with the sensor. For example, the sensor may be a line-scan camera (e.g., a TDI line-scan camera) and the illumination source may be an LED line light or a laser (e.g., a laser having a beam expanded to a line), and the illumination source may illuminate the area being detected by the sensor. The sensor (and, optionally, the illumination source) may rotate at a same or different rate as the open substrate. In some cases, the sensor (and, optionally, the illumination source) may translate across the open substrate in a predefined pattern, such as a spiral pattern. Alternatively, the sensor (and, optionally, the illumination source) may translate radially across the open substrate. In some cases, the sensor (and, optionally, the illumination source) may remain in a same physical location but may rotate about a central axis of the detector system or component(s) thereof. In other cases, the illumination source may illuminate an area of the open substrate that may be larger than an area that is detectable by the sensor in a given scan or collection of scans. However, illumination over a broad swath of the open substrate may promote bleaching of beads and/or fluorophores that may be disposed on the open substrate. Accordingly, the illumination source may be configured to illuminate only a limited area of the open substrate at a given time (e.g., an area that may be, at least partially overlaps with, or is within an area detectable by the sensor).

In another example, a detector system may comprise a sensor (e.g., camera), an illumination source, and one or more optical elements (e.g., lenses, mirrors, prisms, etc.), and the sensor and illumination source may remain stationary while an optical element (e.g., prism) is in motion. For instance, the optical element may rotate at a same rate as the open substrate, or the optical element may translate across the open substrate (e.g., radially or in a predefined pattern, such as a spiral pattern). In some cases, the optical element may remain in a same physical location but may rotate about a central axis (e.g., of the optical element or the detector system). Motion of an optical element of a detector system relative to an open substrate in motion may have the effect of enabling detection at one or more different areas of the open substrate. For example, the movement of one or more optical elements of the detector system may result in illumination of different areas of the open substrate to permit detection of signal associated with the different areas of the open substrate. Distortions of the illumination (e.g., laser light) and variation in detection sensitivities over different areas of the open substrate may be compensated for via subsequent processing (e.g., using a processor, as described herein).

Alternatively, a system of the present disclosure may be configured to analyze a stationary open substrate using a detector system comprising one or more dynamic components. For example, a detector system may comprise a sensor (e.g., camera) and an illumination source. The sensor may be in motion while an optical element (e.g., prism) remains stationary. The illumination source may move in tandem with the sensor. For example, the sensor may be a line-scan camera (e.g., a TDI line-scan camera) and the illumination source may be an LED line light or a laser (e.g., a laser having a beam expanded to a line), and the illumination source may illuminate the area being detected by the sensor. The sensor (and, optionally, the illumination source) may rotate (e.g., about a central axis of the open substrate). In some cases, the sensor (and, optionally, the illumination source) may translate across the open substrate in a predefined pattern, such as a spiral pattern. Alternatively, the sensor (and, optionally, the illumination source) may translate radially across the open substrate. In some cases, the sensor (and, optionally, the illumination source) may remain in a same physical location but may rotate about a central axis of the detector system or component(s) thereof.

In another example, a detector system may comprise a sensor (e.g., camera), an illumination source, and one or more optical elements (e.g., lenses, mirrors, prisms, etc.), and the sensor and illumination source may remain stationary while an optical element (e.g., prism) is in motion. For instance, the optical element may rotate (e.g., about a central axis of the open substrate or about a central axis of the optical element or the detector system) or translate across the open substrate (e.g., radially or in a predefined pattern, such as a spiral pattern). Motion of an optical element of a detector system relative to a stationary open substrate may have the effect of enabling detection at one or more different areas of the open substrate. For example, the movement of one or more optical elements of the detector system may result in illumination of different areas of the open substrate to permit detection of signal associated with the different areas of the open substrate. Distortions of the illumination (e.g., laser light) and variation in detection sensitivities over different areas of the open substrate may be compensated for via subsequent processing (e.g., using a processor, as described herein).

A system may be calibrated (e.g., using an open substrate that does not comprise an analyte, or comprises a known analyte or collection thereof) to facilitate any detection schemes provided herein.

In any of the preceding examples, multiple sensors and/or illumination sources may be used (e.g., to detect different areas of the open substrate, as described herein). The multiple sensors and/or illumination sources may all remain stationary or may all be in motion during a detection process. In other cases, certain sensors and/or illumination sources may be in motion and other sensors and/or illumination sources may be stationary during a detection process. Some or all sensors may analyze the substrate. For example, only sensors in motion, or only sensors that are stationary, may detect signals from the open substrate.

The scan direction of one or more detector systems (e.g., imaging head) may rotate due to non-radial motion of the detector system relative to a substrate. For example, a detector system may have different tangential velocity vectors relative to the substrate while tracing different imaging paths at different radial positions along the substrate, which tangential velocity vectors may point in substantially different directions. Such an effect may be manifested as a rotation of the imaging field as a first detector system traces a first set of imaging paths or as a second detector system traces a second set of imaging paths (see, e.g., FIG. 31A and FIG. 31B).

The present disclosure provides an apparatus in which processing of an analyte on an open substrate and detection of a signal associated with the analyte are performed in the same environment. For example, the open substrate may be retained in the same or approximately the same physical location during processing of an analyte and subsequent detection of a signal associated with a processed analyte. For a system in which the detector system or a component thereof is in motion during detection, the apparatus may comprise a mechanical component configured to affect motion of the detector system of component thereof.

The present disclosure also provides an apparatus in which processing of an analyte on an open substrate and detection of a signal associated with the analyte are performed in different environments. For example, the open substrate may be retained in a first physical location during processing of an analyte and the in a second physical location during detection of a signal associated with a processed analyte. The open substrate may be transferred between various physical locations via, for example, a mechanical component. In some cases, the open substrate may be transferred between various physical locations using a robotic arm, elevator mechanism, or another mechanism. The first physical location may be disposed, for example, above, below, adjacent to, or across from the second physical location. For example, the first physical location may be disposed above the second physical location, and the open substrate may be transferred between these locations between analyte processing and detection. In another example, the first physical location may be disposed adjacent to the second physical location, and the open substrate may be transferred between these locations between analyte processing and detection. The first and second physical locations may be separated by a barrier, such as a retractable barrier.

Figure 12A:
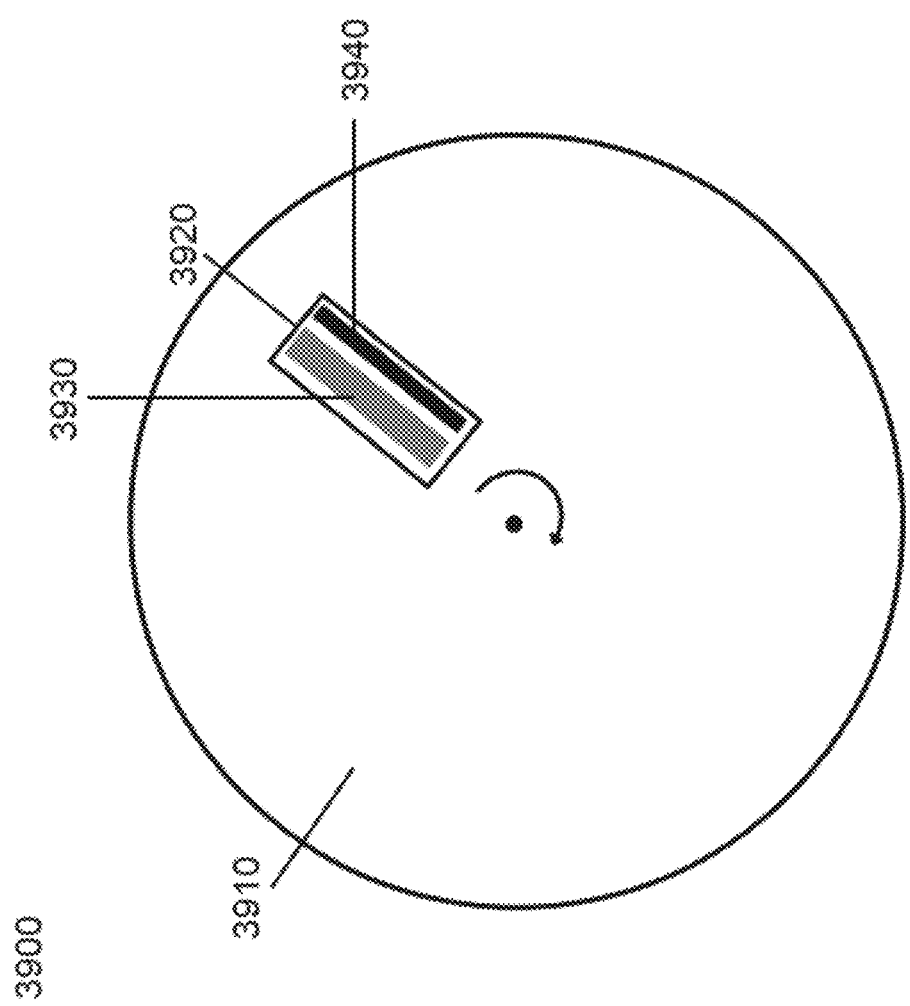
Figure 12B:
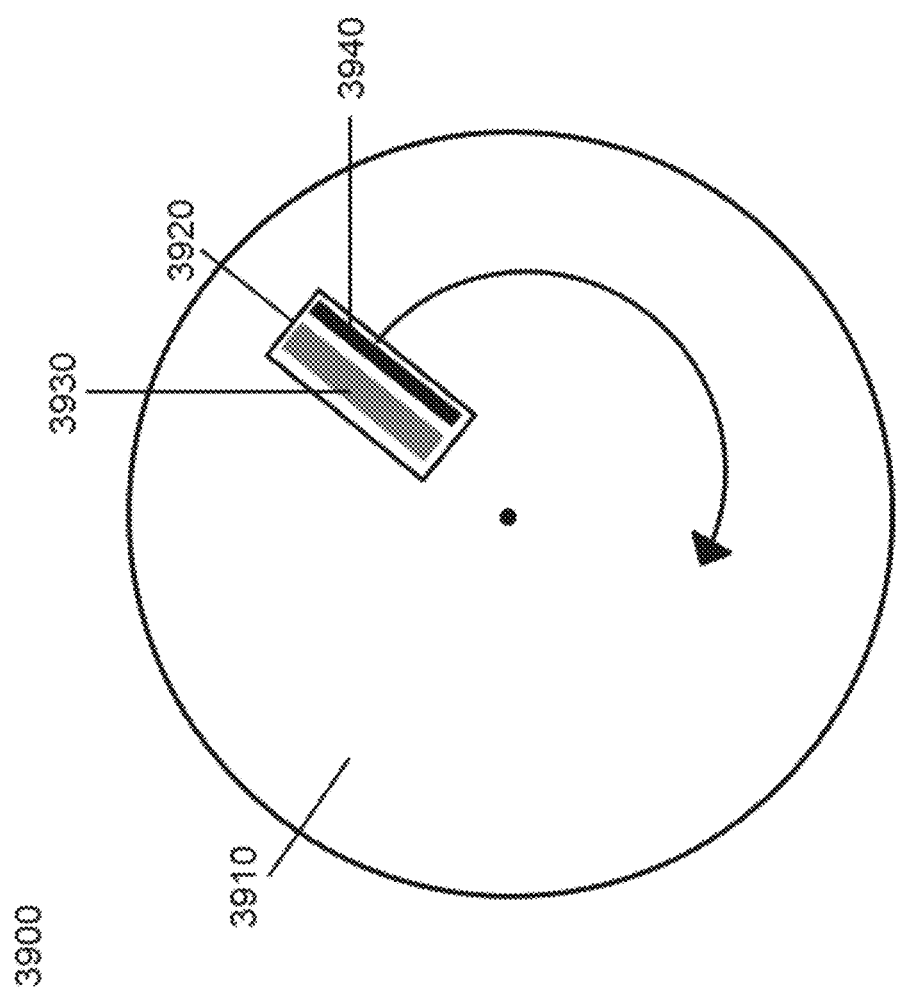

FIG. 12A-FIG. 12C illustrate various detection schemes. FIG. 12A illustrates a scheme involving a system 3900 in which open substrate 3910 rotates and detector system 3920 remains stationary during detection. Detector system 3920 may comprise line-scan camera (e.g., TDI line-scan camera) 3930 and illumination source 3940. FIG. 12B illustrates an alternative scheme involving a system 3900 in which open substrate 3910 remains stationary and detector system 3920 rotates during detection. FIG. 12C illustrates a scheme involving an apparatus comprising a first system 3950 in which open substrate 3910 is subjected to analyte processing. As shown in FIG. 3, first system 3950 may comprise a plurality of fluid channels 3960, 3970, 3980, and 3990, which plurality of fluid channels may comprise a plurality of fluid outlet ports 3965, 3975, 3985, and 3995. The apparatus may be configured to transfer open substrate 3910 to second system 3900, in which open substrate 3910 is configured to remain stationary and detector system 3920 is configured to rotate during detection. While examples described herein provide relative rotational motion of the substrates and/or detector systems, the substrates and/or detector systems may alternatively or additionally undergo relative non-rotational motion, such as relative linear motion, relative non-linear motion (e.g., curved, arcuate, angled, etc.), and any other types of relative motion.

In an aspect, the present disclosure provides a method for analyte detection or analysis comprising providing an open substrate comprising a central axis (e.g., as described herein). The open substrate may be, for example, a wafer or disc, such as a wafer or disc having one or more substances patterning its surface. The open substrate may be substantially planar. The open substrate may have an array of immobilized analytes thereon (e.g., as described herein). The immobilized analytes may be immobilized to the array via one or more binders. The array may comprise at least 100,000 such binders. In some cases, an immobilized analyte of the immobilized analytes may be coupled to a bead, and the bead may be immobilized to the array. An immobilized analyte may comprise a nucleic acid molecule.

A solution having a plurality of probes may be delivered (e.g., as described herein) to a region proximal to the central axis to introduce the solution to the open substrate. The solution may be dispersed across the open substrate such that at least one probe of the plurality of probes may bind to at least one immobilized analyte of the immobilized analytes to form a bound probe. The plurality of probes may comprise a plurality of oligonucleotide molecules. Alternatively, the plurality of probes may comprise a plurality of nucleotides or nucleotide analogs. All or a subset of the plurality of nucleotides or nucleotide analogs may be fluorescently labeled. In an example, the immobilized analytes may comprise nucleic acid molecules and the plurality of probes may comprise fluorescently labeled nucleotides, such that at least one fluorescently labeled nucleotide of the fluorescently labeled nucleotides binds to at least one nucleic acid molecule of the nucleic acid molecules via nucleotide complementarity binding. All or a subset of the plurality of nucleotides or nucleotide analogs may comprise the same base (e.g., the same canonical nucleobase, such as A, T, C, or G). Similarly, all or a subset of the plurality of nucleotides or nucleotide analogs may be reversibly terminated. Reversible terminators and, in some cases, fluorescent moieties such as dyes, may be cleaved from nucleotides (e.g., subsequent to their incorporation into a growing nucleic acid strand) using a cleaving agent, which cleaving agent may be included in another solution provided to the open substrate (e.g., as described herein). The open substrate may also be provided with a wash solution to remove excess probes and other reagents, which wash solution may be dispersed across the open substrate (e.g., during rotation of the open substrate using at least centrifugal force, as described herein).

After generation of the bound probe, a detector system may be used to detect at least one signal from the bound probe. The detector system may comprise a line-scan camera (e.g., a TDI line-scan camera) and an illumination source (e.g., an LED line light or a laser, such as a continuous wave laser). In some cases, the illumination source may comprise a laser and the detector system may comprise an optical element (e.g., a cylindrical lens) configured to change a shape of a beam (e.g., Gaussian beam) emitted by the laser (e.g., as described herein). The open substrate may comprise a first area and a second area, where the first area and the second area comprise subsets of the array of immobilized analytes, are at different radial positions of the open substrate with respect to the central axis and are spatially resolvable by the detector system. The bound probe may be disposed in the first area of the open substrate. The detector system may perform a non-linear scan of the open substrate. The illumination source and the detector system are described in greater detail with respect to FIG. 41.

During the dispersal and delivery processes, the open substrate may be rotating (e.g., in a first physical location). The detector system (e.g., sensor and illumination source) may be stationary during these processes.

During the detection process, the open substrate may be stationary. The sensor and/or the illumination source of the detector system may be in motion during detection. For example, the sensor and the illumination source may be rotating during detection, optionally at the same rate. The sensor and/or the illumination source may rotate about a central axis of the open substrate. Alternatively, the sensor and/or the illumination source may rotate about a central axis of the detector system or a component thereof and remain in a same physical location. The sensor and/or illumination source may translate relative to the open substrate in a predetermined pattern, such as a spiral pattern. Alternatively, the line-scan camera and/or illumination source may translate (e.g., radially translate) across the open substrate. The detector system may further comprise a prism (e.g., a Dove prism), which prism may rotate during the detection process (e.g., about a central axis of the open substrate or about a central axis of the detector system or a component thereof while remaining in a same physical location). In an example, the prism may rotate or otherwise translate relative to the open substrate while the sensor and illumination source remain stationary. Such a prism may be used to disperse light to and from the open substrate, e.g., to disperse light from the illumination source to the open substrate and to detect optical signal from the open substrate, such as fluorescence.

The detector system may be configured to illuminate an area of the open substrate using the illumination source and subsequently detect a signal from the area using a sensor (e.g., line-scan camera). For example, the illumination source may illuminate an area of the open substrate (e.g., a stationary open substrate) prior to its detection by the sensor. In such a situation, the sensor and illumination source may move in tandem relative to the open substrate. One or more optical elements, such as one or more lenses, mirrors, filters, or other optical elements, may move in tandem with these other components of the detector system (e.g., to manipulate light provided to or detected from the open substrate).

During the dispersal and/or delivery processes, an additional probe may be formed, which additional bound probe may be disposed in the second area of the open substrate. During detection, at least one signal may be detected from the additional bound probe at the same time as the at least one signal from the bound probe. These signals may be detected with different sensitivities.

The detector system may compensate for velocity differences at different radial positions of the array with respect to the central axis within a scanned area. The detector system may comprise an optical imaging system having an anamorphic magnification gradient substantially transverse to a scanning direction along the open substrate, where the anamorphic magnification gradient may at least partially compensate for tangential velocity differences that are substantially perpendicular to the scanning direction. Detection may comprise reading two or more regions on the open substrate at two or more different scan rates, respectively, to at least partially compensate for tangential velocity differences in the two or more regions. Detection may further comprise using an immersion objective lens in optical communication with the detector system and the open substrate to detect the at least one signal (e.g., as described herein). The immersion objective lens may be in contact with a fluid that is in contact with the open substrate. The fluid may be in a container, and an electric field may be used to regulate a hydrophobicity of one or more surfaces of the container to retain at least a portion of the fluid contacting the immersion objective lens and the open substrate.

The delivery and/or dispersal processes may be performed in a first environment having a first operating condition, the detection process may be performed in a second environment having a second operating condition different from the first operating condition. The first and second environments may be disposed in the same physical location. For example, the delivery and/or dispersal processes may be performed under a first set of conditions while the open substrate is retained in a first physical location, and the detection process may be performed under a second set of conditions while the open substrate is retained in the same physical location. Alternatively, the first environment may comprise a first physical location in which the open substrate is accessible to a rotational unit configured to rotate the open substrate during the delivery and/or dispersal processes. The second environment may comprise a second physical location in which the open substrate is accessible to the detector system. As noted above, one or more components of the detector system and/or the open substrate may be in motion during the detection process. The second physical location may comprise a mechanism for supporting the open substrate while retaining it in a stationary state as well as a mechanism (e.g., a rotational unit) for moving the detector system or a component thereof relative to the open substrate (e.g., as described herein). The first and second environments may in physical proximity to one another. In an example, the first environment may be disposed in a first physical location of an apparatus that is located above a second physical location of the apparatus that is part of the second environment. In another example, the first environment may be disposed in a first physical location of an apparatus that is located adjacent or somewhat adjacent to a second physical location of the apparatus that is part of the second environment. The first and second environments may be separable by one or more barriers. In an example, a retractable barrier such as a sliding door separates the first and second environments. The retractable barrier may remain in a closed state during delivery and/or dispersal processes and may then be retracted to permit translation of the open substrate from the first environment to the second environment for subsequent detection. The retractable barrier may be retained in a closed state during the detection process. The open substrate may be retained in a container, which container is transferred with the open substrate between the first and second environments.

The first and second environments may comprise one or more different operating conditions. For example, the first environment may comprise a first temperature, humidity, and pressure and the second environment may comprise a second temperature, humidity, and pressure, where at least one of temperature, humidity, and pressure differ between the first and second environments. A given environment may comprise multiple temperature, humidity, and/or pressure zones, and one or more such zones may differ in the first and second environments.

The present disclosure also provides apparatus and computer readable media for implementing the methods provided herein. For example, the present disclosure provides a computer-readable medium comprising non-transitory instructions stored thereon, which when executed cause one or more computer processors to implement the methods provided herein. The present disclosure also provides an apparatus for analyte detection or analysis comprising a housing configured to receive an open substrate having an array of immobilized analytes thereon (e.g., as described herein). The apparatus may comprise one or more dispensers configured to deliver a solution having a plurality of probes to a region proximal to a central axis of the open substrate. The apparatus may also comprise a rotational unit configured to rotate the open substrate about the central axis to disperse the solution across the open substrate at least by centrifugal force, such that at least one probe of the plurality of probes binds to at least one immobilized analyte of the immobilized analytes to form a bound probe. The rotational unit may be disposed in a first area of the apparatus, which first area is distinct from a second area of the apparatus. The apparatus may also comprise a detector system, which detector system may comprise a sensor (e.g., line-scan camera) and an illumination source (e.g., as described herein). The detector system may be disposed in the second area of the apparatus. Alternatively, the detector system may be disposed in the first area of the apparatus. The open substrate may comprise a first area and a second area, where the first area and the second area comprise subsets of the array of immobilized analytes, are at different radial positions of the open substrate with respect to the central axis and are spatially resolved by the detector system. The bound probe may be disposed in the first area of the open substrate, and the detector system may be programmed to perform a non-linear scan of the open substrate and detect at least one signal from the bound probe at the first area of the open substrate. The apparatus may comprise one or more processors configured to, for example, direct dispersal and delivery of one or more solutions to the open substrate or direct the detector system to detect one or more signals from the open substrate. The processor may be programmed to direct the detector system to compensate for velocity differences at different radial positions of the array with respect to the central axis of the open substrate within a scanned area. For example, the processor may be programmed to direct the detector system to scan two or more regions of the open substrate at two or more different scan rates, respectively, to at least partially compensate for tangential velocity differences in the two or more regions. The apparatus may further comprise one or more optics, such as one or more optics that are configured to generate an anamorphic magnification gradient that is, e.g., substantially transverse to a scanning direction along the open substrate (e.g., as described herein). A processor may be programmed to adjust the gradient to compensate for different imaged radial positions with respect to the central axis of the open substrate.

System Architectures for High-Throughput Processing

The nucleic acid sequencing systems and optical systems described herein (or any elements thereof) may be combined in a variety of architectures.

Figure 23A:
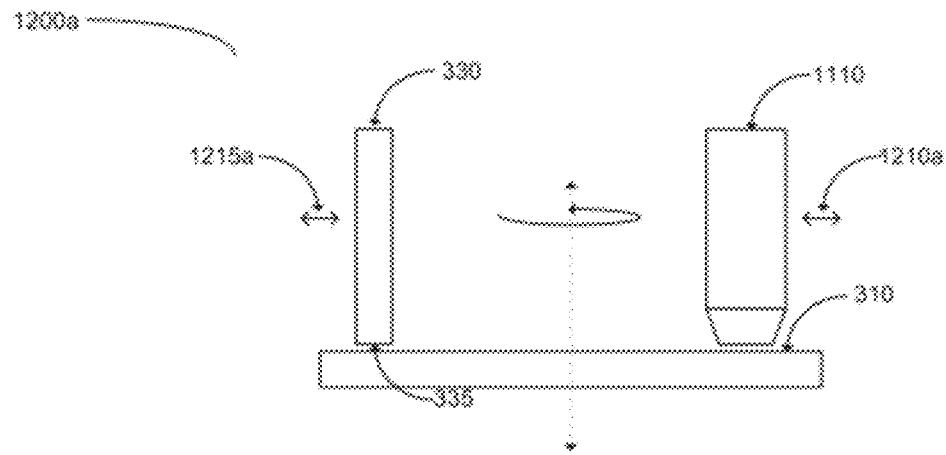
FIG. 23A shows an architecture for a system comprising a stationary axis substrate and moving fluidics and optics.

FIG. 23A shows an architecture for a system 1200a comprising a stationary substrate and moving fluidics and optics. The system 1200a may comprise substrate 310 described herein. The substrate may be configured to rotate, as described herein. The substrate may be adhered or otherwise affixed to a chuck (not shown in FIG. 23A), as described herein. The system may further comprise fluid channel 330 and fluid outlet port 335 described herein, and/or any other fluid channel and fluid outlet port described herein. The fluid channel and fluid outlet port may be configured to dispense any solution described herein. The fluid channel and fluid outlet port may be configured to move 1215a relative to the substrate. For instance, the fluid channel and fluid outlet port may be configured to move to a position above (such as near the center of) the substrate during periods of time in which the fluid channel and fluid outlet port are dispensing a solution. The fluid channel and fluid outlet port may be configured to move to a position away from the substrate during the period in which the fluid channel and fluid outlet port are not dispensing a solution. Alternatively, the reverse may apply. The system may further comprise optical imaging objective 1110 described herein. The optical imaging objective may be configured to move 1210a relative for the substrate. For instance, the optical imaging objective may be configured to move to a position above (such as near the center of) the substrate during periods of time in which the substrate is being imaged. The optical imaging objective may be configured to move to a position away from the substrate during the period in which the substrate is not being imaged. The system may alternate between dispensing of solutions and imaging, allowing rapid sequencing of the nucleic acids attached to the substrate using the systems and methods described herein.

Figure 23B:
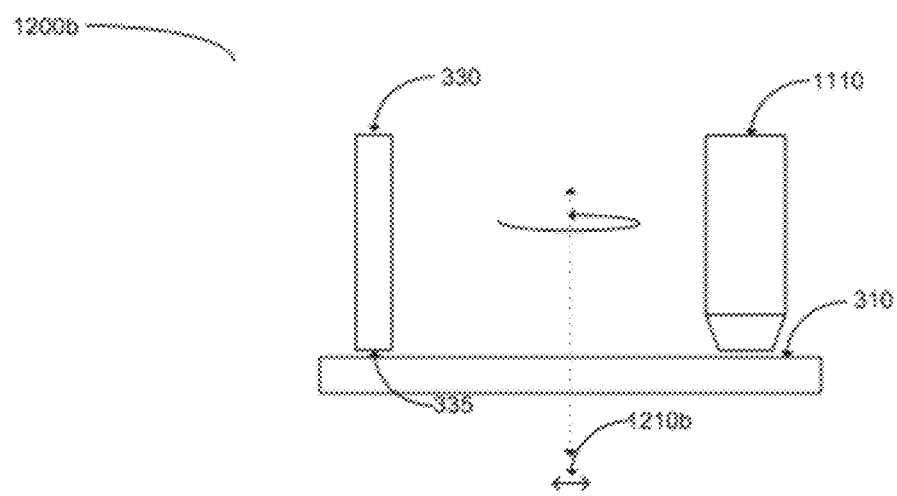
FIG. 23B shows an architecture for a system comprising a translating axis substrate and stationary fluidics and optics.

FIG. 23B shows an architecture for a system 1200b comprising a moving substrate and stationary fluidics and optics. The system 1200b may comprise substrate 310 described herein. The substrate may be configured to rotate, as described herein. The substrate may be adhered or otherwise affixed to a chuck (not shown in FIG. 23B), as described herein. The system may further comprise fluid channel 330 and fluid outlet port 335 described herein, or any other fluid channel and fluid outlet port described herein. The fluid channel and fluid outlet port may be configured to dispense any solution described herein. The system may further comprise optical imaging objective 1110 described herein. The fluid channel, fluid outlet port, and optical imaging objective may be stationary. The substrate may be configured to move 1210b relative to the fluid channel, fluid outlet port, and optical imaging objective. For instance, the substrate may be configured to move to a position such that the fluid channel and fluid outlet port are above (such as near the center of) the substrate during periods of time in which the fluid channel and fluid outlet port are dispensing a solution. The substrate may be configured to move to a position away from the fluid channel and fluid outlet port during the period in which the fluid channel and fluid outlet port are not dispensing a solution. The substrate may be configured to radially scan the objective over the substrate during periods of time in which the substrate is being imaged. The substrate may be configured to move to a position away from the optical imaging objective during the period in which the substrate is not being imaged. The system may alternate between dispensing of solutions and imaging, allowing rapid sequencing of the nucleic acids attached to the substrate using the systems and methods described herein.

Figure 23C:
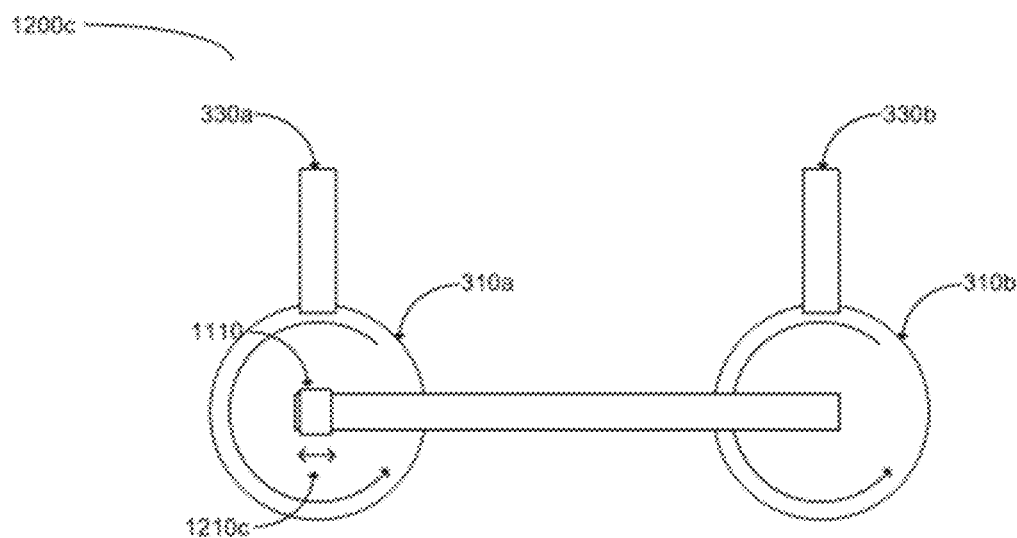
FIG. 23C shows an architecture for a system comprising a plurality of stationary substrates and moving fluidics and optics.

FIG. 23C shows an architecture for a system 1200c comprising a plurality of stationary substrates and moving fluidics and optics. The system 1200c may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 23C), as described herein. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The system may further comprise second fluid channel 330b and second fluid outlet port 335b. Second fluid channel 330b may be similar to fluid channel 330 described herein or any other fluid channel described herein. Second fluid outlet port 335a may be similar to fluid outlet port 335 described herein or any other fluid outlet port described herein. The first fluid channel and first fluid outlet port may be configured to dispense any solution described herein. The second fluid channel and second fluid outlet port may be configured to dispense any solution described herein.

The system may further comprise optical imaging objective 1110. Optical imaging objective 1110 may be configured to move 1210c relative to the first and second substrates. For instance, the optical imaging objective may be configured to move to a position above (such as near the center of, or radially scanning) the first substrate during periods of time in which the first fluid channel and first fluid outlet port are not dispensing a solution to the second substrate (and during which the first substrate is to be imaged). The optical imaging objective may be configured to move to a position away from the first substrate during the period in which the first fluid channel and first fluid outlet port are dispensing a solution. The optical imaging objective may be configured to move to a position above (such as near the center of, or radially scanning) the second substrate during periods of time in which the second fluid channel and second fluid outlet port are not dispensing a solution to the second substrate (and during which the second substrate is to be imaged). The optical imaging objective may be configured to move to a position away from the second substrate during the period in which the second fluid channel and second fluid outlet port are dispensing a solution.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the optical imaging objective may be moved from the second substrate to the first substrate. A solution may then be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 23C, system 1200c may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and/or at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. Each optical imaging objective may be moved between substrates as described herein.

Figure 23D:
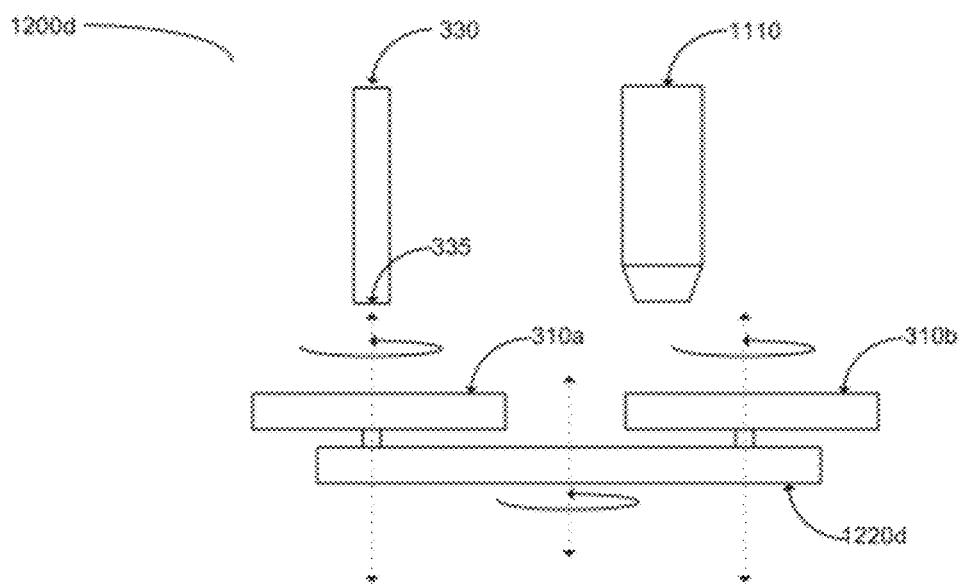
FIG. 23D shows an architecture for a system comprising a plurality of moving substrates on a rotary stage and stationary fluidics and optics.

FIG. 23D shows an architecture for a system 1200d comprising a plurality of moving substrates on a rotary stage and stationary fluidics and optics. The system 1200d may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 23D), as described herein. The first and second substrates may be affixed to a rotating stage 1220d (such as approximately at opposing ends of the rotating stage). The rotating stage may be configured to rotate about an axis. The axis may be an axis through the center of the substrate. The axis may be an off-center axis. The rotating stage may approximately scan the radius of the substrate 310b. The system may further comprise fluid channel 330 and fluid outlet port 335. The fluid channel and fluid outlet port may be configured to dispense any solution described herein. The system may further comprise optical imaging objective 1110. A longitudinal axis of the imaging objective 1110 may not be coincident with a central axis of the second substrate 310b (although this is difficult to distinguish in FIG. 23D). The imaging objective 1110 may be positioned at some distance from a center of the second substrate 310b.

The rotating stage may be configured to alter the relative positions of the first and second substrates to carry out different sequencing operations. For instance, the rotating stage may be configured to rotate such that the optical imaging objective is in a position above or in optical communication with the first substrate during periods of time in which the fluid channel and fluid outlet port are not dispensing a solution to the first substrate (and during which the first substrate is to be imaged). The rotating stage may be configured to rotate such that the optical imaging objective is away from the first substrate during the period in which the fluid channel and fluid outlet port are dispensing a solution to the first substrate. The rotating stage may be configured to rotate such that the optical imaging objective is in a position above or in optical communication with the second substrate during periods of time in which the fluid channel and fluid outlet port are not dispensing a solution to the second substrate (and during which the second substrate is to be imaged). The rotating stage may be configured to rotate such that the optical imaging objective is away from the second substrate during the period in which the fluid channel and fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the rotating stage may be rotated such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, one fluid channel, one fluid outlet port, and one optical imaging objective in FIG. 23D, system 1200d may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The rotating stage may be rotated to place any substrate under any fluid channel, fluid outlet port, or optical imaging objective at any time.

Figure 23E:
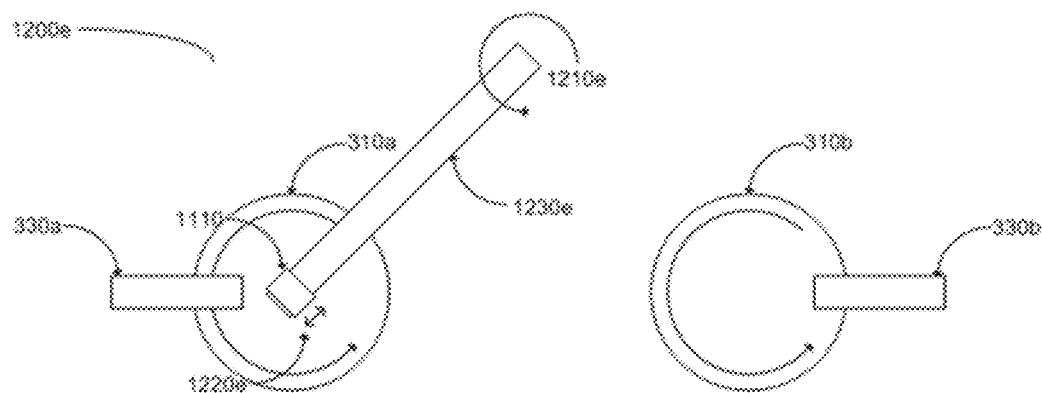
FIG. 23E shows an architecture for a system comprising a plurality of stationary substrates and moving optics.

FIG. 23E shows an architecture for a system 1200e comprising a plurality of stationary substrates and moving optics. The system 1200d may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 23E), as described herein. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein.

The system may further comprise optical imaging objective 1110. The optical imaging objective may be attached to an imaging arm 1230e. The optical imaging objective may be configured to move 1220e along the optical imaging arm to image an entire area of the first or second substrate. The optical imaging arm may be configured to rotate 1210e. The optical imaging arm may be configured to rotate such that the optical imaging objective is in a position above or in optical communication with the first substrate during periods of time in which the first fluid channel and first fluid outlet port are not dispensing a solution to the first substrate (and during which the first substrate is to be imaged). The optical imaging arm may be configured to rotate such that the optical imaging objective is away from the first substrate during the period in which the first fluid channel and first fluid outlet port are dispensing a solution to the first substrate. The optical imaging arm may be configured to rotate such that the optical imaging objective is in a position above or in optical communication with the second substrate during periods of time in which the second fluid channel and second fluid outlet port are not dispensing a solution to the second substrate (and during which the second substrate is to be imaged). The optical imaging arm may be configured to rotate such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the optical imaging arm may be rotated such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 23E, system 1200e may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The optical imaging arm may be rotated to place any substrate under any fluid channel, fluid outlet port, or optical imaging objective at any time.

Figure 23F:
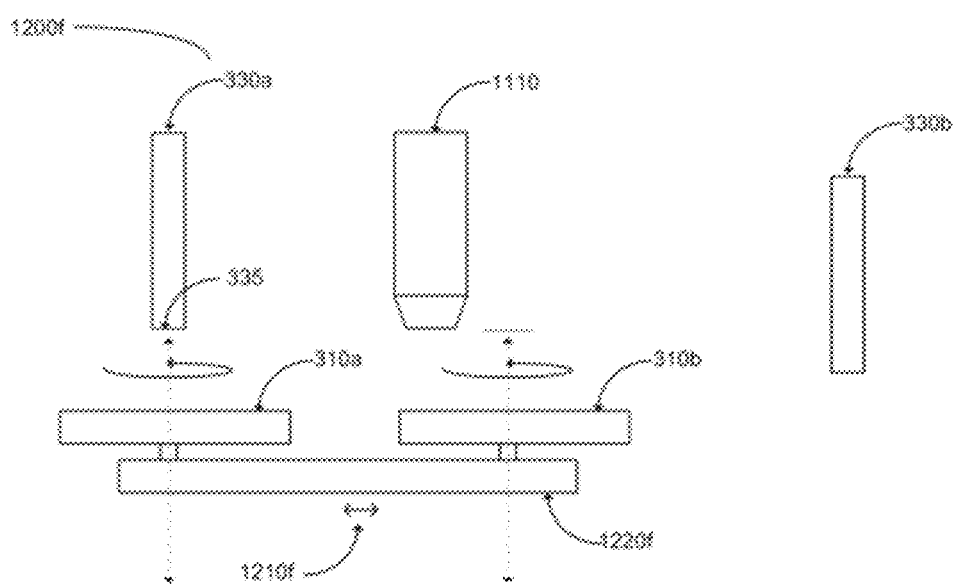
FIG. 23F shows an architecture for a system comprising a plurality of moving substrates and stationary fluidics and optics.

FIG. 23F shows an architecture for a system 1200f comprising a plurality of moving substrates and stationary fluidics and optics. The system 1200f may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 23F), as described herein. The first and second substrates may be affixed to opposing ends of a moving stage 1220f. The moving stage may be configured to move 1210f. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein. The system may further comprise optical imaging objective 1110.

The moving stage may be configured to move such that the optical imaging objective is in a position above or in optical communication with the first substrate during periods of time in which the first fluid channel and first fluid outlet port are not dispensing a solution to the first substrate (and during which the first substrate is to be imaged). The moving stage may be configured to move such that the optical imaging objective is away from the first substrate during the period in which the first fluid channel and first fluid outlet port are dispensing a solution to the first substrate. The moving stage may be configured to move such that the optical imaging objective is in a position above or in optical communication with the second substrate during periods of time in which the second fluid channel and second fluid outlet port are not dispensing a solution to the second substrate (and during which the second substrate is to be imaged). The moving stage may be configured to move such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the moving stage may move such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 23F, system 1200f may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The moving stage may move so as to place any substrate under any fluid channel, fluid outlet port, or optical imaging objective at any time.

Figure 23G:
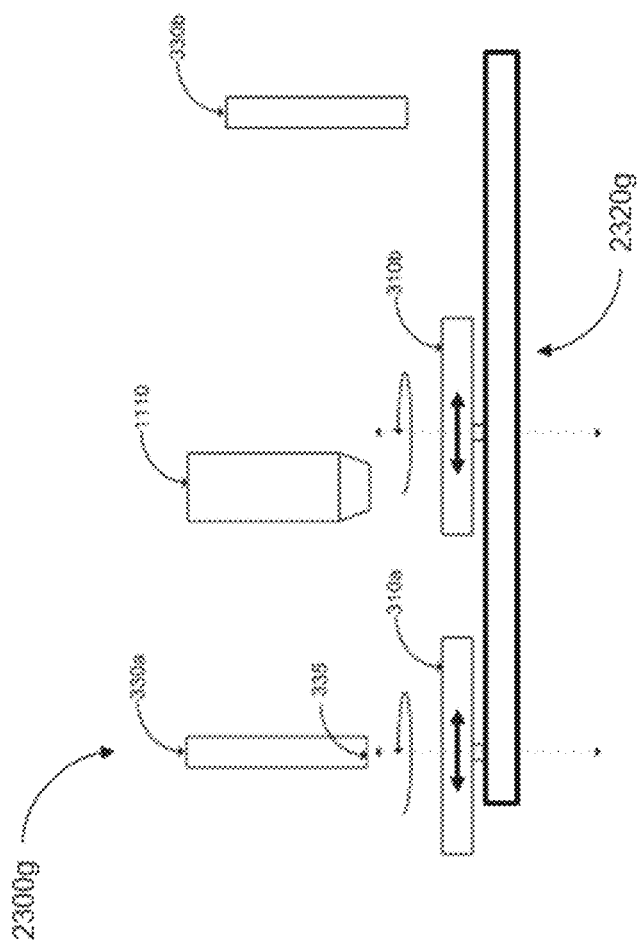
FIG. 23G shows an architecture for a system comprising a plurality of moving substrates and stationary fluidics and optics.

FIG. 23G shows an architecture for a system 2300g comprising a plurality of moving substrates and stationary fluidics and optics. The system 2300g may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 23G), as described herein. The first and second substrates may be configured to translate along a stationary stage 2320g. The first and second substrates may be configured to move between a first fluid station comprising a first fluid channel 330a and first fluid outlet port 335a, a second fluid station comprising a second fluid channel 330b and second fluid outlet port 335b, and an imaging station comprising an optical imaging objective 1110. FIG. 23G illustrates a configuration where the first substrate is positioned at the first fluid station and the second substrate is positioned at the imaging station. In another configuration, the first and second substrates may undergo relative translation with respect to the optical head so that the first substrate is positioned at the imaging station and the second substrate is positioned at the second fluid station. The first and second translating substrates may be configured to move such that the optical imaging objective is in a position above or in optical communication with the first substrate during periods of time in which the first fluid channel and first fluid outlet port are not dispensing a solution to the first substrate (and during which the first substrate is to be imaged). The first and second translating substrates may be configured to move such that the optical imaging objective is away from the first substrate during the period in which the first fluid channel and first fluid outlet port are dispensing a solution to the first substrate. The first and second translating substrates may be configured to move such that the optical imaging objective is in a position above or in optical communication with the second substrate during periods of time in which the second fluid channel and second fluid outlet port are not dispensing a solution to the second substrate (and during which the second substrate is to be imaged). The first and second translating substrates may be configured to move such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the moving stage may move such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 23G, system 2300g may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The translating substrates may move so as to place any substrate under any fluid channel, fluid outlet port, or optical imaging objective at any time.

Figure 23H:
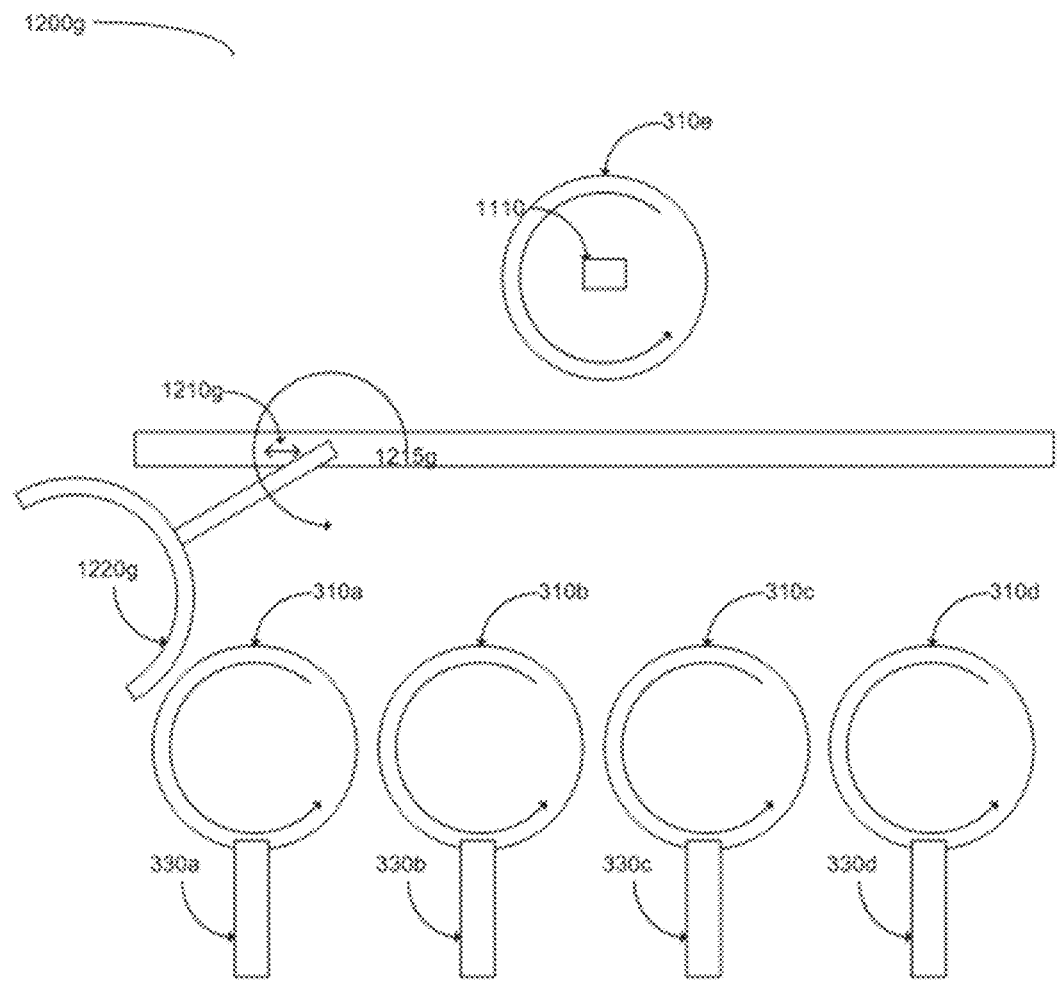
FIG. 23H shows an architecture for a system comprising a plurality of substrates moved between a plurality of processing bays.

FIG. 23H shows an architecture for a system 1200g comprising a plurality of substrates moved between a plurality of processing bays. The system 1200g may comprise first, second, third, and fourth substrates 310a, 310b, 310c, 310d, and 310e, respectively. The first, second, third, fourth, and fifth substrates may be similar to substrate 310 described herein. The first, second, third, fourth, and fifth substrates may be configured to rotate, as described herein. The first, second, third, fourth, and fifth substrates may be adhered or otherwise affixed to first, second, third, fourth, and fifth chucks (not shown in FIG. 23H), respectively, as described herein.

The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The first fluid channel and first fluid outlet port may be regarded as a first processing bay. The first processing bay may be configured to perform a first processing operation, such as dispensing of a first solution to any of the first, second, third, fourth, or fifth substrates.

The system may further comprise second fluid channel 330b and second fluid outlet port 335b. Second fluid channel 330b may be similar to fluid channel 330 described herein or any other fluid channel described herein. Second fluid outlet port 335*b* may be similar to fluid outlet port 335 described herein or any other fluid outlet port described herein. The second fluid channel and second fluid outlet port may be configured to dispense any solution described herein. The second fluid channel and second fluid outlet port may be regarded as a second processing bay or processing station. The second processing bay may be configured to perform a second processing operation, such as dispensing of a second solution to any of the first, second, third, fourth, or fifth substrates.

The system may further comprise third fluid channel 330*c* and third fluid outlet port 335*c*. Third fluid channel 330*c* may be similar to fluid channel 330 described herein or any other fluid channel described herein. Third fluid outlet port 335*c* may be similar to fluid outlet port 335 described herein or any other fluid outlet port described herein. The third fluid channel and third fluid outlet port may be configured to dispense any solution described herein. The third fluid channel and third fluid outlet port may be regarded as a third processing bay or processing station. The third processing bay may be configured to perform a third processing operation, such as dispensing of a third solution to any of the first, second, third, fourth, or fifth substrates.

The system may further comprise fourth fluid channel 330*d* and fourth fluid outlet port 335*d*. Fourth fluid channel 330*d* may be similar to fluid channel 330 described herein or any other fluid channel described herein. Fourth fluid outlet port 335*d* may be similar to fluid outlet port 335 described herein or any other fluid outlet port described herein. The fourth fluid channel and fourth fluid outlet port may be configured to dispense any solution described herein. The fourth fluid channel and fourth fluid outlet port may be regarded as a fourth processing bay or processing station. The fourth processing bay may be configured to perform a fourth processing operation, such as dispensing of a fourth solution to any of the first, second, third, fourth, or fifth substrates.

The system may further comprise a scanning optical imaging objective 1110. The optical imaging objective may be regarded as a fifth processing bay or processing station.

The system may further comprise a moving arm 1220*g*. The moving arm may be configured to move laterally 1210*g* or rotate 1215*g*. The moving arm may be configured to move any of the first, second, third, fourth, or fifth substrates between different processing stations (such as by picking up substrates and moving them to new locations). For instance, at a first point in time, the first substrate may undergo a first operation (such as dispensing of a first solution) at the first processing bay, the second substrate may undergo a second operation (such as dispensing of a second solution) at the second processing bay, the third substrate may undergo a third operation (such as dispensing of a third solution) at the first processing bay, the fourth substrate may undergo a fourth operation (such as dispensing of a fourth solution) at the fourth processing bay, and the fifth substrate may be imaged at the fifth processing bay. Upon completion of one or more of the first, second, third, or fourth operations, or of imaging, the moving arm may move one or more of the first, second, third, fourth, or fifth substrates to one or more of the first, second, third, fourth, or fifth processing bays, where another operation may be completed. The pattern of completing one or more operations and moving one or more substrates to another processing bay to complete another operation may be repeated, allowing rapid sequencing of the nucleic acids attached to the first, second, third, fourth, and fifth substrates using the systems and methods described herein. The alternating pattern of dispensing and imaging may speed up the sequencing by increasing the duty cycle of the imaging process or the solution dispensing process.

Though depicted as comprising five substrates, four fluid channels, four fluid outlet ports, and one optical imaging objective in FIG. 23H, system 1200*g* may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The moving arm may move so as to place any substrate under any fluid channel, fluid outlet port, or optical imaging objective at any time.

Figure 23I:
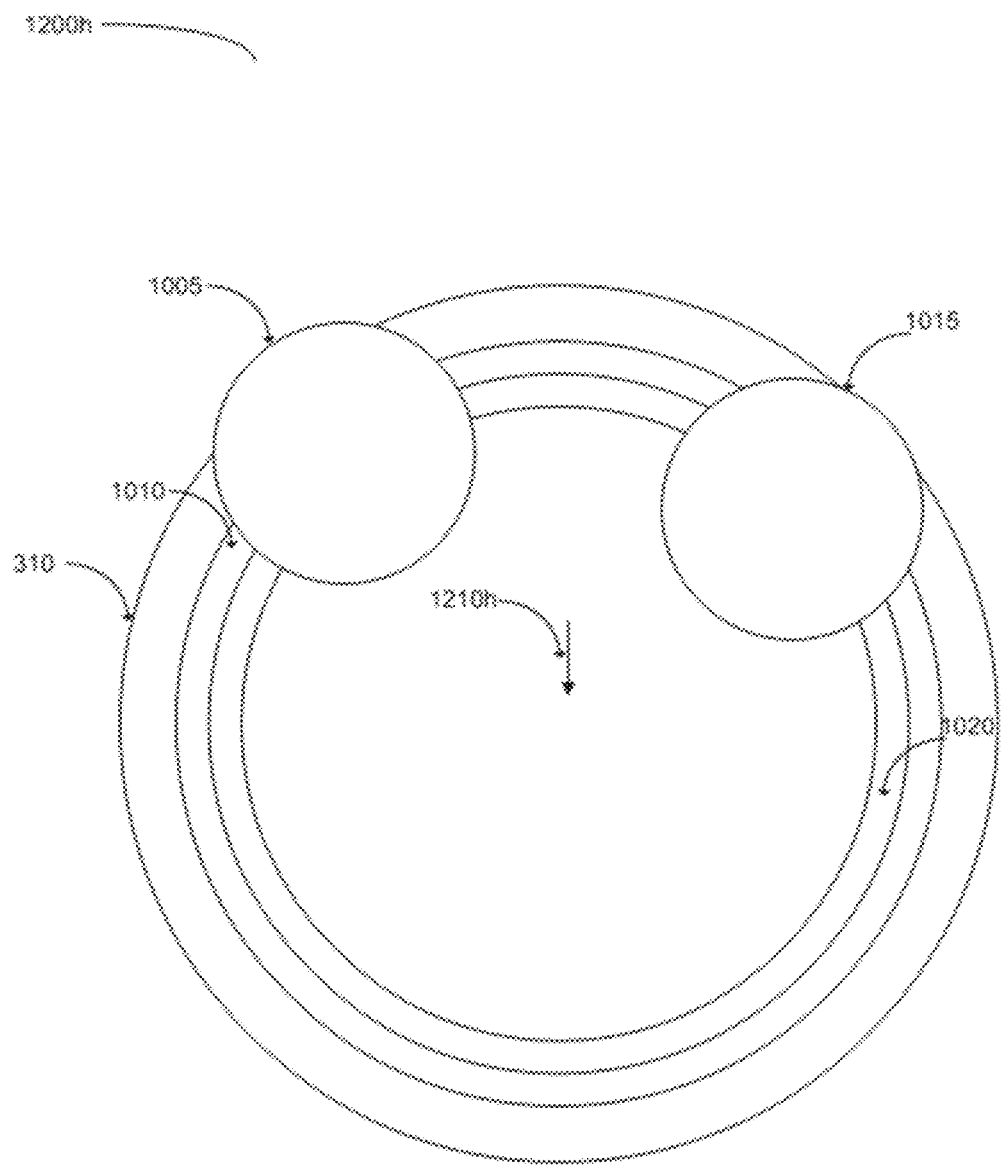
FIG. 23I shows an architecture for a system comprising a plurality of imaging heads scanning with shared translation and rotational axes and independently rotating fields.

FIG. 23I shows an architecture for a system 1200*h* comprising a plurality of imaging heads scanning with shared translation and rotational axes and independently rotating fields. The system may comprise first and second read heads 1005 and 1015, respectively, configured to image substrate 310. The first and second read heads may be similar to any read head described herein (such as with respect to FIG. 14). At a particular point in time, the first and second read heads may be configured to image first and second paths 1010 and 1020, respectively. The first and second paths may be similar to any paths described herein (such as with respect to FIG. 14). The first and second read heads may be configured to move 1210*h* in a substantially radial direction over the spinning substrate, thereby scanning the substrate. In the event that either the first or second read head does not move precisely radially, an image field or sensor of the read head may rotate to maintain a substantially tangential scan direction, as described with respect to FIG. 34. A field rotation may be accomplished using rotating prisms. Alternatively or in addition, mirrors or other optical elements may be used.

Though depicted as comprising two read heads and two imaging paths in FIG. 23I, system 1200*h* may comprise any number of read heads or imaging paths. For instance, the system may comprise at least 1, at least 2, at least 3, at least 4, at least 5, at least 6, at least 7, at least 8, at least 9, or at least 10 read heads. The system may comprise at least 1, at least 2, at least 3, at least 4, at least 5, at least 6, at least 7, at least 8, at least 9, or at least 10 imaging paths.

Figure 23J:
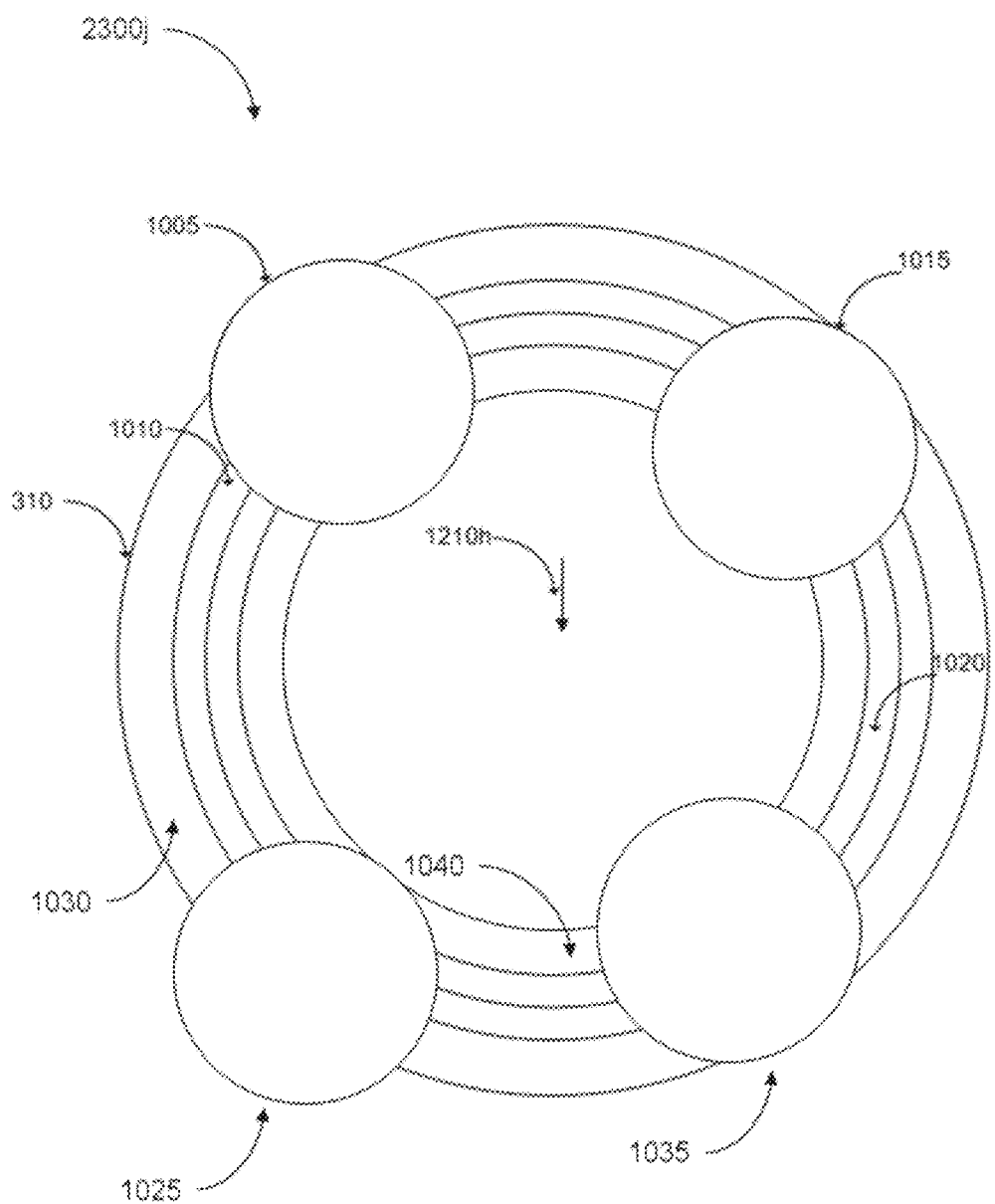
FIG. 23J shows an architecture for a system comprising a plurality of imaging heads scanning with shared translation and rotational axes and independently rotating fields.

FIG. 23J shows an architecture for a system 2300*j* comprising a plurality of imaging heads scanning with shared translation and rotational axes and independently rotating fields. The system may comprise first, second, third, and fourth read heads 1005, 1015, 1025, and 1035, respectively, configured to image substrate 310. The first, second, third, and fourth read heads may be similar to any read head described herein (such as with respect to FIG. 14). At a particular point in time, the first, second, third, and fourth read heads may be configured to image first, second, third, and fourth paths 1010, 1020, 1030, and 1040, respectively. The first, second, third, and fourth paths may be similar to any paths described herein (such as with respect to FIG. 14). The first, second, third, and fourth read heads may be configured to move 1210*h* in a substantially radial direction over the spinning substrate, thereby scanning the substrate. In the event that the first, second, third, and fourth read head does not move precisely radially, an image field or sensor of the read head may rotate to maintain a substantially tangential scan direction. A field rotation may be accomplished using rotating prisms. Alternatively or in addition, mirrors or other optical elements may be used.

Though depicted as comprising four read heads and four imaging paths in FIG. 23J, system 2300*j* may comprise any number of read heads or imaging paths. For instance, the system may comprise at least 1, at least 2, at least 3, at least 4, at least 5, at least 6, at least 7, at least 8, at least 9, or at least 10 read heads. The system may comprise at least 1, at least 2, at least 3, at least 4, at least 5, at least 6, at least 7, at least 8, at least 9, or at least 10 imaging paths.

Figure 23K:
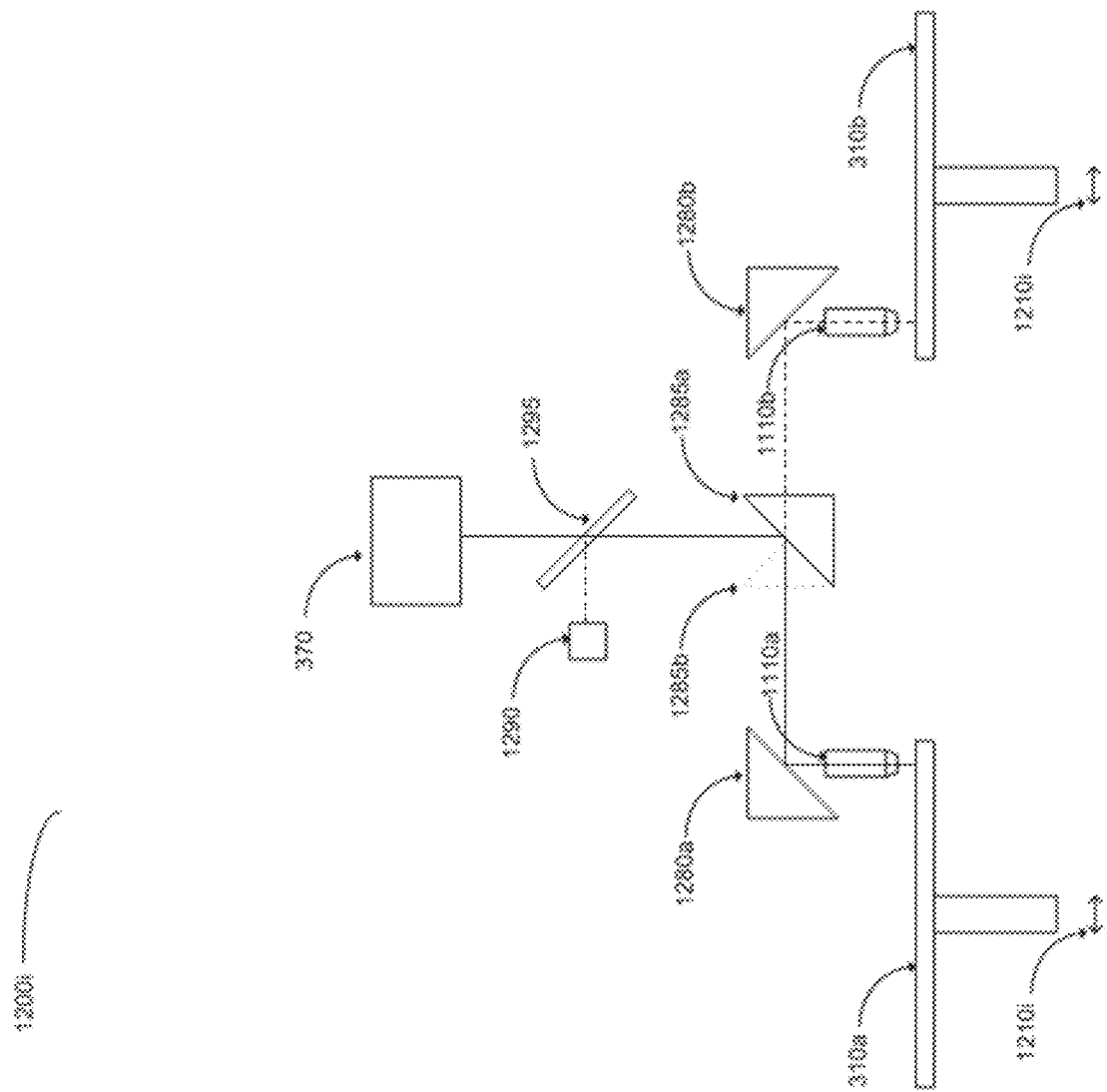
FIG. 23K shows an architecture for a system comprising multiple spindles scanning with a shared optical detection system.

FIG. 23K shows an architecture for a system 1200*i* comprising multiple spindles scanning with a shared optical detection system. The system may comprise first and second substrates 310*a* and 310*b*, respectively. The first and second substrates may be similar to substrate 310 described herein. The first and second substrates may be affixed to first and second spindles, respectively. The first and second spindles may impart rotational motion to the first and second substrates, respectively. The system may comprise first and second optical imaging objectives 1110*a* and 1110*b*, respectively. The first and second optical imaging objectives may be similar to optical imaging objective 1110 described herein. The first and second optical imaging objectives may be configured to collect light from the first and second substrates, respectively. The first and second optical imaging objectives may pass light collected from the first and second substrates, respectively, to first and second mirrors 1280*a* and 1280*b*, respectively. In some cases, only one of the first and second optical imaging objective will collect light at a particular instance in time.

The first and second mirrors may pass the light to a shared movable mirror. When in a first configuration 1285*a*, the shared movable mirror may direct light from the first substrate to a beamsplitter 1295. The beamsplitter may comprise a dichroic mirror. For example, as illustrated in FIG. 23K, the beamsplitter may be configured to reflect an excitation light from an excitation light source 1290 toward a substrate and transmit the light from a substrate toward the detector 370. In an alternative configuration (not shown in FIG. 23K), the beamsplitter may be configured to transmit an excitation light from an excitation light source 1290 toward the substrate and reflect the light from a substrate toward the detector 370. The beamsplitter may pass or reflect light to a detector 370, allowing the first substrate to be imaged. The first substrate may be configured to be translated 12101, allowing different locations on the first substrate to be imaged.

When in a second configuration 1285*b*, the shared movable mirror may direct light from the second substrate to the beamsplitter 1295. The beamsplitter may pass or reflect light to a detector 370, allowing the second substrate to be imaged. The second substrate may be configured to be translated 12101, allowing different locations on the second substrate to be imaged. Thus, by moving the movable mirror, the first and second substrates may be imaged by a shared optical system.

The system may further comprise an excitation light source 1290. The light source may be configured to provide excitation light (such as for fluorescence imaging) to the first or second substrate. The excitation light may be selectively delivered to the first or second substrate using the movable mirror in a similar manner as for detection described herein.

Though depicted as comprising two substrates, two imaging optical objectives, and two mirrors in FIG. 23K, system 12001 may comprise any number of substrates, imaging optical objectives, or mirrors. For instance, the system may comprise at least 1, at least 2, at least 3, at least 4, at least 5, at least 6, at least 7, at least 8, at least 9, or at least 10 substrates. The system may comprise at least 1, at least 2, at least 3, at least 4, at least 5, at least 6, at least 7, at least 8, at least 9, or at least 10 imaging optical objectives. The system may comprise at least 1, at least 2, at least 3, at least 4, at least 5, at least 6, at least 7, at least 8, at least 9, or at least 10 mirrors.

FIG. 23I shows an architecture for a system comprising a plurality of imaging heads scanning with shared translation and rotational axes and independently rotating fields.

FIG. 23K shows an architecture for a system comprising multiple spindles scanning with a shared optical detection system.

Figure 24:
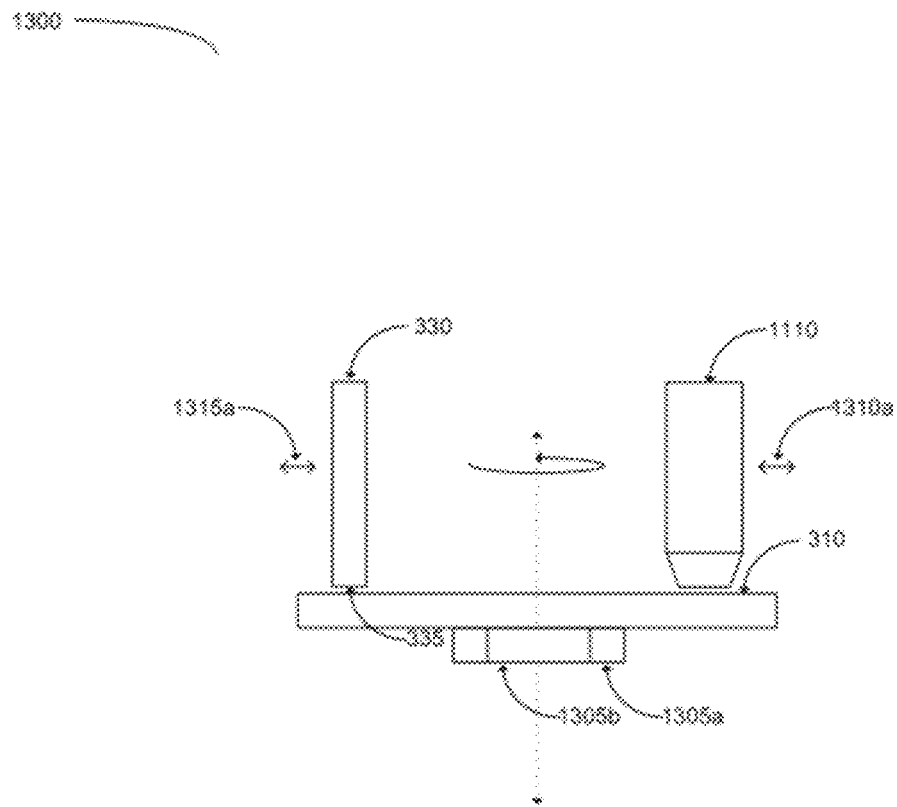
FIG. 24 shows an architecture for a system comprising a plurality of rotating spindles.

FIG. 24 shows an architecture for a system 1300 comprising a plurality of rotating spindles. The system 1300 may comprise substrate 310 described herein. The substrate may be configured to rotate, as described herein. The system may further comprise fluid channel 330 and fluid outlet port 335 described herein, or any other fluid channel and fluid outlet port described herein. The fluid channel and fluid outlet port may be configured to dispense any solution described herein. The fluid channel and fluid outlet port may be configured to move 1315*a* relative to the substrate. For instance, the fluid channel and fluid outlet port may be configured to move to a position above (such as near the center of) the substrate during periods of time in which the fluid channel and fluid outlet port are dispensing a solution. The fluid channel and fluid outlet port may be configured to move to a position away from the substrate during the period in which the fluid channel and fluid outlet port are not dispensing a solution. The system may further comprise optical imaging objective 1110 described herein. The optical imaging objective may be configured to move 1310*a* relative for the substrate. For instance, the optical imaging objective may be configured to move to a position above (such as near the center of, or radially scanning) the substrate during periods of time in which the substrate is being imaged. The optical imaging objective may be configured to move to a position away from the substrate during the period in which the substrate is not being imaged.

The system may further comprise a first spindle 1305*a* and a second spindle 1305*b*. The first spindle may be interior to the second spindle. The first spindle may be exterior to the second spindle. The second spindle may be interior to the first spindle. The second spindle may be exterior to the first spindle. The first and second spindles may each be configured to rotate independently of each other. The first and second spindles may be configured to rotate with different angular velocities. For instance, the first spindle may be configured to rotate with a first angular velocity and the second spindle may be configured to rotate with a second angular velocity. The first angular velocity may be less than the second angular velocity. The first spindle may be configured to rotate at a relatively low angular velocity (such as an angular velocity between about 0 rpm and about 100 rpm) during periods in which a solution is being dispensed to the substrate. The second spindle may be configured to rotate at a relatively high angular velocity (such as an angular velocity between about 100 rpm and about 1,000 rpm) during periods in which the substrate is being imaged. Alternatively, the reverse may apply. The substrate may be transferred between the first and second spindles to complete each of the dispensing and imaging operations.

The system may comprise any number of spindles. For example, the system may comprise at least about 2, 3, 4, 5, 6, 7, 8, 9, 10, 20, or more spindles. Alternatively or in addition, the system may comprise at most about 20, 10, 9, 8, 7, 6, 5, 4, 3, 2, or 1 spindle. A given spindle may be interior or exterior relative to one or more other spindles in the system. In some instances, each of the spindles may rotate independently of each other. In some instances, at least a subset of the spindles may rotate independently of each other. In some instances, at least a subset of the spindles may rotate dependently of each other (e.g., simultaneously at the same angular velocity). The spindles may rotate with respect to the same axis or different axes. In some instances, each spindle may rotate with different angular velocities. In some instances, at least a subset of the spindles may rotate with different angular velocities.

Though depicted as utilizing a moving fluid channel and optical imaging objective in FIG. 24, the system 1300 may be configured in other manners as described herein. For instance, the system may be configured such that the fluid channel and optical imaging objective are stationary, and the substrate is configured to move. The system may be configured in any other manner described herein.

Nucleic Acid Amplification and Sequencing Applications

The methods and systems described herein may be applied to a variety of sequencing and application techniques and methods. The open substrate systems, the solution dispensing methods, the rotating array systems, the substrate systems, the substrate preparation methods, the optical systems, the scanning systems, or the scanning methods disclosed herein, or any combination thereof, may be applied to a variety of sequencing methods, for example including non-terminated sequencing, reversible terminator sequencing, rolling circle amplification sequencing, DNA nanoball sequencing, massively parallel sequencing. A substrate disclosed herein may comprise one or more sequencing components (e.g., adapters, primers, beads, antibodies, DNA nanoballs, nucleic acid templates, polymerases, nucleotides, fluorescent nucleotides, terminating nucleotides, or reversibly terminating nucleotides) suitable for binding or amplifying a nucleic acid. A sequencing component may be affixed to the substrate. In some instances, a sequencing component may be patterned onto the substrate. In some instances, a sequencing component may be affixed to the substrate without patterning. The substrate may comprise a pattern comprising discrete regions distinguished by surface chemistry. For example, the substrate may comprise a pattern comprising one or more regions that recruit one or more sequencing components and one or more regions that exclude one or more sequencing components. In some instances, a first sequencing component may be recruited to the substrate, and a second sequencing component may be recruited to the first sequencing component. Additional sequencing components may be recruited, thereby sequencing a nucleic acid.

One or more sequencing components may be dispensed onto the substrate using the solution dispensing methods disclosed herein. For example, the sequencing components may include samples, processed samples, supports or particles (e.g., beads, etc.), amplification reagents and/or sequencing reagents (e.g., washing solution, buffers, primers, enzymes, catalysts, quenchers, nucleotides, or analogs thereof, dyes, probes, tags, labels, etc.), fluidic components (e.g., surfactant, buffer, etc.), and/or optical components (e.g., reference beads, dyes, etc.). For example, a solution comprising a sequencing component may be dispensed onto the substrate in a spiral pattern. In some instances, a solution comprising a sequencing component may be dispensed in a circular path, an elliptical path, a linear path, or a non-linear path. A sequencing component may be dispensed onto a rotating substrate. A sequencing component may be dispensed on a substrate in a pattern to ensure a consistent reaction time at each region of the substrate contacted by the sequencing component, as disclosed herein. Alternatively, a sequencing component may be dispensed in any manner, including random or semi-random dispensing. A substrate comprising a sequencing component may be scanned using the scanning systems disclosed herein. A substrate comprising a sequencing component, for example a fluorescent component (e.g., a fluorescent nucleotide or a fluorescent antibody), may be imaged using the optical systems disclosed herein. The substrate comprising a sequencing component may be scanned while the substrate is rotating. In some instances, the substrate may be scanned using an optical system comprising one or more objectives. The one or more objectives may be configured to enable efficient scanning of the substrate, as disclosed herein.

Reversible Terminator Sequencing

The systems and methods disclosed herein may be compatible with reversible terminator sequencing methods. In some instances, a reversible terminator sequencing method may comprise adhering a plurality of adaptors to a substrate. An adaptor may bind to a DNA template or a DNA template fragment. The adaptors may be affixed to a patterned substrate. The adaptors may be affixed to a substrate without patterning. A patterned substrate may comprise one or more regions that recruit the adaptors and one or more regions that exclude the adaptors. An adaptor with or without a DNA template or DNA template fragment may be delivered to a substrate. For example, an adaptor comprising a DNA template or fragment thereof may be delivered to a patterned substrate or a substrate lacking a pattern. In another example, an adaptor lacking a DNA template or fragment thereof may be delivered to a patterned substrate or a substrate lacking a pattern. A solution comprising a DNA template or DNA template fragment may be dispensed to the substrate comprising the adaptors, and they DNA template or DNA template fragment may adhere to the adaptors. A solution comprising a DNA template or a DNA template fragment may be dispensed onto the substrate using any of the dispensing methods or patterns disclosed herein. For example, a solution comprising a DNA template or DNA fragment may be dispensed locally to targeted regions of the substrate. In another example, the solution comprising a DNA template or DNA fragment may be dispensed locally and broadly dispersed across the substrate (e.g., spin-coated). In another example, the solution comprising a DNA template or DNA fragment may be dispensed onto the substrate in a pattern (e.g., a spiral pattern, a circular pattern, an elliptical patter, a linear pattern, or a non-linear pattern). The solution comprising a DNA template or DNA fragment may be dispensed while the substrate is rotating.

In some instances, a reversible terminator sequencing method may comprise adhering a plurality of primers to a substrate. In some instance, a primer may adhere to an adaptor. A primer may bind to a DNA template or a DNA template fragment. The primers may be affixed to a patterned substrate. The primers may be affixed to a substrate without patterning. A patterned substrate may comprise one or more regions that recruit the primers and one or more regions that exclude the primers. A solution comprising a DNA template or a DNA template fragment may be dispensed onto the substrate comprising primers using any of the dispensing methods or patterns disclosed herein. The DNA template or DNA template fragment may be recruited to the substrate (e.g., by binding to a primer or an adapter). The DNA template or DNA template fragment may be amplified on the substrate. In some instances, the DNA template or DNA template fragment may be dispensed onto the substrate such that the rate of DNA binding to a region is slower than the amplification doubling rate in the region. For example, the amplification doubling rate of a DNA template or DNA template fragment may be about 2, about 3, about 4, about 5, about 6, about 7, about 8, about 9, or about 10 times the arrival rate of the DNA template or DNA template fragment to the region of the substrate. This may ensure that a DNA template or DNA template fragment is well amplified before arrival of another DNA template or DNA template fragment to the same region.

A solution comprising DNA molecules may be dispensed onto a substrate (e.g., any of the substrates or patterned substrates disclosed herein) with a seeding efficiency determined by the fraction of DNA molecules dispensed onto the substrate that adhere to the substrate. In some instances, the solution comprising the DNA molecules may be dispensed with a seeding efficiency of about 5%, about 6%, about 7%, about 8%, about 9%, about 10%, about 11%, about 12%, about 13%, about 14%, about 15%, about 20%, or about 25%. In some instances, the DNA molecules may adhere to the substrate at a density of about 10,000 DNA molecules per mm$^2$, about 20,000 DNA molecules per mm$^2$, about 30,000 DNA molecules per mm$^2$, about 40,000 DNA molecules per mm$^2$, about 50,000 DNA molecules per mm$^2$, about 100,000 DNA molecules per mm$^2$, about 200,000 DNA molecules per mm$^2$, about 300,000 DNA molecules per mm$^2$, about 400,000 DNA molecules per mm$^2$, about 500,000 DNA molecules per mm$^2$, about 1,000,000 DNA molecules per mm$^2$, about 2,000,000 DNA molecules per mm$^2$, about 3,000,000 DNA molecules per mm$^2$, about 4,000,000 DNA molecules per mm$^2$, about 5,000,000 DNA molecules per mm$^2$, about 6,000,000 DNA molecules per mm$^2$, about 7,000,000 DNA molecules per mm$^2$, about 8,000,000 DNA molecules per mm$^2$, about 9,000,000 DNA molecules per mm$^2$, or about 10,000,000 DNA molecules per mm$^2$.

The DNA molecules adhered to the substrate may be monoclonal amplified. In some cases, at least about 70%, at least about 75%, at least about 80%, at least about 85%, at least about 90%, at least about 95%, at least about 98%, or at least about 99% of the DNA molecules adhered to the substrate may be amplified.

One or more DNA molecules (e.g., one or more DNA templates or one or more DNA template fragments) may be amplified. Amplification may occur while the DNA molecule is adhered to the substrate. Amplification may occur while the DNA molecule is being dispensed on the substrate. The DNA molecules may be amplified using a variety of amplification means, including but not limited to polymerase chain reaction (PCR), recombinase polymerase amplification (RPA), bridge amplification, nucleic acid sequence-based amplification (NASBA), loop-mediated isothermal amplification (LAMP), helicase-dependent amplification (HDA), rolling circle amplification (RCA), or multiple displacement amplification (MDA). A DNA molecule may be amplified using nucleic acids comprising a reversible terminator. In some instances, a nucleic acid may comprise a base, a cleavable linker covalently linked to the base, and a fluorescent molecule covalently linked to the base via the cleavable linker. In some instances, a nucleic acid may comprise a reversibly terminating group covalently linked to the nucleic acid (e.g., at the 3' hydroxyl group). A reversible terminator may comprise 3'-O-azidomethy reversible terminator, a 3'-ONH$_2$ reversible terminator, a 3'-ONH$_2$ reversible terminator, or 3'-OH unblocked reversible terminator (e.g., a virtual terminator or a lightening terminator).

An amplified DNA molecule (e.g., comprising a fluorescent molecule) may be imaged using the optical systems or scanning methods disclosed herein. In some instances, imaging may comprise imaging a plurality of optically resolvable spots. A spot may comprise a DNA molecule (e.g., a DNA molecule comprising a fluorescent molecule). In some cases, at least about 70%, at least about 75%, at least about 80%, at least about 85%, at least about 90%, at least about 95%, at least about 98%, or at least about 99% of the spots comprising a DNA molecule comprise a single species of DNA (e.g., are monoclonal).

Massively Parallel Sequencing

The systems and methods disclosed herein may be compatible with massively parallel sequencing methods. One or more DNA molecules (e.g., one or more DNA templates or one or more DNA template fragments) may be amplified. Amplification may occur while the DNA molecule is adhered to the substrate. Amplification may occur while the DNA molecule is being dispensed on the substrate. The DNA molecules may be amplified using a variety of amplification means, including but not limited to polymerase chain reaction (PCR), recombinase polymerase amplification (RCA), bridge amplification, nucleic acid sequence-based amplification (NASBA), loop-mediated isothermal amplification (LAMP), helicase-dependent amplification (HDA), rolling circle amplification (RPA), or multiple displacement amplification (MDA). In some instances, massively parallel sequencing may comprise labeling an amplified DNA molecule (e.g., a DNA template or a DNA template fragment) with an antibody (e.g., a fluorescently labeled antibody). An antibody may bind to a terminated nucleotide. For example, an antibody may bind to any of the reversibly terminated nucleotides disclosed herein. An antibody may selectively bind to a terminated nucleotide sequence (e.g., a terminated A, a terminated T, a terminated C, or a terminated G). In some instances, an antibody may comprise a plurality of fluorescent molecules.

The DNA molecules may dispensed onto a substrate using any of the methods or systems disclosed herein. The DNA molecules may be dispensed onto any of the substrates disclosed herein (e.g., a pattered substrate or a substrate lacking a pattern). The antibodies may be dispensed onto the substrate in any of the patterns disclosed herein (e.g., a spiral pattern, a circular pattern, an elliptical patter, a linear pattern, or a non-linear pattern). The antibodies may dispensed onto a substrate using any of the methods or systems disclosed herein. The antibodies may be dispensed onto any of the substrates disclosed herein (e.g., a pattered substrate or a substrate lacking a pattern). The antibodies may be dispensed onto the substrate in any of the patterns disclosed herein (e.g., a spiral pattern, a circular pattern, an elliptical patter, a linear pattern, or a non-linear pattern).

A substrate comprising the DNA molecules and the antibodies may be imaged using the optical systems or scanning methods disclosed herein. In some instances, imaging may comprise imaging a plurality of optically resolvable spots. A spot may comprise a DNA molecule. A spot may comprise an antibody (e.g., an antibody comprising a fluorescent molecule). In some cases, at least about 70%, at least about 75%, at least about 80%, at least about 85%, at least about 90%, at least about 95%, at least about 98%, or at least about 99% of the spots comprising a DNA molecule comprise a single fluorescent antibody.

DNA Nanoball Sequencing

The systems and methods disclosed herein may be compatible with DNA nanoball sequencing methods. DNA nanoball sequencing methods may comprise amplifying a DNA template or a DNA template fragment using rolling circle replication. DNA template fragments (e.g., fragments comprising from about 100 base pairs to about 350 base pairs) may be ligated to adapter sequences. The adapter sequences may be ligated to the fragments, thereby circularizing the fragments. The circular fragments may be amplified using rolling circle amplification. In some aspects, rolling circle amplification of the ligated fragments may generate single-stranded copies of the fragments. An amplified nucleic acid molecule comprising concatenated amplified fragments may be compacted into a DNA nanoball.

The DNA fragments may dispensed onto a substrate using any of the methods or systems disclosed herein. The DNA fragments may be dispensed onto any of the substrates disclosed herein (e.g., a pattered substrate or a substrate lacking a pattern). The DNA nanoballs may dispensed onto a substrate using any of the methods or systems disclosed herein. The DNA nanoballs may be dispensed onto any of the substrates disclosed herein (e.g., a pattered substrate or a substrate lacking a pattern). In some instances, the DNA fragments may be amplified while adhered to the substrate.

A substrate comprising the DNA fragments or DNA nanoballs may be imaged using the optical systems or scanning methods disclosed herein. In some instances, imaging may comprise imaging a plurality of optically resolvable spots. A spot may comprise a DNA nanoball. A spot may comprise an DNA fragment. In some cases, at least about 70%, at least about 75%, at least about 80%, at least about 85%, at least about 90%, at least about 95%, at least about 98%, or at least about 99% of the spots comprising a DNA nanoball or DNA fragment may comprise a single fluorescent species of DNA nanoball or DNA fragment.

The systems and methods provided herein may be applicable for any sequencing or amplification scheme, such as those described herein. For any sequencing scheme or amplification, one or more operations may be performed off the substrate and/or one or more operations may be performed on the substrate. For example, in a sequencing scheme, amplification is performed off the substrate and amplified products (e.g., attached to a support) are subsequently deposited onto the substrate for sequencing. For example, in an amplification scheme, library preparation is performed off the substrate and a library of template nucleic acid molecules is deposited onto the substrate for amplification. In another example, both amplification and subsequent sequencing is performed on the substrate. Any sequencing component may be loaded to the substrate, affixed to the substrate and/or dispensed to an object affixed to the substrate, as described elsewhere herein.

Application to Other Analytes

Figure 25:
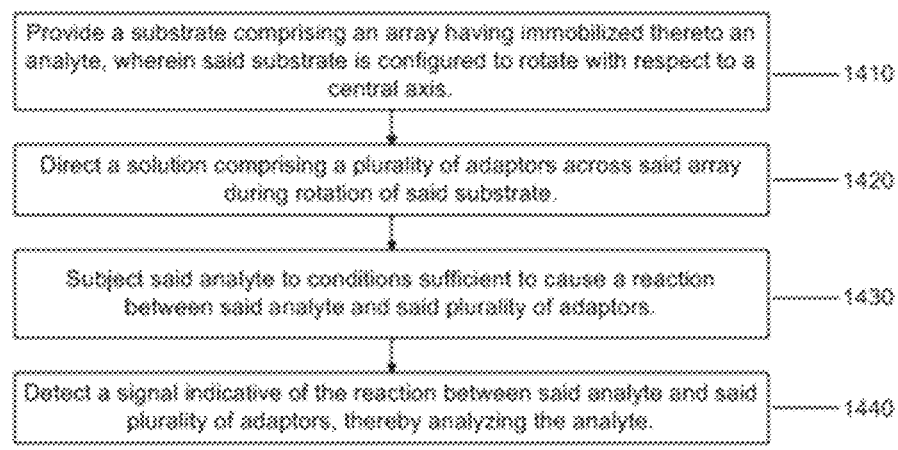
FIG. 25 shows a flowchart for an example of a method for processing an analyte.

Though described herein as useful for sequencing nucleic acids, the systems and method described herein may be applied to other analytes and/or other applications processing such analytes. FIG. 25 shows a flowchart for an example of a method 1400 for processing an analyte.

In a first operation 1410, the method may comprise providing a substrate comprising a planar array having immobilized thereto an analyte, wherein the substrate is configured to rotate with respect to an axis. The axis may be an axis through the center of the substrate. The axis may be an off-center axis. The substrate may be any substrate described herein. In some instances, the planar array may comprise a single type of analyte. In other instances, the planar array may comprise two or more types of analytes. The two or more types of analytes may be arranged randomly. The two or more types of analytes may be arranged in a regular pattern. For example, two types of analytes may be arranged in a radially alternating pattern. The analyte may be any biological sample described herein or derivative thereof. For example, the analyte may be a single cell analyte. The analyte may be a nucleic acid molecule. The analyte may be a protein molecule. The analyte may be a single cell. The analyte may be a particle. The analyte may be an organism. The analyte may be part of a colony. In some cases, the analyte may be or be derived from a non-biological sample. The analyte may be immobilized in an individually addressable location on the planar array. The analyte may be immobilized to the substrate via a linker configured to bind to the analyte. For example, the linker may comprise a carbohydrate molecule. The link may comprise an affinity binding protein. The linker may be hydrophilic. The linker may be hydrophobic. The linker may be electrostatic. The linker may be labeled. The linker may be integral to the substrate. The linker may be an independent layer on the substrate.

In a second operation 1420, the method may comprise directing a solution comprising a plurality of reactants across the planar array during rotation of the substrate. The solution may comprise any solution or reagent described herein. The plurality of reactants may be configured to interact with the analyte immobilized to the planar array. For example, where the analyte is a nucleic acid molecule, the plurality of reactants may comprise a plurality of probes. A given probe of the plurality of probes may comprise a random sequence or a targeted sequence, such as a homopolymer sequence or a dibase or tribase repeating sequence. In some instances, the probe may be a dibase probe. In some instances, the probe may be about 1 to 10 bases in length. In some instances, the probe may be about 10 to 20 bases in length. In some instances, the probe may be at least about 1, 2, 3, 4, 5, 6, 7, 8, 9, 10, 11, 12, 13, 14, 15, 16, 17, 18, 19, 20, 30, 40, 50, or more bases. Alternatively or in combination the probe may be at most about 50, 40, 30, 20, 19, 18, 17, 16, 15, 14, 13, 12, 11, 10, 9, 8, 7, 6, 5, 4, 3, 2, 1 base. In another example, where the analyte is a protein molecule, the plurality of reactants may comprise a plurality of antibodies. A given antibody of the plurality of antibodies may have binding specificity to one or more types of proteins. In other instances, the plurality of reactants may comprise any combination of a plurality of oligonucleotide molecules, carbohydrate molecules, lipid molecules, affinity binding proteins, aptamers, antibodies, enzymes, or other reagents. The plurality of reactants may be hydrophilic. The plurality of reactants may be hydrophobic. The plurality of reactants may be electrostatic. The plurality of reactants may be labeled. The plurality of reactants may comprise a mixture of labeled and unlabeled components. In some instances, the plurality of reactants may not be labeled.

In an operation 1430, the method may comprise subjecting the analyte to conditions sufficient to cause a reaction or interaction between the analyte and the plurality of reactants. In an operation 1440, the method may comprise detecting a signal indicative of the reaction between the analyte and the plurality of reactants, thereby analyzing the analyte. In some cases, a reactant may undergo a reaction with the analyte. Alternatively or in addition, the reactant may bind to or interact with the analyte. One or more of the analyte or the reactant may undergo a conformational change, chemical change, state change, or any combination thereof upon interaction with the analyte.

The method may further comprise, prior to operation 1410, directing the analyte across the substrate comprising the linker. For example, prior to or during dispensing of the analyte, the substrate may be rotated to coat the substrate surface and/or the planar array with the analyte. In some instances, the analyte may be coupled to a bead, which bead is immobilized to the planar array.

The method may further comprise recycling, as described elsewhere herein, a subset of the solution that has contacted the substrate. The recycling may comprise collecting, filtering, and reusing the subset of the solution. The filtering may comprise molecular filtering. The molecular filtering may comprise specific nucleic acid filtering (i.e. filtering for a specific nucleic acid). The nucleic acid filtering may comprise exposure of the solution to an array of oligonucleotide extension compounds which may specifically bind to contaminant nucleotides or nucleic acids.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal. The signal may be any detectable signal. Alternatively or in addition to the optical sensors described herein, the system may comprise one or more other detectors (e.g., acoustic detector, etc.) configured to detect the detectable signal.

In some instances, the method may further comprise, prior to operation 1420, subjecting the substrate to rotation with respect to the central axis.

In some instances, the method may further comprise terminating rotation of the substrate prior to detecting the signal in operation 1440. In other instances, the signal may be detected in operation 1440 while the substrate is rotating.

The signal may be generated by binding of a label to the analyte. The label may be bound to a molecule, particle, cell, or organism. The label may be bound to the molecule, particle, cell, or organism prior to operation 1410. The label may be bound to the molecule, particle, cell, or organism subsequent to operation 1410. The signal may be generated by formation of a detectable product by a chemical reaction. The reaction may comprise an enzymatic reaction. The signal may be generated by formation of a detectable product by physical association. The signal may be generated by formation of a detectable product by proximity association. The signal generated by proximity association may comprise Forster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. For example, the reaction may comprise a hybridization reaction or ligation reaction. The reaction may comprise a hybridization reaction and a ligation reaction.

The method may further comprise repeating operations 1420, 1430, and 1440 one or more times. Different solutions may be directed to the planar array during rotation of the substrate for consecutive cycles.

Many variations, alterations, and adaptations based on the method 1400 provided herein are possible. For example, the order of the operations of the method 1400 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated. Some of the operations may be manual.

Figure 26:
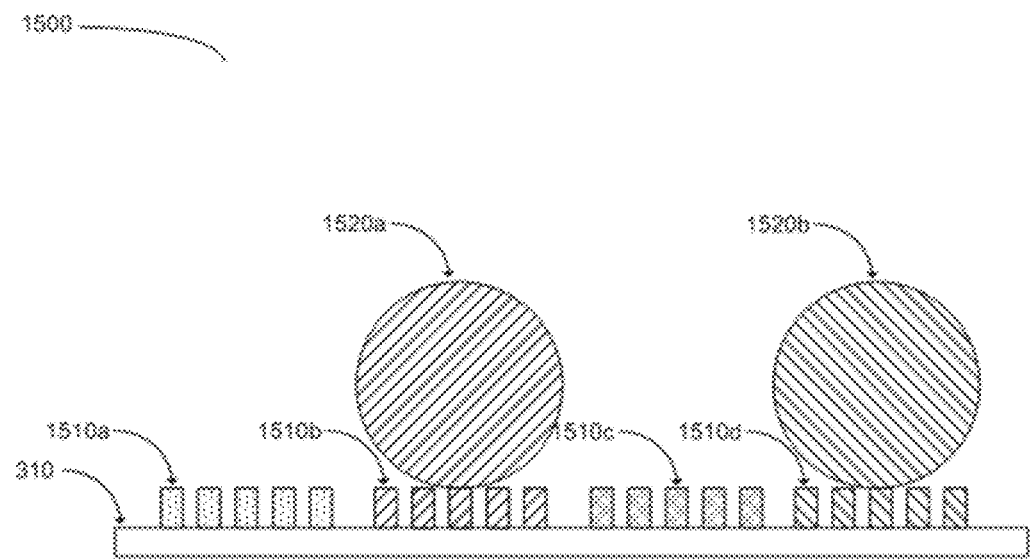
FIG. 26 shows a first example of a system for isolating an analyte.

FIG. 26 shows a first example of a system 1500 for isolating an analyte. The system may comprise a plurality of linkers 1510*a*, 1510*b*, 1510*c*, and 1510*d*. The plurality of linkers may be adhered or otherwise affixed to substrate 310 described herein. For instance, each linker may be bound to a particular individually addressable location of the plurality of individually addressable locations described herein. Linkers 1510*a*, 1510*b*, 1510*c*, and 1510*d* may comprise any linker described herein. Some or all of linkers 1510*a*, 1510*b*, 1510*c*, and 1510*d* may be the same. Some or all of linkers 1510*a*, 1510*b*, 1510*c*, and 1510*d* may be different. The linkers may be configured to interact with analytes 1520*a* and 1520*b*. For instance, the linkers may be configured to bind to analytes 1520*a* and 1520*b* through any interaction described herein. Analytes 1520*a* and 1520*b* may comprise any analyte described herein. Analytes 1520*a* and 1520*b* may be the same. Analytes 1520*a* and 1520*b* may be different. The linkers may be configured to interact specifically with particular analytes and/or types thereof. For instance, linker 1510*b* may be configured to interact specifically with analyte 1520*a*. Linker 1510*d* may be configured to interact specifically with analyte 1520*b*. Any linker may be configured to interact with any analyte. In this manner, specific analytes may be bound to specific locations on the substrate. Though shown as comprising four linkers and two analytes in FIG. 26, system 1500 may comprise any number of linkers and analytes. For instance, system 1500 may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000 linkers, or a number of linkers that is within a range defined by any two of the preceding values. System 1500 may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000 analytes, or a number of analytes that is within a range defined by any two of the preceding values.

Figure 27:
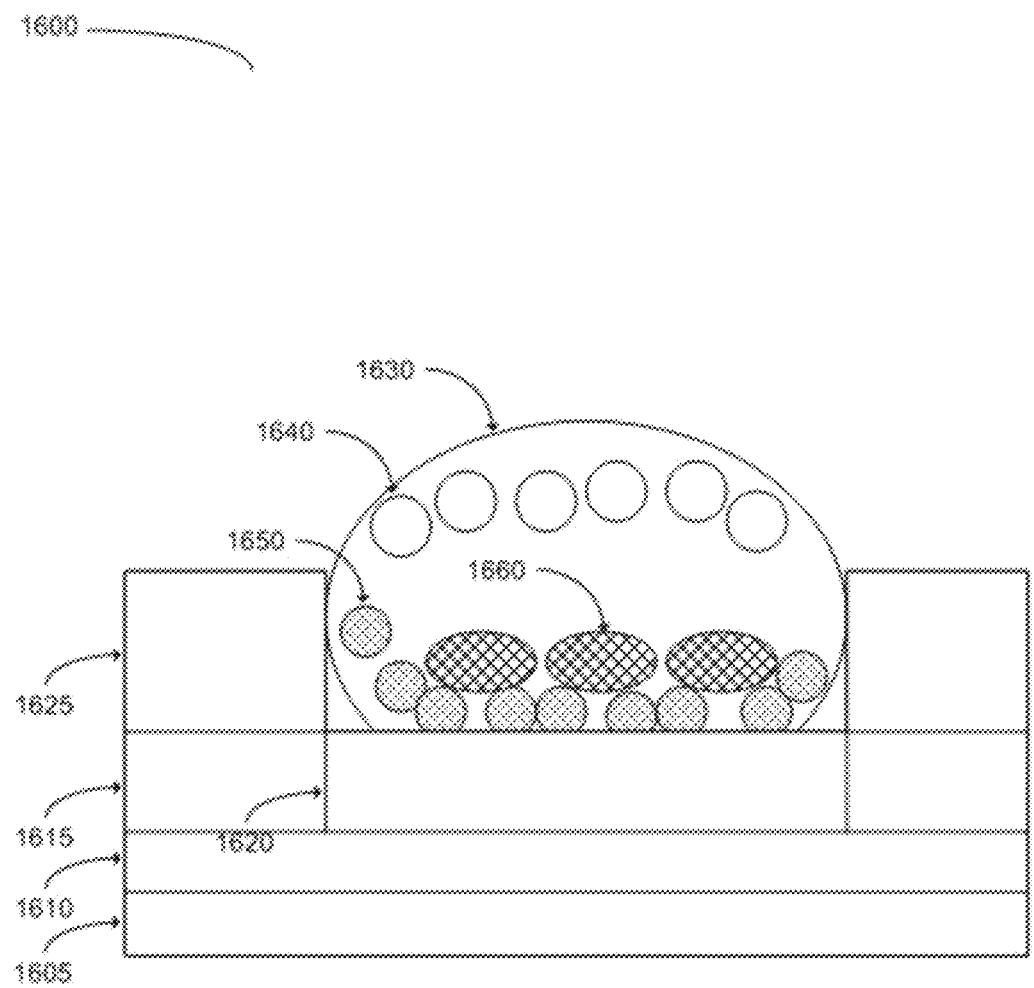
FIG. 27 shows a second example of a system for isolating an analyte.

FIG. 27 shows a second example of a system 1600 for isolating an analyte. The system may comprise a well configured to physically trap a particle. The well may comprise an individually addressable location of the plurality of individually addressable locations described herein. The well may be configured to trap an analyte. For instance, the well may be configured to trap a droplet of blood 1630. For example, the droplet of blood may comprise white blood cells 1640, red blood cells 1650, and circulating tumor cells 1660. The well may be configured to trap any other analyte described herein. The well may be constructed in layers using microfabrication materials and techniques. For instance, the well may comprise a base layer 1605. The base layer may comprise silicon. The well may comprise an oxide layer 1610. The oxide layer may comprise silicon oxide. The well may comprise a metal layer 1615. The metal may comprise nickel or aluminum. The well may comprise a nanotube layer 1620. The nanotube layer may comprise one or more carbon nanotubes. The well may comprise a confinement layer 1625. The confinement layer may comprise a photoresist. The photoresist may comprise SU-8. The nanotube layer and confinement layer may be configured to together trap the cell.

Figure 28:
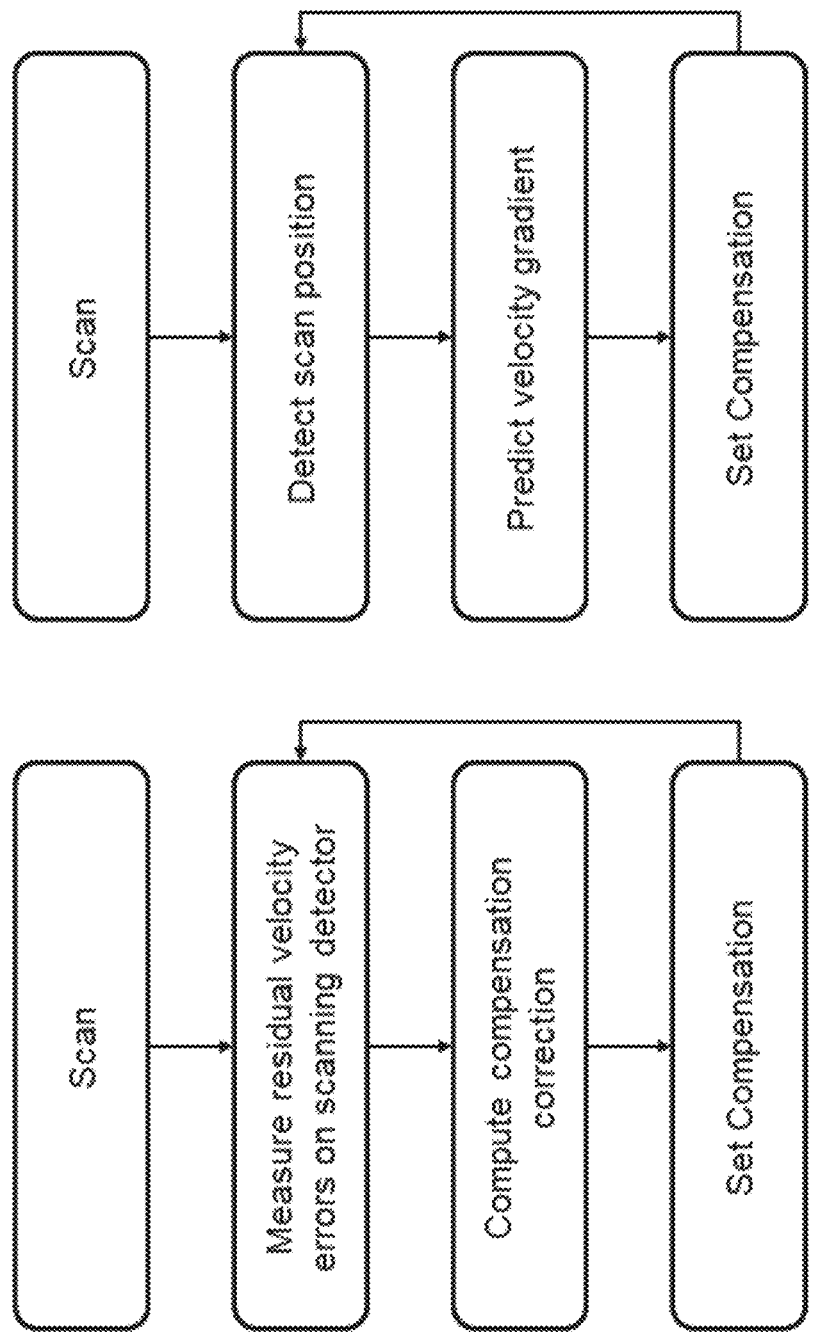
FIG. 28 shows examples of control systems to compensate for velocity gradients during scanning.

FIG. 28 shows examples of control systems to compensate for velocity gradients during scanning. Such control system may algorithmically compensate for velocity gradients. The control system may predictive or adaptively compensate for tangential velocity gradients. In a first control system, illustrated on the left of FIG. 28, the control system may, based on scanning of a rotating substrate, measure residual (uncorrected) velocity errors during scanning, compute a compensation correction factor, and use the compensation correction factor to set (or adjust) a compensation factor to reduce the velocity errors for subsequent scanning results. The first control system may be a closed loop control system that removes (or otherwise reduces) velocity errors. In a second control system, illustrated on the right of FIG. 28, the control system may, based on knowledge of the geometry and relative position of the scanning relative to the substrate, directly compute (or predict) the expected velocity gradient, and set (or adjust) the system to remove the expected gradient.

Multi-Head Imaging Using a Common Linear Motion

Systems and methods described herein may utilize multiple imaging heads (e.g., detector systems, such detector systems comprising a sensor and an illumination source), with each imaging head responsible for imaging different locations on a substrate described herein. For instance, as described herein, a first imaging head may image the substrate along a first imaging path. The first imaging path may comprise a first series of (one or more) rings, a first series of (one or more) spirals, or a different first imaging path. Second, third, fourth, fifth, sixth, seventh, eighth, ninth, or tenth imaging heads may image the substrate along second, third, fourth, fifth, sixth, seventh, eighth, ninth, or tenth imaging paths. The second, third, fourth, fifth, sixth, seventh, eighth, ninth, or tenth imaging paths may comprise second, third, fourth, fifth, sixth, seventh, eighth, ninth, or tenth series of rings, second, third, fourth, fifth, sixth, seventh, eighth, ninth, or tenth spirals, or different second, third, fourth, fifth, sixth, seventh, eighth, ninth, or tenth imaging paths. An imaging path or scan path may be an imaging path or scan path on the substrate or on the sample.

Such multi-head imaging systems and methods may increase a rate of imaging of the substrate and/or decrease an amount of time that may be required to image the substrate. In some cases, multiple imaging heads may move independently relative to the substrate, such as by independently controlling motions of each of the imaging heads. In some cases a first sensor may image a first region of the substrate at a first rate, and a second sensor may image a second region of the substrate at a second rate. The imaging rate of the sensor may be determined based on the linear velocity of the region being imaged relative to the imaging head comprising the sensor. For example, a first sensor may image a first region farther from the axis of rotation of the substrate at a faster rate than a second sensor imaging a second region closer to the axis of rotation of the substrate.

As described herein, during detection (e.g., imaging) of a substrate or region thereof, the substrate may be stationary and one or more detector systems or components thereof may be in motion (e.g., rotating). For example, the substrate may be stationary and both a sensor (e.g., line-scan camera) and an illumination source of a detector system may be in motion (e.g., rotating) during detection. Alternatively, the substrate may be in motion (e.g., rotating) and one or more detector systems or components thereof may be stationary. In some cases, the substrate and a detector system or component thereof may be in motion. For example, the substrate may be rotating, and a sensor and an illumination source of a detector system may be in motion. For instance, the sensor and illumination source may translate (e.g., radially translate) across the substrate or the sensor and illumination source may remain disposed in a same physical location but may rotate about a central axis of the detector system.

The required motions of the imaging heads may be reduced by moving the substrate relative to each of the imaging heads such that each of the imaging heads shares a single linear motion with respect to the substrate. Such an improvement may be achieved by positioning each scan head at a different initial distance (e.g., radial distance) from a center of the substrate and operating each scan head at a different scan rate which depend on the scan head's initial distance from the center of the substrate. The single shared linear motion may be along a linear vector. For example, the single shared linear motion may result in radial motion (e.g., directed through an axis of rotation) or non-radial motion (e.g., not directed through an axis of rotation) of one or more scan heads. In some cases, the imaging heads may be configured to move relative to the substrate in a radial direction, r, in a polar coordinate system comprising radial component r and angular component φ. In some cases, the imaging heads may be configured to move in a linear direction relative to the substrate that is not entirely radial, for example in a direction comprising both r and φ components. The imaging heads may operate on the same side of the axis of rotation of the substrate or on opposite sides of the axis of rotation of the substrate. In the case of non-radial linear motion of the one or more heads, the scan direction of each imaging head may rotate due to a change in angle relative to the axis of rotation. Such rotations may be compensated by counter-rotating (for instance, using a prism) to allow for a fixed scan direction for each imaging head.

FIG. 29A shows motion of a substrate relative to two imaging heads located on the same side of an axis of rotation of the substrate. The substrate 310 may be any substrate described herein. A first imaging head 1005 may be similar to any first imaging head described herein. A second imaging head 1015 may be similar to any second imaging head described herein. At a first moment in time, the first imaging head 1005 and second imaging head 1015 may be located on the same side of an axis of rotation 305 of the substrate, such that the first imaging head 1005 traces a first imaging path 1010 during rotation of the substrate and the second imaging head 1015 traces a second imaging path 1020 during rotation of the substrate. The substrate may be configured to move in a linear, radial direction 1810 relative to the first and second imaging heads. For example, the substrate may be configured to move in a radial direction, r, in a polar coordinate system comprising radial component r and angular component φ. In some cases, the substrate may be configured to move in a linear direction that is not entirely radial, for example in a direction comprising both r and φ components.

Thus, the first and second imaging paths may vary in location with respect to the substrate over the course of time. Each imaging head may be in optical communication with an imaging field. For example, the first and second imaging heads may be in optical communication with a first and second imaging fields, respectively. Each of the first and second imaging fields may be configured to rotate with respect to the substrate, as described elsewhere herein. Rotation of the first and second imaging fields may be independent, or rotation of the first, second, third, or fourth imaging fields may be coordinated.

FIG. 29B shows motion of a substrate relative to two imaging heads located on opposite sides of an axis of rotation of the substrate. In comparison with FIG. 29A, at a first moment in time, the first imaging head 1005 and second imaging head 1015 may be located on opposite sides of an axis of rotation 305 of the substrate, such that the first imaging head 1005 traces a first imaging path 1010 during rotation of the substrate and the second imaging head 1015 traces a second imaging path 1020 during rotation of the substrate. The substrate may be configured to move in a linear, radial direction 1810 relative to the first and second imaging heads. Thus, the first and second imaging paths may vary in location with respect to the substrate over the course of time. Each imaging head may be in optical communication with an imaging field. For example, the first and second imaging heads may be in optical communication with a first and second imaging fields, respectively. Each of the first and second imaging fields may be configured to rotate with respect to the substrate, as described elsewhere herein. Rotation of the first and second imaging fields may be independent, or rotation of the first, second, third, or fourth imaging fields may be coordinated.

FIG. 29C shows motion of a substrate relative to three imaging heads. A third imaging head 1025 may be similar to any third imaging head described herein. At a first moment in time, the first imaging head 1005 may be located on one side of an axis of rotation 305 of the substrate, with respect to a plane containing the axis of rotation, and the second imaging head 1015 and third imaging head 1025 may be located on the opposite side of the axis of rotation of the substrate, such that the first imaging head 1005 traces a first imaging path 1010 during rotation of the substrate, the second imaging head 1015 traces a second imaging path 1020 during rotation of the substrate, and the third imaging head 1025 traces a third imaging path 1030 during rotation of the substrate. The substrate may be configured to move in a linear, radial direction 1810 relative to the first, second, and third imaging heads. Thus, the first, second, and third imaging paths may vary in location with respect to the substrate over the course of time. Each imaging head may be in optical communication with an imaging field. For example, the first, second, and third imaging heads may be in optical communication with a first, second, and third imaging fields, respectively. Each of the first, second, and third imaging fields may be configured to rotate with respect to the substrate, as described elsewhere herein. Rotation of the first, second, and third imaging fields may be independent, or rotation of the first, second, and third imaging fields may be coordinated.

FIG. 29D shows motion of a substrate relative to four imaging heads. A fourth imaging head 1035 may be similar to any fourth imaging head described herein. At a first moment in time, the first imaging head 1005 and the fourth imaging head 1035 may be located on one side of an axis of rotation 305 of the substrate, with respect to a plane containing the axis of rotation, and the second imaging head 1015 and third imaging head 1025 may be located on the opposite side of the axis of rotation of the substrate, such that the first imaging head 1005 traces a first imaging path 1010 during rotation of the substrate, the second imaging head 1015 traces a second imaging path 1020 during rotation of the substrate, the third imaging head 1025 traces a third imaging path 1030, and the fourth imaging head 1025 traces a fourth imaging path 1030 during rotation of the substrate. The substrate may be configured to move in a linear, radial direction 1810 relative to the first, second, third, and fourth imaging heads. Thus, the first, second, third, and fourth imaging paths may vary in location with respect to the substrate over the course of time. Each imaging head may be in optical communication with an imaging field. For example, the first, second, third, and fourth imaging heads may be in optical communication with a first, second, third, and fourth imaging fields, respectively. Each of the first, second, third, and fourth imaging fields may be configured to rotate with respect to the substrate, as described elsewhere herein. Rotation of the first, second, third, or fourth imaging fields may be independent, or rotation of the first, second, third, or fourth imaging fields may be coordinated.

FIG. 29E shows a further embodiment of motion of a substrate relative to four imaging heads. The first, second, third, and fourth imaging heads, 1005, 1015, 1025, and 1035, respectively, may be similar to any imaging head described herein. At a first moment in time, the first imaging head 1005 and the second imaging head 1015 may be located on one side of an axis of rotation 305 of the substrate, with respect to a plane containing the axis of rotation, and the third imaging head 1025 and the fourth imaging head 1035 may be located on the opposite side of the axis of rotation of the substrate, such that the first imaging head 1015 and the fourth imaging head 1035 trace a first half and a second half, respectively, of a first imaging path 1010, and the second imaging head 1015 and the third imaging head 1025 trace a first half and a second half, respectively, of a second imaging path 1020 during rotation of the substrate 310. The substrate may be configured to move in a linear, radial direction 1810 relative to the first, second, third, and fourth imaging heads. Thus, the first, second, third, and fourth imaging heads may subsequently trace first and second halves of a third imaging path 1030 and a fourth imaging path 1040. The first, second, third, and fourth imaging paths may vary in location with respect to the substrate over the course of time. Each imaging head may be in optical communication with an imaging field. For example, the first, second, third, and fourth imaging heads may be in optical communication with a first, second, third, and fourth imaging fields, respectively. Each of the first, second, third, and fourth imaging fields may be configured to rotate with respect to the substrate, as described elsewhere herein. Rotation of the first, second, third, or fourth imaging fields may be independent, or rotation of the first, second, third, or fourth imaging fields may be coordinated.

Figure 29F:
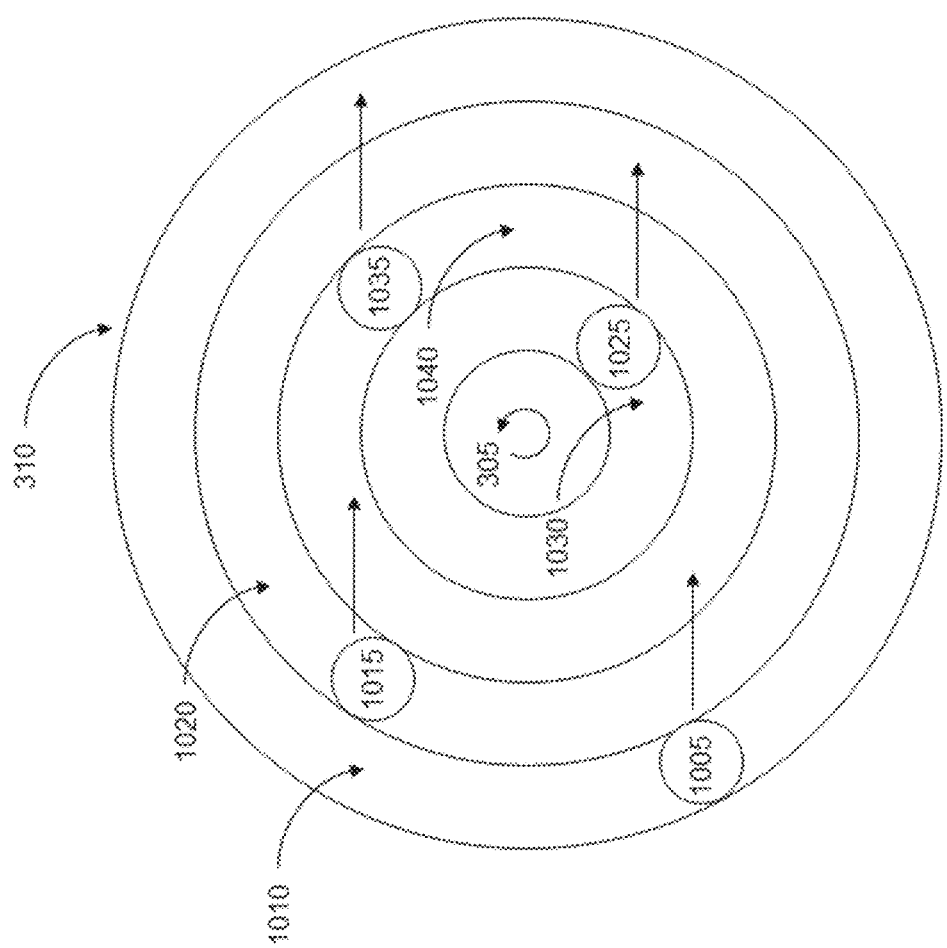
FIG. 29F shows motion of a substrate relative to four imaging heads.

FIG. 29F shows a further embodiment of motion of a substrate relative to four imaging heads. The first, second, third, and fourth imaging heads, 1005, 1015, 1025, and 1035, respectively, may be similar to any imaging head described herein. At a first moment in time, the first imaging head 1005 and the second imaging head 1015 may be located on one side of an axis of rotation 305 of the substrate, with respect to a plane containing the axis of rotation, and the third imaging head 1025 and the fourth imaging head 1035 may be located on the opposite side of the axis of rotation of the substrate, such that the first imaging head 1005 traces a first imaging path 1010, the second imaging head 1015 traces a second imaging path 1020, the third imaging head 1025 traces a third imaging path 1030, and the fourth imaging head 1035 traces a fourth imaging path 1040 during rotation of the substrate. The heads may be configured to translate in a linear direction. The translation may be radial, or the translation may not be radial. Translation of one or more of the first, second, third, or fourth imaging heads may be coupled. Alternatively or in addition, translation of the first, second, third, or fourth imaging heads may be independent. In some embodiments, translation of the first and second imaging heads may be coupled, and translation of the third and fourth imaging heads may be coupled. Thus, the first, second, third, and fourth imaging paths may vary in location with respect to the substrate over the course of time. Each imaging head may be in optical communication with an imaging field. For example, the first, second, third, and fourth imaging heads may be in optical communication with a first, second, third, and fourth imaging fields, respectively. Each of the first, second, third, and fourth imaging fields may be configured to rotate with respect to the substrate, as described elsewhere herein. Rotation of the first, second, third, or fourth imaging fields may be independent, or rotation of the first, second, third, or fourth imaging fields may be coordinated.

Figure 29G:
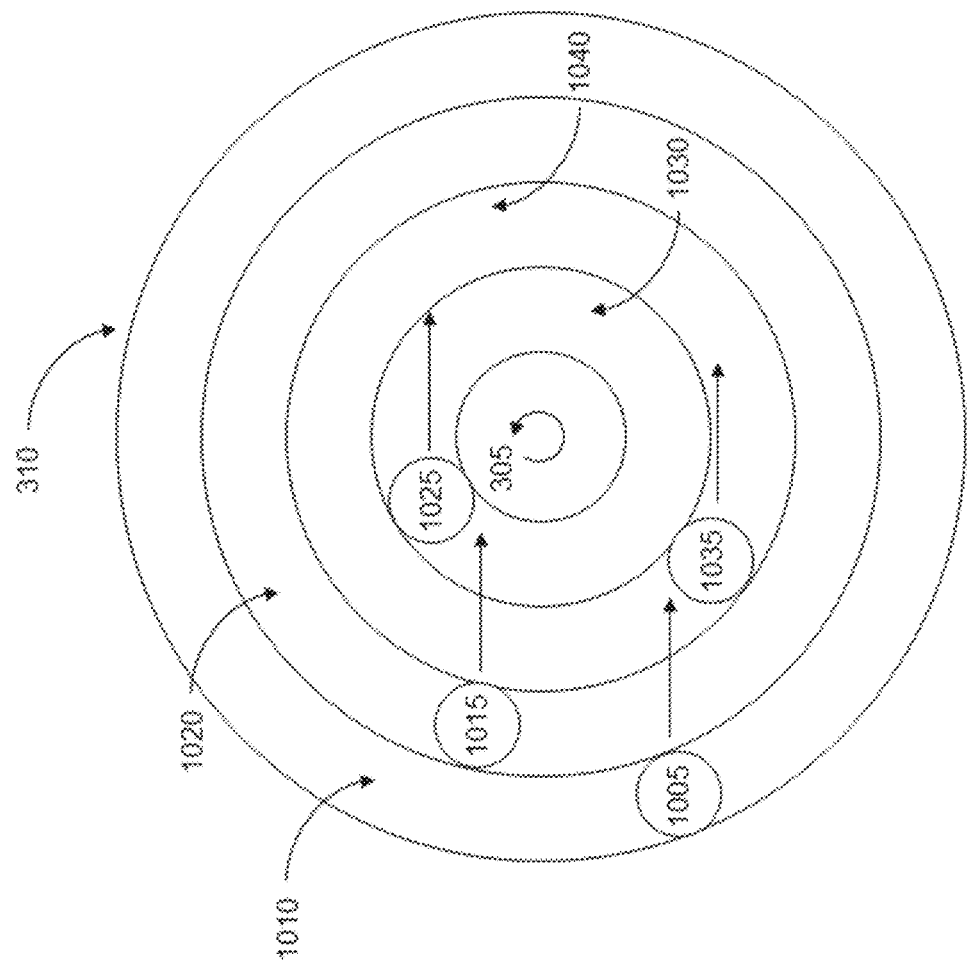
FIG. 29G shows motion of a substrate relative to four imaging heads.

FIG. 29G shows a further embodiment of motion of a substrate relative to four imaging heads. The first, second, third, and fourth imaging heads, 1005, 1015, 1025, and 1035, respectively, may be similar to any imaging head described herein. At a first moment in time, the first imaging head 1005, the second imaging head 1015, the third imaging head 1025, and the fourth imaging head 1035 may be located on the same side of an axis of rotation 305 of the substrate, with respect to a plane containing the axis of rotation. The first imaging head 1005 may trace a first imaging path 1010, the second imaging head 1015 may trace a second imaging path 1020, the third imaging head 1025 may trace a third imaging path 1030, and the fourth imaging head 1035 may trace a fourth imaging path 1040 during rotation of the substrate. The heads may be configured to translate in a linear direction. The translation may be radial, or the translation may not be radial. Translation of the first, second, third, or fourth imaging heads may be independent. Thus, the first, second, third, and fourth imaging paths may vary in location with respect to the substrate over the course of time. Each imaging head may be in optical communication with an imaging field. For example, the first, second, third, and fourth imaging heads may be in optical communication with a first, second, third, and fourth imaging fields, respectively. Each of the first, second, third, and fourth imaging fields may be configured to rotate with respect to the substrate, as described elsewhere herein. Rotation of the first, second, third, or fourth imaging fields may be independent, or rotation of the first, second, third, or fourth imaging fields may be coordinated.

FIG. 30A shows successive ring paths of two imaging heads located on the same side of an axis of rotation of a substrate. At a first moment in time, the first imaging head (not depicted in FIG. 30A) and second imaging head (not depicted in FIG. 30A) may be located on the same side of an axis of rotation 305 of the substrate 310, such that the first imaging head traces a first imaging path 1010*a* at a first time point during rotation of the substrate and the second imaging head traces a second imaging path 1020*a* at the first time point during rotation of the substrate. For example, the two imaging heads may be located and configured as in FIG. 29A. As the substrate moves in a linear, radial direction 1810 relative to the first and second imaging heads, the first and second imaging heads may trace a series of imaging paths during rotation of the substrate. For instance, if the first and second imaging heads are located on the same side of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. When the first and second imaging heads are located on the same side of the axis of rotation, the succession of imaging paths {1010*a*, 1010*b*, 1010*c*, 1010*d*} and {1020*a*, 1020*b*, 1020*c*, 1020*d*} may proceed in the same direction with respect to the substrate. For instance, as depicted in FIG. 30A, the succession of imaging paths {1010*a*, 1010*b*, 1010*c*, 1010*d*} and {1020*a*, 1020*b*, 1020*c*, 1020*d*} may both proceed in a direction toward the center of the substrate.

FIG. 30B shows successive ring paths of two imaging heads located on opposite sides of an axis of rotation of a substrate. In comparison with FIG. 30A, at a first moment in time, the first imaging head (not depicted in FIG. 30B) and second imaging head (not depicted in FIG. 30B) may be located on opposite sides of an axis of rotation 305 of the substrate, such that the first imaging head traces a first imaging path 1010*a* at a first time point during rotation of the substrate and the second imaging head traces a second imaging path 1020*a* at the first time point during rotation of the substrate. For example, the two imaging heads may be located and configured as in FIG. 29B. As the substrate moves in a linear, radial direction 1810 relative to the first and second imaging heads, one of the heads moves towards the central axis and the other head moves away from the central axis, the first and second imaging heads each tracing a series of imaging paths during rotation of the substrate. For instance, if the first and second imaging heads are located on opposite sides of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. When the first and second imaging heads are located on the opposite sides of the axis of rotation, the succession of imaging paths {1010*a*, 1010*b*, 1010*c*, 1010*d*} and {1020*a*, 1020*b*, 1020*c*, 1020*d*} may proceed in opposite directions with respect to the substrate. For instance, as depicted in FIG. 30B, the succession of imaging paths {1010*a*, 1010*b*, 1010*c*, 1010*d*} may proceed in a direction toward the center of the substrate while the succession of imaging paths {1020*a*, 1020*b*, 1020*c*, 1020*d*} may proceed in a direction away from the center of the substrate.

FIG. 30C shows staggered ring paths of two imaging heads located on the same side of an axis of rotation of a substrate. At a first moment in time, the first imaging head (not depicted in FIG. 30C) and second imaging head (not depicted in FIG. 30C) may be located on the same side of an axis of rotation 305 of the substrate 310, such that the first imaging head traces a first imaging path 1010*a* at a first time point during rotation of the substrate and the second imaging head traces a second imaging path 1020*a* at the first time point during rotation of the substrate. As the substrate moves in a linear, radial direction 1810 relative to the first and second imaging heads, the first and second imaging heads may trace a series of imaging paths during rotation of the substrate. For instance, if the first and second imaging heads are located on the same side of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. The succession of imaging paths {1010*a*, 1010*b*, 1010*c*, 1010*d*} and {1020*a*, 1020*b*, 1020*c*, 1020*d*} may be staggered, such that successive imaging paths toward or away from the center of the substrate are traced by alternating imaging heads. When the first and second imaging heads are located on the same side of the axis of rotation, the succession of imaging paths {1010*a*, 1010*b*, 1010*c*, 1010*d*} and {1020*a*, 1020*b*, 1020*c*, 1020*d*} may proceed in the same direction with respect to the substrate. For instance, as depicted in FIG. 30C, the succession of imaging paths {1010*a*, 1010*b*, 1010*c*, 1010*d*} and {1020*a*, 1020*b*, 1020*c*, 1020*d*} may both proceed in a direction toward the center of the substrate.

FIG. 30D shows staggered ring paths of two imaging heads located on opposite sides of an axis of rotation of a substrate. At a first moment in time, the first imaging head (not depicted in FIG. 30D) and second imaging head (not depicted in FIG. 30D) may be located on opposite sides of an axis of rotation 305 of the substrate 310, such that the first imaging head traces a first imaging path 1010*a* at a first time point during rotation of the substrate and the second imaging head traces a second imaging path 1020*a* at the first time point during rotation of the substrate. As the substrate moves in a linear, radial direction 1810 relative to the first and second imaging heads, one of the heads moves towards the central axis and the other head moves away from the central axis, the first and second imaging heads each tracing a series of imaging paths during rotation of the substrate. For instance, if the first and second imaging heads are located on opposite sides of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. The succession of imaging paths {1010*a*, 1010*b*, 1010*c*, 1010*d*} and {1020*a*, 1020*b*, 1020*c*, 1020*d*} may be staggered, such that successive imaging paths toward or away from the center of the substrate are traced by alternating imaging heads. When the first and second imaging heads are located on the opposite sides of the axis of rotation, the succession of imaging paths {1010*a*, 1010*b*, 1010*c*, 1010*d*} and {1020*a*, 1020*b*, 1020*c*, 1020*d*} may proceed in opposite directions with respect to the substrate. For instance, as depicted in FIG. 30D, the succession of imaging paths {1010*a*, 1010*b*, 1010*c*, 1010*d*} may proceed in a direction toward the center of the substrate while the succession of imaging paths {1020*a*, 1020*b*, 1020*c*, 1020*d*} may proceed in a direction away from the center of the substrate.

FIG. 31A-FIG. 31B show rotating scan directions of an imaging head due to non-radial motion of the head relative to a substrate (e.g., motion comprising both r and φ components in a polar coordinate system). For example, as shown in FIG. 31A, the head may be moving along direction 316 relative to the substrate, which is not through the central axis. At a first point in time, the first imaging head (not depicted in FIG. 31A) or second imaging head (not depicted in FIG. 31A) may be located off-axis from a longitudinal axis 315 of the substrate 310. In such a case, the first or second imaging head may have a tangential velocity relative to the substrate that changes in direction as the substrate moves with respect to the first or second imaging head. For instance, as depicted in FIG. 31A, the second imaging head may have a tangential velocity vector 2020*a* relative to the substrate while tracing the imaging path 1020*a* and a tangential velocity vector 2020*b* relative to the substrate while tracing the imaging path 1020*c*. As shown in FIG. 31, the tangential velocity vectors 2020*a* and 2020*b* may point in substantially different directions. Such an effect may be manifested as a rotation of the imaging field as the first imaging head traces the succession of imaging paths {1010*a*, 1010*b*, 1010*c*, 1010*d*} or as the second imaging head traces the succession of imaging paths {1020*a*, 1020*b*, 1020*c*, 1020*d*}.

FIG. 31B shows rotating scan directions of imaging fields of view due to non-radial motion of the imaging head relative to the substrate. For example, a first imaging head (not shown in FIG. 31B) imaging a first field of view 3101, and a third imaging head (not shown in FIG. 31B) imaging a third field of view 3103 may translate relative to the substrate 310 in directions 3111 and 3113, respectively, that are not through the central axis. At a first point in time, the first imaging field 3101 or the third imaging field 3103 may be located off-axis from a longitudinal axis 315 of the substrate 310. In such a case, the first or third imaging field may have a tangential velocity relative to the substrate that changes in direction as the substrate moves with respect to the first or second imaging head. Following non-radial translation, the first and third imaging fields may no longer be positioned perpendicular to the tangential motion of the substrate (indicated by gray rectangles). In some embodiments the first and third imaging fields may undergo a counter-rotation with respect to the substrate following non-radial translation such that the first and third imaging fields may be positioned perpendicular to the tangential motion of the substrate (indicated by dashed rectangles). Counter-rotation may be achieved using any of the methods disclosed herein, such as those described with respect to FIG. 34A-FIG. 34C.

Figure 34A:
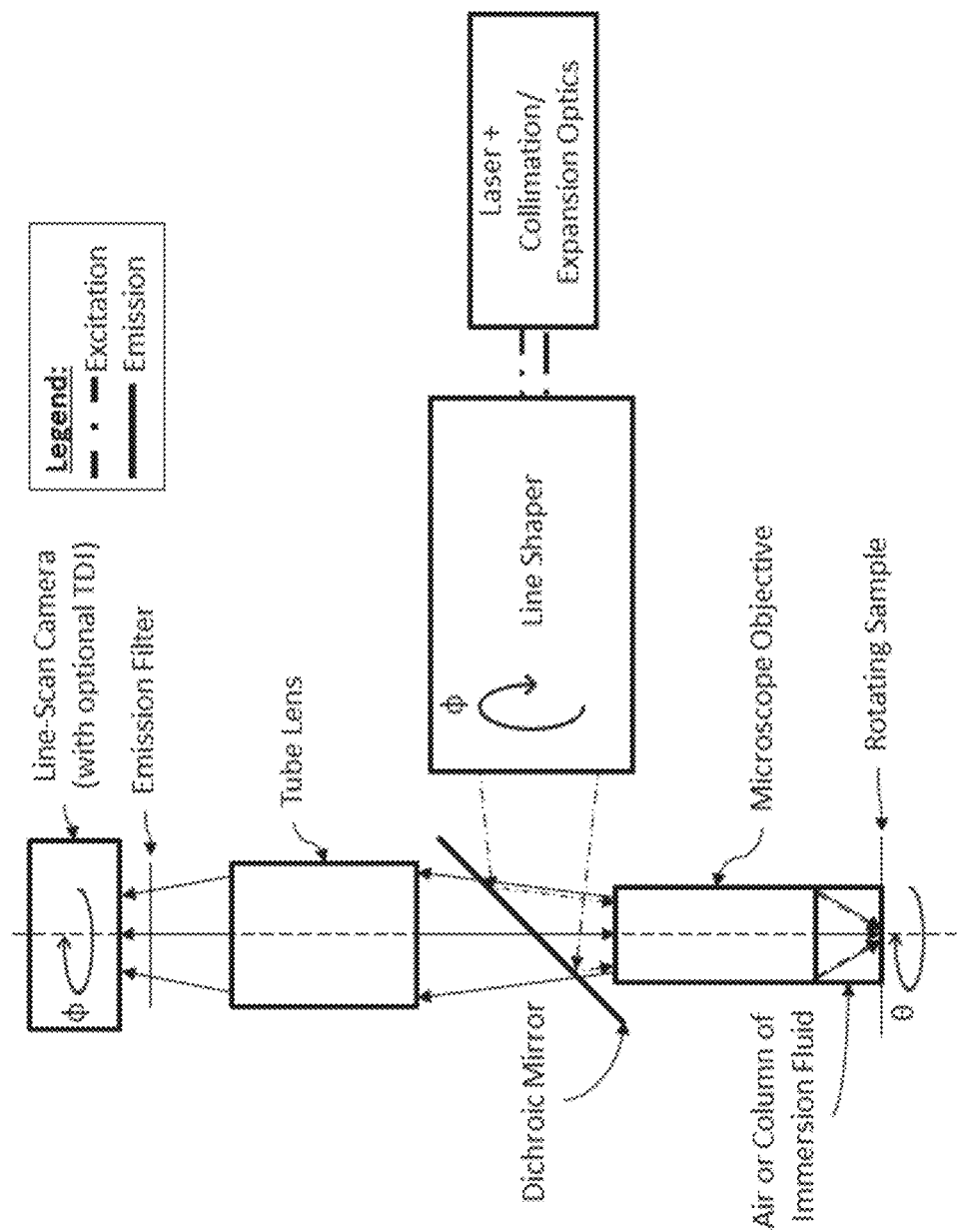
FIG. 34A illustrates schematically an optical system for rotating an imaging field.
Figure 34B:
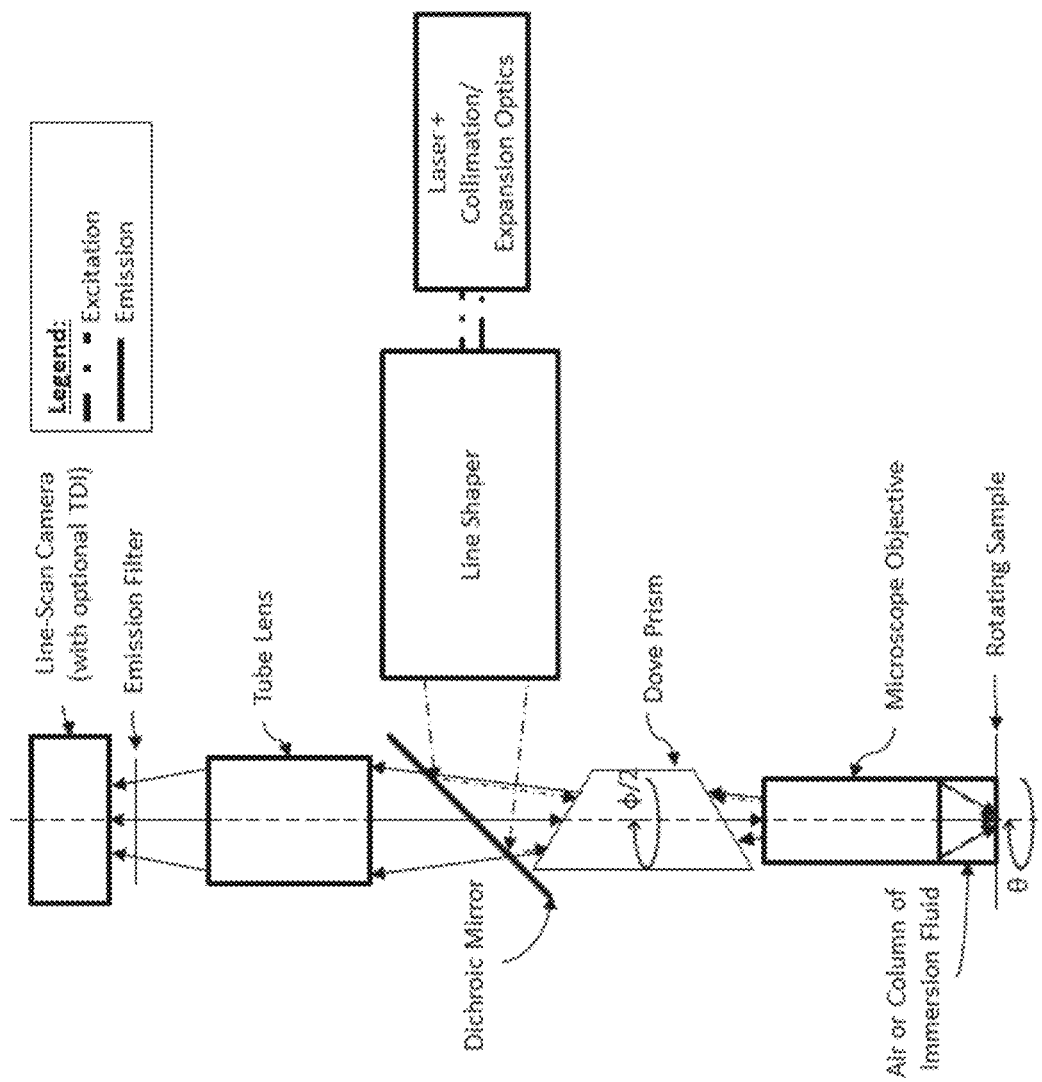
FIG. 34B illustrates schematically an optical system for rotating an imaging field.
Figure 34C:
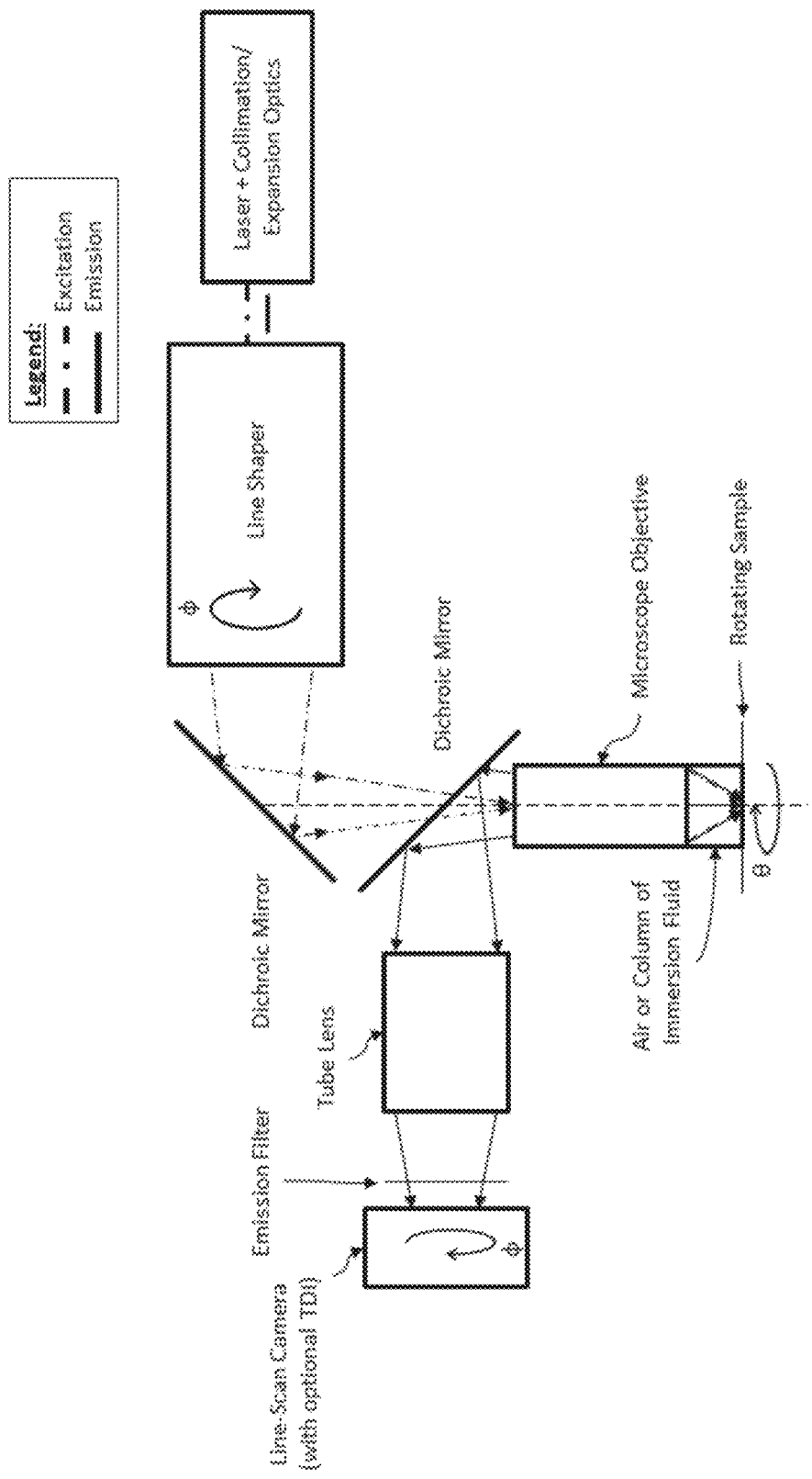
FIG. 34C illustrates schematically an optical system for rotating an imaging field.

FIG. 34A-FIG. 34C shown exemplary optical systems for rotating an imaging field. Such a rotation of the imaging field may be compensated by counter-rotating the imaging field. For instance, the imaging field may be counter-rotated using a prism system, such as a delta rotator prism, a Schmidt rotator, or a Dove prism. An exemplary optical system for counter-rotating an imaging field using a Dove prism is shown in FIG. 34B. Alternatively or in addition, the compensation may be achieved by using one or more mirrors or other optical elements (e.g., beamsplitter (e.g., dichroic mirror)), as described herein. Alternatively or in addition, the compensation may be achieved by rotating one or more sensors in the optical head(s). For example, the compensation may be achieved by rotating a detector (e.g., a line-scan camera) and a line shaping element (e.g., a cylindrical lens). Exemplary optical systems for rotating a detector and a line shaping element are shown in FIG. 34A and FIG. 34C. The imaging field may be rotated about an axis of rotation, which may be counter to the axis of rotation of the surface, to compensate for a relative translational motion that may not intersect the axis of rotation of the surface and the imaging field, as shown in FIG. 33.

Figure 35A:
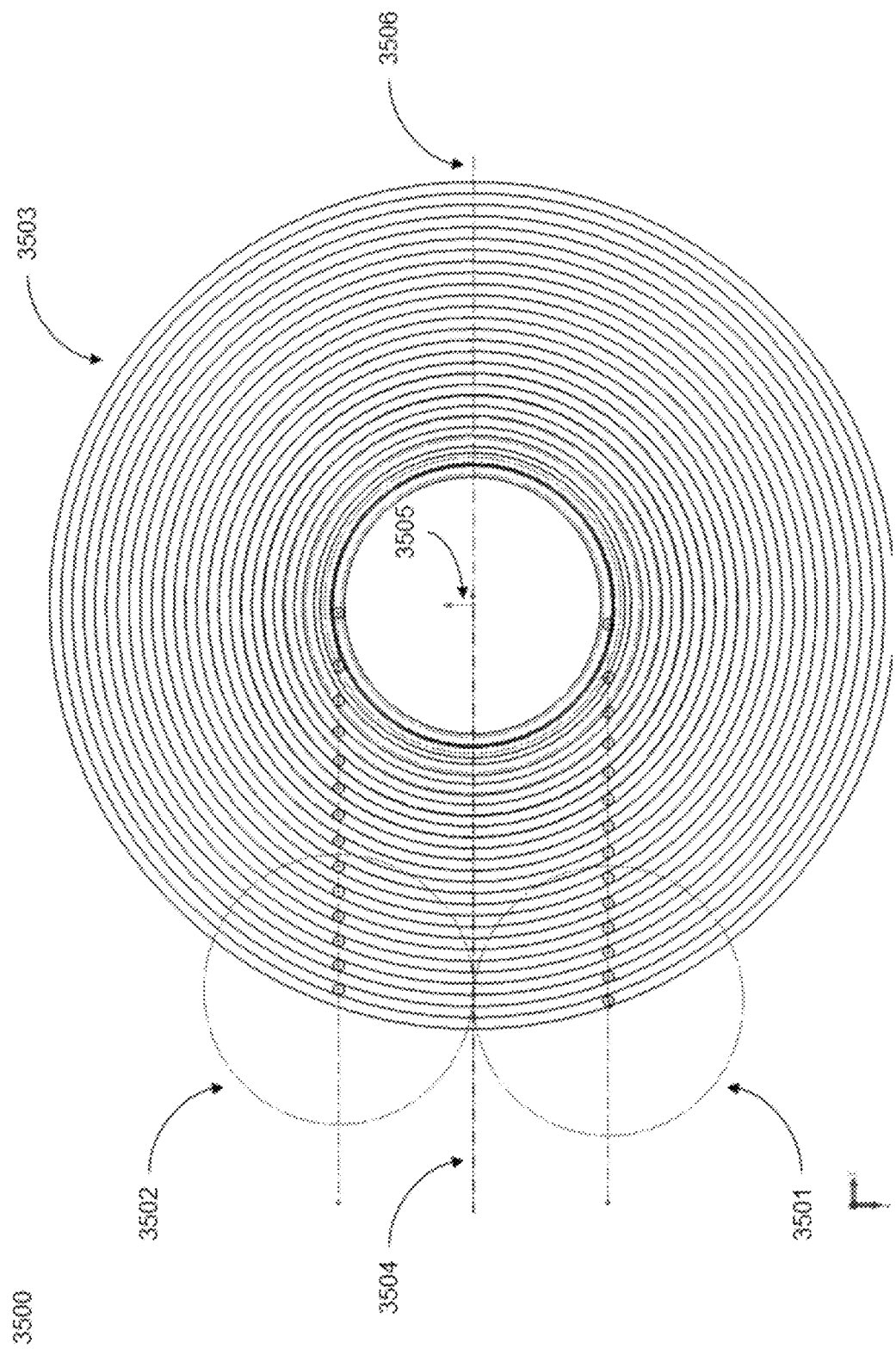
FIG. 35A shows an example of imaging head positioning for optimal scanning efficiency.
Figure 35B:
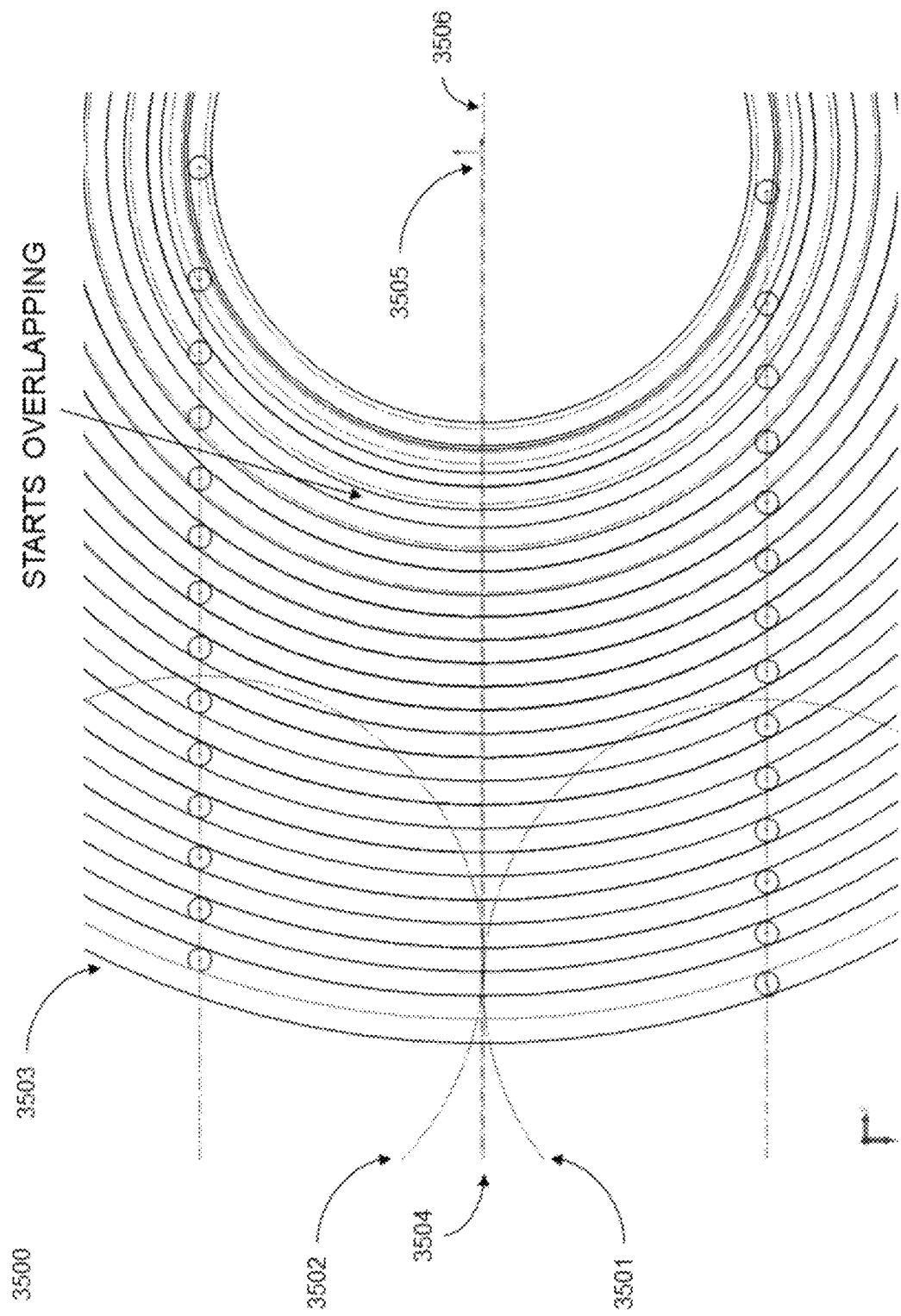
FIG. 35B shows an example of imaging head positioning for optimal scanning efficiency.

FIG. 35A-FIG. 35C illustrate exemplary optical path trajectories of an optical system 3500 comprising imaging heads. Two imaging heads 3501 and 3502, each comprising an objective, may be positioned to image corresponding regions of a substrate 3503, as shown in FIG. 35A. The imaging heads may be positioned on opposite sides of a radial line 3504. In some embodiments, the two imaging heads may be positioned at different distances from the radial line. The distances from the radial line may be determined by the diameter of the objectives and optical path trajectories of the imaging heads. The substrate may be configured to rotate about an axis of rotation 3505 and translate along an axis of translation 3506 with respect to the imaging heads. The substrate may be rotated about the axis of rotation such that the two imaging heads trace circular optical path trajectories. Ideal optical path trajectories in which an entire outer region of the surface is scanned without overlap are outlined with solid lines in FIG. 35A-FIG. 35C. An optical path trajectory resulting from coordinated motion of two imaging heads in which the optical path trajectories partially overlap is outlined with dashes in FIG. 35A-FIG. 35C. For clarity, only the initial position of the imaging heads 3501 and 3502 are shown in FIG. 35A-FIG. 35C.

The first optical path 3511 of the first imaging head 3501 may be concentric to the first optical path 3521 of the second imaging head 3502, as shown in FIG. 35C. Upon translation of the substrate along the axis of translation, the first and second imaging heads may move to second optical paths 3512 and 3522, third optical paths 3513 and 3523, third optical paths, fourth optical paths 3514 and 3524, fifth optical paths 3515 and 3525, sixth optical paths 3516 and 3526, seventh optical paths 3517 and 3527, or more optical paths. In some embodiments, the optical path trajectories of the two imaging heads partially overlap, with the amount of overlap increasing for optical paths closer to the axis of rotation of the substrate. The optical path trajectories and the distances of the imaging heads from the radial line may be optimized for minimal overlap of the optical path trajectories of the two imaging heads, as shown in FIG. 35B. The optical path trajectories may overlap by no more than 0.10%, no more than 0.20%, no more than 0.50%, no more than 1%, no more than 2%, no more than 3%, no more than 4%, no more than 5%, no more than 6%, no more than 7%, no more than 8%, no more than 9%, no more than 10%, no more than 15%, no more than 20%, no more than 30%, no more than 40%, or no more than 50%.

In some embodiments, the optical path trajectories of the two imaging heads do not substantially overlap. In some embodiments, the optical path trajectories of the two imaging heads are partially separated, with the amount of separation decreasing for optical paths closer to the axis of rotation of the substrate. The optical path trajectories and the distances of the imaging heads from the radial line may be optimized to reduce the amount of substrate that is not scanned without substantial overlap of the optical path trajectories of the two imaging heads (not shown in FIG. 32). In some instances, the unscanned portion of the substrate may comprise no more than 0.10%, no more than 0.20%, no more than 0.50%, no more than 1%, no more than 2%, no more than 3%, no more than 4%, no more than 5%, no more than 6%, no more than 7%, no more than 8%, no more than 9%, no more than 10%, no more than 15%, no more than 20%, no more than 30%, no more than 40%, or no more than 50% of the total substrate surface. In some cases, the optical path trajectories of the tow imaging heads may be configured to reduce the amount of overlap in order to reduce the amount of photodamage to the substrate or a reagent on the substrate.

Figure 32:
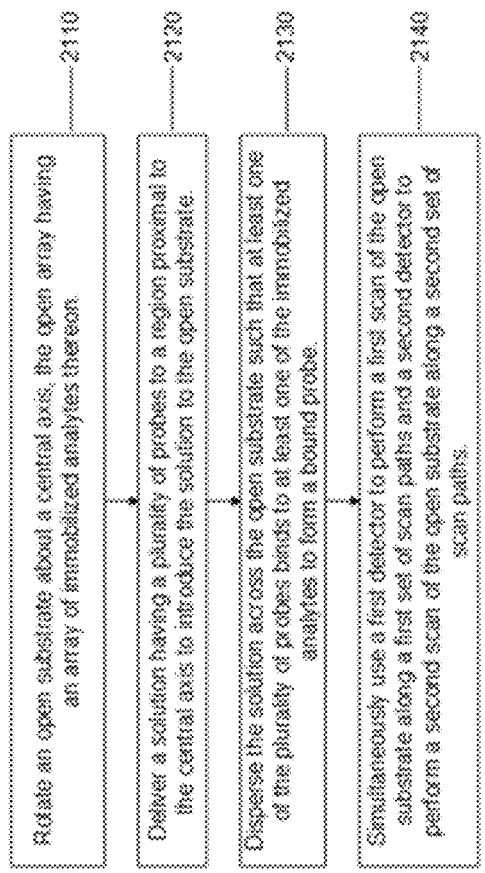
FIG. 32 shows a flowchart for an example of a method for analyte detection or analysis.

The substrate motions described herein, for example those described with respect to FIG. 29-FIG. 31, may be used to scan a surface comprising an analyte. In some cases, scanning the surface may comprise detecting the analyte on the surface. FIG. 32 shows a flowchart for an example of a method 2100 for analyte detection or analysis. In a first operation 2110, the method 2100 may comprise rotating an open substrate about a central axis, the open substrate having an array of immobilized analytes thereon.

In a second operation 2120, the method 2100 may comprise delivering a solution having a plurality of probes to a region proximal to the central axis to introduce the solution to the open substrate.

In a third operation 2130, the method 2100 may comprise dispersing the solution across the open substrate (for instance, at least by centrifugal force) such that at least one of the plurality of probes binds to at least one of the immobilized analytes to form a bound probe.

In a fourth operation 2140, the method 2100 may comprise, during rotation of the open substrate, simultaneously using a first detector to perform a first scan of the open substrate along a first set of one or more scan paths and a second detector to perform a second scan of the open substrate along a second set of one or more scan paths. The first set of one or more scan paths and the second set of one or more scan paths may be different. The first detector or the second detector may detect at least one signal from the bound probe. The first detector may be disposed at a first radial position relative to the central axis. The second detector is disposed at a second radial position relative to the central axis. The first detector and the second detector may undergo relative motion with respect to the central axis along a same linear vector, to generate the first set of one or more scan paths and the second set of one or more scan paths, respectively.

The first detector and the second detector may operate at different scan rates. For instance, the different scan rates of the first detector and the second detector may be a function of the first radial position and the second radial position, respectively. Alternatively, the detectors may operate at a fixed line rate. For example, algorithmic processing may resolve oversampling of the optical head located in the inner radial positions.

The first set of one or more scan paths may comprise one or more circular scan paths having different radii. For instance, the first set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more circular scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 circular scan paths, or a number of circular scan paths that is within a range defined by any two of the preceding values.

The second set of one or more scan paths may comprise one or more circular scan paths having different radii. For instance, the second set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more circular scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 circular scan paths, or a number of circular scan paths that is within a range defined by any two of the preceding values.

The first set of one or more scan paths may comprise one or more spiral scan paths. For instance, the first set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more spiral scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 spiral scan paths, or a number of spiral scan paths that is within a range defined by any two of the preceding values.

The second set of one or more scan paths may comprise one or more spiral scan paths. For instance, the second set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more spiral scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 spiral scan paths, or a number of spiral scan paths that is within a range defined by any two of the preceding values.

The same linear vector may be in a radial direction through the central axis. The same linear vector may not be in a radial direction (e.g., not through the central axis). The method may further comprise compensating for velocity differences (such as tangential velocity differences, as described herein with respect to FIG. 31) of different areas at different radial positions with respect to the central axis. A given scan path of the first set of one or more scan paths may comprise the different areas. A given scan path of the second set of one or more scan paths may comprise the different areas. The compensating may comprise using one or more prisms, such as one or more delta rotator prisms, Schmidt rotators, or Dove prisms.

The first detector and the second detector may be substantially stationary during the relative motion. The open substrate may undergo both rotational and translation motion during the relative motion. The first detector and the second detector may undergo motion during the relative motion. The open substrate may undergo rotational motion relative to the first detector and the second detector and the first detector and second detector may undergo linear motion relative to the central axis. The first detector may undergo the relative motion during rotation of the open substrate. The second detector may undergo the relative motion during rotation of the open substrate. The first detector may undergo the relative motion when the open substrate is substantially stationary. The second detector may undergo the relative motion when the open substrate is substantially stationary.

A given scan path of the first set of one or more scan paths may include an area scanned during the relative motion. A given scan path of the second set of one or more scan paths may include an area scanned during the relative motion. A given scan path of the first set of one or more scan paths may not include an area scanned during the relative motion. A given scan path of the second set of one or more scan paths may not include an area scanned during the relative motion.

The first detector and the second detector may have the same angular position relative to the central axis. The first detector and the second detector may have different angular positions relative to the central axis. The first detector and second detector may have opposite angular positions (e.g., having 180 degrees separation) relative to the central axis.

The first detector may have an angular position of at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more relative to the central axis, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degree, or less relative to the central axis, or an angular position relative to the central axis that is within a range defined by any two of the preceding values.

The second detector may have an angular position of at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more relative to the central axis, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degree, or less relative to the central axis, or an angular position relative to the central axis that is within a range defined by any two of the preceding values.

A given scan path of the first set of one or more scan paths may include a first area and a second area. The first area and second area may be at different radial positions of the open substrate with respect to the central axis. The first area and second area may be spatially resolved by the first detector. A given scan path of the second set of one or more scan paths may include a first area and a second area. The first area and second area may be at different radial positions of the open substrate with respect to the central axis. The first area and second area may be spatially resolved by the second detector.

Reel-to-Reel Processing of Biological Analytes

In some instances, an open substrate system of the present disclosure may comprise a substantially flexible substrate. For example, the substantially flexible substrate may comprise a film. The substantially flexible substrate may have any degree of deformability. In some instances, an open substrate system of the present disclosure may achieve dispensing via contact with a reagent reservoir or bath. In some instances, a substantially flexible substrate may be used with a reagent reservoir or bath. In some instances, a substantially rigid substrate may be used with a reagent reservoir or bath. In some instances, a substantially flexible substrate may be used with other dispensing mechanisms (e.g., nozzles) described herein. In some instances, a substantially rigid substrate may be used with other dispensing mechanisms (e.g., nozzles) described herein.

In an aspect, provided herein are methods for processing a biological analyte, comprising (a) providing a flexible substrate comprising an array having immobilized thereto the biological analyte, wherein the flexible substrate is able to be moved through a reel; (b) bringing the flexible substrate in contact with a reservoir comprising a solution that comprises a plurality of probes; (c) subjecting the biological analyte to conditions sufficient to conduct a reaction between at least one probe of the plurality of probes and the biological analyte, to couple the at least one probe to the biological analyte; and (d) detecting one or more signals from the at least one probe coupled to the biological analyte, thereby analyzing the biological analyte.

In some embodiments, the method further comprises using a recirculation tank.

In some cases, a dimension of the flexible substrate is the width of a field of view of the imaging method.

In some embodiments, the process of bringing the flexible substrate in contact with a reservoir and/or the process of subjecting the biological analyte to conditions sufficient to conduct a reaction is performed while the flexible substrate is moved through the reel.

In some embodiments, the flexible substrate is moved through a reel to contact the solution with the biological analyte. In some embodiments, the flexible substrate is further moved through a second reel to bring the flexible substrate in contact with a second reservoir comprising a second solution. In some cases, the second solution comprises a wash buffer. In some cases, the second solution comprises a plurality of probes, wherein the solution and the second solution are different.

In some embodiments, the processes of bringing the flexible substrate in contact with the reservoir, subjecting the biological analyte to conditions sufficient to conduct the reaction, and detecting may be repeated any number of times, for example, a number of times sufficient to complete an assay (e.g., determining a sequence of a nucleic acid molecule).

In some embodiments, the method further comprises repeating the processes of bringing the flexible substrate in contact with the reservoir, subjecting the biological analyte to conditions sufficient to conduct the reaction, and detecting with an additional plurality of probes that is different than the plurality of probes. In some cases, the plurality of probes can comprise any probe described elsewhere herein. For example, the probe may comprise an oligonucleotide molecule having any length. For example, the probe may comprise oligonucleotides 1 to 10 bases in length. A given probe may be a dibase probe. A given probe may be between 10 to 20 bases in length. In some instances, the plurality of probes may be labeled.

In some embodiments, the biological analyte is a nucleic acid molecule, and analyzing the biological analyte comprises identifying a sequence of the nucleic acid molecule. In some embodiments, the plurality of probes is a plurality of nucleotides. In some embodiments, the plurality of probes is a plurality of oligonucleotide molecules. In some cases, subjecting the biological analyte to the conditions sufficient to conduct the reaction comprises subjecting the nucleic acid molecule to a primer extension reaction under conditions sufficient to incorporate at least one nucleotide from the plurality of nucleotides into a growing strand that is complementary to the nucleic acid molecule. In some embodiments, the one or more signals are indicative of incorporation of at least one nucleotide. In some embodiments, the plurality of nucleotides comprises nucleotide analogs. In some embodiments, the method further comprises repeating the processes of bringing the flexible substrate in contact with a reservoir and subjecting the biological analyte to conditions sufficient to conduct a reaction with an additional plurality of nucleotides that are of a second canonical base type, wherein the second canonical base type is different than the first canonical base type. In some embodiments, the plurality of probes is a plurality of oligonucleotide molecules. In some embodiments, the biological analyte is a nucleic acid molecule, and the subjecting comprises conducting a complementarity binding reaction between the at least one probe and the nucleic acid molecule to identify a presence of homology between the at least one probe and the biological analyte in the detection.

In some embodiments, the detecting is conducted using a sensor that continuously scans the array. In some embodiments, the detecting is conducted using a sensor that scans the array linearly. In some cases, the detecting is conducted using any sensor or sensing mechanism described herein.

In some embodiments, the method further comprises using a pulling mechanism to move the flexible substrate through the reel and into contact with the reservoir, thereby dispensing the solution on the flexible substrate. Any other motion units or mechanisms may be used to actuate the flexible substrate.

In some embodiments, the fluid viscosity of the solution or a velocity of the flexible substrate is selected to yield a predetermined thickness of a layer of the solution adjacent to the array. In some embodiments a squeegee near the substrate may be used to yield a predetermined thickness of a layer. In some embodiments, the flexible substrate is textured or patterned. In some embodiments the flexible substrate is substantially planar.

In some embodiments, the flexible substrate comprises an array which comprises a plurality of individually addressable locations, and wherein the biological analyte is disposed at a given individually addressable location of the plurality of individually addressable locations. In some embodiments, the array has immobilized thereto one or more additional biological analytes.

In some embodiments, bringing the flexible substrate in contact with the reservoir comprises achieving contact at an area of contact between the flexible substrate and the reservoir. In some embodiments, bringing the flexible substrate in contact with the reservoir comprises achieving contact along a line of contact between the substrate and the reservoir.

In some cases, the biological analyte can comprise any analyte described elsewhere herein. The analyte may be a single cell analyte. The analyte may be a nucleic acid molecule or clonal population of nucleic acids. The analyte may be a protein molecule. The analyte may be a single cell. The analyte may be a particle. The analyte may be an organism. The analyte may be part of a colony. The analyte may be immobilized in an individually addressable location on the planar array. The array on the flexible substrate may comprise two or more types of analytes. The two or more types of analytes may be arranged randomly. The two or more types of analytes may be arranged in a regular pattern.

In some instances, the analyte can be immobilized to the flexible substrate via a linker. The flexible substrate may comprise the linker that is coupled to the analyte. The linker can be any linker described herein. The linker may comprise a carbohydrate molecule. The linker may comprise an affinity binding protein. The linker may be hydrophilic. The linker may be hydrophobic. The linker may be electrostatic. The linker may be labeled. The linker may be integral to the substrate. The linker may be an independent layer on the substrate. In some embodiments, the biological analyte is coupled to a bead, which bead is immobilized to the flexible substrate. The method may further comprise, prior to providing the flexible substrate, directing the biological analyte across the flexible substrate comprising the linker. The biological analyte may be coupled to a bead, which bead is immobilized to the substrate. In some instances, for example, the flexible substrate comprising the linker may be brought into contact with a reservoir comprising a solution comprising the biological analyte. Alternatively or in addition, the biological analyte may be dispensed onto the flexible substrate in accordance with any other dispensing mechanism described herein.

The method may further comprise recycling a subset of the solution that has contacted the substrate. The recycling may comprise collecting, filtering, and reusing the subset of the solution. The filtering may be molecular filtering. For example, the solution in the reservoir (after the substrate has passed through) may be recycled.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal. The signal may be generated by binding of a label to the analyte. The label may be bound to a molecule, particle, cell, or organism. The label may be bound to the analyte (e.g., molecule, particle, cell, or organism) prior to deposition on the substrate. The label may be bound to the analyte subsequent to deposition on the substrate. The signal may be generated by formation of a detectable product by a chemical reaction. The reaction may comprise an enzymatic reaction. The signal may be generated by formation of a detectable product by physical association. The signal may be generated by formation of a detectable product by proximity association. The signal generated by proximity association may comprise Förster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. The reaction may comprise a hybridization reaction or ligation reaction. The reaction may comprise a hybridization reaction and a ligation reaction.

One or more processes of the methods described herein may be repeated in a continuous fashion. One or more methods described herein may offer higher efficiency in reagent usage. One or more methods described herein may allow for detection of one or more signals at multiple locations along the array contemporaneously. In some cases, throughput may be altered by changing the dimensions of the flexible substrate. For example, the flexible substrate may be a rectangular film, wherein a wider film allows for increased throughput. In another example, the length of the reel may be changed to match the detection method.

Figure 36A:
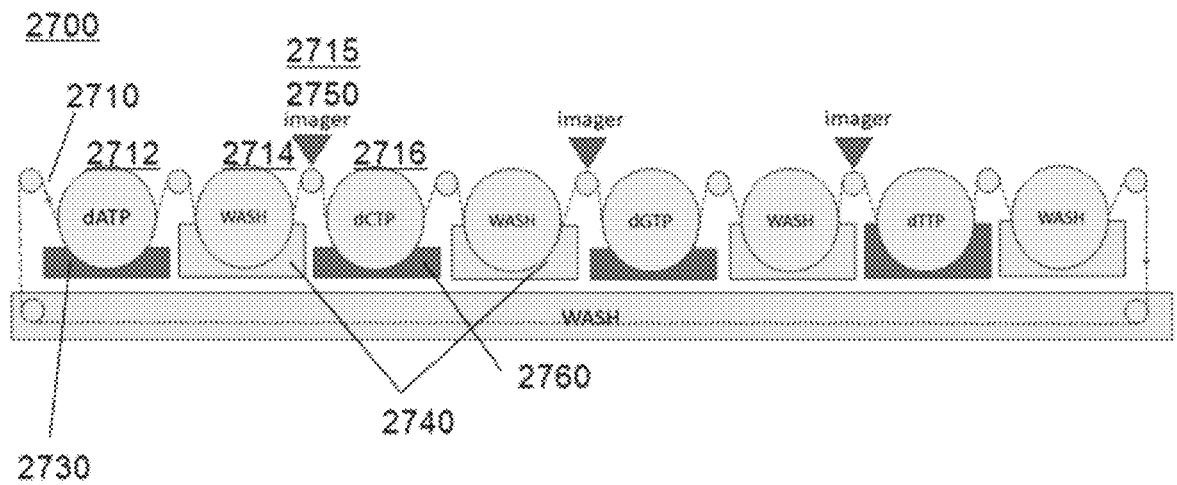
FIG. 36A-FIG. 36B illustrate schematically methods for processing a biological analyte.
Figure 36B:
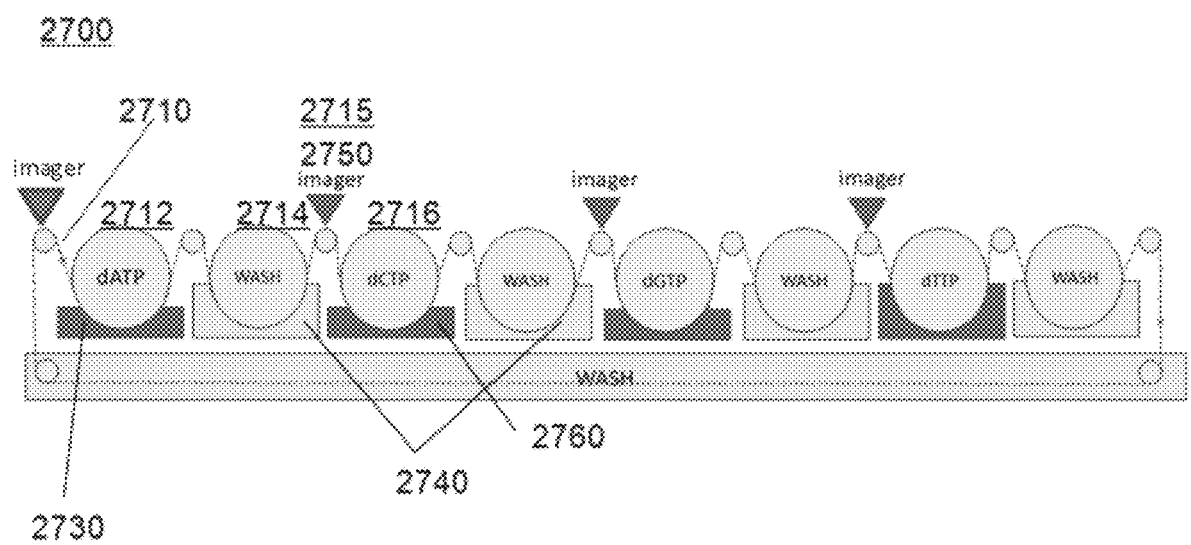

FIG. 36A-FIG. 36B schematically illustrate methods for processing a biological analyte, as shown in FIG. 36A and FIG. 36B. A flexible substrate such as a film 2710 has immobilized thereto the biological analyte. In some cases, the biological analyte is immobilized to the film in an arrayed pattern in individually addressable locations. In other embodiments, the biological analyte is immobilized to the film in a random orientation. The film 2710 comprising the biological analyte immobilized thereto is capable of being moved through a reel or a series of reels. In process 2712, the film 2710 comprising the biological analyte immobilized thereto is moved through a reel and brought into contact with a reservoir 2730 comprising a plurality of probes, such as a plurality of labeled probes. In some cases, the labeled probe is a fluorescently labeled nucleotide. The labeled probes may couple to a subset of the individually addressable locations comprising the biological analyte, e.g., based on sequence complementarity. In process 2714, the film is then moved through a second reel and brought into contact with a reservoir 2740 comprising a wash buffer. The wash buffer may allow for removal of uncoupled probes, such as probes that are unbound or unhybridized to the film. Detection of one or more signals from the at least one probe coupled to the biological analyte may be performed. In process 2715, detection can occur using a sensor, such as an imager 2750, in which an image of the film is taken. In some cases, the field of view of the image is one of the dimensions (e.g., the width) of the film. In some cases, detection may occur a plurality of times during the processing. For example, as shown in FIG. 36A, detection may occur after one or more wash step following treatment with a probe (e.g., dATP, dCTP, dTTP, dGTP, or dUTP). In some cases, a surface may me imaged prior to treatment with a probe, as shown in FIG. 36B. In process 2716, the film 2710 is moved through a third reel and brought into contact with a reservoir 2760 comprising a plurality of probes, such as a plurality of labeled probes. The labeled probes in reservoir 2760 may be different than the labeled probes in reservoir 2730. As in process 2712, the labeled probes in reservoir 2760 may couple to a subset of the individually addressable locations comprising the biological analyte e.g., based on sequence complementarity. Processes 2714, 2715 may then be repeated. In some cases, one or more processes may be performed iteratively.

In some cases, the biological analyte is a nucleic acid molecule or clonal population of nucleic acid molecules, and the film 2710 is moved through a first reel to contact the film with a first reservoir comprising a plurality of adenine (e.g., fluorescently labeled adenine) molecules. The adenine molecules may then hybridize with a thymine molecule within the biological analyte. The film may then be moved through the reel to contact the film with a wash reservoir to remove unhybridized probes. Detection of the hybridized molecules may occur. Since the sequence of the probe molecule is known, detection of one or more signals may yield knowledge of the sequence of the biological analyte. Subsequently, the film may then be brought into contact with a reservoir comprising a labeled cytosine, a labeled guanine, or a labeled thymine, etc. Again, as each sequence of the probe is known, detection of one or more signals may yield knowledge of the sequence of the biological analyte. As will be appreciated, the specific nucleotide added to each reservoir can vary; e.g., the first reservoir may comprise an adenine, cytosine, guanine, thymine, etc, and the next reservoir may comprise an adenine, cytosine, guanine, thymine, etc.

As will be appreciated, any of the processes within the method described herein may occur at any convenient step. For example, the flexible substrate may first be brought into contact with a first reservoir, followed by a wash reservoir, followed by a second reservoir, prior to detection. In other examples, the flexible substrate may be brought into contact with a plurality of reservoirs comprising probes prior to detection. In other examples, the flexible substrate may be brought into contact with a detector prior to or following contacting the flexible substrate with any number of reservoirs. Additionally, any number of reels may be used. For example, it may be desirable to use a single reel for an operation. In some cases, more than one reel may be used. For example, 2, 3, 4, 5, 6, 7, 8, 9, 10, 20, 30, 40, 50, 60, 70, 80, 90, 100, 200, 300, 400, 500, 600, 700, 800, 900, 1000 or more reels may be used.

In some cases, the detection method may comprise multi-channel imaging.

Immersion Optics

Disclosed herein, in certain embodiments, are systems for using optical sensors, such as optical imaging objectives. The present disclosure provides systems for modulation and management of temperature for one or more systems or methods of the disclosure. In some embodiments of one or more systems and methods described herein, an optical imaging objective is used during the detection method. In some cases, the optical imaging objective is immersed in a fluid in contact with the substrate, and the optical imaging objective is in optical communication with the detector. In some embodiments, the substrate performs optimally at a non-ambient temperature (e.g., ~50 degrees Celsius). In some cases, the optical imaging objective may be close to ambient temperature. In such cases, a substrate that is operating at a higher temperature (e.g., ~50 degree Celsius) may be in contact with the objective that operates at ambient temperature (~20 degrees Celsius), thereby generating a temperature gradient between the substrate and the optical imaging objective. In some cases, it may be desirable to control the temperature gradient location and the magnitude of the temperature gradient. Thus, provided herein are methods and systems for temperature modulation.

Figure 16:
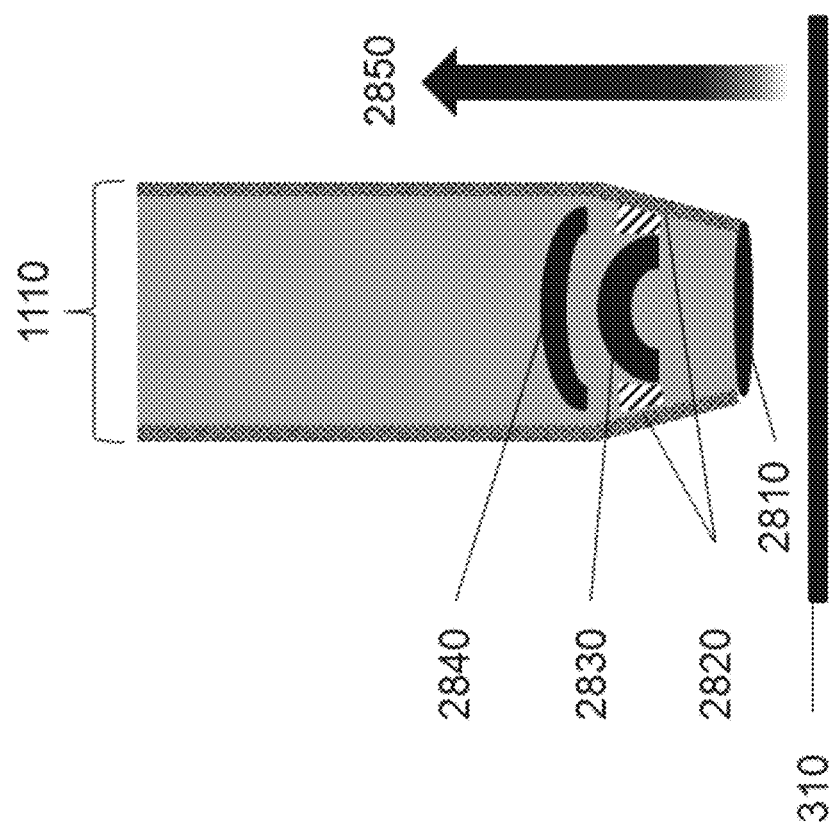
FIG. 16 illustrates schematically an exemplary temperature gradient during optical imaging.

FIG. 16 illustrates schematically an exemplary temperature gradient that may arise between an optical imaging objective and a substrate. The optical imaging objective 1110 (e.g., as described with respect to FIG. 15) may comprise a first element 2810, a second element 2830, a third element 2840, and, in some cases, one or more spacers 2820. For example, the first element 2810 may comprise a front lens or a meniscus lens, the second element 2830 may comprise a first lens group such as a triplet lens group, and the third element 2840 may comprise a second lens group such as a doublet lens group. Alternatively or in addition, the first element 2810 may comprise a planoconvex lens, the second element 2830 may comprise a meniscus lens, and the third element 2840 may comprise an achromatic lens. The optical imaging objective 1110 may be at ambient temperature. The substrate 310 may be a substrate described herein and may comprise a biological analyte. In some cases, the substrate 310 is heated to a temperature that is greater than ambient temperature. In some cases, the difference in temperature between the substrate 310 and the optical imaging objective 1110 may generate a temperature gradient 2850. The temperature gradient 2850 may result in heat transfer between the substrate and the optical imaging objective 1110 as well as the surrounding environment. In some cases, it may be desirable to modulate or regulate the temperature of the system or the substrate so that the substrate maintains a constant temperature.

FIG. 17A-FIG. 17E illustrate schematically example methods to regulate temperature of the substrate. FIG. 17A illustrates an embodiment of such a temperature regulation method of a system. The system may comprise a substrate 310, which may be any substrate described herein, an optical imaging objective 1110 as described herein, and an immersion fluid 1140. In some embodiments, it is desirable to maintain the substrate 310 at an elevated temperature (e.g., 50 degrees Celsius) while keeping other components of the system (e.g., 2830, 2840, 2820) at ambient temperature. In some cases, heat 2920 may be applied to the substrate 310. The heat may transfer to other components of the system, such as the immersion fluid 1140, and part of the optical imaging objective 1110. In some cases, the first element 2810 of the optical imaging objective 1110 may be robust to a large temperature gradient and may not be critical to the optical path or detection method. In one non-limiting example, the first element 2810 may be a substantially flat (e.g., planar) surface. In such cases, the first element 2810 may be robust to a large temperature gradient and may not influence the optical path, detection, or magnification of the substrate or contents disposed thereof. In some cases, the heat 2920 applied to the substrate 310 may be transferred conductively away from the optical imaging objective 1110. For example, the heat 2920 applied to the substrate 310 may transfer to the immersion fluid 1140, to the first element 2810, to the one or more spacers 2820, then toward the outer layer 2930 of the optical imaging objective. The transferred heat may then travel convectively away from the optical imaging objective 1110. In some cases, the heat may be transferred away from the optical imaging objective and may travel from the substrate 310 to the immersion fluid 1140, to the first element 2810. The heat may travel convectively to the second element 2830 and to the one or more spacers 2820 and may travel convectively away from the optical imaging objective 1110. In some embodiments, the thermal resistance of one or more components of the optical imaging objective 1110 may be modulated. For example, the outer layer 2930 of the imaging optical imaging objective 1110 may be configured to optimally disperse heat (e.g., using brass or a low resistivity material, designing thin layers, etc.).

In some embodiments, the method may comprise heating the immersion fluid. In some cases, the immersion fluid 1140 may be pre-heated and applied to the substrate 310, so that the substrate maintains an elevated temperature (e.g., 50 degrees Celsius). The immersion fluid may be continuously replenished. For example, the system may comprise a fluid flow tube (e.g., 1130 in FIG. 15) that is configured to deliver immersion fluid in an enclosed system. In such cases, the heat may be transferred away from the optical imaging objective via convection and conduction. In some cases, additional heat may be transferred away from the optical imaging objective using a cooling element 2910a, such as a fan, which may direct heat (e.g., convectively) away from the optical imaging objective 1110 and reduce the temperature of the components of the optical imaging objective 1110.

FIG. 17B illustrates schematically another embodiment of a temperature regulation method of a system. The system may comprise a substrate 310, as described herein, an optical imaging objective 1110, as described herein, and an immersion fluid 1140. In some embodiments, the immersion fluid 1140 may be heated. In some embodiments, heat 2920 is added to the substrate 310. In some embodiments, the system comprises an insulating spacer 2935, which may be configured to generate an insulated region 2940, comprising the second element 2830 and the third element 2840, which is insulated from the elevated temperature region (e.g., the first element 2810, the immersion fluid 1140, and the substrate 310). In such cases, the greatest temperature gradient may occur in the space between the first element 2810 and the second element 2830. In some cases, the insulating spacer 2935 may have a higher thermal resistance than glass. In some embodiments, a cooling element 2910a may be used to further cool the optical imaging objective 1110. In some embodiments, the first element 2810 may be configured to rapidly disperse heat (e.g., may be thin). In some embodiments, the insulating spacer 2935 may have a higher resistance than the first element 2810, which may reduce heat transfer to the second 2830 and third 2840 elements. Alternatively or in addition to the insulating spacer, there may be a gap (e.g., air gap) disposed between the first element 2810 and the rest of the objective 1110. In some embodiments, the first element 2810 may have optical properties that are insensitive to temperature. In some embodiments, the first element 2810 may have zero or very low optical power, e.g., may be a window or substantially flat (e.g., planar) element, thereby reducing the sensitivity of the first element 2810 to temperature or thermally induced dimension fluctuations.

FIG. 17C illustrates schematically another embodiment of a temperature regulation method of a system. The system may comprise a substrate 310, as described herein, an optical imaging objective 1110, as described herein, an immersion fluid 1140, and a heating element 2910b. In some embodiments, the optical imaging objective 1110 may be heated to a desired temperature (e.g., 50 degrees Celsius) or to a temperature to match the desired temperature of the substrate 310. In some cases, resistive heaters may be used for the optical imaging objective. Heating of the optical imaging objective may result in heat transfer to the substrate 310. In some cases, heat 2920 may also be applied to the substrate 310. In some embodiments, the heating element 2910b may be used to apply heat to the optical imaging objective, e.g., via convection.

FIG. 17D illustrates schematically another embodiment of a temperature regulation method of a system. The system may comprise a substrate 310, as described herein, an optical imaging objective 1110, as described herein, and an immersion fluid 1140. In some embodiments, the optical imaging objective 1110 may be cooled. For example, cooled immersion fluid 1140 may be continuously circulated between the optical imaging objective 1110 and the substrate 310. In some cases, the immersion fluid 1140 may be recycled to minimize reagent use, as described elsewhere herein. In some embodiments, heat 2920 may be applied to the substrate 310.

FIG. 17E illustrates schematically another embodiment of a temperature regulation method of a system. The system may comprise a substrate 310, as described herein, an optical imaging objective 1110, as described herein, and an immersion fluid 1140. In some embodiments, the optical imaging objective 1110 may be cooled while the substrate 310 is heated. For example, cooled immersion fluid 1140 may be continuously circulated between the optical imaging objective 1110 and the substrate 310. In some cases, the flow rate of the immersion fluid 1140 may be controlled such that the temperature gradient 2850 exists primarily in the immersion fluid 1140, and the immersion fluid 1140 close to the substrate is at an elevated temperature, but the immersion fluid 1140 close to the optical imaging objective 1110 is cooled. In some cases, the immersion fluid 1140 may be recycled to minimize reagent use, as described elsewhere herein.

As will be appreciated, any combination of mechanisms for temperature regulation and/or modulation may be used. For example, the optical imaging objective may comprise (i) an outer layer that may conduct heat away from the optical imaging objective and (ii) a flat or planar first element with zero or low optical power that is robust to temperature. In some cases, the immersion fluid may be heated in addition or alternatively to using an optical imaging objective with a conductive outer layer and/or flat first element. Similarly, a cooling element may be implemented with any of the described methods and systems. Any suitable combination of temperature modulation methods may be used in conjunction with the systems and methods described herein.

Also disclosed herein, in certain embodiments, are methods for fluid and bubble control in optical detection systems. In some embodiments, an optical imaging objective is used during the detection method. In some cases, the optical imaging objective is immersed in a fluid in contact with the substrate, and the optical imaging objective is in optical communication with the detector. In some cases, the optical imaging objective may comprise a camera or may be connected to a camera. In some cases, the camera or the optical imaging objective comprising the camera may be in fluidic communication with the substrate. In some embodiments, the optical imaging objective or camera is located at a suitable working distance from the substrate. In some cases, the optical imaging objective may be immersed in a fluid. In some embodiments, the optical imaging objective or camera comprises an adapter that is configured to maintain a fluid-filled cavity around the outlet of the optical imaging objective or camera. In some cases, the adapter may allow for imaging of the substrate (or an uncovered surface thereof) at greater working distances. The adapter may be attached to or encase the optical imaging objective or camera. In some cases, the adapter comprises a hydrophobic region, such as the area that interfaces with the immersion fluid. The hydrophobic region may allow for fluid to be directed towards or stay near the imaging region of the optical imaging objective. For example, the hydrophobic region may be configured to retain a volume of fluid between the optical imaging objective or camera and the imaged region of the substrate (or uncovered surface thereof). In some cases, the adapter comprises a hydrophilic region, such as the area that interfaces with the immersion fluid. The hydrophilic region may allow for fluid to be directed towards or stay near the imaging region of the optical imaging objective. For example, the hydrophilic region may be configured to retain a volume of fluid between the optical imaging objective or camera and the imaged region of the substrate (or uncovered surface thereof). In some cases, the adapter comprises both a hydrophilic and a hydrophobic region, which may allow for fluid to be directed towards or stay near the imaging region of the optical imaging objective or camera.

FIG. 19 illustrates schematically an exemplary adapter that may be attached to or encase the optical imaging objective. The adapter 3100 may allow for imaging of the substrate at greater working distances (e.g., greater than 500 microns). In some cases, the adapter simulates a shorter working distance by forming a fluid-filled cavity around the optical imaging objective 1110. In some embodiments, the adapter 3100 comprises one or more inlet ports 3110, which may dispense the immersion fluid. In some embodiments, the adapter 3100 also comprises one or more other ports 3120 (e.g., outlet ports, additional inlet ports, etc.). Fluid may be directed to a cavity 3130 surrounding the optical imaging objective 1110. In some cases, the fluid may be immersion fluid and may be dispensed on the substrate 310. In some cases, the adapter 3100 retains a volume of immersion fluid between the adapter and the substrate 310, e.g., via surface tension. Use of an adapter may allow for greater working distances while maintaining immersion of the optical imaging objective 1110 in the immersion fluid. In some cases, the adapter may comprise a hydrophobic region that allows for the immersion fluid to remain or be directed toward the imaging path of the optical imaging objective 1110.

Suitable working distances between the optical imaging objective and the substrate may be any suitable distance for imaging the substrate. In some cases, a working distance between 100 and 500 microns (μm) is suitable. For example, a suitable working distance may be 100, 150, 200, 250, 300, 350, 400, 450, 500 microns. In some cases, a working distance may be less than 100 microns. For example, a working distance may be 1, 2, 3, 4, 5, 10, 15, 20, 25, 30, 35, 40, 45, 50, 55, 60, 65, 70, 75, 80, 85, 90, or 95 microns. In some cases, a working distance may be greater than 500 microns. For example, a suitable working distance may be 550, 600, 650, 700, 750, 800, 850, 900, 950, or 1000 or more microns. In some cases, a suitable working distance may be more than 1000, 1500, 2000, 2500, 3000, 3500, 4000, 4500 or more microns. In some cases, the optical imaging objective may be a long working distance objective. For example, the optical imaging objective may have a working distance of greater than 5, 6, 7, 8, 9, 10, 15, 20, 25 or more millimeters (mm).

In some cases, a working distance may be sufficiently small such that an immersion fluid may be retained (e.g., via surface tension) between the optical imaging objective and the substrate. In some cases, a working distance may be greater, such that the immersion fluid does not touch the optical imaging objective or the substrate. In some cases, an adapter may be added to the objective that can form a fluid-filled cavity around the objective, such that an immersion fluid may be retained (e.g., via surface tension) between the optical imaging objective and/or adapter and the substrate.

In some embodiments, bubbles may form in the immersion fluid, which may affect the optical and/or detection performance of the system. For example, bubbles may form in the optical path of the optical imaging objective, which may reduce the performance of imaging, focusing, and the path of light (e.g., laser, LED, transmitted light, etc.). In some cases, it is desirable to prevent bubble formation and/or remove bubbles from the optical path. Thus, provided herein are methods and systems for preventing formation of bubbles and for removal of bubbles from the optical path.

FIG. 18 demonstrates schematically the formation of bubbles in an immersion fluid. An optical imaging objective 1110, as described herein, may be positioned over a substrate 310, such as a rotatable substrate, a planar substrate, and/or any substrate described herein. Disposed between the optical imaging objective 1110 and the substrate 310 is an immersion fluid 1140, as described herein. In some cases, the immersion fluid may comprise bubbles 3010. The bubbles 3010 may occur along the optical path of the optical imaging objective 1110, which may reduce the imaging performance of the detection method.

In some embodiments, the method may comprise substrate modification to prevent bubble formation. In some cases, the method comprises degassing the immersion fluid before use in imaging. In some cases, the substrate modification may comprise immersion lithography. In some cases, a hydrophobic material, such as a resist, may be deposited onto the surface of the substrate. Increasing the hydrophobicity of the substrate may increase the contact angle of a fluid on the surface of the substrate and reduce bubble formation.

In some cases, e.g., in immersion lithography, it may be desirable to minimize the exposure of the immersion fluid to the substrate. Thus, the method may comprise methods to minimize the area and duration of immersion fluid contact with the substrate. In some embodiments, the method comprises dispensing and recovery ports that dispense immersion fluid onto the substrate and remove the immersion fluid from the substrate, respectively. Recovery of the fluid may be obtained by a variety of means such as application of pressure or aspiration, gravity forces, centrifugal forces, capillary forces, electric forces, magnetic forces, etc. In some cases, the dispensing and recovery parts may be used to minimize usage of reagents (e.g., immersion fluid). In such cases, the immersion fluid may be recycled, as described elsewhere herein.

FIG. 21 illustrates schematically a method for dispensing and removing immersion fluid onto a substrate. The substrate 310 may be any substrate described herein. The immersion fluid 1140 may comprise an imaging buffer. In some cases, minimization of amount of immersion fluid may be desired, or minimization of exposure of the substrate 310 to the immersion fluid 1140 is desired. In some embodiments, the method comprises dispensing the immersion fluid 1140 through a dispensing port 3210 and recovering the immersion fluid 1140 through a recovery port 3220. In some cases, the dispensing port is located close to the optical imaging objective 1110. In some cases, the recovery port is located outside, i.e., radially outward, of the optical imaging objective 1110 and the dispensing port 3210. In some cases, a plurality of dispensing and recovery parts may be used. As will be appreciated, any number of dispensing and removal ports may be used. For example, 1, 2, 3, 4, 5, 6, 7, 8, 9, 10, 20, 30, 40, 50, 60, 70, 80, 90, 100 or more dispensing ports or removal ports may be used. In some embodiments, the number of dispensing ports used may not be equal to the number of removal ports used. In some cases, more dispensing ports may be used than removal ports. In other cases, more removal ports are used than dispensing ports. In some embodiments, the dispensing and removal ports may be part of an adapter 3100 (see FIG. 19).

In some embodiments, the generation of bubbles may be minimized by controlling the flow rate of the immersion fluid. In some cases, e.g., in immersion lithography, the flow rate of fluid dispensing may be optimized. For example, the flow rate of fluid dispensing may be 1 picoliter/min, 10 picoliters/min, 100 picoliters/min, 1 nanoliter/min, 10 nanoliters/min, 100 nanoliters/min, 1 microliter/min, 10 microliters/min, 100 microliters/min, 1 milliliter/min, 10 milliliters/min, 100 milliliters/min, or up to 1 liter/min. The flow rate of fluid dispensing may be between any of these flow rates. Alternatively, the flow rate of fluid dispensing may be at most any of these flow rates. The flow rate may be sufficiently low such that bubble generation is minimized. In some embodiments, the flow rate may allow air or bubbles to rise above the objective and away from the optical path.

In some embodiments, the method may comprise dispensing a fluid on the substrate and then using the optical imaging objective to displace bubbles. FIG. 20A-FIG. 20B illustrate schematically a method to displace bubbles. In FIG. 20A, a substrate 310 may have dispensed thereto an immersion fluid 1140, as described herein. The immersion fluid 1140 may comprise bubbles 3010. In FIG. 20B, the optical imaging objective 1110 may be brought into contact with the immersion fluid 1140, thus displacing the bubbles 3010. In some embodiments, the optical imaging objective 1110 may have attached thereto an adapter 3100 (not shown). In some cases, the adapter 3100 may comprise a plurality of dispensing and recovery ports. In such cases, the dispensing port or the recovery port may be used to pull the fluid (e.g., via pressure differences, capillary forces, etc.) into the adapter and thus away from the optical imaging objective.

In some embodiments, the method may comprise using an adapter to prevent bubble formation, or to trap or capture bubbles. As described herein, the adapter may be attached to the optical imaging objective. In some cases, the adapter may interface with the immersion fluid. In some cases, the adapter comprises dispensing ports that may dispense the immersion fluid onto the substrate. In some embodiments, the surface of the adapter that interfaces with the immersion fluid may be flat. In some cases, a thin layer of glass may be placed between the optical imaging objective and the substrate to form a closed cavity to minimize bubble formation. In such an embodiment, the thin layer of glass may be placed between the objective and the wafer to form a closed cavity. The closed cavity may be filled with an immersion liquid without bubbles. On the other end of the thin layer of glass, the fluid may be introduced between the thin layer of glass and the substrate.

In some embodiments, the adapter may be used to remove bubbles from the immersion fluid. In some cases, the adapter comprises one or more dispensing and/or recovery ports. In some embodiments, the dispensing ports may be used to rapidly flush immersion fluid onto the substrate, thereby breaking or disrupting larger bubbles into smaller bubbles, which may be cleared by a separate mechanism, or which may break. A high rapid flush may also push bubbles out of the adapter or away from the optical imaging objective.

In some embodiments, the adapter may comprise ports that may be used to remove bubbles. For example, a suction (i.e., negative pressure) port may be placed in the adapter that may attach to the optical imaging objective. In some embodiments, the suction port may be used to remove bubbles in the vicinity. In other cases, the adapter may comprise a dispensing port that rapidly dispenses fluid onto the substrate to move bubbles toward another area of the substrate. The adapter in some cases may also comprise a suction port to aspirate the bubbles. As will be appreciated, any combination of the features of the adapter (e.g., dispensing port, recovery port, suction ports) may be used.

In some embodiments, the adapter may be flat relative to the plane in which the adapter interfaces with the immersion fluid, for example as shown in FIG. 22A. In some embodiments, the adapter may be convex along the plane or area that interfaces with the immersion fluid, for example as shown in FIG. 22B. In some cases, the bottom surface of the adapter may interface with the immersion fluid and may be partly angled, e.g., in a cone shape. The angled shape may reduce the area of contact between the immersion fluid and the adapter. In some cases, the angled shape may guide or direct fluid to the optical path. In some cases, the optical imaging objective may be the closest part to the substrate and/or immersion fluid. In some embodiments, the adapter may be asymmetrical in shape to reduce the area of the adapter in contact with the immersion fluid.

In some embodiments wherein the adapter is angled, the angle between the adapter and the immersion fluid may be any suitable angle. The angle may be, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 degrees. In some cases, the angle may be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 degrees. In some cases, the angle may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 degrees. In some cases, the angle may be a non-integer angle.

In some embodiments, the adapter may comprise a trap that may capture and remove bubbles from the optical path. For example, the adapter may comprise a cavity that may direct bubbles into an internal region of the adapter. Alternatively, the cavity may be connected to an outlet port that allows for disruption of the bubble or removal of the bubble.

FIG. 22A-FIG. 22B illustrate schematically a method for trapping bubbles. FIG. 22A illustrates an exemplary adapter 3100, as described herein, which encases an optical imaging objective 1110, as described herein. The adapter 3100 may be flat or may be angled (see, FIG. 22B). The adapter 3100 may interface with an immersion fluid 1140, which may comprise bubbles 3010. The adapter 3100 may comprise a cavity that can capture entrained bubbles 3010. In some cases, the bubbles may disrupt, break, or pop in the cavity. In other cases, the cavity may be connected to a port (not shown). In FIG. 22B, the adapter may have an angled bottom, which may reduce the area of contact between the immersion fluid 1140 and the adapter 3100. The angle, θ, may be any suitable or useful angle.

In some cases, one or more components of the system may be moved (e.g., translated) to remove bubbles. In one non-limiting example, the optical imaging objective may be moved vertically away from the substrate and then repositioned to an imaging position, thereby allowing entrained bubbles to displace and/or break. In some cases, the substrate may be moved relative to the objective, thereby allowing entrained bubbles to displace and/or break. In another non-limiting example, the substrate may be moved in the plane, e.g., in a circular motion or linear motion (e.g., as shown in FIG. 23A-FIG. 23J). In some cases, motion of the substrate may generate a shear force and velocity field that causes bubbles to displace and/or break. In some cases, a combination of motion planes may be employed. For example, either the optical imaging objective or the substrate, or both, may be moved both in a vertical and planar direction. At any step in the motion, an immersion fluid may be dispensed onto the substrate.

In some embodiments, the immersion fluid may be recollected and recycled (or recirculated). In some cases, the immersion fluid may be treated prior to recycling or recirculation. Treatment may comprise removing debris, removing analytes (e.g., nucleotides, proteins, lipids, carbohydrates, etc.), removing beads, or any other contaminants. Treatment may comprise degassing, de-bubbling, or removing entrained air. As will be appreciated any treatment may comprise any combination of these processes in any convenient order.

Optical Layouts

Figure 41:
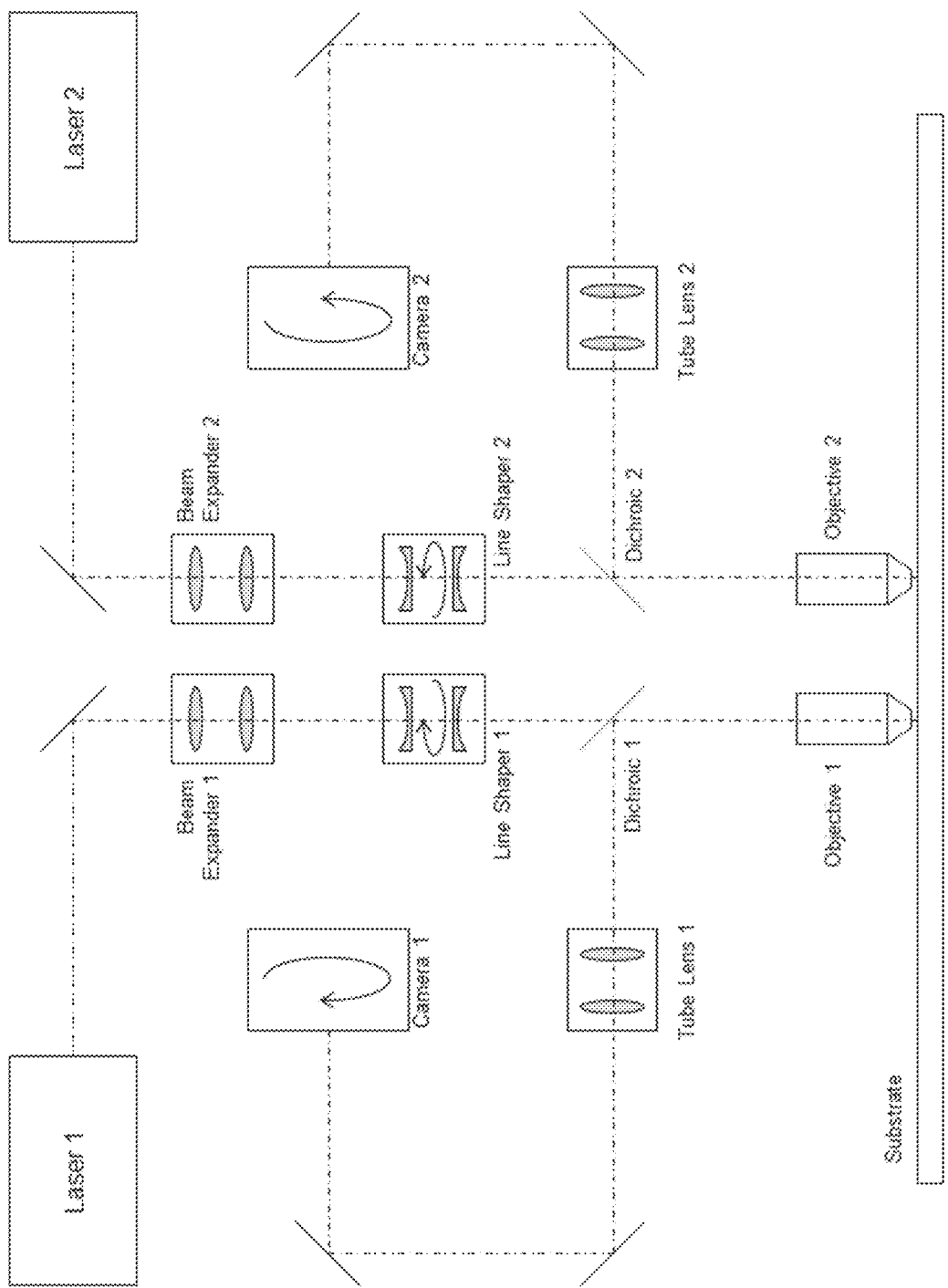
FIG. 41 illustrates schematically an exemplary optical layout.

The present disclosure provides optical systems that are designed to implement the methods of the disclosure. FIG. 41 shows an exemplary optical system that may be used to scan a substrate as disclosed herein, for example a rotating substrate. The optical system may comprise one or more distinct optical paths. The one or more optical paths may comprise mirrored optical layouts. In some embodiments, the optical system may comprise 1, 2, 3, 4, 5, 6, 7, 8, 9, 10, 11, 12, 13, 14, or 15 distinct optical paths. For example, the optical system may comprise two distinct optical paths, as shown in FIG. 41.

An optical path may comprise an excitation path and an emission path. The excitation path and the emission path may each comprise a plurality of optical elements in optical communication with the substrate. In some embodiments, the excitation path comprises one or more of an excitation light source, a beam expander element, a line shaper element, a dichroic, and an objective. In some embodiment, the emission path may comprise one or more of an objective, a dichroic, a tube lens, and a detector. The objective in the excitation path may be the same as the objective in the emission path. The objective may be an immersion objective, or the objective may be an air objective. In some embodiments, the objective is immersed in water, buffer, aqueous solution, oil, organic solvent, index matching fluid, or other immersion fluid. The objective may be a 10×, 20×, 50×, or 100× objective.

The dichroic in the excitation path may be the same as the dichroic in the emission path. The dichroic may be a short pass dichroic, or the dichroic may be a long pass dichroic. In some embodiments, the dichroic passes the excitation light and reflects the emission light. In other embodiments, the dichroic reflects the excitation light and passes the emission light. The dichroic may have a cutoff wavelength of about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, about 1050 nm, or about 1100 nm. The dichroic may have a cutoff wavelength of from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 900 nm to 950 nm, from 950 nm to 1000 nm, from 1000 nm to 1050 nm, from 1050 nm to 1100 nm, from 250 nm to 400 nm, from 350 nm to 500 nm, from 450 nm to 600 nm, from 550 nm to 700 nm, from 650 nm to 800 nm, from 750 nm to 900 nm, from 850 nm to 1000 nm, or from 950 nm to 1100 nm.

The excitation light source may be configured to emit light, for example coherent light. The excitation light source may comprise one or more light emitting diodes (LEDs). The excitation light sources may comprise one or more lasers. The excitation light sources may comprise one or more single-mode laser sources. The excitation light sources may comprise one or more multi-mode laser sources. The excitation light sources may comprise one or more laser diodes. A laser may be a continuous wave laser or a pulsed laser. A beam of light emitted by a laser may be a Gaussian or approximately Gaussian beam, which beam may be manipulated using one or more optical elements (e.g., mirrors, lenses, prisms, waveplates, etc.). For example, a beam may be collimated. In some cases, a beam may be manipulated to provide a laser line (e.g., using one or more Powell lenses or cylindrical lenses). The excitation light source may be coupled to an optical fiber.

The line shaper may be configured to expand the excitation light source along one axis, for example as shown in FIG. 11A and FIG. 11B. The line shaper may comprise one or more lenses. In some embodiments, the line shaper comprises one or more cylindrical lenses. The one or more cylindrical lenses may be convex cylindrical lenses, concave cylindrical lenses, or any combination thereof. In some embodiments, the line shaper is positioned in a rotating mount, for example a motorized rotating mount. The rotational mount may be configured to rotate the expanded excitation light source about a central axis without substantial deviation of the central point of the excitation light source. In some embodiments, the line shaper element may be configured to rotate about the central axis in response to, concurrent with, or in anticipation of a translation of the substrate with respect to the optical system. For example, the line shaper element may rotate about the central axis such that the axis of the expanded excitation light maintains a defined orientation with respect to the rotational axis of the substrate upon translation of the substrate with respect to the optical axis in a direction that is not directly toward or away from the rotational axis.

The beam expander may comprise one or more lenses. For example, the beam expander may comprise two lenses. The lenses may have different focal lengths. In some embodiments, the lens closer to the excitation light source may have a shorter focal length that the lens farther from the excitation light source. The beam expander may be configured to expand the excitation light source about 2×, about 3×, about 4×, about 5×, about 10×, about 15×, or about 20×. The beam expander may be configured to collimate the excitation light source. The beam expander may be configured to focus the excitation light source.

The tube lens may comprise one or more lenses. For example, the tube lens may comprise two lenses. The lenses may have different focal lengths, or the two lenses may have different focal lengths. The tube lens may be configured to expand the excitation light source about 2×, about 3×, about 4×, about 5×, about 10×, about 15×, or about 20×. The tube lens may be configured to collimate the emission light. The tube lens may be configured to focus the emission light.

The detectors may comprise any combination of cameras (e.g., CCD, CMOS, or line-scan), photodiodes (e.g., avalanche photo diodes), photoresistors, phototransistors, or any other optical detector known in the art. In some embodiments, the detectors may comprise one or more cameras. For example, the cameras may comprise line-scan cameras, such as TDI line-scan cameras. In some embodiments, the TDI line-scan camera may comprise two or more vertically arranged rows of pixels, as shown with respect to FIG. 8A-FIG. 8D. The detector may be configured to rotated with respect to the substrate to correct for tangential velocity blur, as described herein. In some embodiments, the detector may be configured to rotate in response to, concurrent with, or in anticipation of a translation of the substrate with respect to the optical system. For example, the detector may rotate such that the axis of the imaging field maintains a defined orientation with respect to the rotational axis of the substrate upon translation of the substrate with respect to the optical axis in a direction that is not directly toward or away from the rotational axis. The detector may be configured to rotate concurrently with a rotation of the line shaper element, such that the imaging field maintains a defined orientation with respect to the axis of the expanded excitation light. The detector may be configured to rotate independently of the line shaper element.

The optical path may comprise additional optical components not shown in FIG. 41. For example, an optical path may comprise additional splitting, reflecting, focusing, magnifying, filtering, shaping, rotating, polarizing, or other optical elements.

One or more optical elements in the optical path may be positioned in a mount. A mount may be a rotational mount. A mount may be a kinematic mount. A mount may be a translational mount. A mount may be a stationary mount. In some embodiments, a mount may have one or more degrees of freedom. For example, a mount may have one or more of one-dimensional translation, two-dimensional translation, three-dimensional translation, one dimensional rotation, two-dimensional rotation, or three-dimensional rotation.

The optical systems of this disclosure may further comprise one or more autofocus systems (not shown in FIG. 41). In some embodiments, each optical path in the optical system comprises an autofocus system. The autofocus system may comprise an autofocus illumination source configured to direct autofocus light through the objective toward the surface. In some embodiments, the autofocus illumination source may comprise an infrared (IR) laser, for example, a speckle-free IR laser. The autofocus light may pass through one or more of the optical elements in the optical path. In some embodiments, the optical path comprises one or more optical elements to differentially reflect or combine one or more of the excitation light, the emission light, or the autofocus light. The one or more optical elements may comprise one or more dichroics. The autofocus light may reflect, refract, or scatter off the surface toward an autofocus detector. The autofocus detector may be a position-sensitive detector. The autofocus light may coincide with the autofocus detector at a discrete position when the surface is in focus on an emission detector (e.g., the camera illustrated in FIG. 41). The autofocus illumination source and the autofocus detector may be configured such that a change in a position of the surface relative to the objective results in a change in position of the autofocus illumination on the autofocus detector. For example, a change in a distance between the surface and the objective or a tilt of the surface relative to the objective may cause a displacement of the autofocus illumination position on the autofocus detector. The autofocus system may send a signal to a focusing system in response to the change in position of the autofocus illumination on the autofocus detector. The focusing system may adjust the position of the surface relative to the objective such that the position of the autofocus illumination on the autofocus detector returns to the discrete position when the surface is in focus on the emission detector.

The optical systems of this disclosure may be aligned such that the excitation light and the emission light pass substantially through the center of the optical elements. In some embodiments, the excitation light may be aligned with respect to the line shaper element such that the position of the excitation light after passing through the line shaper does not change substantially upon rotation of the line shaper. The line shaper may be rotated during alignment and the position of the excitation light source, the line shaper, or both may be adjusted to minimize motion of the position of the excitation light after passing through the line shaper upon rotation of the line shaper. In some embodiments, a position of the detector is aligned with respect to a rotating mount. For example, the detector is centered within the rotational mount by illuminating the center of the detector, rotating the rotational mount, and adjusting the position of the detector within the mount so that the position of the illumination does not move upon rotation of the rotational mount. In some embodiments, the position of the excitation light is aligned at two or more points thereby defining both a position and an angle. In some embodiments, the position of the emission light is aligned at two or more points thereby defining both a position and an angle.

The one or more imaging heads of this disclosure may be aligned with respect to the substrate. In some embodiments, the positions of the one or more imaging heads are adjusted in zero, one, two, or three translational dimensions (e.g., x, y, and z) and zero, one, two, or three rotational dimensions (e.g., $\alpha$, $\beta$, and $\gamma$). In some embodiments, the position of one or more optical elements may be adjusted in any combination of translational or rotational dimensions. The optical systems of this disclosure may be coarsely aligned at low excitation power. The alignment of the optical systems of this disclosure may be precisely aligned at higher excitation powers. In some embodiments, the alignment of the optical systems may change upon increase of the excitation power. In some embodiments, the optical system may be aligned during one or more of rotation of the substrate, translation of the substrate, or translation of one or more imaging heads. The optical systems of this disclosure may be aligned using any alignment method known in the art.

Computer Control Systems

The present disclosure provides computer control systems that are programmed to implement methods of the disclosure. FIG. 1 shows a computer system 101 that is programmed or otherwise configured to sequence a nucleic acid sample. The computer system 101 can regulate various aspects of methods and systems of the present disclosure.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine-readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, nucleic acid sequencing information to a user. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105.

Numbered Embodiments

The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A method for scanning a surface, the method comprising: (a) scanning a scanning field comprising a portion of a surface using a scanning system, wherein the scanning field has an orientation with respect to a rotational axis of the surface; and (b) rotating (i) the surface about the rotational axis of the surface and (ii) the scanning field about a rotational axis of the scanning field such that the scanning field substantially maintains the orientation with respect to the rotational axis of the surface prior to, during, or subsequent to translation of the surface relative to the scanning field. 2. The method of embodiment 1, wherein the scanning field has a substantially rectilinear shape. 3. The method of embodiment 1, wherein the scanning field has a long axis, and wherein the orientation comprises a line coinciding with the long axis of the scanning field passing through the rotational axis of the surface. 4. The method of embodiment 1, wherein the scanning field traces an arc on the surface. 5. The method of embodiment 1, wherein scanning the surface comprises imaging the surface. 6. The method of embodiment 1, wherein the scanning field comprises an imaging field. 7. The method of embodiment 1, wherein the scanning field traces a scanning path on the surface, and the scanning path comprises an imaging path. 8. The method of embodiment 1, wherein the scanning system comprises an imaging system. 9. The method of embodiment 1, wherein the orientation comprises a long axis of the scanning field, wherein the long axis is parallel to a radial line passing through (i) the rotational axis of the surface and (ii) the rotational axis of the scanning field. 10. The method of embodiment 1, wherein translation of the surface relative to the scanning field comprises translating in a direction that is not directly toward or away from the rotational axis of the surface. 11. The method of embodiment 1, wherein translation of surface relative to the scanning field comprises translating along a translation path, wherein a line comprising a net displacement along the translation path does not intersect both the scanning field and the rotational axis of the surface. 12. The method of embodiment 1, wherein the scanning field rotates with respect to the surface around the rotational axis of the scanning field. 13. The method of embodiment 12, wherein the rotational axis of the scanning field is substantially perpendicular to the surface. 14. The method of embodiment 12, wherein the rotational axis of the scanning field is substantially parallel to the rotational axis of the surface. 15. The method of embodiment 12, wherein the rotational axis of the scanning field passes through an axis of symmetry of the scanning field. 16. The method of embodiment 1, wherein the scanning field is rotated by rotating an objective. 17. The method of embodiment 1, wherein the scanning field is rotated by rotating a lens. 18. The method of embodiment 1, wherein the scanning field is rotated by rotating a prism. 19. The method of embodiment 1, wherein the scanning field is rotated by rotating a mirror. 20. The method of embodiment 1, wherein the scanning field is rotated by rotating a camera. 21. The method of embodiment 1, wherein the scanning field is rotated by rotating a diffractive optical element (DOE). 22. The method of embodiment 1, wherein the scanning field is rotated using a motor. 23. The method of embodiment 1, wherein the surface is substantially circular and wherein the scanning field is translated along a chord of the surface. 24. The method of embodiment 12, wherein the surface is substantially circular and wherein the rotational axis of the scanning field is translated along a chord of the surface. 25. The method of embodiment 24, wherein the chord does not pass through the rotational axis of the surface. 26. The method of embodiment 1, wherein the scanning field is translated by moving the surface. 27. The method of embodiment 1, wherein the scanning field is translated by moving the scanning system. 28. The method of embodiment 1, wherein the scanning field traces a circle on the surface. 29. The method of embodiment 1, wherein the scanning field traces a spiral on the surface. 30. The method of embodiment 1, wherein rotating the surface and translation of the surface are performed simultaneously. 31. The method of embodiment 1, wherein the translation of the surface is linear with respect to the rotational axis of the surface. 32. The method of embodiment 1, wherein the translation of the surface is not substantially circular with respect to the surface. 33. The method of embodiment 1, wherein the translation of the surface increases or decreases a distance between the rotational axis of the scanning field and the rotational axis of the surface. 34. The method of embodiment 1, wherein the scanning system comprises an objective in optical communication with the surface. 35. The method of embodiment 1, wherein the scanning system comprises a camera. 36. The method of embodiment 1, wherein the scanning field is in optical communication with a camera. 37. The method of embodiment 35, wherein the camera is a time delay integration (TDI) camera having a line rate. 38. The method of embodiment 35, wherein the camera is a multi-line TDI camera. 39. The method of embodiment 35, wherein the camera comprises an array of sensors and the rotational axis of the scanning field passes through a center of the sensor array. 40. The method of embodiment 37, wherein the line rate is set such that the camera takes an image when the scanning field has advanced along the surface from a first location to a second location, which second location is adjacent to the first location. 41. The method of embodiment 37, wherein the line rate is variable. 42. The method of embodiment 37, wherein the line rate is higher when the objective is located farther from the rotational axis of the surface. 43. The method of embodiment 1, wherein the scanning system further comprises a tube lens. 44. The method of embodiment 34, wherein the scanning system comprises two objectives, the objective and a second objective, in optical communication with the surface. 45. The method of embodiment 44, wherein the two objectives are on a same side of the surface with respect to a plane normal to the surface and intersecting the rotational axis of the surface. 46. The method of embodiment 44, wherein the two objectives are on opposite sides of the surface with respect to a plane normal to the surface and intersecting the rotational axis of the surface. 47. The method of embodiment 44, wherein the two objectives trace circular paths on the surface. 48. The method of embodiment 47, wherein the circular paths are concentric. 49. The method of embodiment 48, wherein the objective and the second objective trace alternating circular paths. 50. The method of embodiment 48, wherein the objective traces the circular paths closer to the axis of rotation, and the second objective traces the circular paths farther from the rotational axis of the surface. 51. The method of embodiment 44, wherein the two objectives trace individual spiral paths on the surface. 52. The method of embodiment 51, wherein the spiral paths are interleafed. 53. The method of embodiment 51, wherein the spiral paths are concentric and the objective traces the spiral path closer to the rotational axis of the surface, and the second objective traces the spiral path farther from the rotational axis of the surface. 54. The method of embodiment 44, wherein the objective traces a first path, the first path having a first width corresponding to a first width of the scanning field, and wherein the second objective traces a second path, the second path having a second path width corresponding to a second width of a second scanning field. 55. The method of embodiment 54, wherein the first path width and the second path width overlap by no more than 30%, no more than 20%, no more than 10%, no more than 5%, no more than 1%. 56. The method of embodiment 34, wherein the scanning system comprises four objectives in optical communication with the surface. 57. The method of embodiment 56, wherein the four objectives are positioned on a same side of the surface with respect to a plane normal to the surface and intersecting the rotational axis of the surface. 58. The method of embodiment 56, wherein a first two of the four objectives are positioned on a first side of the surface and a second two of the four objectives are positioned on a second side of the surface opposite the first side with respect to a plane normal to the surface and intersecting the rotational axis of the surface. 59. The method of embodiment 34, wherein the scanning system comprises 5, 6, 7, 8, 9, 10, 11, 12, 13, or more objectives in optical communication with the surface. 60. The method of embodiment 1, wherein the surface is rotated at a constant angular velocity. 61. The method of embodiment 35, wherein the camera is configured to take images at a given frequency and the surface is rotated relative to the objective at a variable angular velocity. 62. The method of embodiment 35, wherein the angular velocity is varied such that, at the given frequency, the camera takes an image when the scanning field is at a first location and when the scanning field is at a second location, which second location is adjacent to the first location. 63. The method of embodiment 1, further comprising illuminating a portion of the surface defined by an illumination field. 64. The method of embodiment 63, wherein the illumination field is illuminated using a laser. 65. The method of embodiment 63, wherein the illumination field is illuminated using a light emitting diode (LED) or a lamp. 66. The method of embodiment 64, wherein a power of the laser is adjusted to maintain a constant brightness on the surface and/or not saturate the camera. 67. The method of embodiment 63, wherein the illumination field at least partially overlaps with the scanning field. 68. The method of embodiment 63, wherein the scanning field encompasses the illumination field. 69. The method of embodiment 63, wherein the illumination field has a shape that is substantially similar to the scanning field. 70. The method of embodiment 63, wherein the illumination field is a substantially rectilinear shape. 71. The method of embodiment 63, wherein the illumination field has a long axis. 72. The method of embodiment 63, wherein the scanning system further comprises a plurality of illumination fields. 73. The method of embodiment 72, wherein one or more of the plurality of illumination fields have a shape that is substantially linear. 74. The method of embodiment 63, further comprising rotating the illumination field such that the illumination field maintains a defined orientation with respect to the rotational axis of the surface. 75. The method of embodiment 63, wherein the illumination field maintains a fixed orientation with respect to the scanning field. 76. The method of embodiment 74, wherein the defined orientation comprises a line coinciding with the long axis of the illumination field passing through the rotational axis of the surface. 77. The method of embodiment 74, wherein the defined orientation comprises the long axis of the illumination field being parallel to a radial line, wherein the radial line passes through the rotational axis of the surface and the rotational axis of the illumination field. 78. The method of embodiment 63, wherein the scanning field and the illumination field are rotated together. 79. The method of embodiment 71, wherein the long axis of the illumination field is parallel to the long axis of the scanning field. 80. The method of embodiment 63, wherein the illumination field rotates around a rotational axis of the illumination field. 81. The method of embodiment 80, wherein the rotational axis of the illumination field is substantially perpendicular to the surface. 82. The method of embodiment 80, wherein the rotational axis of the illumination field is substantially parallel to the rotational axis of the surface. 83. The method of embodiment 80, wherein the rotational axis of the illumination field passes through an axis of symmetry of the illumination field. 84. The method of embodiment 80, wherein the rotational axis of the illumination field is the same as the rotational axis of the scanning field. 85. The method of embodiment 63, wherein the illumination field is rotated by rotating a lens. 86. The method of embodiment 63, wherein the illumination field is rotated by rotating a diffractive optical element (DOE). 87. The method of embodiment 63, wherein the illumination field is rotated by rotating a prism. 88. The method of embodiment 63, wherein the illumination field is rotated by rotating a mirror. 89. The method of embodiment 63, wherein the illumination field is rotated by rotating a laser. 90. The method of embodiment 63, wherein the illumination field is rotated using a motor. 91. The method of embodiment 1, further comprising scanning a second portion of the surface defined by a second scanning field. 92. The method of embodiment 91, wherein the second scanning field is scanned using a second scanning system. 93. The method of embodiment 91, wherein the second scanning system comprises a second objective in optical communication with the surface. 94. The method of embodiment 93, wherein the second objective is focused independently of a first objective. 95. The method of embodiment 93, wherein the second objective has a fixed position relative to the first objective. 96. The method of embodiment 91, wherein the second scanning field has an orientation with respect to the rotational axis of the surface. 97. The method of embodiment 84, wherein the second scanning field is radially adjacent to the scanning field. 98. The method of embodiment 91, wherein the scanning field and the second scanning field have the same orientation with respect to the rotational axis of the surface. 99. The method of embodiment 91, wherein the second scanning field is rotated independently of the scanning field such that the second scanning field maintains the orientation with respect to the rotational axis of the surface. 100. The method of embodiment 91, wherein the second scanning field is rotated in coordination with the scanning field. 101. The method of embodiment 93, wherein the first objective and the second objective are part of a scanning module, and the scanning module is translated relative to the surface along a line extending radially from the rotational axis of the surface. 102. The method of embodiment 93, wherein the surface is substantially circular and wherein at least one of either the first objective or the second objective is not translated along a chord that passes through the rotational axis of the surface. 103. The method of embodiment 93, wherein the first objective and second objective are on a same side of the surface with respect to a plane normal to the surface and intersecting the rotational axis of the surface, and both the first objective and the second objective are translated together toward or away from the rotational axis of the surface. 104. The method of embodiment 93, wherein the first objective and second objective are on an opposite side of the surface with respect to a plane normal to the surface and intersecting the rotational axis of the surface. 105. The method of embodiment 104, wherein (i) the first objective is translated toward the rotational axis of the surface when the second objective is translated away from the rotational axis of the surface or (ii) the first objective is translated away from the rotational axis of the surface when the second objective is translated toward the rotational axis of the surface. 106. The method of embodiment 93, wherein the surface is substantially circular and wherein the first objective and second objective are translated along parallel chords on either side of a plane normal to the surface and intersecting the rotational axis of the surface and equidistant from the rotational axis of the surface. 107. The method of embodiment 1, wherein the surface is mounted on a rotational module. 108. The method of embodiment 107, wherein the rotational module is translated relative to the scanning system. 109. The method of embodiment 107, wherein the rotational module is stationary and the scanning module is translatable. 110. The method of embodiment 107, wherein the scanning module is stationary and the rotational module is translatable. 111. The method of embodiment 107, wherein the rotational module is mounted on a track. 112. The method of Embodiment 1, wherein the scanning module is mounted on a scanning module track. 113. The method of embodiment 112, wherein the scanning module track is linear. 114. The method of embodiment 107, wherein a plurality of surfaces are mounted on a plurality of rotational modules and wherein the plurality of rotational modules are mounted on a stage and the stage is rotated to bring each of the rotational modules in optical communication with the scanning module. 115. The method of embodiment 107, wherein subsequent to scanning the surface, the rotational module is moved to a chemistry module. 116. The method of embodiment 107, further comprising translating a second rotational module such that a second surface is in optical communication with the scanning module. 117. The method of embodiment 1, wherein the surface comprises an array of nucleic acid colonies. 118. The method of embodiment 117, wherein the nucleic acid colonies are labeled with a fluorophore. 119. The method of embodiment 117, wherein an intensity of the fluorophore is indicative of a sequence of the nucleic acid colony. 120. The method of embodiment 1, wherein a laser excites the fluorophore at a first wavelength and a camera detects an emission from the fluorophore at a second wavelength. 121. The method of embodiment 1, wherein the laser illuminates an illumination field and the camera scans a scanning field. 122. The method of embodiment 1, wherein two or more of scanning, rotating the surface, rotating the scanning field, and translation occur simultaneously. 123. The method of embodiment 1, wherein three or more of scanning, rotating the surface, rotating the scanning field, and translation occur simultaneously. 124. The method of embodiment 1, wherein scanning, rotating the surface, rotating the scanning field, and translation occur independently. 125. The method of embodiment 1 further comprising repeating steps (a) and (b). 126. The method of embodiment 125, wherein steps (a) and (b) are repeated for each base in a nucleic acid polymerization reaction, thereby sequencing the nucleic acid.

127. A scanning system comprising: a surface configured to rotate about a rotational axis of the surface; a detector in optical communication with the surface, wherein the detector has a scanning field comprising a first portion of the surface; and an illumination source configured to illuminate an illumination region comprising a second portion of the surface, wherein the illumination region and the scanning field at least partially overlap, wherein the detector is configured to maintain an orientation of the scanning field with respect to the rotational axis of the surface during (i) rotation of the surface about the rotational axis and (ii) translation of the surface relative to the scanning field. 128. The scanning system of embodiment 127, wherein the scanning field traces an arc on the surface. 129. The scanning system of embodiment 127, wherein scanning the surface comprises imaging the surface. 130. The scanning system of embodiment 127, wherein the scanning field comprises an imaging field. 131. The scanning system of embodiment 127, wherein the scanning field traces a scanning path along the surface, and wherein the scanning path comprises an imaging path. 132. The scanning system of embodiment 127, wherein the scanning system comprises an imaging system. 133. The scanning system of embodiment 127, wherein the detector comprises a line scan camera. 134. The scanning system of embodiment 133, wherein the line scan camera comprises a TDI-line scan camera. 135. The scanning system of embodiment 134, wherein the TDI-line scan camera images a first scanning field on a first camera region. 136. The scanning system of embodiment 135, wherein the TDI-line scan camera images a second scanning field on a second camera region. 137. The scanning system of embodiment 134, wherein the TDI-line scan camera images a first scanning field on a first camera region and images the first scanning field on a second camera region. 138. The scanning system of embodiment 137, wherein the first camera region and the second camera region detect different wavelengths. 139. The scanning system of embodiment 137, wherein the first camera region and the second camera region detect different dynamic ranges. 140. The scanning system of embodiment 127, wherein the surface is configured to translate along an axis of translation with respect to the scanning field. 141. The scanning system of embodiment 140, wherein the axis of translation intersects the rotational axis of the surface and a center point of the scanning field. 142. The scanning system of embodiment 140, wherein the axis of translation does not intersect the rotational axis of the surface and a center point of the scanning field. 143. The scanning system of embodiment 142, wherein an orientation of the scanning field changes from a first orientation to a second orientation with respect to the rotational axis of the surface upon translation of the surface. 144. The scanning system of embodiment 143, wherein the scanning field is configured to rotate about a rotational axis of the scanning field with respect to the rotational axis of the surface to correct the orientation of the scanning field from the second orientation to the first orientation with respect to the rotational axis of the surface. 145. The scanning system of embodiment 144, wherein the scanning field is configured to rotate by rotating an objective. 146. The scanning system of embodiment 144, wherein the scanning field is configured to rotate by rotating a lens. 147. The scanning system of embodiment 144, wherein the scanning field is configured to rotate by rotating a prism. 148. The scanning system of embodiment 144, wherein the scanning field is configured to rotate by rotating a mirror. 149. The scanning system of embodiment 144, wherein the scanning field is configured to rotate by rotating the detector. 150. The scanning system of embodiment 144, wherein the scanning field is configured to rotate by rotating a diffractive optical element (DOE). 151. The scanning system of embodiment 127, wherein the illumination source comprises a laser or a light emitting diode (LED). 152. The scanning system of embodiment 127, wherein the illumination source comprises a substantially circular illumination profile. 153. The scanning system of embodiment 127, wherein the substantially circular illumination profile is expanded along a single axis. 154. The scanning system of embodiment 153, wherein the substantially circular illumination profile is expanded along a single axis using a cylindrical lens. 155. The scanning system of embodiment 153 further comprising a plurality of illumination sources having substantially circular illumination profiles, wherein the substantially circular illumination profiles are expanded along a single axis. 156. The scanning system of embodiment 127, wherein the illumination source passes through a grating. 157. The scanning system of embodiment 127, wherein the first portion of the surface is configured to move with respect to the scanning field. 158. The scanning system of embodiment 157, wherein a first region of the first portion of the surface is configured to move at a first velocity with respect to the scanning field, and a second region of the first portion of the surface is configured to move at a second velocity with respect to the scanning field. 159. The scanning system of embodiment 158, wherein the first region is closer to the rotational axis of the surface than the second region and the first velocity slower than the second velocity. 160. The scanning system of embodiment 158, wherein an image of the first region is magnified on the detector by a first magnification factor and an image of the second region is magnified on the detector by a second magnification factor. 161. The scanning system of embodiment 160, wherein the first magnification factor and the second magnification factor are different. 162. The scanning system of embodiment 161, further comprising a lens having a lens axis positioned in an optical path between the scanning field and the detector, wherein the lens axis is not perpendicular to the surface. 163. The scanning system of embodiment 127, further comprising an objective positioned in an optical path between the scanning field and the detector. 164. The scanning system of embodiment 163, wherein the objective is in fluidic contact with the surface. 165. The scanning system of embodiment 163, wherein the objective and the surface are different temperatures. 166. The scanning system of embodiment 163, further comprising a temperature gradient across a fluid contacting the surface and the objective. 167. The scanning system of embodiment 166, wherein the objective comprises an insulating spacer in contact with the fluid. 168. The scanning system of embodiment 167, wherein the insulating spacer comprises an air gap. 169. The scanning system of embodiment 163, wherein the objective is heated to reduce the temperature gradient. 170. The scanning system of embodiment 163, wherein the objective is cooled to increase the temperature gradient. 171. The scanning system of embodiment 163, wherein the fluid is configured to exchange during rotation. 172. The method of embodiment 1 further comprising (i) scanning a focal region of the surface using an autofocus system to generate a focal map of the focal region and (ii) adjusting a focus of the surface relative to the scanning system based on the focal map while scanning the scanning field. 173. The method of embodiment 172, wherein the surface rotates about the rotational axis of the surface with respect to the scanning field while scanning the focal region of the surface using the autofocus system. 174. The method of embodiment 172, wherein the focal region comprises the scanning field. 175. The method of embodiment 172, wherein the focal region comprises a field in close proximity to the scanning field. 176. The method of embodiment 175, wherein the focal region does not comprise the scanning field. 177. The method of embodiment 172, wherein the focal region is scanned prior to scanning. 178. The method of embodiment 172, wherein the focal region is scanned while scanning. 179. The scanning system of embodiment 164, wherein the objective is configured to maintain fluidic contact with the surface while the surface is rotated about the rotational axis of the surface with respect to the objective. 180. The scanning system of embodiment 164, wherein the objective is configured to move in a direction approximately normal to the surface to leave and re-enter fluidic contact with the surface. 181. The scanning system of embodiment 180, wherein the objective is configured to retain a droplet of fluid adherent to the objective when the objective leaves fluidic contact with the surface. 182. The scanning system of embodiment 181, wherein the objective is configured to displace bubbles between the surface and the objective when the objective re-enters fluidic contact with the surface. 183. The scanning system of embodiment 182, further comprising an adaptor attached to the objective and configured to facilitate bubble displacement. 184. The scanning system of embodiment 163, further comprising a chamber surrounding the surface and the objective configured to maintain a higher humidity in the chamber as compared to outside the chamber. 185. The scanning system of embodiment 184, wherein the chamber comprises a reservoir beneath the surface configured to collect fluid. 186. The scanning system of embodiment 185, wherein the reservoir comprises a fluid level, and wherein the reservoir is configured to maintain an approximately constant fluid level. 187. The scanning system of embodiment 186, wherein the reservoir is configured to dispense a volume of fluid approximately equal to a volume of fluid collected by the reservoir. 188. The scanning system of embodiment 185, wherein a top portion of the chamber is held at a first temperature, the objective is held at a second temperature, the surface is held at a third temperature, and the reservoir is held at a fourth temperature. 189. The scanning system of embodiment 188, wherein the first temperature is higher than the second temperature. 190. The scanning system of embodiment 188, wherein the third temperature is lower than the fourth temperature. The scanning system of embodiment 188, wherein the second temperature is higher than the third temperature and lower than the first temperature.

Additional Numbered Embodiments

The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A method for sequencing a nucleic acid molecule, the method comprising: a. providing an array of nucleic acid molecules on an uncovered surface; b. dispersing a layer of a solution over the uncovered surface at a rate of at least 1 nanoliter per second when measured at a temperature of 25 degrees Celsius, wherein the solution comprises reagents including at least one nucleotide that incorporates into a growing nucleic acid strand that is complementary to a nucleic acid molecule of the array of nucleic acid molecules; and c. detecting one or more signals that are indicative of the nucleotide incorporated into the growing nucleic acid strand. 2. The method of embodiment 1, wherein the uncovered surface is exposed to an atmosphere. 3. The method of embodiment 1 or 2, wherein the layer comprises a first surface and a second surface, wherein the first surface contacts the uncovered surface and the second surface contacts a gas. 4. The method of any one of embodiments 1-3, wherein the uncovered surface is not a flow cell. 5. The method of any one of embodiments 1-4, wherein the uncovered surface does not have a surface facing the uncovered surface. 6. The method of any one of embodiments 1-5, wherein the uncovered surface is substantially planar. 7. The method of any one of embodiments 1-6, wherein the layer has a thickness of less than about 100 micrometers (μm) on the uncovered surface. 8. The method of any one of embodiments 1-7, wherein (b) comprises dispersing the solution to the uncovered surface across a non-solid gap. 9. The method of any one of embodiments 1-8, further comprising repeating (b) with a plurality of different solutions, wherein each solution of the plurality of different solutions is dispersed over the uncovered surface using its own dedicated fluidics. 10. The method of any one of embodiments 1-9, wherein the layer of solution is dispersed over the uncovered surface by rotating the uncovered surface. 11. The method of any one of embodiments 1-10, wherein the uncovered surface is rotated at a first angular velocity that directs the solution along a direction away from a central axis of rotation. 12. The method of any one of embodiments 1-11, wherein the solution comprises a fluid that is thixotropic. 13. The method of any one of embodiments 1-12, wherein the uncovered surface comprises a rim near an outer edge of the uncovered surface such that an amount of the solution that flows over the outer edge in (b) is reduced. 14. The method of any one of embodiments 1-13, wherein a viscosity of the solution is selected such that less than about 50% of the solution dispensed in (b) flows over the outer edge in (b). 15. The method of any one of embodiments 1-14, wherein (c) is performed by rotating the uncovered surface at a second angular velocity while the uncovered surface is in proximity to a camera. 16. The method of any one of embodiments 1-15, wherein the uncovered surface is capable of folding or bending. 17. The method of any one of embodiments 1-16, wherein the uncovered surface is textured or patterned. 18. The method of any one of embodiments 1-17, wherein the layer of solution is dispersed over the uncovered surface by passing the uncovered surface through and in contact with a reservoir of the solution. 19. The method of any one of embodiments 1-18, wherein (c) is performed by passing the uncovered surface under a camera. 20. The method of any one of embodiments 1-19, wherein the uncovered surface moves through a series of solutions, including the solution, by moving against a plurality of rotating reels. 21. The method of embodiment 20, wherein the series of solutions comprise a series of nucleotide solutions having reagents sufficient to incorporate one of the nucleotides (A, T/U, C or G) into the growing nucleic acid strand. 22. The method of embodiment 21, wherein the uncovered surface is passed through and in contact with a washing solution after each of the nucleotide solutions. 23. The method of embodiment 22, wherein the uncovered surface is imaged subsequent to passing through each of the washing solutions. 24. The method of any one of embodiments 1-23, wherein the layer of solution is dispersed over the uncovered surface by spraying the solution over the surface. 25. The method of any one of embodiments 1-24, wherein the layer of solution is dispersed over the uncovered surface by subjecting the uncovered surface to vibration. 26. The method of any one of embodiments 1-25, wherein the layer of solution is dispersed over the uncovered surface by blowing a gas to displace a volume of the solution over the uncovered surface. 27. The method of any one of embodiments 1-26, wherein the layer of solution is dispersed over the uncovered surface by contacting the solution with a solid surface and moving the solid surface across the uncovered surface. 28. The method of any one of embodiments 1-27, wherein the uncovered surface is contained in a housing that encloses an atmosphere, wherein the atmosphere has a higher humidity than ambient atmosphere. 29. The method of any one of embodiments 1-28, wherein less than about 50% in volume of the layer of solution dispersed on the uncovered surface evaporates prior to (c). 30. The method of any one of embodiments 1-29, wherein the solution comprises reagents configured to reduce an evaporation rate of the solution. 31. The method of embodiment 30, wherein the solution comprises glycerol. 32. The method of any one of embodiments 1-31, wherein the uncovered surface is maintained at a temperature near the dew point. 33. The method of any one of embodiments 28-32, wherein the housing contains a second surface that is separate from the uncovered surface, wherein the second surface has a temperature that (i) encourages condensation on the second surface and/or (ii) inhibits condensation on or above the uncovered surface. 34. The method of embodiment 33, wherein the housing comprises walls that are shaped to direct condensation away from the uncovered surface. 35. The method of any one of embodiments 33-34, wherein a fluid flows in the housing to direct condensation away from the uncovered surface. 36. The method of any one of embodiments 1-35, wherein (c) is performed by a camera in fluidic communication with the uncovered surface. 37. The method of embodiment 36, wherein the camera includes an adapter configured to retain and/or replenish an immersion fluid between the camera and the uncovered surface. 38. The method of embodiment 37, wherein the hydrophobicity or hydrophilicity of the adapter is selected to retain a volume of fluid between the camera and the uncovered surface. 39. The method of any one of embodiments 36-38, further comprising removing one or more gas bubbles trapped between the camera and the uncovered surface. 40. The method of any one of embodiments 36-39, wherein the camera has numerical aperture of at least about 0.10. 41. The method of any one of embodiments 36-40, wherein the camera detects a single wavelength. 42. The method of any one of embodiments 36-41, wherein the camera has an intentional blur. 43. The method of any one of embodiments 1-42, further comprising repeating (b) and (c). 44. The method of any one of embodiments 1-43, wherein (b) and (c) are repeated for each of four nucleotide solutions dispersed during (b). 45. The method of any one of embodiments 1-44, wherein (b) is repeated at least twice within a period of time of less than about 30 seconds (s). 46. The method of any one of embodiments 1-45, wherein (b) is performed within a period of time of less than about 30 seconds (s). 47. The method of any one of embodiments 1-46, wherein the solution comprises a plurality of nucleotides that are not reversibly terminating nucleotides. 48. The method of any one of embodiments 1-47, wherein the solution comprises a plurality of nucleotides that are labeled. 49. The method of embodiment 48, further comprising cleaving off a label from a nucleotide of the plurality of nucleotides that are labeled subsequent to (c). 50. The method of any one of embodiments 1-49, wherein the solution comprises a plurality of nucleotides that are not labeled. 51. The method of any one of embodiments 1-50, further comprising washing non-incorporated nucleotides from the solution off of the uncovered surface between (b) and (c). 52. The method of any one of embodiments 1-51, further comprising collecting at least a portion of the solution subsequent to (b). 53. The method of any one of embodiments 1-52, further comprising recovering a reagent from the solution subsequent to (b). 54. The method of any one of embodiments 1-53, wherein the solution comprises a plurality of nucleotides, and wherein at least 50% of the nucleotides are natural nucleotides. 55. The method of any one of embodiments 1-54, wherein the one or more signals are fluorescent signals. 56. The method of any one of embodiments 1-55, wherein the solution comprises a polymerase, and wherein the polymerase is native. 57. The method of any one of embodiments 1-56, wherein the solution comprises a polymerase, and wherein the polymerase is not replenished after each repetition of (b) and (c). 58. The method of any one of embodiments 1-57, wherein the solution comprises a polymerase, and wherein the polymerase remains affixed to the nucleic acid molecule following (c). 59. The method of any one of embodiments 1-58, wherein the array of nucleic acid molecules is affixed to the uncovered surface. 60. The method of any one of embodiments 1-59, wherein nucleic acids of the array of nucleic acid molecules are affixed to beads which are arranged over the uncovered surface. 61. A method for processing a plurality of nucleic acid samples, comprising: (a) providing said plurality of nucleic acid samples, wherein said plurality of nucleic acid samples comprises a first nucleic acid sample comprising a first set of nucleic acid molecules and a second nucleic acid sample comprising a second set of nucleic acid molecules, wherein each sample of said plurality of nucleic acid samples has an identifiable sample origin; (b) loading said first nucleic acid sample onto a first region of a substrate as a first array of said first set of nucleic acid molecules and loading said second nucleic acid sample onto a second region of said substrate as a second array of said second set of nucleic acid molecules, wherein said first region is different from said second region; (c) dispersing a solution across said substrate, wherein said solution comprises reagents sufficient to react with nucleic acid molecules of said first array or said second array; (d) detecting one or more signals that are indicative of a reaction between said reagents and said nucleic acid molecules of said first array or said second array; and (e) based at least in part on (i) said one or more signals and (ii) locations, from said first region and said second region, from which said one or more signals are detected, analyzing said first nucleic acid sample and said second nucleic acid sample, and determining (1) a first subset of said nucleic acid molecules of said first array or said second array as originating from said first nucleic acid sample and (2) a second subset of said nucleic acid molecules of said first array or said second array as originating from said second nucleic acid sample. 62. The method of embodiment 61, wherein said nucleic acid samples comprise nucleic acid molecules affixed to beads. 63. The method of embodiment 61, wherein said determining in (e) is performed without determining a barcode sequence of said nucleic acid molecules of said first array or said second array. 64. The method of embodiment 63, wherein said first set of nucleic acid molecules and said second set of nucleic acid molecules do not have a barcode sequence indicative of an originating nucleic acid sample. 65. The method of embodiment 61, wherein said first region and said second region are on a same surface of said substrate. 66. The method of embodiment 61, wherein said analyzing in (e) comprises sequencing said nucleic acid molecules of said first array or said second array. 67. The method of embodiment 66, wherein said solution comprises reagents sufficient to incorporate at least one nucleotide into a growing nucleic acid strand that is complementary to a nucleic acid molecule of said nucleic acid molecules of said first array or said second array. 68. The method of embodiment 67, further comprising repeating (c)-(e) with various nucleotides in said solution to provide sequence information for said nucleic acid molecules. 69. The method of embodiment 61, wherein said plurality of nucleic acid samples comprises n number of nucleic acid samples, and (b) comprises loading said n number of nucleic acid samples to n number of separate regions of said substrate. 70. The method of embodiment 69, wherein n is at least 3. 71. The method of embodiment 69, wherein n is at least 5. 72. The method of embodiment 69, wherein n is at least 10. 73. The method of embodiment 61, wherein said first nucleic acid sample or said second nucleic acid sample comprises 1000 nucleic acid molecules. 74. The method of embodiment 73, wherein said first nucleic acid sample or said second nucleic acid sample comprises 10,000 nucleic acid molecules. 75. The method of embodiment 74, wherein said first nucleic acid sample or said second nucleic acid sample comprises 100,000 nucleic acid molecules. 76. The method of embodiment 61, wherein (b) comprises depositing said first nucleic acid sample to said substrate from a dispenser through an air gap. 77. The method of embodiment 61, wherein (b) comprises depositing said first nucleic acid sample to said substrate through a closed flow cell. 78. The method of embodiment 61, wherein said first region and said second region have different sizes. 79. The method of embodiment 61, wherein said first region and said second region have the same size. 80. The method of embodiment 61, wherein said first region and said second region comprise different numbers of individually addressable locations on said substrate. 81. The method of embodiment 61, wherein said first region and said second region comprise the same number of individually addressable locations on said substrate. 82. The method of embodiment 61, wherein, subsequent to (b), said first set of nucleic acid molecules is attached to a plurality of beads, which plurality of beads is immobilized to said substrate 83. The method of embodiment 82, wherein a bead of said plurality of beads comprises a plurality of nucleic acid molecules attached thereto, wherein said plurality of nucleic acid molecules comprises a colony of nucleic acid molecules. 84. The method of embodiment 83, wherein said colony of nucleic acid molecules are amplification products derived from a nucleic acid molecule of said first set of nucleic acid molecules. 85. The method of embodiment 83, wherein said plurality of nucleic acid molecules are attached to said bead prior to (b), and (b) comprises dispensing said plurality of beads to said substrate. 86. The method of embodiment 82, wherein, subsequent to (b), said second set of nucleic acid molecules is attached to a second plurality of beads, which second plurality of beads is immobilized to said substrate 87. The method of embodiment 61, wherein said substrate comprises a plurality of individually addressable locations. 88. The method of embodiment 87, wherein an individually addressable location of said plurality of individually addressable locations is configured to associate with a nucleic acid molecule of said nucleic acid molecules of said first array or said second array. 89. The method of embodiment 88, wherein said individually addressable location is configured to associate with a bead, wherein said bead comprises said nucleic acid molecule attached thereto. 90.

The method of embodiment 89, wherein said bead comprises a plurality of nucleic acid molecules, including said nucleic acid molecule, attached thereto. 91. The method of embodiment 90, wherein said plurality of nucleic acid molecules comprises a colony of nucleic acid molecules that are amplification products derived from said nucleic acid molecule. 92. The method of embodiment 89, wherein said first set of nucleic acid molecules are attached to a first plurality of beads and wherein said second set of nucleic acid molecules are attached to a second plurality of beads, wherein said first plurality of beads and said second plurality of beads are associated to said plurality of individually addressable locations. 93. The method of embodiment 92, wherein said first plurality of beads and said second plurality of beads are distinguishable. 94. The method of embodiment 93, wherein said first plurality of beads and said second plurality of beads emit a different wavelength of signals. 95. The method of embodiment 93, wherein said first plurality of beads and said second plurality of beads emit a different intensity of signals. 96. The method of embodiment 92, further comprising, subsequent to (b), subjecting individually addressable locations unassociated with said first plurality of beads and said second plurality of beads to conditions sufficient to disallow association of subsequent sample beads to said individually addressable locations unassociated with said first plurality of beads and said second plurality of beads. 97. The method of embodiment 96, further comprising, subsequent to (b), contacting said substrate with a plurality of blank beads such that individually addressable locations unassociated with said first plurality of beads and said second plurality of beads are associated with blank beads. 98. The method of embodiment 97, wherein said plurality of blank beads has a higher affinity for said plurality of individually addressable locations than said first plurality of beads or said second plurality of beads. 99. The method of embodiment 61, wherein said first nucleic acid sample and said second nucleic acid sample are distinguishable by a fluorescent dye. 100. The method of embodiment 61, wherein said nucleic acid molecules each comprise a synthetic sequence of no more than 6 bases in length. 101. The method of embodiment 100, wherein said synthetic sequence is no more than 4 bases in length. 102. The method of embodiment 101, wherein said synthetic sequence is no more than 2 bases in length. 103. The method of embodiment 102, wherein said synthetic sequence is no more than 1 base in length. 104. The method of embodiment 100, wherein a total number of said nucleic acid molecules is greater than a total number of unique synthetic sequences. 105. The method of embodiment 100, wherein a subset of nucleic acid molecules originating from the same nucleic acid sample of said plurality of nucleic acid samples each comprise a common synthetic sequence, which common synthetic sequence is different from synthetic sequences of another subset of nucleic acid molecules originating from a different nucleic acid sample. 106. The method of embodiment 61, further comprising rotating said substrate with respect to a reference axis of said substrate. 107. The method of embodiment 106, wherein said rotating is performed subsequent to said dispersing in (c). 108. The method of embodiment 106, wherein said rotating is performed during said dispersing in (c). 109. The method of embodiment 106, wherein said rotating is performed prior to said dispersing in (c). 110. The method of embodiment 106, wherein said dispersing in (c) comprises movement of said solution from a first location on said substrate to a second location on said substrate due to centrifugal forces from said rotating, wherein said first location and said second location have different radial distances from said reference axis. 111. The method of embodiment 106, wherein said first region and said second region are disposed at least 1 millimeter (mm) distance from said reference axis on said substrate. 112. The method of embodiment 111, wherein said first region and said second region are disposed at least 1 centimeter (cm) distance from said reference axis on said substrate. 113. The method of embodiment 61, wherein said first region and said second region are arranged radially around said substrate with respect to a central axis of said substrate. 114. The method of embodiment 113, wherein said substrate comprises a plurality of radially alternating regions, including said first region and said second region, wherein said plurality of radially alternating regions comprises a first set of regions of a first type and a second set of regions of a second type. 115. The method of embodiment 113, wherein said first set of regions are chemically distinct form said second set of regions. 116. The method of embodiment 113, wherein said first set of regions and said second set of regions are separated by barriers. 117. The method of embodiment 113, wherein said first set of regions and said second type of regions are distinguishable only by nucleic acid samples loaded on said first set of regions and said second set of regions. 118. The method of embodiment 61, wherein said first region and said second region are directly adjacent. 119. The method of embodiment 61, wherein said first region and said second region are separated by another region on said substrate. 120. The method of embodiment 61, wherein said first region and said second region overlap. 121. The method of embodiment 61, wherein in (e) said first subset and said second subset does not include a third subset of said nucleic acid molecules of said first array or said second array that is located proximate to within 0.5 millimeter (mm) of a border of said first region and said second region. 122. The method of embodiment 61, wherein (b) is performed in a first station different from a second station in which (c) or (d) is performed. 123. The method of embodiment 61, wherein said substrate comprises a physical demarcation, wherein said physical demarcation is used as a reference to spatially index said substrate. 124. The method of embodiment 123, wherein said demarcation comprises one or more of an indentation, notch, physical feature, dye, and ink on said substrate. 125. The method of embodiment 123, wherein said demarcation comprises a control nucleic acid sample. 126. The method of embodiment 61, wherein said first region and said second region are separated by a barrier on said substrate 127. The method of embodiment 126, wherein said barrier remains fixed to said substrate during (c) or (d). 128. The method of embodiment 127, wherein said barrier remains fixed to said substrate during (c) and (d). 129. The method of embodiment 126, wherein said barrier is removable. 130. The method of embodiment 129, further comprising removing said barrier subsequent to (b). 131. The method of embodiment 130, wherein said barrier dissolves. 132. The method of embodiment 130, wherein said barrier evaporates. 133. The method of embodiment 130, wherein said barrier sublimes. 134. The method of embodiment 130, wherein said barrier melts. 135. The method of embodiment 126, wherein said barrier comprises an injection molded guide. 136. The method of embodiment 126, wherein said barrier comprises polyethylene glycol (PEG). 137. The method of embodiment 126, wherein said barrier comprises a viscous solution. 138. The method of embodiment 137, wherein said viscosity varies in proportion to temperature. 139. The method of embodiment 126, wherein said barrier comprises a fluid that is immiscible with a loading solution comprising said first nucleic acid sample and said second nucleic acid sample. 140. The method of embodiment 126, wherein said barrier comprises a hydrophobic region, and wherein said first region and said second region comprise hydrophilic regions. 141. The method of embodiment 126, wherein said barrier comprises an air knife. 142. The method of embodiment 61, wherein prior to (b), said substrate is masked with one or more masks such that said substrate comprises a subset of one or more masked regions and a subset of one or more unmasked regions, wherein said subset of one or more unmasked regions comprises said first region and said second region. 143. The method of embodiment 142, further comprising, prior to (b) masking said substrate with said one or more masks. 144. The method of embodiment 142, further comprising, subsequent to (b), unmasking said substrate from said one or more masks, and loading a third nucleic acid sample onto a third region of said one or more masked regions. 145. The method of embodiment 61, wherein (b) comprises (i) masking said substrate with said one or more masks such that said substrate comprises a subset of one or more masked regions and a subset of one or more unmasked regions, wherein said subset of one or more unmasked regions comprises said first region and said subset of one or more masked regions comprises said second region; (ii) loading said first nucleic acid sample; (iii) unmasking said substrate from said one or more masks; and (iv) loading said second nucleic acid sample 146. The method of embodiment 61, wherein (b) comprises contacting said substrate with a first loading fluid comprising said first nucleic acid sample and a second loading fluid comprising said second nucleic acid sample, wherein said first loading fluid and said second loading fluid are immiscible. 147. The method of embodiment 61, wherein (b) comprises loading said first nucleic acid sample and said second nucleic acid sample simultaneously 148. The method of embodiment 61, wherein (b) comprises loading said first nucleic acid sample and said second nucleic acid sample at discrete times 149. The method of embodiment 148, wherein said first nucleic acid sample is loaded prior to loading of said second nucleic acid sample. 150. The method of embodiment 149, wherein said substrate is dried between loading of said first nucleic acid sample and said second nucleic acid sample. 151. The method of embodiment 61, wherein (b) comprises applying a magnetic field to direct said first nucleic acid sample to said substrate. 152. The method of embodiment 151, wherein said magnetic field is applied by one or more magnets. 153. The method of embodiment 151, wherein said first set of nucleic acid molecules are attached to a plurality of magnetic beads. 154. The method of embodiment 151, wherein a loading fluid comprising said first nucleic acid sample comprises a ferrofluid. 155. The method of embodiment 61, further comprising, prior to (b), activating said first region or said second region for loading using temperature. 156. The method of embodiment 61, further comprising, prior to (b), activating said first region or said second region for loading using electromagnetic radiation. 157. The method of embodiment 61, wherein said first region attracts said first nucleic acid sample. 158. The method of embodiment 61, wherein said second region repels said first nucleic acid sample. 159. The method of embodiment 61, wherein said substrate comprises a third region that repels said first nucleic acid sample. 160. The method of embodiment 61, further comprising, subsequent to (b), washing nucleic acid molecules unassociated with said first region or said second region from said substrate 161. The method of embodiment 160, wherein said washing comprises aspirating 162. A method for processing a plurality of nucleic acid samples, comprising: (a) providing said plurality of nucleic acid samples, wherein said plurality of nucleic acid samples comprises a first nucleic acid sample comprising a first set of nucleic acid molecules and a second nucleic acid sample comprising a second set of nucleic acid molecules; (b) loading said first nucleic acid sample onto a substrate to associate said first set of nucleic acid molecules to a first array of individually addressable locations; (c) imaging said substrate to identify said first array of individually addressable locations; (d) loading said second nucleic acid sample onto a substrate to associate said second set of nucleic acid molecules to a second array of individually addressable locations; (e) imaging said substrate to identify said second array of individually addressable locations; (f) dispersing a solution across said substrate, wherein said solution comprises reagents sufficient to react with nucleic acid molecules of said first array or said second array; (g) detecting one or more signals that are indicative of a reaction between said reagents and said nucleic acid molecules of said first array or said second array; and (h) based at least in part on (i) said one or more signals and (ii) locations, from said first array of individually addressable locations and said second array of individually addressable locations, from which said one or more signals are detected, analyzing said first nucleic acid sample and said second nucleic acid sample, and determining (1) a first subset of said nucleic acid molecules of said first array or said second array as originating from said first nucleic acid sample and (2) a second subset of said nucleic acid molecules of said first array or said second array as originating from said second nucleic acid sample. 163. The method of embodiment 162, wherein said analyzing in (h) comprises sequencing said nucleic acid molecules of said first array or said second array 164. The method of embodiment 163, wherein said solution comprises reagents sufficient to incorporate at least one nucleotide into a growing nucleic acid strand that is complementary to a nucleic acid molecule of said nucleic acid molecules of said first array or said second array. 165. The method of embodiment 164, further comprising repeating (f)-(h) with various nucleotides in said solution to provide sequence information for said nucleic acid molecules. 166. The method of embodiment 162, wherein said plurality of nucleic acid samples comprises n number of nucleic acid samples, and (b) comprises loading said n number of nucleic acid samples to n number of separate regions of said substrate. 167. The method of embodiment 166, wherein n is at least 3. 168. The method of embodiment 166, wherein n is at least 5. 169. The method of embodiment 166, wherein n is at least 10. 170. The method of embodiment 162, wherein said first nucleic acid sample or said second nucleic acid sample comprises 1000 nucleic acid molecules. 171. The method of embodiment 170, wherein said first nucleic acid sample or said second nucleic acid sample comprises 10,000 nucleic acid molecules. 172. The method of embodiment 171, wherein said first nucleic acid sample or said second nucleic acid sample comprises 100,000 nucleic acid molecules. 173. The method of embodiment 162, wherein (b) comprises depositing said first nucleic acid sample to said substrate from a dispenser through an air gap. 174. The method of embodiment 162, wherein (b) comprises depositing said first nucleic acid sample to said substrate through a closed flow cell. 175. The method of embodiment 162, wherein said first array of individually addressable locations and said second array of individually addressable locations have different sizes. 176. The method of embodiment 162, wherein said first array of individually addressable locations and said second array of individually addressable locations have the same size. 177.

The method of embodiment 162, wherein said first array of individually addressable locations and said second array of individually addressable locations comprise different numbers of individually addressable locations on said substrate. 178. The method of embodiment 162, wherein said first array of individually addressable locations and said second array of individually addressable locations comprise the same number of individually addressable locations on said substrate. 179. The method of embodiment 162, wherein, subsequent to (b), said first set of nucleic acid molecules is attached to a plurality of beads, which plurality of beads is immobilized to said substrate 180. The method of embodiment 179, wherein a bead of said plurality of beads comprises a plurality of nucleic acid molecules attached thereto, wherein said plurality of nucleic acid molecules comprises a colony of nucleic acid molecules. 181. The method of embodiment 180, wherein said colony of nucleic acid molecules are amplification products derived from a nucleic acid molecule of said first set of nucleic acid molecules. 182. The method of embodiment 180, wherein said plurality of nucleic acid molecules are attached to said bead prior to (b), and (b) comprises dispensing said plurality of beads to said substrate. 183. The method of embodiment 179, wherein, subsequent to (b), said second set of nucleic acid molecules is attached to a second plurality of beads, which second plurality of beads is immobilized to said substrate 184. The method of embodiment 162, wherein said substrate comprises a plurality of individually addressable locations. 185. The method of embodiment 184, wherein an individually addressable location of said plurality of individually addressable locations is configured to associate with a nucleic acid molecule of said nucleic acid molecules of said first array or said second array. 186. The method of embodiment 185, wherein said individually addressable location is configured to associate with a bead, wherein said bead comprises said nucleic acid molecule attached thereto. 187. The method of embodiment 186, wherein said bead comprises a plurality of nucleic acid molecules, including said nucleic acid molecule, attached thereto. 188. The method of embodiment 187, wherein said plurality of nucleic acid molecules comprises a colony of nucleic acid molecules that are amplification products derived from said nucleic acid molecule. 189. The method of embodiment 186, wherein said first set of nucleic acid molecules are attached to a first plurality of beads and wherein said second set of nucleic acid molecules are attached to a second plurality of beads, wherein said first plurality of beads and said second plurality of beads are associated to said plurality of individually addressable locations. 190. The method of embodiment 189, wherein said first plurality of beads and said second plurality of beads are distinguishable. 191. The method of embodiment 190, wherein said first plurality of beads and said second plurality of beads emit a different wavelength of signals. 192. The method of embodiment 190, wherein said first plurality of beads and said second plurality of beads emit a different intensity of signals. 193. The method of embodiment 189, further comprising, subsequent to (b), subjecting individually addressable locations unassociated with said first plurality of beads and said second plurality of beads to conditions sufficient to disallow association of subsequent sample beads to said individually addressable locations unassociated with said first plurality of beads and said second plurality of beads. 194. The method of embodiment 189, further comprising, subsequent to (b), contacting said substrate with a plurality of blank beads such that individually addressable locations unassociated with said first plurality of beads and said second plurality of beads are associated with blank beads. 195. The method of embodiment 190, wherein said plurality of blank beads has a higher affinity for said plurality of individually addressable locations than said first plurality of beads or said second plurality of beads. 196. The method of embodiment 162, wherein said first nucleic acid sample and said second nucleic acid sample are distinguishable by a fluorescent dye. 197. The method of embodiment 162, wherein said nucleic acid molecules each comprise a synthetic sequence of no more than 6 bases in length. 198. The method of embodiment 197, wherein said synthetic sequence is no more than 4 bases in length. 199. The method of embodiment 198, wherein said synthetic sequence is no more than 2 bases in length. 200. The method of embodiment 199, wherein said synthetic sequence is no more than 1 base in length. 201. The method of embodiment 197, wherein a total number of said nucleic acid molecules is greater than a total number of unique synthetic sequences. 202. The method of embodiment 197, wherein a subset of nucleic acid molecules originating from the same nucleic acid sample of said plurality of nucleic acid samples each comprise a common synthetic sequence, which common synthetic sequence is different from synthetic sequences of another subset of nucleic acid molecules originating from a different nucleic acid sample. 203. The method of embodiment 162, further comprising rotating said substrate with respect to a reference axis of said substrate. 204. The method of embodiment 203, wherein said rotating is performed subsequent to said dispersing in (f). 205. The method of embodiment 203, wherein said rotating is performed during said dispersing in (f). 206. The method of embodiment 203, wherein said rotating is performed prior to said dispersing in (f). 207. The method of embodiment 203, wherein said dispersing in (f) comprises movement of said solution from a first location on said substrate to a second location on said substrate due to centrifugal forces from said rotating, wherein said first location and said second location have different radial distances from said reference axis. 208. The method of embodiment 203, wherein said first array of individually addressable locations and said second array of individually addressable locations are disposed at least 1 millimeter (mm) distance from said reference axis on said substrate. 209. The method of embodiment 208, wherein said first array of individually addressable locations and said second array of individually addressable locations are disposed at least 1 centimeter (cm) distance from said reference axis on said substrate. 210. The method of embodiment 162, wherein said first array of individually addressable locations and said second array of individually addressable locations are arranged radially around said substrate with respect to a central axis of said substrate. 211. The method of embodiment 210, wherein said substrate comprises a plurality of radially alternating arrays of individually addressable locations, including said first array of individually addressable locations and said second array of individually addressable locations, wherein said plurality of radially alternating arrays of individually addressable locations comprises a first set of regions of a first type and a second set of regions of a second type. 212. The method of embodiment 210, wherein said first set of regions are chemically distinct form said second set of regions. 213. The method of embodiment 210, wherein said first set of regions and said second set of regions are separated by barriers. 214. The method of embodiment 210, wherein said first set of regions and said second type of regions are distinguishable only by nucleic acid samples loaded on said first set of regions and said second set of regions. 215. The method of embodiment 162, wherein said first array of individually addressable locations and said second array of individually addressable locations are directly adjacent. 216. The method of embodiment 162, wherein said first array of individually addressable locations and said second array of individually addressable locations are separated by another array of individually addressable locations on said substrate. 217. The method of embodiment 162, wherein said first array of individually addressable locations and said second array of individually addressable locations overlap. 218. The method of embodiment 162, wherein in (h) said first subset and said second subset does not include a third subset of said nucleic acid molecules of said first array or said second array that is located proximate to within 0.5 millimeter (mm) of a border of said first array of individually addressable locations and said second array of individually addressable locations. 219. The method of embodiment 162, wherein (b) is performed in a first station different from a second station in which (f) or (g) is performed. 220. The method of embodiment 162, wherein said substrate comprises a physical demarcation, wherein said physical demarcation is used as a reference to spatially index said substrate. 221. The method of embodiment 220, wherein said demarcation comprises one or more of an indentation, notch, physical feature, dye, and ink on said substrate. 222. The method of embodiment 220, wherein said demarcation comprises a control nucleic acid sample. 223. The method of embodiment 162, wherein said first array of individually addressable locations and said second array of individually addressable locations are separated by a barrier on said substrate 224. The method of embodiment 223, wherein said barrier remains fixed to said substrate during (f) or (g). 225. The method of embodiment 224, wherein said barrier remains fixed to said substrate during (f) and (g). 226. The method of embodiment 223, wherein said barrier is removable. 227. The method of embodiment 226, further comprising removing said barrier subsequent to (b). 228. The method of embodiment 227, wherein said barrier dissolves. 229. The method of embodiment 227, wherein said barrier evaporates. 230. The method of embodiment 227, wherein said barrier sublimes. 231. The method of embodiment 227, wherein said barrier melts. 232. The method of embodiment 223, wherein said barrier comprises an injection molded guide. 233. The method of embodiment 223, wherein said barrier comprises polyethylene glycol (PEG). 234. The method of embodiment 223, wherein said barrier comprises a viscous solution. 235. The method of embodiment 234, wherein said viscosity varies in proportion to temperature. 236. The method of embodiment 223, wherein said barrier comprises a fluid that is immiscible with a loading solution comprising said first nucleic acid sample and said second nucleic acid sample. 237. The method of embodiment 223, wherein said barrier comprises a hydrophobic region, and wherein said first region and said second region comprise hydrophilic regions. 238. The method of embodiment 223, wherein said barrier comprises an air knife. 239. The method of embodiment 162, wherein prior to (b), said substrate is masked with one or more masks such that said substrate comprises a subset of one or more masked regions and a subset of one or more unmasked regions, wherein said subset of one or more unmasked regions comprises said first array of individually addressable locations and said second array of individually addressable locations. 240. The method of embodiment 239, further comprising, prior to (b) masking said substrate with said one or more masks. 241. The method of embodiment 239, further comprising, subsequent to (b), unmasking said substrate from said one or more masks, and loading a third nucleic acid sample onto a third array of individually addressable locations of said one or more masked regions. 242. The method of embodiment 162, wherein (b) comprises (i) masking said substrate with said one or more masks such that said substrate comprises a subset of one or more masked regions and a subset of one or more unmasked regions, wherein said subset of one or more unmasked regions comprises said first array of individually addressable locations and said subset of one or more masked regions comprises said second array of individually addressable locations; (ii) loading said first nucleic acid sample; (iii) unmasking said substrate from said one or more masks; and (iv) loading said second nucleic acid sample 243. The method of embodiment 162, wherein (b) comprises contacting said substrate with a first loading fluid comprising said first nucleic acid sample and a second loading fluid comprising said second nucleic acid sample, wherein said first loading fluid and said second loading fluid are immiscible. 244. The method of embodiment 162, wherein (b) comprises loading said first nucleic acid sample and said second nucleic acid sample simultaneously 245. The method of embodiment 162, wherein (b) comprises loading said first nucleic acid sample and said second nucleic acid sample at discrete times 246. The method of embodiment 245, wherein said first nucleic acid sample is loaded prior to loading of said second nucleic acid sample. 247. The method of embodiment 246, wherein said substrate is dried between loading of said first nucleic acid sample and said second nucleic acid sample. 248. The method of embodiment 162, wherein (b) comprises applying a magnetic field to direct said first nucleic acid sample to said substrate. 249. The method of embodiment 248, wherein said magnetic field is applied by one or more magnets. 250. The method of embodiment 248, wherein said first set of nucleic acid molecules are attached to a plurality of magnetic beads. 251. The method of embodiment 248, wherein a loading fluid comprising said first nucleic acid sample comprises a ferrofluid. 252. The method of embodiment 162, further comprising, prior to (b), activating said first array of individually addressable locations or said second array of individually addressable locations for loading using temperature. 253. The method of embodiment 162, further comprising, prior to (b), activating said first array of individually addressable locations or said second array of individually addressable locations for loading using electromagnetic radiation. 254. The method of embodiment 162, wherein said first array of individually addressable locations attracts said first nucleic acid sample. 255. The method of embodiment 162, wherein said array of individually addressable locations repels said first nucleic acid sample. 256. The method of embodiment 162, wherein said substrate comprises a third array of individually addressable locations that repels said first nucleic acid sample. 257. The method of embodiment 162, further comprising, subsequent to (b), washing nucleic acid molecules unassociated with said first array of individually addressable locations or said second array of individually addressable locations from said substrate. 258. The method of embodiment 257, wherein said washing comprises aspirating. 259. A method for processing a plurality of nucleic acid samples, comprising: (a) providing said plurality of nucleic acid samples, wherein each of said plurality of nucleic acid samples comprises a fluorescent dye; (b) separating said plurality of nucleic acid samples into a first set of one or more samples and a second set of one or more samples; (c) loading said first set of one or more samples onto a first set of regions on a substrate, with one sample per region in said first set of regions; (d) imaging said substrate to identify (i) locations within said first set of regions and (ii)

locations within a second set of regions on said substrate, wherein said second set of regions are different from said first set of regions, where said first set of one or more samples are associated; (e) loading said second set of one or more samples onto said second set of regions on a substrate, with one sample per region in said second set of regions; (f) imaging said substrate to identify (i) locations within said first set of regions and (ii) locations within said second set of regions where said second set of one or more samples are associated; (g) dispersing a solution across said substrate, wherein said solution comprises reagents sufficient to react with nucleic acid molecules of said first set of one or more samples or said second set of one or more samples; (h) detecting one or more signals that are indicative of a reaction between said reagents and said nucleic acid molecules; and (i) based at least in part on (i) said one or more signals and (ii) locations, from said first set of regions and said second set of regions, from which said one or more signals are detected, analyzing said each of said plurality of nucleic acid samples. 260. The method of embodiment 259, wherein said fluorescent dye is attached to a sequencing primer of a nucleic acid molecule of said each of said plurality of nucleic acid samples. 261. The method of embodiment 259, further comprising (j) loading a primer comprising a label to said substrate, (ii) subjecting a nucleic acid molecule of said plurality of nucleic acid samples to conditions sufficient to interact with said primer, and (iii) detecting a presence of said nucleic acid molecule using said label. 262. The method of embodiment 259, wherein said analyzing in (i) comprises sequencing said nucleic acid molecules of said first set of regions or said second set of regions. 263. The method of embodiment 262, wherein said solution comprises reagents sufficient to incorporate at least one nucleotide into a growing nucleic acid strand that is complementary to a nucleic acid molecule of said nucleic acid molecules of said first set of regions or said second set of regions. 264. The method of embodiment 263, further comprising repeating (g)-(i) with various nucleotides in said solution to provide sequence information for said nucleic acid molecules. 265. The method of embodiment 259, wherein said plurality of nucleic acid samples comprises n number of nucleic acid samples, and (c) comprises loading said n number of nucleic acid samples to n number of separate regions of said substrate. 266. The method of embodiment 265, wherein n is at least 3. 267. The method of embodiment 265, wherein n is at least 5. 268. The method of embodiment 265, wherein n is at least 10 269. The method of embodiment 259, wherein said nucleic acid sample comprises 1000 nucleic acid molecules. 270. The method of embodiment 269, wherein said nucleic acid sample comprises 10,000 nucleic acid molecules. 271. The method of embodiment 270, wherein said nucleic acid comprises 100,000 nucleic acid molecules. 272. The method of embodiment 259, wherein (c) comprises depositing said first set of one or more samples to said substrate from a dispenser through an air gap. 273. The method of embodiment 259, wherein (c) comprises depositing said first set of one or more samples to said substrate through a closed flow cell. 274. The method of embodiment 259, wherein said first set of regions and said second set of regions comprise different numbers of individually addressable locations on said substrate. 275. The method of embodiment 259, wherein said first set of regions and said second set of regions comprise the same number of individually addressable locations on said substrate. 276. The method of embodiment 259, wherein, subsequent to (c), said first set of one or more samples is attached to a plurality of beads, which plurality of beads is immobilized to said substrate 277. The method of embodiment 276, wherein a bead of said plurality of beads comprises a plurality of nucleic acid molecules attached thereto, wherein said plurality of nucleic acid molecules comprises a colony of nucleic acid molecules. 278. The method of embodiment 277, wherein said colony of nucleic acid molecules are amplification products derived from a nucleic acid molecule of said first set of nucleic acid molecules. 279. The method of embodiment 277, wherein said plurality of nucleic acid molecules are attached to said bead prior to (c), and (c) comprises dispensing said plurality of beads to said substrate. 280. The method of embodiment 276, wherein, subsequent to (c), said second set of nucleic acid molecules is attached to a second plurality of beads, which second plurality of beads is immobilized to said substrate 281. The method of embodiment 259, wherein said substrate comprises a plurality of individually addressable locations. 282. The method of embodiment 281, wherein an individually addressable location of said plurality of individually addressable locations is configured to associate with a nucleic acid molecule of said nucleic acid molecules of said first array or said second array. 283. The method of embodiment 282, wherein said individually addressable location is configured to associate with a bead, wherein said bead comprises said nucleic acid molecule attached thereto. 284. The method of embodiment 283, wherein said bead comprises a plurality of nucleic acid molecules, including said nucleic acid molecule, attached thereto. 285. The method of embodiment 284, wherein said plurality of nucleic acid molecules comprises a colony of nucleic acid molecules that are amplification products derived from said nucleic acid molecule. 286. The method of embodiment 283, wherein said first set of nucleic acid molecules are attached to a first plurality of beads and wherein said second set of nucleic acid molecules are attached to a second plurality of beads, wherein said first plurality of beads and said second plurality of beads are associated to said plurality of individually addressable locations. 287. The method of embodiment 286, wherein said first plurality of beads and said second plurality of beads are distinguishable. 288. The method of embodiment 287, wherein said first plurality of beads and said second plurality of beads emit a different wavelength of signals. 289. The method of embodiment 287, wherein said first plurality of beads and said second plurality of beads emit a different intensity of signals. 290. The method of embodiment 286, further comprising, subsequent to (c), subjecting individually addressable locations unassociated with said first plurality of beads and said second plurality of beads to conditions sufficient to disallow association of subsequent sample beads to said individually addressable locations unassociated with said first plurality of beads and said second plurality of beads. 291. The method of embodiment 286, further comprising, subsequent to (c), contacting said substrate with a plurality of blank beads such that individually addressable locations unassociated with said first plurality of beads and said second plurality of beads are associated with blank beads. 292. The method of embodiment 287, wherein said plurality of blank beads has a higher affinity for said plurality of individually addressable locations than said first plurality of beads or said second plurality of beads. 293. The method of embodiment 259, wherein said first nucleic acid sample and said second nucleic acid sample are distinguishable by a fluorescent dye. 294. The method of embodiment 259, wherein said nucleic acid molecules each comprise a synthetic sequence of no more than 6 bases in length. 295. The method of embodiment 294, wherein said synthetic sequence is no more than 4 bases in length. 296.

The method of embodiment 295, wherein said synthetic sequence is no more than 2 bases in length. 297. The method of embodiment 296, wherein said synthetic sequence is no more than 1 base in length. 298. The method of embodiment 294, wherein a total number of said nucleic acid molecules is greater than a total number of unique synthetic sequences. 299. The method of embodiment 294, wherein a subset of nucleic acid molecules originating from the same nucleic acid sample of said plurality of nucleic acid samples each comprise a common synthetic sequence, which common synthetic sequence is different from synthetic sequences of another subset of nucleic acid molecules originating from a different nucleic acid sample. 300. The method of embodiment 259, further comprising rotating said substrate with respect to a reference axis of said substrate. 301. The method of embodiment 300, wherein said rotating is performed subsequent to said dispersing in (g). 302. The method of embodiment 300, wherein said rotating is performed during said dispersing in (g). 303. The method of embodiment 300, wherein said rotating is performed prior to said dispersing in (g). 304. The method of embodiment 300, wherein said dispersing in (g) comprises movement of said solution from a first location on said substrate to a second location on said substrate due to centrifugal forces from said rotating, wherein said first location and said second location have different radial distances from said reference axis. 305. The method of embodiment 300, wherein said first set of regions and said second set of regions are disposed at least 1 millimeter (mm) distance from said reference axis on said substrate. 306. The method of embodiment 305, wherein said first set of regions and said second set of regions are disposed at least 1 centimeter (cm) distance from said reference axis on said substrate. 307. The method of embodiment 259, wherein said first set of regions and said second set of regions are arranged radially around said substrate with respect to a central axis of said substrate. 308. The method of embodiment 307, wherein said substrate comprises a plurality of radially alternating arrays of individually addressable locations, including said first set of regions and said second set of regions, wherein said plurality of radially alternating arrays of individually addressable locations comprises a first set of regions of a first type and a second set of regions of a second type. 309. The method of embodiment 307, wherein said first set of regions are chemically distinct form said second set of regions. 310. The method of embodiment 307, wherein said first set of regions and said second set of regions are separated by barriers. 311. The method of embodiment 307, wherein said first set of regions and said second type of regions are distinguishable only by nucleic acid samples loaded on said first set of regions and said second set of regions. 312. The method of embodiment 259, wherein said first region and said second region are directly adjacent. 313. The method of embodiment 259, wherein said first region and said second region are separated by another region on said substrate. 314. The method of embodiment 259, wherein said first region and said second region overlap. 315. The method of embodiment 259, wherein (e) is performed in a first station different from a second station in which (g) or (h) is performed. 316. The method of embodiment 259, wherein said substrate comprises a physical demarcation, wherein said physical demarcation is used as a reference to spatially index said substrate. 317. The method of embodiment 316, wherein said demarcation comprises one or more of an indentation, notch, physical feature, dye, and ink on said substrate. 318. The method of embodiment 316, wherein said demarcation comprises a control nucleic acid sample. 319. The method of embodiment 259, wherein said first region and said second region are separated by a barrier on said substrate 320. The method of embodiment 319, wherein said barrier remains fixed to said substrate during (g) or (h). 321. The method of embodiment 320, wherein said barrier remains fixed to said substrate during (g) and (h). 322. The method of embodiment 319, wherein said barrier is removable. 323. The method of embodiment 320, further comprising removing said barrier subsequent to (g). 324. The method of embodiment 321, wherein said barrier dissolves. 325. The method of embodiment 321, wherein said barrier evaporates. 326. The method of embodiment 321, wherein said barrier sublimes. 327. The method of embodiment 321, wherein said barrier melts. 328. The method of embodiment 319, wherein said barrier comprises an injection molded guide. 329. The method of embodiment 319, wherein said barrier comprises polyethylene glycol (PEG). 330. The method of embodiment 319, wherein said barrier comprises a viscous solution. 331. The method of embodiment 330, wherein said viscosity varies in proportion to temperature. 332. The method of embodiment 319, wherein said barrier comprises a fluid that is immiscible with a loading solution comprising said first set of one or more samples and said second nucleic acid sample. 333. The method of embodiment 319, wherein said barrier comprises a hydrophobic region, and wherein said first region and said second region comprise hydrophilic regions. 334. The method of embodiment 319, wherein said barrier comprises an air knife. 335. The method of embodiment 259, wherein prior to (g), said substrate is masked with one or more masks such that said substrate comprises a subset of one or more masked regions and a subset of one or more unmasked regions, wherein said subset of one or more unmasked regions comprises said first region and said second region. 336. The method of embodiment 335, further comprising, prior to (g) masking said substrate with said one or more masks. 337. The method of embodiment 334, further comprising, subsequent to (g), unmasking said substrate from said one or more masks, and loading a third set of one or more samples onto a third region of said one or more masked regions. 338. The method of embodiment 259, wherein (g) comprises (i) masking said substrate with said one or more masks such that said substrate comprises a subset of one or more masked regions and a subset of one or more unmasked regions, wherein said subset of one or more unmasked regions comprises said first region and said subset of one or more masked regions comprises said second region; (ii) loading said first set of one or more samples; (iii) unmasking said substrate from said one or more masks; and (iv) loading said second set of one or more samples. 339. The method of embodiment 259, wherein (g) comprises contacting said substrate with a first loading fluid comprising said first set of one or more samples and a second loading fluid comprising said second set of one or more samples, wherein said first loading fluid and said second loading fluid are immiscible. 340. The method of embodiment 259, wherein (g) comprises loading said first set of one or more samples and said second set of one or more samples simultaneously 341. The method of embodiment 259, wherein (g) comprises loading said first set of one or more samples and said second set of one or more samples at discrete times 342. The method of embodiment 341, wherein said first set of one or more samples is loaded prior to loading of said second set of one or more samples. 343. The method of embodiment 342, wherein said substrate is dried between loading of said first set of one or more samples and said second set of one or more samples. 344. The method of embodiment 259, wherein (g) comprises applying a magnetic field to direct said first set of one or more samples to said substrate. 345. The method of embodiment 344, wherein said magnetic field is applied by one or more magnets. 346. The method of embodiment 344, wherein said first set of nucleic acid molecules are attached to a plurality of magnetic beads. 347. The method of embodiment 344, wherein a loading fluid comprising said first set of one or more samples comprises a ferrofluid. 348. The method of embodiment 259, further comprising, prior to (g), activating said first set of regions or said second set of regions for loading using temperature. 349. The method of embodiment 259, further comprising, prior to (g), activating said first set of regions or said second set of regions for loading using electromagnetic radiation. 350. The method of embodiment 259, wherein said first set of regions attracts said first set of one or more samples. 351. The method of embodiment 259, wherein said set of regions region repels said first set of one or more samples. 352. The method of embodiment 259, wherein said substrate comprises a third set of regions that repels said first set of one or more samples. 353. The method of embodiment 259, further comprising, subsequent to (g), washing nucleic acid molecules unassociated with said first set of regions or said second set of regions from said substrate. 354. The method of embodiment 353, wherein said washing comprises aspirating. 355. A method for processing a biological analyte, comprising: (a) moving a substrate through or along a reel, wherein a surface of said substrate comprises an array having immobilized thereto said biological analyte, wherein said; (b) bringing said surface of said substrate in contact with a reservoir comprising a solution, wherein said solution comprises a plurality of probes; (c) subjecting said biological analyte to conditions sufficient to conduct a reaction between a probe of said plurality of probes and said biological analyte, to couple said probe to said biological analyte; and (d) detecting one or more signals from said probe coupled to said biological analyte, thereby analyzing said biological analyte, wherein said substrate is substrate is moved through or along said reel through in the same direction for at least two consecutive cycles of (b)-(d). 356. The method of embodiment 355, further comprising using a recirculation tank. 357. The method of embodiment 355, wherein a dimension of said substrate corresponds to a size of a field of view of an imaging system used in (d). 358. The method of embodiment 355, wherein (a) is performed to bring said surface of said substrate in contact with said reservoir. 359. The method of embodiment 355, further comprising moving said substrate through or along a second reel. 360. The method of embodiment 355, further comprising bringing said surface of said substrate in contact with a second reservoir comprising a second solution. 361. The method of embodiment 360, wherein said second solution comprises a wash buffer. 362. The method of embodiment 360, wherein said second solution comprises a second probe, and the method further comprises subjecting said biological analyte to conditions sufficient to conduct a reaction between said second probe and said biological analyte, to couple said second probe to said biological analyte. 363. The method of embodiment 360, further comprising bringing said surface of said substrate in contact with n numbers of different reservoirs comprising n number of solutions. 364. The method of embodiment 355, further comprising repeating (b)-(d) during said moving in (a) with additional reservoirs comprising different solutions a number of times sufficient to complete an assay of said biological analyte. 365. The method of embodiment 364, wherein said biological analyte is a nucleic acid molecule, and said assay comprises determining a sequence of said nucleic acid molecule. 366. The method of embodiment 355, wherein said probe comprises an oligonucleotide molecule. 367. The method of embodiment 366, wherein said oligonucleotide molecule comprises 1 to 10 bases in length. 368. The method of embodiment 366, wherein said oligonucleotide molecule comprises 10 to 20 bases in length. 369. The method of embodiment 366, wherein said probe comprises a dibase probe. 370. The method of embodiment 355, wherein said probe is labeled. 371. The method of embodiment 355, wherein said biological analyte comprises a nucleic acid molecule. 372. The method of embodiment 371, wherein said analyzing comprises identifying a sequence of said nucleic acid molecule. 373. The method of embodiment 371, wherein said plurality of probes comprises a plurality of oligonucleotide molecules. 374. The method of embodiment 373, wherein (c) comprises conducting a complementarity binding reaction between said probe and said nucleic acid molecule to identify a presence of homology between said probe and said biological analyte. 375. The method of embodiment 371, wherein said plurality of probes comprises a plurality of nucleotides. 376. The method of embodiment 375, wherein (c) comprises subjecting said nucleic acid molecule to a primer extension reaction under conditions sufficient to incorporate at least one nucleotide from said plurality of nucleotides into a growing strand that is complementary to the nucleic acid molecule. 377. The method of embodiment 375, wherein said plurality of nucleotides comprises nucleotide analogs. 378. The method of embodiment 375, wherein said one or more signals are indicative of incorporation of at least one nucleotide. 379. The method of embodiment 355, wherein said detecting is conducted using a sensor that continuously scans said array. 380. The method of embodiment 379, wherein said sensor scans said array linearly. 381. The method of embodiment 355, further comprising using a pulling mechanism to move said substrate through or along said reel. 382. The method of embodiment 355, wherein said substrate is textured or patterned. 383. The method of embodiment 355, wherein said substrate is substantially planar. 384. The method of embodiment 355, wherein said array comprises a plurality of individually addressable locations, and wherein said biological analyte is disposed at an individually addressable location of said plurality of individually addressable locations. 385. The method of embodiment 384, wherein said biological analyte is attached to a bead, wherein said bead is immobilized to said individually addressable location. 386. A system for analyzing a biological analyte, comprising: a substrate comprising a biological analyte, wherein said substrate is maintained at or above a first temperature that is higher than an ambient temperature of an environment exposed to said substrate; and an optical imaging objective in optical communication with said substrate and exposed to said environment, wherein said optical imaging objective is subject to a temperature gradient between said first temperature of said substrate and said ambient temperature of said environment, wherein said optical imaging objective comprises a first optical element and a second optical element adjacent to said first optical element, wherein said second optical element is disposed farther from said substrate than said first optical element, wherein said first optical element is configured to be at least partially immersed in an immersion fluid in contact with said substrate, wherein said second optical element is in optical communication with said substrate through said first optical element, and wherein said first optical element is configured such that a second temperature of said second optical element is maintained at or below a predetermined threshold. 387. The system of embodiment 386, wherein said first optical element is a window configured to allow optical communication between said substrate and said second optical element. 388. The system of embodiment 387, wherein said window is substantially flat. 389. The system of embodiment 388, wherein said window is flat. 390. The system of embodiment 386, wherein said optical imaging objective comprises one or more spacers between optical elements, and an outer layer enclosing said optical elements of said optical imaging objective, and wherein a primary heat flux path from said substrate to said environment through said optical imaging objective comprises conductive heat transfer from said substrate to said immersion fluid to said first optical element to said one or more spacers to said outer layer, and convective heat transfer from said outer layer to said environment. 391. The system of embodiment 386, wherein said first temperature is at least 40 degrees Celsius. 392. The system of embodiment 386, wherein said first temperature is at least 50 degrees Celsius. 393. The system of embodiment 386, wherein said first temperature is about 50 degrees Celsius. 394. The system of embodiment 386, wherein said predetermined threshold is an ambient temperature. 395. The system of embodiment 386, wherein said predetermined threshold is at most 30 degrees Celsius. 396. The system of embodiment 386, wherein said predetermined threshold is at most 25 degrees Celsius. 397. The system of embodiment 386, wherein said predetermined threshold is about 20 degrees Celsius. 398. The system of embodiment 386, wherein at least 50% of said temperature gradient occurs within said first optical element. wherein at least 70% of said temperature gradient occurs within said first optical element. 399. The system of embodiment 398, wherein at least 90% of said temperature gradient occurs within said first optical element. 400. The system of embodiment 386, wherein at least a portion of said first optical element is at a temperature of at least 40 degrees Celsius. 401. The system of embodiment 386, wherein at least a portion of said first optical element is at a temperature of at least 50 degrees Celsius. 402. The system of embodiment 386, wherein at least a portion of said first optical element is at a temperature of about 50 degrees Celsius. 403. The system of embodiment 386, wherein at least a portion of said first optical element is at an ambient temperature. 404. The system of embodiment 386, wherein said first optical element is at a temperature of at most 30 degrees Celsius. 405. The system of embodiment 386, wherein said first optical element is at a temperature of at most 25 degrees Celsius. 406. The system of embodiment 386, wherein said first optical element is at a temperature of about 20 degrees Celsius. 407. The system of embodiment 386, wherein said immersion fluid is maintained at a third temperature such that said substrate is maintained at or above said first temperature and said second temperature of said second optical element is maintained at or below said predetermined threshold. 408. The system of embodiment 407, further comprising a fluid flow unit configured to replenish said immersion fluid in contact with said substrate and said first optical element to maintain said third temperature of a volume of said immersion fluid in contact with said substrate. 409. The system of embodiment 407, wherein said third temperature is at least 40 degrees Celsius. 410. The system of embodiment 407, wherein said third temperature is at least 50 degrees Celsius. 411. The system of embodiment 407, wherein said third temperature is about 50 degrees Celsius. 412. The system of embodiment 407, wherein said third temperature is within 5 degrees Celsius of said first temperature. 413. The system of embodiment 407, wherein said third temperature is an ambient temperature. 414. The system of embodiment 407, wherein said third temperature is at most 30 degrees Celsius. 415. The system of embodiment 407, wherein said third temperature is at most 25 degrees Celsius. 416. The system of embodiment 407, wherein said third temperature is at most 20 degrees Celsius. 417. The system of embodiment 386, wherein said optical imaging objective comprises an insulating spacer disposed between said first optical element and said second optical element, wherein said insulating spacer is configured to insulate heat transfer from said first optical element and said second optical element. 418. The system of embodiment 417, wherein said insulating spacer has a thermal resistance higher than a thermal resistance of said first optical element. 419. The system of embodiment 386, wherein said optical imaging objective comprises a cooling element configured to decrease temperature of an outer layer of said optical imaging objective. 420. The system of embodiment 386, further comprising a fluid flow unit configured to dispense said immersion fluid to said substrate. 421. The system of embodiment 420, wherein said fluid flow unit is configured to dispense said immersion fluid at a rate of less than about 1 milliliter per second. 422. The system of embodiment 421, further comprising a container configured to at least partially enclose said optical imaging objective with a cavity disposed between said optical imaging objective and a wall of said container, and a pressure unit configured to draw in a volume of said immersion fluid disposed outside said container into said container after said optical imaging objective is in contact with said immersion fluid. 423. The system of embodiment 422, wherein said dispensing unit is configured to replenish said immersion fluid in contact with said first optical element at a rate of at least 1 nanoliter per second. 424. The system of embodiment 420, wherein said dispensing unit is configured to dispense said immersion fluid to said substrate prior to bringing said optical imaging objective in contact with said immersion fluid. 425. The system of embodiment 424, further comprising a container configured to at least partially enclose said optical imaging objective with a cavity disposed between said optical imaging objective and a wall of said container, and a pressure unit configured to draw in a volume of said immersion fluid disposed outside said container into said container after said optical imaging objective is in contact with said immersion fluid. 426. The system of embodiment 386, further comprising a container configured to at least partially enclose said optical imaging objective, wherein a surface of said container interfaces said immersion fluid, wherein said surface is angled with respect to a surface of said first optical element that interfaces said immersion fluid 427. The system of embodiment 386, further comprising a casing that at least partially encloses said first optical element, wherein said casing comprises a cavity adjacent to said first optical element, wherein said cavity interfaces said immersion fluid and is configured to direct one or more bubbles in said immersion fluid away from said first optical element. 428. The system of embodiment 427, wherein said cavity is annular or surrounds said first optical element. 429. The system of embodiment 427, wherein said first optical element is substantially flat. 430. The system of embodiment 386, further comprising a movement unit operatively coupled to said substrate or said optical imaging objective, wherein said movement unit is configured to subject said substrate to movement relative to said optical imaging objective. 431. The system of embodiment 430, wherein said movement is in a vector that includes a vertical component that is substantially perpendicular to a plane of said substrate. 432. The system of embodiment 430, wherein said movement is in a vector that includes a horizontal component that is substantially parallel to a plane of said substrate. 433. The system of embodiment 430, wherein said movement is linear. 434. The system of embodiment 430, wherein said movement is non-linear. 435. The system of embodiment 430, wherein said movement unit is configured to subject said substrate to movement during dispensing of said immersion fluid to said substrate. 436. The system of embodiment 430, further comprising one or more computer processors operatively coupled to said optical imaging objective and said movement unit, wherein said one or more computer processors are individually or collectively programmed to (i) direct said movement unit to subject said substrate to movement relative to said optical imaging objective during detection of said substrate by said optical imaging objective, and (ii) use said optical imaging objective to detect one or more signals from said biological analyte. 437. A method for analyzing a biological analyte, comprising: (a) providing a substrate comprising a biological analyte, wherein said substrate is at a first temperature that is higher than an ambient temperature of an environment exposed to said substrate; (b) providing an optical imaging objective in optical communication with said substrate and exposed to an environment, wherein said optical imaging objective is subject to a temperature gradient between said first temperature of said substrate and said ambient temperature of said environment, wherein said optical imaging objective comprises a first optical element and a second optical element adjacent to said first optical element, wherein said second optical element is disposed farther from said substrate than said first optical element, and wherein said first optical element is at least partially immersed in an immersion fluid in contact with said substrate; (c) controlling or maintaining a second temperature of said first optical element to regulate a magnitude or location of said temperature gradient through said optical imaging objective such that a third temperature of said second optical element is maintained below a predetermined threshold; and (d) using said optical imaging objective to detect one or more signals from said biological analyte, during movement of said substrate relative to said optical imaging objective. 438. The method of embodiment 437, wherein said first optical element is a window configured to allow optical communication between said substrate and said second optical element. 439. The method of embodiment 438, wherein said window is substantially flat. 440. The method of embodiment 439, wherein said window is flat. 441. The method of embodiment 437, wherein said optical imaging objective comprises one or more spacers between optical elements, and an outer layer enclosing said optical elements of said optical imaging objective, and wherein a primary heat flux path from said substrate to said environment through said optical imaging objective comprises conductive heat transfer from said substrate to said immersion fluid to said first optical element to said one or more spacers to said outer layer, and convective heat transfer from said outer layer to said environment. 442. The method of embodiment 437, wherein said first temperature is at least 40 degrees Celsius. 443. The method of embodiment 437, wherein said first temperature is at least 50 degrees Celsius. 444. The method of embodiment 437, wherein said first temperature is about 50 degrees Celsius. 445. The method of embodiment 437, wherein said predetermined threshold is an ambient temperature. 446. The method of embodiment 437, wherein said predetermined threshold is at most 30 degrees Celsius. 447. The method of embodiment 437, wherein said predetermined threshold is at most 25 degrees Celsius. 448. The method of embodiment 437, wherein said predetermined threshold is about 20 degrees Celsius. 449. The method of embodiment 437, wherein at least 50% of said temperature gradient occurs within said first optical element, wherein at least 70% of said temperature gradient occurs within said first optical element. 450. The method of embodiment 449, wherein at least 90% of said temperature gradient occurs within said first optical element. 451. The method of embodiment 437, wherein at least a portion of said first optical element is at a temperature of at least 40 degrees Celsius. 452. The method of embodiment 437, wherein at least a portion of said first optical element is at a temperature of at least 50 degrees Celsius. 453. The method of embodiment 437, wherein at least a portion of said first optical element is at a temperature of about 50 degrees Celsius. 454. The method of embodiment 437, wherein at least a portion of said first optical element is at an ambient temperature. 455. The method of embodiment 437, wherein said first optical element is at a temperature of at most 30 degrees Celsius. 456. The method of embodiment 437, wherein said first optical element is at a temperature of at most 25 degrees Celsius. 457. The method of embodiment 437, wherein said first optical element is at a temperature of about 20 degrees Celsius. 458. The method of embodiment 437, wherein said immersion fluid is maintained at a third temperature such that said substrate is maintained at or above said first temperature and said second temperature of said second optical element is maintained at or below said predetermined threshold. 459. The method of embodiment 458, further comprising, maintaining said third temperature of a volume of said immersion fluid in contact with said substrate using a fluid flow unit configured to replenish said immersion fluid in contact with said substrate and said first optical element. 460. The method of embodiment 458, wherein said third temperature is at least 40 degrees Celsius. 461. The method of embodiment 458, wherein said third temperature is at least 50 degrees Celsius. 462. The method of embodiment 458, wherein said third temperature is about 50 degrees Celsius. 463. The method of embodiment 458, wherein said third temperature is within 5 degrees Celsius of said first temperature. 464. The method of embodiment 458, wherein said third temperature is an ambient temperature. 465. The method of embodiment 458, wherein said third temperature is at most 30 degrees Celsius. 466. The method of embodiment 458, wherein said third temperature is at most 25 degrees Celsius. 467. The method of embodiment 458, wherein said third temperature is at most 20 degrees Celsius. 468. The method of embodiment 437, wherein said optical imaging objective comprises an insulating spacer disposed between said first optical element and said second optical element, wherein said insulating spacer is configured to insulate heat transfer from said first optical element and said second optical element. 469. The method of embodiment 468, wherein said insulating spacer has a thermal resistance higher than a thermal resistance of said first optical element. 470. The method of embodiment 437, wherein said optical imaging objective comprises a cooling element configured to decrease temperature of an outer layer of said optical imaging objective. 471. The method of embodiment 437, further comprising dispensing said immersion fluid to said substrate using a fluid flow unit. 472. The method of embodiment 471, wherein said fluid flow unit is configured to dispense said immersion fluid at a rate of less than about 1 milliliter per second. 473. The method of embodiment 472, further comprising at least partially enclosing said optical imaging objective with a container comprising a cavity disposed between said optical imaging objective and a wall of said container, and drawing in a volume of said immersion fluid disposed outside said container into said container using a pressure unit after said optical imaging objective is in contact with said immersion fluid. 474. The method of embodiment 473, wherein said dispensing unit is configured to replenish said immersion fluid in contact with said first optical element at a rate of at least 1 nanoliter per second. 475. The method of embodiment 471, wherein said dispensing unit is configured to dispense said immersion fluid to said substrate prior to bringing said optical imaging objective in contact with said immersion fluid. 476. The method of embodiment 475, further comprising at least partially enclosing said optical imaging objective with a container comprising a cavity disposed between said optical imaging objective and a wall of said container, and drawing in a volume of said immersion fluid disposed outside said container into said container using a pressure unit after said optical imaging objective is in contact with said immersion fluid. 477. The method of embodiment 437, further comprising at least partially enclosing said optical imaging objective with a container, wherein a surface of said container interfaces said immersion fluid, wherein said surface is angled with respect to a surface of said first optical element that interfaces said immersion fluid 478. The method of embodiment 437, further comprising least partially encloses said first optical element with a casing, wherein said casing comprises a cavity adjacent to said first optical element, wherein said cavity interfaces said immersion fluid and is configured to direct one or more bubbles in said immersion fluid away from said first optical element. 479. The method of embodiment 478, wherein said cavity is annular or surrounds said first optical element. 480. The method of embodiment 478, wherein said first optical element is substantially flat. 481. The method of embodiment 437, operatively coupling to said substrate or said optical imaging objective a movement unit, wherein said movement unit is configured to subject said substrate to movement relative to said optical imaging objective. 482. The method of embodiment 481, wherein said movement is in a vector that includes a vertical component that is substantially perpendicular to a plane of said substrate. 483. The method of embodiment 481, wherein said movement is in a vector that includes a horizontal component that is substantially parallel to a plane of said substrate. 484. The method of embodiment 481, wherein said movement is linear. 485. The method of embodiment 481, wherein said movement is non-linear. 486. The method of embodiment 481, wherein said movement unit is configured to subject said substrate to movement during dispensing of said immersion fluid to said substrate. 487. The method of embodiment 481, further comprising using one or more computer processors operatively coupled to said optical imaging objective and said movement unit, wherein said one or more computer processors are individually or collectively programmed to (i) direct said movement unit to subject said substrate to movement relative to said optical imaging objective during detection of said substrate by said optical imaging objective, and (ii) use said optical imaging objective to detect one or more signals from said biological analyte. 488. A method for storing a substrate comprising a nucleic acid molecule-coated surface, comprising: (a) providing said substrate having a surface comprising a first set of nucleic acid molecules immobilized thereto, wherein nucleic acid molecules of said first set of nucleic acid molecules are configured to capture sample nucleic acid molecules derived from one or more nucleic acid samples; (b) bringing said substrate comprising said surface comprising said first set of nucleic acid molecules into contact with a second set of nucleic acid molecules under conditions sufficient to yield a treated surface in which at least 90% of nucleic acid molecules of said first set of nucleic acid molecules are hybridized to nucleic acid molecules of said second set of nucleic acid molecules, wherein said second set of nucleic acid molecules are not said sample nucleic acid molecules; and (c) storing said substrate having said treated surface for a time period of at least 1 hour. 489. The method of embodiment 488, further comprising, subsequent to (c), removing said nucleic acid molecules of said second set of nucleic acid molecules from said treated surface. 490. The method of embodiment 489, further comprising, subsequent to said removing, using said first set of nucleic acid molecules immobilized to said surface for hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof. 491. The method of embodiment 489 or 490, wherein said nucleic acid molecules of said second set of nucleic acid molecules are removed from said treated surface via enzymatic degradation. 492. The method of embodiment 489 or 490, wherein said nucleic acid molecules of said second set of nucleic acid molecules are removed from said treated surface via denaturing via chemical or thermal stimulation. 493. The method of embodiment 492, wherein a chemical stimulus is used to remove said nucleic acid molecules of said second set of nucleic acid molecules from said treated surface. 494. The method of embodiment 493, wherein said chemical stimulus comprises sodium hydroxide. 495. The method of any one of embodiments 488-494, wherein, during storage of said treated surface, each nucleic acid molecule of said first set of nucleic acid molecules that is hybridized to a nucleic acid molecule of said second set of nucleic acid molecules does not hybridize to another nucleic acid molecule. 496. The method of any one of embodiments 488-495, wherein at least 95% of nucleic acid molecules of said first set of nucleic acid molecules are hybridized to nucleic acid molecules of said second set of nucleic acid molecules. 497. The method of any one of embodiments 488-496, wherein said treated surface is stored at temperatures between about 18° C. to about 30° C. 498. The method of any one of embodiments 488-497, wherein said treated surface is stored for at least 6 hours. 499. The method of embodiment 498, wherein said treated surface is stored for at least 24 hours. 500. The method of embodiment 499, wherein said treated surface is stored for at least 2 days. 501. The method of any one of embodiments 488-500, wherein said second set of nucleic acid molecules is provided to said surface of said substrate in a solution. 502. The method of any one of embodiments 488-501, wherein each nucleic acid molecule of said second set of nucleic acid molecules comprises a sequence that is substantially complementary to a sequence of said first set of nucleic acid molecules. 503. The method of embodiment 502, wherein said sequence of said first set of nucleic acid molecules comprises at least 6 bases. 504. The method of any one of embodiments 488-503, wherein said nucleic acid molecules of said first set of nucleic acid molecules are immobilized to said surface at independently addressable locations. 505. The method of embodiment 504, wherein said independently addressable locations are substantially planar. 506. The method of embodiment 504 or 505, wherein said independently addressable locations comprise one or more wells. 507. The method of any one of embodiments 488-506, wherein said nucleic acid molecules of said first set of nucleic acid molecules are immobilized to said surface of said substrate according to a predetermined pattern. 508. The method of any one of embodiments 488-507, wherein a density of said first set of nucleic acid molecules on said surface is at least 1,000,000 molecules per mm2. 509. The method of any one of embodiments 488-508, wherein each nucleic acid molecule of said first set of nucleic acid molecules comprises the same nucleic acid sequence. 510. The method of any one of embodiments 488-509, wherein said first set of nucleic acid molecules comprises one or more different nucleic acid sequences. 511. The method of embodiment 510, wherein said first set of nucleic acid molecules comprises a first subset of nucleic acid molecules comprising a first nucleic acid sequence and a second subset of nucleic acid molecules comprising a second nucleic acid sequence, which first and second nucleic acid sequences are different. 512. The method of embodiment 511, wherein said first subset of nucleic acid molecules and said second subset of nucleic acid molecules both comprise a third nucleic acid sequence. 513. The method of embodiment 512, wherein said third nucleic acid sequence comprises a poly(T) sequence. 514. The method of any one of embodiments 488-513, wherein said second set of nucleic acid molecules comprises DNA nucleotides. 515. The method of any one of embodiments 488-513, wherein said second set of nucleic acid molecules comprises RNA nucleotides. 516. The method of any one of embodiments 488-513, wherein said second set of nucleic acid molecules comprises a mixture of RNA and DNA nucleotides. 517. The method of any one of embodiments 488-516, wherein each nucleic acid molecule of said second set of nucleic acid molecules comprises at least 6 bases. 518. The method of any one of embodiments 488-517, wherein said surface of said substrate is substantially planar. 519. The method of any one of embodiments 488-518, wherein said substrate comprises one or more particles immobilized thereto. 520. A method for nucleic acid processing, comprising: (a) providing a substrate having a treated surface comprising a first set of nucleic acid molecules immobilized thereto, wherein at least 90% of nucleic acid molecules of said first set of nucleic acid molecules are hybridized to nucleic acid molecules of a second set of nucleic acid molecules, wherein nucleic acid molecules of said first set of nucleic acid molecules are configured to capture sample nucleic acid molecules derived from one or more nucleic acid samples, wherein said second set of nucleic acid molecules are not said sample nucleic acid molecules, and wherein said substrate having said treated substrate has been stored for a time period of at least 1 hour; and (b) removing said nucleic acid molecules of said second set of nucleic acid molecules from said treated surface. 521. The method of embodiment 520, further comprising, subsequent to (b), using said first set of nucleic acid molecules immobilized to said surface for hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof 522. The method of embodiment 520 or 521, wherein said nucleic acid molecules of said second set of nucleic acid molecules are removed from said treated surface via enzymatic degradation. 523. The method of any one of embodiments 520-522, wherein said nucleic acid molecules of said second set of nucleic acid molecules are removed from said treated surface via denaturing via chemical or thermal stimulation. 524. The method of embodiment 523, wherein a chemical stimulus is used to remove said nucleic acid molecules of said second set of nucleic acid molecules from said treated surface. 525. The method of embodiment 524, wherein said chemical stimulus comprises sodium hydroxide. 526. The method of any one of embodiments 520-525, wherein, during storage of said treated surface, each nucleic acid molecule of said first set of nucleic acid molecules that is hybridized to a nucleic acid molecule of said second set of nucleic acid molecules does not hybridize to another nucleic acid molecule. 527. The method of any one of embodiments 520-526, wherein at least 95% of nucleic acid molecules of said first set of nucleic acid molecules are hybridized to nucleic acid molecules of said second set of nucleic acid molecules. 528. The method of any one of embodiments 520-527, wherein said treated surface has been stored at temperatures between about 18° C. to about 30° C. 529. The method of any one of embodiments 520-528, wherein said treated surface has been stored for a time period of at least 6 hours. 530. The method of embodiment 529, wherein said treated surface has been stored for a time period of at least 24 hours. 531. The method of embodiment 530, wherein said treated surface has been stored for a time period of at least 2 days. 532. The method of any one of embodiments 520-531, wherein each nucleic acid molecule of said second set of nucleic acid molecules comprises a sequence that is substantially complementary to a sequence of said first set of nucleic acid molecules. 533. The method of embodiment 532, wherein said sequence of said first set of nucleic acid molecules comprises at least 6 bases. 534. The method of any one of embodiments 520-533, wherein said nucleic acid molecules of said first set of nucleic acid molecules are immobilized to said surface at independently addressable locations. 535. The method of embodiment 534, wherein said independently addressable locations are substantially planar. 536. The method of embodiment 534 or 535, wherein said independently addressable locations comprise one or more wells. 537. The method of any one of embodiments 520-536, wherein said nucleic acid molecules of said first set of nucleic acid molecules are immobilized to said surface of said substrate according to a predetermined pattern. 538. The method of any one of embodiments 520-537, wherein a density of said first set of nucleic acid molecules on said surface is at least 1,000,000 molecules per mm2. 539. The method of any one of embodiments 520-538, wherein each nucleic acid molecule of said first set of nucleic acid molecules comprises the same nucleic acid sequence. 540. The method of any one of embodiments 520-539, wherein said first set of nucleic acid molecules comprises one or more different nucleic acid sequences. 541. The method of embodiment 540, wherein said first set of nucleic acid molecules comprise a first subset of nucleic acid molecules comprising a first nucleic acid sequence and a second subset of nucleic acid molecules comprising a second nucleic acid sequence, which first and second nucleic acid sequences are different. 542. The method of embodiment 541, wherein said first subset of nucleic acid molecules and said second subset of nucleic acid molecules both comprise a third nucleic acid sequence. 543. The method of embodiment 542, wherein said third nucleic acid sequence comprises a poly(T) sequence. 544. The method of any one of embodiments 520-543, wherein said second set of nucleic acid molecules comprises DNA nucleotides. 545. The method of any one of embodiments 520-543, wherein said second set of nucleic acid molecules comprises RNA nucleotides. 546. The method of any one of embodiments 520-543, wherein said second set of nucleic acid molecules comprises a mixture of RNA and DNA nucleotides. 547. The method of any one of embodiments 520-546, wherein each nucleic acid molecule of said second set of nucleic acid molecules comprises at least 6 bases. 548. The method of any one of embodiments 520-547, wherein said surface of said substrate is substantially planar. 549. The method of any one of embodiments 520-548, wherein said substrate comprises one or more particles immobilized thereto. 550. A kit, comprising: a substrate comprising a treated surface, wherein said treated surface comprises a plurality of pairs of bound nucleic acid molecules, wherein each pair of said plurality of pairs comprises a first nucleic acid molecule of a first set of nucleic acid molecules at least partially hybridized to a second nucleic acid molecule of a second set of nucleic acid molecules, wherein said first set of nucleic acid molecules is immobilized to said surface, wherein at least 90% of nucleic acid molecules of said first set of nucleic acid molecules are paired with a nucleic acid molecule of said second set of nucleic acid molecules, wherein nucleic acid molecules of said first set of nucleic acid molecules are configured to capture sample nucleic acid molecules derived from one or more nucleic acid samples when said nucleic acid molecules of said first set of nucleic acid molecules are not paired with nucleic acid molecules of said second set of nucleic acid molecules. 551. The kit of embodiment 550, wherein said treated surface is stored for at least 24 hours. 552. The kit of embodiment 551, wherein said treated surface is stored for at least 2 days. 553. The kit of any one of embodiments 550-552, wherein, during storage of said treated surface, each nucleic acid molecule of said first set of nucleic acid molecules in said each pair of said plurality of pairs does not hybridize to another nucleic acid molecule. 554. The kit of any one of embodiments 550-553, further comprising a chemical stimulus configured to remove second nucleic acid molecules from said treated surface. 555. The kit of embodiment 554, wherein said chemical stimulus comprises sodium hydroxide. 556. The kit of any one of embodiments 550-555, wherein at least 95% of nucleic acid molecules of said first set of nucleic acid molecules are at least partially hybridized to nucleic acid molecules of said second set of nucleic acid molecules. 557. The kit of any one of embodiments 550-556, wherein said treated surface is stored at temperatures between about 18° C. to about 30° C. 558. The kit of any one of embodiments 550-557, wherein said second nucleic acid molecule comprises a sequence that is substantially complementary to a sequence of said first nucleic acid molecule. 559. The kit of embodiment 558, wherein said sequence of said first nucleic acid molecule comprises at least 6 bases. 560. The kit of embodiment 558 or 559, wherein said sequence of said second nucleic acid molecule comprises at least 6 bases. 561. The kit of any one of embodiments 550-560, wherein said first nucleic acid molecule and said second nucleic acid molecule comprise the same number of nucleotides. 562. The kit of any one of embodiments 550-561, wherein said first nucleic acid molecule and said second nucleic acid molecule comprise different numbers of nucleotides. 563. The kit of any one of embodiments 550-562, wherein nucleic acid molecules of said first set of nucleic acid molecules are immobilized to said surface at independently addressable locations. 564. The kit of embodiment 563, wherein said independently addressable locations are substantially planar. 565. The kit of embodiment 563 or 564, wherein said independently addressable locations comprise one or more wells. 566. The kit of any one of embodiments 550-565, wherein a density said first set of nucleic acid molecules on said surface is at least 1,000,000 molecules per mm2. 567. The kit of any one of embodiments 550-566, wherein each nucleic acid molecule of said first set of nucleic acid molecules comprises the same nucleic acid sequence. 568. The kit of any one of embodiments 550-567, wherein said first set of nucleic acid molecules comprises one or more different nucleic acid sequences. 569. The kit of embodiment 568, wherein said first set of nucleic acid molecules comprises a first subset of nucleic acid molecules comprising a first nucleic acid sequence and a second subset of nucleic acid molecules comprising a second nucleic acid sequence, which first and second nucleic acid sequences are different. 570. The kit of embodiment 569, wherein said first subset of nucleic acid molecules and said second subset of nucleic acid molecules both comprise a third nucleic acid sequence. 571. The kit of embodiment 570, wherein said third nucleic acid sequence comprises a poly(T) sequence. 572. The kit of any one of embodiments 550-571, wherein said second set of nucleic acid molecules comprises DNA nucleotides. 573. The kit of any one of embodiments 550-571, wherein said second set of nucleic acid molecules comprises RNA nucleotides. 574. The kit of any one of embodiments 550-571, wherein said second set of nucleic acid molecules comprises a mixture of RNA and DNA nucleotides. 575. The kit of any one of embodiments 550-574, wherein each nucleic acid molecule of said second set of nucleic acid molecules comprises at least 6 bases. 576. The kit of any one of embodiments 550-575, wherein surface of said substrate is substantially planar. 577. The kit of any one of embodiments 550-576, wherein said surface of said substrate comprises a plurality of wells. 578. The kit of any one of embodiments 550-577, wherein said substrate comprises one or more particles immobilized thereto. 579. A kit, comprising: a substrate comprising a surface comprising a first set of nucleic acid molecules immobilized thereto, wherein said first set of nucleic acid molecules comprises one or more first nucleic acid molecules, which one or more first nucleic acid molecules are configured to capture sample nucleic acid molecules derived from one or more nucleic acid samples; and a solution comprising a second set of nucleic acid molecules, wherein said second set of nucleic acid molecules comprises one or more second nucleic acid molecules, which one or more second nucleic acid molecules are not said sample nucleic acid molecules; wherein said second set of nucleic acid molecules is selected such that, upon bringing said solution in contact with said surface, at least 70% of said one or more first nucleic acid molecules bind to a second nucleic acid molecule of said second set of nucleic acid molecules to generate one or more pairs of bound nucleic acid molecules, wherein each pair of said one or more pairs comprises (i) a first nucleic acid molecule of said first set of nucleic acid molecules and a second nucleic acid molecule of said second set of nucleic acid molecules, and (ii) a section of substantially complementary sequences. 580. The kit of embodiment 579, further comprising a chemical stimulus configured to remove second nucleic acid molecules from said surface. 581. The kit of embodiment 580, wherein said chemical stimulus comprises sodium hydroxide. 582. The kit of any one of embodiments 579-581, wherein, upon bringing said solution in contact with said surface, at least 90% of said one or more first nucleic acid molecules of said first set of nucleic acid molecules bind to a second nucleic acid molecule of said second set of nucleic acid molecules. 583. The kit of any one of embodiments 579-582, wherein each nucleic acid molecule of said first set of nucleic acid molecules in each pair of said one or more pairs does not hybridize to another nucleic acid molecule. 584. The kit of any one of embodiments 579-583, wherein said section of substantially complementary sequences of each pair of said one or more pairs comprises a first sequence of a first nucleic acid molecule of said one or more first nucleic acid molecules and a second sequence of a second nucleic acid molecule of said one or more second nucleic acid molecules, which first sequence is substantially complementary to said second sequence. 585. The kit of embodiment 584, wherein said first sequence and said second sequence each comprise between about 6-20 bases. 586. The kit of any one of embodiments 579-585, wherein a first nucleic acid molecule of said one or more first nucleic acid molecules and a second nucleic acid molecule of said one or more second nucleic acid molecules have the same number of nucleotides. 587. The kit of any one of embodiments 579-586, wherein a first nucleic acid molecule of said one or more first nucleic acid molecules and a second nucleic acid molecule of said one or more second nucleic acid molecules have different numbers of nucleotides. 588. The kit of any one of embodiments 579-587, wherein said first set of nucleic acid molecules is immobilized to said surface at independently addressable locations. 589. The kit of embodiment 588, wherein said independently addressable locations are substantially planar. 590. The kit of embodiment 588 or 589, wherein said independently addressable locations comprise one or more wells. 591. The kit of any one of embodiments 579-590, wherein said first set of nucleic acid molecules is immobilized to said surface according to a predetermined pattern. 592. The kit of any one of embodiments 579-591, wherein a density said first set of nucleic acid molecules on said surface is at least 1,000,000 molecules per mm2. 593. The kit of any one of embodiments 579-592, wherein said first set of nucleic acid molecules comprises one or more different nucleic acid sequences. 594. The kit of embodiment 593, wherein said first set of nucleic acid molecules comprises a first subset of nucleic acid molecules comprising a first nucleic acid sequence and a second subset of nucleic acid molecules comprising a second nucleic acid sequence, which first and second nucleic acid sequences are different. 595. The kit of embodiment 594, wherein said first subset of nucleic acid molecules and said second subset of nucleic acid molecules both comprise a third nucleic acid sequence. 596. The kit of embodiment 595, wherein said third nucleic acid sequence comprises a poly(T) sequence. 597. The kit of any one of embodiments 579-596, wherein said second set of nucleic acid molecules comprises DNA nucleotides. 598. The kit of any one of embodiments 579-596, wherein said second set of nucleic acid molecules comprises RNA nucleotides. 599. The kit of any one of embodiments 579-596, wherein said second set of nucleic acid molecules comprises a mixture of RNA and DNA nucleotides. 600. The kit of any one of embodiments 579-599, wherein each nucleic acid molecule of said second set of nucleic acid molecules comprises at least 6 bases. 601. The kit of any one of embodiments 579-600, wherein said surface of said substrate is substantially planar. 602. The kit of any one of embodiments 579-601, wherein said surface of said substrate comprises a plurality of wells. 603. The kit of any one of embodiments 579-602, wherein said substrate comprises one or more particles immobilized thereto. 604. A method for storing a substrate comprising a nucleic acid molecule-coated surface, comprising: (a) providing a substrate having a surface comprising a first set of nucleic acid molecules immobilized thereto, wherein nucleic acid molecules of said first set of nucleic acid molecules are configured to capture sample nucleic acid molecules derived from one or more nucleic acid samples, and wherein each nucleic acid molecule of said first set of nucleic acid molecules comprises a first nucleic acid sequence and a second nucleic acid sequence, which second nucleic acid sequence is substantially complementary to said first nucleic acid sequence; (b) generating a treated surface by subjecting said surface to conditions sufficient to bind said first nucleic acid sequence of a nucleic acid molecule of said first set of nucleic acid molecules to said second nucleic acid sequence of said nucleic acid molecule to provide an immobilized hairpin molecule; and (c) storing said substrate having said treated surface for a time period of at least 1 hour. 605. The method of embodiment 604, further comprising, subsequent to (c), separating said second sequence from said first sequence of said immobilized hairpin molecule. 606. The method of embodiment 605, wherein said separating comprises an enzymatic degradation or denaturation using a chemical or thermal stimulus. 607. The method of embodiment 606, wherein said chemical stimulus comprises sodium hydroxide. 608. The method of any one of embodiments 605-607, further comprising, subsequent to said separating, using said first set of nucleic acid molecules immobilized to said surface for hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof. 609. The method of any one of embodiments 605-608, wherein each nucleic acid molecule of said first set of nucleic acid molecules comprises a cleavable base, which cleavable base is disposed between said first sequence and said second sequence of said nucleic acid molecule. 610. The method of embodiment 609, further comprising, subsequent to separating said second sequence from said first sequence of said immobilized hairpin molecule, cleaving said nucleic acid molecule at said cleavable base, thereby removing said second sequence of said nucleic acid molecule from said surface. 611. The method of any one of embodiments 604-610, wherein, during storage of said treated surface, each nucleic acid molecule of said first set of nucleic acid molecules does not hybridize to another nucleic acid molecule. 612. The method of any one of embodiments 604-611, wherein, during storage of said treated surface, at least 70% of nucleic acid molecules of said first set of nucleic acid molecules are present as immobilized hairpin molecules. 613. The method of any one of embodiments 604-612, wherein said treated surface is stored at temperatures between about 18° C. to about 30° C. 614. The method of any one of embodiments 604-613, wherein said treated surface is stored for at least 6 hours. 615. The method of embodiment 614, wherein said treated surface is stored for at least 24 hours. 616. The method of any one of embodiments 604-615, wherein said first sequence and said second sequence each comprise at least 6 bases. 617. The method of any one of embodiments 604-616, wherein said nucleic acid molecules of said first set of nucleic acid molecules are immobilized to said surface at independently addressable locations. 618. The method of embodiment 617, wherein said independently addressable locations are substantially planar. 619. The method of embodiment 617 or 618, wherein said independently addressable locations comprise one or more wells. 620. The method of any one of embodiments 604-619, wherein a density said first set of nucleic acid molecules on said surface is at least 1,000,000 molecules per mm2. 621. The method of any one of embodiments 604-620, wherein said first set of nucleic acid molecules comprise one or more different nucleic acid sequences. 622. The method of embodiment 621, wherein said first set of nucleic acid molecules comprises a first subset of nucleic acid molecules comprising said first nucleic acid sequence and said second nucleic acid sequence and a second subset of nucleic acid molecules comprising a third nucleic acid sequence and a fourth nucleic acid sequence, which third nucleic acid sequence is substantially complementary to said fourth nucleic acid sequences, and which first nucleic acid sequence is different from said third and fourth nucleic acid sequences. 623. The method of embodiment 622, wherein said first subset of nucleic acid molecules and said second subset of nucleic acid molecules both comprise a fifth nucleic acid sequence. 624. The method of embodiment 623, wherein said fifth nucleic acid sequence comprises a poly(T) sequence. 625. The method of any one of embodiments 604-624, wherein said surface of said substrate is substantially planar. 626. The method of any one of embodiments 604-625, wherein said surface of said substrate comprises a plurality of wells. 627. The method of any one of embodiments 604-626, wherein said substrate comprises one or more particles immobilized thereto. 628. A method for storing a substrate comprising an nucleic acid molecule-coated surface, comprising: (a) providing a substrate having a surface comprising a first set of nucleic acid molecules immobilized thereto, wherein nucleic acid molecules of said first set of nucleic acid molecules are configured to capture sample nucleic acid molecules derived from one or more nucleic acid samples, and wherein each nucleic acid molecule of said nucleic acid molecules of said first set of nucleic acid molecules comprises a first nucleic acid sequence; (b) providing a second set of nucleic acid molecules, wherein each nucleic acid molecule of said second set of nucleic acid molecules comprises a second nucleic acid sequence that is substantially complementary to said first nucleic acid sequence, and wherein said second set of nucleic acid molecules are not said sample nucleic acid molecules; (c) bringing said surface comprising said first set of nucleic acid molecules into contact with said second set of nucleic acid molecules to generate a treated surface in which at least 70% of nucleic acid molecules of said first set of nucleic acid molecules are hybridized to nucleic acid molecules of said second set of nucleic acid molecules; and (d) storing said treated surface for at least one hour, wherein, for each nucleic acid molecule of said first set of nucleic acid molecules hybridized to a nucleic acid molecule of said second set of nucleic acid molecules, said first nucleic acid sequence is hybridized to said second nucleic acid sequence, and wherein said first nucleic acid sequence hybridized to said second nucleic acid sequence at least partially denatures between about 40° C. and 60° C. 629. The method of embodiment 628, wherein said first nucleic acid sequence hybridized to said second nucleic acid sequence at least partially denatures between about 50° C. and 60° C. 630. The method of embodiment 628 or 629, further comprising, subsequent to (d), removing said nucleic acid molecules of said second set of nucleic acid molecules from said treated surface. 631. The method of embodiment 630, further comprising, subsequent to said removing, using said first set of nucleic acid molecules immobilized to said surface for hybridization capture, single nucleotide polymorphism (SNP) genotyping, sequencing library capture, synthesis of nucleic acid molecules, on-surface amplification, downstream processing or analysis of nucleic acid molecules or derivative thereof, or combinations thereof. 632. The method of embodiment 630 or 631, wherein said nucleic acid molecules of said second set of nucleic acid molecules are removed from said treated surface via enzymatic degradation. 633. The method of embodiment 630 or 631, wherein said nucleic acid molecules of said second set of nucleic acid molecules are removed from said treated surface via denaturing via chemical or thermal stimulation. 634. The method of embodiment 633, wherein said nucleic acid molecules of said second set of nucleic acid molecules are removed from said treated surface by denaturing said first nucleic acid sequence hybridized to said second nucleic acid sequence. 635. The method of embodiment 633 or 634, wherein said nucleic acid molecules of said second set of nucleic acid molecules are removed from said treated surface by heating said treated surface to between about 40° C. and 60° C. 636. The method of any one of embodiments 633-635, wherein said nucleic acid molecules of said second set of nucleic acid molecules are removed from said treated surface by heating a solution in contact with said treated surface to between about 40° C. and 60° C. 637. The method of any one of embodiments 633-636, wherein a chemical stimulus is used to remove said nucleic acid molecules of said second set of nucleic acid molecules from said treated surface. 638. The method of embodiment 637, wherein said chemical stimulus comprises sodium hydroxide. 639. The method of any one of embodiments 628-638, wherein, during storage of said treated surface, each nucleic acid molecule of said first set of nucleic acid molecules that is hybridized to a nucleic acid molecule of said second set of nucleic acid molecules does not hybridize to another nucleic acid molecule. 640. The method of any one of embodiments 628-639, wherein at least 90% of nucleic acid molecules of said first set of nucleic acid molecules are hybridized to nucleic acid molecules of said second set of nucleic acid molecules. 641. The method of any one of embodiments 628-640, wherein said treated surface is stored at temperatures between about 18° C. to about 30° C. 642. The method of any one of embodiments 628-641, wherein said treated surface is stored for at least 6 hours. 643. The method of embodiment 642, wherein said treated surface is stored for at least 24 hours. 644. The method of embodiment 643, wherein said treated surface is stored for at least 2 days. 645. The method of any one of embodiments 628-644, wherein said second set of nucleic acid molecules is provided to said surface in a solution. 646. The method of any one of embodiments 628-645, wherein said first nucleic acid sequence and said second nucleic acid sequence each comprise at least 6 bases. 647. The method of any one of embodiments 628-646, wherein a given nucleic acid molecule of said first set of nucleic acid molecules and a given nucleic acid molecule of said second set of nucleic acid molecules comprise the same number of nucleotides. 648. The method of any one of embodiments 628-647, wherein a given nucleic acid molecule of said first set of nucleic acid molecules and a given nucleic acid molecule of said second set of nucleic acid molecules comprise different numbers of nucleotides. 649. The method of any one of embodiments 628-648, wherein said first set of nucleic acid molecules is immobilized to said surface at independently addressable locations. 650. The method of embodiment 649, wherein said independently addressable locations are substantially planar. 651. The method of embodiment 649 or 650, wherein said independently addressable locations comprise one or more wells. 652. The method of any one of embodiments 628-651, wherein said first set of nucleic acid molecules is immobilized to said surface according to a predetermined pattern. 653. The method of any one of embodiments 628-652, wherein a density said first set of nucleic acid molecules on said surface is at least 1,000,000 molecules per mm2. 654. The method of any one of embodiments 628-653, wherein said first set of nucleic acid molecules comprises one or more different nucleic acid sequences. 655. The method of embodiment 654, wherein said first set of nucleic acid molecules comprises a first subset of nucleic acid molecules comprising said first nucleic acid sequence and a second subset of nucleic acid molecules comprising a third nucleic acid sequence, which first and third nucleic acid sequences are different. 656. The method of embodiment 655, wherein said first subset of nucleic acid molecules and said second subset of nucleic acid molecules both comprise a fourth nucleic acid sequence. 657. The method of embodiment 656, wherein said fourth nucleic acid sequence comprises a poly(T) sequence. 658. The method of any one of embodiments 628-657, wherein said second set of nucleic acid molecules comprises DNA nucleotides. 659. The method of any one of embodiments 628-657, wherein said second set of nucleic acid molecules comprises RNA nucleotides. 660. The method of any one of embodiments 628-657, wherein said second set of nucleic acid molecules comprises a mixture of RNA and DNA nucleotides. 661. The method of any one of embodiments 628-660, wherein each nucleic acid molecule of said second set of nucleic acid molecules comprises at least 6 bases. 662. The method of any one of embodiments 628-661, wherein said surface of said substrate is substantially planar. 663. The method of any one of embodiments 628-662, wherein said surface of said substrate comprises a plurality of wells. 664. The method of any one of embodiments 628-663, wherein said substrate comprises one or more particles immobilized thereto. 665. A method for detecting or analyzing an analyte, comprising: (a) providing an open substrate comprising a central axis, said open substrate comprising an array of analytes immobilized adjacent to said open substrate, wherein at least one analyte of said array of analytes is bound to a probe; and (b) using a detector system to perform a non-linear scan of said open substrate to detect at least one signal or signal change from said bound probe, wherein said detector system comprises a line-scan camera and an illumination source, wherein said illumination source is configured to generate an illuminated region on said open substrate, wherein said open substrate comprises a first area and a second area, wherein said first area and said second area: (i) comprise different subsets of said array of analytes, (ii) are at different radial positions of said open substrate with respect to said central axis, and (iii) are spatially resolved by said detector system; and wherein said bound probe is disposed in said first area of said open substrate, and wherein said non-linear scan is performed during relative non-linear motion between said open substrate and one or both of (i) said line-scan camera and (ii) said illuminated region. 666. The method of embodiment 665, wherein said illuminated region has a maximum dimension of at most about 2 millimeters. 667. The method of embodiment 665 or 666, wherein said illuminated region has a maximum width of at most about 0.5 millimeters. 668. The method of any one of embodiments 665-667, wherein said line-scan camera is a time delay and integration line-scan camera. 669. The method of any one of embodiments 665-668, wherein said illumination source comprises a laser. 670. The method of embodiment 669, wherein said laser is a continuous wave laser. 671. The method of embodiment 669 or 670, wherein said detector system comprises an optical element configured to change a shape of a beam of light emitted by said laser. 672. The method of embodiment 671, wherein said optical element comprises a cylindrical lens. 673. The method of any one of embodiments 665-668, wherein said illumination source comprises a light emitting diode. 674. The method of any one of embodiments 665-673, wherein during (b), said open substrate is rotating. 675. The method of embodiment 674, wherein during (b), said line-scan camera of said detector system is stationary. 676. The method of embodiment 674, wherein during (b), said line-scan camera of said detector system is rotating. 677. The method of embodiment 675 or 676, wherein during (b), said illuminated region is rotating. 678. The method of embodiment 677, wherein during (b), said illuminated region is rotating at a same rate as said line-scan camera. 679. The method of embodiment 674, wherein during (b), said line-scan camera of said detector system translates radially across said open substrate. 680. The method of embodiment 674 or 679, wherein during (b), said illuminated region translates radially across said open substrate. 681. The method of any one of embodiments 665-673, wherein during (b), said open substrate is stationary. 682. The method of embodiment 681, wherein during (b), said line-scan camera of said detector system is rotating. 683. The method of embodiment 681 or 682, wherein during (b), said illuminated region is rotating. 684. The method of embodiment 683, wherein during (b), said illumination region is rotating at a same rate as said line-scan camera. 685. The method of embodiment 681, wherein during (b), said line-scan camera is stationary. 686. The method of embodiment 685, wherein during (b), said illuminated region of said detector system is rotating. 687. The method of any one of embodiments 665-686, wherein said detector system further comprises a prism, which prism is rotating during (b). 688. The method of any one of embodiments 665-687, wherein said detector system is configured to detect a signal from said illuminated region using said line-scan camera. 689. The method of any one of embodiments 665-688, wherein said array of analytes comprises a second analyte bound to an additional probe, which additional probe is disposed in said second area of said open substrate, and wherein during (b), at least one signal or signal change is detected from said additional probe at the same time as said at least one signal or signal change detected from said bound probe. 690. The method of any one of embodiments 665-689, wherein said detector system compensates for velocity differences at different radial positions of said array with respect to said central axis within a scanned area. 691. The method of any one of embodiments 665-690, wherein said detector system comprises an optical imaging system having an anamorphic magnification gradient substantially transverse to a scanning direction along said open substrate, and wherein said anamorphic magnification gradient at least partially compensates for tangential velocity differences that are substantially perpendicular to said scanning direction. 692. The method of any one of embodiments 665-691, wherein (b) comprises reading two or more regions on said open substrate at two or more different scan rates, respectively, to at least partially compensate for tangential velocity differences in said two or more regions. 693. The method of any one of embodiments 665-692, wherein (b) further comprises using an immersion objective lens in optical communication with said detector system and said open substrate to detect said at least one signal or signal change, which immersion objective lens is in contact with a fluid that is in contact with said open substrate. 694. The method of embodiment 693, wherein said fluid is in a container, and wherein an electric field is used to regulate a hydrophobicity of one or more surfaces of said container to retain at least a portion of said fluid contacting said immersion objective lens and said open substrate. 695. The method of any one of embodiments 665-694, wherein said array of analytes comprise nucleic acid molecules, wherein said plurality of probes comprises fluorescently labeled nucleotides, and wherein at least one fluorescently labeled nucleotide of said fluorescently labeled nucleotides binds to at least one nucleic acid molecule of said nucleic acid molecules via nucleotide complementarity binding. 696. The method of any one of embodiments 665-695, wherein said open substrate is substantially planar. 697. The method of any one of embodiments 665-696, wherein an analyte of said array of analytes is immobilized adjacent to said open substrate through one or more binders. 698. The method of any one of embodiments 665-697, wherein said open substrate comprises at least 100,000 binders, wherein a binder of said at least 100,000 binders immobilizes an analyte of said array of analytes immobilized adjacent to said open substrate. 699. The method of any one of embodiments 665-698, wherein an analyte of said array of analytes is coupled to a bead, which bead is immobilized to said open substrate. 700. The method of any one of embodiments 665-699, wherein an analyte of said array of analytes comprises a nucleic acid molecule. 701. The method of any one of embodiments 665-700, wherein said plurality of probes comprises a plurality of oligonucleotide molecules. 702. The method of any one of embodiments 665-700, wherein said plurality of probes comprises a plurality of nucleotides or analogs thereof 703. An apparatus for analyte detection or analysis, comprising: a housing configured to receive an open substrate having an array of analytes immobilized adjacent thereto, wherein at least one analyte of said array of analytes is bound to a probe; and a detector system, wherein said detector system comprises a line-scan camera and an illumination source, wherein said illumination source is configured to generate an illuminated region on said open substrate, wherein said open substrate comprises a first area and a second area, wherein said first area and said second area: (i) comprise subsets of said array of immobilized analytes, (ii) are at different radial positions of said open substrate with respect to said central axis, and (iii) are spatially resolved by said detector system; wherein said bound probe is disposed in said first area of said open substrate, and wherein said detector system is programmed to perform a non-linear scan of said open substrate and detect at least one signal or signal change from said bound probe at said first area of said open substrate, wherein said non-linear scan is performed during relative non-linear motion between said open substrate and one or both of (i) said line-scan camera and (ii) said illuminated region. 704. The apparatus of embodiment 703, wherein said illuminated region has a maximum dimension of at most about 2 millimeters. 705. The apparatus of embodiment 703 or 704, wherein said illuminated region has a maximum width of at most about 0.5 millimeters. 706. The apparatus of any one of embodiments 703-705, further comprising a processor programmed to direct said detector system to compensate for velocity differences at different radial positions of said array with respect to said central axis within a scanned area. 707. The apparatus of embodiment 706, wherein said processor is programmed to direct said detector system to scan two or more regions on said open substrate at two or more different scan rates, respectively, to at least partially compensate for tangential velocity differences in said two or more regions. 708. The apparatus of any one of embodiments 703-707, further comprising one or more optics that are configured to generate an anamorphic magnification gradient substantially transverse to a scanning direction along said open substrate, and wherein said anamorphic magnification gradient at least partially compensates for tangential velocity differences that are substantially perpendicular to said scanning direction. 709. The apparatus of embodiment 708, further comprising a processor programmed to adjust said anamorphic magnification gradient to compensate for different imaged radial positions with respect to said central axis. 710. The apparatus of any one of embodiments 703-709, wherein said line-scan camera is a time delay and integration line-scan camera. 711. The apparatus of any one of embodiments 703-710, wherein said illumination source comprises a laser. 712. The apparatus of embodiment 711, wherein said laser is a continuous wave laser. 713. The apparatus of embodiment 711 or 712, wherein said detector system comprises an optical element configured to change a shape of a beam of light emitted by said laser. 714. The apparatus of embodiment 713, wherein said optical element comprises a cylindrical lens. 715. The apparatus of any one of embodiments 703-710, wherein said illumination source comprises a light emitting diode. 716. The apparatus of any one of embodiments 703-715, wherein said detector system and said rotational unit are disposed in different areas of said apparatus. 717. The apparatus of any one of embodiments 703-716, further comprising a rotational unit configured to rotate said detector system or an element thereof, and wherein said detector system is programmed to detect said at least one signal from said bound probe while said line-scan camera of said detector system is rotating. 718. The apparatus of embodiment 717, wherein said detector system is programmed to detect said at least one signal from said bound probe while said illuminated region of said detector system is rotating. 719. The apparatus of embodiment 718, wherein said detector system is programmed to detect said at least one signal from said bound probe while said line-scan camera and said illuminated region are rotating at a same rate. 720. The apparatus of any one of embodiments 703-719, wherein said detector system is programmed to detect said at least one signal from said bound probe while said open substrate is stationary. 721. The apparatus of any one of embodiments 703-719, wherein said detector system is programmed to detect said at least one signal from said bound probe while said open substrate is rotating. 722. The apparatus of any one of embodiments 703-716, wherein said detector system is programmed to detect said at least one signal from said bound probe while said line-scan camera translates radially across said open substrate. 723. The apparatus of embodiment 722, wherein said detector system is programmed to detect said at least one signal from said bound probe while said illuminated region translates radially across said open substrate. 724. The apparatus of any one of embodiments 703-716, wherein said detector system further comprises a prism, and wherein said detector system is programmed to detect said at least one signal from said bound probe while said prism is rotating. 725. The apparatus of any one of embodiments 703-724, further comprising an immersion objective lens in optical communication with said detector system and said open substrate, which immersion objective lens is configured to be in contact with a fluid that is in contact with said open substrate. 726. The apparatus of embodiment 725, further comprising a container configured to retain said fluid and an electric field application unit configured to regulate a hydrophobicity of one or more surfaces of said container to retain at least a portion of said fluid contacting said immersion objective lens and said open substrate. 727. The apparatus of embodiment 725 or 726, wherein said immersion objective lens separates a first environment from a second environment, wherein said first environment and said second environment have different operating conditions. 728. The apparatus of embodiment 727, wherein said immersion objective lens forms a seal between said first environment and said second environment. 729. The apparatus of any one of embodiments 703-728, wherein said open substrate is substantially planar. 730. The apparatus of any one of embodiments 703-729, wherein an analyte of said array of analytes is immobilized adjacent to said open substrate through one or more binders. 731. The apparatus of any one of embodiments 703-730, wherein said open substrate comprises at least 100,000 binders, wherein a binder of said at least 100,000 binders immobilizes an analyte of said array of analytes immobilized adjacent to said open substrate. 732. The apparatus of any one of embodiments 703-731, wherein an analyte of said array of analytes is coupled to a bead, which bead is immobilized to said open substrate. 733. The apparatus of any one of embodiments 703-732, wherein an analyte of said array of analytes comprises a nucleic acid molecule. 734. The apparatus of any one of embodiments 703-733, wherein said plurality of probes comprises a plurality of oligonucleotide molecules. 735. The apparatus of any one of embodiments 703-733, wherein said plurality of probes comprises a plurality of nucleotides or analogs thereof. 736. A computer-readable medium comprising non-transitory instructions stored thereon, which when executed cause one or more computer processors to implement a method for detecting or analyzing an analyte, the method comprising: providing an open substrate about a central axis, said open substrate comprising an array of analytes immobilized adjacent to said open substrate, wherein at least one analyte of said array of analytes is bound to a probe; and using a detector system to perform a non-linear scan of said open substrate to detect at least one signal or signal change from said bound probe, wherein said detector system comprises a line-scan camera and an illumination source, wherein said illumination source is configured to generate an illuminated region on said open substrate, wherein said open substrate comprises a first area and a second area, wherein said first area and said second area (i) comprise different subsets of said array of analytes, (ii) are at different radial positions of said open substrate with respect to said central axis, and (iii) are spatially resolved by said detector system; wherein said bound probe is disposed in said first area of said open substrate; and wherein said non-linear scan is performed during relative non-linear motion between said open substrate and one or both of (i) said line-scan camera and (ii) said illuminated region. 737. The computer-readable medium of embodiment 736, wherein said line-scan camera is a time delay and integration line-scan camera. 738. The computer-readable medium of embodiment 736 or 737, wherein said illumination source comprises a laser. 739. The computer-readable medium of embodiment 738, wherein said laser is a continuous wave laser. 740. The computer-readable medium of embodiment 738 or 739, wherein said detector system comprises an optical element configured to change a shape of a beam of light emitted by said laser. 741. The computer-readable medium of embodiment 740, wherein said optical element comprises a cylindrical lens. 742. The computer-readable medium of embodiment 736 or 737, wherein said illumination source comprises a light emitting diode. 743. The computer-readable medium of any one of embodiments 736-742, wherein during said detecting, said open substrate is stationary. 744. The computer-readable medium of embodiment 743, wherein during said detecting, said line-scan camera of said detector system is rotating. 745. The computer-readable medium of embodiment 744, wherein during said detecting, said illuminated region is rotating. 746. The computer-readable medium of embodiment 745, wherein during said detecting, said illuminated region is rotating at a same rate as said line-scan camera. 747. The computer-readable medium of embodiment 743, wherein during said detecting, said line-scan camera translates radially across said open substrate. 748. The computer-readable medium of embodiment 747, wherein during said detecting, said illuminated region translates radially across said open substrate. 749. The computer-readable medium of any one of embodiments 736-742, wherein during said detecting, said open substrate is rotating. 750. The computer-readable medium of embodiment 749, wherein during said detecting, said line-scan camera of said detector system is stationary. 751. The computer-readable medium of embodiment 750, wherein during said detecting, said illuminated region of said detector system is rotating. 752. The computer-readable medium of embodiment 749, wherein during said detecting, said line-scan camera of said detector system is rotating. 753. The computer-readable medium of embodiment 752, wherein during said detecting, said illuminated region is rotating. 754. The computer-readable medium of embodiment 753, wherein during said detecting, said illuminated region is rotating at a same rate as said line-scan camera. 755. The computer-readable medium of embodiment 749, wherein during said detecting, said line-scan camera translates radially across said open substrate. 756. The computer-readable medium of embodiment 755, wherein during said detecting, said illuminated region translates radially across said open substrate. 757. The computer-readable medium of any one of embodiments 736-756, wherein said detector system further comprises a prism, which prism is rotates during said detecting. 758. The computer-readable medium of any one of embodiments 736-757, wherein said detector system is configured to detect a signal from said illuminated region using said line-scan camera. 759. The computer-readable medium of any one of embodiments 736-758, wherein said detector system compensates for velocity differences at different radial positions of said array with respect to said central axis within a scanned area. 760. The computer-readable medium of any one of embodiments 736-759, wherein said detector system comprises an optical imaging system having an anamorphic magnification gradient substantially transverse to a scanning direction along said open substrate, and wherein said anamorphic magnification gradient at least partially compensates for tangential velocity differences that are substantially perpendicular to said scanning direction. 761. The computer-readable medium of any one of embodiments 736-760, wherein said detecting comprises reading two or more regions on said open substrate at two or more different scan rates, respectively, to at least partially compensate for tangential velocity differences in said two or more regions. 762. The computer-readable medium of any one of embodiments 736-761, wherein said detecting further comprises using an immersion objective lens in optical communication with said detector system and said open substrate to detect said at least one signal or signal change, which immersion objective lens is in contact with a fluid that is in contact with said open substrate. 763. The computer-readable medium of embodiment 762, wherein said fluid is in a container, and wherein an electric field is used to regulate a hydrophobicity of one or more surfaces of said container to retain at least a portion of said fluid contacting said immersion objective lens and said open substrate. 764. The computer-readable medium of any one of embodiments 736-763, wherein said array of analytes comprise nucleic acid molecules, wherein said plurality of probes comprises fluorescently labeled nucleotides, and wherein at least one fluorescently labeled nucleotide of said fluorescently labeled nucleotides binds to at least one nucleic acid molecule of said nucleic acid molecules via nucleotide complementarity binding. 765. The computer-readable medium of any one of embodiments 736-764, wherein said open substrate is substantially planar. 766. The computer-readable medium of any one of embodiments 736-765, wherein an analyte of said array of analytes is immobilized adjacent to said open substrate through one or more binders. 767. The computer-readable medium of any one of embodiments 736-766, wherein said open substrate comprises at least 100,000 binders, wherein a binder of said at least 100,000 binders immobilizes an analyte of said array of analytes immobilized adjacent to said open substrate. 768. The computer-readable medium of any one of embodiments 736-767, wherein an analyte of said array of analytes is coupled to a bead, which bead is immobilized to said open substrate. 769. The computer-readable medium of any one of embodiments 736-768, wherein an analyte of said array of analytes comprises a nucleic acid molecule. 770. The computer-readable medium of any one of embodiments 736-769, wherein said plurality of probes comprises a plurality of oligonucleotide molecules. 771. The computer-readable medium of any one of embodiments 736-769, wherein said plurality of probes comprises a plurality of nucleotides or analogs thereof.

EXAMPLES

Example 1. Imaging of Sequencing of a Nucleic Acid Molecule

Figure 42:
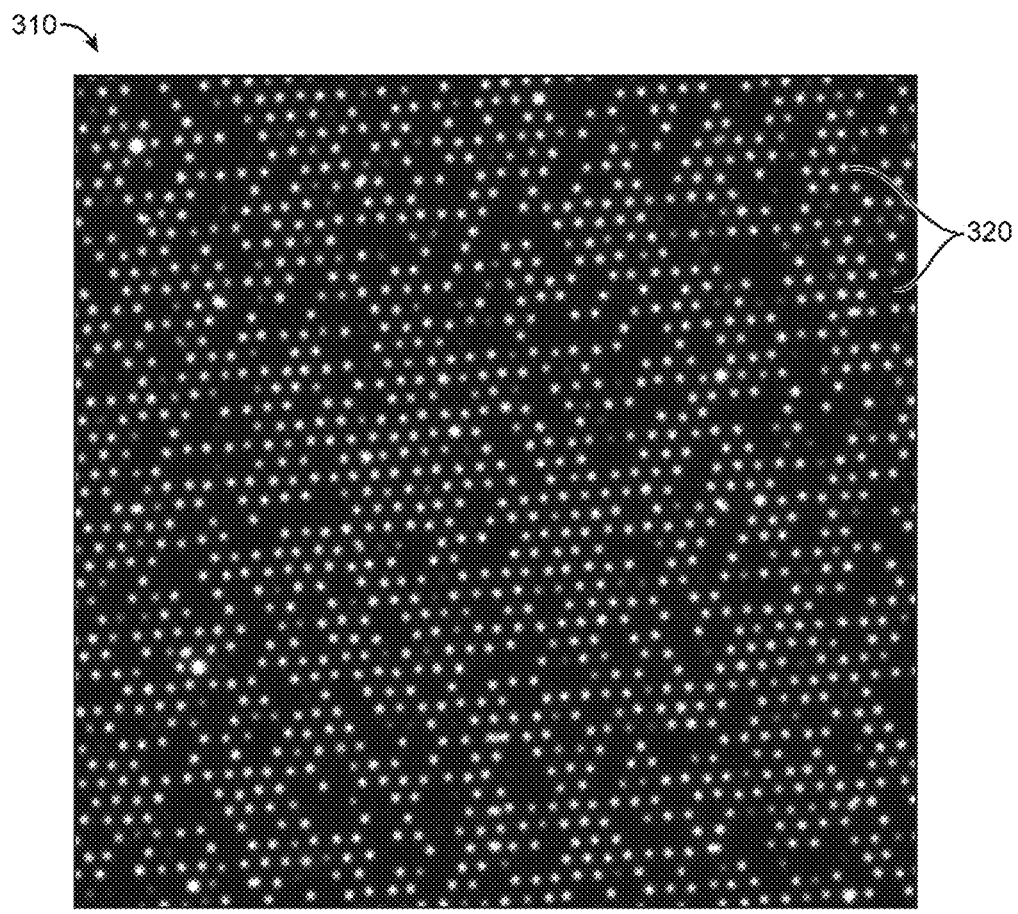
FIG. 42 shows an example of an image generated by imaging a substrate with an analyte immobilized thereto.

FIG. 42 shows an example of an image generated by imaging a substrate with an analyte immobilized thereto. A substrate 310 comprising a substantially planar array has immobilized thereto the biological analyte, e.g., nucleic acid molecules. The substantially planar array comprises a plurality of individually addressable locations 320, and a plurality of the individually addressable locations comprises a biological analyte, e.g., one or more nucleic acid molecules. The individually addressable locations 320 may be randomly arranged or arranged in an ordered pattern. The biological analyte may be attached to a bead, which is immobilized to the array. A single bead may comprise a plurality of analytes, such as at least 10, 20, 30, 40, 50, 100, 150 or more analytes. A bead may be associated with an individually addressable location. A plurality of fluorescent probes (e.g., a plurality of fluorescently-labeled, A, T, C, or G) is dispensed onto the substrate 310. In some embodiments, the substrate is configured to rotate with respect to a central axis; a fluid flow unit comprising a fluid channel configured to dispense a solution comprising a plurality of probes to the array, wherein during rotation of the substrate, the solution is directed centrifugally along a direction away from the central axis and brought in contact with the biological analyte. In other embodiments, the substrate is not rotated. The substrate 310 is then subjected to conditions sufficient to conduct a reaction between at least one probe of the plurality of probes and the biological analyte, to couple the at least one probe to the biological analyte. The uncoupled probes are washed away. The coupling of the at least one probe to the biological analyte is detected using photometry, which comprises imaging at least a part of the substrate 310 (e.g., via scanning or fixed field imaging) and measuring the signal of each individually addressable location 320. Nucleic acid molecules comprising a nucleotide complementary to the fluorescent probes are fluorescent in an individually addressable location 320. The operations may then be iterated, and signals from an image are collated with signals from prior images of the same substrate to generate traces of signals in time for each biological analyte in each individually addressable location 320. The sequence of the plurality of fluorescent probes is known for each iteration of the operations, generating a known sequence for the analyte in each of the individually addressable locations 320.

Example 2. Diagnostic Procedure for Nucleic Acid Incorporation

Figure 43:
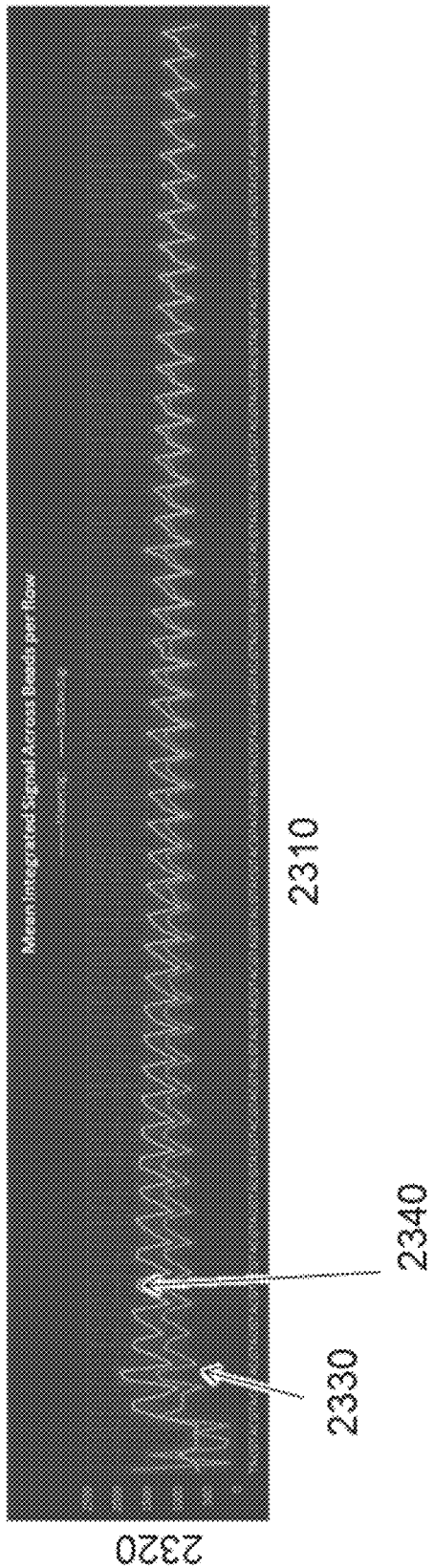
FIG. 43 shows an example of data obtained from a diagnostic procedure.

Diagnostic procedures are run to determine whether a probe has coupled with a biological analyte (e.g., nucleic acid molecule). FIG. 43 shows example data of such a diagnostic procedure, running approximately 29 giga base pairs (Gbp) from about 183 million beads. A substrate, similar to that depicted in 310 for example in FIG. 15-FIG. 23, comprises an array configured to immobilize the biological analyte. The biological analyte may be attached to a bead, which is immobilized to the array. A single bead may comprise a plurality of analytes, such as at least 10, 20, 30, 40, 50, 100, 150 or more analytes. The biological analyte in some cases is genomic DNA from E. Coli bacteria. In some cases, human DNA may be used as the biological analyte. In some cases, the biological analyte is a shotgun library of DNA from a clonal population. In some cases, the substrate is configured to rotate with respect to a central axis. In other embodiments, the substrate is not configured to rotate and may be stationary. In other embodiments, the substrate is not configured to rotate and may be movable laterally or longitudinally, as described elsewhere herein. In some cases, a fluid flow unit comprising a fluid channel is used to dispense a solution comprising a plurality of probes (e.g., fluorescently labeled nucleotides) to the array, wherein during rotation of the substrate, the solution is directed centrifugally along a direction away from the central axis and brought in contact with the biological analyte under conditions sufficient to couple at least one probe (e.g., nucleotide) of the plurality of probes to the biological analyte. In other cases, the probes may be dispensed on the substrate via nebulization, a spray, a pressurized gas (e.g., blown gas) system, etc., as described elsewhere herein. The substrate 310 is then subjected to conditions sufficient to conduct a reaction between at least one probe of the plurality of probes and the biological analyte, to couple the at least one probe to the biological analyte. The uncoupled probes are washed away. The coupling of the at least one probe to the biological analyte is detected using photometry, which comprises imaging at least a part of the substrate. Nucleic acid molecules comprising a nucleotide complementary to the fluorescent probes are fluorescent in an individually addressable location. One or more of the processes may be repeated or iterated in a cycle.

From the images, the signal 2320 of each individually addressable location or a plurality of individually addressable locations is measured. The mean signal 2330 of multiple individually addressable locations can also be obtained for each cycle. Since the probe applied to the substrate is known each cycle, the mean signal 2330 can be plotted as a function of the known nucleotide sequence 2310. Additionally, the standard deviation of the signal 2340 can also be plotted for each cycle. The plot 2300 may then yield information on the nucleic acid sequence of the biological analyte. One or more of these operations may be performed in real time.

Example 3. Scanning Image Pattern of a Biological Analyte

Figure 44:
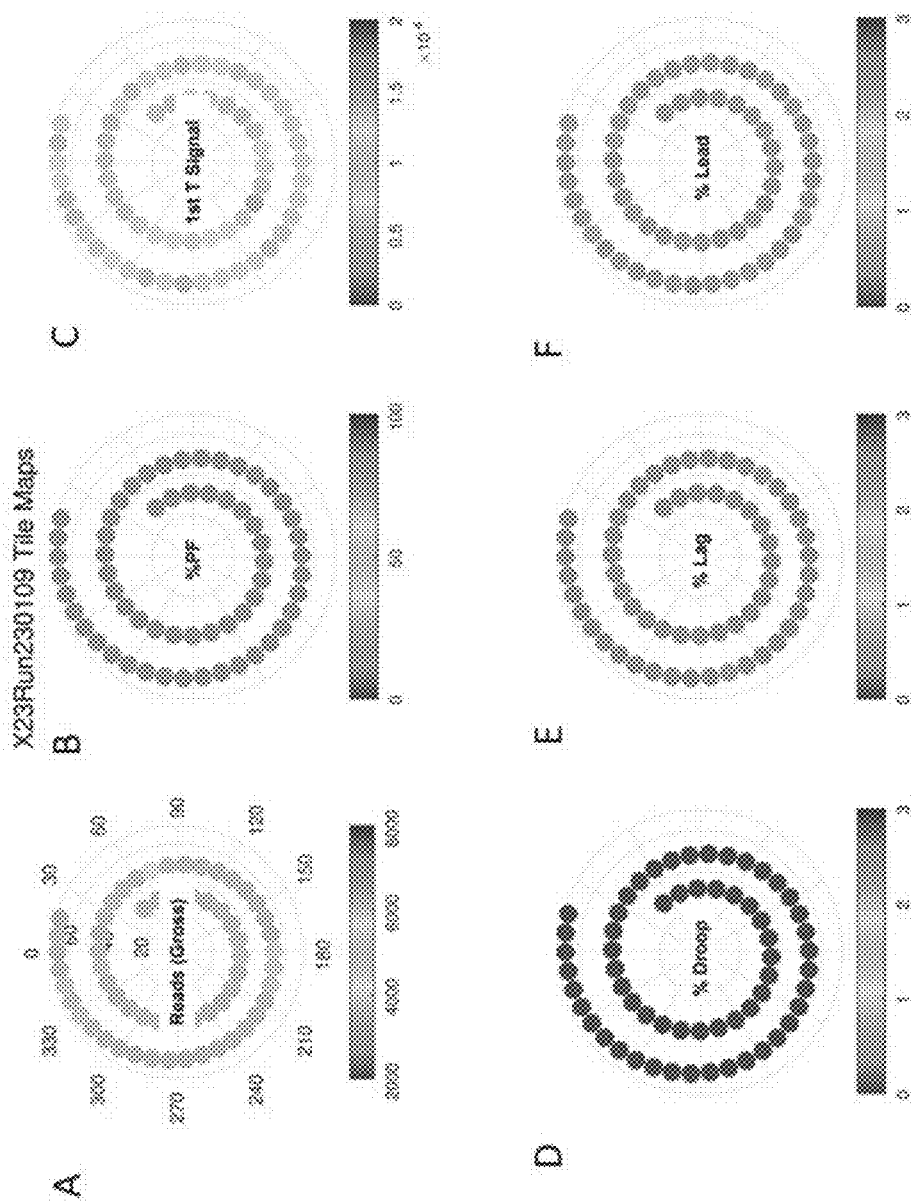
FIG. 44 shows example data of a diagnostic procedure. Panels A-F show spatial plots of diagnostic metrics computed on scanned images at different individually addressable locations.

FIG. 44 shows example data of a diagnostic procedure that informs quality control metrics of scanning imaging. A substrate, similar to that depicted in 310, may be subjected to rotation. The substrate in some cases is rotatable with respect to a central axis. In other embodiments, the substrate may not be rotatable or may not be rotated. The substrate comprises the biological analyte, such as human and *E. Coli* shotgun libraries. In one example, the substrate comprises a shotgun library and ~15% synthetic monotemplates that are spiked into the sample. In such an example, the shotgun library and synthetic monotemplates may be labeled (e.g., fluorescently). In other examples, the shotgun library and synthetic monotemplates are associated with a bead, which may associate with the substrate (e.g., via a linker). In some cases, the beads may associate with the substrate in a pattern. In some cases, a subset of beads on the substrate may be detected in a pattern, such as a spiral pattern (e.g., according to a scan path). The library and synthetic monotemplates may be detected directly using an optical measurement. In other examples, a plurality of probes is added to the substrate and the substrate is subjected to conditions sufficient to conduct a reaction between at least one probe of the plurality of probes and the biological analyte, to couple the at least one probe to the biological analyte. One or more signals are detected from the at least one probe coupled to the biological analyte.

Diagnostic metrics may be computed of imaged segments. FIG. 44A-FIG. 44F show plots depicting image or process metrics at different individually addressable locations (e.g., varying R and θ on a circular substrate). Each scan field of view is depicted as a small circle on each plot (Panels A-F). The images may then be analyzed for the number of reads per image (Panel A), percentage of reads passing filter (Panel B), mean first incorporation signal of a nucleotide (Panel C), droop (signal loss per cycle, Panel D), lag phasing, which may be indicative of false negatives, e.g., the fraction of the clonal population that fails to advance per cycle (Panel E), and lead phasing, which may be indicative of false positives, e.g., the fraction of the clonal population that incorrectly advances per cycle (Panel F). Uniform signal level and lead/lag phasing across R and θ indicate consistent fluidic and biochemical reactions over the course of many incorporation cycles in this instance and predict high quality sequence reads.

Example 4. Linearity and Accuracy of Homopolymers

Figure 45A:
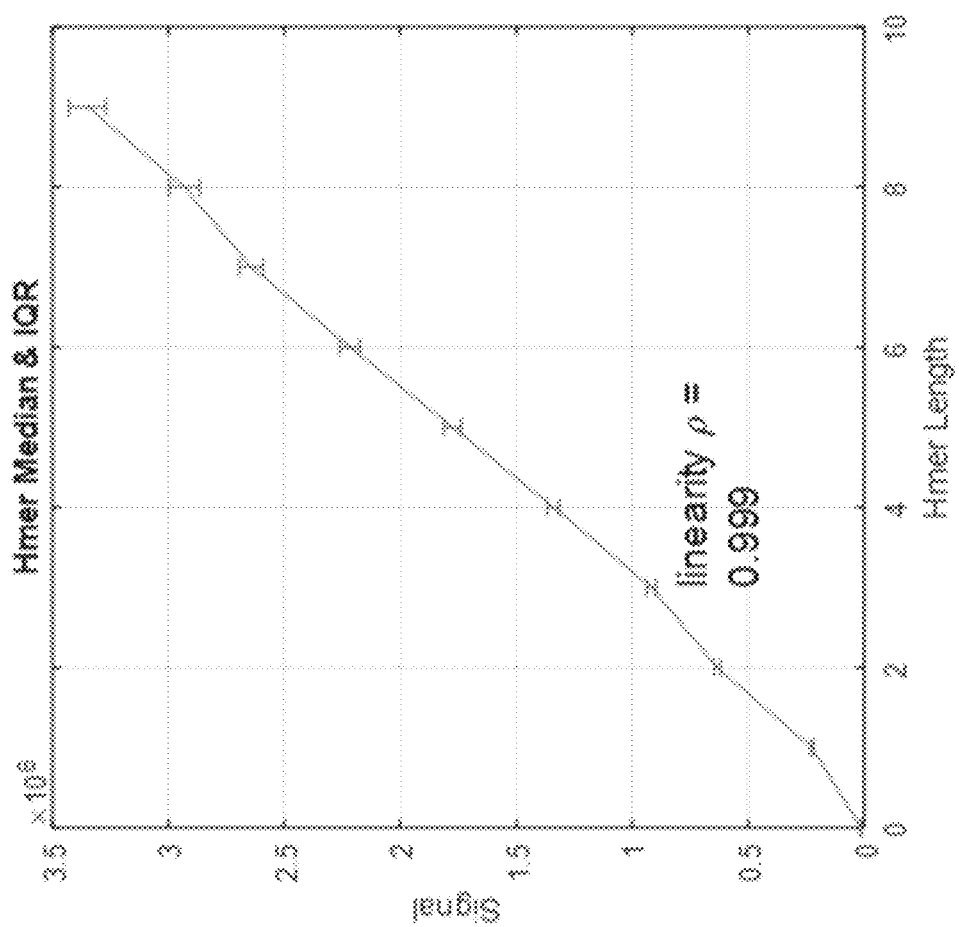
FIG. 45A shows example data of flow-based sequencing.

In sequencing by synthesis chemistries based on single nucleotide flows it is necessary to determine the length of hompolymers as they are synthesized in order to determine the sequence. A homopolymer can be of varying lengths and comprise a sequence of identical nucleotides (e.g., one nucleotide, two nucleotides, three nucleotides, four nucleotides, five nucleotides, six nucleotides, seven nucleotides, eight nucleotides, nine nucleotides, and ten nucleotides, wherein the nucleotides are all the same, i.e., all A, all T, all C, all G, etc.). FIG. 45A shows exemplary data of flow-based sequencing by synthesis. Many homopolymers of different lengths were coupled to the substrate. A complementary probe was added to the substrate, and the substrate was washed and imaged, and the process was repeated. Signal was measured from each bead position. As can be visualized in the plot, the signals from the images are quite linear with the homopolymer length, up to the maximum of 9 nucleotides tested here. Thus, the signal from the obtained images (e.g., of an individually addressable location) can be used to determine the homopolymer length up to 5 bases with sufficiently high accuracy and low noise (>99% accuracy).

Example 5. Sequencing of Nucleic Acid Molecules and Signal Processing

Figure 45B:
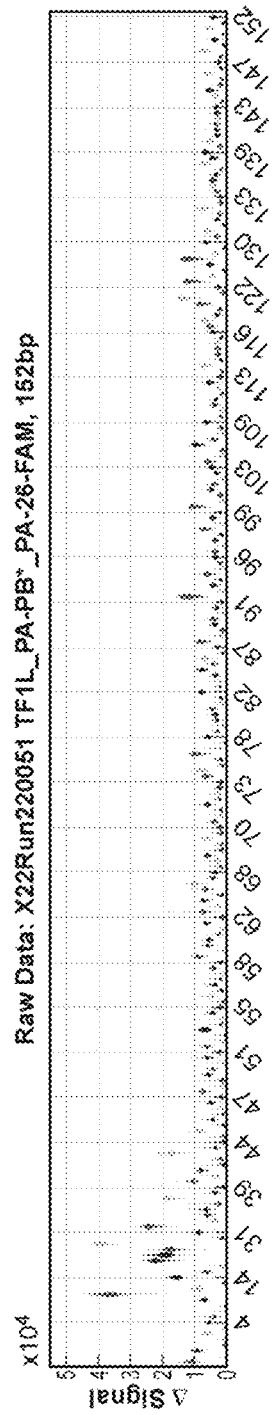
FIG. 45B-FIG. 45C illustrate exemplary data from processed images.
Figure 45C:
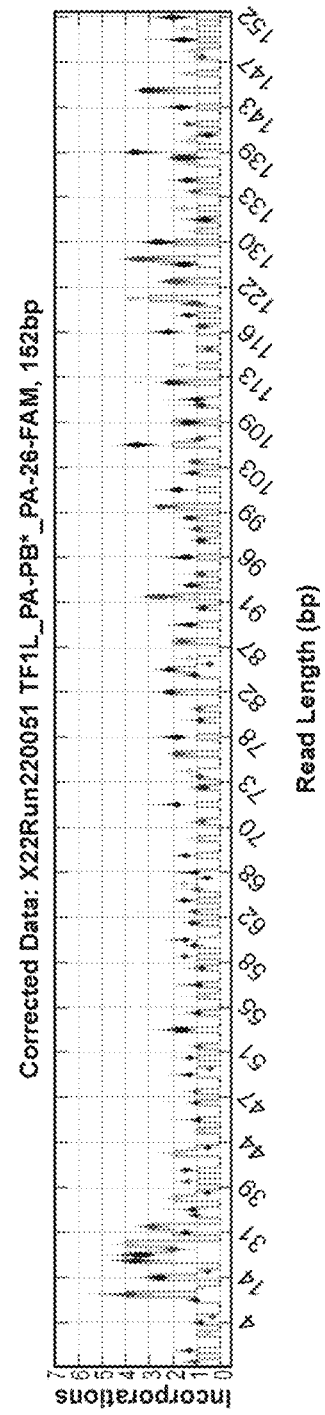

A substrate comprising a substantially planar array has immobilized thereto the biological analyte, e.g. nucleic acid molecules from *E. coli*. Sequencing by synthesis was performed using a flow-based chemistry. Imaging was performed, as described elsewhere herein. FIG. 45B shows the signal distributions for a set of several hundred colonies, each a replicate of a single synthetic monotemplate. The x-axis is labeled with the length of the sequencing after each cycle (e.g., each chemistry flow step). In FIG. 45C, the same data have been processed with a parametric model. The parametric model accounts for different template counts (amplitude) and background level for each colony. The signal is deconvolved with a model of lead and lag phasing and also accounts for global signal loss per cycle. In the example depicted here, the nominal phasing was 0.54% lag, 0.41% lead, and a signal loss of 0.45%. The residual systematic variation may be attributable to signal variation with sequence context can be further corrected using other algorithms (not shown).

Example 6. Sequencing of Shotgun Library from *E. coli*

Figure 46A:
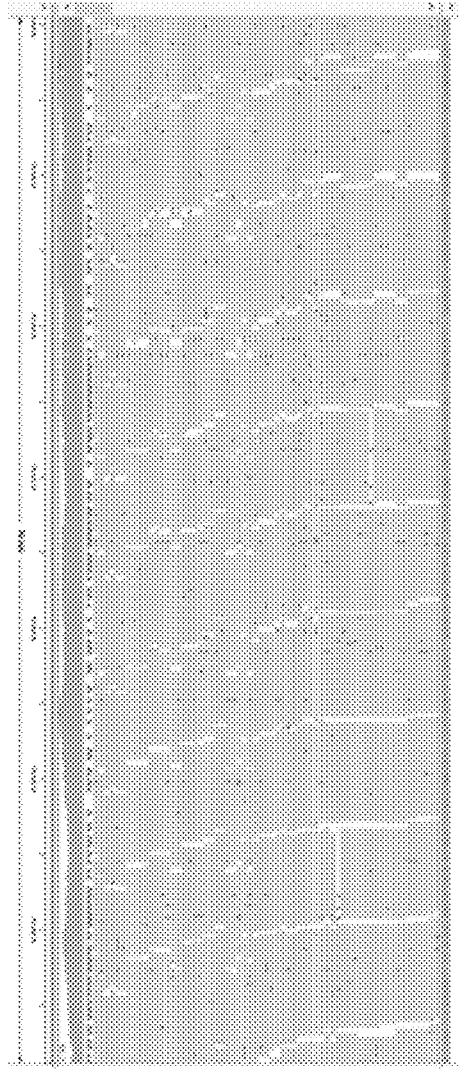
FIG. 46A shows a plot of aligned genomic reads.
Figure 46B:
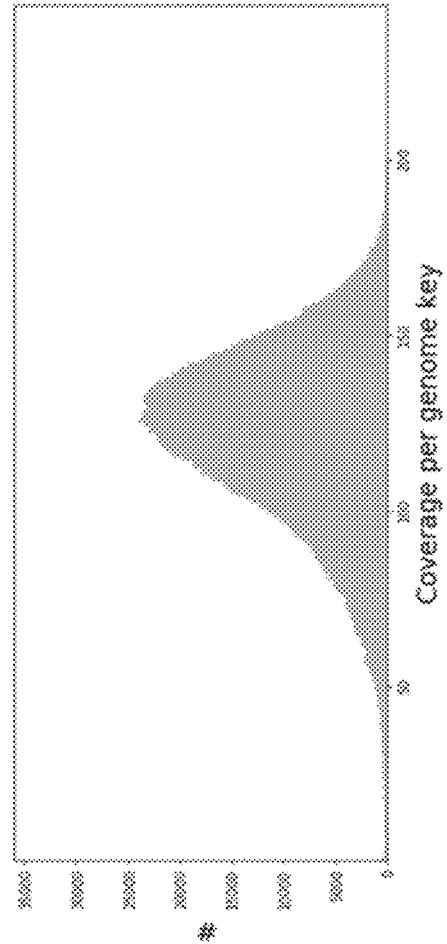
FIG. 46B shows aligned coverage distribution over a reference genome.

A substrate comprising a substantially planar array has immobilized thereto the biological analyte, e.g. nucleic acid molecules from *E. coli*. Sequencing by synthesis was performed using a flow-based chemistry. Imaging was performed, as described elsewhere herein. Images were then processed. FIG. 46A shows individual aligned reads for a segment of the *E. coli* reference genome. FIG. 46B shows a plot derived from the image processing of the aligned read depth for each position in the *E. coli* genome for a set of shotgun reads. The x-axis shows the coverage level at each *E. coli* reference key position and the y-axis shows the frequency.

Example 7. Calculation of Reel-to-Reel Dimensions

A flexible substrate comprising a biological analyte may be designed in a manner such that the throughput of processing nucleic acid molecules is improved. In one example, biological analytes are nano-imprinted on a flexible substrate, such as a film, that is pulled through a first reel to contact the flexible substrate with a reservoir comprising a solution comprising a plurality of probes. The dimensions of the film may be modulated to be compatible with the detector (e.g., an optical sensor). In some cases, the length of the film may be rolled around a reel. The film may be ~85 meters long and 7 millimeters (mm) wide, yielding an area of 6000 square centimeters ($cm^2$). Compared to a planar, circular substrate that has a diameter of 5.9 centimeter (cm), the usable area of the film may be over 60 times greater than the usable area of the planar, circular substrate. Given an optical sensor rate of 10 centimeters per second (cm/s), the entire film may be imaged within ~14 minutes. Alternatively, the dimensions (e.g., length and width) of the film may be modulated to improve the detection rate, the imprinting rate, the contact area, etc.

Example 8: Preparation of a Substrate for Sequencing

Nucleic acid molecules may be sequenced using the methods and systems provided herein. A substrate used in a sequencing process may be a substrate 310. The substrate may comprise a substantially planar array that may comprise a plurality of individually addressable locations 320. The plurality of individually addressable locations may be randomly arranged or arranged in an ordered pattern. At least a subset of the plurality of individually addressable locations may be coupled to a plurality of nucleic acid molecules in preparation for a sequencing process. The individually addressable locations of the subset of the plurality of individually addressable locations may be randomly arranged or arranged in an ordered pattern. The substrate may be configured to rotate with respect to a central axis. A fluid flow unit comprising a fluid channel may be coupled to the substrate and may be configured to dispense a solution to the array. When the solution is dispensed during rotation of the substrate, the solution is directed centrifugally along a direction away from the central axis and may be brought into contact with one or more biological analytes (e.g., nucleic acid molecules) coupled to the substrate. However, the substrate may not be rotated during preparation for sequencing or during a sequencing process. In some cases, the substrate may undergo continuous rotation during preparation for and performance of a sequencing process. In other cases, the substrate may be stationary for at least a portion of such a process.

Preparation of a substrate for sequencing a nucleic acid molecule may comprise dispensing one or more nucleic acid molecules on the substrate. Dispensing of nucleic acid molecules onto the substrate may be carried out in an ordered or random fashion. Nucleic acid molecules coupled to the substrate may be directly or indirectly immobilized to the substrate. For example, nucleic acid molecules may be coupled to a plurality of particles, which plurality of particles may be directly immobilized to the substrate (e.g., via one or more oligonucleotide molecules or another mechanism, as described herein). The plurality of particles may comprise a plurality of beads. A given particle of the plurality of particles may comprise one or more nucleic acid molecules coupled thereto. For example, a given particle of the plurality of particles may comprise a clonal population of nucleic acid molecules coupled thereto. In an example, the plurality of particles comprise a plurality of primer molecules coupled thereto, which plurality of primer molecules are configured to hybridize to sequences of nucleic acid molecules of a library of nucleic acid molecules. Nucleic acid molecules of the library of nucleic acid molecules may be coupled to the plurality of particles via hybridization of the plurality of primer molecules to sequences of the nucleic acid molecules. An amplification process may be performed to amplify nucleic acid molecules coupled to the plurality of particles, which process may provide one or more clonal populations of nucleic acid molecules coupled to the plurality of particles. The amplification process may comprise emulsion PCR. Following the amplification process, the plurality of particles may be dispensed onto the substrate (e.g., in an ordered or random fashion) (e.g., as described herein). Alternatively, the plurality of particles may be dispensed onto the substrate prior to interaction with nucleic acid molecules of the library of nucleic acid molecules, and an amplification process may be performed while the plurality of particles are immobilized to the substrate.

The substrate may comprise adapters or primers of one or more types suitable for binding and amplifying nucleic acid molecules. These adapters may be affixed to the substrate in patterns or without patterns. A pattern may comprise regions attractive to adapters as well as regions repulsive to adapters. Examples of patterns that may be applied to a substrate include spiral pattern, single or concentric rings, and checkered patterns. In an example, the substrate is divided into two portions (e.g., a disc-shaped substrate is bisected to provide two portions), one of which comprises a first region attractive to a first adapter type and another of which comprises a second region attractive to a second adapter type, where the first and second adapter types are not the same. Adapters may be dispensed onto the substrate via a dispensing head that may provide a specific localized concentration of nucleic acid molecules to the substrate in a given pattern. For a continuous process amplification, a concentration may be such that the rate of binding of nucleic acid molecules to a localized volume (e.g., spot) shall be substantially less (at least about 4×) than the amplification doubling rate. This may ensure that most seeds are well-amplified before a second seed in the spot. Loading may take place repeatedly at a modest seeding efficiency, such as an about 10% seeding efficiency. Patterns such as repeated rings and spirals may be generated. Sequential seeding may be used to ensure that most spots are seeded and nearly monoclonally amplified (e.g. at least about 90% of spots, and at least about 90% monoclonal). Alternatively, templates may be seeded to an unpatterned surface with a concentration such that the seeding density is at least about 50 k/mm$^2$, 100 k/mm$^2$, 500 k/mm$^2$, 1M, 2M, 4M, or more. During or after seeding, solid phase amplification may be performed.

Amplification of nucleic acid molecules (e.g., coupled to a plurality of particles, such as a plurality of particles coupled to the substrate) may comprise PCR, bridge amplification, recombinase polymerase amplification, Wildfire amplification, template walking amplification, strand displacement amplification, rolling circle amplification, or any other useful method. An amplification method may comprise kinetic exclusion amplification. For example, an amplification reagent may undergo reaction to product amplification sites each having a clonal population of amplicons from a given nucleic acid molecule, which reaction may comprise simultaneously transporting nucleic acid molecules including the given nucleic acid molecule to the sites at an average transport rate and amplifying the nucleic acids molecules that transport to the sites at an average amplification rate, where the average amplification rate exceed the average transport rate. Nanoball sequencing methods may also be used in combination with the methods and systems provided herein. For example, nucleic acid molecules may comprise template fragments, and adapter sequences may be ligated to the fragments to effect circularization of the fragments. The circular fragments may then be amplified using rolling circle amplification, which may provide concatenated amplified fragments that may be compacted into nucleic acid nanoballs.

Example 9: Sequencing Nucleic Acid Molecules Using Blocked or Terminated Nucleotides Nucleic acid molecules may be sequenced using the methods and systems provided herein. A nucleic acid molecule may be immobilized to a substrate (e.g., directly or via a support such as a bead, which bead may comprise a plurality of nucleic acid molecules coupled thereto, such as a clonal population of nucleic acid molecules). The substrate (e.g., a substrate 310, as described herein) may comprise a substantially planar array, which substantially planar array may comprise a plurality of individually addressable locations (e.g., individually addressable locations 320, as described herein). The plurality of individually addressable locations may be randomly arranged or arranged in an ordered pattern. The nucleic acid molecule may be associated with an individually addressable location of the array. For example, a bead to which the nucleic acid molecule is coupled may be associated with an individually addressable location of the array. The nucleic acid molecule may be coupled to the array (e.g., via a support coupled to the substrate) via an oligonucleotide such as an adapter or primer molecule. The substrate may be configured to rotate with respect to a central axis; a fluid flow unit comprising a fluid channel configured to dispense a solution may be coupled to the substrate such that, during rotation of the substrate, the solution is directed centrifugally along a direction away from the central axis and brought in contact with the biological analyte (e.g., nucleic acid molecule). Alternatively, the substrate may not be rotated.

The nucleic acid molecule may comprise a double-stranded region, which double-stranded region may comprise an adapter sequence in a first strand and a sequence complementary to the adapter sequence in the second strand. The nucleic acid molecule may comprise a target sequence (e.g., a library insert sequence), which target sequence may be flanked by one or more adapter sequences and one or more other sequences, such as one or more barcode or identifier sequences, primer sequences, or other sequences. The nucleic acid molecule may derive from a sample, such as a sample comprising a biological fluid (e.g., blood or saliva). The nucleic acid molecule may comprise deoxyribonucleic acid or ribonucleic acid. For example, the nucleic acid molecule may comprise genomic DNA.

Sequencing of the nucleic acid molecule may proceed by providing a first nucleotide that is complementary to an available position of the nucleic acid molecule. The first nucleotide may comprise a blocking or terminating group, such as a reversible terminator. The blocking or terminating group (e.g., reversible terminator) may be coupled to the first nucleotide via a sugar moiety, such as to a 3' position of the sugar moiety. The blocking or terminating group may comprise an azido moiety. For example, the blocking or terminating group may be a 3'-O-azidomethyl blocking group. Alternatively, the blocking or terminating group may be another group that does not significantly affect incorporation of subsequent nucleotides into a template, such as a small, stable group. The first nucleotide may be labeled (e.g., may be coupled to a fluorescent label). Alternatively, the first nucleotide may be unlabeled (e.g., may not be coupled to a fluorescent label). The first nucleotide may be provided in a first solution (e.g., a reaction mixture), which first solution may comprise one or more additional nucleotides. The first solution may be provided to the substrate via the fluid channel of the fluid flow unit coupled to the substrate (e.g., during rotation of the substrate or while the substrate is stationary). The first solution may comprise a plurality of identical nucleotides comprising the first nucleotide. Alternatively, the first solution may comprise a first plurality of identical nucleotides comprising the first nucleotide and a second plurality of identical nucleotides, where the first nucleotide and a second nucleotide of the second plurality of identical nucleotides may have different chemical structures. For example, the first nucleotide and second nucleotide may comprise different bases (e.g., canonical bases, such as A, G, C, and U/T), labels (e.g., fluorescent labels), linkers (e.g., linkers connecting labels to bases, sugars, or phosphate moieties of a nucleotide), sugar moieties (e.g., sugar moieties comprising or not comprising blocking or terminating groups), or a combination thereof. In an example, the first solution comprises a first plurality of identical nucleotides comprising the first nucleotide, a second plurality of identical nucleotides, a third plurality of identical nucleotides, and a fourth plurality of identical nucleotides, wherein each plurality of identical nucleotides comprises bases of a different canonical type (e.g., A, G, C, and U/T). Each nucleotide of each plurality of identical nucleotides may comprise a blocking or terminating moiety, which blocking or terminating moiety may be the same or different for different types of nucleotides. Each nucleotide of each plurality of identical nucleotides may be unlabeled. Alternatively, all or a portion of each nucleotide of a given plurality of identical nucleotides may be labeled (e.g., with fluorescent labels). For example, all or a portion of each nucleotide of each plurality of identical nucleotides may be labeled. The first solution may comprise other reagents for performing a reaction, such as a buffer, cations, an enzyme (e.g., a polymerase enzyme), or other reagents.

The nucleic acid molecule coupled to the substantially planar array of the substrate and the first nucleotide may be subjected to conditions sufficient to incorporate the first nucleotide into an available position of the nucleic acid molecule (e.g., into a growing strand coupled to a nucleic acid strand comprising a target sequence). The blocking or terminating group of the first nucleotide may prevent incorporation of an additional nucleotide (e.g., of a same type, such as for a homopolymer sequence, or of a different type).

Incorporation of the first nucleotide into the nucleic acid molecule may be detected via imaging, such as by imaging a label coupled to the first nucleotide or a label of a reporter moiety. The array may be interrogated with a detector such an optical detector. Imaging may be performed during rotation of the substrate or while the substrate is stationary. Imaging may comprise scanning or fixed field imaging. For example, an optical detector may be translated and/or rotated relative to the substrate during imaging. Imaging may detect a signal (e.g., fluorescence emission) of a label (e.g., of the first nucleotide or of a reporter moiety coupled thereto). The signal may be indicative of the type of nucleotide incorporated into the nucleic acid molecule. Alternatively, the signal may be indicative of the type of reporter moiety coupled to the nucleic acid molecule, and thus of the type of nucleotide incorporated into the nucleic acid molecule.

Additional details of such methods are described in the Examples below. After detection of the incorporation of the first nucleotide into the nucleic acid molecule, the process may be repeated using a second solution comprising a second nucleotide, etc., to determine a sequence of the nucleic acid molecule.

Example 10: Sequencing Nucleic Acid Molecules Using Non-Terminated Nucleotides

Nucleic acid molecules may be sequenced using the methods and systems provided herein. A nucleic acid molecule may be immobilized to a substrate (e.g., directly or via a support such as a bead, which bead may comprise a plurality of nucleic acid molecules coupled thereto, such as a clonal population of nucleic acid molecules). The substrate (e.g., a substrate 310, as described herein) may comprise a substantially planar array, which substantially planar array may comprise a plurality of individually addressable locations (e.g., individually addressable locations 320, as described herein). The plurality of individually addressable locations may be randomly arranged or arranged in an ordered pattern. The nucleic acid molecule may be associated with an individually addressable location of the array. For example, a bead to which the nucleic acid molecule is coupled may be associated with an individually addressable location of the array. The nucleic acid molecule may be coupled to the array (e.g., via a support coupled to the substrate) via an oligonucleotide such as an adapter or primer molecule. The substrate may be configured to rotate with respect to a central axis; a fluid flow unit comprising a fluid channel configured to dispense a solution may be coupled to the substrate such that, during rotation of the substrate, the solution is directed centrifugally along a direction away from the central axis and brought in contact with the biological analyte (e.g., nucleic acid molecule). Alternatively, the substrate may not be rotated.

The nucleic acid molecule may comprise a double-stranded region, which double-stranded region may comprise an adapter sequence in a first strand and a sequence complementary to the adapter sequence in the second strand. The nucleic acid molecule may comprise a target sequence (e.g., a library insert sequence), which target sequence may be flanked by one or more adapter sequences and one or more other sequences, such as one or more barcode or identifier sequences, primer sequences, or other sequences. The nucleic acid molecule may derive from a sample, such as a sample comprising a biological fluid (e.g., blood or saliva). The nucleic acid molecule may comprise deoxyribonucleic acid or ribonucleic acid. For example, the nucleic acid molecule may comprise genomic DNA.

Sequencing of the nucleic acid molecule may proceed by providing a first nucleotide that is complementary to an available position of the nucleic acid molecule. The first nucleotide may be a non-terminated nucleotide (e.g., may not comprise a blocking or terminating group). The first nucleotide may be labeled (e.g., may be coupled to a fluorescent label). Alternatively, the first nucleotide may be unlabeled (e.g., may not be coupled to a fluorescent label). The first nucleotide may be provided in a first solution (e.g., a reaction mixture), which first solution may comprise one or more additional nucleotides. The first solution may be provided to the substrate via the fluid channel of the fluid flow unit coupled to the substrate (e.g., during rotation of the substrate or while the substrate is stationary). The first solution may comprise a plurality of identical nucleotides comprising the first nucleotide. Alternatively, the first solution may comprise a first plurality of identical nucleotides comprising the first nucleotide and a second plurality of identical nucleotides, where the first nucleotide and a second nucleotide of the second plurality of identical nucleotides may have different chemical structures. For example, the first nucleotide and second nucleotide may comprise different bases (e.g., canonical bases, such as A, G, C, and U/T), labels (e.g., fluorescent labels), linkers (e.g., linkers connecting labels to bases, sugars, or phosphate moieties of a nucleotide), sugar moieties, or a combination thereof. In an example, the first solution comprises a first plurality of identical nucleotides comprising the first nucleotide, a second plurality of identical nucleotides, a third plurality of identical nucleotides, and a fourth plurality of identical nucleotides, wherein each plurality of identical nucleotides comprises bases of a different canonical type (e.g., A, G, C, and U/T). Each nucleotide of each plurality of identical nucleotides may be unlabeled. Alternatively, all or a portion of each nucleotide of a given plurality of identical nucleotides may be labeled (e.g., with fluorescent labels). For example, all or a portion of each nucleotide of each plurality of identical nucleotides may be labeled. In an example, the first solution may comprise a plurality of nucleotides comprising the first nucleotide, in which each nucleotide includes the same canonical base. The plurality of nucleotides may comprise a plurality of labeled nucleotides and a plurality of unlabeled nucleotides. For example, at least 20% of the nucleotides of the plurality of nucleotides of the first solution may be labeled nucleotides. Any % of the nucleotides of the plurality of nucleotides may be labeled nucleotides. The first solution may comprise other reagents for performing a reaction, such as a buffer, cations, an enzyme (e.g., a polymerase enzyme), or other reagents.

The nucleic acid molecule coupled to the substantially planar array of the substrate and the first nucleotide may be subjected to conditions sufficient to incorporate the first nucleotide into an available position of the nucleic acid molecule (e.g., into a growing strand coupled to a nucleic acid strand comprising a target sequence). The absence of a blocking or terminating group may facilitate incorporation of an additional nucleotide (e.g., of a same type, such as for a homopolymer sequence, or of a different type) in a position adjacent to that into which the first nucleotide is incorporated.

Where the first solution includes nucleotides comprising the same base (e.g., canonical base, such as A, G, C, and U/T), detection of incorporation of the first nucleotide and, in some cases (e.g., where the target sequence comprises a homopolymer sequence), one or more additional nucleotides may be detected by imaging a label coupled to the first nucleotide and/or the one or more additional nucleotides, or by detecting a label of a reporter moiety provided to the nucleic acid molecule (e.g., a reporter moiety configured to specifically bind to a nucleotide of a given type). A label coupled to an incorporated nucleotide may be removed (e.g., by contacting the incorporated nucleotide with a cleaving reagent) subsequent to detection, such as prior to contacting the nucleic acid molecule with a second solution comprising a second nucleotide. A label coupled to a reporter moiety may be similarly removed. Alternatively, a sequencing process may proceed without cleaving a label associated with a nucleotide incorporated into the nucleic acid molecule.

Where the first solution includes nucleotides comprising different bases, detection of incorporation of the first nucleotide and, in some cases (e.g., where the target sequence comprises a homopolymer sequence), one or more additional nucleotides may be detected by imaging a label coupled to the first nucleotide and/or the one or more additional nucleotides, which label may be different from other labels coupled to nucleotides comprising bases of different types. For example, the first nucleotide may comprise a label of a first type and a second nucleotide included in the first solution may comprise a label of a second type. The different labels may provide different signals, such as different fluorescence signatures, such that detection of the fluorescence signature of the label coupled to the first nucleotide indicates incorporation of the first nucleotide, rather than the second nucleotide. Alternatively, a labeled reporter moiety may be used to detect incorporation of a nucleotide of a given type.

The array may be interrogated with a detector such an optical detector. Imaging may be performed during rotation of the substrate or while the substrate is stationary. Imaging may comprise scanning or fixed field imaging. For example, an optical detector may be translated and/or rotated relative to the substrate during imaging. Imaging may detect a signal (e.g., fluorescence emission) of a label (e.g., of the first nucleotide or of a reporter moiety coupled thereto). The signal may be indicative of the type of nucleotide incorporated into the nucleic acid molecule. Alternatively, the signal may be indicative of the type of reporter moiety coupled to the nucleic acid molecule, and thus of the type of nucleotide incorporated into the nucleic acid molecule.

Additional details of such methods are described in the Examples below. After detection of the incorporation of the first nucleotide into the nucleic acid molecule, the process may be repeated using a second solution comprising an additional nucleotide, etc., to determine a sequence of the nucleic acid molecule.

Example 11: Detecting Nucleotide Incorporations Using Reporter Moieties

As described in the preceding Examples, detection of incorporation of a nucleotide into a nucleic acid molecule may comprise detection of a label coupled to a nucleotide. Detection of incorporation of a nucleotide may alternatively comprise detection of a label coupled to a reporter moiety.

A labeled (e.g., fluorescently labeled) reporter moiety may be provided to a nucleic acid molecule coupled to a substantially planar array of a substrate (e.g., via a particle). A first nucleotide may be incorporated into the nucleic acid molecule (e.g., as described in the preceding Examples). The first nucleotide may comprise a blocking or terminating moiety. Alternatively, the first nucleotide may be a non-terminated nucleotide. The first reporter moiety may be provided in a first solution (e.g., a first solution providing the first nucleotide to the nucleic acid molecule for incorporation therein) or in a second solution that is provided to the nucleic acid molecule (e.g., after removal of the first solution via centrifugal action and optional application of a washing solution). The second solution may be provided during rotation of the substrate or while the substrate is stationary. The first reporter moiety may comprise an antibody. The first reporter moiety may comprise a fluorescent label. The first reporter moiety may be configured to bind to a nucleotide incorporated into a nucleic acid molecule. For example, the first reporter moiety may be base-specific. The first reporter moiety may be configured to bind to a nucleotide comprising a blocking or terminating group. For example, the first reporter moiety may be a base-specific, 3' block-dependent first reporter moiety, such as a base-specific, 3' block-dependent fluorescently labeled antibody. The first reporter moiety may be configured to bind to the first nucleotide. The first reporter moiety may be configured to not bind to a nucleotide of a type other than that of the first nucleotide. The solution comprising the first reporter moiety (e.g., the second solution) may comprise a plurality of identical first reporter moieties comprising the first reporter moiety. The solution comprising the first reporter moiety may also comprise a plurality of identical second reporter moieties specific to a second nucleotide type (e.g., of a second plurality of identical nucleotides), a plurality of identical third reporter moieties specific to a third nucleotide type (e.g., of a third plurality of identical nucleotides), and a plurality of identical fourth reporter moieties specific to a fourth nucleotide type (e.g., of a fourth plurality of identical nucleotides). Each plurality of identical reporter moieties may comprise a label of a different type. The first reporter moiety and the nucleic acid molecule may be subjected to conditions sufficient to bind the first reporter moiety and the first nucleotide incorporated into the nucleic acid molecule. Unbound reporter moieties may be removed (e.g., via removal of the second solution via centrifugal action and optional application of a washing solution). The array may be interrogated with a detector such an optical detector. Imaging may be performed during rotation of the substrate or while the substrate is stationary. Imaging may comprise scanning or fixed field imaging. For example, an optical detector may be translated and/or rotated relative to the substrate during imaging. Imaging may detect a signal (e.g., fluorescence emission) of a label of the first reporter moiety. The signal may be indicative of the type of reporter moiety coupled to the nucleic acid molecule, and thus of the type of nucleotide incorporated into the nucleic acid molecule.

Subsequent to imaging, the nucleic acid molecule coupled to the array may be subjected to conditions sufficient to remove the first reporter moiety coupled to the first nucleotide. For example, a washing solution may be provided that may comprise a reagent configured to cleave the blocking or terminating group from the first nucleotide and remove the first reporter moiety. Subsequent to the cleaving/washing process, the first nucleotide may no longer comprise a blocking or terminating group, such that the incorporation and detection process may be repeated one or more times. In this manner, a sequence of the nucleic acid molecule coupled to the array may be determined. This process may be used to identify sequences of a plurality of nucleic acid molecules, such as one or more clonal populations of nucleic acid molecules coupled to the array. For example, this process may be used to identify sequences of multiple different clonal populations of nucleic acid molecules coupled to a plurality of beads coupled to a plurality of individually addressable locations of the substantially planar array of the substrate.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
   (a) dispensing a first solution comprising a plurality of labeled nucleotides of a base type from a first dispenser to an open substrate; and
   (b) dispensing a second solution comprising a plurality of unlabeled nucleotides of said base type from a second dispenser to said open substrate, wherein said open substrate is moving relative to said first dispenser and said second dispenser during or subsequent to each of said dispensing in (a) and (b) to disperse said first solution and said second solution, respectively, across said open substrate.

2. The method of claim 1, further comprising allowing said first solution and said second solution to combine on said open substrate to form a mixture comprising said plurality of labeled nucleotides and said plurality of unlabeled nucleotides.

3. The method of claim 1, further comprising dispensing a third solution from a third dispenser to said open substrate.

4. The method of claim 3, wherein said third solution comprises a washing solution.

5. The method of claim 1, wherein dispensing said first solution and dispensing said second solution are performed at substantially a same time.

6. The method of claim 1, wherein dispensing said first solution and dispensing said second solution are performed at different time points.

7. The method of claim 1, further comprising imaging said open substrate.

8. The method of claim 7, wherein imaging said open substrate occurs after dispensing said first solution.

9. The method of claim 7, wherein imaging said open substrate occurs and dispensing said first solution are synchronized.

10. The method of claim 1, wherein said open substrate is moving with respect to said first dispenser and said second dispenser during dispensing said first solution and dispensing said second solution.

11. The method of claim 10, wherein said moving comprises rotation with respect to a rotational axis that is perpendicular to a surface of said open substrate.

12. The method of claim 1, wherein said open substrate is moving subsequent to dispensing said first solution and dispensing said second solution.

13. The method of claim 12, wherein said moving comprises rotation with respect to a rotational axis that is perpendicular to a surface of said open substrate.

\* \* \* \* \*

UNITED STATES PATENT AND TRADEMARK OFFICE
CERTIFICATE OF CORRECTION

PATENT NO. : 12,031,180 B2
APPLICATION NO. : 17/543521
DATED : July 9, 2024
INVENTOR(S) : Beckett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 123 days.

Signed and Sealed this
Twelfth Day of November, 2024

Katherine Kelly Vidal
Director of the United States Patent and Trademark Office